United States Patent
Wei et al.

(10) Patent No.: US 6,878,808 B2
(45) Date of Patent: Apr. 12, 2005

(54) ISOLATED HUMAN TRANSPORTER PROTEINS, NUCLEIC ACID MOLECULES ENCODING HUMAN TRANSPORTER PROTEINS AND USES THEREOF

(75) Inventors: Ming-Hui Wei, Germantown, MD (US); Jiayin Li, Potomac, MD (US); Fangcheng Gong, Germantown, MD (US); Andrei Gabrielian, Rockville, MD (US); Karen A. Ketchum, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 203 days.

(21) Appl. No.: 10/274,990

(22) Filed: Oct. 22, 2002

(65) Prior Publication Data

US 2003/0054491 A1 Mar. 20, 2003

Related U.S. Application Data

(62) Division of application No. 09/734,674, filed on Dec. 13, 2000, now Pat. No. 6,498,022.

(51) Int. Cl.[7] ............................................. C07K 14/705
(52) U.S. Cl. ........................................ 530/350; 514/2
(58) Field of Search ............................... 514/2; 530/350

(56) References Cited

FOREIGN PATENT DOCUMENTS

EP      0 892 052 A      1/1999

OTHER PUBLICATIONS

Wang, C–Z– et al. "The Na+–Driven Cl–/HCO3–Exchanger Cloning Tissue Distribution, and Functional Characterization." Journal of Biological Chemistry, American Society of Biological Chemists, Baltimore, MD, US 'Online! vol. 275, No. 45. Nov. 10, 2000. XP002182614.

Wang et al. "*Homo sapiens* SLC4A10 mRNA for NCBE, Complete CDs." Database EMBL 'Online! Nov. 21, 2000. Database accession No. AB040457. XP002217229. & Wang et al. "Mus Musculus SLc4A10 mRNA for NCBE, Complete CDs." XP002217230.

Sulston et al. "*Homo sapiens* BAC Clone RP11–220I15 From 2, Complete Sequence." Database EMBL 'Online! Apr. 26, 2000. Database accession No. AC062022. XP002217231.

International Search Report dated Nov. 18, 2002. PCT/US01/47463.

Results of BLAST search of SEQ ID NO:2 against Derwent (FastAlert and GeneSeqP) and NCBI (pataa) protein patent databases on Mar. 17, 2003.

*Primary Examiner*—John Ulm
(74) *Attorney, Agent, or Firm*—Celera Genomics; Lin Sun-Hoffman

(57) ABSTRACT

The present invention provides amino acid sequences of peptides that are encoded by genes within the human genome, the transporter peptides of the present invention. The present invention specifically provides isolated peptide and nucleic acid molecules, methods of identifying orthologs and paralogs of the transporter peptides, and methods of identifying modulators of the transporter peptides.

4 Claims, 92 Drawing Sheets

```
   1 CGGCCGCGTC GACGTGATTT GATATCTTGA TGATGGCTTA AACAGATACT
  51 GATGGACAGA TCTGTTGTTT GATATTTTTT TCACTAGCCC TGAAGATGCT
 101 GAGACATAGA GATGGCTGTG ATTATCTTTT GTAAGACAGG AAATGCAGTC
 151 TTTAGGGGTT TCTGGAAATA GAAAGGTCAT GCAGTCTGGA ACCTGTGAGC
 201 CTTTTCAATC TCTAAGTCAT CAGAGAAATG ATGAAGAAGC AGTTGTGGAT
 251 AGAGGTGGAA CTCGTTCTAT TCTCAAAACA CACTTTGAGA AAGAAGATTT
 301 AGAAGGTCAT CGAACACTAT TTATTGGAGT ACATGTGCCC TTGGGAGGAA
 351 GAAAAAGCCA TCGACGTCAC AGGCATCGTG GTCATAAACA CAGAAAGAGA
 401 GACAGAGAAA GAGATTCAGG ATTAGAGGAT GGAAGGGAGT CACCTTCTTT
 451 TGACACCCCA TCACAGAGGG TACAGTTTAT TCTTGGAACC GAGGATGATG
 501 ACGAGGAACA CATTCCTCAT GACCTTTTCA CAGAACTGGA TGAGATTTGT
 551 TGGCGTGAAG GTGAGGACGC TGAGTGGCGA GAAACAGCCA GGTGGTTGAA
 601 GTTTGAAGAA GATGTGGAAG ATGGAGGAGA AAGGTGGAGC AAGCCTTATG
 651 TGGCTACTCT TTCATTGCAC AGCTTGTTTG AATTGAGAAG TTGTATTCTG
 701 AATGGAACTG TGTTGCTGGA CATGCATGCC AACACTTTAG AAGAAATTGC
 751 AGATATGGTT CTTGACCAAC AAGTGAGCTC AGGTCAGCTG AATGAAGATG
 801 TACGCCATAG GGTCCATGAG GCATTGATGA AACAGCATCA TCATCAGAAT
 851 CAGAAAAAAC TCACCAACAG GATTCCCATT GTTCGTTCCT TTGCTGATAT
 901 TGGCAAGAAA CAGTCAGAAC CAAATTCCAT GGACAAAAAT GCAGGTCAGG
 951 TTGTTTCTCC TCAGTCTGCT CCAGCCTGTG TTGAAAATAA AAATGATGTT
1001 AGCAGAGAAA ACAGCACTGT TGACTTTAGC AAGGGACTGG GAGGCCAACA
1051 AAAGGGGCAT ACTAGTCCAT GTGGGATGAA ACAAAGGCAT GAAAAAGGAC
1101 CTCCACACCA GCAAGAGAGA GAGGTTGATC TGCATTTTAT GAAAAAGATT
1151 CCTCCAGGTG CTGAAGCATC GAACATCTTA GTGGGAGAAC TGGAGTTCTT
1201 GGATCGAACA GTAGTTGCGT TTGTCAGGTT GTCTCCAGCT GTATTGCTTC
1251 AAGGACTGGC TGAAGTCCCA ATCCCAACCA GATTTTTGTT CATTCTTCTG
1301 GGACCCCTGG GAAACGGTCA ACAGTACCAT GAGATTGGCA GATCAATTGC
1351 AACCCTAATG ACAGATGAGG TATTTCATGA TGTTGCCTAT AAAGCTAAAG
1401 ATCGTAATGA CTTGGTATCA GGAATTGATG AGTTTCTGGA TCAGGTTACT
1451 GTTCTCCCTC CTGGAGAATG GGATCCAAGC ATTCGAATAG AGCCTCCCAA
1501 AAATGTTCCT TCCCAGGAGA GAGGAAGAT TCCTGCTGTA CCAAATGGAA
1551 CAGCAGCTCA TGGGAAGCA GAGCCCCACG GAGGACATAG TGGACCTGAA
1601 CTCCAGCGAA CTGGAAGGAT TTTTGGGGGA CTTATTTTAG ATATCAAAAG
1651 AAAAGCTCCA TACTTCTGGA GTGACTTCAG AGATGCTTTC AGCCTGCAGT
1701 GCTTAGCATC TTTTCTATTT CTCTACTGCG CGTGTATGTC TCCTGTCATC
1751 ACGTTTGGAG GACTGCTGGG AGAAGCAACT GAAGGGCGTA TAAGTGCAAT
1801 TGAATCTCTC TTTGGAGCAT CCATGACCGG GATAGCCTAT TCTCTCTTTG
1851 GTGGACAGCC TCTTACCATA TTAGGCAGTA CAGGACCAGT TTTGGTGTTT
1901 GAAAAGATTT TGTTTAAATT TTGCAAAGAA TATGGGCTGT CATACCTATC
1951 TTTAAGAGCT AGCATTGGAC TTTGGACTGC AACTCTATGT ATCATACTTG
2001 TGGCCACAGA TGCTAGTTCC CTTGTCTGCT ACATCACTCG GTTTACTGAA
2051 GAAGCTTTTG CTTCCCTGAT TTGCATCATT TCATTTATG AGGCCCTGGA
2101 GAAGTTGTTT GAACTCAGTG AAGCATATCC AATCAACATG CATAATGATC
2151 TGGAACTGCT GACACAATAC TCGTGTAACT GTGTGGAACC GCATAATCCC
2201 AGCAATGGCA CATTGAAGGA ATGGAGGGAA TCCAATATTT CTGCCTCTGA
2251 CATAATTTGG GAGAACCTAA CTGTGTCAGA ATGCAAATCA TTGCATGGAG
2301 AGTATGTTGG ACGGGCCTGT GGCCATGATC ACCCATATGT TCCAGATGTT
2351 CTATTTTGGT CTGTGATCCT GTTCTTTTCC ACAGTTACTC TGTCAGCCAC
2401 CCTGAAGCAG TTCAAGACTA GCAGATATTT TCCAACCAAG GTTCGATCCA
2451 TAGTGAGTGA CTTTGCTGTC TTTCTTACAA TTCTGTGTAT GGTTTTAATT
2501 GACTATGCCA TTGGGATCCC ATCTCCAAAA CTACAAGTAC AAGTGTTTT
2551 CAAGCCCACT AGAGATGATC GTGGCTGGTT TGTTACGCCT TTAGGTCCAA
2601 ACCCATGGTG GACAGTAATA GCTGCTATAA TTCCAGCTCT GCTTTGTACT
2651 ATTCTAATTT TTATGGACCA ACAGATTACA GCTGTCATCA TCAACAGGAA
2701 AGAGCATAAG CTAAAGAAAG GTTGTGGGTA CCATCTGGAC CTATTAATGG
2751 TGGCTGTCAT GCTCGGTGTA TGCTCCATCA TGGGCCTGCC ATGGTTTGTG
2801 GCTGCCACAG TCCTCTCCAT CACTCATGTC AATAGCCTAA AACTGGAATC
2851 AGAATGCTCA GCTCCAGGAG AACAACCCAA ATTTCTCGGC ATTCGGGAGC
2901 AAAGGGTTAC TGGGCTTATG ATTTTTATTC TTATGGGTTC ATCAGTCTTT
2951 ATGACCAGTA TTCTGAAGTT TATTCCCATG CCAGTGCTAT ATGGAGTGTT
3001 TCTTTATATG GGTGCTTCAT CTCTAAAGGG AATTCAGTTC TTTGATAGGA
3051 TAAAGCTCTT CTGGATGCCG GCAAAACATC AACCAGATTT TATATACCTA
```

FIGURE 1A

```
3101 AGGCACGTAC CGCTTCGAAA AGTGCATCTC TTCACAATTA TTCAGATGAG
3151 TTGCCTTGGC CTTTTGTGGA TAATAAAGT  TTCAAGAGCT GCTATTGTCT
3201 TTCCCATGAT GGTGTTAGCC CTGGTATTTG TAAGAAAGTT GATGGACTTG
3251 TTGTTCACGA AGCGGGAACT CAGCTGGTTG GATGATTTGA TGCCCGAGAG
3301 TAAGAAAAAG AAACTGGAAG ATGCTGAAAA AGAAGAAGAA CAAAGTATGC
3351 TAGCTATGGA AGATGAGGGC ACAGTACAAC TCCCATTGGA AGGGCACTAT
3401 AGAGATGATC CATCTGTGAT CAATATATCT GATGAAATGT CAAAGACTGC
3451 CTTGTGGAGG AACCTTCTGA TTACTGCCGA TAACTCAAAA GATAAGGAGT
3501 CAAGCTTTCC TTCCAAAAGC TCCCCTTCCT AATCACTCTA GAAGCTGATT
3551 CCCCAAAGCA TTGAAAGCCG AAAAGAGAAG AAAGCTGACT CAGGGAAAGG
3601 TGTTGACAGG GAGACTTGTC TATGACTCGA TCTTCAATTT ATTTTTTACA
3651 TATATATGAG AAGAGTGTCA CAATTATTAA TAAAACTGCT TTGATCATGT
3701 ATTGTAAATT CTGTCCCTCA ACCCAAATCC ACCTTCATAC TGTAAGTAGT
3751 GCAATACTTG TTTCATTTCT GTGTTTAAAC TTCTGAGCAG TGAGACATCC
3801 CTGTGAGCAG ATACAATAGC CAATGCAAGA ATCTGTGTGT TCCTTGCTGT
3851 ACGTTAGACA TTTGTAAACT GGATTCTGAT TGTCAGTTTT ATGAGAGCAA
3901 TAGCTTCCTT AAAGAGATAA GTCATATTTA CCTAGTTTGT ATTTTCCTAC
3951 TTTAGTGACC TGAAGATGCC TGATAATTTC ATTCAGAAGA ATTTTTGAAA
4001 GGTAGTCTTA CTTCTTTTTA GTTTTTATAG CTTAGCATTA GTGACTTATT
4051 TCAAAAGACC CAAATCAAAA AGTTAGTTTG AAAGCATTTT TTAATAATTG
4101 TATTTATGCA TTTCCTTGAT TTAATATGAT AAATTTAATA CTTAACAATT
4151 TATATGTAAC TAAAACTTAA AGTCATTTGA AAAATATATA GAAACCTATT
4201 TACAACTTGT TAAGGACAAT CAGACATAAT GCAGAGTTAA GTAGTATTTG
4251 CTTAAAATTC AAGTTGTGAC TAATGATCAA ATACTAGGCT TGTACGAAAT
4301 GCTTTAGAAA AACTTTGTAA CAGTTTTGTG GGATTTTTCA ATATAAACCT
4351 TTATCAGAAA TATACTAAGT TTGTCTCCCA CTGACAACAG ATGTTTTCCA
4401 AATAAACATA TTCTATACAT ACTTGTGGAA TGCCACATGG TGAATCATTG
4451 TATATGAAAT TCCACTCCTG TACAGTTACT CTGCAGCTAA TGGTCATGCA
4501 CTGCTTAATG CTGGTCCTGA ATCATGTTCT CATGTTAGAC CAACAGCTCT
4551 CCAATTGTCA TTTTTTTTCT GCAGAGTTTT TTTTTTTCCA CTTTTAAATT
4601 AAATGCATGT TGTGGAAAAA CAGTCTTTTA AAATGAAATT TCAGATTCCA
4651 TTTGAGAAGG TTCTGTAGAT ATTTCAGTCC ATATAAAATA ATACATCTTT
4701 ACTAAACTTA TATAAGGGGA GAGAAAGTTA TGAAGTTTTG GACATTACTA
4751 AAAGTACAGT ATTTGATTTC ACTTTCAATG AATGTGAAGT TAATAAAACT
4801 AAATCTCATA ATGCTCTTGG TTCCTAAGAA TGAGTAGTAA TCATCAACTT
4851 TATAATACTC CAATATTCCG TTTTATAATA ATTCAGAGCC CTGTGGCTTT
4901 TACACACCGT TAATTATGTA CTCTGTTGGA AGTGCACATG AAAAGTGAAG
4951 AAAAGTTCCT CTTGTGATTA AACTAATGGG AGGAAATAAA TCAACAAAGT
5001 CTCCATTAAG TTCTACATTT TGAGACCTTT TAAAAATTCC CCTCACAATT
5051 CTTTAAGGAG CCCCCCTTTT TATGGAACAT GAGCCTAAAA ATTATAGAAA
5101 GAAGAATTTT AAGTTAATAA AGTTTGTATT TATAAATGCT GAAAAAATAC
5151 AGAAACTTTC TGTTCCAAAT GTGTTGCCTT TGTGTATTTT ATAATACAGA
5201 TACTACATTG TAAACATTTC CATTGTTTTA TGATTTAGCC AGTGATTCCC
5251 CAAAGCAGCC TCTTAGTGTT TTAATATATT AATAACTGTT TTGTTAAAAA
5301 TGATCATAGT GAATTTAAAT CTTCACATGA TCACCTATTT GAATAAGCAA
5351 TCATATCCAA TGAAATTCTG TATTTCTGAG TATTTTTATA GTCATTTTGT
5401 TCTTGTGTGA ATTTAAAGC  TATCCCTATG TTAATCCTAA TATTTTGAAA
5451 TCATATAAAA TATAATAAAA ATGTAGTATT ATATATTTAC TTCTAATTTC
5501 AGATTCCTGG TCAAAATTAC TAAATATCTT GAATGTAATT TAGTGCCAAG
5551 TTTAAATAAT GTGTAAATGT GACTAGGATA TTGTGTTTTT CACAATTAAG
5601 AAATGTTATG TGGAAATAAA TATTTATCCT AACTTCCTTG CACATTTTAA
5651 ATTGTGATAC AAAGTGTCTT GTCTTTTTTC TTTGTTTTAA TTAGTAAATC
5701 AGTGTAAAAC AAAAAAAAAA AAAAAAAAAA AAAAA   (SEQ ID NO:1)
```

FIGURE 1B

FEATURES:
5' UTR: 1
Start: 179
Stop: 3530
3' UTR: 3533
HOMOLOGOUS PROTEINS:
Top 10 BLAST Hits:

```
                                                              Score   E
gi|10946960|ref|NP_067505.1| sodium bicarbonate cotransporter i...  1702  0.0
gi|4759134|ref|NP_004849.1| solute carrier family 4, sodium bic...  1677  0.0
gi|3882199|dbj|BAA34459.1| (AB018282) KIAA0739 protein [Homo sa...  1671  0.0
gi|10436051|gb|AAG16773.1|AF089726_1 (AF089726) sodium bicarbon...  1626  0.0
gi|4507029|ref|NP_003606.1| solute carrier family 4, sodium bic...  1503  0.0
gi|6650104|gb|AAF21720.1|AF053755_1 (AF053755) bicarbonate tran...  1473  0.0
gi|6502527|gb|AAF14345.1|AF069511_1 (AF069511) putative sodium ...  1288  0.0
gi|5702100|gb|AAD47142.1|AF080106_1 (AF080106) NBC-like protein...  1288  0.0
gi|5051628|gb|AAD38322.1|AF047033_1 (AF047033) sodium bicarbona...  1266  0.0
gi|5669564|gb|AAD46389.1|AF070475_1 (AF070475) NBC-like protein...  1260  0.0
```

EXPRESSION INFORMATION FOR MODULATORY USE:
library source:
Expression information from PCR-based tissue screening panels:
Human testis
Human fetal brain
Brain
Placenta
Bone marrow

FIGURE 1C

```
   1  MQSLGVSGNR  KVMQSGTCEP  FQSLSHQRND  EEAVVDRGGT  RSILKTHFEK
  51  EDLEGHRTLF  IGVHVPLGGR  KSHRRHRHRG  HKHRKRDRER  DSGLEDGRES
 101  PSFDTPSQRV  QFILGTEDDD  EEHIPHDLFT  ELDEICWREG  EDAEWRETAR
 151  WLKFEEDVED  GGERWSKPYV  ATLSLHSLFE  LRSCILNGTV  LLDMHANTLE
 201  EIADMVLDQQ  VSSGQLNEDV  RHRVHEALMK  QHHHQNQKKL  TNRIPIVRSF
 251  ADIGKKQSEP  NSMDKNAGQV  VSPQSAPACV  ENKNDVSREN  STVDFSKGLG
 301  GQQKGHTSPC  GMKQRHEKGP  PHQQEREVDL  HFMKKIPPGA  EASNILVGEL
 351  EFLDRTVVAF  VRLSPAVLLQ  GLAEVPIPTR  FLFILLGPLG  KGQQYHEIGR
 401  SIATLMTDEV  FHDVAYKAKD  RNDLVSGIDE  FLDQVTVLPP  GEWDPSIRIE
 451  PPKNVPSQEK  RKIPAVPNGT  AAHGEAEPHG  GHSGPELQRT  GRIFGGLILD
 501  IKRKAPYFWS  DFRDAFSLQC  LASFLFLYCA  CMSPVITFGG  LLGEATEGRI
 551  SAIESLFGAS  MTGIAYSLFG  GQPLTILGST  GPVLVFEKIL  FKFCKEYGLS
 601  YLSLRASIGL  WTATLCIILV  ATDASSLVCY  ITRFTEEAFA  SLICIIFIYE
 651  ALEKLFELSE  AYPINMHNDL  ELLTQYSCNC  VEPHNPSNGT  LKEWRESNIS
 701  ASDIIWENLT  VSECKSLHGE  YVGRACGHDH  PYVPDVLFWS  VILFFSTVTL
 751  SATLKQFKTS  RYFPTKVRSI  VSDFAVFLTI  LCMVLIDYAI  GIPSPKLQVP
 801  SVFKPTRDDR  GWFVTPLGPN  PWWTVIAAII  PALLCTILIF  MDQQITAVII
 851  NRKEHKLKKG  CGYHLDLLMV  AVMLGVCSIM  GLPWFVAATV  LSITHVNSLK
 901  LESECSAPGE  QPKFLGIREQ  RVTGLMIFIL  MGSSVFMTSI  LKFIPMPVLY
 951  GVFLYMGASS  LKGIQFFDRI  KLFWMPAKHQ  PDFIYLRHVP  LRKVHLFTII
1001  QMSCLGLLWI  IKVSRAAIVF  PMMVLALVFV  RKLMDLLFTK  RELSWLDDLM
1051  PESKKKKLED  AEKEEEQSML  AMEDEGTVQL  PLEGHYRDDP  SVINISDEMS
1101  KTALWRNLLI  TADNSKDKES  SFPSKSSPS   (SEQ ID NO:2)
```

FEATURES:
Functional domains and key regions:
[1] PDOC00001 PS00001 ASN_GLYCOSYLATION
N-glycosylation site Number of matches: 7
```
    1        187-190    NGTV
    2        290-293    NSTV
    3        468-471    NGTA
    4        688-691    NGTL
    5        698-701    NISA
    6        708-711    NLTV
    7       1094-1097   NISD
```

[2] PDOC00004 PS00004 CAMP_PHOSPHO_SITE
cAMP- and cGMP-dependent protein kinase phosphorylation site Number of matches: 2
```
    1        238-241    KKLT
    2        255-258    KKQS
```

[3] PDOC00005 PS00005 PKC_PHOSPHO_SITE
Protein kinase C phosphorylation site

Number of matches: 15
```
    1         72-74     SHR
    2        107-109    SQR
    3        148-150    TAR
    4        241-243    TNR
    5        446-448    SIR
    6        490-492    TGR
    7        603-605    SLR
    8        690-692    TLK
    9        753-755    TLK
   10        690-692    TLK
   11        753-755    TLK
   12        759-761    TSR
```

FIGURE 2A

```
     13     794-796  SPK
     14     898-900  SLK
     15     960-962  SLK
```

[4] PDOC00006 PS00006 CK2_PHOSPHO_SITE
Casein kinase II phosphorylation site

```
Number of matches: 17
      1        46-49  THFE
      2        92-95  SGLE
      3      116-119  TEDD
      4      130-133  TELD
      5      177-180  SLFE
      6      198-201  TLEE
      7      249-252  SFAD
      8      291-294  STVD
      9      426-429  SGID
     10      483-486  SGPE
     11      551-554  SAIE
     12      690-693  TLKE
     13      700-703  SASD
     14      710-713  TVSE
     15      806-809  TRDD
     16    1039-1042  TKRE
     17    1044-1047  SWLD
```

[5] PDOC00007 PS00007 TYR_PHOSPHO_SITE
Tyrosine kinase phosphorylation site

```
          978-985  KHQPDFIY
```

[6] PDOC00008 PS00008 MYRISTYL
N-myristoylation site

```
Number of matches: 11
      1         5-10  GVSGNR
      2        38-43  GGTRSI
      3        68-73  GGRKSH
      4        93-98  GLEDGR
      5      301-306  GQQKGH
      6      339-344  GAEASN
      7      539-544  GGLLGE
      8      558-563  GASMTG
      9      563-568  GIAYSL
     10      571-576  GQPLTI
     11      609-614  GLWTAT
```

[7] PDOC00009 PS00009 AMIDATION
Amidation site

```
Number of matches: 2
      1        68-71  GGRK
      2      253-256  IGKK
```

[8] PDOC00040 PS00041 HTH_ARAC_FAMILY_1
Bacterial regulatory proteins, araC family signature

```
          921-961  RVTGLMIFILMGSSVFMTSILKFIPMPVLYGVFLYMGASSL
```

FIGURE 2B

Membrane spanning structure and domains:

| Helix | Begin | End | Score | Certainty |
|---|---|---|---|---|
| 1 | 371 | 391 | 0.629 | Putative |
| 2 | 520 | 540 | 2.036 | Certain |
| 3 | 555 | 575 | 1.439 | Certain |
| 4 | 605 | 625 | 1.559 | Certain |
| 5 | 634 | 654 | 0.689 | Putative |
| 6 | 734 | 754 | 1.972 | Certain |
| 7 | 774 | 794 | 1.593 | Certain |
| 8 | 821 | 841 | 2.189 | Certain |
| 9 | 867 | 887 | 2.222 | Certain |
| 10 | 922 | 942 | 2.278 | Certain |
| 11 | 945 | 965 | 1.230 | Certain |
| 12 | 994 | 1014 | 1.557 | Certain |
| 13 | 1017 | 1037 | 0.669 | Putative |

BLAST Alignment to Top Hit:

```
>gi|10946960|ref|NP_067505.1| sodium bicarbonate cotransporter isoform
    3 [Mus musculus] >gi|7385123|gb|AAF61705.1|AF224508_1
    (AF224508) sodium bicarbonate cotransporter isoform 3
    kNBC-3 [Mus musculus]
    Length = 1089

Score = 1702 bits (4360), Expect = 0.0
 Identities = 835/1120 (74%), Positives = 956/1120 (84%), Gaps = 49/1120 (4%)

Query:  13  MQSGTCEPFQSLSHQRNDEEAVVDRGGTRSILKTHFEKEDLEGHRTLFIGVHVPLGGRKS  72
            M +G+ EP   LS+QR DEEAVVD+GGT +IL  H+EKE+LEGHRTL++GV  +PLG R+S
Sbjct:   1  MPAGSNEPDGVLSYQRPDEEAVVDQGGTSTILNIHYEKEELEGHRTLYVGVRMPLG-RQS  59

Query:  73  HRRHRHRGHKHRKRDRERDSGL---EDGRESPSFDTPSQRVQFILGTEDDDEEHIPHDLF  129
            HR HR  G KHR+R    R G    E+G E+ + DTPSQRVQFILGTE+D EEH+PH+LF
Sbjct:  60  HRHHRTHGQKHRRRGG-RGKGASQGEEGLEALAHDTPSQRVQFILGTEED-EEHVPHELF  117

Query: 130  TELDEICWREGEDAEWRETARWLKFEEDVEDGGERWSKPYVATLSLHSLFELRSCILNGT  189
            TELDEIC  +EGEDAEW+ETARWLKFEEDVEDGGERWSKPYVATLSLHSLFELRSC++NG+
Sbjct: 118  TELDEICMKEGEDAEWKETARWLKFEEDVEDGGERWSKPYVATLSLHSLFELRSCLINGS  177

Query: 190  VLLDMHANTLEEIADMVLDQQVSSGQLNEDVRHRVHEALMKQHHHQNQKKLTNRIPIVRS  249
            VLLDM A+++EEI+D++LDQQ     L++ VR +V EAL+K HHHQN+++  N IPIVRS
Sbjct: 178  VLLDMRASSIEEISDLILDQQELLRDLSDSVRVKVREALLKKHHHQNERRRNNLIPIVRS  237

Query: 250  FADIGKKQSEPNSMDKNAGQVVSPQSAPACVENKNDVSRENSTVDFSKGLGGQQKGHTSP  309
            FA++GKKQS+P+SMD++  GQ  +SPQSA     +E KN V+  E+S VD SK
Sbjct: 238  FAEVGKKQSDPHSMDRD-GQTMSPQSATN-LEVKNGVNCEHSPVDLSK-----------  283

Query: 310  CGMKQRHEKGPPHQQEREVDLHFMKKIPPGAEASNILVGELEFLDRTVVAFVRLSPAVLL  369
                            VDLHFMKKIP GAEASN+LVGE++ LDR +VAFVRLSPAVLL
Sbjct: 284  ----------------VDLHFMKKIPTGAEASNVLVGEVDTLDRPIVAFVRLSPAVLL  325

Query: 370  QGLAEVPIPTRFLFILLGPLGKGQQYHEIGRSIATLMTDEVFHDVAYKAKDRNDLVSGID  429
             GL EVPIPTRFLFILLGP+GKGQQYHEIGRS+AT+MTDE+FHDVAYKAK+R DL++GID
Sbjct: 326  SGLTEVPIPTRFLFILLGPVGKGQQYHEIGRSMATIMTDEIFHDVAYKAKERDDLLAGID  385

Query: 430  EFLDQVTVLPPGEWDPSIRIEPPKNVPSQEKRKIPAVPNGTAAHGEAEPHGGHSGPELQR  489
            EFLDQVTVLPPGEWDPSIRIEPPKNVPSQEKRK+P VPNG   H E EPHGGHSGPEL+R
Sbjct: 386  EFLDQVTVLPPGEWDPSIRIEPPKNVPSQEKRKMPGVPNGNVCHIEPEPHGGHSGPELER  445

Query: 490  TGRIFGGLILDIKRKAPYFWSDFRDAFSLQCLASFLFLYCACMSPVITFGGLLGEATEGR  549
            TGR+FGGL+LD+KRKAP++WSD+RDA SLQCLASFLFLYCACMSPVITFGGLLGEATEGR
Sbjct: 446  TGRLFGGLVLDVKRKAPWYWSDYRDALSLQCLASFLFLYCACMSPVITFGGLLGEATEGR  505
```

```
Query:  550  ISAIESLFGASMTGIAYSLFGGQPLTILGSTGPVLVFEKILFKFCKEYGLSYLSLRASIG  609
             ISAIESLFGASMTGIAYSLF GQPLTILGSTGPVLVFEKILFKFCK+Y LSYLSLRA IG
Sbjct:  506  ISAIESLFGASMTGIAYSLFAGQPLTILGSTGPVLVFEKILFKFCKDYALSYLSLRALIG  565

Query:  610  LWTATLCIILVATDASSLVCYITRFTEEAFASLICIIFIYEALEKLFELSEAYPINMHND  669
             LWTA LCI+LVATDASSLVCYITRFTEEAFASLICIIFIYEA+EKL  L+E YPI+MH+
Sbjct:  566  LWTAFLCIVLVATDASSLVCYITRFTEEAFASLICIIFIYEAIEKLIHLAETYPIHMHSQ  625

Query:  670  LELLTQYSCNCVEPHNPSNGTLKEWRESNISASDIIWENLTVSECKSLHGEYVGRACGHD  729
             L+ L+ Y C CV P NP+N TL+ W++ NI A+++ W NLTVSEC+ +HGE++G ACGH
Sbjct:  626  LDHLSLYYCRCVLPENPNNHTLQYWKDHNILAAEVNWANLTVSECQEMHGEFMGSACGHH  685

Query:  730  HPYVPDVLFWSVILFFSTVTLSATLKQFKTSRYFPTKVRSIVSDFAVFLTILCMVLIDYA  789
              PY PDVLFWS ILFF+T + +TLK FKTSRYFPT+VRS+VSDFAVFLTI  MV++D+
Sbjct:  686  GPYTPDVLFWSCILFFATFIVPSTLKTFKTSRYFPTRVRSMVSDFAVFLTIFTMVVLDFL  745

Query:  790  IGIPSPKLQVPSVFKPTRDDRGWFVTPLGPNPWWTVIAAIIPALLCTILIFMDQQITAVI  849
             IG+PSPKLQVP+VFKPTRDDRGWF+ P+GPNPWWTVIAAIIPALLCTILIFMDQQITAVI
Sbjct:  746  IGVPSPKLQVPNVFKPTRDDRGWFINPIGPNPWWTVIAAIIPALLCTILIFMDQQITAVI  805

Query:  850  INRKEHKLKKGCGYHLDLLMVAVMLGVCSIMGLPWFVAATVLSITHVNSLKLESECSAPG  909
             INRKEHKLKKGCGYHLDLLMVAVMLGVCSIMGLPWFVAATVLSITHVNSLKLESECSAPG
Sbjct:  806  INRKEHKLKKGCGYHLDLLMVAVMLGVCSIMGLPWFVAATVLSITHVNSLKLESECSAPG  865

Query:  910  EQPKFLGIREQRVTGLMIFILMGSSVFMTSILKFIPMPVLYGVFLYMGASSLKGIQFFDR  969
             EQPKFLGIREQRVTGLMIF+LMG SVFMT++LKFIPMPVLYGVFLYMG SSL+GIQFFDR
Sbjct:  866  EQPKFLGIREQRVTGLMIFVLMGCSVFMTAVLKFIPMPVLYGVFLYMGVSSLQGIQFFDR  925

Query:  970  IKLFWMPAKHQPDFIYLRHVPLRKVHLFTIIQMSCLGLLWIIKVSRAAIVFPMMVLALVF  1029
             +KLF MPAKHQPDFIYLRHVPLRKVHLFT++Q++CL LLW+IK S AAIVFPMMVLALVF
Sbjct:  926  LKLFGMPAKHQPDFIYLRHVPLRKVHLFTLVQLTCLVLLWVIKASPAAIVFPMMVLALVF  985

Query:  1030 VRKLMDLLFTKRELSWLDDLMPESKKKKLEDAEKEEEQSMLAMEDEGTVQLPLEGH----  1085
             VRK+MDL F+KRELSWLDDLMPESKKKKL+DA+K+EE+    M D G  + PLE
Sbjct:  986  VRKVMDLCFSKRELSWLDDLMPESKKKKLDDAKKKEEEEAEKMLDIGGDKFPLESRKLLS  1045

Query:  1086 ------YRDDPSVINISDEMSKTALWRNLLITADNSKDK 1118
                   +R DPS INISDEM KT +W+ L I + N+K+K
Sbjct:  1046 SPGKSSSFRCDPSEINISDEMPKTTVWKALSINSGNTKEK 1085 (SEQ ID NO :4)

Hmmer search results (Pfam):
Model      Description                                    Score      E-value   N
PF00955    HCO3- transporter family                       1273.1     0         1

Parsed for domains:
Model      Domain    seq-f    seq-t    hmm-f   hmm-t    score     E-value
PF00955    1/1       145      988  ..  1       875  []  1273.1    0
```

FIGURE 2D

```
   1 GCCTTGGGAG CTGTGAGAAA TAAATATTTG TTGTTGTGGC ATTTTGTTAT
  51 AGCAGCCCAA ATGGACTAAG ATACACTCTT TTGGCTCTCT CTTCATTCAG
 101 TCCAAGGGTG TTCTGCTAGG TTTTGGCTAC TCTTCATTTC TTTTATCAAA
 151 TATTTGTTAA GGCTTATTAG GGCCTAAAGT CTAGAGGCAT TCTGCTTTAC
 201 TATTATGACC ATATCTTAAT AACACTGGTA TGAGTAACAT ACTGTATGAG
 251 TAAATAATTT GTTTTAGAGC AATGGTTTTC TAAAAATGGG AGATCATAGT
 301 TTTTAGTAAT TAATTGTGTT AAATTACTAT TAAGAGGGTC AAGTAATAGA
 351 TGTTAAGTAA TTTTTTGGAT TAAATAGATC TTATCAACTA GATAATAGAG
 401 AGATTAAGAG CTGCTTTGCA CTCAGGTTTC ATGTTTTTAT TGCAAAGATC
 451 AATTGTGCTT ACAAGAAAAC ACTGAAGGAA ATTGGGGATT ATATATACTA
 501 ATTAATAACA TCCAGAGAAT GATAAAAATA TCAGTGTTTG TATTCTTGCT
 551 GTGACAAAAT ACCTGAAGGA AAAGTTCAAT TTTCTTATTT TTCATTATTG
 601 ATTCATTTAA TAACTTTGAT ATGTAATAGT ATAGGAGATT AGGAATGAAC
 651 CTTGCTTGAT GTTTCGCTTT TCCTCATTTC TCACATTCAA TCCCTGAATT
 701 CTATCTTTTT TCAATAAGAT GTGTATCTGG ATCTATTCAT TTCTCTTCAT
 751 TCCTATTGCC ACTTCTTTGG TTCAGGCCAT CATCATCCCC TGATTGAAAT
 801 TATTTAACAT TCTCCTGATT TGTCTCCCGT CCTCCAGTTT TGTTTTACTC
 851 AATTGATTGT CTATAGAGTA GCCGGGATAT TTTAAACCTG ATTATGCTGA
 901 CAGTTTGTCA TTTCCCTAAG GGTAAAGCTC ACACTCTTTA AATGGCTCCT
 951 GACGCTTACC GTGACTGGGC CTCACTTCTC ATCTCTTCCC TCTGTTCTTA
1001 CACTTTATGG TCTAACCTAT GTTGTATTTG CCATTCCTTG AATGTGACTA
1051 GATCAGAATC TTCTGTTTTA ACAGTACTTC CCTAAGGAAA TCTTTTCTGA
1101 TCCCTAGATT AGGGTAGGAT GCCTTGCTAC GGCTTTCATG TCAACTTTTA
1151 ATTCTTCAGT TATAACAAAA CATGCTGTT TGATTTATCT GCTTTCTGTG
1201 ATGGCAGGTT TTGTGTTGTT TGTTATGGAG TCCCTAGCAC CTATATAGTA
1251 CCTGACACAT AGTAAGAATT CAATATTTC TACAGGAAAG AATGAATATA
1301 GAAAGAGAGA CGATGTAGCT TAGGAAGGCT TTATTGAGAA GATAGGTCTT
1351 AAAGGATGAG TACCTATTTT GATTATAATA AGAGGGTAAA TACTACATAG
1401 ATGGAAATAT TTGTTTACAT GTGATTTTTC ATTCAGATGT GTTATAGTAT
1451 ACATACAGCA GAATACCAAG CTCTGTGTCT CCAACCTGTG CAGTTAGAGT
1501 CAGTAGTTTT TCTAAAAGTA TAATTTGGAT CAGCCCAGTT TCTTAAGACT
1551 CATTGTGACT AGTCTCCATC AAATGTTGTG AGTGAAAGAA GGGAAACTAT
1601 TCACAGGTAA ATAAAGTGTT CATAGAGTCG TGAATTCAGG CTATTCATAA
1651 TGTGAGGGCT GTTTCAGGAT AAATATGTTGC ACTTGGTGTC TTAATTTTGA
1701 ATGTAGTTGA ATTGACTATA ATCTTAGTCT TTTTTTTTTT TGGTTTGTGT
1751 TTTCTTTAGT TATAAAACAC AACCTTTTGT CACACGGTAA AGAGAAAGCA
1801 TTTCCAATTA TAATTTTTGA GATATTGATT CTATATTAGA ACACTTTATC
1851 AATCTTAAAG TTCCCTGATT CTGCTATGTT GTGGTAAAAG AAAACAGTAC
1901 TCAAACTTTA ATAAATAAGA CACAGTGAAA ATCCATAGTA AAAATGCCAA
1951 CAACTTACAT AGGTTTCATT ACTAGACTTA ACCGTGCAGT TTTAGCATTT
2001 GATAATACCA CATTATCTTT TGCATGTAAA TTCTTTAGAA GAAGATATTA
2051 AATAAAAAGA TAAATGTAT GTTGGTATGA AGAATCTGAA ACATAAATGA
2101 AATCCCTGAA AATTAAAAGG TGAATATGTA TTTACCTATT TACTATTTAC
2151 ACAACTATCA AAGATTGCCA AAATAAAAAT CCTGTATAGG CGCTCATCAT
2201 TTTGATGGGT GGATAAGTCG TGATACCCAT AGTTTGGAAG GAAGATTCCT
2251 TCAAGAGAGT ACAATTTGC TTGGTAAATC TTTTGCATGT TAAACTTTTT
2301 AGAAGAAGAA ATTAAATAAA AATATAAAAT GTATGTTGGT ATGAAGAATC
2351 TGAAACATAA ATGAAATTCC TGAAAATTAA AGGGTGAATA TGTATTTACC
2401 TATTTACTAT TTATACAACT ATCAAAGATT GCCAAAATAA AAATCCTTTT
2451 TAGGCACTCA TCATTTTGAT GGGTGGATAA GTGATGATAT TCAGAGTTTG
2501 GAGGGAAAAT TCCTTTAAGA GAGTATAATT TGCTTGGTA AGTCATAAAG
2551 CCTAAAGCTT AGTCACATAT AGAGAAAGCT GCCTAATAAT TAAGAGTTGA
2601 CATTTTAACA TGGTATTTGC AACAGACACA TTGGATACTT AATTAAATGG
2651 AAAACTGCTT ATTTTAAAG GACTGAAAAA ATTCAACTCT CCTTGGCAAA
2701 TGAAGTCTTC ATAGTATCGA AAATGGGGAA ATCTGAAGGA TGTGGCTCAT
2751 TCTCTGTTTC GATGATGCAG AATTGCTCTA AGCAGTAAGC TTACAGTTTT
2801 CAGACAGCAT CAGCAAATAC AACTGTGTCA GTCTCTCTTA GTATGGGGTG
2851 TTTGTAACTG CACAGGGGAG ATGATAAATA GTATATGTGA TTTGATATCT
2901 TGATGATGGC TTAAACAGAT ACTGATGGAC AGATCTGTTG TTTGATATTT
2951 TTTTCACTAG CCCTGAAGAT GCTGAGACAT AGAGATGGCT GTGATTATCT
3001 TTTGTAAGAC AGGAAATGCA GTCTTTAGGG GTTTCTGGAA ATAGAAAGGT
3051 CATGCAGTCT GGAACCTGTG AGCCTTTTCA ATCTCTAAGT CATCAGGTAT
```

FIGURE 3A

```
3101  GACCTCATGA ATTATGATGA TAATATTAGA ATGTAGGGTG CTTGCTTTTT
3151  CTAGTTCTTA CTCATTGAAA ATATATTCAT TAATGTAATT GTTTATTGTC
3201  AGACTTTCCT TAGGATATTT GAACAAGTAA GATTTATGGC AGCTAAACAA
3251  TATGATTATT AGAAATGTGT GTGTATGTGT GTGCCTGTGT GTGTGTATGT
3301  GTTTAAATTT GTGTTTACTT TAGCTTTTTG GGGGAGAGGG CGGTAAAGGA
3351  AGAGATTCTT TGAATGTGAT TAAAAGCAAG GTTTGGGGCA CTTCAGATTT
3401  TTCCAGATTA AGCCTGAATA GAGTCAATCT TTATATTTTA CTTCAAGTGA
3451  TAAAAATAGT ATAAATCGAT CAAACTGATA AGGATACATC GTAGCTAGCT
3501  GCTTACAGAT ACTGATATAT TGCAAATATT TTTATTATTT GGAATTTCTT
3551  AACCATAGAA ACTGATGCTG CTACCATTGT AGTGTGCTAC ATAGCAAAGG
3601  AAGTTTGGTG AATAGAATCA TCTTTGTCAG CATCTGACCT ATAAACTAAT
3651  TTCCTGAAAT TTATGTTGCA TTATCTGAAC TGTTGTAAAG ACACTGGTTT
3701  TAATCATTTC TCAGATCTAT TGAAATATTG ATGCTCTTGG TGCTTTTAAG
3751  GTAGATATAT ACTAACGTAT TGTTCATAGA AGAAAGGAGA CTATAAATCT
3801  GTTTTTCACA AGAAAGCTT GTGACATTTA AGCTTGTTGA AGATTTTTG
3851  ACCCAGAGAG CTTCGTCCTT TGCTTACTTT CATTTTCAAA CTGAAAATAC
3901  TTGACTATGT TAAACATGCA AATGATTTGG ATTTCGATGT CCATTTGTA
3951  CTGAAACTCT GCCATTTATT TTAAACTATT TTCACCCATC AAGTTATATA
4001  TAATGCATTT AACTTTGATT TGTTACAGCA TGTCCTCAGA ATTATATACT
4051  TGGATAAGAA ACTACCTATA TTTGACATTC AGATTTTGAA GGAAATATAT
4101  TTCATTTTC AAAATATTGT ACATGCTTCT GCCTCAATGT TAGAGAACTT
4151  TTCAGGTACT CCATATTAAA TGATCAAAAA GAGAGAAATA TATTGCAGCA
4201  GTTCTCAACA GCAAGATGGT TTTGTCTTTA TGATTCTGTA GCCTGATTGT
4251  AATTTAATGC CTTATCAGGG TGAAATGACA TAGATTAAAA AAATGAATAT
4301  ATTTAAGGAA GTCTGAAACA ATGAATTGAT TCAGTTAAGG GGTTTCTCCT
4351  TTTTAATTAA AAACACATTC TGCCTACTGA TATTGACTAT AATTTATATG
4401  TTATTCAGGC TACTTAGCCA GCTTATATTC TTATTAGTAG GGAAGATTGG
4451  CATATTCTTA AGCTTGATTA ATTTTGAAAT GATTTGAATA TACCTTTTAA
4501  TTGCAACAAA ATATGTCTAA TCTGTTAGAA TTTATTTCCA GTATTTGCAT
4551  GTATTAGTCA TTATGAGTAC ATTCTGTTTC TTGGCATTGC TTTGGGATTC
4601  CTCTTGGTAT TGGTTTCACA GCATTCTGCT ATTTTTCACT GTATTCCTGA
4651  CCTTTCAAGA GAACCAAACT GTAAAGATTT TTAGTTACTT TCTGTTAGTG
4701  GCATTTAAAT GAGGATATCG ATAATTTGT AAGGTGGAAA AAAATTACTA
4751  TTTTAGAATT GTCATTTCTG TCACAAATCA GAGAAATTTT TCTCTATTAC
4801  TATTTCAAAA TATACTACAA TAAAAAGCAA AGACTGGTTA GAATGTAGTT
4851  AAATGCAATG TCAATCTTTC TTCTTGCATG GCAGGATAAT CTTGATCTTT
4901  GGAATGATAA AACTGATTGT AAACTTGCCC AGTAATGATT GGTCATCTTC
4951  CTTACAAAGG CTGCCTTCGT TTATACTATT TTACATGCAT TTCATTATAC
5001  ATCATAAAGG TTTTAAAGGT AAGCTGCCTA TAAAAACTAT TTGAGTAATT
5051  CTTCAATTCA GTAAACATAG TAAAGGCTGA GCATTGGATG ATACTGTATG
5101  TATTTGGTGT TATGAGGAAT GCAGAAAAGA AAAAGTCATT TCCGGCTTTC
5151  AAGGAGATTA GTGAATATAT GCAATGAATT GTGTTCACAT TTGAATTGA
5201  TTTTTGATAG GCAGTATGCT ACAATCAGTT TTAACTTAAT CTATAAGCTG
5251  ATGAATCCTA GAAGGAGTTA CATGTAACCT TTTTTCCTCA TGTAAATTTC
5301  TTGATATTAG ATAAATGAAG GCTTAGGTCA AACTGTATCA TTATGCATCC
5351  CATAACTTTA TTGAAAATTG CATTAAAGAC TTTTAGAGTG CATAGTTTCT
5401  CGTATAGGGC TTTATAAACT GTGAATCAGT AAAATAGCAA AATAGCTTTG
5451  CATGTTGTAT AAGCCATCAT TGTCAGTATG AGACTGAAGG TGCACCCAGT
5501  CCACTGGCAG GAGGCAGAAG TGTCAGCTCA ACATAGAGAC TTGATCAATC
5551  CTGTCTAATT CCAGGCTCAG TGTGGGTAAT TAAGTATTAT GGAAGGGGTT
5601  TTGACTTTAT AGGGATAAAA CTTGGAAATA AAGAGTAGCA AGTATGGAAG
5651  TGTCTGTTAC TAACTAGGTC ATTGGAGAG TCCTTTGAAT AAAATGGGGG
5701  AATAGGATTT ACCTCAGGTT CTGAGAAAGC GGATCAGGAC CAACTAATTA
5751  TGGAAGTGGA CCTTAGCTGC TGCTTGGTGA ACAGTCAGGC ATTACTCTCT
5801  TCTCTTTCAT TCCAATATGT TTGCTGAAAG TTGCAGGAAG GTGGGTGGAG
5851  AAGATGCAAA GCCCTTGTTT CCCCAGAATC CCAAACTGGA ACACGCTGCC
5901  TGATAGTGCC TCCAAAGTGC CTGTTTCCTT GTATTAGACG AATAGAAAAT
5951  TGATTTGCAA ATTCTTCTGG TTTGTAATGG CTGGCTGCAG TAAGAGGCTT
6001  GTGCAATGGT TCAGTGTCTG GACTGCCATG TTCTCTGGGT TCAAATCTTA
6051  GCTATGCTAC TTACTGGCTG CATGATCTTG GCTTGTTTCC TGATGTGTAA
6101  TATAGGGATA ATAATGGCAC CTACCTCAAA GAGTTGTGGT AAACATTAAG
6151  TGAGTTAATG TATGTGAAAC ACTTATAAGA GTACCTGACA TATATCAAAC
```

FIGURE 3B

```
6201  ATATTATTGT CAACATCCTT TGTCGACAGA CTTTGTTATA GACATTCTAA
6251  GAGGTTGGAT GGGCTATTGG CAAGACTTTG TAACAGTCAT CATGCAGTTT
6301  AGTTTTGTTC CCTCTCCCTT AATCTCTTTA TCAAATAAGA AATTCAGCCA
6351  AAAATATATG CTACACTGAA ATATAGTTAT AAAAATGCAA ACAAAGAACA
6401  ACATGCTATA TCTGATTCAA TTCTAACATT TACTGACAAT AAGAATTGTG
6451  ACTTGATGAA AGATTTTGTG TTTAAACTTT ACATCTACCT GCTAGGCTGA
6501  TCCAAACTCT CTTAGAATTC TATGTGTGCA GATTCTTTGC TTCTCTGTAT
6551  TACACCAACT ACTTTATTCA TGACTGAAAG ATTACTAGGA CTTTGGGAAA
6601  ATTTAACAGC AACTTAAGGT CTTTCTTGTT TATTGTTTAA GACTAAAATT
6651  AAGGGGTAAA AAAAAGCCTT TCTTTAAAGG CTTAAAAAAA ATAATAGGGG
6701  CAAATTTACC TAGCATAGAT TTAGTGATAC TTAGTCATCA AAAATGTCCA
6751  AGACAAAAAA TTTTACCGAA AGTCAAACAC AACTTGTTTT TAATAATTTT
6801  ATTTCTTGGC ATTTTTATTC TAGATGAAAC ACTAAATGAA ATATATTATA
6851  AATAGAATGC TACATATATA AGTAGAACAA TTCAAGTTCC CATTTGATAG
6901  AGTATAATAT TTGAATTGC TGGTGATTAT TTAATGTAAA AACATTTATC
6951  TGCTTAAAAT TCTCAATAAA CTTCAAAGAG AAGTGAGTAA TATGATATTT
7001  GGATTAAATT TACATGCTTA AATATGGCAT TTTATTACAT CTCTGAATTT
7051  CACTTCTCTT CTCTGAAGAA ATTTCCTCAG TGTGCTGCTG TTTCCCCCAA
7101  ATTGGCAGAG TCAGTTGAAT CTCAGAATAA TGCAATTTTT AAAAACAAAT
7151  ATACAAAATC CTACAATGTT CTAGAAAGAA TTGTACTGGG CAAGGATATA
7201  AAAGTCTGTA GGTCTCTGCC TTCAGGAGGT CACAGGTAAT GGGTTGTAAC
7251  TACAAAATAC AAGTAACTAT GGCAGAATAT GAAAGTAGTG AATGCCATGA
7301  GGTAGTCTTG AAGACTGGCC AACATAGAGA GAAAAGGTCA TTTCAGGCAG
7351  AGGAAACAAC ATCATTAAAG GTAGGGAGGC AGAAAGCAAA TAATAGAATA
7401  GTTCATTTTG GCTATAGCCT AGTGGGATAA CTTAGACTTA CCACAGGAAA
7451  GGTTTGTTGG GACCAGATAA GTGTAGAATC TTGAATGCTA GACTATGATT
7501  TCTAAACTGA GAACATTTCT TTGCTGATGT ACGTATTCCT GGAAAAAATA
7551  AAATAAAAAA AACAAAGAG CACTACCTAT ATTTTGAAGT CATTTTCAGA
7601  GCTCTAACCC TCTTGAGACT TTGAGAATGA AAATTAAATT CCTGAGTAGA
7651  TTTAGTAGTT AGTAGACAAG GTAGGGGGTA GAAACAAACT GAAGGATTTT
7701  AATAAAATTT TCTATCAAAA TTGCACATGA GAGCATTTCT CAGTCTATCC
7751  ACAAGCACTC AAAAGTCCTA GATTTCAGAT CCTAAGAGAC CTCCTGCTTG
7801  TCCGTGATGT AAACTCCATT TTATTGGTAC GTAATCTGAT TTAGCTTTGG
7851  CTTTGTTTTT GACATTTCCT AAAGCAAGGA CAATCTAGTG GGATCATTTT
7901  AATACAATGA ATACTCATGT TACTATGGTG AATAGTTGGA TAAAAAGGAC
7951  TTTGTCTTAG GGAAAATTGG AAATTAAAAT TGCCATTTTG AATCACGGAA
8001  GTCGCTGAAT ATTTTACCTT TGTTCTCTGT TCATTTAAAA ATCATAAAGT
8051  AAACCATGTT TGCAAATACT TTTAATATCG CCTTCTTCTA CTCCATACAC
8101  CAGAGGCATT TTAGTATTGC ATGAGGTTAG TAAAAAAGCT GGATACCTTC
8151  CAAGAGCAGA TTTCCTTTAG ATGTGACAGC TGGGATGTGA CTTTTGGTAT
8201  CAGATGCAGG AAGACGTCAT TTGTACATGG TAATTGTGAA AAAATTGGAA
8251  CTTATTACTC TCAGTATAAA TGATCCATAA AAAGTATGTC AGAAGTAAAA
8301  CTCCTGGAAT TCTACAGGGA GAGTTAAAAT AAAACCAGAC ACAGGTGCTC
8351  ATCTGACTCT ATTTTTAGAA CAATAGGAGA CTCATATAAC TGAGAATGCT
8401  CTGTACTTCC TGTATAAATC TACATTATTT GAAAGTCGTA TTTTCTAGAA
8451  GTTCCTGTGA AGTTGTACTT ATTAATCTTT GCAACTTCAC ATTGCCTAGG
8501  AAAGAGCCAT TCACCTGGTA GGAACCCAAC AAATTTTCAG TGCTTGTCTT
8551  AGAATCATAG TCCCATTTCT GAAAGAAACC TTGAATATCA TTGGGCTTCA
8601  AGTTGTTCTA AAAATGTTTA AGCATTTAAA CATGGTTTTC TTTCTCAAAA
8651  AGCAAATAGA AGGCATTTAG AGGAAAAGGA CCCTTTCTTC ACCTTAAGAC
8701  TTTTAAAAAT GGCAATATGG GAAGATTAAT AAGAAGAATA AGTTAACGGA
8751  GAATTCAATA TTCCTCCATG AAACTACTCT TTCTAAAAGG CAACAGAGAC
8801  TGGTTCCAGT GAAGCATATT ATGATGTGTG GCGTGTAAAT GTATATCATT
8851  ATCCCTACTC ATCTTTTTCC CCAAATTCAA TTTAATACTC ATAAGAATTT
8901  ATTGAGGCTA CTGTATAACA TGGAGGAAAG CTGTATACCA CAGTAGCAAG
8951  GAGCTAGGGC TCCACAGCGG GACTCCTGTG TTATGATCCC ATATCTTCCA
9001  CTTACTGGC AATTTTTATC TTAGGAAGTT ACTTAATCTC TCTTTTCTTC
9051  AGTGTTTTCA TCTGTGAAAT GAGGACACTA ATACGTTAAT CTCTAGAGTT
9101  GTAATGAAAA TCAAATAAAA TAATAAATTA ATACTTCAAA CAGTGCCTAG
9151  AGTGTTTGAT ACAGTGCCTA GCTTTTGGTT ATTATAATTA TCCCCACTGA
9201  ACTAGGTAAA TGCTACAAAT ATGTATGTGT ATATTTGTGT GTATACACAC
9251  AAATATGCAT ATATGTACAC ACACATACTG TACATCCTAT GTAAACACAA
```

FIGURE 3C

```
 9301  TTTTAGTATG TATGTATGTC TATACATACG TATACATTCT ACCTTAAGTA
 9351  TATATAGTAT ACTGAAAAAG AAATTTAGTA GTTTGCCCAA GATCAAAATT
 9401  GCCTGCAAAG GATAGGACAA TTTGAGTTTC AAACCCAGAA AGTCTAGCTC
 9451  TACAGCTGTT GGCCTTAACT ACTGTTTCAT ACTGTTTAGA GTATAAACAC
 9501  CTGAATTAGA TAGCCATGTA TAAATTAGCA TATTCTAAAT GCCAAATTGA
 9551  GACTAAAGAC ATGAAGGTAA ACTGAAACTA CTGTGAAAGA CTTAATGGAA
 9601  GAATTGTGAC TTTTATTTGA TTTTAAGTTC TGGGATACAT GTGCAGGATA
 9651  CGCAGGTCTG TTACATAGCT AAATGTGTGC CAAGGTGGTT TGCTGCACCT
 9701  ATCAACCCAT CACCTAGGTA TTAAGCCCAG CATGCATTAG CTATTTTTCC
 9751  TTATGCTCTC CCTCTTCTCA CACACCCCTC AGCAGACCCC AGTGTGTGTT
 9801  TTTCCCCTGC CTGTGTCCAT GTGTTCTCAT CTTTCAGCTC CCAGTGAGAA
 9851  CATGTGGTAT TTGGTTTTCT GTTCCTGCGT TAGTTTGCAG ATGATAATGG
 9901  CTTCCAGCTC CATCCATATC CCTGTAAAAG ACATGATCTA ATTCCTTTCT
 9951  ATGGCCACAT AGTATTCCAG GGTGTCTATG TACCACATTT TCTTTATCCA
10001  GCCTATCATT GATGGGCATT TGGGTTGATT CCATGCCTTT GATATTGTTA
10051  ATAGTGCTGC AATGAATATA CGCACGCATG TATCTTTATA ATAGAATGAT
10101  TTATATTCCT TTGAGTGTAT ACCCAGTAAT AGGGTCAAAT GGTATTTCTG
10151  GTGCAGGTCT TTGAGGAATT GCCACACTGT TTTCTACAAT GTGTGAACTA
10201  ATTTACATTC CCACCAAAAA TGTAAAAGTG TTTCTGTTTC TCCACAGCCC
10251  TCGCTAGCAT CTGTTGTTTC TTGACTTCTT TATAATCACC ATTCTGACTG
10301  GCATGAGATG GTATCTTATT GTGGTTTTAA TTTGAATTTC TCTAATAATC
10351  AGCAATATTA AGCTTTCTCT AAATATGTTT TTTGGCTGCT TATATATCTT
10401  CTTTTGAGAA GTGTCTGTTC ATGTCCTTTG CCCACTTTTT GATGGGTTTT
10451  TTTTTTTTCT TGTAAATTTG TTTATGTTCC TTGTAGAGTC TGGATACTAG
10501  GCCTGTGCCA GATGGATGGA TTGCAAAAAT CTCCCATTCT GTAGGTTGTC
10551  TGTTTTCTCT GATGATAGTT TCTTTTGCTG TGCAGAAGTT CTTTAGTTTA
10601  ATTAGATCCC ATTTGTAAAT TTTTGCTTTT GTTGCAATTG CTTTTGATAT
10651  TTTTGTCATG AAATCTTTGC CCGTGCCTAT GTCCTGAATG GTATTGCCTA
10701  GATTTCTTC TAGGGTTTTT ATAATTTTGG GTTTTACATT TAAGTCTTTA
10751  CTCCATCTTG AGTTAATTTT TGTAAAAGAT GTAAGCAAAA GGTCCATTTT
10801  CAATTTTCTG CACTATTTAT TAAATAGGGA ATCCTTTCTC CATTGCTTGT
10851  TTTTGTCAGG TTTGTTGAAG ATCAGACAAT TGTAAATGTA TGGTCTTATT
10901  TCTGAGTTCT CTATTCTGTT CCATTGGTCT ATGTGTCTGT TTTTGTACCA
10951  ATACCATGCT GCTTTGGTTA CTGTAGCCTT GTAGTACAGT TTGAAGTTGG
11001  GTAGGGTGAT GTTGCCAGCT TTATTCTTTT TTCTTTAGGA TTGTCTTGAC
11051  TATACCAGCT CTTTTCTGGT TCCATATGAA TTTTAAAATT TTTTTTCTAA
11101  TTCTGTGAAG AATGTCATTG GTAGTTTAAT CATTGAATCT ATAAATTACT
11151  TTGGGCAGTA TGGCCATTTT CATGATGTTG ATTCTTCTTA TCCATGAGTG
11201  TGGATTGTTT TTCGATTTGT TTGAGTCATC TCTGATTTCC TTGAGCAGTG
11251  GTTTGTAGTT CTCCTTGAAG AGGTCCTTCA CATTCCTTGT TAGCTGTATT
11301  CTAGGTATTT TATTCTCTTT GTAGCAATTG TGAATGGGAG TTCATTCATG
11351  ATTTGGCTTT ATGCTTGTCT GTTGTTGGTG TATAGGAATA CCTGTGATTT
11401  TTGCATGTTG ATTTTTTATC CTGAGATTTT GCTGAAGTTG CTTATCTGCT
11451  TAAGAAGCTT TTGGGCTGAG ATGATGGGGT TTTCTAGGTA TGGGATCATG
11501  TCATGGGCAA AGACAATTTG ATTTCTTCTC TTTCTATTTG AATACGCTTT
11551  ATTTATTTCT CTTTGCCTGA TTGCCCTGGC CCAGAACTTC AATACTATT
11601  TGAATAGGAG TGGTGAGAGA GCATCCTTGT CTTGTGCCAG TTTTCAAGGG
11651  GAATGCTTCC AGCTTTTGCC CATGCAGTAT GATATTGGCT GTGAGTTTGT
11701  CATAAATGGC TTTTATTATT TTGAGGTATG TTCCTTCAAA CCTAGTTTAT
11751  TTAGAGTTTT TAAGACGAAG GGATGTTGAA CTTTATCAAA GTCCTTCTTC
11801  TGCATCTAAT GAGATAATCA CGTGGCTTTT TTCTTTAGTT CTGTTCATGT
11851  GGTGAATTAT GTATATTGAT TTGCATACGC TGAACCACCC TTGCATCCCA
11901  GGGATGAAGT AGACTTGATT GCGATGGATA AGCTTTTTGA TGTGCTGCTG
11951  GATTCATTTT GCCAGCATTT TCTTGAAGAT TTTTGCATTG ATATTCATCA
12001  GGGATATTGG CCTGAAGTTT TCTTTATTTG TTATATCTCT CCCAGGTTTT
12051  GGTGTGAGGA TGACGCTGGC CTCATAAAAT GGTTTACAGA GGAGTCCCTC
12101  CTTTCCAATT GTTTGGAATA GTTTCAGAAG AAATGGTACC AACTCCTCTT
12151  TGTACCTCTG GTAGAATTCA GCTGTAAATT CATCTGGTCC TGGGCTGTTT
12201  TGTTTGGGAG GCTATTTTTA CTGCCTCAAT TTCAGAACTT GTTATTGGTT
12251  ATTGGTTATT GATTATTCTT CAGGGAATCA ACTTCTTTGT GGGTCAGTGT
12301  GAGCAGGGTG TATGTGTCCA GGAATTTATC CATTTCTCCT AGATTTTCTA
12351  GTTTGTTTGC ATAGAGGTGT TTATAGTATT CTCTGATGGT TGTTTGTATT
```

FIGURE 3D

```
12401  TCTGTGATAT  CCCCTTTATC  ATTTTTACTG  TGTCTATTTG  ATTTTTCTCT
12451  TTTTTCTTCT  TTATTAGTCT  AGCTAGTGGT  CTAGCTATTT  TATTAATTTT
12501  TTAAAAAAAT  CACCTCCTGG  ATTCGTTGAT  TTTTTGAAGG  GTTTTTTTGT
12551  GTGTCTCTCT  CCTTCAGTTC  TGCTCTGATC  TTGCTTATTT  CTTGTCTTCT
12601  GCTAGCTTTG  GGGTTTGTTT  GCTCTTGGTT  CTCTGTAAAT  AGTTCTTTCA
12651  GTTGTGATGT  TAGGATGTGG  GTTTGAGATA  TTGCTAGCAT  TTTGATGGCA
12701  GCATTTAGTG  CTATAAATTT  CCCTCTTAAC  ACTGCTTTAG  CTGTGTCCCA
12751  GAGATTCTGG  TATGCTCTCT  TTGTTCTCAT  TAGTTTCAAA  GAACTTCCTG
12801  ATTTTTGCCT  TAATTATTTT  ATTCACCCAG  AAGTCATTCA  GGAGTGGGTT
12851  GTTCAATTTC  CATGTAGTTG  TGTAGTTTTG  AGTGAGTTTC  TTAATTTTGA
12901  ATTCTAATTT  GATTGTGCCA  TGGTCTGAGA  GACTGTTGTG  ATTTCAGTTC
12951  TTTTGCATTT  GCTGAAGAGT  GTTTTACTTC  CACTTATGTG  ATCAGTTTTA
13001  GAGTAGGCAC  CATGTAGTGC  TGAAGAAGAT  GTATATTCTG  TTGTTTTTGG
13051  GTGGAAAGAT  CTGTAGATAA  CTATCAAGTT  CACTTGATGC  AGAGCTGACT
13101  TCAAGTCCTT  TGTTGATTTT  CTGTCGTGAT  GATGAGTCTA  ATATTGACAG
13151  CAGGGTGTTA  TTATCTCCCA  CTGTTTTTTT  TATTATTATA  CTTTAAGTTT
13201  TAGGGTACAT  GTGCACAATG  TGCAGGATAG  TTACATATGT  ATACATGTGC
13251  CATGCTGGTG  TGCTGCACCC  ATTAACTCCT  GCTTGAGCAA  TAGTGGTATC
13301  TCCTAAGGTA  AACTTTCCCC  CTCCCCTAAC  CCACAACAGG  GCCCAAAGTG
13351  GGTTGGTCCC  CCTTCTTNNN  NNNNNNNNNN  NNNNNNNNNN  NNNNNNNNNN
13401  NNNNNNNNNN  NNNNNNNNNN  NNNNNNNNNN  NNNNNNNNNN  NNNNNNNNNN
13451  NNNNNNNNAA  TATATGTGGC  TCCATCTTGG  TTCACACTGC  TACTCAGTGT
13501  ACTACAAATC  ACAGTGAGTT  TGAATGCCAT  TCATATTACT  GCAAACGACA
13551  TTTTATTTAT  TTTTATTGCC  AGTGCATATC  CATCATGCCA  GAACAAGAAA
13601  ATAAGAGAAA  AATGAACTTT  GATTGTCATG  CTTTTATAGC  ACAGTGGAGT
13651  GTGAATTATT  TTATTTAATT  AGATGACAAA  ATATGTATTT  ATTATGTAAA
13701  GACTCTATAG  CTATGCTAAA  AGAATAGAAT  ATATCTCCAC  ATAACCAGAT
13751  TAATCACTCA  TCACAATATT  CCTGACTCAC  AAGAAGACAA  CAGTCATAAA
13801  TATTAGAAGG  CTTAAAATGG  AATCTCTCAT  TATAGCAGAG  TTTTCCTACA
13851  AAACAAAAAG  GACAGTGAGA  CTTCAACCAA  TGTACATTTC  TGAATGGCTC
13901  ACTTGTTAGC  CAAGTATGCC  CTTATAAGAC  TGTGGCACTC  TAAACAGGGC
13951  TTTCACAATG  TCCACCCACA  CAATACCTGC  CTTAATGAAA  AGCTCAGTAC
14001  CAGTTTCAGG  CAATTTAAAA  ATCTTAGCCT  TTATTATATT  GAAATTAAGT
14051  CGAATTATTT  TTCTATTATG  ATCCCTTTTG  AAATAAGCTT  TTACACATTT
14101  CTAATGCTTT  CTTCAGAGCG  GCTCATATAA  ATCAATGATT  TTTTAAAAAA
14151  TTCTTTCATT  TCGATTTAAT  CTATTAATAC  TTTAGATCTC  ACTCTCAGGG
14201  AAAAATTACT  TTATTGCATG  TAAAGTAATT  CAAATAGAAT  ATAGTTTACA
14251  ATTTTCTTCC  AAATTAAGCT  TGAGCCTGGA  TAAAAATATT  TTTAAGTGCC
14301  CAACAATATT  TAGATATTAT  TTGCCATGTT  TCTATTTTCA  TAGGAAGAGA
14351  TAATATGTTT  AATAAAAAAT  ACATATCTAA  AAGGATAATC  TGATGTTGTA
14401  AAATTATAAA  TTCTAATTTT  CTGTCAAAAC  AACCCTGAAT  GTGAACTTAT
14451  CAGAATCTTG  TCTGTGTGAC  TGCAACCCCT  CCCCCAACCT  TAAAAAACAT
14501  ACCACCAGCC  CCACTCTCCA  CCAGTGTGGC  CAAACCAAGG  GAAGTGAGAA
14551  GCAGGAACAT  AGCTACACAG  GTCAGAGCTA  AATATTAAGA  GTAAAAATAG
14601  TATCTTGAGC  TTTCAGAACC  ACAAATTTTC  AAAGTGAGCC  AGAGGACAGA
14651  GCAGCAGCTG  CATTTTCAAA  CAGAAGCAAC  TACATTTTTC  TAATCAACTG
14701  CTGTGTTATG  GAACATGAAC  TGCAGGAAAT  GATGGACTAA  TGTCCTTTTA
14751  TGTATCAGAT  AAGCAGGAGG  AAGTATCAGT  GGTGTGCTTT  ACTTGGTGAG
14801  TGAATCTTGA  TAAACATATT  CAATAAATAT  CTTCCACTTA  TGTCCTTTAA
14851  TTCAGTACAA  TGCTTTTTAA  AAATATTCA  ACTTGTGTGT  ACATCGACCA
14901  GAAAATGTTC  TATATAAAAA  CTGTATTTTG  CTTGGGTTTC  GAGATGAATG
14951  TTTCATAAGA  TATCTATATA  TGTATTAAAA  TTATTTAAAT  ATGAGGAAAA
15001  AGAACTTGTT  TGCTGTTGGC  GATGAAATCA  TGTTTAATTA  TAGTACTGAA
15051  AAAAATGTGC  CAAGAGTAAA  CAAACTTGTT  TAGTGCTGCT  AGTGTTTAGG
15101  TGAGAACCAT  TGCTTGAAGA  GTTGGGGACA  CTGGGAGCAA  CATAGATGGT
15151  CAATGAAAAA  ATGACAGAAG  ACTACGTCA  CCAAAGTGTG  GAGTAGGAAA
15201  CCTTCGTCCC  CACCACAAAC  ACACCAATTC  AGGAACAATT  CACAGAAAAA
15251  TTCCCTTTGT  GGGAAATCCA  GCAACTAATT  GAAGGGCTCC  TGCACCCTGG
15301  GTGAATGCAA  AATCAGATCC  ATCGAAGCTG  GTGAGGATAT  TCACGACAGC
15351  TGTCTGCCAA  AATTTCTACC  CCCAACGCAA  CACCATACAA  TTGGGAAAAG
15401  AGTCTCAGCT  CTCAGCTTCT  CCCAGAGGAG  GTTTGTACAT  CCAATACCCC
15451  AACTTCGATG  GGGGCTACCC  AAAGGACTGG  CTTCTGTCTT  CTCTGTCTTA
```

FIGURE 3E

```
15501  AAGTGCTAAT GGTGTGGAAT TATCTAGCCA CCTGGGGGAG AATAGAGATG
15551  GTGGCTTAGA TTGGTAGCCA CCATAGCTTT TCCTCCCTAG CTCAGAGCAT
15601  AGAGCAAGCA AACAAAATCC CCACCTTTCA GCTTCTCCCT GGGGATGGAA
15651  AGAGTTGGTA CATACATTAA ACTTTCTGGG GGTTTTCCAA AGGATTGGCT
15701  GAAATCCCAA AGAATTCAGT CTCACTCATC CTGGTGCACT CACAAGACCT
15751  GGCAAACCCT AGACACCTGG GGCTACAAGA AATACACAAG CAAATAAGTT
15801  GAACAAGCAT GAGGTTTAAG AAGCTTTAGA ATCTCTTCCT GGACTTATTG
15851  GTGGGGATCT TCCATATAAG GCCAGCTCTT TGTGAAGACT CAGAGAGAAG
15901  TCTGCTTTAT CTGATGCAAA GACACCAATG CATAGAGTCA AGTAAGATGA
15951  AAAAACAGGA AAATGTGTTC CAAACTAGGT AACAGAAAAA TCTCCAGAAA
16001  TTGACTCTAA TGAAACAAAG ATACACAATT TACCTGGAAA AGAATTTAGA
16051  ATAACTGTCA TAAAGATGCT CACTGAGGAT AAGAGAACGT TGCATGAACA
16101  AAGTGAGAAT TTCAGCAAAG AGATAGAAAA TATCTTAAAA GTACCAAACA
16151  GGAATCATGA AGTTGAAGAA TAAAATAATT AAATTGAAAA ATTCACTAGA
16201  GGGATTCAAC AACATACTAG TATCAAGCTA AAGAAAGAAT CAGTGAACTT
16251  AAGGACAGGC CATTGGAACT TGCTGAGTCA GAGAAACAAA AAGGACAAAA
16301  TAATGAAAAA GAATAAAAAA AGCTTAAAGG ACTTACGAGA CACCATCAAG
16351  TGGATCAATA TATGCATTAT GAGAATTCCA GAAGGAGAAG AGAGAAGGAA
16401  AGAACCAGAA GATTTATTCA AAGAAATAAT AGCTAAAAAC TCCCAAGTAT
16451  GGAAAGGAA ATGTGTAATC CAAGGACCCC CAAAAAGGAA AACTTAGAGA
16501  TATCAACACT AAGCACCTT ATAATCAAAT TGTCAAAAGT CAATCACAAA
16551  GAGAAAAAGC AACAAGGGAA AAGTTACTTG TTCGGGTACA AGGGAAATTT
16601  CATAAGAGTA TAAGTAGATT TTTCTTCAGC AACTTTTTTG CAGATGAGAA
16651  GGAAATGAGA TGATAGATTC ACAATGCTGG GGGAAAAAGC CAACCAGGAA
16701  ACCTAGACCA AATGAAACTG TCCTTCAACC AGGAAAACTA GACCAAATGA
16751  AACTGTCATT CAATCATGAA AGAGAGATAA AGTCTTTTCC AGACAAACAA
16801  AAACTAAGGA AGTTCATCAC CACCAGACCT CCCTACAAAA AATGCTAAGG
16851  GAACCTCCTT AACTTGAAAT GAAAGGACAC TAAACAGCAA CAAGATAGCA
16901  TAAGAAAGTA TAAAAGTATT GGTAAAGGTA AATATATAGA CAAATGCAGG
16951  ACCGTAATAC TGCAATAGTG GTAGGTAGAC CACTTGTAAT TCAAGTAAAA
17001  AAGTTAAAAG ACAAAGTAGC AAAATACTTT CAATAACTAA AATACTTTTA
17051  ATAAGTAAAA CTATGTTAAT AGATACACAA TATAAAGAAA TGTTAACTGT
17101  GACAACAATA ACAAAATGTG TATGGGAAGG AGAGTAAAAA GAGGCATATT
17151  TTTGTATGTC ATTGAACTTA AGTTGTTATC AGGAAAAAAT AGACTGTCAT
17201  TACTATAAGG TATTATATAA ACCCCATGGT ATCTAATGAG AAAATACCTA
17251  TAGAAAGGTA TCAAAGATTC CCAACAAAAA AAAATCAACA AAACATGAAA
17301  AATGAGAGCA AGAGAGGAAA AAATGCACAA AATAATTACA AGGCTAACAG
17351  AAAACAGTAC ATGACAATAA TAAATCCTTC TCTATCAATA ATTACTTTAA
17401  AACTAAATAA ATTATACTTC CCAATCAAAG ACATAGGGTG GTTGAATGGA
17451  TTAAATGTAT AATGGAATCA CATGCTGTTA TCAAGAGACT CCCTTTAGAA
17501  TTTAGGCTCA ATGTGAAAGA ATGGAAAAAA AAATTCCACG AAAATGTTAA
17551  TGAAAACGA GCAAGAGTGA CTATACTTAT ATCAGATAAA ATAGACTATA
17601  AGTCAAAACT CTCTCAAAAG ACTGAGAAAG ACATCTTATA ATGATAAAAG
17651  GATCAATTCA CCAGGAATAT ATAACAATTG TAAGTAGTTA TGCACCCAAC
17701  GATTAAGCAC CTAAACATAT AAAGCAAACA TTGACAAAAC TGAAGAGAGA
17751  AACAGGCAGC AACACAATAA TAGTAGGATA TTTCAATACC TCATTTTGAA
17801  TGATGGGTAA AACATATTAT CCATTACCCA CGGGCAAAAC AGAGCAAAAG
17851  GAAATAAAGG ACTTCAACAA CCTTATAGAA AAAAATGGAC CCAATAGACA
17901  TGAACATTTC ACTCAATAGC AGCATAATAC ACATTCTTCT CAAGTGCAGC
17951  CAGAATATTC TCCAGAATAG ATCACATATT AAGCTGAAAA GTATGTTTTA
18001  AAAATTTAAA GTGATCAAAA TTGTACCAAC TATTATTTCT GACTACAATG
18051  GAATGTGAAA GTAGAAATCA ATAGCCATGG GAAAACTGAA AATATTATAA
18101  ATATGTGGAC ATTAAACAAA ACACTCTTGA CAACTAATG GGTCAGAAAG
18151  AATTCAAAAG AGACATTAGA AAATATCTTG AGAGACATGA AGATGAAAAC
18201  ATAATATACC AAAACTTATG GTATACAGCC AAAGCACTAT AAAAGATAA
18251  GTTTATAATG ATAAAAGTCT ATATGAAAAA AGAAGACAGA TCTCAAATTT
18301  GCAACCTAAT TATACATTTG AAGGGACTAG AAAAAAAAAA CACACTAGAC
18351  CCAAAGTTAG CTGATAGGAA GAACTAGCAA AGATCAGAGC AGAAATAAAC
18401  AAAATAGATA ATAGAAAACA ATAGGAAAAA ATCAATGAAA TTGGGTTTTT
18451  TTTTAAAAGA TAAAATTGAC AAACCTTTGG CTAGACTTAG AAAAAGAGA
18501  GGATTCAAAT AAATATAAAT CATATATTAA AGAGGAGGTA TTACCACTGA
18551  TATCACATAA GTTAAAAAGT TCATAAGTAT CTATGATAAA CAATTATATG
```

FIGURE 3F

```
18601  CTAAGAAACT CTATGACCTT AAAAATGGAT AAATTCCTAG GAACATAAAA
18651  TCTACCAAAC ACGAAACAAG AAGATATAGA AAATCTGGAC AGACAAATAA
18701  CAAGCAAGAA AATTAAATCA GTAATAAAAG ACCTCCAAAC AAAGAAAATC
18751  CCAGGAACAG ATGGCTTCAC TGGTGAATTT TACCAAACAT TTGAAGAAGA
18801  TTTATGTCAA ACTTTTTTTT ATCTTGAAGA AGAGGAAATA CCTCCAAACT
18851  CATTGTATGA TGCCAGCATT ACCCTGATAC CAAAGCCAGA CAAAGACACT
18901  GCAAGATAAG AAAATTACAT AATAATATCT CTGATGAACA TAGATGCAAA
18951  AATTCTTAAC AACAAAAACT ACCTAGCAAG CTGAATTCAA CAGTACATTA
19001  AAAAGTCATA TGATATTTAT TATAGGAAGC AATGGATACC CTGGGCTGGG
19051  GTTCATTATA TACAAATCAA TAAATGTGAT GTGCCACATT CACAGAGTAA
19101  AGAACAAAAA ATATATTATT ATTTAACATC GTTTCATGAT AAAAACTCTC
19151  AACAAATTAG CTGTAGAAGG GATGTAGCTC AACACAATAA AGGCCATATA
19201  TGACAATCCT ACAGTTTACA TCATACTCAA TGATGAAAAG TTGAAAGCTT
19251  TTCCTCTAAG TTCAGGAACA AGGCAAGGAT GTCTACTCTT GCTACTTCCA
19301  TTCAACATAG TACTAGAAGT CCTAGGAAGA GCGATTAGGC AAGAAAATTT
19351  TTTCATGTGC AGATGAGAAA AAATGTATAT TCTGTGGTCG TTGAATGGAA
19401  TGTTCAGTAG ATGTTATTA GGTCCATTTG GTCAAGAGTG CAGTTTAAGT
19451  TCAGAGTTTC TTTGTTAGTT TTCTGCTTTA ATGATCTGTC TAGTGCCATC
19501  ATTGGGATGT TGAAGTCCTC CACTGTTATT GTATATCTGT CTGTCTCTTT
19551  TCTGAGGTCT AATGGCATTT GCTTTATAAA TCTGGGTGGT CAGGTATTGG
19601  GTATAAATAT ATTTAGGATA GTTAAATCTT CCTGTAGAAT TGAACTCTTT
19651  GTCATTATAT AATGTTATTC TTTGTCTTTT TTTTAACTAT TATTGGTATA
19701  AATTCTGTTT TTTTCTGATG TAAGAATAGC AACCTATGCT CTTTTTTGTT
19751  TTCCATTGTG TGATATACCT TTCTCCACTC CTTTACTTTG AGCCTGTGGG
19801  TGTCCTTTCA CATTAGATGG ATCTCTTGTA GTCAGCAGAT GTTGAGTCTT
19851  GTTCTTAAA TGCAATTTGA CAATCTATAT CTTCATTTAG GTCATTTCTG
19901  TTCAAAGTTA ATATTGACAT GTGAAGTTTT GTTCCAATCA TAGTACTGTT
19951  AGCTAATTGC TTTGTAGTCT CAGTGGTGTG ATTGCTTTAT AGGATCTTTG
20001  GATTTTGTAC TTATATGAGC TTTTATGACA GGAGAGTATT GTCCTATATT
20051  CTTTTATGAC ATAAAAGAGT ATACTCTTTT CTGTTCGAAG TTTATGCTTT
20101  ATGACATAAA AGAGTATACT CATTTCTGTT CAAAGTTAAT ATTGACGTGA
20151  AATTTTGTTC CAATCATAGT ATTGTTAGCT AGTTGCTTTG CAGTCTCAGT
20201  AGTGTAATTG CTTTTTAGGA TCTTTGAGTT TTGTACTTAT ATGAGCTTTT
20251  ATGACAGGAG AGTATTGTCC TATATTCTTT TATGACATAA AAGAGTATAC
20301  TCTTTTCTGT TCAAAGTTTA TGCTTTATGA CATAAAAGAG TATACTCATT
20351  TCTGTTCAAA GTTAATATTG ACATGTGAAG TTTTGTCCCA ATCATAGTAT
20401  TGTTAGCTAG TTGCTTTGCA GTCTCAGTGG TGTAATTGCT TTATAGGATC
20451  TTTGAATTTT GTACTTATAT GAGCTTTTAT GACAGGAGAG TATTGTCCTA
20501  TGTTCTTTTA TGACATAAAA GAGTATACTT TTTTATGACA AAGAGTATTG
20551  TCCTTTTTCC CCACGTTTAC AACACCTTTG AGCATTTCTT ATAGCACCAG
20601  TCTCATGGTG ATGAATTTTC TTAATATTTG CTTGTTTGAG AAAGACTTTA
20651  TTTCTCCTTT GCTTATGAAG CTTAGTTAGG CAGGATATAC AATTTGGGGC
20701  TATAATTTTT TGTCCTCAAG AAGGCTAAAA ATAGGCCCCC TATCTTTTTG
20751  GCTTATATGG TTTCTGTTGA GAAAGCCACT GCTAGTCTGA TGGAATTTCC
20801  TTTACAGGTG ACTTGACTGT TCTCTCTAAC TCTCTTTAAG ATTTTTTCTT
20851  TAGCATTGAC CTTGGTTAGT CTGATGACTA TATGCCTTGA TGATGTTCAT
20901  CTTATATAGT ATCTTGCAAG TGTTTTCTGA ATTTCTTTTA TCTGGATGTC
20951  TACCTCCCAA CAAGATCAGG GAAATTTTTC TGAATGATTC CTTTAAATAT
21001  GTTTCCAAAT TGCTTACTTT TCCTTCTTTC TCAGCAATAC CTATAAGCTA
21051  TAGGTTTGGT CAATTTACCC CCTATACCAT CTTTCTCAAA TATTTTGTTT
21101  ATTTTTAAAA TGCTTTTCTA TTTATTTTTG TCTGACTGGA TTAATTTGAA
21151  AGACCAATGT TTAAGCTCTG AAATTCTTTC TTCTACTTGG TCTAGTCTTT
21201  TGTTAATGTT TTCAATTGTA CATTGAAATT ACTTTTGTGA ATTTTTTTAT
21251  TTTCAGAAGT TCTATTTTTA TAAATATAGC TATCTTGTCT TTCATTTTCT
21301  GAGTTGTTCT TCTGGTTTCT TTGTATTGGT TTTAACATT CTCTTGGATA
21351  TCATTGCACT TCTTTAGAAT CCGTATCTTG AATTCCTTAT CAGTCATTTT
21401  TTATTTTGTT TAGGATCCAT TGCTAGAAAT CTAGCCTGAT CCTTTCAAGG
21451  TGTTAAAACA CTCTGTCTTT TGTACCACT GGAGTTCTTG CACTGATTCC
21501  TTCCCATGCG AAGGAGTTGT TGCTTCTAAG TTTTGAATTT GCTATTGTTT
21551  GAATGGGACT TTATCATGTT TATTCTTTTT TCCCTTGAGG GTATGACTGT
21601  GGTGTATGTT GTATGTGATT GTTTGGCTTC TTTTCTGGGG TTTCTCGGTG
21651  CCAAGACTCT GCATGGGCTC CTTGGTTATG GATAGCCTTT GTGTGGTGGC
```

FIGURE 3G

```
21701  TTTCTCAAAT GCTGCTTGTT GTAGACATGT ATTGGGCATA TGAGCCAACA
21751  CACTATTTTC TGTGTGACTA GGAGAGCAGA GGTCTCAGTA AACTTATCTT
21801  GTACACTAGT ACTATACCCT TCTGACAGTA GGTTTTTTAT TTGGTGGTGC
21851  AATTCAGTCT TCAGTCAAGT AGGAGGTGCT TAAGAGTAAG AATCCACTCA
21901  CCCTCAGGCA GTCTAATGAT GAAGGAAGAC AACTGTCCTA ATTGAGGTTA
21951  GTGTGGGGAG CTTGTGTTGG AGTGAACTGG TCTTGGTGGT AGGGGCAGGG
22001  GGCCTGCATT AGCCCCTCAT CCTGGGCAGG CAGGAATGTG ATCCGTTTTC
22051  CTATCACACC TTTCTGTCAC AGGGCTCATG ATCTTCAGCA TATAGACATT
22101  GTTCTTTGGC TCCCAAGCTG AAGTGTGACT GAGGTCTGGA GAAATGCCCC
22151  TTTGGTGGCT ACCACCAAAA TGAGCTCAGG GCAGAGCCTC TTCCCAGAGC
22201  CCAGAGCAAA CAGTTTTTCA ACTTGTCTGC CCTTCGTTGC TGGGACACTG
22251  CCATTCTGTG TTGGGATGGG GAGACAGGTC CCACCTTTCA TGCATGCCTA
22301  GGTGGCATTG GCTCACTTTC AATGAGGTGT AGCTGCCACG AAGAGTGCTG
22351  GAAAGGCTGT CTCCAAGTGC AATCAGGTCA GCCCTCATCA GGAAAAAGCC
22401  TCTGCTGCAT CCACAACAGT GCCTGCACTG AGGGCTAGAT TTCCATGGAA
22451  CCTGCAGCTC CCCAGAGACC CGCCAGTCTC CTGTGGTTGC CAAAGTCAGA
22501  AGGGGTTCTG AGGTATGTTT GCAGGGGATC TTGTAGTGTG CAACACAAG
22551  GACTAAGGTT CCTTGGACAG GGCACTGGCC CACAATGAGT GCACAACCAG
22601  TGTGGCACCT GCCATCTCAG TTAGGGCCTG AGGGGAGTGT GGGCACACCA
22651  GCACGAGCTG GCCACCTGAG GCTCCACCC CAGAGAGTTC CCAAATTGCC
22701  ACCAACTGCA TTGCCTGGGA TTTCAAGGGC AGAGGGGTTC TCTGACAATT
22751  TGTCAGTCAG CAGTTAGTCA CAGGAGTGAG GGGAGCAGAG AAGCACCCCA
22801  ACCTATCCTT TACATGGGAC TCTGAGTTCC TCAGGAGTCA GTGTCTGCCA
22851  GACTTTTGCT GCTTTCCTTG TCTGCACCCC AGTTTCTTCC CATGGGCTCT
22901  CTGAAAGCTC GTGGCTCTCT TCCCTCAGCT TTCCATTTGG ATCATGACCA
22951  TTCAACTGTA ACTTTGATCT TTCTACAAAC TGGTGTCTGA CATCTCTAGT
23001  CAGCCATCTT GAAAAAAAAA AGCTACATTA AAGTTATAAA AATAAAAGTA
23051  ATTGCACTGT GATGTTACAA AGGCTACTAT ATCACTAGGT GACAAGAATT
23101  TTTCAGCCCT ATTATAGTTT TATGGTACCA CTATTTTATA TGCGATCCAT
23151  CATTTGACTG AAACATCATT ATGTATGACT GTACATAACA AATTGCAAT
23201  AGAATTAGAA AGTGCTTTCT ACTTCTGGAA ATCAATGTTG TCTTCACAGA
23251  GACAGAGGTG GGCTTTGAAG GATAAATAGG AGTTCAGGAG GCAAAGAAGG
23301  AAGGATCTGT TATATTCTGG GAATGGCAAA TATGATGTGG ATAAAGCATT
23351  GGGATTGTGT CTGGGGCAT AAAATGTGAC TGGATATAAA GTTTAAATCT
23401  TTACATAAGG TAGGTCAAAT TGTGGAGAAT GAATTAATCC TTGAAGTCAC
23451  TCTATCTGAT AAGCACATTA TTATCTCCAT TTCACAGATA AAGAAACTAA
23501  GGTACAGAAG ATTAAATGAC TTAAATAGGT CACCTGACTA GTAAGTCGTA
23551  TGGCAGTGAT TCAAACCCAC AAGGAAGACT TGTACATATT TATTGACTTT
23601  TTCATGATGA TTTTTAAAAA GTTGAGAATA TTCTATTATA AAGCAATAAA
23651  GAATTTGATA TTTAGTAACC ATATCACAAT AGTTTTACAA ATGTTTTAGC
23701  AAAAGTTTGA AAGTTTTATA GTTAGAAAAT TCCCATTGAA CTAAGATTTA
23751  TTCCCATAAT TAGGAAAGCC ACTCTCCCAT TGGAGACTAC TTTTATTATA
23801  GCCTCATGTT CTCTTACTTT AAATTATCTT CTCTGCTGTA CCACAAAATA
23851  AAAAGTCTTA TAATTTCCTT ATTTCAAATG TTTTTTCTTT GAAAAAGAAC
23901  CATTTATTTC TGGTATTATT AGTTGATTAA TTTTTGTGCA ACTTAGTAGT
23951  GTTGATATAG GATCAATGTC AACTGGTGGA GCAATTCTAA GGGTGTTTGC
24001  TCCATTAGTA ATAACCAGTG GAGTTAATTA ATTACACAGG CATTTGAAAT
24051  TGTAGGTTTT GCCTGTTAAA CACTGGATAT TTCAGGATGA GAAATGTGGA
24101  GGTGGACTAA TACTGAACAT TTTATTTCAG AAAATACAGC CAATAGTAAA
24151  TTTCAGTCTT TTATTGAGCT ATCTTTGACA CCTGTGCACA TCTTATAATA
24201  AACTGTTCTG TTTTTCAATG GGTATCCTAG GAACAAGAAC TAAATAAGAG
24251  ACAATTATTT TAAAGTCTTC AATAATAGAA TTTACTTTTG TGTGGGCAAA
24301  AGACACGAAC AGACACTTCT CAAAGAAGA CATACATGCG GCTGACATAG
24351  GAAAAAAAAG CTCAACATCA CTAATCATTA GAGAAATGCA AATCAAAACC
24401  TCAATAAGAT ATCATCTCAC ATCAGTCAGA ATGGCTATTA TTAAAACGTC
24451  AAGAAACAAC AGATGCTGGT GAGGTTGTGG AGAAAAAGGA TTCCTTTACA
24501  CTATTGGTGG AAACGTAAAT TAGTTCAACC ATTGTGGAAG ACAGTGTGGC
24551  AATTCCTTAA AGACCTAGAG GCAGAAATAC CATTTGACCC AACAATGCCA
24601  TTAATGTGTA TATACCCAAA GGAATATAAA TCATTCTATT ATAAAGATAC
24651  ATGCACGCAC GTGTTCATTG TAGTGCTATT CACAATAGCA AAGACATGGA
24701  ACCAACTAAA ATGCCCATCA GTGATAGACT GGATAAAGAA AATGTTGCAC
24751  ATGTATACCC TGAAATGCTA TGCAGCCATA AAAAGGAACA AGATCATGTC
```

FIGURE 3H

```
24801  CTTTGCAGGG ACCTGGATGG AACTGGAAGC CATTACCCTC AGCAAACTAA
24851  AGCAGTAACA GAAAACTAAA TACCACATAT TCTCACTTAT AAGTGGGAGT
24901  AGAATGATGA GAACACATGG ACACATGAGA GGAAACAACA CACACTGAGG
24951  CCTGTTGGAG GGTAGGAGGT GGGAGGAGGG AGCACATCAG GAAGAATAGC
25001  TGATGGACTC TGGGCTTAAT ACCTAGATGA TGGGTTGATC TGTGCAGCAA
25051  ACCACCGTGG TACACATTTA CCTATGCAAC AAAACTGCAC ATATTGCCCT
25101  TGTACATCTG AACTTCAAAA TAAAAGTTGG AGATTAAAAA ACGAAATTAC
25151  TTTTGTTCCA GAATTAACTC TCAGATGTTC CATGTTTCAT CACTTTATTT
25201  TTTCACATAA TTTGTGTATG TGACTCACAT CAATTCATTT TGATATATAA
25251  TTGATTTCTG ATATTTTGTT TGTTTGAAGT GAGAGGTAAC TGGGTAATTA
25301  TCTATACTCT GCTTTTACCA TGCATTTTAT TTCCAGGTAA ATTTGAAAAA
25351  TCTAAATTAT TTTTCTAAAT TTGATCATGG TTTATTTGAC AGTTTACAAG
25401  TACTTGCAGG CATGTGTTTG CATGTGGATA ATAACAAATA ACTAAGAAAT
25451  CTTACAAAAG TATAGCTTCA TAATTTGGGG GTCCTGGTTA TACATTTTAC
25501  ATCTCTAAGT TAGGAACTCA TATTGTTAAT CTCCCTTCAT AGTTCCTTAT
25551  AACTAAACTC TGTTTAGTAT GAGTTTCTAC TTATCAAAGG CATAATAACT
25601  CACTCACTAT TTGGTATATT TGCTCTTTAA TGTGACATGA CATGTTTCT
25651  GTGGATAAGG AGAACTGTGT ATTTGTGCGT ATATGTATAT ATAATGTTTT
25701  CAACCAATCA CTATTTCAGA GAAAAATGG ATGAAATAA ACTTGTATTC
25751  ATTACATTAA ATATAATCCT ATACATATTA AGAGGAAATT TTACAGCAGG
25801  AAATTGTTCC TTTAATCATT ATTTTTCTTG AAAATTATTT AATACTTTTA
25851  AGACAAACCA CGGATGACCA AAGTCTCTTA ATATTACCA CATAGATTTA
25901  TATTAACACT ATATTTTGT TTTAAGTTTT CTAGACATCT GAGACTTAAA
25951  TATGTTCTTA TTTAAAGACT TTAATAGTAT GGCAGTTGTA CCATGAAGGT
26001  GGCATAGTGA AGGAGATCAA CTTAGTCTAC TTTTTGACTA AATTCTTAAA
26051  TCTCTATTTC AGCTGTCTTC CCCCTAGAAC TATAGCTTAA AAGCTCCTCA
26101  GCTGCATACA GCACATAGCC TTCACAGGTT ATCGCCTTTC TATAGAGTCC
26151  TCTCACAATA TAAACAGGTG TAGCTACCAA TTAGGACATG TCTCAAGAAA
26201  TTGTTAACAC TCACCAATAT TAATTAAGTG CTAATAGGGT ACTGAGCCAA
26251  ACACTGAGGG TGCTGAGCCA AATTTCCATT TCACATTCTT CATTCTCCAA
26301  GGAGGTTTAG ATACTGGTGC TGTCAATAGG GTGCTTGAGT TCTAGAACCC
26351  ATGGGGAAAA ATAAATTACT GTGGCCACTT TGCACATAAA TGTTTAAATT
26401  TAAAATATCA ATTGATATAA ATACTGATAA TAATGAATAA ATATTAAATA
26451  ATAATTGAAA GGGATGATGT TCTTGGTTTG GGGGATAATA CCCATAATCT
26501  TAGCAGTACC AGAATCATTG CAACCCTAAT AGGATTAATT CCATTTTGGA
26551  ATATCAGTAT TCTGAGATTA CTATTTGAA TGTTCTCGTT TATATTTTCT
26601  TCAAGTAAAC TTTTTTGCTT CTTCATTCTT TTTCAGAAAT TTTATTATTT
26651  TTAAAATTGA CAGATAAAAT TGTATGTATT TATTATGTAC AACATGATGC
26701  TTTGAAATAT ATATATCTAT GCACTGTAGA ATAACTAAAT ATAGCTAATT
26751  AACATATGCC TTACCTCACA TAGTTATTAT TTTTGTAGTG AAAATACTTA
26801  TCCACTCTCA CTATTTTTCA GGAATACAAT ATGTTATTAA CTATTGTCAC
26851  TATGCTGTAC AATAGATCTC TTGAACTTAT TTCTGCTGTC AAACTAGAAT
26901  TTTATATCCT TTGACTAGCC CCTTCCTCAG CCCCCCAAGT GCCCCAGCCC
26951  CTAGTAGCCA TCATTCTACT CTCTAGTTCT ATGTGTTTGC CTCCTCGTTC
27001  TATCTTTCCT CTTCCTCACT ACCTAGTCAT TCCTAGTGCC CACAGTGTGT
27051  CACAACTGCT GAAAGCATGG TGAAAAATA TCTGTTTTCT TTTCTTCCCT
27101  TCTCTCTCTC TTCTTAATGC GTTTCAGGTG GGAAGATAAT AAAAGAAACC
27151  AAAATGATTG AAATCATTAT TAGCAGAAAG TAAAATTTTA ATTTCCTGCT
27201  GGTACAATAA GCTTTTGTCT GGGCTCTGGG GACAAAAAGA TTATGAATAT
27251  TCTTTTGTGC CACTTTCAAA CTGCTTCTAA ATATCTTAGG TACATTTGTA
27301  ATATGAAAAT ATGGCAGCCT TATTAGCAAA ATAATTTCTA ATTTTGAGCT
27351  AAATTGTATA AGATTATGCA TGTTTTTCTT TTGCATAACT CAATTTGTTT
27401  CCTGTAATGA TAATTGCCAT GATTGAATTA GAAGATAATA TAGCATAAAA
27451  AAATTTTATG ACATCACAGT GATTAATCCA AAACTATCAG CATCAATGAA
27501  GTTAATAACA ATATTGTTCA TGAAAACAAA GGTCATGTTT ATGAAATTGA
27551  AACATTGTTT ATATGTGAGT GGCCTATTTT TCTCATGCTA CTGCACTAAT
27601  TTTATCTTAG GGTTTATAAA TATGAATCCT AAATATTAAA GTAGTGCTAT
27651  TTATCGCCAA CTCTAGTGGC CTTCTGTCCT CAGCCTTTTT GAATTCACAA
27701  AATTCCTGTA AACTGTGGAC TATTTTCCCC AACTTACAAA TAAAGAAATT
27751  GAGGTTCAAA AAAGTAACTC GCCAATAAAT AGGTTCTAGA TATCTACTAT
27801  ACAGCATAGT GCCTATAGCT AAAAATACTG TATCGTATAC TTAAAATCTT
27851  CCAAGAGGGT GGATCTTATG TTGTATTCTT ACCACGCACA TACAAATAAT
```

FIGURE 31

```
27901 AATAATGATA GTAAAGGCAT TAGGGAGCTT TGGGATGTGA TAGATATATT
27951 TCCATGTGTA AGTGCTGTAA GAGTTCACAA GGGCATAACC CAAGTGCCCC
28001 AGATATGGCC CTTCTGTATT GAATATACCT AAGGTAGACA CACTGAAGAA
28051 GATGGATATA TGAAAAAGTC TAATATACTA GCCTTATTGA GGTAAATTGA
28101 TCAGTTCACA TTGGGTATAG AACATTGTCA GCAACTAGAA AAAGAAAATG
28151 AGGTTGTTCC GTCTCTATGT TCACACGAGG CATGAGGCAG CGACGTTCTA
28201 ATAATCCTCC TGCTCTTCTC CCTTACCCTC CTGCCTCCTC AATAGCCTTA
28251 ATTTGTAGCA TTTTCCAATA TCTGTGGTTA AATTCTTTCC CTATGGCCAA
28301 TTTTATACCA CTGAGGTGTT TTCCCCTGAA CATAAAGTTA GGAAGAGATG
28351 CGTGTAACTG GCACTGGTGA GCTGGGGTAA GCCAGCTCTA GCATACCACT
28401 GCTGCCAGGT TATCTACCGT AGAGTGTAAG CCATAGTTTT CATCAAAAGT
28451 GTCCTGCAAA AAAAAACAT TGAAAAATGA GAAACAGTTT CTGTATGTCA
28501 ATATAAGTCA ATTTTATTG CAATGAATAT TGAAGGAGGT AAAATTTTTT
28551 TTTACTTCCT GATGAAAACA GATGAAGTAT GTTAATATAT GTCCCTGGGC
28601 CCTCTGTGTT TCTGTGCCTC CCCTCACAAG GCATGCTATT TTTCTGTACC
28651 TGCCAATACA TATCTTATCT TCCTTACAGG CCTCTCTCCT CTGTTTTTGA
28701 CTATTTCAGC CTACTCCAGC TTGTAGTGCT GTAGAAAAGG CTTTAGATTC
28751 ATTTATTTAT TCAAGAAACA CTTACTGAGC TTTTAATATG CCAGGTACTG
28801 AGAATATAAA CATGATTAGA CAGACCATGC TATAGCTTTG ATTGTATGGC
28851 TTTGGGGCAA TTGCTTTTTT TGTTTTTTAA CTTACTGAGG GATGACTGAC
28901 ATGTAAAAAG CTGTACATAT TTAATGTATA CAACTCAATG AGTTTGGAAT
28951 ATACACCCAT GAAATCATTA CTAGCATCAA AGCCACAGAT ATATCTATCA
29001 CCTCCCAAAG CTTCCTAATG CCTTTATTAT TATTACTATT ATTTTTATTA
29051 TTATTAGTAT GTGTGTGTGT GGTAAGAACA CAACATAAGA TTCAACCTCT
29101 TGGAAGATTT TAAGTATACA ATGCAGTATT GTTAGCTATA GGCACTATGC
29151 TGTGTAGTAG ATCTCTAGAA CCTATTTATC GGAAAGTTAC TTTTTTGAAC
29201 CTCAATTTCA TTATTTGTAA GTTGGGGAAA ATAGTCCATA GATTGCAGCG
29251 ATTTTGTGAA GATTAAATGA GAAAATATAA ATAAAACACT TAGCATAGTA
29301 GATGGTACAT TGTAGATTTT CTATAAAGGC TAGTTTCTTT TTTTTAACTC
29351 TAAACTCTTA TAGCTATCTT AAGTGCCAAA TGAATCGGCA TTTATTTATA
29401 TTCTGCCTTG GATGTTGCTT GCCTTCTCTA GTATCCTCAG CTTGTACCTT
29451 TATGCAGGTT CTTATACATA ATTTGTTGTT CCTATCAACA TTGATCACAA
29501 TGTAGTATCA ATACTTTCTG ATTCTTGGTT CTTAATTTGC CTGCCCATTG
29551 AGATATTGGT CATAAGTTAA CATTTTCCCA TTATTTTCCA TTTTGAATCA
29601 CTTTCCTGGT ACTTTCAATT TTGTATTTTA TATCCTGTCC ATCTGTATTT
29651 TATAATTTTA AATTTTTTCT TCCAAATAAA TTTTAGCATT CAGCTATTGC
29701 TGTGTCACAA TCCATTTCCA AACGCAGTGG CTTCAAACAG CAACATTTTA
29751 TTTAGGTCAT AATTCTGTAG GTTGTGAATT TGGGTTGGAC TCAGCTAGTT
29801 AGTTCTTCTA ATGTGAATCA GCTGGCGCCC GCTTCTACAA TCAGCTGATG
29851 ATTTCACAAC TGAGGCCGGC TGGTTTGTGA AGTCCTCAGC TGGATGACTG
29901 CCAGCTAGGG CTTCTCTCTT CATGGTCTCT GATCTGATCC AGCCAGCTAG
29951 GCTGGGCATG TTTACATGGT GGCATGACTT CCAGAAGCAA CAGCAGGTAA
30001 GAACCTATGC ATAAGAACCC TTCAAACCTC TGTGTCACAT TTGCTAATGC
30051 CCCATTGATC CAGATTCAAG GGTTGGAGGA ATATATTCCA ACTCTTGTTG
30101 GAACAAGCTG CTAAATATT GTGGCCATTT TAAGAGAATC TACCACATTA
30151 TCTATGTATT TTTCATTTGT AAACATCTAT ACAGAAATGC CAAGTGTTTT
30201 TATCTTTGAT TTCAGATATT TTAATTGTTT CACAGTTGAA TTTCATAAAC
30251 TTTCCTCATG GAAATCTGTT TTTCTCCTCA GCAACTTCTC GGTTTTTCCA
30301 GGCAAGCCTT TCTGTTCTTA ATTACTGTAA TTTTCAGAAT GAGCTACTTT
30351 CTACATGTGC ACATGTCTTT TAAATTAATA TAATACAAAA CTAAATCTGG
30401 AAAATTTTAG TTTTACATTT TTTTGTTCAT CTCCTAACCT ATTTCCCTGA
30451 AGCAAAGTGA CAGGTCTGTT CAGAATTTAT AATTTAATTA AGATGAGATT
30501 GGGGAGGTAA GGAAGTACCA CTTTCTCTTT TGCATTCATT TTTTAAGGAT
30551 CTCAGGACAT ATGTTGATCT ATTTTCTTTC TCTTCCTTGC AAATTAAAAC
30601 AAAATGTTTT AAAATAAATG TTTTAAAATA ATAGTGAAAT TGCGAGCTTT
30651 GCTGATTATA AAAATATATG CTCTATGTCA TCTTGCCTTT TCTTCCCTGC
30701 TCTAATATGA ACTTCACATT ATCCCTTCAA TTGCTCTTCT GTTTTTGCTC
30751 ACGTTATCTC CTTTTTCTAA ATTTTTCACT CCTCTGCTGA TGTAAAACCT
30801 GCTTATTGTT TAAGAGCAAC TCAAGTCCTA CATCCTCCAT GAAATTTTCA
30851 CTGATTGCCC AGGTTATCCT TGATTTTACT CTATTGTGAA CTCCTACAGC
30901 ATTTGATGGC TGGTACCACA CAGTAACATT TGCCTCATTA CAGGTTGGTA
30951 TTGTTTAATG CTTTTAATGT GTATTTTTAA TTTGTATTGT TTGCTGCTGT
```

FIGURE 3J

```
31001 TTTCATTGCT GGGCTTGATT CGTTAGCCAG TTTTTTTTTT TACTGATTTG
31051 CACTCCTGGC TCTCTAAGTG CTGTAAATGT CCAGGATTAA GCTGTTTTAT
31101 AATATACCAA AATTGGGAGT TCTCAAGTCA TTTTTTTTAT AAGAAAACAC
31151 ATATTTTTAG GTTTCATTCA CTTATTCAAG ATATATTAAA TGCTTATTAT
31201 GTTTCAAGAT TAAAAATAAA CACTATCTCA AGACACAAAG TTAATTTAGT
31251 TGCTATGTTT TGCTCAAGAC GGTGTTATAA ACTTGTAAGA AACAGTATTT
31301 TTGAAAATGT GCCACAGTAC CTTCTAAACT AGTAAATCTC AGTTAGTGGC
31351 CCTTTTGATG AGCAACTTTA GGACTTTCAA GATTTCTACT TTCTATCTAG
31401 AATAGTCATA GTCATGAAGC CTTTTGTTTT ATAATGATTA TAAATACCCT
31451 TCCCAGGGTC AGGTAACTAT GACCAGCACT AGTTAACAC TGTCTTTTTC
31501 TTTTAGCAAA ACAACACAAG GAACAATGGC ACAGTAGCCT AGTAATACCT
31551 CTTTGCTATA AACATACACT CACTCCCATC CTCTCAGTCT CTTTGTTTCT
31601 CTGTTACTCT CCCTTAGCAG AAATTTTCCA TTGGACTTCT AGTGCTTTGA
31651 TGTATTATGA TCAATGATGA CTTGTGTTTT CTGACTCTGT TAGAGTCTCC
31701 ATGGAATTAA AGATTATATG CTTATTCAGC TTAATGTACT TGACCTTTTT
31751 GTATGATTGA CACATCTAAA TTTCTGTAGC AACTCAGTCA TTATGCAACA
31801 GCTGTGTTAT ATTCATTTCA TGTAAAAAGC AAAAACAAAA GACATAGAGT
31851 TCTCTTCAAG AGTAGATACC TTGACCCCTT CCCTCCCAGC TAAATAAAGA
31901 ATAGTTTATT AATAACATTA TTAATCAGTT TCCAAATGCG CTCCCTTTCC
31951 TCACCGCATT TTATAAACAT TCAGTATACT GTGACCATAG TCACATCAAG
32001 AATCATTTCA ATACTGATCC TTATTATATA ATTAAAATAT TCAATAATTC
32051 TGAGTCTGTT GAACATAATA ATAGCCACAC AACTTAAGTG TCAAACATCT
32101 AGGATTTGTT AGCAAGATTT GTGCTCAGAA AATAATATGT ACAAACCTTT
32151 GATTTTCTTA ATGATGAAAC TGTATTTTGT CTGAATTGAC ATATGTGTCT
32201 TTAAGTTAGA GAGAAAAAAC CTTGACATTT TTCTGTGACT TTTCCTTATC
32251 AACAGCTGTG TTCTACCTGC GTTTATTTTT CTCAGAATTC ATTATGAATT
32301 CTGTATAGGC CTTCAGAAGG CCTATACAGG CTTTCTAACA GAGATTCTAT
32351 AGGAAAAAGT TTTGGTTAAC TGTTTGAAGT ATTAGTTGAA GAAGGCATTC
32401 TAGATAAGGT TTTACAAGAC AGAAGAAAAG AATCAATTCA TTTTTAGTTC
32451 TGAGCCTGAA TTGTGGAAAC TGTACTAACT GCAGATAAAC TCTGAATAAA
32501 TTCTAGTGTT CTCTGCTTAT CTCAAAAAAT CTTTTCTTTT AATGATACTG
32551 TTCCATGCTC ACTAATGTTT TCAAAACATA TTCATATCTA AATGGTTTTG
32601 TATTTTTATT AAATTTTGGA TTTTTTGCAT TACATAAAGT TAATTTTGTT
32651 GACCATTTTA TGAATTTAAG AAATGTCCAC TTGAAAGGAC TCGCTCCTTT
32701 AATTAAATTT TTGGCCTTTA TTTATAAAAT AAAAATTATT CTTTATATGT
32751 TCTTGAAAAG TAAATCAGAT TAGGATTAAT AATTGTCAAG TCATTTTAGA
32801 ACAATGACAT CTATCATTAA ATTTCTTGAA TTTTTTGCCT TCTCAACTGA
32851 TAGCTATCCG GGTGAAAAAT TCAATTATGG ATATTGGAAA AATTGATGGT
32901 AATATTAATC TGGAAATGTT ATTTCTGTAC TATTCTTTAC AGGACCTGAG
32951 GGGATTCTCT AGTTCTTTAG GCCAGTGTTA TAATGTTAGG ATTTACAAAA
33001 GTTGGTAATA TAGAGAGAAA CAGGAAGAAA ATGAAATGGG ACAGGAAAAT
33051 ATCATTCCTT CTTCTTATTC CTTCCTCTAA GTCACTGGCA TTGTGAAGGG
33101 AAAAGGGAAC TAACATGTAT TAGTGTCTAC CATGTAACAG GCATTGTCTT
33151 TCATATTTTA TATTTATCGT ATTAGCTCAT GTAATCTTTG TGGAAAATCT
33201 CCTAAATCTA TTAGTAGGTC TTTAATATCT ATGTTTATTT ATTTTGTCCT
33251 GAAAACAAAT GAAGTTTTTG GATCAAGACA GAGAATTATT ATTACTTATA
33301 GCAATAACCA CCTTGGAAAG AAGGCACACA GTTATGCGCA CAGGAGGGGA
33351 GCCATGAAAT TATGAATCTG GGAATTTATA TAGGAATTAC TATATAAACT
33401 CTTTATATAG TAAATGGTCT TCTCCTGTCT TCTCCTTTTC TGAAAGAGGA
33451 AGAGAAAGTT TATCTCCGTT ATATACAATA AGCAAATCTT TAGGGGAGAG
33501 AATGAGAAGG TCCTGGTTTA AACCCTTTGA AATGTAAACC AGTAGCTCTG
33551 GGATTTTGTT CTCTTTTGAA ATGTAAACAC AGAGCTGTAG AAAATAAGTG
33601 TCTGCATATC TCTGAGGGTC TCTGTCTATT CAGTCCACCT TTAATCCAGA
33651 TTTCAGTTTG TCTTGCTTTA TAACTCCTTA ACCATGCAGA AGCATGAAAA
33701 CATTTTCTCT GTAGTTCCAC ATCATGAATT TTAGCAGTTT TAGTACTGTT
33751 GCTAAAAAAT TGTGGCTATT AGCTTGTTTC CATTCCTTTC ATAAAGTGTT
33801 TAGTAGCATA ATGCATTATT AGGTCTACTT TCTATCTATT ATACTTGAAA
33851 ACCATCCTCT CTATGTAAAA TATCTATTTA TTCAATGGAT ATTTATTGAG
33901 CACCAAAAAC TGTCAAGCAT TGTTCTAGGT ATTTGGGATA CATCAGTCGA
33951 CAAATCAAAG ATACCTGCCT TGCTTGTATT TACAAACTTT GGGGTTAGAA
34001 TGCATAAAAT TGAGATTATG GAGGGGTTGT AATTATTGCC AATGAAAAGC
34051 CTAGGATGAA AGATCACTGG AAGACTAAAG TTTAAGGAAT TGAAAGGCCA
```

FIGURE 3K

```
34101  GAATATCAAA AGAATCATCT ATATGTGTTT TGAAATCTTA TGAATTAAGG
34151  CAGTATCGAA GAGAATGACA GTATGCAAAG AGCTCAAATG GTTGAGTGGG
34201  AATTACCTGG ACCTTAGTGG ATAACAGCAA CCATGAGGCA AAGTATGTAG
34251  TGAGTAATGT CGACCATGAG ATTTAAATCT GAAGGATGTC AGGAAGGATA
34301  TGGGGAAATG GTCTGAAAAT GTCAGAATGG AGCAAAGAAA TACCACTTTG
34351  CTTATTCCAC TCACCCAACC AGAGGTCGCA GGAACAAGAA TGACACCTTT
34401  CCATCTTGCA TAAGAACTGT GGGAGAGAAG CAGCCATCAC TGAGAGATTG
34451  TAGGGGAGGC ATTGTCCTCC AGAGAAAGAC AGGTTTATGT TTCAGCTAGG
34501  AAAGTAAAGG GAACACTTAG AAAATTGATT TTTGGCTCAC TGGAAGGGTT
34551  TCAGCAGTTG GGAGAGAACA AAGGTAATTT TTACCAGCTT GTAACTTCAC
34601  ATGTATTAAC TGTGTTGCAA AACTAATGAA ACTTACTGTC TATTCTCTTG
34651  CTTTATCTGA TAATATAGAT AAGGGTGTCA CCTGTAATCA TTGTTACCAT
34701  ATTTCTTGAG GCCATTTTCT TATTCTCATT TAACTTTTCT ACTTGTTTCT
34751  TCTTTATTTG TATTTTTCTC TGTTTTTAAT CTTGCTCTTT TTATCATTTC
34801  TGTCTCTTTA TATCCTACTT ACCTCTTAAT CTTTTTGCCC AACTTCTCTC
34851  TTAATATATA TATATTTTTG CTCTTTACTA TTTCTCTTAT CTTTCTATTT
34901  CAAAATTACA CTGTCTGCTG TTTTCTCCAA CTCCCCACAA CTCACCTTAG
34951  GTGTAGTTGG GACTATGCAA TATGCCATCA CACAGGTAGT ACTAATTTTG
35001  ACAGGTAGCA TCTCTACTTC AAACAAAGAA AGCTTTAACC AAAAAGGAAT
35051  TACAGGAGAG AAGACAGTAT TCTCCCCAAC TGATGCTAAC ATTGCCACCT
35101  ACACTTTTGA CGCTTTCTTC AACAGTTAAG ACGTAGCAAC TTATTACTTC
35151  CCCAAATTCC CTGTGCTCTG TTGATCTGTC TTAAACTCTA AAGGGAGAGA
35201  AAGTAGGTTT GTTCATTAGC TGTGGGACTT AAAATGTGAC TTAACTTTTT
35251  TGAACCTTTT GTTTCGTGAA TGATAAAAAA ACACTTTCTG AATGATATAG
35301  CTACTAATAT TTTCATTTTA TAGATAAAGT GAAAGATAAA GTACTTTTTT
35351  TAAAGGTTGC ATAAATATAA GTGACACACA CTGATATGAA TGTAAGCATT
35401  TGACTCAATC CCAGAGATCA TGTTTTAATG AATACTCTAT TGTTTCTCAC
35451  ATAATATAAC TTAATATTGT GGTCAATAAA ATAATAAATA GGACCAGACA
35501  CATATATGTA TTAATTCACT TCCCTTTATT TCCTTTTTCC AAAATTGAGC
35551  CTTATTGGTA AAGGGCTTTT TGTGCATTTT AATTGTCTAT AATCAGGTAC
35601  TTGAACCAAT TATAATTTTT CACTTGCCTG CATGAATCCA TACAGGACAA
35651  AAACCTGAAT ATAGAAACTA TCTTTCAGCT TTCGGTTTGC CAGAGGATTA
35701  ATCTATAATT ATTTTTAGGA TTATAAAAGA TTTACATCCG TTCTTAAAAT
35751  ATACATAATA TCGGATTTTT TTCCAGCAAT AGAGGAATAA CTAATTCTAT
35801  AGTTTCATGC CAATCTCACC TCCAGTCCTT CTAGAATTTG GAGGTAATTT
35851  AACCCCGTGT ATAAAAAATA AATATTTTCT TTTTTGCGTT TTATTGAAAA
35901  AATCACGTAA TTTAAGTACA AATATATCCA CTAAAGTAGG CAAATTTATT
35951  TTAGTAGAAT TCAGTTATCC CTTTCAAAGA AACACTATCA GCCTAAGTGT
36001  TATACATTGG ATATTTTAGA AATCTTACAA TTTCAATTAC ATGTCTTCTG
36051  AAACTCATTA TTGTAAGGCT TTGTTTTAGG CTTTCCTTGC TGTATTAGTT
36101  GACTGGGGCT GCCAGAAAAA AATACCACAG GCTGGGCAGC TTAAACTACA
36151  GAAATGTATT TTCTCACAGT TCTGGAGGCT GGGACACCTA AGATCAAGAT
36201  GGCTAGCCAG GTGGGTCTCA TTCTGAAGAC TTTTCTCTTG GCTTTAGGTG
36251  GTTACCATCT CCTTGCATCA TTGTGTTACC TCTTTGTGTG CTTGGACAGA
36301  GAGCAAGAGA GGTAGCTCTT TGGTGTTTCT TCTTTTAAGA ACACTAATTG
36351  GATGGATCCA GCCCCACTCC TATGGCCTCA TTTAACCTTA ATTACCTCTA
36401  TAAAGGCCCT ATCTCTAAAT ACAGTCACAT TTGGGGTTGG GACTTTAAAA
36451  TATAAACCTC GGGGACATA AGCCTTCATC CACAGTATTG CCATTATAAT
36501  ATTTTGTGTA CTTTGGCACT TGAGAAAGTA AGATTTTTTT TAACCTAGTA
36551  TTTTAATGTT TTCTTTAGAG GTTTTTTCCC TGATACAACA CTCTCCTATA
36601  CATGATCTAC TTGGTAACAC AAATATCCCT TTGTTTGCTT GTACTTTTGC
36651  TTCCTCATAA ATTTTTCTGT AGCTACAAAT GTTAACTTTG TTGGATAGGC
36701  TTTATTTTTT AGATCAATTT TAAGTTTATA AAAATACTGC ACAGAAAGTT
36751  GAGACAGTTC CCATGTATTT CCTCTCCCTG CTGCACACAA TTTCTTCTCT
36801  TATTAACATT TTACATTAGT GCAGTACATT TGTTACAATT GATAAACCAA
36851  CATTAATAGG TTATTATCAA CCAAAGTCCA TAGTTTACAT TAGGGTTCAC
36901  TCTGTGTTAT ACAGTTCTAT TGGTCTGGAC AAATGTTTAA TGACATGTAT
36951  CTACCATTAC ATTATCAAGG ATGGTTTGAC TTCCCTAAAA ATGCCCTGTG
37001  CTCCACCTGT TCATCCCTAT ACCTTCTCCC TGAAGCCCTG ACAACTGCTG
37051  ATATTTTTAC TGTCTCTATA GTTTAGCTT TTCCAGAATG TCATACAGTT
37101  GGAATAATAC AGTATGTAGC TTTTAAAACC ATCTTCTTTC ACCTAGCAAT
37151  ATGCATTAAC AGTTCTCTCA TGTCTTTTTT GTGGTTGACA GCTCATTTCC
```

FIGURE 3L

```
37201  TTTTCCAGTA GTCCCACTTT ATCTGTAGAG GATACGTTCT AAGACCCCCA
37251  AAAGATGCCT GAAACCTCAG ATAGTACTGA ACCCTATATA TACTGTGTTT
37301  TTCCTTTACA TACATACCTA TGATAAAATT TAATTTATAA ATTAGGCACA
37351  GTAAGAGATT AACAGTAGCT AATAATAAAA TTGAACAATT ATAACAATAT
37401  GCCAGAGTCG AAACTCTTGT GCCTTGGGAC TTTTATTAAG TATAATAGGT
37451  GGCCAATATC AAGTGTAACA TATAGAAATA GGAAAACAGA AAAACCTCTG
37501  TGGAATTTGG CATTAACATA GACCTTAGCG AAACCTGTTT TATTAGAGAC
37551  AGTGATTTTT TAAAAACACT TAACTGTGAA GGGAAGGGAT TTGATGAGAT
37601  AACACAATTG TCTGAAGGTA GAGAGAATAA AAAACAATTT TTTTTCTAAT
37651  GAGAAGAGTA TAATTAAGCA TGGGAACAG ACACATAGAG ATTATAAAGG
37701  AAGTGATGAT TGCAAATAT TTAACCAAAT AATTAGTATT ATACATGTTT
37751  GTGATAGAGC TATGGTACAC TTAATTAGGT AAAATGCCAA AAGACAGTGC
37801  CACGCTCCAA GCTTTATGTA TCATAAACAT CAAAAATGAC TTGCTGAATT
37851  AAATTAAATT GAGTCTCCAT TAACATGTAA ATCATCATAT CTGTGCCCTG
37901  GAATAATTCA GAGTTTAATT TGTGGGTTTG CTTCCTTATG AAGGTCATCG
37951  AACACTATTT ATTGGAGTAC ATGTGCCCTT GGGAGGAAGA AAAAGCCATC
38001  GACGTCACAG GCATCGTGGT CATAAACACA GAAAGAGAGA CAGAGAAAGA
38051  GATTCAGGAT TAGAGGATGG AAGGGAGTCA CCTTCTTTTG GTAAGAATCC
38101  TTCTCCTTGT TTTTATTAAG TTAATTATTG TAATATACTT GCTTATACAA
38151  TTATGATTAG GAGTAATACC TTATACTCAT AAAATTGTTT ATACTTTTAT
38201  AAAAGACTTT GGGCCGGTTG GAGAGAAGTG GGAGAGATAA AGCTTGATCT
38251  TTGTTTTTCT CTTATATATT TGCATTGAGA AGCTGAGAAT TGATGAAGAT
38301  TTATGATATA GGAAATAACA TTGAGTAAAG CTCAAAAACT CTTGATAATT
38351  TATACAAATA ATCATCATTA CTCAAAGTGG TTTGAAAATC CAGGGCAAAA
38401  TGCCTTAATT TAGTTCCCAT TTGCACTTTT ACTGATAGTG CCCAAGTTTC
38451  AGTCTTAGGA TGTTGTATTA GTCCGTTTTC ACACTGCTGA TAAAGACATA
38501  CCCGGACTAG ACAATTTACC AAAATAAAAA AGAGGTTTAA TTGGACTTAC
38551  AGTACCACAT GGCTGGGGAA GCCTCACAAT TATGGTGGAA GGCAAGGAGA
38601  AGCAAGTCAT GTCTTACATG GGTGGCAGCA GGCAAAGAGA GCTTGTGCAG
38651  GAAAACTCCC CCTTATAATA ACTATCAGAT CTCATGAGAC TTACTCACTA
38701  TCACGAGAAA AGCACAGGAA AGACCTGTCC TCATTATTCA ATTAACTCCC
38751  ACTGGGTCCC TCCCACAACA CATGGAAAAT TCAAGATGAG ATTTGGGTGA
38801  GGACACAGCC AAACCATATC GTTCCACCCT TGGGCCCTCC CAAATCTCAT
38851  GTCCTCACAT TTCAAAACCA ATCGTGCCTT CCCAACAGTC CTCCAAGGTC
38901  TTAACTTATT TCAGCTTTAA TTCAAAAGTC TATAGTCCAA AATCTCATCT
38951  GAGATAAGGC AAGTCCCTTC CACCTGTGAG CCTGTAAAAT CAAAAGCAAG
39001  CTAGTTACTT CCTAGATACA ACTGGGGTAA AGGCATTAGG TAAATACAGC
39051  CATTCCAAAT GGGAGATATT GGCCAAAACA AAGGGGCTAC AGGCCCAATG
39101  CAAGTCCAAA ATCCAGCAAG GCAATCAAAT CTTAAAGCTC CGAAATGATC
39151  TCCTTTTACT CCATGTCTCA CATGCAGGTC ATGCTGATGG TTCTCATGGT
39201  CTTGGGCAGC TCTGCCCTCG TGGCTTTGCA GGATATAGCC CACCTCCTGG
39251  CTGCTTTCAT GGGCTGGCGT TGAGTGTCTT GTTGCTTTTC CGGACACACT
39301  ATTCAAGCTG TCAGTGGATC TTCCATTCTG CAGTCAGGAG GACAGTGGCC
39351  CTTTTCTCAC AGCTCCACTA GGTGGTGTCC CAGTAGGGAC TCTGTGGGGG
39401  CTGTAACCCC ACATTTCCCT TCTGCACTGC CCTAGCAGAG GTTCTCCATG
39451  AGGGCCCTGC CCCTGAAGCA AATTTCTGCC TGGGCATCCA GGCATTTCCA
39501  TACATCCTCT GAAATCTAGG CAGAGGTTCC TAAACCCCAA TTCTTGACTT
39551  CCGTACACCT GCAGGCTCAA CACCACATGG AAGCTGCCAA GGCTTGAGGC
39601  TTGCACCCTC TGAAGCCACA GCCTGAGCTC TACATTTGTC CCTTTCAGCT
39651  ATGGCTGGAG CAGCTGAAAC ACAGGGCACC AAGTCCCTAG GCTGTACACA
39701  GGATGGGTAC CCTGTGCCTG ACTGAGAAAA CCACTTTTTC TTCCTGGGCC
39751  TCTGGGTCTG TGATGGGAGG GGCTGCCATA AAGACCTTTG ACATGCCCTG
39801  GAGACATTTT CCCCATTGTC TTGGGGATTA ACATTTGGCT CCTCATTACT
39851  TTTGTGAATT TCTGCATTTG GCTTGAATTT CTCCTCAGAA AATGGAATTT
39901  TCTTTTCTAT TGCACTGTCA GGCTGCAAAT TTTCTGAACT TTTATCCTTT
39951  GCTTCCTTTA TAAAACCGAA TGTCTTTAAC AGCATCCAAG TCACTTCTTG
40001  AATGCTTTGC TGCTTAGAAA TTTCTTCTGC CAGATACCCT AAATCATCTC
40051  TCTCAAGTTC AAAGTTTCAC AGATCTCTAG GCAGGGGTA AAACACTGCC
40101  AGTCTCTTTG CTAAAACATA ACAAGAGTCA CCTTTGCTCC AGTTCCCAAC
40151  ACGTTCTTCA TCTCCACCTG AGACCACCTG AGATTGCCTG GACCTTATTG
40201  TCCATATCAT TATCAAGCTT TTGGTCAAAG CCATTCAACA CGTCACTAGG
40251  AAGTTCCAAA CTTTCCCACA TTTTCCTATC TTCTTCTGAC CCCTCCAAAC
```

FIGURE 3M

```
40301  TGTTCCAACT TCTGCCTGTT ACCCAGTTCC AAAGTCACTT CCACATTTTC
40351  AGGTATCTTT TCAGCAGCAC CCCACTCTAC TGGTATCAAT TTACTATATT
40401  AATATGTTTT CACACTGCTG ATAAAAACAT ACCTGAGACT AGGCAATTTA
40451  CAGAAGAAGG AGGTTTAATT GGACTTACAG TTCCACATGA CTGGGGAAGC
40501  CTCACAATCA TAGCGGAAAG CAAGGAGGAG CAAGTCACAT CTTATGTGAA
40551  TGGCAGCAGG TAAAGAGACC TTGTGCAGGA AAACTCTGCC TTATAATAAC
40601  CATCAGATCT CATGGACTTA CTCACTATCA TGAGAACAGC ACAGGAAAGA
40651  CCTGCCCCCC ATGATTCAAT TACCTCCCAC CAGGTCCCTC CCACAACATG
40701  TGAGAATTCA AGATGAGATT TGGGTGGGGA CACAACCAAA CCATATCAAA
40751  TGTGAACCTT TTACTATTGT GAATGCTCTC TCATTGAAAG CATATTCAGA
40801  ATACCACAAT AAGTGTTTTC GTAGTTGTTA AAAGGTTCTG AATGCCATGA
40851  GAGCCCATGT ACATGACATA ACTGAGAACC TGGCTCTCAG TTCCTTGACC
40901  ATCCCATCTC TTATGACCTT CTCTGTCATT GCACTTGTT CACCTTCTCA
40951  ACCATATTCA CTCCATCCCT GAAGTCACTA ATTCATTTAT CTTTCTGTCT
41001  GACCACAGCT TCACTCCTTT CTTGCTGTGC AGCTACTTAA CCCCTCTACT
41051  TTTCTTCTAT CCATAAGTTT GTCTTTATTT GTTTATCCTA GTCTGATTGC
41101  ATAGCATGCA GTCTTAGGAA TACTTTAGCA TTACTAGTAT TCCATTTGTA
41151  TTACTAGTAG TCTATTTAGT AATACTAGTA TTCTAAATAT CTTAGGTTCT
41201  AAGTTTTAGT TTTCTTCATA CCTTTACTGC CTCTTTTATT TTCATTTTTA
41251  ATAGGAAGCA GCATTTTATT TAAAATGTTT TTAATAGATT TCTTAAAGAT
41301  GTAAATAATC GAATTAAACT TAGTCTATAT TACTTGTATG AATTAATTTA
41351  CATTTTGTTC ACATTCGTGA AAAATAATTT AGCTAGGTAT GCAATTCCAA
41401  ATTGACAAGT ATTTTAACTC AGCACTTTGA ACATAATATC TATTTATTTA
41451  TCAATTTCAT GAAGATGTTA AGAAAGGAGA TAAAAATCTA TTGTTGCTCT
41501  ACAGTTAATT TGGATTTTAT ATTTTTATGA ATTTAAATCA TTTCCTTTAT
41551  TTTGGTATTT AGTTTTACAT TTATTATGAT ATTTTCAGAC ACACATATAT
41601  GCCTTTTATG CTTTTCTTGG TTGATATTTA ATGAGAATGT ATATTATTAG
41651  TTCTTTAAAA TGCTTAAACA TGTCCTATTT TCTATTATTT TCTCTCCCAC
41701  TTATTTAAAT TCTTTCTTCA AATATTCATT AAGCATATTC CTTTCAATTT
41751  CATTTTCGAT TTATTTTGAT CCCTCTTTTA TATTTTTTCA TCATTTTCTC
41801  CTTGTCCTGA CATTGAAGTG TTTATTTTAG CTAATTCATT TATTCATATT
41851  TTAGCTCATA GTTTTGCCT TGCTCATATC CCTTTACTTT CTTTAAACAT
41901  TTTGACTACA TGTGTCTTTC ACTTCTTTTA CTTTGGATTC GGGGGCATGT
41951  GTGCAGGTTT GTTACATAAG TATGTTGTGT GATGCTGGGG TTTGGGATAT
42001  GGATGGTCCT ATCACCTAGG TAGTGAGCAC AGAGTATAGT TTTACAACCC
42051  TTGTTCCCCA CCCTCCTTCC CTGCTCTGGT GATTCCCAGT GCCTATTGTT
42101  CCCATCTTAA TGTACATAAG TACCCAATGT TTAGCCCCAC TTATGAGTGA
42151  GAACATGCAG TATTTGGTTT TCTGTTCCTG AGTTAATTTT TTTAGGATAA
42201  TGATCTCCAG CTGCATTCAT GTTGCTGCAA AAGGATATGA TGTCATTCTT
42251  TTTATGGCCA CATAGTATTC CATGATATAT ATGTACCACA TTTTCTTCAT
42301  CCACTTTACC ATAAGGAAAC CTAGTTGATT CCATGTCTTT GCTATGGTGA
42351  ATAACACTGC AGTGAACATA CCAGTGCATG CATCTTTTTG GTGGAATGAT
42401  TCATTTTTCT TTGAGTATAT ACCCAGTAAT GGGATTGCTG GGTTGAATGG
42451  TAGTTCTGTT TTAATTTCTT TGATAAATCT CCAAACTGCT TTCCACAGTG
42501  GCTGAACCAA TTTATATTCC CACCAACAGT GTATAAGCAT TCCGTTTTCT
42551  CTGCAGCCTT GTCAGCATCT ATTATTTTTT GACTTTTTAA TGTTCACCAT
42601  TCTGACTGGT GTGACATGGT ATCTCATTGT GGTTTTGACT TGCATTTCAT
42651  TTGTTGACTG CTTGTATGTT TTCTTTTGAG AAGTGTCTGT TCGTGTCCTT
42701  TGCCCATTTT TAGTAGAATT ATTTGTTTTT TGCTTGTTGA TTTGTTTAAA
42751  TTTTGCTTGT GGATTCGGGG TATCAGACAT TTTTTGAATG CATAGTTTGC
42801  AAATATTTTC TCCCATTCTG TAAGCTATCT GTTTAGACTA TTGAGATTTG
42851  CTGTGCAGAG GCTCTTTAGT TTAATTAGGT CCCACTTGTC AATTTTTGTT
42901  TTTGTTCAA TTGCTTTTGG AGACTTAGCC ATTAATTCTT TGTCAAAGTT
42951  AATGTTGGGA AGGGTATTTC CTAAGCTTTC TTCTAGAATT ATTATAACTT
43001  AAAGTCTTAC ATTTAACTCT TTAATCCAAC TTGAGTTAAT TTTTGTATAT
43051  GGTGAAAAGT AGGTATCCAG TTTCATTATT TTGCATATGG CTTGACAGTT
43101  ATCCAGCAC CATTTATTTA ATAGGGAGTC CTTTCTGTAT TAGTTATTCT
43151  TGGTGACTTT GTTGAAGAGC AGACTGTTGT AGGTGTTTGA CTTTATTTCT
43201  GGATTCTCTA TTCTATTCCA TTAGTGTGTG TGTCTGTTTT TTGTACCAGT
43251  ACAATGCTGT TTGGGTTAAT GTAGCCATAG AGTACAGTTT GAAGTCAGGT
43301  AATATGATGC CTCTGACTTT GTTCTTTTTG CTTAGAATTG CTTTGGCTAT
43351  TTGGGCTCTT TTTTGATTCC ATATTAATTT TAGAATAGTT TTTCTAATTC
```

FIGURE 3N

```
43401  TGTGAAAAAC AACATTGGTG TTTTGATAGA GATCGGTATT GAATTCTGTA
43451  AATTGCTTTG GGCAGTATGG CCATTTTAAT GATATTGATT CTTCCTATTC
43501  ATGAGTGTGG AACATTTTTA CATTGTTTG  TGTTGTCTCT GATTTCTTTC
43551  AGCAGTGTTT TGTAGTTCTC CTTGTAGAAA TCTTTCACCT CTTTGGTTAG
43601  ATGTATTACA TTTTTTTGTG TGCCTATTGT AAATGGGATT GAGTTTTTGA
43651  CTTGGCTCTC TGATACAATG TTATTGCTGT ACAGAAATAC TATTGACTTT
43701  TGTACATTGA TTTTGTCTCC TGAAACTCTA CTGAAATTGT CAATTCTAGT
43751  TGCCTTTTGG TGGAGTCTTT AGGGTTTTCT ATTTCTAAAA TTATAATCAT
43801  CAGCAAAGGA GAGATAGTTT GACTTCCTCT CTTCCTATTT GAATGCCTTT
43851  TATTTCTTTC TCTTGCCTGA TTGCTCTGGC TAGGTCTTCC TTATACTATG
43901  TTAAATAGGA GTGGTAAGAG TAGGCATCAC TTTCTTGTTC TGGTTCTCCA
43951  GGGGAATAGT TATAGCTTTT GCCCATTCAG TATGATTTTA GCTGTGTGTT
44001  TTTCATAGAT GGCTCTTATT GTTTGAGGT  ATGTTTCTTC AATGACTAGC
44051  CTGTTGAGGG TATTTTATCA TGAAGGGATT TGGGATTCTC TTGAAGGCCT
44101  TTTCTGTATC TATCGAGATA ACCATATGGT TTTGATTTTG ATTCTGTTTA
44151  TGCGATGAAT CATATCTAGT GAATTGTGTA TGTCGAACCA ACCTTGCATT
44201  CCAGGAATGA AGCCCACTTT TCTCATAGTG AATTAGATTT TGATGTGCTG
44251  CTGAATTCAG TTTGCTAGTA TTTTGTTGAG GATTTTGTGT CTATGTTCAT
44301  CAGGGAGTTT AGCCTGAAGT TTTCTGTTTT TGTGTCTCTG CCAGATTTTG
44351  GTATAAGGAT GATGATGACT TTGTATAATA TGTTAGTGAG AAGCCTCCCC
44401  TCATCCTCAA TTTTTTGGAA GACTTTTAGT AGGATTGGTA CCAGTTCTTC
44451  TTTGTAACTC TAGTAGAATT CAGCTGTGAA TCCGCCTGGT TCAGGGCTTT
44501  TTTTGGTTGG TAGGTTTTTT TAAAATTACC GATTCAATTT CAGAACTTGT
44551  TATTGGCTTA TTCATGTTTT CACATTATCC CTTGTCAAC  CTTGGATGGT
44601  TTTGTGTTTC TGAGAACTTA TCCATTTCCT CTAGATTTTC TAATTTGTTT
44651  GCACAGAGGT GTTCATAATA GTCTCTGAAT ATCTTTTGTA TTTCTGTGGG
44701  ATTGGGTGTA ATGTCATTTG TCATTTTTGA TTGTGCTTAT TTGGGTCTTC
44751  TCTTTTTTG  TTAATCTAAC TAGTAGTCTA TCAATCTTAT TTATTCTTTC
44801  AAAAAACAAA CTCTGTTTCA TTTATCTTTG TATGGACTTT TGCATCTCAA
44851  TTTCTTTCAG TTGTTCTCTG ATTTTAGTAA TCTCTTTTCT TCTGCTAGCT
44901  TTTAAAGCCA TACTTATGTT GGGGTTCCTC CATTTTTCCA TTTTCTCCTT
44951  GCCTCCACAA GCAGATATAC TCTGCTGGAA ATCATCATTC AACAAGGCAG
45001  ATTGTAACCA TTATGAAGTT ATGACTCAAG GAGACCTTCA ACATCTCCTC
45051  CTAATTTCAT TGTGTATCTT TTTTGACATT TGAAATAATT ATTTTTCAAC
45101  TTTCTTCGCC TTCTTCATCA TTCTCCAACA TCCTCTCTTT TCACCATTAC
45151  TTGATAGTAA TCTTGCTTTG TACTTCAGAG GGAAAATATA TCATCAGAAA
45201  GAACTCACTT TACTTTCTTC CTGTTAAAAA GTTATAGCTG AAACCTTTCT
45251  TCCTATTAAA CGGTTAAAAC TGCAAGAAAA TAAGGAAGTT TTCTTTTCCT
45301  TTATGTTTAT TTTCTATTCC CTCTCACCAC TCTGGAAACT TATGCCATTT
45351  CTAATTTAAT TGACCTCTTC CTCTTGAAAT GAATTTTTCT TATCATCTTT
45401  GAAACATGAT AGAGTCTCCA CCATTTTAAG CAGTTCTCCA ACCTCCTGCA
45451  AACCCACCTT TAGTCATTCA GATATGTAAG TTAACTGCAT ATAAATGTTC
45501  TGGGTAGCAA TTTTACTTTT AAATATCTCT CCATATTGCT TTATTTGGTT
45551  TATTCAATAT CTGGCTTCAG TAACTATTGC AGATAAGTCT ATAGTCTCTC
45601  TATTTTTATT TTTTAGGTTT ATGTATTTTA ATCCTGAATG TTTATAGACA
45651  TTTTTCTGTG TCCCTTAATG AAGAAAATTG CTAAGATTGA CCTAATGGTA
45701  GGTGTATTAA AAAACTTTTC CATCCCGCAT ACACGAATAG TTTTCCACCT
45751  AGGGAACATT TTCCTATTAT GTTTCATTCT GTTCCATTTA CTTTGATCTC
45801  TTTGTGAAGA CTTTCTTTGC TCATATCCCT CTACTTTCTT CAAACATTTT
45851  AACTACATAT ATCTTTCATT TTTTTTTAAC TTTGAATTTG GGGGTACATG
45901  TGCAGGTTTG TTACATGAGT ATGTTGTATG ATGCTGAGGT TTGGGGTACA
45951  GATGGTCCTA TCACGCAGGT AGTGAGCACA GAGTATAGTC AATTTTACAA
46001  CCCTTGTTCC CTACCCTCCT TCCCAGCTCC GGTGATTCCA AGTGCCTATT
46051  GTTCCCATCT TTATGTCCAT GAGTACCCAA TGTTTATCTC CCATTTATGA
46101  GTAACAACAT GCAGTATTTG GTTTTCTGTT CCTGAGTTAA TTTGCTTAGA
46151  GTAATGGCCT CCAGCTGCAT TCATGTTACT GCAAAGGAT  ATGATGTCAT
46201  TCTTTTTATG GCTGCACAGT ATTCCATGGT GTATATGTAC CACATTTTCT
46251  TTATCCACCT CACCCTAATG GTACCTAGTT GATTCCATGT CTTTGCTATG
46301  GTGAATAGCA CTAAGATGAA CATGCACGTA TATGTCAGAT TTCTGATTTC
46351  TGCTCTGTAT CCTTTTCCTC TGTAGTTTAA TGTTAGTCTT TTATATTACC
46401  ATTTGATTAT CTGCAGAATA AATTCTGCAT TTCCTACTT  TTATTATGAG
46451  TTTTGGTTTT GCTGTTGCAT TTTTAGTTTT CATTAATTTC TTTCTTATTT
```

FIGURE 3O

```
46501  CATCCTATTT TCTTTACATT TTAGCCTGTC CTTTCCTGAA TACTTTTTAT
46551  TTTTTTCTGG TTGGTAGAGT GTATCCCCAG TGATTTCTGG ACGTTTTCAT
46601  TTTATCCTAA AGTAGACAAT TTTCAGAGCT ATGCTTTTCC TTTGGACTGT
46651  CAGATTATTT TTACTCTCCA TTGATTTTTA GTATTTTTA TGGACTCCTA
46701  GGTTTTTTCC TTTTTTTCTC ATTTTTAAAC AAGGAAAGGT AGATTCCTAC
46751  TATATCTACC TAGCTATATC TTAAGATTGC TTAATGAGGC TGCTGTCAGT
46801  ATGCTCCATG TTTCCAACAG TATGTATAAT AAGCATCACA CTTATCCAAA
46851  TGCCCTGTAC TTCTGCCAGG GGCAGCATAG TTGTTGGTGG CAGAGTATGT
46901  AAAGAAAAGT ACTCTAGGTA TCCTGCACCA CCATGATAAA GAAGGATGGT
46951  TGTCCATAAG AATGGGCAGA TGGGCTGAGA GTGTAGGATA TACTAAGTAT
47001  CTTCTGCATT TTCAGATGTT GTCTCTTTCA TGAAGGAACG TCTTAGAGTG
47051  TAAAAAAATG ACAATTTGGC ATATTTTTCT CATTCAAGTT CCATCTGCTT
47101  ATAGTTAGCA GAGATGCCCT CTTAGACTGC AGGAATGGAT TATCTGTAGG
47151  GCTATGCGCT AATGATGAGT TTTCATCATT TTCTAGTATT TGAGAAAATA
47201  TATTTATATC ATCTTACAAG TATTTCATGA GCAAATAAAA ATAAGCTGTA
47251  TTTATCATTT GTTTGTTCCC TGTGCCTCTT CTTTATTTTT CCCTAACTGG
47301  AGGCATTATG CCAGTTTTTC TAGAACAGTG GTTCTCAATA ATGACTGCAT
47351  TTGAGAATTC TAAAACCGTG CTAATGCTCA ACCCGTACAC CAACCAGAAT
47401  CTCTGTGCCT GGGGCCTAAG CATGAGTATT TTTTGAAAAG TACCCCCAGG
47451  TGATTCTTCT GTGGAGCTGT TGATAGCTCC ACAGAAGGTT GATATCCACT
47501  GTTCTGGAAA CTTTGCTATT TAAATTTAGT TCATCAGGGG TCTAATATCC
47551  AGAATCTATA AGGAACTTAA ACAACTCAAC AAGCAAAAAT CAACGTGATT
47601  AAAAAGTGGG TAAAGACATG AACAGACACT TCTTAAAAGA AGACATATAA
47651  GCAGCCAATA AACATATGAA GAAATGCTCA ATATCACGAA TCATCAGAGA
47701  AATGCAAACC AAAACCACAA TGAGATACTA TCTCACACCA GTCAAAATGG
47751  TGATTATCAA AAACTTAAAA AATAACAGAT TCTGACAAAG CTGCAGAGAA
47801  AAGGGTATGC TTACACACTG TTGGTGGGAA TATAAATTGG TTCAGCCACT
47851  GTGGAAAGCA GTTTGGAGAT TTCTCGAAGA ACTTAAAACA GAACAACTAT
47901  TGACCCAGCA ATGTCATTAC TGGGCATATA CCCAAAGGCA AATGAATCAT
47951  TCTATCAAAA GGCACATGGA CACGACTGTT AATCACAGTG CTATTCACCA
48001  TGGCAAAGAC ATGGAATCAA CCTAGGTGCT CATCAACAGT GGATTGAATA
48051  AAGAAAATAT ACTCCATGGC ATACATTGCA GCCCTAAAAA AGAGCAAAAT
48101  CATGTTCTTT GCAGCAACAT GTATACAACT GGAGGTCATT ATCCTAAGTG
48151  AATTAATGCA GGAACAGAAA ACCAAATACC ACATGTTCTC ACTTATAAGT
48201  GGGAGCTAAA CATTGGGTAG TTGTGAACAT AACGATGGCA ACAATAGACA
48251  CTGGAAACCA CCAGAGAGGA GAGGGAGGGT GGGGAACTAG GGTTAAAAAA
48301  GTAACTATTG GGTACTATAC TGCCCACTAC TTGGGGGACA GGATCAGTCA
48351  TACCCCAAAC CTCAGCATCA TTCAATATGC CCATATAACA AGCCTGCACA
48401  TGTACTCCCT GAATCTAAAA TAAAAGTAGA AATTATTTTT AAAACTTACC
48451  AAACGTAAAG AAAGAAACCT GTACTGCTAG CTTTTAAAAG TTATTTAATA
48501  AATAAACCTA TTTTATAACA AAAATAGTAA AAATAAATTT CTACTTCAAA
48551  GTATAAAGCC AACAATATTA GCATTAAATT TAAACTTGCC AGAAATGCAG
48601  AATCTCAGGC CCCATCCAGA CCTCTTGAGT CAGGACCTGT ACATTAAAAA
48651  TATATTTAGG TAACTGGTAT GGTTTGGCTC TGTGTCCCCA CCAAAATCTC
48701  ATCTCCATTT ATAATCCCCA TGTGTTGAGG GAGGGACCTG TAATCCCCAT
48751  GTGTCCAAGG AGGGAGGTGA TTGGATTTTG GGGCGGTTT CCCTCATGCT
48801  GTTCTCGTGA TGGTGAGTGA TTTCTCATGA GATCTGAAGG ATTTATAAGG
48851  CAGTGTTCCC AGCTCTTTGC TCGCTCGCTC TTCTGCCGCC TTGTGAAGAA
48901  AGTGCCTACT TCTCCTTCCG CCATGATTGT AAGTTTCCTG AGGCCTCTCC
48951  AGGCATATGG AGCTGTGAGA CAATTAAACT TCTTTCCTTT ATAAATTACC
49001  CAGCCTCAGG GAAGCTCTTT ATCACAGTGG TGAAACAGAC TAATAACAGT
49051  AACGTATATG AATCTTAAAA TTTGACGCCA AGCGATGCTC TAGAACATTG
49101  CTTATCAAAC CCTTCTGGCA CATTGGGAAT CACTTGAGAA GCTTTAAAAA
49151  AATTATTGAT GCTAGGCTTC AACCTCGAAG GATTTTATT TAATTAATCT
49201  TGGGTGTTTC CCTAGGCACT GGTATTTTA AAAAGTACCC CAAATTATTT
49251  AATAACCACT TAAATAATTG ACCAAGAATC AGATTCTGAG AAGCTTCTGC
49301  CTCTCAATTT GGTGAAACTT GGAAATAAGT CGGGTGGCCC AGATTCTCCC
49351  TCTTATTTTT TGCCACTATT TTTGGATGCC ACCTACCTTT TTCCTTCTTC
49401  AATCATCTGA GTATCTTCAG TGACATTTAG ACCTAAATGT GGTTTATCAG
49451  TGACAAATGT TTGGCACTTG GTGGTTTCTA AGCAATGGAA TTTTCTAGAT
49501  TTCACTTTTT TCAGTTTCTC TAGTACTAAT CTTCTGCCTT CATCCTTATT
49551  CCACACTCAG TTTATTTGCT ATAATAAGTA CTCAGTCACA CACAGAGACT
```

FIGURE 3P

```
49601  TCAACCAAAC CCTAAACACC ATCCTATCTG ATTTGGGTTT TGATATTCTG
49651  CATAGTGAGA ATATATGACA TTTCCATGCT GAAGGCATTA AAGAAAATTT
49701  CTGCCTACTT AAGAAATAGT TATTTTACGT GGAAGCATTC CAAAGAAAAT
49751  ATTTTGAAGA TATTTCTGCA GGTGCCTCAA AATTCTTTGG AATTCAACTT
49801  CCGAAGAAGT ATAGGATAGA GGAGAATTTA AGAGAGTATC AGGTCTCTCT
49851  GCTATGAAGC TAGATATATG TTGTTAATTG CAGTATGAAT CTGTGAAATC
49901  ATGGAATCAT TAGGGCCCAA ATTATGAAGC AAGCATCAAT TTAACAAAAC
49951  GATTTTTGGA AAAACGTTTG AATTTGGGCA CTCTTTTTTT TATTATTATA
50001  CTTTAAGTTT TAGGGTACAT GTGGACAACG TGCAGGTTTC TTACATACGT
50051  ATACATGTGC CATGTGTGGT GTGCTGCACC CATTAACTCG TCATTTAGCA
50101  TTAGGTATAT CTCCCAATGC TATCCTTCCC CCCCTCCCCC CACCCCACAA
50151  CAGTCCCCAG TGTGTGATGT TCCCCTTCCC TGTGTCCATG TGTTCTCATT
50201  GTTCAATTCC CACCTGTGAG TGACAACATG CGGTGTTTGG TTTTTTGTCC
50251  TTGCAATAGT TTGCTGAGAA TGATGGTTTC CAGCTTCATC CATGTCCCTA
50301  CAAAGGACAT GAACTCATCA TTTTTTATGG CTGCATAGTA TTCCATGGTG
50351  TATATGTGCC ACATTTTCTT AATCCAGTCT ATCATTGTTG GACATTTGGG
50401  TTGGTTCCAA GTCTTTGCTA TTCTGAATAG TGCCGCAATA AACATACATG
50451  TGCATGTGTC TTTATGGCAG CATGATTTAT AGTCCTTTGG GTATATACCC
50501  AGTAATGGGA TTGTTGGGTC AAATGGTATT TCTAGTTCTA GATCCCTGAG
50551  GAATCGCCAC ACTGACTTTC ACAATGATTG AACTAGTTTA CAGTCCCACC
50601  AACAGTGTAA AAGTGTTCCT ATTTCTCCAC ATCCTCTCCA GCACCTGTTG
50651  TTTCCTGACT TTTTAATGAT TGCCATTCTA AGTGGTATGA GATGGTATCT
50701  CATTGTGGTT TTGATTTGCA TTTCTCTGAT GGCCAGTGAT GATGAGCATT
50751  TTTTCATGTG CCTGTTGGCT GCATAAATGT CTTCTTTTGA GAAGTGTCTG
50801  TTCATATCCT TTGCCCACTT TTTGATGGGA CTGTTGTTT TTTTCTTGTA
50851  AATTTGTTTA AGTTCATTGT AGATTCTGGA TATTAGCCCT TTGTCAGATG
50901  AGTAGGTTGC GAAAATTTTC TCCCATTTTG TAGGTTGCCT GTTCACTCTG
50951  ATGGTAGTTT CTTTGCTGT GCAGAAGCTC TTTAGTTTAA TTAGATCCCA
51001  TTTGTCAATT TTGGCTTTTT GTTGCCATTG CTTTTGGTGT TTTAGACATG
51051  AAGTCCTTGC CCATGCCTAT GTCCTGAATG GTATTGCCTA GGTTTTCTTC
51101  TAGGGTTTTT ATGGTTTTAG GTCTAACATT TAAGTCTTTA ATCCATCTTG
51151  AATTAATTTT TGTATAAGGT GTAAGGAAGG GATCCAGTTT CAGCTTTCTA
51201  CATATGGCTA GCCAGTTTTC CCAGCACCAT TTATTAAATA GGGAATCCTT
51251  TCCCCATTGC TTGTTTTTCT CAGGTTTGTC AAAGATCAGA TAGTTGTAGA
51301  TATGCAGTGT TATTTCTGAG GGCTCTGTTC TGTTCCATTG ATCTATATCT
51351  CTGTTTTGGT ACCAGTACCA TGCTGTTTTG GTTACTGTAG CCTTGTAGTA
51401  TAGTTTGAAG TCAGGTAGCG TGATGCCTCC AGCTTTGTTC TTTTGGCTTA
51451  GGATTGACTT GGTGATGTGG GTTCTTTTTT GGTTCCATAT GAACTTTAAA
51501  GTAGTTTTTT TCCAATTCTG TGAAGAAAGT CATTGGTAGC TTGATGGGGA
51551  TGGCATTGAA TCTATAAATT ACCTTGTATC TCCCACTGTT ATTGTGTGGG
51601  AGTCTAAGTC TCTTCATAGG TCTCCAAGAA TGTGTTTTAT GAATCTGGGT
51651  GCTCCTGTAT TGGGAGCATA TAATTAGG ACAGTTAGCT CCTCTTGTTG
51701  AATTGAACCC TTTACCATTA TATAATGCCC TTCTTTGTCT TTTTCGATCT
51751  TTGTTGGGTT AAAGTCTCTT TTGTCAGAAA CTAGGATTTC AACTCCTGCT
51801  TTTTTCTGCT TTCCATTTGC TTGGAAAATT TTCTCCCTCC CTTTATTTGA
51851  GCCTATCTGT ATCTTGGCAT GTGAGATGGA TTTCTTGAAT ACAGCACGCC
51901  AATGAGTCTT GACTCTTTTT TTTTTTCTTT TTTTTCTTGA TGCAGAGTCT
51951  TGCTCTGTCA CCCAGGCTGG AGTACAGTGG CATGATCTTG GTCACTGCAA
52001  CCTCTGCCCC CAGGTTCAAG TAATTCTCCT GCCTCAGCCT CCCAAGTAGC
52051  TGGGATTACA GGCATGTGAC ACCACGCCCA GCTAATTTTT GTAGTTTTAG
52101  CAGAGATGGG GTTTCACCAT GTTGATCAGG CTGGTCTTGA ACTCCTGTCC
52151  TCAGGTGATC CACCCACCTC GGCCTCCCCA AAAGTGCTTG GATTACAGGC
52201  ATGAGCCAGG GCCTTGACTC TTTATCCAGC TTACCATTCT GTGTCTTTTG
52251  ATTTGGGCAT TTAGCCCATT TAATTGAAGA ATAATATCTT TATGTGTGAA
52301  TTTGATCCTG TCATCATGAT GCTAGCTAGT TATTTTGTAG ATTTGTTAGT
52351  GTAGTTGCTT CATAGAGTCA TTGGTCTGTG TACTTCAGTG TGTTTTTGTA
52401  GTGGCTGCTA ATGATTTTCC CTTTCATATT TAGTGCTTTT CTCAGGAGCT
52451  CTTACAAGGC AGGCAGGCCA GGTGGTGACA AATTCCCTCA GTATTTGCGT
52501  GTCTGAAAAG GGTTCTATTT CTCCTTCACT TATGAAGCGT GGTTTAGCCA
52551  GATATGAAAT TTGGGTTAG AAATTCTTTT CTTTAAGACT GTTGAATATT
52601  GGCCCCCAGT CTCTGCTGGC TTATAGGGTT TCCACTGAGA TGTTTGCTGT
52651  TAGTCTGATG GACTTCCCTT TGTAGGTGAC CTGGCTTTTC TCTCTGCGCT
```

FIGURE 3Q

```
52701  GCCCTTAACA TTTTTTCCTT CATTTCTACC TGGAGAATCT GATGACTATA
52751  NNNNNNNNNN NNNNNNNNNN NNNNNNNNNN NNNNNNNNNN NNNNNNNNNN
52801  CTAAATTATT ACATTCAATG AAATGTAATA ATTGACAAAA TTTTATTTTA
52851  TTTTATTATT ATTATACTTC TAGGGCACAT GTGCACAGCA TGCGGGTTTG
52901  TTACTTATGT ATACATGTGC CATGTTGGTG TGCTGCACCC ATTAACTGGT
52951  CATTTACATT AGGTATATCT CCTAATGCTA TCCCTCCCCC CTACCCCCAC
53001  CCCATGACAG GCCCCAGTGT GTGATGTTCC CCTTCCTGTG TCCAAGTGTT
53051  CTCACATTGT TCAGTTCCCA CCTATGAGTG AGAACATGTG GTGTTTGGTT
53101  TTTTGTCCTT GCGATAGTTT GCTGAGAATG ATGGTTTCCA GCTTCATCCA
53151  TGTCCCTACA AAGGATATGA ACTCATCCTT TTTATGGCTG CATAGTATTC
53201  CATGGTATAT ATGTGCCACA TTTTCTTAAT CCAGTGTATC ATTGATGGAC
53251  ATTTGGGTTG GTTCCAAGTC TTTTTTTTTT TTCATTGTTA TTTTTTCCAG
53301  ACTTTTTTTT TTTTATTATA GGTTCCAAGT CTTTGCTATT GTGAATAGTG
53351  CCGCAATAAA CATATGTGTG CATGTGTCTT CATAGCAGCA TGATTTATAA
53401  TCCTTTGGGT ATATACCCAG TAATGGGATT GCTGGGTCAA ACGGTATTTC
53451  TAGTTCTAGA TCCCTGAGGA ATCGCCACAC TGACTTTCAC AATGATTGAA
53501  CTAGTTTACA GTCCCACCAA CAGTGTAAAA GTGTTCCTAT TTCTCCACAT
53551  CCTCTCCAGC ACCTGTTGTT TCCTGACTTT TTAATGATTG CCATTCTAAG
53601  TGGTATGAGA TGGTATCTCA TTGTGGTTTT GATTTGCATT TCTCTGATGG
53651  CCAGTGATGA TGAGCATTTT TTCATGTGCC TGTTGGCTGC ATAAATGTCT
53701  TCTTTTGAGA AGTGTCTGTT CATATCCTTT GCCCACTTTT TGATGGGACT
53751  GTTTGTTTTT TCTTGTAAA TTTGTTTAAG TTCATTGTAG ATTCTGGCTA
53801  TCAGCTCTTT GTCAGATGAG TAGGTTGCGA AAATTTTCTC CCATTTGTA
53851  GGTTGCCTGT TCACTTTGAT GGTGATTTCT TTTGCTGTGC AGAAGCTCTT
53901  TAGTTTAATT AGATCCCATT TGTCAATTTT GGCTTTTGTT GCCATTGCTT
53951  TTGGTGTTTT AGACATGAAG TCCTTGCCCA TGCCTATGTC CTGAATGGTA
54001  TTGCCTAGGT TTTCTTCTAG GGTTTTTATG GTTTAGTCT AACATGTAAG
54051  TCTTTAATCC ATCTTGAATT AATTTTTGTA TATGGTGTAA GGAAGGGATC
54101  CAGTTCAGC TTTCTACCTA TGGCTAGCCA GTTTTCCCAG CACCATTTAT
54151  TAAATAGGGA ATTCTTTCCC CATTGCTTGT TTTTGTCAGG TTTGTCAAAG
54201  ATCAGATAGT TGTAGATATG CGGCATTATT TCTGAGGGCT CTGTTCTGTT
54251  CCATTGATCT ATATCTCTGT TTTGGTACCA GTACCATGCT GTTTTGGTTA
54301  CTGTAGCCTT GTAGTATAGT TTGAAGTCAG GTAGCGTGAT GCCTCCAGCT
54351  TTGTTCTTTT GGCTTAGGAT TGACTTGGTG ATGTGGGTTC TTTTTTGGTT
54401  CCATATGAAC TTTAAAGCAG TTTTTTCCAA TTCTGTGAAG AAAGTCATTG
54451  GTAGCTTGAT GGGGATGGTA TTGAATCTAT AAATTACCTT GGGCAATATG
54501  GCCATTTTCA TGATATTGAT TCTTCCTACC CATGAGCATG GAATGTTCTT
54551  CCATTTGTTT GTATCCTCTT TTATTTCATT GAGCAGTGGT TTGTAGTTCT
54601  CCTTGGACGA GGTCCTTCGC ATCCCTTTTA AGTTGGAGTT CTAGGTATTT
54651  TATTCTCTTT GAAGCAATTG TGAATGGGAG TTCATTCATG ATTTGGCTCT
54701  CTGTTTGTCT GTTATTGGTG TATAAGAATG CTTATGATTT TTCCACATTG
54751  ATTTTGTAT CCTGAGACTT GTTGTAGTTG CTTATCAGCT TAAGGAGATT
54801  TTGGGCTGAG ATGATGGGGT TTTCTAGTAT ATACAATCAT GTCATCTGCA
54851  AACAGGGGAC AATGTGACTT CTTTTCCTAA TTGAATGCCC TTTATTTCCT
54901  TCTCCTGCCT GATTGCTCTG GCCAGAACTT CCAACACTAT GTTGAATAGG
54951  AGTGGTGAGA GAGGGCATCC CTGTCTTGTG CCAGTTTTCA AAGGGAATGC
55001  TTCCAGTTTT TGTCCATTCA GTATGATATT GGCTGTGGGT TTGTCATAGA
55051  TAGCTCTTAT TATTTTGAGA TACATCCCAT CAATACCTAA TTTATTGAGA
55101  GTTTTTAGCA TGAAAGGTTG TTGAATTTTG TCAAAGGCCT TTTCTGCATC
55151  TGTTGAAATA ATCATGTGGT TTTTGTCTTT GGTTCTGTTT ATATACTGGA
55201  TTACATTTAT CGATTTGCAT ATGTTGAACC AGCCTTGCAT CCCAGGGATG
55251  AAGGCCACTT GATCATGGTG GATAAGTTTT TGATGTGTTG CTGTATTCAG
55301  TTTGCCAGTA TTTTATTGAG GATTTTGCA TCAATATTCA TCAAGGATAT
55351  TGGTCTAAAA TTCTCTTTTT TTGTTGTGTC TCTGCCAGGG TTTGGTATCA
55401  GGATGATGCT GGCCTCATAA AATGAGTTAG GGAGGATTCC TTCTTTTTCT
55451  ATCGATTGGA ATTTGGGCAC TCTTAAAAG TTTTATTACT CCAACGTATA
55501  AGCAACATCA GCAGAATCCT ACTTTATTAT GAGACCCAAT CATAGAATAC
55551  AGTGTTGTTA AAACATCCTA GTTGCATTAG TGTTGCATTC AGGTAAAAGA
55601  ATAGGCCTTT AATATAGACG GAAGAGTTTA TGCTTACATC ATAGGAAAAC
55651  AATGACTGGT TCAAGCCTAC CATATGTCAT GGTTGGGCTG TGATTCCTAG
55701  GTGAGTCTAA AGAGGAACTG GCTTTTGGTC TGTGTGGTAG TGGTGGTGGT
55751  GATGTTTTGC TCATACAAAA AACTTTTAAT GCCCACAAAT AAGTTCAACC
```

FIGURE 3R

```
55801  TACTTTGGCT ACTGTACTTA ATAAATATAA TAAATATATT AATTTGTTTA
55851  GATGAATGTG ATGATGATTA ATTAATTCTC CTTCCTATTG CAATCAACTC
55901  CCCAGTAACA AAGCTGCTAA AATTTCACTT TTTTTTTTTG AGACAGAGTC
55951  TCACTCTGTT GGCCAGGCTG CAGTGCTGTA GCACAGTCTT GGCTCACTGC
56001  AACCTCTGCC TCCCTGGTTC AAGCGATTCT CCTGCCTCAG CCTCCTGAGT
56051  AGCTGGGATT ACAGGCACCT GCCACCACAG CCAGCTAATT TTTTGTATTT
56101  TTAGTAGAGA CGGGGTTTCA CCATGTTGGC CAAGCTGGTC TCGAACTCCT
56151  GACCTCGTGA TCCACCCGCA CCAGCCTCCC AAAGTGCTGG GATTACAGGA
56201  ATGAGCCACC GCATCCAGCC CACATTTGTT ATTTTTAATG TCATCTTCTA
56251  TTCTCTTTGT ATAATTTGAA ACTATATTTT CAACTGGGAA CATGGATGAG
56301  CTGCTTTAAA TTGGTAAGTT TGAAGCATAA GCTTGAAGTC AGTGAAAATA
56351  TGAAAGATGA TGAGGGAAAT TTGTAACACT TCAACGTTTA TTTTTTTCCT
56401  CAACCTCCCT GAAAAGAATC TAATAGAAAA GATGATAGGA TTATGCCAAT
56451  TACAATTAGC TAATGTATAA GAAGTAGAAA TAAATCTAAA AGATACAGAC
56501  TATTAAACAC ATGTTTAAAA TATGGTACAC AAAGATACTG AATAAATTAA
56551  CACAGTCCTG GAATTATAAT AGGATTTTGT CAGTCTTAGG TGGTAAATTG
56601  TGCACACTCT TTAGGAGAAA TGAAGCAAAT ATAGAAAACA TGACCTCAAA
56651  GAGCAATTTT TTGATGGACA GTGGCTTCCT GTTCCTATTT TAATGACCAA
56701  TTAGGTGCTA TATGAGAATA TCAAGGTGTT TTTACAAATG TATTTTATTG
56751  TAAAGTATAA GACAAGCATT CACAAGTGTT AAAGCATAGA AACATACATA
56801  TAAAACCCAA TGAATTATCA CACCAGAACA TCTGTGTAAT ACCACCTTGG
56851  CTGGCACTCT AGAAACTCAC TTTGTGCTCA TTACCAGTCA TTAGGTTTTC
56901  CATCCTCCTC AAAAGAATCT CTGGCCTTTC TTTTTACAAT GGGTATTTTG
56951  CTTGTTTTTG AACGTTATAT CTGAATGAAATC ATATAAGAGG AATTAATTGC
57001  TCAGTGTTCT GTTTATGGAA TTCACCAATG TTTTTGATGT AGCTTCAGCC
57051  TATTCATTTT CATTATTGTA TAGTATGTTA ATGTGCTTCT ATATGCACGG
57101  TATGTATGCA TTCTACTATT GATGGTCATT TGGATCATAT GCAATTAGAA
57151  GCTACTACAA GTAATAATGC TGTGAACATT TTTCTATATG TCTTTTGGTA
57201  TACATATGCA TTTCTCATAC CGATGAATGA AATTATCAAT TGCTGAGTCA
57251  TAGGACATGC ATATTTTCAG TTTTGGTAGA TAATGCCAAA TAGATTTCCA
57301  AAATTGGGGT ACATATTTAC ATTCCCACCA ATAAAGTGTG AGAACTTATG
57351  TTTTTTTTGCA TCCTTACTAA CACTTGGTAA TTCCATTCTT TTAACATTAG
57401  CCATTCTCTT AAGGTATGTA ATTATATCTT ATTGTTTTAA TTTATATTTC
57451  TTGATTACCA ATGAAATTGA GTAACTTTGC ATATGCCTTT GGCCATTTGG
57501  ATATTCTCTT CTAGGAAGTG CCTACCAAAG TCATATTTTT AATGAGCTTT
57551  TATTGATTTG TAGAAGTTCT TTACATGTTA TGGAAATAAG TCCTTTGTTA
57601  GTTTTATGTG TTTTAAATAT CTTCTCACTA TTGTGGGTTC TGATTTCACT
57651  CTCATAATGG TATTTTTTTG ATGTGGCTAC AGATTCCAGC AGAGTCTGCT
57701  AAGAGGCTGA TACCTTTATT CTTTAGGCAA ATTTTTCTAT GTTATTTATT
57751  TCCATTATAT GTTTTAGTAT ATATAGAAGC AGACCCATAT CTTGATCTTC
57801  CATAATCTTG GCTGAAGTTT GTATTTCACT GCTCTATGGT TTCAGTGGCT
57851  ATCATAAAAA TAAACATCCA TCAACACAGG AGAAATATTC TATTAACTTA
57901  GACAATTCTG CCAGGTGCTG TAGCTCACAC CTATAAACCC AGTTACTTAG
57951  AAGGCTGAGG TGAGAGAATT GCTTGAGCCC AGGAGTTCAG GGTTACAGTG
58001  ATCATGCCAT TGCACTCCAG ACTGTGTGAC AGAACAAGAC AGCATCTCTA
58051  ATAAAAATAA CAATTTTTAA CAGGAAGATT TTTTCTGATT TTGATAGTAC
58101  TGCAATTTAC ATGAAATATG TAATACTATT TTAAGGTGTC TATTTTTAAT
58151  AGACATGAAA AATGGGTGTT GAATTACACA TTTGGAAAAT TTACTGTATT
58201  GAAACATAAT CTTAATCCCT TTTTAAGATC TTAAAAATAT GTTAGTAGGA
58251  TGGTTATGAA AAATCTTTTG TGAAAATAAC CTAATACCTA TAAAATCATT
58301  TCTATTTTAA AGAATGAAGG CCTGATACAG GAACCATAC GTTATCTTGA
58351  ATCAAAATAA AATATTTCTT GTCGCTGAAT AGATGACCCT ATTTCAATAA
58401  ATTATTATTT TCTTTACCAT TGCTGCTATC ATTGTGTTTT AGGGAAGCCT
58451  TTTGAATACC TGACACCCTA TCTCACACTT TCAAATACTC CTTATTCATA
58501  ACTGTGAGGG TGTTATAACC ACATGTTTAC TTACAAATAG TATTTTAAAG
58551  GTGTGTAGTG AGTAAGCCTC ATGCTTTATA AAAGGAAACA CTAATAAGCC
58601  TTAAAATTAA CACTCATGTA CATAGCAATT GAGATTTGGG GGTTGGATGC
58651  ATGGTATTAT AGACATCCAG ATTACTGATG AAGAGTGAAC TGAAATAAGT
58701  CTTTGGAAAC AGTGATGAGA GAAATGTTT CAGAGACATG GGGACCCTAA
58751  TACCAATGTG GAAGCATGGC TGCTATGAGA TGTGACCTCT GAGAAGTGAT
58801  TGGGTAGTCA GAACTGGTTG TCATGCAACA CAAAATGACT ATGTCTGCTC
58851  ACACTGGGTC AGTCTAATGG GAATATTTAA TTGATTTCTT AGTGTAACTC
```

FIGURE 3S

```
58901 TAGAATCACA AATTGTGCTT TTTTTTAAAT GGCTATTCAA AGTACTGATA
58951 TTTTTTCTAG ACCAACTAGT CTGAGAGATA ACAGGCTAAT TAAAAATGCA
59001 GTTGACCCTT GAACAATATG GGTTTGAACT GTGCAGGTCC ACTTACACAT
59051 AGACTTTTAC ATTTATATGT ATATTATGTA GTTTTTGTAT ATTATGTATT
59101 TTTATATTAA AAATGTATGG GCCAGGCGCA GTGGCTCATG CCTGTAATCC
59151 CAGCCTTTTG GGAGGCCTAG AAACACAGAT CACTTGAGGC CAGGAGTTGG
59201 AGACCATCAT GGCCAACATG GCAAAACCTC CTCTCTGCTA AAAATACAAA
59251 AATTAGCTAG ACATGGTGAT GCGCACCTGT AGTCCCAGCT ATTTGGGAGC
59301 CTGGAGCAGG AGAACTGCTT GAACCCAAGA GGTGGAGGCT GCAGTGAGCC
59351 AAGACAGTGC CACTGCACTC CAGCCTGGAT GGCAGAAAGA AACTGTCTCA
59401 AAAAAAATTA TGTGTATATA TATATACTTT TTTTTTAGAT TTGTGACATT
59451 TTGAAAAAAC TCACAGATAA ACTGCATAGC CTAGAAATAT AAAAAAATTA
59501 GGAAAAAAGT ATGTCATGAA TGCATAACAT ATAGGTAGAT ACTAGTCTAT
59551 TGTATCACAT ACTACCATAA AATCTACACA AATCTATTAT AAAAGTTGAA
59601 ATTTATCAGG CCTTATGTAC ACAAACACTT ATAGATTGTG CATGGTGTCA
59651 TTGGCAACTG AGAGAAATGT AAACAAGTGC AAAAAATGCA GTATTAAATC
59701 ATAACTGCAT ACAGTTTACT GTTGTACTTA ATGTACTACT GTAATAATGT
59751 TGTAGCCACT TGCTGTTGCT ATTGTGTGAG TGCAAGTGTT TCCAGTATCC
59801 ACTTAAAACA CCTTGTGATG CTAATCACGT CTACCTGAGC AGTTCATCTC
59851 TTCAGTAAAC AGCATATTGC CGTAAAAAGA ATGATCTCTC ATGGTTCTCA
59901 CATATTTTTC ATCATGTTTA GTATAATATT GTGAACCTTG AATATAACCA
59951 CGGAACCCGT ATGAAGTGCC ACAGTGATGC TCGAAGTGCT CCCAAGAAGC
60001 AGAGAAAAGT CATAACATTA CAAGACAAAG TTGAATTGCT TGACATGTAC
60051 TGCAGATTGA GGTTTGCAGC AGTGGTTGCC CACCGTTTCA GGCAGATAAC
60101 ATAAAAAGAT GCAGAAACTT ATCAACAAAT ACAGTAAAGT ACTGTAAGTG
60151 TATTTTCTTT CATTTATGAT TTTTGTAAGA GAAAGGATAT CTGCTTGAAC
60201 AGGTTTTTAA AGCAGACGAA AGTGCCCAAT TCTGGGGGGA AAATGCCACA
60251 AAGGAAGAGA ACATCAGTAT TTAAAGCAGA AAGGAATAGG CTAACTACTG
60301 TTTTTTGGCA ATTGCCGCTA GGTTTATGAT CAAGACTACC CTTATCTATA
60351 AAACTACTAA CCCTAGATCC TTGAAAGGAA AAGATGAGTA CTGCCTGCCA
60401 GTCTCTTGGT TGTACTAAAA GGCCTGGACA ATGAGAATCC TTTTTCTACT
60451 TTGGTTCTAT CGATGCTTTG TCCCTGAAGT CAGGAAGTAC CTTACCGGTA
60501 AGGAAATGCC TTTGAAAATC CTTTCAATGT TGGACAATGC CTCTGGCCGT
60551 GTAGAAACCC AGGAGCTAAT GTTCATGAAG GTGTTAAAGT GATCTACTTG
60601 CCCCAAAACA CAAAACTTAT AATCAGCTTC TAGATCAGGT TTTGTAAGGA
60651 CCTTTAAGGT TCATTACACA TGGTACCCTA TGGAAAGCAT CGTCAATAAT
60701 GTGGAAGAGA ACCCCAATAG AGAAGACATC ATGAAACTCT AGATGGATTA
60751 CACCATTAAA GATGCCTTCA TTGCTACAGA AAAATCCATG AAAGCCATCA
60801 AGCTTGAAAC CACAAATTCC TGCTGGAGAA AACTGTGTTC CAGTGTGCAT
60851 GACATCACAA GATTTACAAC ACAGCCAATC AAGGAAATTA TGAAACAGAT
60901 TGTGAATATG GCGAAAAAGG TGGGGGTAAA AGGTATCAGG ATATGGATCT
60951 TGGAGAAACT CAACAGCAAA CAGAAACCAT GTCAGAGGAA TTAATAGAAG
61001 ATGACTCGAT GAAGATGAGT ATTTCTAAAC CAGCGCCAGA AGATAAGGAA
61051 GAAAACATTG AAAAAGCAGT GCCAGAAAAC AAATTCACAT TAGACAATCT
61101 GGCAGAAGAG TTACAATTAT TCAAGACTAG GTTCAACTTT TTTTACAACA
61151 TGGACCCTTC TATAATATGT GCACTGAAAC TAAAATAAAT GGTGGAAGAA
61201 GGATCGCATC TCATGGAAAC AGTTTTAGAG AAATGAAAAA GCGAAAAGGT
61251 CAGAAATTAC AATTTATTTC CATAAAGTTA CATCAAGTGT GTCTGCCTCT
61301 CTTGCCTCCC CTTCTACCTT TTCTGCCTCT GCCACTCCTG AGATAGCAAG
61351 ACCAACCCCT CCTCTTCCTC CTCCTCAGCA TACTCAACAT GAAGACAATG
61401 AGGATCAAGT CCTTTATATA ATCCATTTTC ACTTAATGAG TAGTAAATAT
61451 ATTTTCTCTT CTTTGTGATT TTCTTGTTTT CTCCAGTTTA TTGTAAAAAT
61501 ACAGTACATA ATACACATAA TATACACATT ATGTGTTAAT TGACTATGTT
61551 ATCATTAAGG CACCTGGTCA ACAGTAGGCT ATTAGTAGTT AAGTTTTGAG
61601 GGAGTCAAAA GTTATATACA GATTTTCAGC TGTGTGGGAG ATCAGCACCT
61651 TTAAGACCTG TGTTATTCAA GAGTCAACTG TAGTTGCTTT TTTTTCTTTT
61701 CTACCTTGAA CATCTTCCTG CAGATGCTCC ATCATCTTCC TAGCTCTAGT
61751 TTCTTATCTC TAATGGAGGT AAAGCAGGAA AGTTCTTACT TCACTGCTAC
61801 TGTGGCAAGT TAATGTCACA CTCCTTAGGC TTAGCAAGAA TTTGAGTTTA
61851 TTCATTCTCT CCTGGAGGTT TTCTCACCTG CACTCTTTTC TGCGTTACTA
61901 TTTATTCCTC TTCATCCCCT AGGCATTCAG TTATAATGAT AGAGTCTCTC
61951 TGCTGAAATA TTCTCAGTGC TCTGTGGCAG CCCAAGATGA CTCTATATTC
```

FIGURE 3T

```
62001 CACACCCTCT CTCTCTCTTC TCCCCGCTCC CCTCTCATGT GTGTGGCTTA
62051 TGTATGATTC ACAGAAGACA CACACACACT CAGATTGAGT GCTCTGGTAA
62101 ATACTGAAAG TGTGTGTTAT TGAATGCAGC AATGTCAGCC ATCAGCAGCT
62151 AGGCTGACTT TATGTTTCTC AGGTAAGAAT CATACCCCTA CTGCCATCCC
62201 TTTTAAGGAG AATAAGTAAA TGTCAGACTC ATGTTACAGC TCTTTCCGAA
62251 GAACTCTAAA ATGTGTCTGT TTCATCTCAT GATCCTTTAT AGCCAGCCTC
62301 TGTGTGGGTG AAAAATTAGA GTCACATAAC TAGGTTTTTA GAGCATGGTT
62351 TGCAAATTCT GCATATAATC TTATATCCCA TGTGGAAATA AATATCTGTT
62401 CTTGGTGCTT CATCTGAAAC ATTCATTTTA CCAATCTATT ACCCTGTAAT
62451 GAAATTACTA ATTAGAATTG ATAATATTAT ATTATTTCAA TTATGTAAAT
62501 GAATTAAAAT CTAGAAATTT CAATGAATAG ATTGTGCATG ACATTCAAAT
62551 ACTATGAACA CAATTTTAAA GTTCAACTAA AAATGGAAAA TATTATTGAG
62601 CTTCAAGGAG ACTGGAGACA TAAATTTGGA ACAGAACTAC CAAACTTGTC
62651 ATAATTTCAT AAGATAGATT ATCTGAATAT GGATTCATCT GAACTATAAC
62701 AAAGATAAAG AGGAAGAAAA GTGTCTGTGA TTCAGAAATT CACAATGGTA
62751 AGCATTTTGT GAATCTGTTC TCTTAAGCTA AATGTCATAG TAACCAAGGC
62801 TTGTGTACTT CATGACAGCA AGATTACATA TTAAAATGGA AGTTTTTCAA
62851 TTCACTTCTG TCATTGTACT TGTAATGCTG GCATGATAAA TATATATTCT
62901 CAACATATTT GTAAATATT GTCCAGAAAG TGTCTAAAAA ATAGAGTGCT
62951 TTTGGAGAGG GCCTGCAAAA GGAGAGTATT TCACTGATT ATTAGGAACT
63001 ATCTCTTTAA GCCCTGGTTA ATTAGTATGT GAGTTATTAA GGCAATATAA
63051 GTAATATAGC TAATAATGCA AAGATAGAAG TTTGCTAAGG AATTTGTTGT
63101 TTCCAGTTAT GATTCTACAA GGGCTTTCCT CAGATAGCAT AATGATTTAA
63151 ATTTGATTTT CTTAACTAAT TATTTGTTGA AAATACAGTC CATATTCCAA
63201 ATGGAAATAC CTTATTTCTC TATTTCTGAT TATAACAGTA ATAAATGTTC
63251 TTTGGAATTC CAGTGCTATT GAAAATTAGG CTAGCCAGAT CTTCTTTCTC
63301 TTAACACAGT TCTCATTGAC CACCCTACAA CATCCAACAT TATTGACTTC
63351 TTATTCTTTT TAAATTCTTT TCTACTTTGT TCCTGGTTAT ACTACTCTCT
63401 CCGTGAGATG TATGTTCCAT GAAGGCAGAG GCTTTTTTTC TGTTTATATC
63451 TGTCTTATTC ACTACTTAGT ATGGTATCTG ACAAAAGAAA GGTGTTCATT
63501 AAATGTTTGT GTAATGTATT AATCCTTTTA CATATTTATT CCTTTTCCGA
63551 TTCTTTTGTT AACTTATTTT CCTTCTGCCA AATCTTAAAC CTTATTACTT
63601 CTCCAGTGTT GAGTCTTCTT CTCTCTCAAG ACTTTCATTT TGAGTCATCA
63651 TCATCATTGT AATCATGTGA TATCTTTAGT TAAATGTTAT CTATGTCTCT
63701 ATCTCTGTCC CTGCTCTCTC TTCCAGAATC CAATCTCAAA TCTCCAACTG
63751 CCTTATGACC TTCTTCATAT GATGGTCCCT TAGTCACCTC AAAGTTAGCA
63801 TATGCAAAAG TTATCTTTGG AGCACCCAAC CTACAATGCT GGCTCTCATT
63851 CTGACAACTC TCTTTTAATT AATGGCATGA TTATTCTACC TGCTTCAATT
63901 TGTAAAGCTC TCTATTTCTG GTAGGTAATT CTATATCATC ATTATAACCA
63951 TCACCCCCTA TCTCTAATAT AATCATCAGT AATATTATGT GATTCTTTTT
64001 TTTTTTTTGA GACGGAGTCT CGCTCTGTCA ACCAGGCTGG AGTGCAGTGG
64051 CGCGCGATCT CGGCTCACTG CAAGCTCCGC CTCCTGGGTT CACACCATTC
64101 TCCTGCCTCA GCCTTCCGAG TAGCTGGGAC TACAGGCACG CCCGCACCAG
64151 GCCGGCTAAT TTTTTGTATT TTTAGTAGAG ACGGGGTTTC GCCATGTTAG
64201 CCACCATGGT CTCGATCTCC TGACCTCGTG ATCCGCCCTT CTCGGCCTCC
64251 CAAAGTGCTG GGATTACAGG CGTGAGCCCC CGCGCCCGGC CAATATTTAT
64301 GTGATTCTTT ATTGCTTGAA AAGTATTTTT ACATCTATAA TTTCCTCTTT
64351 TGGGGCTTGG TCCAATCTTC TGGGAGACTA ATTCTGGCAG GTAGAAATAT
64401 AAGGAGGCCA ATATCAGTAC ATTGCTTATT CACCATTGCT AGCGTCTTAC
64451 TCCTGGGTTT ACTCTGACTT TGGTCCCCAG CTCTCCAGTG CTATTATTTC
64501 TTTGCTTCTT TCTGTTATCC ATATTCCTGT CTTGCAACCA AGTTTCCCTT
64551 TAATGAGATA TTCTATTTCA CTCCAGTTTT CCTATGATGG AACCACTTTG
64601 CTAGACAAAG CCTGCGCATT TGGACTTGTG CTCATTACAT GATGCAAACT
64651 AGTGTGATAA ACCTAGTTAT TGTATTTAT TAACTTCTTA CAAAACAGTA
64701 TTCATGACTC ACTTGTTCCT TTACTTCTGC CTGCAGATCT GCTTTTGGA
64751 ATTTCATTTT TGTACTACTG ACCCTTGGAT TGCTTACAA AACTAAATTA
64801 CTGTTTTTTT CTTGAGCTTT TGAATTTTTG ATATTGACTG CTTCCAGTTT
64851 GGTCCACACT AATTTCAACC AGTCATCAAT TATTAAAGAT ATAATCCTCA
64901 TTTAAAATGT TATATATCTC TATATATTTT AAATATGTAG TATAATTTTA
64951 TATATGCTTA TTTTTATTTG TATATATAAA TATATACATA TTATTTACCA
65001 TATATTATAT ATACATGCAT AGGAAAGGAC TCTTTCTGGT TCCCTAGTAT
65051 TGGAATTTTT GCTTTCTTC TCTCTGGTAT TTTTTCATCC TTGTTTGATT
```

FIGURE 3U

```
65101  CAGACAACCT  GGCTATTGTT  TTACTGCTTA  CCCGGGATCT  TAATGCTTCA
65151  GGTTCGGCTG  GATTCCAGCT  TTTCCTTGGT  TTTAATTCTA  ATTCATATAT
65201  ATATATATAT  ATATATATAT  ATATATATAT  ATATATGTAT  AATCTACATC
65251  TGCATCAAAT  CCCTCTCTAG  AGCATGCAGT  GGATTTCAGA  CCTGGGATTT
65301  CATCTTGAAC  TTCAGCTACT  GAGGATATTT  TCTTGCATTA  TTCTATTTCT
65351  AAATTATTCT  ATTAGAATAA  TTCTATTAGA  ATTATTCTAT  TTCTATATTA
65401  TTGTATTTCT  AAATCCATTG  CCTAAACCAA  ACCATTAATT  TTGTCTCAGT
65451  AATCCTGGAT  CTTTTTCTTT  TACCATATAG  TCAAAAATAT  TATGTCCTTA
65501  ATGCTGGTGT  GGCCTGACTT  AATCCCACCT  CTTCTTGTGA  AAACCTCCTT
65551  GACCGTGTAG  CCTTCATTTG  TTTTTACACC  TCTTTACCCT  TATAGCACTA
65601  AGCACCAGAC  ATGTTAGTGC  TTAATTATTA  TTGTCTTACA  TTGTCTGTTA
65651  TTATGTATTC  ATCTTATTTT  TAAAACCAGA  TTATAAGCAA  TTTAAGAACA
65701  ATAAATATGG  TATAGCATTT  ATGTGAACTG  GAATAGATAC  TATCCTACAG
65751  TTAATGAATT  GACCAAGCAA  CTATTCAAAG  TACAGCCAGG  CTGAAGACGG
65801  CAGTATGTTG  TTTTTTTAAA  AGATACTTTA  TTTGCTCAAT  AAATCTAGGA
65851  AGAAATCAGC  CTCACATTTT  TTTGAACTGC  AACTTCTTTG  CTTGCCATCA
65901  TTTAATTAGT  TGCCGAGTTA  AAGGACCCTC  TTGGCTAATA  AGATAGCAAA
65951  ATTGTCATGG  ATTCTCATGA  ATCTCAATAT  AATTGAACTT  ACAATTCATC
66001  TAAATTATTC  CACTTTGTTT  TTTATACTAT  TTGCAGTAAT  TTCATTCCAC
66051  TTGAATAATA  AGGGAATGTT  TTCTCATGTT  CTGTAAATAT  ATTATTTGAG
66101  GATATTTTAC  TTTTTTTCTA  TATTTATGTA  TTGGTCTGTT  TTCATGCTGC
66151  TGATAAAGAC  ATACCTGAGA  CTGGGTAATT  TATAAAGAAA  AAGAGGTTGA
66201  ATGGATCACA  GTTCCATATG  GCTGAGGAGG  CCTCACAATC  ATGGCGGGAA
66251  GCAAAAGGAA  GGCACATCTT  ACATGGCAGC  AGACAAGAGA  GAATAAGAGC
66301  CAAGCAAAAG  GGGTTTCCCC  TTATAAAACC  ATCAGATCTC  ATGAGACTTA
66351  TTCACTACCA  CGGGAACAGT  ATGGGGAAAC  TGTCCCCATG  ATTCAATTAT
66401  CTCTCACTGG  GTCTCTGCCA  CAACACATAA  GAATTATGGG  AGCTAAAATT
66451  CAAGATGAGA  TTTGGGTGAG  GACACAGCCC  AACCATACCA  ATTTCTTTCT
66501  ATAGAATATA  CATTTAAAAA  TTGACATAAG  TGTGCTAAGT  GCTCTGCACA
66551  TTTCAGCTCC  CAAGGAATGC  ATATTGTAGG  AACTAAAGCA  AAAAAAAAAA
66601  AAAAATAACA  ACAACCAGGG  CAGTTTTATT  GAGTTCAGTA  AAGAATATGT
66651  TTCCCTATAT  TTTAATAACC  ACATCTATTC  TTATCTGATT  TACTTTAAGA
66701  ATCTATTTTC  CTCTTTAATG  CAGTTAACTA  ATACTATTTC  TTATACAATG
66751  GCAGTTTGAA  ATATTAATCC  AAACATTTTT  ACAATTTTTC  CATCCATTTT
66801  CATAACATGC  CAGTGTTATA  TTTAGTTTAA  TAGGCTAAGG  TTACCTTTCA
66851  TATTGATGGA  TTTACTCTGA  ACTTCTAGCT  GCTCTTAAGG  TAGTTGTGAG
66901  GTTTTTTTTT  TTTCCTGTTA  TTGTAATTAC  AGTTACAGAA  TAAGACTGGA
66951  AACTTTGAGC  AAGTTTATTT  TCTGTTTTA  AAAAAACCC  AGAAACAAAC
67001  AAGCTGACAT  GTTGATGAGA  TATATTTTAT  TACCCTACTT  TACCCAGAAA
67051  GCTATGCATA  AAGTTCATAC  AACAAGATAA  AATTTTAAAA  AAAAGCCAAA
67101  AGTGTACAAA  ATACATCTTG  GCTTCATCTT  TTAAATAAAT  TAATATTTGT
67151  TAAACCTTTG  ATATTTACTG  AGGATATAGC  AGTGAATAAA  ACAAACATGG
67201  TTTCTGCCCT  TATATTTCAT  CCATTCTAGC  AAAAAGATAG  ATGCAAAATC
67251  AATTATTGCA  CAATTAATTA  TTAGTTGCAA  TTGTGATAAG  TAGATCAAGA
67301  GATGTAGGGT  GCTATAAGTT  AGGATAGCAG  GGGCCTGATT  TGTTTGTATA
67351  TGAATATGCT  TAGATGTGGA  TATGTATGTG  TTCATATGTC  TGTTTTACAA
67401  AGATGATTAG  GTAGGTGTGC  CAAAGTATAC  TACATTTAAG  CAGAGAGTAG
67451  ATGTCTAAGA  CAGCTACAAG  ATTCTGACGT  AGGGAAGAGC  ATGATATTTT
67501  TAAAGTCTT  AAAGAAGGCT  AATGTACCTA  GACTGTAATA  GCAAGGGAAA
67551  GACTGGCAGA  AGATGAGGCT  AATGAGTTAG  GCAAGAGTTA  CCACAGATAT
67601  TTATTTACAC  AGAAATATGA  CACTATATTA  TCATTGTGTG  TTTATTTTTC
67651  ACCTTTGCCC  TCTGAAATAC  TCTCAATTAT  GACTTAGTTG  TAATCTAATT
67701  ATTTCAATAA  CTTATTAATT  GGTTTATTTT  CATATATGAA  ATGATTAATA
67751  TTATAGATTT  CAGTAATTGC  TCTATAGCTG  TTACTGATTT  ACTCATTCTT
67801  TTGTGTTTTA  AAAAGTTTAA  AACATACCAG  ATGTTTTATT  GAACTAACAT
67851  TGAATTCATG  ATTTTTTTTT  ATGACTAAGG  CTTCCTCATC  ATTCAATAAA
67901  GTTTTATAAT  TTTTATCACA  AATATGCTAC  ATAATTTGC  TGGATTTATT
67951  CCTAATATTA  TATTTTTCTT  CTAAGGTAAA  TGAATTTTTT  TCTGGCTAGA
68001  CTAATAGTTT  TTGCTGCCCT  ATAGGAATAG  TATGGATTTT  CTTTTTAAGA
68051  CCTAGTAAAG  ATTTCTAGGT  AAAAATCATA  TAATCTGTAC  AAAATATAAT
68101  GAAAAGGAA  ATAATGAAAG  CAAATCCCA  AGAATTCTTT  TTTCCCCCCT
68151  CAAAGAATGC  GTTGAAGAAT  GGGCAAATAA  AATCGGGAAT  ATTTAGAGGT
```

FIGURE 3V

```
68201  AGGAAGGTGG TGAAAAGGTT CACAAAGAAG TTTCAATTTC AACAAAAAGC
68251  TTTTAATTCA AAGATTTTTC TTTCTTTTTC TGAGAGTGAT CAGAACATGA
68301  AGATGGCTGT TGGGAGACAA ATCTCCATGT ATCCTTTATG TTCCCAAACA
68351  TCTTTTGGGC AAAGGCACTA AGTGCCTTTG TGCCTGTCTG TCTTTACAAG
68401  TATGTTTATA TCGTGAACAC ACTAGGAAGA TATAGATAGT GTCTCTCTCT
68451  GGAGCAAAGG GTAGGTTTTT TATCTTTATA CAGTAAAGAT AATGTCTCCT
68501  TATGGGCAA CAATCAGTGA GGATTATTGT CCATTATGAA AGACCTGAGT
68551  TCCTTACCTT GGTTCTCCCC TGTCACATAT CCCGCTACAT GTGCAGCATC
68601  TCCTGGCCCT TTGCACACCC TTCTGTGGGA GTTGGGGCTC AGAATGCAAC
68651  ACAAATGATG ATACTCTAGG TACTACTATT CTGTGCATAA TAAACCATCT
68701  TTTGTCTCTG ACTCAAGAGT CTCATGGCTT TTGCTAGCAT CCATAAAACT
68751  GGCAGGGCAA ATCCTGATAC CCTTCACAAT TCTTGGCAGT TTTGGCAGTG
68801  AGGAAGGGAT ACTGACAGAG ACATGGCTTT TGGAAAAAGA AGGATGATGG
68851  CCTCACAGCT AATTAATAGA CTTTGAAAGA AGTCCATTGG TATTGGTAGC
68901  AAACTTGTGG ACCAAATTGT CTAGTAAGCA GAGCAATAAA TATTCTTCTA
68951  CTCTATTGCT CATTAATGAG GAGGATTTGG GGAGGTAGTT GCAAGCTGAG
69001  AACCAGGCAA CAGATATGAT TTAACTGTCC TTTAGGCAGG GAGATTACAG
69051  TCTGGCAGTA GTCTCAGGTT CACCTATTGT AACAATTAGT ACTTAGATTC
69101  ATTTGGGCTG TGGGGTGGGG AGAGAGGAAC AAGTTTGCAT TTTCTTTTTT
69151  TGTTGTTGTT GTTTTGTTTT GTTTGTTTT GTTTTCAGA CAGAGTCTCA
69201  CTCTGTCGCC CAGGCTGGAG TGCAGTGGCG CGATCTCAGC TTACTGCAAG
69251  CTCCGCCTCC CGGGTTCACG CCATTCTTCT GCCTCTGCCT CCCGAATAGC
69301  TGGGATTACA GGCGCCTGCC ACCACGCCTG GCTAATTTTT TGTATTTTTA
69351  GTAGAGACGG GGTTTCACCG TGTTAGCCAG GATGGTCTGC ATCTGCTGAC
69401  CTCGTGATCC GCCCGCCTCA GTCTCCCAAA GTGCAGTGTT GGGATTACAG
69451  GCGTGCGCCA CCGCGCCCGG CCGCATTTTC TTTCAGACAA CAATTTTAGA
69501  GATACATACC TACAGTGAGC ATGAGAGGAA AATTTATGAC TATTATGTAC
69551  AGAAACCAGG CAAATTATTA GAACTTTGGC TGATTTTCTT GGAAAATGAG
69601  TGAGGTGGGT CATGGAATGT TGGTAATAGA AGAATGGCCA AAACTGGGAT
69651  ATCTTTTTTG CTCAGACTCT CCTACCATCA TGCCAACTTG TAATCCATCT
69701  GGAGATGACA GTAGAAAGTC TTGGAATTTT CTGTAATGGG TTCTATCTGC
69751  TGTAAAATAA CTTTGGCCCT TTTATGGAGA TTTCTCTGGA AGAGACAAAA
69801  TCAAGGGGAA ACTATAGATG AGGCATTAAT TAGTATTGCA CTCTTACAGC
69851  CCCAGATTGG TTTCATAATG CTAATATAAG TGACCCCTG GAGAATGAAA
69901  AGGTCATCAA AGAAATTTAG ATAAATTCTT GTGGTCAGCC TGAAGTTCTA
69951  GAAAAGTTCT TTCACCCTTA TGTTGGAACC AGGCAAGAAC TTAATAAATG
70001  TTGTATTGAT AGTAGGGCAG CAGGTACATC TATCTAGTCT GAGGATGTTG
70051  TTGCTGTTAC AGCCAATTAG TTTATTCTAG ACACACCATG TGACCCTTGA
70101  AACTAATCTA TGTTATGTAT TCAGATTTCT GAACCATTCA CAGTCAGAGA
70151  GTCATGCACT TTTTAATCCC CAAAGCCATA CAACAATTGG CTGATAATCA
70201  AGGTATGTGA TAGACCTTCC ACATTTCCTA TCATCCATCG GCATCTGGTA
70251  TTGTTAAATG TTGGAAGGGC TTCTTCAAAA ATTAAAAAAA GTTTCCAACT
70301  CTGCCTCTCT CACCTCCTTC TGGTGCACAC ATATAAGTAA GATGGTTTGG
70351  TCACTGAATG TGGCTTCTGC AGAAACTGAT CATCTCCTCT CAGCCTCTAT
70401  GTGGATAATA AGATGAAAGG GTTAAGATTT TATATAAACT TATATTGAAA
70451  AATCAGTGTT CCACCATGAC CATTTCTGGG CATAATGCGT TATTCTTTCT
70501  TATTACAGAA ACCTCAGGCC AGCCTGATTG GTACATCCTC CAAATGGTAG
70551  TCCAGCTAAA GGGAGGCCTC AGGAATTTTT ATTTAATTCT TGTATAGCTA
70601  ACTGGATATG CTTGTTGGCT TCATTTGGTC CTACATTGTA AGAGTAGTAA
70651  CCATTTAGTT GAGTACACAG CTTGCCAAGA CCCCCTGCAA TTGCCCAAAT
70701  GTACCATTAA TGTAGGGGAC ATAATGAGTC TCTGTAAATT TTATAAAAAT
70751  GCCCTTTTCT CCCTTATTCT GACCCTTCCC AACAAAAGAT TTGGGTATGA
70801  TAGAGGATGG TTAGAAAAAA AGTGAAATTA TAGCTACCGG AATGGAACAC
70851  ACTCTGCATT TCAGGTGCAG GAGTAAAATC AATGATCTTT CAGAACTTCC
70901  CCTGGAGCCT CCCACATAAA GAAAAGTCCT TGGTGTGAGT CTCTCAAACT
70951  GTGGTAAATG CTTTAAATGT AATTTCCTTC TGGCTTAACA TTCTTCATCA
71001  GATGTCTCTG CCTGCATTTT GATCATCATT GCTTTTAACC TTGAGGAGAA
71051  GTTTATTAGA AACATCAGGG AAAGATCCTT TATCGCCTAC ACACACACAC
71101  ACACACACAC ACACACACAC ACACACACAA AACCTATTAA CACCTTTGGG
71151  TGTCTTCTTT ACCCCTCTTT CTATAACCAT CAATCACTCA TTCCATGGGG
71201  TGGATGAATG CCATGTAGTG GCTTGCATGG ATAAATAGAT CAGATTGGAC
71251  TGACTGTCCC CAAGCAGTTT CTCTAAAAAA CAGCAATAAT CTCAATTATC
```

FIGURE 3W

```
71301 TGAACTGAAC TGAGAACCCC AAGGCCAACT AGCTGGCCTG GAGGCCCTGT
71351 TGGAGACATT GCCAATCTGT TTCTTCTAAC TGACATCGGT CCATTTTTGG
71401 GGTCACAGTC ATCGTAAATA ACATGTTCTT TCTAGGACCA TTGTGTGAAC
71451 CCTTAAGACT ATATGTCTTT TTTTTTTTTT TTGAGACGGA GTCTTGCTCT
71501 GTCACACAGG CTGGAGAGCA ATAGCGCAAT CTTGGCTCAC TGCAACCCCC
71551 ACCTGCTGGG TTCAAGCAAT TCTTCTGCCT CAGTCTCCTG AGTATCTGAG
71601 ACTACAAGCA CGTGCCACCA TGCCCAGCTA ATTTTTTGTA TTTTTAGTAG
71651 AGATGGGATT TCACCATGCT GGCCAGGCTG GTCTTGAACT CCTGACCTTG
71701 TGATCCGTCC ACCTCGGCCT CCCAAAGTGC TGGGATTACA GGCATGAACC
71751 ACTGCGCCCG GCCAAGACTG CATGTCTTAT GTCCAAATCA TGCATTATTT
71801 TCCCTCCCTA TCCAAAATAT AGTGACTTGA ACCACAGGGA TGGTCATAAG
71851 AGACCTTTGA ATGTTTAAGC AAACACCACC AGTAGATTAT GTAAGCTTCA
71901 GACGATTTCG GAGAGAACTC CAAAATCTAC ACTTGGCTAT GAGGATGAGC
71951 TTCCTGGAGG GATAATTGAC TTATTAGTTT TGTGTGCCCT ACAGGCAGTT
72001 ATCCCTACAA TGGTAATCAT CAAATTAGAA AAATTGGTGA GAAATTTGCC
72051 CCTGAATTTA ATCTAAAAGA TTAATGATAC AATTCCAGTC TTCTTTAGCC
72101 TCAGTTCATG GACTAACGTT TTTATGGATG ATAGGATTGC CCTCAGCTAC
72151 CTCCTTGTGG TCCAAGGAAG AGACTGTGCA ATTGCTTATA TATCCTGCTG
72201 TACCTGATCT AATGCCTCCG GCCAAGTGGA AAGGTTAATA TAGAAACTTA
72251 AGGAGAAAGT CACATGGCTT TGTAAGGGAA ACCTTTATGG TTTGGGGGAT
72301 TTATTCAGTT TGTTGGGTTC AGCAGCTGAA TACATCAGCA GTGTGGTTGA
72351 GGTATATACT GTAGATTGGT CCCATCCTTC TGCTTTGAGT CCTGTTGATA
72401 GTGACCTTAA GTAAAGACAT GTATGAGACA AAGTGGATGA ACTTTTTTCC
72451 AGCATCTGTT GGTTAGATTT ATCCGTGACT GATGGCGTAT TTATGGGAAA
72501 ATTAGTCAGA GAAAAGATGA TGTCAAGACA AGCTGTGGCT ATTGTTGATG
72551 ACTGTTCTCA GTTGATTCTG CTGTCACTAT ATCAGAAGCG AAGAGAAAGA
72601 GTATGAAGCA AACAGACAGA AAACTATGGA AGAAATAATT GAAGACAGTT
72651 GTGGTGGCTC ATGCCTGTAA TCCCAGCACT TTGGGAGGCT GAGGCAGGCA
72701 GATCACTTGA GGTCAGGAGT TTGAGACCAG CCTGGCCAAC ATGGCAAAAC
72751 CCCATCTCTA CTAAAAATAC AAAAATTAGC TGGGTGTGGT GGTGCATGCC
72801 TGTAATCCCA GCTACTTGGG AGGCTGAGGC AGGAGAATCA TTTGAACCTG
72851 GGAGGCAGAG GTTGTAGTGA GCAGAGATCA CACCACTGCA CTCCAGTGTG
72901 GGTGACAGAG TGAAAGAAAG AAAAGAAAGA AAAGGAAGAA AAAGAAAGAA
72951 AGAAAGAGAG AGAGAGAGAG AGAAAGAAAG AAAGAAAGAA AGAAAGAAAG
73001 AAAGAAAGAA AGAAAGAAAG AAAGAAAGAA AGGAAGGAAG GAAAGAAATG
73051 AAAGAAAAGA AAGAAAAGAA GAAAGAAAAT TTCTGGAAAA AAAAAAACCC
73101 CATAAACTTA CACATTGAAG AAGCTCAGGG TTCCCACAGG ATAAATGCTA
73151 AAATAAACAA ACACCAAAAC AAAACCCCAA ATCCCAAAAT TATTAAAAAG
73201 TATCATAACC AAGCTTCTGA AAACTAAAAA CAAAGAAAAT ATTCTAATAG
73251 TAGCCAGAGA AAAATGCAAC AATGATTCCA ATGATTGCAG ATTTCTCATT
73301 AAGAAATATG AGGGCTAAAA GGAAATGGAA CAGCATTTGA GAATGCTGAA
73351 AGAACATTTA GTCCAGGATT CTATATCCAC TGACATATTC TTTAGGCATG
73401 AAAGTTAAAT AAAGGCATTC TCAGACAAAG GGAAACTGAC ATCATACTTA
73451 TTCATGAAAG ACTGTTTTCC CCCTGTGACC AGGAACAAAG TAAGCCTGGC
73501 CACTCTCATC ACTGCCACTT AATATCGTAC TGGAATTCTA GCCAGTATAA
73551 TAATAAATAA ATAAATAGAG AAAAGAGCTT GGAAAGGAAAA AATAAAATGG
73601 TTCATATTCA CATATATATG ATCTCTACCT GGAAAATTCC GTGGAACCTA
73651 CAAAAAAATT AGAAATAATA AGTAAGTTTA ATAAGGTTGA AGGATACAAG
73701 GTCACATGAA AATAAATCAC ATTTCTCTAC ACTAGCATTA AAAATTGGAA
73751 ACAAATTAAA AAATATAATA GCCTCAAGAA ATGAAATATC TAGGTATAAA
73801 TTTAACAAAG CAGGTAGAAG ATCTGTGTTC TGGAATTAT AAAACCTGAT
73851 GGAAGTAAAT ATTTTGAAAT GAAAGAAGAC CTAAATAAAT GAAGATACAC
73901 ATAGTTTCCA TGGGTTGGAA AAATCATTAC ACTTAAGGTA CTATTCTCCC
73951 TAAATTGATC CATAGATTTA GTGCAATATC AATCAAATTC CAAGCAGGAA
74001 TTTTGTAGAT ACAGAAAAAC TTGTTCTAAA ATGTATATCA AAAGGCAAAA
74051 AGATTAGAAT AGCCAAACAG TTTGAAAAAA GAAGAGCAAA GTTGGGAGAC
74101 TCATACCATC TGACTTTAAG AATTACTCTA AAGCTATAGT AATCAAAAAA
74151 GTGTGGTATT GTCAAAGGAA TAGACAAAGC AATGAACTAA ATGTTTGTGT
74201 TCCCCCAAAA CTCATAGGTT GATATTCTCA CCCCAATATG ATGGTATTAG
74251 GAGATCGGGC CTTTGGGATG AAATTAGGTC ATGAGGGTGA AGCCCTTATG
74301 ATTGGGATTA GTGCCCTTAT AAAATGAACC TGCTCTCTCA GCCTTTTCCA
74351 CCATGTGATA TTACAAGGAG AAAACAGCAG TTTGCAACCC AGAATAAGTC
```

FIGURE 3X

```
74401  CTTCACTAGA ACCTAACCAT GTTGGCACCC TGATTTCAGA CATCCAGGCT
74451  TCAGAACTGC AAGAAATAAA TTTCTGTTGT TTATAAGCCA CTCAATCTAT
74501  GGTACTTTGT TATAGTATCC TGGACTGACT GAAATATAGG CCTAGATCAA
74551  TGGGACATTT TAGAAAGTCC AGAAAAACAG TCCAAACAAA TATAACTAAT
74601  TGATTTTTGA AAACGGCACA AACCATGAAG AATATACTTT TTCTGTGTCT
74651  TTTATTTGGG TCTTTTCCAT AAATGGTATG ATATTGGAAC AATTTAACAT
74701  CCATATGCAA AAAATAAAAA AAAAACCCTT GAATTAAACC TCATATCTTA
74751  TACCAAAATT AACTCAAAAT GGACCATAGC TTCAAGATGT AAAATATAAT
74801  ATATGAAACT TTAGAAGAAA ACATAAAAGA AAATCTTTGT GACCTTTAGG
74851  CAGAGAGTTT TCAAATTTGA TACCAAAGCA TAATTTATAA CACACACACA
74901  CAAATCAGAA TTTATCAAAA TTTAAAACTT TTCCTCAGTG AAAGACACTG
74951  CTAAAGAAT ATAAAGTCAA ACTATAAATG GGGAGAAAAG ACAAATATTG
75001  CAAATCATAT GTTCAAAAAA TGTCGTGTAT CCAGAATGTA TAAAGAAGTC
75051  TCAAAACTCG ACAGTAAGGA ACAGACAACC CAATAAAAAT AAGCAAAATG
75101  TTTTCATAAA CACTTTGCCA GAGAATAAAT ATGGATGTCA AATAAACTCA
75151  GGAAAAATTG TCAACAATAA CCATTATAGA AATGTAAAGT AACACCACAA
75201  TGAAATACCA CTACATAGAA TGGCTACAAA ACAACTGATA ATACCAAGTG
75251  CTGGTGAAGA TTCAGAACAA CTGCAACTCT CTTGCATTGC TCCTGGGAAT
75301  GCAAATGGT ACAGCCATTC TGGAAAGCAG TTTGGCAGTG TCTCAGAAAG
75351  CTGAACATAA ACTTATCATA TGACTAGCAA TCCTACTTCT AGGTATTTAC
75401  CCTAGAGAAA TAAAATTTAT GTTACACCA AAGCCTACAC AAGAATACTT
75451  ATAGCAGTTG TATTTATAAT TGGGCCAAGC ACTAGAAACC CAAATGTCCT
75501  CCAGCAGGTG AATGCATAAG CAAAGAGTGG TACATTCCTG CAATGGACTG
75551  TTACTCAGCT ATGAAAAAGA ATGAACTACT AATACACACA ATGACAGATA
75601  AATCTCAAAA TCTCAAAGGC ATTTGCTAAG TGAATAAAGC CAGTCTCAAA
75651  AGGTTATATG CTGCGTTTCC ACTTACATGA CATTTTGCAA AGGCAAAGCT
75701  AGCAGCAGAG ACCAGATCAG TGGTTGCTGG GGGCTACAAA AGGGAGGTAG
75751  GAATGACTAC AAAGGAGGAT CACAAGGGAG TTTTTTTGGT GAATAACATT
75801  CTGCATAGTT TTAGTATAAA TGAATTTTAT CATGATCTAC TCTTCTGAAT
75851  ATTACCCATA AAATATACCA TATATGATGA GAGAAAATGA GTATATGTGT
75901  CTGAGAAATA GAAATAGTCT CCATGAGTGT TAAAAATAAT CCAAAATAAT
75951  AATCATATTT TATTTATTAT TTATTATATG TATACATTAA TATATACATT
76001  TTACATATTT ATTTTCCCCA ATTATACTGG ACTTCATGTA ATGATGAATT
76051  TGGTTTTAGT TCCTGAGTTT GATTTGGATG AGTGTTGCAG TGGGGAGCAG
76101  GGGAGGTGTG AGCTTGGGGT GGTGCGAGCT TGGGGTGGTG CTGAAGGCAG
76151  TGACTGGGAC ATTTTAAGCT CAGGGTCGTG GTAATACATG TTCATGGTAA
76201  TACATGTCTC TGATTTTTA GACACCCCAT CACAGAGGGT ACAGTTTATT
76251  CTTGGAACCG AGGATGATGA CGAGGAACAC ATTCCTCATG ACCTTTTCAC
76301  AGAACTGGAT GAGATTTGTT GGCGTGAAGG TGAGGACGCT GAGTGGCGAG
76351  AAACAGCCAG GTGAGGATTT TTGTTAAAGG GTGAAGGTAT ACTAAAGAAT
76401  TTTCATGTTA CTAGAAAAAG AGATTTCTAA TGCAACAATT TTGCAAACAT
76451  CTATGATTGC TGCTGATTTT AGAAGTTGCT CATCTAGCCT GAGCATATCC
76501  TATAACGGGA TATGGGTCAG AAAGAAATCT GAAGGCAGTA ATTACAGTAA
76551  ACGGTGATGC AGAGCCAGCA ACAGCTGCAG TCTTAAAGAT AAACAGTAAC
76601  ATAATTTGTG TGTCATCAAC AAAACAAAAG AAATCTAAAA GTAGTTTATT
76651  TCTATTTTTT CAGCTGCTGG CTTGCACCTA AATTTATGAT AGTATATGAT
76701  AACTTGAAAG TGGGCTTTTT TTAAAAGAAA GGGCAAATAT TATGATAAAA
76751  TGCTTTATGT ACAGTCCTGG ATTTCATGTG CTCTTTCATG AGGATAAAAA
76801  TAATTTGTAA TATGTTTCTA GGATATGCAT ACATTTAAGC ATAGTGGTTT
76851  TTAAAAATAT CTTTTAAAAT CACTTTTTCT ATCATTTGTA ATTAAGATTT
76901  TTACATTGCT ATATAATTGA TAGAGTTCTG TAAAGTTGGA ATTAAATTTT
76951  GTGTTTACTT TTCATTCATT CTTTCTGATT TGCTCAGTTA ACAAACATTT
77001  ATGGAGTGTC CATTATGTGC CAAGTGCAAT GGATATGGCA CAACAACAAA
77051  AATCTTAGAT CTTGCCTTTA GGGATCTTGC AGTCTAATTT AGACAAGAAA
77101  ACAAAGTTGT AAATGCTGTA TAATGAAAGC TGTGATACAG GTGTCCACAA
77151  GAAACTGTGG GCACACCCAG GGTTGTCATT TACCCACTTT TTCACAAATT
77201  TTAATGTGAC TACCAATCAC CTGGAATATT GTTTAAAATG TAGACTTAGT
77251  AGGCCTCAGG CATAGTCAGA CCATGAGGAT GTCGTGTAAA ATGTTTTGGG
77301  TTTGAGAACC AAACTTTGAG TAGCAGTTAT CTAAACCACG AGGTGAAAGA
77351  GAGGATCAGG GTAGCTTCCC TGGAGGAGGC GATTCTTGAG CTAGCTCTTG
77401  TGAGTTGGGT TGGAGTTAGC TAGGCAGAAA AGCAGAGGGG ACAGTATTCT
77451  AGGCAGAGAT AGCAGGACGT GCTTAAATAT ATCATTGACA CAGGTTTAGT
```

FIGURE 3Y

```
77501  GTTTATTTAT TTATTTATTT ATTTGTCTGA GACAGAGTCT CACTCTGTCC
77551  CCCAGGGTGG AGTGCAGTGA CGAGATCTTG GCTCATTGCA ACCTCTGCCT
77601  CCCTGGTTCA AGCCATTCTC CTGCCCCAGC CTCCCTAGTA GCTGAGACCA
77651  CAGTCATCTG CCACCGCGCC CAGCTAATTT TTGTATTTTT AGTAGAGACA
77701  GGGTTTCACC ATGTTGGCCA GGCTGGTCTC GAACTCCTGA CCTCAAGTCC
77751  TCTACCTGCC TCAGCCTCCC AAAGTGCTGG GATTGCAGGT GTGAACCACC
77801  ATGCCCCTGC TGACACAGGT TTATTGTTT TGTTAGGCTA TCTCTTCCAC
77851  TGTAGGACAG CATTATTATT AGAAAGACTT TATCTTAAGC ATATTTATTA
77901  GTGGTCCTCA GATTGCAATT GCTGTCTGAA AGCCACAGTA ATTCCATTGG
77951  ATCATGTTAA ACTTGTAGCT GCATTTATTC ATTGACTTTA CTCAGTGTAG
78001  AAATAAATGC TCAATTATGA AAAGAATGT TGTGAATAAC AATGGCCCAG
78051  TTAATTCTTG TTTGATATAT TTCAGTGGT CTTTACAGCT CTCCTTTATT
78101  TAAAAAACAC TAAAAACGAG ACAACCAAAA TGGTTACCAA CTAGTTTATC
78151  CTTATTAACA TTTTAAAGTA AATAAAACTA ATAACTGCCA GTATTTAAAA
78201  TTCACAAGGT ATAGGATGGC AGAAAAGTAA AAATACTTCT CTATGCTTAT
78251  TCACAGTATC TCTTTTCAAA AGTAATCACT GTTAATCTTT TCTGTGCATC
78301  TTTCCCCCAA AATTTAATAG CTAAATCTGC GTGTAAATAT ATGCCCTTTT
78351  AAATTTACAC AATAGGGATT ATATAATATA CAGTGTTCAT ATCTTATCTT
78401  TTCCACTTCA TATATTTGGA ACATTTTCCA TATCAGCAAT TCAAATTTAT
78451  ATCATCTATT TGATGATTGC ATTGCATTCA ATTATATGGA TGAACTTTCA
78501  TTTATTTATT TATCAGTTAG TCTTGATAGA CATTTAGGTT ATTTATTTTT
78551  TTCCATAAAA ACCACTGCAG TGATTGCTCA CACAAATATT TTGTCATTAT
78601  TTTGTAGGTA TTTCTGTAAA GTGAATTTCT AACAATGGCA ACATATGTAG
78651  CAAAGAGAGC AGACATTTTT TCCTTTGATA AATACTGTAA ACTTACCTTC
78701  ATAAAATGTT TTTCTAATTT ACACTTCTAT CAACAGTGTA TGAGAGTGCT
78751  TATTTCCTCC ACATCCTTTC ACAGTAAATT ATCAAACTGC TTAAAATGTC
78801  TTTTCCAGTT TTATAAATAA AACATAAATC TCATTGTTTT AATTTGATTA
78851  TTCAAATTAT TAGTGAGGTA CAACATCTTT TCCTATGTTT TTATTTTTTT
78901  CATGTGAACG AACTATTCAT TTCCTTTATT TATTTTATAT AAATCATTCA
78951  TTATTTTCTT TATTTGCCTT TTGGAACACT TTAAATTGGT GGCATGTTAT
79001  TCAGTATGAA CTAACCTTTT TAATAAAATA ATTTACATAA GTTCCTCAT
79051  GATGTTTTGT ATTGTAATAC TTTAAATATA GACTTAAATT TAAAATAGTT
79101  TTTATTTAAC CTGGTACATA TTAAGATTAA GAGACTTCTA CCTTACTTTT
79151  TGTCCCAACT GCATCAAAAA CTACGTAGTA GTTTTAAAAA TGTGTAATAT
79201  ATGTGCTCAT CTTCTTTATT TGGTGACAGA AAGGGAATAT AAGATCATTT
79251  TTTCCACAGA TTAGTGATAT AACTTGCTCT TTTATGATTT TGATAAGTTA
79301  AAGTTCCTCC CTCCCTGTTT AAGACCAGAA GCATCTGTCT GCCACGAGTT
79351  ACAAGGAACA GATGTTCCTA TGTGACTTGA AGGAAGGCGA TCTGGTGATT
79401  GTGATGACTA GACAGCTCTG GTTAGTTAGA GTCTCTTTAA CCTATTGCTA
79451  AGAAGTATTT TGTTGAAGCA TTTATTTTAG AGTTCCTTCT TTACCCTCAT
79501  ACTACATAAT AGAGCTGAAA AGTAAAATTG AATATATAT TTGGGCAAGA
79551  GTAACTCACT TATTCTTACA GTGATTGGTG ATTTTTCATC TTACAGATCA
79601  AATAGTGACC CATTCATTTT AACCAATAAT TTCTTGTAAC TTGCCCACTC
79651  TCATAAAGCT AGGAGATTGC AGAAGCGATA CTAGAATATA GCACTCTCAC
79701  TTTGTTACAG TTGAGCAGGT AGGTTTTTGT TATGCTCTAA TGGATTAACT
79751  CAATAACATG TTTGTCCTAA ACCATCAAAA TATATTGCTG TTGATTTATA
79801  AAGAATAAAA AGATAGTCCA TTTAATTATA CACATTCTCT AATATTATTA
79851  GATGGACCTA TGTTTGTAGC CAAGCTTCTA GAATCTAATG CATGCTATAG
79901  CTGTTTGAGC TTCAGGGAGA CATCTGATGA GCAATGGAAA TAATAACAGA
79951  TATTGAAGGG GAGGGTAGAT GAATTTAAC AGAGACACAA TGATTCAGGG
80001  AAGGGCAGAA CATATTTATT GAGGATTTCG AAAAGTAACA GGTTTTAAAG
80051  TGGCAGAAGT AATTTTGTTC TGATTGCCCT AATTCATCTA AAAACACTAA
80101  TTTTTGTTAA TTCATGACTC CATCTGATTT TTCACATGCA ATTTAATTCT
80151  AGAAAATCAT TAGCATCACC ATTTAAAGCA CTTCTTTCTT TTGATTAGTA
80201  TTCCAGATGG GATTAATAAT TTTCTACCCT CACAGCAGAA ACAAAAAGAT
80251  ATTTTATCAG CTCATTCCAC CTGTCACGTA TCACATCTTG CATAATTTAT
80301  GCCCACTGTC ATTGCCAAGT AAAACTTAAG CAAAGTTTTA GGTTTTGAAG
80351  CTAAATTTTT GAATCATAAT TATTTAATAA ATGTTCGTAA AAACCAGCTG
80401  GTCACTTTTA AAAACCCTAA AAGAAGCCAT ATGAAGAGAC TAATGAAATC
80451  AACACAATTA CAATGTCCTG CTTATAAATA ACATGTAATG TTATTAATAG
80501  AAAAGTGAGC AAAGCTACCA CAGCTGTGCA GTTGTGGCGA CAACATGTTT
80551  GACTCACTGT AGTTACCCTT TATAAAAGCT TCCCACTAAT GAACTCAGAA
```

FIGURE 3Z

```
80601  GAGGCAAAGC AGGGGGTAGC GTTAGGCTTC TGATACATAC ATACATGGCA
80651  GAATAGAAAA GGATTATTAC ATCAGAACAA TTTTATTGAT GCTGTGAAGG
80701  CATTTGATCT TCAAAATTAG TAATGGTTTA AGTCATCTGG ATTTTTTACG
80751  GGAAAATAAT GTGGATTAAG AACAGGTGTG AAAATAATAT GGATTAAGAA
80801  CAGTTAATGT CTATAAACAC TAGGTTTGGA TGTATATCAT TTCCCCTTAA
80851  GATGACTATA GGTATTCTTT GATTACATGT TATTCTCTAG CTCCACCCCA
80901  GCCATGTCCC CCAACTATCC TAAAAGAGGA TGTTTTTTTC TTGAGACATC
80951  CATTATTTCC CCGAAGGCTA TAATTTTGGA TGATATAATA ACTCCTTTTG
81001  GATGATAGAC TTACTCTTTT TTTGTTTGGG TAGAATGAGA GGATTAAAAA
81051  TCTTAGAAAA GTTAAACTGA GTTAGTGAGA ATAGAACACC CAGAAAGAGT
81101  TAAGTTCTCT AGAAAAAACC TTCTCTAGAA GCACCTAATT GGCAGAATAA
81151  TTTTATTCTG TATATTTTAA TAGGAGTATT GTAGAGGAGA TTATAATAAA
81201  CTTAATCCTC AAAGAATTCA TGAAACACCT ATTTAATGTT GCTTAGTGGA
81251  AAGAGACTCC AATGTGCTAA TCTTGGATGA AAACAGATCC AGACATACTG
81301  AAGGAAATGA AAATAATCTT CTCAGGGTTT AAATCCACCC CTCTCTCCCC
81351  ACAGAAAAGG TCGTGCAATT GGCCAACAGT TTTATTTATT TATTTTTTAG
81401  CATTATCCCT CACATCTCAT TCATGCTTTG AAACTCTTGT TTGCCTTGGT
81451  TTGCTGTTCA AACAAATGTC AGCAGAGTTT ATTTGAAAAC TGGAACAAAT
81501  TGCAGCACTT TAGGTCATTA ACTGCAATCA GGCATTTGC AACTGACAGT
81551  ATATTCAGTG ATTACAAATC TTGAAACAGT GTCTGGTGTG CTCCCAGATC
81601  TGTTCATGTC TATCTTTGAA GGATGAAATG GGATTAAAA GAACAGAAAA
81651  GAGAGATATA GTTATGTATT TATGTGTATG TATTATTTTT AATAGTCTCT
81701  TTAACAATAT TCATTTAAAT ATCTCTTAAA GAATTGGCAT CATTCTGGAG
81751  CTGGCATAGA GCACTGAATC TTGAAATGTT TAGTATCTTT AGTAACTTGA
81801  TATTTGTAAC ATGTGGGCAC CTTTTTATGG AAAGTACCTT CTGCCTCCTC
81851  CTATAATACT CATAAAACCT ATGGGTACAT CAAACCATCC ATGCATATAA
81901  CTTATATTTG GTCATCTTAA CTAACAAACT GTTTGGAACT CCCTGAAGTT
81951  CCAAACTCTC TGAAAAGAAC TCCATTCTTT TCTCAGAGAA TTAAGCCCTC
82001  AACTTGAAGA AAATTATTCT AAAGGAAGGA AGAATAATTG GATTTTTTAA
82051  AATGTCATTT CAGACACATA AATCACTGGA ACGGAATAGA GAACTAAGAA
82101  ATAGACCAGC ACAAGTAAAG CTTACTGATT TTTGACAAAA GACAAAAACT
82151  ATTAAATGAA GGAAAATAA TCTTTTTGAA AAATAATGTT GGAGCAATTA
82201  GACACCTACA GGCAAAAAAT TAGCCTTGAT ATAAACCTCA CCATGTACAT
82251  AAAAATTAAT TTAAAATAGT TTATAGATTT AAATTTGAAA CATAAAGCCA
82301  TGAAATTTTT AGAAGAAAAT ATTAGATAAA ATCTTCAGGA CCTAGGGCTA
82351  GGTGGCAAGT TTTTAGACAT AACACCAAAA GCGCAATTCG TAAAAGGAAA
82401  TATTTATAGA TTGAACTTTA CCAAAATTAA AATGTTTGTG CTGTGAAAGA
82451  TTCTGTTAAG TGGATGAAAA GGCAAGCTAC AGACAGAAAG TATTTGTAAA
82501  CCAGATATTC AACAAAAGTG TTATATGTAG AACATATAAA GAACTCTCAA
82551  AGTTCAACAG TATGAAAATA AATCAACTAG AAAAGTGGGC AAAAGGCACA
82601  AACAGACATT TCACCAAAGA AGAGATACAT ATGGCGAATA GCACATGGAA
82651  AAATGTTCAA TATCATTAGT CATCAGGAAA ATGCAAATTA GAACTGCTCT
82701  GAGATATTAC TGCATACCTA ATAGAATAGT AAAAATGAAA AAATAGTCAT
82751  AATAACAAAT GTTGGTGAGG ATTGAAAAA ACTAGATCTT TCATACATTG
82801  CTGGTGTGAA TGTAAAATGG TAGAGCCACT TATGGAAAAC AGTTTGACAG
82851  TTTCTGATAA AACTAAACAT GCATTTACTA TATGATCCAG CAATTGGACT
82901  CTTGGGCATT TATCCCAGAG TAATGAAAAC ATGTTCACAC AAAGACCTCT
82951  GCATGAGTGT TCACAGCAAA TTTATTTGTA ATGGCAAAAC CTGCAAACAA
83001  CCTGAATGTC CCCCATGGGT GACTGATTAA ACAAACTGAT ACATCCATCT
83051  TTATAATGGA ATATTACTCT GCAATAAAAA GGAACAAACT ACTGATACAC
83101  ACAATAACTT GAATGTATAT CAAGGGCATT ATGCTTAGTA AAAAAGTGTC
83151  AATCTCAAAA GGTTGCAAAC TATATGATTC CATTTATATA ACACCGTCAA
83201  AATAACAAAA GTATGGTGAT GAAGAATAGA TTAGTGGTTT CCAGGGGACA
83251  GAAATAGAGT GAGGATTGAG AATATAAAGG TGCAGCACAA GGGATTTCTT
83301  TTGTGGTGAT GGAACAGCTT CGTATGTTGA TTGTGGTAGA GGTTACATCT
83351  ATCTATACAT GGGATAAAAA TGCATAGAAT GGAGGCAGGG CATGGTGGCT
83401  CATGCCTGTA ATCCCAGCAC TTTGGGTGGT CAGCTAAGGC AGGAGGATTA
83451  CTTGAGGCCA GGAGTTCAAG ACCAGCCTGG GTAACATAGT GAGACCCCCA
83501  TCTCTATTAA AAAATACAA AAAAAAAAA GCCAGACATA GTACCTGGCT
83551  ATGTAGTCCC AGCTACTTGG AAGGCTGAGG TGGAAGGATC ATCTGAACCC
83601  AGGAGGTTGT GGCTGCAGTG AGCTGTGATT GCACCACAGC ACTCCAGTCT
83651  GGATGACAGA GTGAGACTAT GTCTCAAAAA AGTTTTTTTT AATGCATAGA
```

FIGURE 3AA

```
83701  ACTGCACACA CACACACATA CACACACACA CACACAGCAA CACACAGAGC
83751  CCACATCTTA TCAGTATTCT TTTTTTTTTT CTTTCCAACT TTTATTTTAG
83801  GTTCAAGGGG TATATGTGCA GGGTTGTTTC ATGGGTAAAT TGTGTGTTAC
83851  AGGTTGGTG TACAGATAAT TTTGTCAGCT GTTAGGTAGT TTTTCAATCC
83901  TCCCATTCCT CCACCTTACC TGATAGATAT TTTTTGTCAC TGAATAGGTA
83951  GTTTTCGATC ATCCCACTCT CCACCCTCAA CTAGGCCTCA GTGTCTGTTG
84001  TTCCCTTCTT TGTAGTCCAT GTGTATGAAT GTTTAGCTCC CACTTGTAAG
84051  AACTTGCAGT ATTTAGTTTT CTGTTCCTGC ATTAGTTCAC TTAGGATAAT
84101  GGCCTCTAGC TCTATTCATG TTGCTGCAAA GGCCATTATC TCATTTTTA
84151  TAGCTGCATA TTATTGCATG GTGTATATGT ACTACATTTT CTTTATACAG
84201  TCCACCACTG GTAGGCACAT AGGTTGATTC CATGTCTTTG CTATTGTGAA
84251  TAGTGCTGCA ATGAACATAC ATGTGCATGT GTCTCTATGG TAGAACGATT
84301  TATATTCCAT TGGTTATATA CTGAGTAATA GGATTGCTGG GATGAATGAT
84351  AGTTCTGTTT TAAGTTCTTT GAGAAATGTC CAGACTGCTT TCCACAGTGG
84401  CTGAACTAAT TTACATTCCC ACCAGCAATG TATAAGCATT CCCCTTCCTC
84451  TGCAACCTCA CCAGCTTCTG TTATTTTTG ACTTTTTAGT AATAGCCATT
84501  CTGACTGGTG TGTGATGGTA ACTCATTGTA GTTTTGGTTT AGATTTCTGT
84551  AATGATTAGT GATACTGAGC ATTTTTTCAT ATGCTTGTTG CTACTTGTAT
84601  TAGTATGTCT TCTTTTGAGA AGTGTCTGTT AATATCTTTT GCCCACTTTT
84651  TAAATAGGGT TGTTTGTTTT TTGCTTGTTG ATTTATTTGA GTTCCTTAAA
84701  GATTCTGGAT ATTAAACCTT AGTCAGATGC ATAGTTTGCA AACATTTTCT
84751  CCTACTCTGT AGGTTGTTTA CTCTGTTGAT AGTTTCTTTT ACTGTGCAAA
84801  AGCTCTTTAG GTCAATTAAA TTCCACTTGT CAATTTTTGT TTTTGTTGCA
84851  ATTGCTTTTG GCATCTTCAT CATGAAGTCT TTTCTTTGGC TGATGTCCAG
84901  AATGGTATTT CCTGGATTTT CTTCTAGAGT TTTTATAGTG TTTTTGGCCT
84951  TACATTTAAG TCTTTAATTC ATCTTGAGTT GACTTTTGTA TATGGTGAAA
85001  TGTAGGGGTC CCGTTTCAAT CTTCTGCATA TGGCTAGCCA GTTATCCCAG
85051  CAGCATTTAT TGAGTAGGGA GTCCTTTCCT CATTGGTTAT TTTTATTGGC
85101  TTTGTTGAAG ATCAGATGGT TCTACATATG TGGCTCTATT TCTGGGTCCT
85151  TTAACCTGTT CCATTGGTCT ATGTGTCTGT TTTTATACTG ATACCATGCT
85201  GTTTTGGTTA CTGTAGCCTT GTAGTATAGT TTGAAGTCAG GTAGTGTGAT
85251  GCCTCCAGCT TCATTCTTTT TGTTCAGGAT CACTTTGGCT ATTTGGGATC
85301  TTTTTTGGTT CCATATGAAT TTTAGAATTT TTTTCTAATT TTGAAAAATG
85351  TGCACTTTTT TCTAATTTTG TAAAAATGTT ATTGGTAGGT TGATAGGAAT
85401  AGCACTGAAT CTGTAAATTG CTTTGGGCAG TATGCCATTT TAATTTTGAT
85451  TTTTTTCCTA TCCATGAGCA TGGAATGTTT TTCCATTTGT TTGTGTCATC
85501  TCTGATTTAT TTCAGCAGTG TCTTGTAATT CTCGTTGCAG AGATCTTTTA
85551  CGTCCCTGTT TAGTTGTATT CCTAGGTATT TTATGATTTT CATGGCTATT
85601  GTGAATGGGA TTGCATTCTT GATTTAGCTC TCAGCTTGAA TGTTATTGGT
85651  GTATATAAAC ATATACCATT TGCATATTGA TTTTTGTATC TTAAAACTTT
85701  GCTGAAGTTG TTTAGCAGAT CTAGGAGCCT CAAGCAGAGA TTATGGTTTT
85751  CCTAGGTATA GTATCATATC ATTTGCGAAG AGAGATGATT TGACTTCCTC
85801  TTTCTCTATC TGGATGGCTT TTATTTTTTA TTCTTTTCTG CTTCTCTGGT
85851  TAGGACTTCC AGGACTTATG TTGAATAAGA ATGGTGAGAG TGGGCATCCT
85901  TGTCTTGTAC CAGTTTTCAA GGAGAATGCT TTCAGCTTTT GCCCATTCAG
85951  TATGATGTTG GCTGTAGGTT TGTTGTAGAT AACACTTATT ATTTTGTGGT
86001  GTACACCTTC AATGCCTAGT TTTTTGCGGG TTTCAAACAT GAGGGGATGT
86051  TTAATTTTAT CAAAAGCCTT TTCTGCATCT TCTGAGATGA TCATGTGGTT
86101  TTTGTTTTA GTTCTGTTTA TGTAATAAAT AACATTTATT GATTTGCATA
86151  TGTTGAACCA AACTTGCCTC CAGGAATAA AGCCTATTTG ATCATGGTGG
86201  ATTAGCTTTT TGATGTGCTG CTGGATTTGG TTTGCTAGTA TTTTGTGGAG
86251  GATTTTTGCA TCTATGTTTA TCAGGGGTAT TGGTCTGAAG ATTTTTGTTG
86301  TGAATCTGCC TGGTTTTAGT ATGAGAATGA TGCTGGCCTC ATAGAATGAA
86351  TTGGACAGGA GCCCCTCCTC CTTGTTTTTT GGAATAGTTT CAGTATCCGT
86401  TCTTCTTTAC ACATCTGGTA GAATTTGGCT GTGACTCCAT CTGATCCAAG
86451  GCTTTTTTCT GGTTGATAGG TTTTTTTTAT TACTGATTCA AGTTTGGAAC
86501  TCATTATTGG TGTGTTCATG GTTTCAATTT CTTTCTGGTT AGGCCAGGTA
86551  CACGGCTCAC ACCTCTAATT CCAGCACTTT GGGAGGTTGA GGTGGGTGGA
86601  TCACTTGAGC CCAGACATTT GAGACCAGCT TGGCCAAAAT GGCAAAACCC
86651  TGTCTCTACT AAAAATACAA AAAATTAGC TAGACACAGT GGTGTGCACC
86701  TGTAGTCCCA GCTACTTGTG ATGTGAGGCA GGAGAATCAC TTGAGTGCAG
86751  GAACAGAGGT TGCAGTGAGT CAAGATTGTG CCACTGCACT CCAGTCTGGG
```

FIGURE 3BB

```
86801  TGACAGAGCA AGACTCTGTC TCAAAAAAAT AAAATAAAAT AAAATAAAAA
86851  TAATTTATTT CTGGTTTAAT CTTGGGCAGT TGAATATTCC CAGGAATTTA
86901  TCCATTTCTT CTAGCTTTTC TAGTTTGTGA GCACAGAGGT GTTCATAATA
86951  GTCTCTTAGG GTTTTTGTAT TTCTGTCGGG TTAGTAGTAA TGTCTCCTTT
87001  GTTTTCTGAT TGTGTTTATC TTTATCTTCT CCCTTTTAAA AAATTAGTAT
87051  AGCTAATAGT ATATCAATGT TATTTATTCT TTCAAAGAGC CAAGTCTTGG
87101  TTTTGTTGAT CTTTTGTGTG ATTTTTCTCA TCTCCATTTT ATTCTGTTCA
87151  GCTATATTTT GGTTATTTCT TTTCTTCTGT TATATTTGGG ATTGGTTGGC
87201  TTTTGTTTTT CAAATTCCTT CAAGTGTAAT GTTAGGTTGT TAACTTAAGT
87251  TGTAAGTTTT TCTTTTTTAT GTCGACATTT AGCAGTATAA ACTTTCCTCT
87301  CAACACTGCT TTTGCCCTGT CCCAGAGATT CTAGTATGTT GTATCTTTGT
87351  TTTCATTAGT TTCAAGGAAT TTCTCGGTTT CTACAGTTAC TTCATTGTTT
87401  ACCCAAATCA TTCAGGAGTA GGTTGTTTAG TTTCCATGTA ATTGTATGCT
87451  TTTGAGAGAT CTTCTTGATA TTGATTTATA TTTTTACTGC ATTGTGTTCT
87501  GAGAGCATGT TTGGTATGAT TTTGGTTTTG TAAAATTTGT TGAGAATTGC
87551  TTTATGGCTA AGTATGTGGT CAATTTTAGA ATATGTGCCA TCTGCAGATG
87601  AAAAGAATGT ATATTCTGTT TTTGTTGGGT GGAGTGTTCT GTAGATGTCT
87651  GTTAGGTTCA TTTGGTCAAG TGTTAAGTTT AGGTCCCAAA TATCTCTTGT
87701  TAGTATTCTG CCTCAGTGAT CTGTCCAATG CCATCAGTAG GGTGTTGAAG
87751  TCTTCCATGA TTATATTGCC ATTATCTAAG TCTCTTCCTA AGTCTCTAAG
87801  AACTTGTTTT ATGAATCTGG GTGTTCCAGT ATTGGGTGCA TATATATTTA
87851  GGATAGTTAA GTCTTCTTGT TTAATTGAAC ACTTTATTTT TATGTAATCC
87901  TCTTCTTTTT ACTTCTGAA TGTTTTGGT TTAAAGTCAT TCTTTTCTGA
87951  AATAAAAACA GCAACCCCTT TTTAGCATTC TTAAAATTTA AAATTTTACT
88001  TTCAAAGGAG CCAAGATGAA ATGATTTAGA TGCTTTGTCA CTTATTTAGT
88051  CATCTTCACT GTTATCCAGA AGTAAATTTT AACTATAAAT TTTATTATAA
88101  GAAAGGGTTT TCATTCTA TATAGATCAA GAGGCCCAGG AGTATTTTAA
88151  AAGTGAATTT GTTATTAATG TTATTACAGC TTACAAACAA TATTATTGTA
88201  TGGGTAAGTT TATAGAGTTA CACTTAAGTA GTTAAGAAAC AATATGATTT
88251  TTTAGTAATG TACGAAGACT TTTCAGGATT TTGTACTTGA GTATAATTTT
88301  TGGAGATTAC ATTTAATTCA GTTTATTTAT TTGTTCTTTT GAGGCAGGAT
88351  CTCACTCTAT CAGCCAGGCT AGAGTGCAGT GGCGTTATCA TGGCTCACTC
88401  CAGCCTCGAT CTCCTGGGCT CAAGCAATCC TGCCATCTTA GCCTTCTGAG
88451  CAGCTGGGGC TACAGGCATT CACCTCTACA CCTGGTTAAC ATTTTTTATT
88501  TCTTGCAGAG ACGTCATCTC ACTGTTACCC ATCGCCTCAC TGTTACAACA
88551  TTTTAGAATC AATTGTATAA ACAGGGATGA CAGAAAGTAC CATAGTTCTA
88601  GAAACCTTAA TTGAGGACAT TTTCCATAGA GAAAAACCTG TATTTCCTTA
88651  AATAGCATTA CACCCTTTTA AAACTCTAGG TTTTCTTTAC CACCAAATAG
88701  ACTAGAAAGT AAATTTCCAA TTTAACAAAG TTCTTCAGTC AAAATAACAC
88751  CAGCATACAT GCTATTATAT AGTCTCCCTT CCTTTTGCTC TTTTTATCTG
88801  AAATCCACAG CATATGTCAG TAGATTATAA TTTAATTAGA AGATTTAATA
88851  AAAGTTGTAT CCACTCCCCT GATGCCACTT CCTTATGGAA AGTTTCATTA
88901  TAGCCCTTCC ACAGAATAGT ATGTTTGAGT CTTATTCACA AAGGAAAACC
88951  ATCTATTTTT ATCTAGCACA GTAGGCAATA AGAAAACAA ATTGGAATAA
89001  TATAAAAGAA AAAGTGAGAA CAAAGAACAT TTTGCAACTT AAGATTGGCT
89051  CCAGACATGG ATGAAAATTA AATGTTAAAT CAGTTGTTTC TGCTATAAGC
89101  ATTAGCATAA GATCTTTGAA CTGAAAAGGA CTATAAATTC AATTCAAATT
89151  ACTATATTAT GGTGGGAAAT GGGCACAGAC TCTGGAGAAA AACAAAATTT
89201  TAAAAAAAAC TTAGAGTTGG ATCCTGGCTT GACAAGGTCA CTGGCTAGGT
89251  GATCTTTGGA AAATTATTTA ATGTGTTTAA TTTGTCTCAT CATTTTACCT
89301  GTGAGAAAAC TGACCCAGAG AAGTTAAAAG ACTTTCCTTT TATTACATGG
89351  TGGTTTAGCT GTATAGAAAA AATATAAATG TCTTTTTATT CTCAACTAGT
89401  TGAAGACACT TTATGTAATA CTATTCCATT AAAATGTCTG CCAAGAGGTT
89451  GTTCCTTTGT GATATTGAAA TCATAATGTG ACTATGGCCT TATTCTCATA
89501  TCTGACAAGA AATAGTAATT TATATTTATT AAAATCATAT TTACTTTCAC
89551  CATTAATTCT GATTAGGATT TTTATGCTGA TATGATTAAC GAAATGGTG
89601  ATCTATGTCA GTTGGGATAG CTAAATTAT GCTATAAAAA ATACCCTGCA
89651  ATCTCAGTGG CTTAAACCCA TTTATTTATG GCTCACAATT CATGTCCATC
89701  ATGAATCATT GGGGTTTTGC TCATCTGTTC ATTGTATTAA ATATGACTT
89751  AGAAACCTCA GCTGATAGAT CAGTCTTCAC CTTGAACTTT GCTTGTTGCA
89801  TGTCAAGGAA AGGATGAGCT CCAGAGGATA TCCTCTTGCC AATTAAATAC
89851  TCCAGTCTGA AAGTGACACA CACATAATTT CTGTTCCCAC CTCATTTCCA
```

FIGURE 3CC

```
89901  GATTTAATCA CAGACACATG GACTCACCCA ATTAAAAGGG AGCCAGGTAG
89951  TGATGTTCTA CACTTTCCTA GGAAGAGAGG GAGAACCAGT TATGACATGA
90001  TATGACCATC ACATGATCTA TGAGGTATTA TGGCCCTGTT TAGGACTGAA
90051  AAACTTTAGG AATAACTAAT ATGAAAACTT TCTGTGTAGA CAAAAATGTT
90101  CTATAAAATT CCCAGCCTTG AAGAGATATA CTGTTGGTGA TTTGTGGCTT
90151  AAATGTAAGT TTTTTCAATA TGGCATATCT ATTCTTACCT GATTGTAAAT
90201  TTTGGCAGGT ATAAGTATTC TTTTCTATTG GCTTCCTTTT CACTTTCTGA
90251  CATTTTTTTT TCTTTTTGCT TCCTAAACAC TAAAAACAGA TCCATAGCTT
90301  TCCTGATCTC TCTTACTACT CTGCACATTA ATCATTCTGA CTGTCTCTTT
90351  TGGTTAGTTA CTTTTGGCTA ATCCACTTGA TTCCCTAACT AGTTACTCCC
90401  ACATATTTGT TGTGTGTTGA AGGTGGATCA TTTTATTACA CAAAATAGTA
90451  AGATAATATA ATATAGAGGA TTTGAATGAT ATTGCTTGGA GAGAGAAATT
90501  GGGGTCAAAA ATGACTAAGG AGAAAAGGAA TGAGGGAAAT GGTGGAGATG
90551  GAGGTAGGCA AGAAGATTTA GGCTAAGGTT CATTAGAAAT GGTGAAACTA
90601  AATTGGTCAT CTATTAGGAT TAGAGACCAA ATTCCTAAAC GGATAAGAAT
90651  TAAGTGGCTT GTGCCAGAGC AATAAAATCA CTGGTTTCTC TTTATCTGTT
90701  CCATTTATCT TGCTTATAGA CAATCTAGGT ATTACTATTC ATTTCAGTCC
90751  AAGAAGACAG TGGTCCCCCA TTTGACATCA TGACATCAAG GTTCTTCTCT
90801  GATTATCCAT CCTGGCAGAA ACACCCAGGG ATGGGTCTG AGCTCAATTC
90851  TCACATATTC AGTCCCTAGG AAGTGACTGC TATCACTAGC TTTCATCCAA
90901  GCAAGCCTAA CAAGGATTTT TCCTATGCAA CAGGCCCCTA ATTATGCTAG
90951  CCTCCCTCAA GATCTTATAA GAAATTACC AAGAGACTAA AATATTCAGG
91001  TTTAAGACCT CCCACTAAGG AAAAATAAGT ATTCTTTCAT TTTCTTTTTC
91051  AATTACCATT AACTTTCCAT GAAGTATACA CTCTTTATTA GTGCTACATA
91101  AGATTTTCTC TGACCACTGG TTAAACAATT ATATTTAAAT ATTTCTTCAG
91151  AGTTAGACAA GTTAACAAAA TAACATGAGT TTTCCTTTTT TTCAATTATT
91201  TTTTAATTGC AAAAAGAATA TGAGTTAAAT GGAATTAAAA TGAAATAAGC
91251  CAAATGGCTT AGACTAGCTT TTATATACTT CCAAACCTA TGAACCAAGA
91301  CACAATATGA CTATTTTTCT ATTTCAACCT TTTATTTTTG GTATAAAGGA
91351  TCATTAACCT ACAATATAAT ATAAACTGTG CTGATAATAT TTGTTTGTAT
91401  AGGTGGTTGA AGTTTGAAGA AGATGTGGAA GATGGAGGAG AAAGGTGGAG
91451  CAAGCCTTAT GTGGCTACTC TTTCATTGCA CAGCTTGTTT GAATTGAGAA
91501  GTTGTATTCT GAATGGAACT GTGTTGCTGG ACATGCATGC CAACACTTTA
91551  GAACAAATTG CAGGTATATC TTTTCCCCCT TAGTGTATTT TATAGGTACA
91601  GCTAATTTTT TGTTACTCTC TTTTCCTTAT AATTCAATAT ACGTATGAAC
91651  TTTGGAAAAC TAATTCTCAT AATCACTGCA TAAGGTCTTA AAAGTCATTT
91701  TCTTTTACCC TGTTATTTGA GATAAAAGAA GTTGAATCTC AGAGAAATAT
91751  GCTCTAGTTT GGCAGTGCCA AGTCTAGGAC AAGAACCTAG ATATCTTGAT
91801  TCCCATTCAC CATTTATTTT CATTATCATA TTTAGACTCT CACCATTAGA
91851  AAATTAAAGG AAAAAACCTT AGAGCTAGAT ACTTATTTTC AATATTCAAA
91901  CATATGAAAT AACCAAATGA AAAAATTTCA ATATACAGAA AAATGTTGGT
91951  TTAGAATGGA CACAGAAAGG TACGGCCATT CATTTAAAC TTAATTAAAA
92001  CCCTTGAATT CCAGAGGAAG CCAAGTGATA CAGTTAGGAT TCGTTTTGTA
92051  ATTCAATACT ATAAACTGAT GAATGATTAG TATTATAATT CAATGATATC
92101  TTATAATACA GACAGGTATA TTTAGGAAAT GTTATTATTA CAGAAATTGA
92151  GTCAAAGAAC TCCTGTATCT TTTGACCAGA AGGCAAACAT ATTTTAGTAA
92201  AAACAAAATA ATACAAAAAG ACAGAAATGA ATTTTGAAAG AGTATAAATG
92251  AAATAATTGA TGGAGGTTTT AAAAACACAA ACAAAGAAAA GAGGCAGTTG
92301  AAAAGTTATT AGTTTGGGAA AAAATAAAAT TCATTCCATA TGATTTGTAT
92351  TTGTGAAGTG AAAAAACTTA ATATCTTAAT CATATTGTAG AGATGAAAAA
92401  CTATATGTGT GTTTTTAATC ATGTATATGA AAATAATATA TTAGAAAAAT
92451  AACATATCTA CTTTAATCTG CAGAACAGCC CCATGAAGTA GATGTCATTC
92501  TCATTTTCCA ATCACAAAAT AGAAACTCTA AAATTGTCAT GGCCTAGATT
92551  TCACCCAAGG GCCCCTGACT TTAAGCCTAG TGTTTTTTCT ATTACACTAC
92601  AACTGCTGTC TGAAGAAAAA GAAATGTCTT GAAGTGAATG TCACCCAAAT
92651  TTTGATGGCA CATTTATCAC CTTAAAAATT ATTGATTTAG TCATTGGTGC
92701  TGATAGGCAC TGCAGTATGT GTGAAAAGAA AAGTAAGTAC TGAAAGATAC
92751  TTTGGCTTGA ATATTAAGC AAAAACTCCA AAAATACTAA AACACACACA
92801  CACACACACA CACACACACA CACACACACA CACACCACAC TGCCCCAAAT
92851  AGGAAAGATA AGCGGTCCTC TTCTGTTTCA TGTAACACCT ATAAAGAGAT
92901  TATTCTTTAA GTTACATAGC TAGAGCCTGA AAGACTTTAT AAAGTTAAAC
92951  ATAAATGTAT AATTTTCAGA AATATCCAGG CTACTGTAGC TGCACTAAAT
```

FIGURE 3DD

```
93001 CAAGAGAAAA TAGAGAAAAT GATTAACTCA GAAATAAGCA AACTCCCTAA
93051 GAATGCTGAA ATAGTTAGCT ATCCAGCTCA ATTTCTTAGC TTTACATTAT
93101 ATGGTCTTGC TAATACCCAA TAAACATTTT TATATTTTAA TTAGGAATGA
93151 AACAGCAGGC TTTTCACAGT ACTTTCAAGT ATGGGAAGCT CTTAAGTTTG
93201 TAATTATCTT TTTAATGCTC AAACCTGGTT CTTAGTATTA TTATTGTTAT
93251 CCTTATTTAA TAAAGAAAAA AACTAAGATT TAAAAGGTTA AAGGCCTTGC
93301 TCTAAGGCGT TTATTTCTGC CGCTTAAATC GATGATGGCG CTACCTTTAA
93351 AAATAGATTA ATCCAAATAC ATTTTGAAAT GGGAAACAAA ACTGTCACAT
93401 TCTACCACCT GGCAAAATTA GCCTCAGAAC ATACCCTTTA TACTTTTACC
93451 AGTCTTCACA TTTCTTAAAT TATGTAATTT CTAATGCTTT CCTCAGAAAG
93501 TTATTCCTAT GAAGAAATTT TCTCCCAGTA ATTTGACTAA AACACTTCAT
93551 TTTATCACTT TAGTTCACTT TCATTGTCCA AAATTATGCA AATTTTTCCT
93601 AACTCTGTCC CTGTTTCCCA AGCTCAATTC TGTAGAATAT GTGAAGGTTA
93651 ACTGGGTTAA ATCTAGCCTT TTCAAGCAAA TTACATTCTC TAAGTCTACC
93701 CTTACAGTGA AAGTAGTTCA GTTGACGTCT TGATACCCTA AATAGCTTTT
93751 TAGTATTCTT TCTGCTCTTC TAATTAGTGT GTATCTTTCT GACTTTGAAG
93801 TAGCCCAACC TGAATGTCCC ATTTTTCAGT GTAGAACAGC CTGTAAAATG
93851 ACATTTAGAA TGTGTCAGTG GTTAATGCT AACATCACAA AGAAAAATAT
93901 GATTACAAAT ATTTGTGTTG ATCATTATTA CTTTAGATTC CTTTACTGTC
93951 ATTACTAAGA AGAGATTTCC TCTCATTGAA AACTATAATT TGGCTAAATT
94001 TAAAAGTTAC TTATTTATCC CCTCAATATA AACTCATTAA AATATTTTCT
94051 CTCTATAGTT TGTAATTATT TTCTTATTTT TTACTTCTCC TATTTTCATT
94101 TTATAAAAAT TGAGCGGCAT TACTAAGTTT GTAATAAATA AGCATGCTTT
94151 CCGTTTTTAA GACTTCTAAC TTTGCAAAGT ATTTCCACAT AATTATGTTT
94201 TATTATCATA ACAACATATA AAGTAGGAAA GAGACTATTT CACCATAAAC
94251 AGATAAATAG AAAGTTCTTT ATCAAAGATG ACCTTTGCAG AAATAAAAAT
94301 AATTTTTTTA TTAACCTATA ATCATAATAT TTGGGGATGG GATCTCCTAT
94351 GTTGCCCAGG CTGGTCTTGA ACTCCTGGGT TCAATTGATC CACCTGCCTC
94401 AGCTTCCCAA AGTGCTAGGA TTACAGGCAT GAGTCACTGT GCCCAACCAT
94451 AATTTTTGTT TTATTCTGTT TCATGATCAT TTGTGGCCAT AGTGATTAAC
94501 AATCAGCCCT GAAACTTTTT CCTCAGCTCT TATTTACCAT GATTTTTCTC
94551 TGTTAGCCAT AATTCACATA CATTAGTCAC TAGTTTCAGT TTTACAAACG
94601 CTAAGTGTAA GAGCTTACCT TTAAGGGTTC TAATCCCTAG TACTTTGTGA
94651 ATACACAGGC TTTACAGTAT TGATGTTTTT CAGACATTTC CTACTAGATG
94701 AATATGACCC AGATATTGTT TTGTAATGAT CAAGGATTTT TATATCAATG
94751 TTTTGATATG TTTTTAACAG ACTCGGATAA TTCCTTAAGA GATTTTTGTA
94801 GACTTAGTAG CAGAAAATCC CATTTGTATC TGGCAGATCT GTCAAGAATT
94851 TCTGATATAA TTAAAGTAGG ATTTTCTTTT GGCTAAGTTA ATTTAAAATA
94901 TATCTGTTTC CCAATGTTTC AGGAAACTCA ATAAATTTAA ACTTTATCCT
94951 TCAAAATATT ACTTAACCTT TCAAATCCA AAATTCTCCA GATATATCTT
95001 CTTACCACAA TTTACTCTGA TATGGAGATT AATTGTATTG AAATATGCTTC
95051 TGAATTATAT TCATATAAAT TACAGGGAAT TTTATGGTCT ATGTTAATCT
95101 CTTTGAAATT AAGCATTATA AAGATTAATG ATGGAAATAT CCTCTCTGCA
95151 GTGTGTGTAT ACTTTAACCT AATTCTGTCA ATGAGAGTTA GGAAGAAATT
95201 AAAACCAAAC CAAAGTTGGT ACCATGGACA GATTATCAAT CATAGCTCCC
95251 AACTCATTTA AACAACCTTT GTTGTTTAAA ATCTTTCATT GAAGGAAGAA
95301 TCTACAGTTT GCTCCACTGA ATGTAATCTG TAGAGTTGGG AGTATAGGAA
95351 TAACCATATA TTTTTTAACC TGCCTATACT GTGACAATCC TTGGTCTGAA
95401 AAGTAAGTAT TCTATTACAG TTTACATCTT TAGTACACAC ATCCCTGTTA
95451 GTGCTGGCAA CCAAACCACA GAATTTAGGA ACTTCGTATC ATATTCCCCC
95501 CCACCTCTCC CAATATCTTT TAAAGTTAAG ACAATGGGTT TTCAAAGCAT
95551 TGATATGATG ATCTTCAAAA AGGCAGAGAT TTATGTAGAA TCTGCAATAT
95601 GTCATAACCT CTAGGGGCTT TCATTCAAGA TACATTATGA TAAAATAGTT
95651 ATCTGATAGG ATGAAAAACA ATTTTTCATT TTTCTGAGGC CTTTTTCCAC
95701 AAGTGCTACT AGTTTTTCTT TTCTTTTCTT TTCTTTTTTT TTTTTTTTTT
95751 CGAAGTCTCG CTCTGTCGCC AGGCTGGAGT GCAGTGGTGC GATCTCAGCT
95801 CACTGCAGCC TCCGCCTCCT GGGTTCAAGC AATTCTCCTA CTTCAATCTC
95851 TTGAGTACCT GGGACTACAG GCACACGGCA ACATGCCCAG CTAATTTTTT
95901 TGTATTTTAG TAGAGACGGG GATTCACCAC GTTGGACAGG GTGGTCTCAA
95951 AGTGCTACTA GTTTTCTAG AGTCTGCTTA GTGTTAGCAG AGTGTGACCT
96001 ATTTGTCCTT TTTTTCTTTT CTTTCTTTTT CTTTTTTTTT TTTTTTTTTT
96051 TTTTTGAGGC GGAGTCTTGC TTTGTCTCCC AGGCTGGAGT GCAGTGGCGC
```

FIGURE 3EE

```
96101  AATCTCGGCT CACTGCAAGC TCCGCCTCCC GGGTTCACGC CATTCCCCTG
96151  CCTCAACCTC CCGAGTCGCT GGGACTACAG GCGCCCGCCA CCACGCCCGG
96201  CTGATTTTTT GTATTTTTAG AAGTGACGGG GTTTCACCGT GTTAGCCAGG
96251  ATGGTCTCTA TCCCCTGACC TCGTGATCCG CCCGCCTCGG CCTCCCAAAG
96301  TGCTGGGATT ACAGGCGTGA GCCACCGCGC CTTTTCTCTT ATCACCCAGA
96351  TCCTGGGGCA GAATAGACTG TATTATGTAG GCATAATAGC TTGCTGAGAT
96401  TGCAGGACTT CACTCTGGAC CCAACGTCAT TATGGTCCGT TATTCTTTCA
96451  CACTTTTCAA ATTAATACTA ATATGTATTG TAGTGGTGAA AAGAACAATG
96501  TAAGTGATTA CTAATTCAGA TTCCTTTTGG TACTTAAATG TCACCCTAGT
96551  ATAAATTATA TTCTTAAGCA AAATGAGTAA TTTTTTCCAG ACAAGTAGAT
96601  ATAATTTGAT ACAGTTATAC TTTGGAGAAG TTTGCTGTGT ATTTCTCTGT
96651  AACTAATGAA CAGATGAGTG TGTTTTTTAA TATTTACTTT TCTTTACATA
96701  ACTGTTTCAA ATAAAAATCT TATCTTTGAA AAACTGTGAA GATAGTGACC
96751  TATGGCTTTT TTAGTGTTCG AGCCTGGAAA CATTGTGCTT AATAGAAAT
96801  TAAAAATAAT AAACATATGT AGGGTTTATT ATGTGATTAC TTTTGATTCT
96851  GACTAGAATA TTGAACTGGG AATTCATATC ATGGCTTATA TTTGGAACTG
96901  CTTTACAATA ATATCATATT GATATTCTAA TAACCTACTT TACAACTTCC
96951  ATTATGAAGT ATATGCATAT TTTATATACA TTTTTCCATC TTAGCAAGGT
97001  TTCAGTGTAA TGTCATATAC GTTGACAATT TATTATTTCC TTTATTTCAG
97051  ATTAACCCAG GGGTATTATA ACTACTGATC TCCAAAGAAC TGAAAAATAG
97101  ATTTAAATAT TATTCTATAG TATCACACAT TTTCAGAATT GGAAGGGACC
97151  TTTGAGGTAA TTATAGTGAC TGACTTTCAA ACATTCCAGG TATATAATAT
97201  GGGTAACTTC CAAATATTCT TTCTACCTCT TTCCATTGTA AACACAAAAA
97251  TGATAGAGCA CACTATATCC CACGTGCCAC ATATGGCCGA CTGCCTGATT
97301  TTGTAGGGCA TTTGAGCTAA GAATGGTGAT TATATTTTAA ATGGTTGAAA
97351  AATAATAAAA AAGAAGTTAA TATGTTGTGA TGTGAATATT ATATGAAATT
97401  CAAGTTTCAG CATCCTTAAA AAAGTTTCAT TGGAGCATAA CCAGGCTCAT
97451  TTGTGTACAT GTTGCCTGTG GCTGCTTTCT TGCTACAAAG GCAAAATTCA
97501  GTATTTGTGA CAGAGATCAT ATGGCCTACA ATGCCTAAAA TATTTGTTAT
97551  CTGGCTCTGG ACAAAAAGAG CTTGTCTTTC TCTGGTTTAG AGAATTAACT
97601  CTAGAGTGAA GCGCAGTTCT TGATTAGCCT GTCAGTCATA TGAATACCAT
97651  CTCCTTTGCC AGTGATTGGT TCAAGATGGG CAGGGCTATG TCAGTTAGAC
97701  TTAGGATAAT TTTTCCTGGC CAGGTGAAAA ATAACTCATC TAAGAGAAAG
97751  TCACAAAAAA ACAATATATT TCTCACTGGA TATGAACAAA AATATATATT
97801  TCCTTGTTGC TGCTGGAAGC CACCTTATGA CCATAAGGAA AATCAGCCTG
97851  AGGTTAAAGC TTACCCTAGA GGAGGAGGAA GTTAACAAAA TCACAGAGAA
97901  GCAGAATTAT AGCCAACCTA ACTTTGATCT TTCTATTTAT GTGAGCCAAT
97951  AAAATTGTTT TATGTAGTTT AATTTGGGTT TTCTGCTATT GATAAGCCCA
98001  GCTTTGTCTC TACTTGATAA GCTGTCACAA AATATGAACA TATTGAAACC
98051  ACCACAAATT TCAAACCAGG AACCCATAAT CTACATTATG AAAATTACAA
98101  AGAAAATCTT GTTCTGGGAA ATATTTACTG ATAGCCTCAA TATTCCAATC
98151  AGTGCATCAG GTGCCTTATG TCATTAGTCT TGGCACCAAT ATATGATATA
98201  GATATTATTA TCTCCATTTT ACAAATAAGG ACACTTAGGT TATTCAACTT
98251  TGCAAAGTTG TCTAGCTAGA ATGTCATAAA GTGGCCCAAA TCTGTCTCCT
98301  AGTTCATTTC CATTTCACAC TGAAGGAAAA CATTGTTGGT AAGGGAGCAT
98351  TCTGCTAACT TTGAAACCTT TATTGTACTC AAAAAGGCAG TGGAAGGCAG
98401  CTCATTGTAA TCTGCTTTAC ATAAGATGTT AATGCCTAAA AAACAATTAG
98451  AGTTAATGTT TGATAATCAG AAAGCAGATT AATTACACAA ACATCCATTG
98501  ATGTGATCTT TATATCACTA AGAAACTTAA AATACCTTTA CTTATCTATT
98551  TTACTGACAT TTTTGATACT ATGTATGGTA AATAATCTGC TTAATTATAG
98601  ACTTCTGAAA TCTCACCTTC CAGTCTTTGT TTTGCAGGTA TAGAATATCT
98651  TTTTAATCTA ACATTCTCAA GGGAGTGTGT TTCCAGCAAA GTTGAGAAA
98701  GGGCTGATTT TCTATCCATA TGAAACAGAA TTGTTTACTC TCCAAATTCA
98751  GTAACTATAT CACTTCATAG GCCTCTTTGC ATCAGATTTT CACAGATAGA
98801  CTTTTGTTCA CTTAATGGGG AAACAAGGAA ATTAGTCTGT ACTAGAAAAT
98851  GGGAAAAAAA TTAAAATATA AGTATAAAAC CAATTTTCAA ATTCAAACAC
98901  GTTATGAATT GTGAATTCAA ACACATTATG AATTTTCAAA TTCAAACACA
98951  TTATGAATTT TGATATTATC TCTACAGCTA TTCCTCCCAT CAGTGTGGAT
99001  AATAAATAAA TAAAGAACTT TCTTCTCAAT GCAACTATTC CCATTTGAAA
99051  AATAATACTT CATAAGAATT ATATATTTAA ATAGAATGGT TTATAATGAA
99101  AATTTGCCCA AATCTTTCTT ATTCAACATT TCTACAATGG AAGATAAATT
99151  TCCATTTATA ACAGCATGCT TAGAGATTTT TTAAAGAAGT TATTTCTATT
```

FIGURE 3FF

```
99201  TCAAGATGAA TAATATTGTT TAGGGCTTGC ATATTTGGAC TCAGTGGTTC
99251  ACGGCTGGCA CACGTTCTAG AGGAAAGCTG TGCTTATCTT CTTCCGGCCT
99301  TTTCTCTTCA GATATGGTTC TTGACCAACA AGTGAGCTCA GGTCAGCTGA
99351  ATGAAGATGT ACGCCATAGG GTCCATGAGG CATTGATGAA ACAGCATCAT
99401  CATCAGAATC AGAAAAAACT CACCAACAGG ATTCCCATTG TTCGTTCCTT
99451  TGCTGATATT GGCAAGAAAC AGTCAGAACC AAATTCCATG GACAAAAATG
99501  GTAAATGTTT ATTTATTGTG CTCTTTATGT CTACTATAGG TCTCTGACAT
99551  ATCAAAGCGC TTCTAAATCT TTTAAAACTT GTTTTATTTG AAAATGATTT
99601  TTTGAAATTC AGATTATTGT AGAATTCTTT TCACATGAGT ATATATTCTT
99651  ATTATCAAGC ATCAAGTTGT AAAAATTTTA GAAAGAACT TAAGTTTCCT
99701  GAAAGGTTCA GGAAAAAAAT GCAAAGAAAA CTAATATTTA ATAAAAAAAC
99751  TTTTAGATTT GGCTGCAGAA AACATAAACA GAGCATCTGT GGCATACCAA
99801  ATAAGGTCCT AGTCTCTGTC CTGTAGCTTA AAAATGTAAT GCAGGGCTTT
99851  GACTTACGCC ATAGATGGTC TTTTAGTTTA AAGGAATCAT GATCATCATC
99901  TAGTGTTTGT GGAAAAAGA TATTGGTTTC ATGTTGCTCA TAGTCAACAA
99951  ATTCCATTAG AGAAATGAT TGAAAGACC AGCCAGTGCA TTGTTTGTGG
100001 CTTTACATAC ATTATGGCTG ATTCCGGTTC AAGGGCTCAT GCTGTTTGT
100051 AATGCAGCAT CTTCAACATC CATGGAGCCA CCCCACTTAC TATCTTCATA
100101 AACCAACATA GATGACCACC ATTGTTCCT AGCAATCAAC TTACTATGAT
100151 TTATGCTTCA GACTATTTTG TCTTTCCTGT ATTTTTGTT CTCTCCTTGC
100201 GTTTATTTAA CCCCTCATCA TTTGCAATAA GGAAGTTGCT TAGGAATCTC
100251 CTGTTATCAT CCATCCTTTC TATTAGTCTC ATGAGAGAAA ATGAAGTTAC
100301 CATGAAGATG ATATGAATTT GTTAAACTTC TGTAGGCTTT AAAAGTTTCC
100351 AGTTCTAGGC CGGGCGCAGT GGCTCACTCC TGTAATCCCA GCACTTTGGG
100401 AGGCCGAGGC GGGCGGATCA AGAGGTCAGG AGATCGTGAC CATCCTGGCT
100451 AACACGGTGA AACCCCGTCT CTACTAAAAA TACAGAAAAA TTAGCCGGGC
100501 GTGGTAGTGG GTGCCTGTAG TCCCAGCTAC TCGGGAGACT GAGGCAGGAG
100551 AATGGTGTGA ACCTGGGTGG CGGAGATTGC AGTGAGCCGA GATCGCGCCA
100601 CTGCACTCCA GCCTGGGCTA CACAGCTAGA CTCTGTCTCA AAAAAAAAA
100651 GTTCCAGTT CTAAAAGATA AAATTAATG AAAAGTATTT TCAAATGCTT
100701 TACTGGAAAG ACTGATTTCC ACGAATGGAT GAAAGCACAT GTAATGACAG
100751 CGTGAAATAT CATGTAATCT CACCCTTATT TTCAAAAGCT TCAGAGATGC
100801 CTTAAATAAA ATGTATGAAA ATTAGTTTTC TTCAGATTTG CTTCATATTA
100851 ATCAGTTTTC ATGCTACTGT ATCAAATATA CATAAAAATA TAGGGTAAAT
100901 GCTTTATTAA ATAGATAAAG ATGATTAGAT GTAATTTGT CTCAGAATGT
100951 AGAACCAGTT CTTAATGACA AAATCATTTT TGAGATAGTT GATTTTTAGG
101001 GCTTTTCAAT GACTGAATAT AAGTCATTTT TGTTACATAC AAGAGTCTAT
101051 AGATGTGCAC ACTTAAGTTC AATAAAATTA TTATGAATAC TTTATGGTGA
101101 ATACCAACTT GTGTTTGTAG ATTCCACTGA ACATTCTGAG GAGATATAAC
101151 TTGCTTTGAA TCAATCATA TATTTAAAAC ATATTTATAT TCTAAATCAC
101201 AATTTGCTTT AAAATATGTG ATACATAAGA TAACAAAACT TGAGGCTTTT
101251 ATATTCTAAG AGATGTATTA CAAATGCAGT GCTTTGTTA TGCTTATAAT
101301 GCTAGTATTT ATTTGGTATG GTAGTGTTAA AATAGACTCA GTTATTTACT
101351 AATTTTGGCT ATGGGATTAT GTCTACATGA TTCCAAAAAC TTTATTAGAA
101401 TTAACTTCCT AAGAATGCAT GCAGTTTTA TAAAAATGAA CTTTTACCTT
101451 CATAACTTTT GCTAGAAATC AGATAAGATA TATGTCTTTA AGAAAGAGGT
101501 ATGTTTCTTC AAAGAGGCAA GGATCTTGCA TTTTGAACTA GTTAAAATTT
101551 ATACCTTAAA TTTCATTGGA GATAATGTTT ACTATAACAA TAATTTCATT
101601 GCATTTTTT TTCAGGCAAG AGACTACAGA ATTTATTGGA GCAATGATTT
101651 ATTGTAAATAT GCAGATCTAG GCACACTGTT TGTTACTGCT TTAAACTTCT
101701 ATTAAACATT AGAAGAGATG TTAGAATTAT AACTGTGAAT CACAAATCTA
101751 CATATAGTCA CAAGGTTTTC TGAGAGCCTG CTTTTTGTCT TATTTAGGAA
101801 ATGGTTTAGT TTTCCCAAAA ATCAGAATCT GAGTGGTTCT AAAGTGATTC
101851 TGTCACCATC TGTACAATCA GCCTTTATCT GAACACATAC AAATCTTTTC
101901 GAGGCATACG TAAGGGCAAT AAAAACTTGG AAACATTTCT AATAAGATTC
101951 ATATACCCAA TTAAGTATTG TTGTAGAGTA TGCTGTCAGA AGTGGTTTTC
102001 TAAGCCTAAG CTTATAACAC CTCCTTATGA CTCTGTTTTG CTTCCTCACA
102051 CACTTTGCAT AATTATGTGT GTTGAGAATT CTGAAAATAT GTATAGACTT
102101 CACCAATTTA GAAGTAAATC TCCTACCCAA AAGTGAAAAA AAGTACAAAA
102151 GACCTTTACT GCTAAGGTTC TTAATCTACT TATGAACTCT AAAGCCTGAC
102201 AAACTCTAGA TATATAAACA AATTGAAATT AATAGCCGTA AATGTAAATT
102251 GGAAATTCTG TTTTAAATAT GCAATCAAGA TTTAAATTTT TGTGCAATAG
```

FIGURE 3GG

```
102301  TTCAGAGAGA  TGCAAAAGGA  TTTCAAAACA  TCAAAAAAGT  AAAGGTAATA
102351  CTATTAATTT  TTAAAAATCT  CCTTAGTAAA  ATCCATTATG  CAAAAAGATT
102401  GACTTTTTTA  AAAAAAAAGA  TTATAGAATA  GAAATTAAAT  AGAGCAAAGA
102451  TTTTTCCAGA  AACTTTAAAA  CAGAACACAT  TTTCCTCCCT  AAGCATAGTG
102501  GTAGAAATAA  GTCCCCGTTT  CTTGTTTAAT  GTGCTAAAAT  TATCTCAAAA
102551  AGGGGATCCT  CTAGAGTCCA  NNNNNNNNNN  NNNNNNNNNN  NNNNNNNNNN
102601  NNNNNNNNNN  NNNNNNNNNN  TCCCGGAAGC  AGAGCGGGAG  AAAGAAGGCC
102651  CCGTTTCGGG  GTGAATGTGC  GAAAAGGAGC  GCAAAAACAA  AGTGAAGCTG
102701  ATGTAGATAA  ACCTGAAAGA  GTCAGATAGA  AGAAAGTTAG  TACGTCCTGA
102751  AGTGACTTGT  GTCTTGAGCA  TGTTACCTTG  TGAGTACTCT  CCGGGGTTAA
102801  ACATTCAGAC  ACTGTATTTC  AAACGGGGTC  TTCCCCATTT  TAAAGATTAG
102851  ATTAATAAAA  TAGTGCATTT  CCTTGCTCTT  CTCCTTCCCA  AGTCTACCAT
102901  TCTTTGTCCA  TTCCTTTTTT  AGTGATTTGT  GATAATTTGT  CAATCTCATC
102951  TCTAAACACA  CTAGTTCACT  CGTTTGAATA  ATTTTTTTCT  TCGTATTCCG
103001  CATTCTCTTC  AGGGCTAATG  TGAAGGATGC  TATGGATTCA  CCATGCATTT
103051  TTAATGCCAC  CATGCTGTGT  TTAACTTTCA  CTTTTCATTA  AGCATCAAAA
103101  CTGTGAGAAT  TAAATGTCTG  ATTCTGATGT  TTCAATAAAA  AGTGACAGTT
103151  ACATTTGGCA  AAACAACAGC  AAAAATAATA  GAAAATAAT   ATCTACTTTG
103201  ACATTAGTAC  CCTGAAAAGG  GTATGGGTGG  TAAAGCACTC  AAAATAAATG
103251  TATCGAAAAT  ATTAAAATAA  TTATTTGAAT  TAGGAAGATT  TTCTAAAACT
103301  AAAAATAAAA  CTTTTAAGGG  ATCTAGAAGA  CAAATTTTAT  CAGTATCTGT
103351  ATTTATCATT  TAGGTCATGT  ATTCAATTAC  CTTTTGAGAC  ATTGGGATTA
103401  TAAATCTATT  ATAAAATATT  ATTATCCTTA  TGATAATTTT  TATATTTTTG
103451  AAGATAATTT  GGGATTATTA  GTTTTCTTAA  GTATAGGATG  TCTTTATTCT
103501  GCTCTATCCT  TTACTAATAA  TTTCTAACTC  TGTTCGTTTT  CCTTCACATA
103551  TCTTTTGTCT  CTCCTAATCT  GAATACTTTC  CAGTTGTACC  TTTTATTTAG
103601  GATCTCAAAA  GGAGTTACAG  TGCAGAAAGT  CTCTAACTAC  TGTTCAACGC
103651  CATAAGTTAC  TGAAAAGCAG  TTAGATTTGG  GAGCCTGGGA  CATAAAGTTC
103701  ACTCTTTAGG  CCTGGGTAGA  TTTCAGCCCT  TAAAGCAATG  TACACATATG
103751  TATTGTGCAT  AATATTTATT  TATGGTTTTG  GAAATCAGAC  CTATTACATT
103801  GTAGTTACTT  CTTTTACAAA  TGCTGTACTT  TTAATTTTCA  GATGCATGCT
103851  GTCTTTACGT  ATTTAGATAT  ATATGCTTTC  TTGCTTTTTT  AATACAATGG
103901  TCTCATAAAT  AAGATATCCA  GGATTTAAAA  TTTATCCCTC  ATAATGTTCT
103951  ACCTTTGAAG  AAAAAATAAA  GCTAGAATAA  TAATTCTTGA  GATTGCTTGA
104001  AAGAAAACTT  ATTAAAGAT   TTGTGTATAT  TAAATAATTA  AACATTGTTT
104051  AATAAATATG  ATATTTTCCA  CCGCTCCAAG  AAAATCAAGA  TGACATTGTT
104101  GACACAACTG  ATGGGCCTGC  CCAGAGGCTA  TATTGTCATT  ACAGTTTTGG
104151  AATGTCAAGA  CTAGATTTTA  AGAGCAAACA  TAATTCTAGT  ATGAAGTGTT
104201  TGAATTTGTT  ATTTCTTATA  TTGCATTAAT  TATTTTCAGG  CATACTAATT
104251  TTTCTCCGAG  TTTAATTGTT  TGCATACTTC  TCATGTTTTT  GAAGTGTAGC
104301  TCACCTAATC  AGCATTTTCT  AAATATTTAG  CCCTTCTTTC  TTCATGTTTT
104351  CTATTCCCAT  GAATAAATGT  ATTGTTACAC  ATGTATGTAA  CTTTGTCATT
104401  CATCTTTATA  TTTCTTTATT  TTGCTCTGTC  TTGTGTCTGT  CTCTAACAGG
104451  CTCATCTCAT  CTCTGTACCT  CCCTCATCTC  CTACCCTTTG  GGTACTCTAA
104501  ATGCGTTGAA  GGTTTCTGAG  GTAGTGTAAA  CCAGCTTGGT  CTCTAGGTTA
104551  ATAGTAATGT  ACCTCCATGT  CTTCATCCCA  GTTTCCTTCT  AGTGCACGTG
104601  ATTTACAGTG  GATTAAGCAG  TAGAAAATAA  TGATACATTT  ATGCAATATA
104651  TTCTATTGAT  ACGAATTTGG  CCAACTATAA  ATTTAAAAGT  TGCTAAGCTG
104701  CTGTTTTATA  ATACATATGT  GCATACTTAA  AGAAGAAGAG  AACTATAGCT
104751  AAAGACAAAT  GAGTTAATAT  AATACTCAAC  AGGGTTTTTG  AGAATATACC
104801  TTTTTTTCCA  ATAATGAAGT  GTTTTAAAAT  ACTGCTATTA  ATTAAAGTCA
104851  TGAAATAGTA  CTTTTGATGT  AATCTCATGT  TCCTTCCTTT  ATGATAAAGA
104901  AACTGTATGA  TAAAGAAAAT  GACTTTACCA  GTCTCACAAT  ACACTTAGTG
104951  AAAAATTTAT  GGTGTAACAA  GCAGAAAAAC  AGCTTCATTT  TTCTAGTTAG
105001  TATTTACTCA  AAATACTCTC  AGTTTTCTCC  TATGCTAGCC  CCATATCTAT
105051  TATAATTTGC  CCTAGAAAAA  TTCATGGTCT  ATAATAACTT  TTTATCTGAC
105101  ACATATGATC  CCTACATGAA  GACTCAAAGA  AAAAAAAATG  AATTTGTAAC
105151  TCAAAGAAAA  GTAATTCAAA  CAGGTGCTAA  TATGAATACT  ATATAATATA
105201  TATCTTAATT  GGTAAGATAT  CAAACAAATA  TTAGAAATTT  TGATTTAAGG
105251  TGAAGAACTG  TTGAGCTTAA  CAAGTCATAA  AAATGTATTT  AGTAAATAGC
105301  AGAGGAGATA  TTAGGTTTCT  CAAATGTTTC  CATTTACGTT  TAAATAGTCA
105351  CAGATACCAG  TTAACCTTAG  TGATATCTAC  TTTTCATCAG  TTTTTTAATA
```

FIGURE 3HH

```
105401  ACTTACCATG AATATAATAG ATTACTCAAT GTCTTTTTTT CATAGTCATC
105451  CTCATGCCTC AAAATTTTCT AGGTATTATA AAAACAGAAA TAATTGAACA
105501  TTGCAATGAC ATTCATTTAT AGGAAATAAT ATGGGTAGTG ATCAGTGGAC
105551  AAAGGTAATA TAAAGAAACA GGTAAAAAGC ATTTCTTTGT AAGTACTGTG
105601  GTATAGCACT TTAAAAAAAT TACAGTATAC AATTAGCATT CATAAAGCTT
105651  CCACACATAT ATGAGTGCTA AATCCTAAAC TTATACTAAT TTTTTTCCGT
105701  GAGGGAAAAA TATCCTAGCA AATCTTTGT TATTCTATTA GGAAAATTTT
105751  TACTTCTGGC TGAAGGTAAA ATTCTGTACC TGAAAATTGC CATTCTGTGA
105801  ACCATTATTG CCTTAGACAT CAGCAAGAAA ATAAGAGATG CCCTTCCAAA
105851  ATCTGAATTT ATTGATTCTT CTTATGTAAT AGTATTTCAG TTAATGAAAT
105901  TAATTTTGAA ATTTAATCCA TCATCTTCTT TTGAAAGATG GTAATAATTG
105951  GCATAAACTA AATAATTGGC ATAGAGAAAA ATATATTTAA ACAATGATTA
106001  CAATTGATAA TAGAACTATA AAATCATTTT TAATTTATGA GGTTTCAATT
106051  AGTTCTATAT ACTATAATTC ATGCTTGAAT ATTGGTTTTA TATATACAGC
106101  AAATAAAATG TTAAGCTTTT TAAAAGACTT CTATTTTTC AAAATAACCC
106151  AAATCAAACT TGTTAGCTTA ATTTTTAAAT AGTATCTATA CATCGTTCTA
106201  TATACTACCA AGTTGTGAAA ACTGCCTTGA GGATATACAC ATTTAATGTA
106251  CATTGTTTCA ACTTTAACAA ATTAACTTAC ATTTTTAGAA ATAATAGACA
106301  AGAAATAACA AGATTTGAAG TGCTACTTAA ACTTCGCAGG ACTTTTGATG
106351  TGATTAAATA TATTTAATTA TGAATATTAA CGCCTATCAT TTAACTACTG
106401  CTCTGAAATA TAAACGATAT ACAATTTGTG GTCTTTATGT CTATGTCATA
106451  GGCTAGTAGT TTTTATGGCT TTTTATATTA GCATACATTC TATACACATA
106501  CCTAGAATCT AGGACTAGCA AGAAGTTTAC TGTCATCTGA TGTGTCTGCT
106551  GCTAGTTAAA CTCTCAACTA GGTCATTATC AACATCACTT AAAATATTTA
106601  TAAAAATAGT TTCTAAATCC CTTCTTCATT ATCAACCTTA TAAAGTAATA
106651  TTTTCTAAAA TTGTTCTTGT TTTAGAACAA GAATAGCATA CAACAATCTC
106701  AAAATATATT ATTAATTA TTACATAAAA TATTAATTAT TAATTACTGT
106751  AATTATTTAC AAGGAGAAAT ACAAGTATTA ATATTTAAA CATACTACCT
106801  GAGCTGAAGG TAATTTATGA AATGCTCTGC TTAAAGTATA CAAATGAAAA
106851  CATAAGGTAT TCAATTTCTT CAAATGTTAA GTTCCGCATA TTTTCTATCC
106901  AATTCAAAAT TTAATCTCTT CAAAGTTAAT GACTTTGCAC TGGGTTGACT
106951  TTTGTTTTGT ATGTGTTTGG TGATAGAACT AAATAATTGT TCTTCCATGT
107001  AGATTTATAC CACACGAAAT GAATTATTAT AAGAAAGCAG ATATGTGTTT
107051  ATTTAATTTA TCCATGACTT GAGTTTCACC ACTCAATTTT ACAGAACATT
107101  CAATAAATTT AGTTTTAAAT ATATCTAATG TTCTAACTCA TTAAAATATG
107151  GAGAAATGAT GTGAAACTGG TGATTGAAGA CATCTGTTGG TAGCACAAAT
107201  GCATTATGTA AAAGATTTTT TTAAAACTAC AGTTATTATT TTGAGAATGG
107251  TAAATTGAAT GGCTGCTAAT GAACAGTTCA CAGTCATAGC TGCACATTGT
107301  GGTTAGAAAT GGGAGAATGA GAATAATTTA TGTAGCTTGT GTGACATTTA
107351  TCTGAAGTTT ATATATTTCC CTAGAATATG CTATACTCAG AATTTGTGAA
107401  CATGGTTTGA GGTGAACTTA TTTTAAAAAG TCATTTTATT TTCATCTTCT
107451  CCAAATATAT TCTTTTACAT TTTTTAATGA AAGTAGTGAA ATCCTTAAGT
107501  TCTAGAAGAA TATTAAGCCT ATTACTTTCT GGCATTATAA CAACTTTAAA
107551  CCATAAAATT ACTCCTATTA ATAAATGACC CCTGCTTGAG AGGCTTACTA
107601  GTCCAAAAAG CAAACTTATA GTAATATTTG AAAGTAAATA ATTAGTATTT
107651  TTAACCACAG TTGGTAATTT CTAGGTAACA AAGAATAAGT GGGTTTTCAG
107701  GAGAGAATTT AAGGGAAAGC GTTTTTGTGG GGTTTTTTTG CATTTACACT
107751  GGGAGTTTAG AGAATTTCAG TCAGAGACTG AAGTGATTAG AGATGACACT
107801  AAAGGTGAAT TTAGAATAAA ATTGGGATTT AGGTAGGTAG AGAGAAGAGC
107851  CAGACAGAGA GAGTATTTCT AACATCTACA ACTGACGTGA ATAAAAGCAG
107901  TATTTTGAGT CATTGAGTTA TTATCATAAA TATGAGCAAG GCTTCAGAGT
107951  TGAGTTGTCT TTATTCATTT CACAGAAAAA AAAAAGATGG GGAGATGTTT
108001  AATTTTCATT GCATTGCTAA CTATGAACAA ATTTCATATG ACTTACTGCA
108051  AACAATGTTT CATATTTAGT GAATGATGGA ATTAACCTT TTCTAGCCAT
108101  TGCCACACTC CCAGAGCTAC TATCCACTTA ATTCTCATCA TCTTCCCTAT
108151  AATAGGGAAA AGAACTACAA GATAATTTTG TTTAATTTA CTGTTAATGC
108201  AAAACTAATA CAATTCAAGT TTTTATCTTT TCTCACATCA CAGACTAGTA
108251  CCAGTATGCT TATATAATAG AATAGTCAGA GGCATAAAAT CATATCCATA
108301  GTGTTCATAC TGTGTGAAAT AAAGGTATTT CTAACTGAAC CCCCTTATAT
108351  AGAAACTGT AAGAGTTATG GCCAAAGAAA TTTTTTTCAT TGGTTTGGCT
108401  TTTTAGATGC AATAGAACCT AAAAATATAC TGTGAATTT TCAGATAAAT
108451  ATCCGTCCTT TTTAATGCTT TACATTTTAA ATTCTTCAGG CTGAGCTTAC
```

FIGURE 3II

```
108501  ATCTTAACAG ATGTCTATCT TGTCTTTTTA TATACGCCAT TAGTTTTGGT
108551  TGGAATCTAG AAATCAATGA TGCTTCAAAA TCCTGGTAAC ATTTACATAT
108601  TTTGTAGATA ATCCTTATTG AAAATAATCT TTTAGAGTTT TTATCTGAAA
108651  ATATGTTTAT TTTTTACTGA ATTCTCCCAT TTCTACCTGT TACTGATAAT
108701  AAGAATGTTT GTATTAATAT AGATTTATTT ATATTGACCC TTCATTCTTA
108751  CATCATAAAT TTATTAAGAA ACCTGTTAGT CTAGTTTAAT TGAAGTGCCT
108801  ATTTCACTCA GTATGTCTAC AACTATGTAA GTAATTGTTT GTATTCTGTC
108851  ACAACAATCT CTTTTAGCAG GTCAGGTTGT TTCTCCTCAG TCTGCTCCAG
108901  CCTGTGTTGA AAATAAAAAT GATGTTAGCA GAGAAAACAG CACTGTTGAC
108951  TTTAGCAAGG TGAGCTTTTC TCCCTCTCAT CTAAGTAAGT TGCTAAATTA
109001  CTACTAGAAA TTACTACCCA TTTTAAGAGG TGTTGACACA ATATTTTGCA
109051  TGCGCTTTTT GTTTCTTGTC AAAGCTTGAT ATTGTTACAG AAAATGTTAG
109101  CATTAAGTCC ACATGTAACA TTTTGCCTAT TCAAAAAAAA AAAAAAAACT
109151  GAACCTGTGA GTTTTATGCA TAGTATTCAT GTTTCAGCCA CTTGGTATAA
109201  TGTTATCTCT TCCAATAAAA AGAATAACTG GGCTTCACAG GGAATTTAAC
109251  AGAAGTTTAA TCTATTTTTG TTTGTTGTG TTTGTTGTTC TTTGTTTGTT
109301  TGTTTGAGGC AGAGTCTCGC TCTGTCACCC AGGCTGGAAT GCAGTGGTGC
109351  AATCTTGGCT CACTGCAACC TCCGCCTCCT GGGTTCAAGC AATTCTCAAG
109401  CCTCAGCTTC CCGAGTAGCT GGGATTACAG GCGTGCACCA CTATGTCTGA
109451  CTAATTTTTG TATTTTTAGT AGAGACGGGG TTTCACCATC TTGGACAGGC
109501  TGGTCTCGAA CTCCTGACCT CAGGTGATCC GTCCGCCTCA GCCTCTCAAA
109551  GTGCTGGGAT TACAGGCGTG AGCCACCCCG CCCGGCCAAG TTTAATCTAT
109601  TGTTTAAAAA CTTTGGCTAG TTTGTGTTCA AAATCACTTT TCTTCTATTT
109651  GTGGGAAAGC AAATCATAAT ATAAACTGA ATTGTTAATG TAATTAAGGA
109701  AAAGTCATTA CTGTAAGGAA ATCCTAGAAG GACACAGCAA AACTGAGCAG
109751  AGTTTTAAAT AAAAACATAT TAAGAACTGA CTGTGTTGAG GGATACATCT
109801  AATTGGAGAC AACTGAAGTG AAATCATTAA CTTGAATGTA TTCTTAGAAA
109851  ATGAGTCAGT GACAATGATG TGATTTTGAT TAGCAAATTC CTGACATTGT
109901  ATATGTGCCA TTGCAAGCTA TGGCAAAGTA ACAATTGAGT GGAAAAGAGG
109951  AGTTTCTAGC CGGGTGTGGT GGCGCGTGCC TGTGGTTCCA GCCACTTGGG
110001  AGGCTGAGGT GGGAGGATTG CTTGAGCCTA GGAGGCAGAG ATTGCAGTGA
110051  GCTGAGGTCG TGTCACTGCA CTCCAGCCTG GGTGACAGAG TGAGACCACA
110101  TCTCAAAAAA AAAAAAAAAA AAAAAAAAA GACAATGCAA AAGAGAAGGA
110151  GTTGAATAC TTGGTGAAAA TACGGCAGGT TAACAATTCT CTTTATCTGA
110201  GTGGCTGAAA TAGAAGTAAC TCAGAGTAAT ATTTTAATAA AGCCCTTAGC
110251  ACTGGCAATA ATTATAGTAG TGGGAGGAGG TGGGAATGGA TGGAAGCAGT
110301  AGAGGAAGTA GCCTGAATCA AGGTTCTGAA AAGATTAATA GTGATCAGCT
110351  CCTTGGACCT GTTTCAGAAT CCCTCTGACA ATGCCTAAAT AATCTAGATC
110401  TAGTTACGTG CATGCTCTCC CTCTGGTGCC TGGCGGAGTC TCCGTGGGAG
110451  CATGGTGTAC CAGCTTAAGT CTGTTAATTA TGCGTGCAGG GACTGGGAGG
110501  CCAACAAAAG GGGCATACTA GTCCATGTGG GATGAAACAA AGGCATGAAA
110551  AAGGACCTCC ACACCAGCAA GAGAGAGAGG TGAGGGCATA CTCGGGCTCT
110601  ATTTCTACAG TGGTTCAAAG CTCATTTCAC TGTATGGAGG CATGTGATTC
110651  AAACATTAAG CCAGTTGAAA TGTATTCCAT CTGCCACTCT AAGAACTATC
110701  TTTTTAAAGC ATTGCATCTT CATTCATCTG CAAGTTGGAA AAAGTTGTCA
110751  CAAACTGCCA TACATTAAT TTCTGATATT CTTAATTTGA AATGATCTTA
110801  AAAGCAATAA TGTAACGAGC TGCATATTTA TGTATAAATG CATTAACAAC
110851  ATAAAGAAGG CATATTTAAC ATCCTCAGAA ACAATCATTA TAAAGCACAT
110901  AGCTCCTCCT TTCAAATAAA TTGTGATTTA ACTTTTAAA AATAATATAA
110951  CCTTTATACA CTGATTGTGT ATCTCCATAT CATGTTGCTT TTGGTTGTGT
111001  GACCTGCCTT TGCAGCCTTC AAGAATACTT CATCACATAT GAAAGAAAAT
111051  GAAGATTGCC AGTTGTAGGC AGTAGTCTCA TCTTCTGGTC CCCCCTCAAA
111101  CAGTTAAAAC TATGGAAGAG TCAAACTTCG ATTTCCTTTC TTTTAATCCT
111151  TTTCTTTCTC TTCACATTTG CGATCACTGG CCCGTTTCAT CTTTTAATAG
111201  GCAAGTTAAA TTTCTAGAGC CCTCTACTTA GTGTCAGCTG TTGTTCATAG
111251  CATGGCACAC TGGAAAGTCT CTTGTTCATA GCATGGCACA CTGGAAAGAA
111301  TGTGGCTTTT GAGAAACAGC ATGAGATCTT GAATCCCAAC TCTGGCATTA
111351  TAAACTAGCT GATCTTGGAG AAGTTCTCTA AAGTTCAGCC TTCTCATTTG
111401  CAAAGTAAGA AAACTATTTA CAATTTCGTT GTGAAGATTT AATGAGCTAA
111451  TATAGAGGGA GGTGCTGGAA CAGTGCTTGA CTTGTAGCAG GTATTTAATA
111501  AAAGGTGGTT ACACTTATTA GTGTGGTTAT TAGTAGTAGT AGAGATAATA
111551  GTGTCAGAAA TGAAACACCA GACCATAATT GAATGTTTTG GTCTCCACTG
```

FIGURE 3JJ

```
111601  GGTCTTTAGT GCCTTGAATA GTATTTGGTA TATATTTGTT GAATGAATCC
111651  TTCAAGATTC AAAATAATGT AAGCCCAGTT TTGGAATTTA AAAAAGACTA
111701  AGTAAGATTT TTTACTTTAA AGTCTGAGAG GGCAGAAAAG TAGAGTTTGA
111751  AAAGAGCAAT TGTGATCTAT CACTATGGAA ACAAATTTTA GTGCCAGATT
111801  TTGCAGGTGC ATGAGTTGAT ATTTTTTAGC CTTATGATTT TAGTTTAGTA
111851  GTGAATTTAT CAGAATTCAC CTAGTCTCCA GGTTAGTTCT CTGTTTTAAT
111901  ATTTTAAGTC TTAATATACA GATTCCAAAA CCCCAGAATC TTAATATGCA
111951  GATTCCAAAC ATTTTGAGGT GTTAAGAAAA AAAAGGTCTT TATTCATCTT
112001  ATATGATTTG ATCATATTTA TTCCATCTAC ATTCAACCTA CATATTTGTA
112051  ACCCTTCCAG TGGATAGACG TATCAAACTT ACTTAAGGAA TGATTAGGAA
112101  AATAACTGGA ATTATCAGGT TTTAGCTTCC CATAATACTT TTAAAAAGCA
112151  GATGTGTCAA AGCAATATTT GTTTTTGTTT TTCAAGCTGA CAGTGGAACG
112201  TAGGTATTTT ATGTTGGTGG TGTTTTCTTT TACTTCAAAT GACCCAGAGA
112251  TGGCTTCACA TAATTTTCTA CATAGAAAGA ACTTCCGTCT GCATCTAGCT
112301  TTAGTGTATG AAACATATTA GAGAGAGTTG TATTATTTAA TCCTAGAACT
112351  GTAGGAAACC TTAGACATCT CCTCATTTAG TCAGCAAGAA AGCTGAATTA
112401  TAGAGTGATT AAGAGAGCTG CTCAAGATCA CTGGCGAGTT AGTGTCAAGA
112451  CACCATTTCT TCCCAGAGAA TCCCTATGAA GTTTCTTGTA CTTTCTATAA
112501  GGGGCTGAAG GCTTAAATTT TCTCCTTAAA TTTCCATCTG TTTTTCCTTT
112551  AACTCTTAGC GTGTAGTTTG CCCAGACACT TCCAATTTCA CCTTGGTCTT
112601  CTATCTAATC TCATTCCTTG TTCCCTAGAA ATGTAACTGT TTCTCATCCA
112651  CAGATTAAGT ATCAAAGGCC CAGAAAGAAA TCTTTCCACT ACCAGCATAA
112701  AGGTGAGGTC TGGGCAGCCC AGAAGCATGA GTGTAAATAC AGACCCAGAA
112751  GAGTATAGCT CGATTTCTTC AAGATCCTAT TCAGAGGACC AGAAACTTCC
112801  AGGATTTCCT TCTTGTCCAT TCCAAGTGTT TGTGTTCACT TGACAGTTTT
112851  CTTAGGGATG TAGTTCAACC TAGATTCTCT AGAGCTGCTT TACATATTTA
112901  TAATTTTATA AGAGGTCACA TTCAGGTCTT TAAACATAAT ATTTTATTAT
112951  ATTAAAAGTT GCTTAGGGGG CCAAGGGCAT GGTGGCTGAC ACCTGTAATC
113001  CCAGCATTTT GAGAGGCCAA GTCAGGAGGA TCACTTGAGC TTAGGAGTTC
113051  GAGATCAACC TAGGCAACAT GGTAAGACCT CATCTCTACA AAATCTAGAA
113101  AAAATCAGCC AGGCATGGTG GCGCACCTGT AGTCCCAGCT ACTCAGAAGG
113151  CTGAAATGGA AGGATCAGGA TGGCTTGAGC CAGGAAGTTC GAGGCTGCAG
113201  TGAGCTGGGA TCGCACCACT GCACTCCACT CTGGATGACA CAAGGAGACC
113251  CTGTCTCAAA AACTTAACCA AACCAAAAAA GATAGTTGGT TTGTCAAATA
113301  AGTTTCTTCA TGAAGTATAT AGTACACAAA CACAAAATAT AGGGTTGCCC
113351  CACGAATAAT ATAATATGTA ACTATACATA ATATAGGAAT AATATAATTA
113401  GATAATATAT AATCGATTAC TTCCCAAAGT ATATGATTAC TCCAAGAATA
113451  ATGTAATGTA ATGAGTATAA TACAATGGCT ACCCCAGATA TGTGCTATAG
113501  TACTATAACT TATTCCATTT GAAGTCAAAA GATGAATTTG CTTATCCTGA
113551  ATTTAAATTC TGTATATTTT AATGTTTTTT CTAAATAACA GGTATCAATG
113601  ATATATTAGG TATTTTGTAA ATTTAAAGAT CATATGTAAT GACCATATAT
113651  TTTCTTTTAC AAAATTTAAC TATTTTAACA TACTATGTAC TTCTTGATTT
113701  AATTAAATTT CATCTTTAAA CAGTTATTTC TATAATCACC AGTTGCCCGA
113751  GGCACAGACT TTCATAGTTA AGACAATGGC ATTTGTCAAG CAATAAATGA
113801  GTTTATAGAA TTTTCAAGGT GGAATTTAAA TTTCAGGTAT TATCAATATA
113851  ATTCATATTA TCAATTATGG ATTTTAAAAA AAGATGTTTT CTCATTTTAA
113901  ATTTTGTTCA GTATATTTAT ATTGTATCAT TGTTCTTTCC ATTGAGAGAG
113951  AAAACTTAAC TGTTTATTCT TTTAGTAACA GAAAGGATTA TGAGATTTAT
114001  TATGTTTTCC TCACAGAGCT GATAGTATAT GGGAAATCTT CTATTCCCTC
114051  CTTGGGAATT TTGGCATTAC AATAAAAATG TAAAGCATTA CTAATTTAAA
114101  GCATCTTAAA TGTGTACATT TCTCCTAACT AGATAAATAC CTACAAAAAT
114151  ACCACAATAA ATCCCATGAA ATTTAACCTT ACTTATTATA GTAAATAAAT
114201  ACTTTTGCTA TCTATAAACT AAAAGATCAG ATTCCACAAA AGCAAAATAT
114251  TTGCTGTATA ATCCAGTGTA CATTAATTAT GAATTTACAA ATTTATATTT
114301  GGAGTACATT TGTAGCTTAA AAATTTTGGA TGTATAATAT TTGTTAGATA
114351  TTTTTATAGG CAGTTTTGCT TTGTTAAATC ATTCTTCCTT TCCTTTAAAA
114401  TAAAATAATG ATTCTATTTA ATATTTTTGA TGGAGTACTG TAGGATATTT
114451  TTATATTTAA TCCTTGTGAA AGAACATATG CTTCCTATAC TAGGTTATAT
114501  ATTTTGTGGT ATCCTTATTC TTTGGAAAGA TTAATTAGTT ACAAAACTTA
114551  CAAATAGCTG TACTATCATC TTGATTTCAG AAAGCAACAT ATTTAATGTA
114601  GTCACTAAGT ATTACTATGG ATTTTTTCAT TTTAAATTTT TGAGAAAAAT
114651  ATTCTCAAAT CATTAAACCT GCAAAAGAAC TATCTAGGCT AAAAAAAATC
```

FIGURE 3KK

```
114701  TTCTCAGCCC CACTCATATT TGCCAGAGCT CATTCCTCTC TCGGCTATTC
114751  TCACTTTGAT CTTTGGCCCT CATTTCATTA ACATCAGAGC ATAAGATCAA
114801  TTACTAGAGC AGATAAATTC TTACTCCCCT AAAAACAGAG TTTCATAAAA
114851  AGCTACTCAA GTGAATTAGA AACAAGACAT AGATCTTGTA CAATTTACAT
114901  TAAAGTCACT GCTTGTCTTT CACTGAGGCC CTATGCATAA AAATTGATAT
114951  TTATTGTTAA GGATATTTTG CATTCATTTT TTAGACTTCA CCCTTTATTC
115001  TTAGCATTTC TTCTCGTTAA TGATCACTTT TGCTTTGTGT ACATTCATTT
115051  CGATCACAAA CATCTCATGT CAGAAATTCA ACTATAGCTC TTCAGTAACT
115101  CCAAATGTTA ATATTTTTTT CTTATTTTTT TCTACTGTGT CATATCTAAA
115151  TTCTCAGATG AAAAACCAAT ATTGAAGAAT TACCAGGCCA AGTATATAAT
115201  GTGAAGAATA TAGAACAACT AGAAAAGAGA AGAAGGTTAA AGTCATAATT
115251  TATACTGTAA AGAGAAACAG GATTATATTT CTTTTGACAT AAGCATATTT
115301  GAGTATCAAT TAAAATGTAT TATGTACAAA AATTAGGTAA TGTAGTATAA
115351  AATATTAAAT CTGTTGGCAA ATGCTAATTA AATTATGGTT AAAGAATAGT
115401  TATTTAACTG AACTCACATA CTTTTCCCTG TCTAAAATTT CAAGATTGTT
115451  GAGGCTGGAG AAACTTCTTT TAAAAATAAT AAATAGAAGT ACCAGAGTAC
115501  TCAGCTTATT GATGACAAGT TAAAATAATC CACAAGTAAA GAAAAAAGGT
115551  TATTATAGAA AAAGGGCAAA TGAGATGTTT AACTGTGTGT ATTTATTTAA
115601  ACTATATTTA TTCATGGATT ACTATATGTG AAGCACTGTG CAAGAATATG
115651  ATTTACCAGA TTTTTCCAAT TTGATTTAT CATATTTACC TGGTGATGCT
115701  TGCAGGTTGA TCTGCATTTT ATGAAAAAGA TTCCTCCAGG TGCTGAAGCA
115751  TCGAACATCT TAGTGGGAGA ACTGGAGTTC TTGGATCGAA CAGTAGTTGC
115801  GTTTGTCAGG TTGTCTCCAG CTGTATTGCT TCAAGGACTG GCTGAAGTCC
115851  CAATCCCAAC CAGGTAAAAA GTATAAAAGC GTCTTTTGTA TTTTTCTTAA
115901  ACCATCTTTT CATGGAAAGA AAATGAGGAT TCAATGTAAT TTTCTGTTAG
115951  AGTTTTGACT AGAAACTAAT GTGAAATCCA CAAAACTACT ATTAATTTTT
116001  GTTTGTGGAG GAGGGGAAAA GTGCTTTAAA AATTATTCTC TTCTTTCCTC
116051  CCTTCTCTCA AACTTCTGCT TCATTTTAGG CACATTCCTC ATCTCAAGGT
116101  ACCCTGAAGC CATATGAATC CTTTTTTTTT TTTTTTTTTT TACATTTTTG
116151  GTAAAGAAG TGGTAACATG TTAGCTTTTT CTCAAAGATT GCATTAAATT
116201  GTCTGCTATA GAAAGAAAGG ATCCTGTGCA TGAGTGCGGT CAAACTCAAA
116251  AACAGCAAAG TTACTAAGGT TTGCTTACAC TTGAATAAGA AGGCCTTCAA
116301  AATGCATGTA AGTGCCATCG TTAGGATAGC GTCAAATATA TGTTTCAATC
116351  CTAGGCACAG TGGGCTTCCG ACACACAGGG TCTGTAGAAA CACTGGTAGA
116401  AGTATTATCG CAGTGTGGTT GGATGTGAGT TAAAGGTACA AATTTAATTT
116451  GATGATCAGA ACTTGTTTCT CATTTAACAA TAAAATAACA ACTTAGGGAT
116501  AATACAAACT GAATTATGCT TTTCTCATTT TTTAGAATAA GGCTATCCAT
116551  TACTAAAACT GTAAAAAAAA GAAAAAGATA AAAAAAAGAA AGGAAACACA
116601  GAATATTGAC TTTAGCACAT TAATTTCCAA GCAATTTACC CAGGAACCTT
116651  GTTTTCTTCC ATACTTCTAC CATCAGTGTG ATTCCAAAAT GCAGATAGCC
116701  TTTTACTCTA GTCCTATTCC CACAGCAAAA CATGTATATT TAGGGCCCCG
116751  TTCCCATATG GCTGGTGCCC TTTGTTTGAT GCTACAGCTA TCTCAAAAGC
116801  TGTTAGTGCG CCTCCTCTTC CAAACATTGA ATACCTTAGC CAAGTTACTT
116851  GATGAAAAGT TCAGGTACTG TATCAACTGT AGAATATATG TCCTCTATGA
116901  ATCTTTGGCC TTAACTCAAA ATATAGCAGA TTACATAACT CCATGCTTTG
116951  ATTATGGATA AAATATTCTA CAACTATGGA ACAGCACAGC AGGAGAGGC
117001  CTCATTTTTT AAGAGCTCAG CTGACTGGAA CGGGATTCAG TGGTTAAGTA
117051  CCTATGTCTG ACTATGGTTT GGGGGAGGAA TCTAGTTACT GTTCAGATTA
117101  TAGAAAGAAG TCTATGTTTA TCCTGTTTGA GAGTTACTGA GATGACTGAT
117151  ACACATCAAC TTTTATGTAC AAAGGGAAAG GATGAACTGA GCACATTAAA
117201  GTGGCATCTG ACTGTGTGAT TCAGGCTATA TGTTTCTAT GGACAACCTG
117251  TAACCTATTC AAGGTTCTG GGAGTCTGGG ATTTATATCT AAGATGTTAA
117301  ACTTGCTAAT GGTAGAGTTA CTATTATAGC AGTTTAAAAT TTCTTTTCAG
117351  TCCTCCAAGC AGTGCATTTG TGTTCCACCA CTTAGGAAGG TGTCTGGTGA
117401  ACTATGAGCA ATGATGGCT ATTTACGACA ATGATAGTGC TTGTATTTCA
117451  AAAGAAGGAA AAGAAAATT CCCATGAGTA GAAAAAGCC GTGATGGGGT
117501  TATATACCCT TACTGTGAAA ACTGTCAGGT TTAAGTGACC TTATTTCATA
117551  CTGAGATAGC AAAATATGT TAGAGAACAA CGGAGAAAAA AATTAGGGCC
117601  ACTGTAGAGC AACTGTATGA GAAAGATTT AAAGACAAGA CTATTTAGTT
117651  AGGAAAGGTG AAAAATGGAA GATTAGTTGG ACAAACAAAA TAAAGAAAGC
117701  CATTCAGGGT TTCTTATTAT CCTTTTTTTG GAAGACAAA AGGCATCCTA
117751  TTAATACGAT GGCAACACAT AGTAGAAAGG TCAGAAAATA ATCTTTTAGA
```

FIGURE 3LL

```
117801  TCTTTAAAAA TAGCCCATGG AATGGAAACC TGAAAAATAG CAAGATGTAC
117851  ATAGGTTAGG AAGTTTCTTA AAAAGCTATT ATAGTTGATA AAGCACCTGC
117901  TACCGAATTA AACCATTCCT GTTTTTAATG TATACTGGAC ATTTCTACAT
117951  AGTAGAAATT GGCTTGGGTT CAGTTGTCAC TGCACACAC AAAAAATATT
118001  GTCATATCCT CTACAATTGT GTAATATTTG CCTCATGTAA AAACATGTAC
118051  AATCTCTAAA GATTACAACT AAATGAGGAG TAGAATTATA GTAACTATTT
118101  TAGTACACCT TGTGAAGTCA TTAGTCTTCA TACTTAACAG CATAAACCAT
118151  TTAACAAATT AACACCACAG AATGATATGG CAGAATATAG GGCATTCTTT
118201  AATTTTCAAA ATTTCCAGA AGGATTGACC TTCTCAGAGA CAGGGCAATT
118251  ACCAGTCTGC TAAAGTTAGA GTATCTATTG ATTTCTTTAA AAGCACCACT
118301  TGTGATGATG AATTTGCCAA ATGTTCGACC TAATATAGAT GGAATATTAT
118351  AGTGCAGATG CTATTTTTAT TCCTCAGCAT TATAAATAAT AGATCATTAA
118401  CTCCCCATTT TCTTCTACGT GGCTGATCTT TGATTCCTGA CAATAATTTT
118451  TTATAATGAA AATTGCACAT ACACCTACTG TTTTTGACT CTATATTTTC
118501  TCTGTTTTGC TACTGTGTTA CCTTTGTCCC CTTTGAACTA TTCGCCATTT
118551  TGCATACAAG TGAGTTTTCT TCCTTCCAAT TTAGAAAGGT CTAATCAGAT
118601  TTTACTTTTC CCACTTTCCT TCTCTAAGGA TCATAGAATC CTTAAAATTC
118651  CCAATAACAA CTGCACATGC TGTACAGATA ACTAAACGGA GAAACACTGT
118701  GATAAAAAAA AAAACACGG AAAACCATGC ATTCCCATTG CTTGAGGATC
118751  TTAAGCATAA GGGTCAATCA TGGTAAAATT TTTCAAAATA ATAATGAACT
118801  ATGAAAAACT ATGGAAGTAT TTGCCATCAC AATCTCCATT TTCAGTAATT
118851  CCTTTGAGAT GAGTGATTCT GTATTACTAA AATTATTTTT ATATTTCTAC
118901  CTTAAAACAT TTTTTTTCTT CTTAATTACA GATTTTTGTT CATTCTTCTG
118951  GGACCCCTGG GAAAGGGTCA ACAGTACCAT GAGATTGGCA GATCAATTGC
119001  AACCCTAATG ACAGATGAGG TATTTATTCA AGTTCTTTGG GAACATTTTC
119051  CCCCATTAGG TATACCTAAA ACTTTTGGAG GTCCTCTTTT CATGACAGTT
119101  TGTTGTGAAT CAGATTTCTC TGTATTGAAT CCCATTCTCC CATGCTTCTG
119151  CTATAAAATC TCCTTTAGAA AAATGTTTCC CAAAGGGATA ATAAATTAAC
119201  ACCCATGAAT ATAATATTTT AAAACTTCAT AGTGTAAAGA AATTTTTTCA
119251  GTGACACTTA GAATATATTA TTAATATTCC CTTTATGGTA TATGTGCTAC
119301  CAAAGTAAGC ACCATTGTTA ATATCAATGG AAATCTTGTT TTGAGTAAAG
119351  AATTTCGAAG TCTAAAGAAA AAACAATAGC AGTTTATCTG AATAGTATAC
119401  ATGACACCAA AATGCATGCA ACATCTATCA ACTCTCTACA GTTGCCTGAA
119451  TGTAGATATT TTTAACCTGG GAGTCTGGGG ACTATTAGAG AAGCTGTAGA
119501  TAGATTTCAA GGAGCTTGTG ATTTCTGTAA CAGAGCATGT AAATTTTTCT
119551  ATGTAAAAAA TTTGTATGTA GATTTTTTGG GACTGGAAAA AGCTTTCATC
119601  AGCTCTTCAA AGAAGTGTAT GTCTCAAAAA TATAAGATCT TTAAAGTAAG
119651  AACATAAAAA GTAGCATCAT ACCACTATTT TCCTTTACTT GGGTTCTCCA
119701  ACACATTATG GAAATTTGTT GTTATTGTTA ACGGGAAGAG CAGATGCAGT
119751  AGATCACAGA AGGGCATTA AATCAAAATT CAGTTGTAAA TGAACAAATG
119801  GGATTATATA CTTCTAGATT TCATCTAAAT AATTTAATAA TGTTTTTATT
119851  GAAATACATG GCTGCAGATA TTTGAAAATT CTGTAAAAAG AGCCAATTAG
119901  TATTGTATAT TACTTTTTCT ATGTTTACAA TAGCTAAAAT TTGAACTTGT
119951  TTTGGGGGTT AAATATTATA AATTCTTCAA TCTGTCCAAA TTATGTTTTA
120001  TAGTGTTATA TGAATTAGTT TTTGATATTT ATGCACAAGA AAGCAAAAGC
120051  AAGAAGAAAA ACATTTTTTC CCTCAGTTTT CAAAAGGAAC CAACTTAATG
120101  AGTGTATTAG TTTACAACGA CTGCCATAAG AAACTACTAC AAATTGGGTG
120151  GTTTAAAATG ACAGTAGTTT GTTTTCTAAC ATTTTTGAGG CTAGAAGTTT
120201  GAAGTCAAGG TGTCAGCAGG GCCACAATCC CTTCGAAGTC TCTAGGGGAG
120251  GATCCTTCCT TGTCTCTTCC ATATTCTGGT GGCTCTTGGT CTTCCCTGGC
120301  TTGTGGCAAT AGACCTTTGT TCTCTGTCTC CATCTTCACA TGGCTTTCTC
120351  CCAGTTGTCT CTGTGTGTCT TCTTATTTTC TGTTATGAAG ACAGACATTT
120401  GTCATTTGAT TTAGGGCCCA TCCTAAATCC ATCCAAATCA TTGGATTTAG
120451  GGCCCATCCT AATTCAGGAT AATTTCATCT TGAGATACTT ACCTTAATTA
120501  CATCTGCAAA AATCCTTATT TCAAATAAGG CCACATTCTG CGGCTCCAGG
120551  TTGATGTGTA TTTTGGGAGG AAATTATTCA ATCCACTGTA ATGAATAACT
120601  TATTCTATTT AGGAAATTTG TGAGAAGACA GGAGGATGAA AAAAATAACT
120651  TAATGAGGGC CATACACCTG ATTTAGCAGA ACTCTCTCTG AGAAAACACT
120701  CACAGTATAA AAGCTCTTAG TATTTCTATA TTGATTTGTA TTGTTATTCT
120751  ATGATTTAAG TATTATCACT TTCACATACA TTTGTTTAAT ATTTTGTTAT
120801  ATTTCAGACA AAAAATGTTT CCCCATCTAA GAAATTAGGG CAATATTTTA
120851  AGATATCTGT GGGGCATGAG ACACGTGATA ATGTGAGAGG ATCCTACTAT
```

FIGURE 3MM

```
120901  GTCATGGGAA GTACATGTAT ATCAATGTAT CTCTCTTCTC TTCATCCTCT
120951  ACTTCCCCAA TTGGGAATCA AGATTTTTCT CGACAGAAAG ATGTCAGTTC
121001  CAAAGTTTTC TTGACTAACC AAGTGGACAC AGAACAGGGA AACATCCATG
121051  TTCTATAAAT TTCAGATTTA GGATGAGAAC AGAGAAGGGG CTTCCACCTA
121101  TTTCTTTGAT TAGTGAGAGC TACCTAATTT GAGAATAAGC ATCAATCACA
121151  TAATAAAGAC TGAAATTTGA GCATAAGCAT CAGTCATCTA TTTTTTCAAT
121201  TATTTAGACT TGAAAGTTTC AGAGCATGGC TTTAGGTAAT CATTGTAGAT
121251  TATGGGATAG AGAAGCAGAA ACTCAACCAG AAAGCTACTC TAAAAGATAA
121301  GAGCCATTAG TTATAATAGG ACATGTTAAT TACAACAGGA CATTGATTGA
121351  ATATCAAAGA ATGTTTAAAT ATTTTTTAAA AGAGAAAACA GATTTGTATT
121401  TCTCAAAGCC TCGGTGAGGC AATTGTTCTG CTTATCTAAT TGCTTTGAAG
121451  GCTATTGAAT AATTGTACTA GGCCAGGTGT AATGGCTTAC ATCTGTAATC
121501  CCAGCACTTT GGGAGGCCAA GGTGGATGGA TCACCTGAAG TCAGGAGTTC
121551  GAGATCAGCC TGGCCAACAT GGTGAAACCT CGTCTCTACT AAAAATACAA
121601  AAATTAGCTG GGTGTGGTGG CAGGTGCCTG TGGTCCCAGC TACTTGAGAG
121651  GCTGAGAGGG GAGAATCACT TGAACCTGGG AAGTGGAGAT GGCAATGAGC
121701  CAAGATTGCA TCACTGCACT CCAGCCTGGG TGATGGAGCG AGACTCTGTC
121751  TCAAAAATAA ATAAATAGAT AAATAAATAA GAAAGAAAAA GAAAAAAGAA
121801  AAGAACAATT GTACTCATTA AGAATAGAAT TTAATATGTT GATTCATAGT
121851  TTACTTTGGT TAAAAAAAAT AGTGCATTGG AGTGCATTAT CAAACATAAA
121901  TTCCATGAGA ACAGTTAGCA TTTTAGCATT CAGTATTCGT TTTTATGACC
121951  TGATTCTTCC AAGTGCTCAA ATAAATATCC ATTGAGCTAA GTTCTGTTTT
122001  CTTTCCCTTC TCTGTACTTG GAACACTTTC TAGGTAGACT GTCTTCCTTT
122051  TGTATTTTTA GACTTATTAT GAGTGTCTGA CCCTCAGTCA GGGTTCAATA
122101  AATCTTTAGA ACATGAATCA ATTACTGAAT ATTCTAGACA TCATACCAAT
122151  ATTCTATCTT GAATCAAGCC AATAATTTAT TTTCTTCATT TCTGTTGAGC
122201  TTTGCTAGAG ATAAATCATA TGATTATGCT TATCAACACT GCTACCAATG
122251  TGTTGATCCC TTCACATTCT CAAAAATTAC TAAGCACCCC AAAGAACTTT
122301  TGTGTATGTA GATATGTTGG TATTTACCAT AGGAGAACTT AAAACTGAGA
122351  AATTTAAAAA GTATGTGTTA ATGAATTCAT TTAAAAATAA TAATAGAACG
122401  GGTTCAGTGG CTCACACCTG TAATCCCAGA ACTTTCAGAG CCTAAGGCGA
122451  GTGGATCACT TGATGTCACA AGTTTGAGAC CAGCCTGGGC AGCATGGTGA
122501  AGCCCTGTCT CTACCAAAAA ATTCAAAAAA ATTTAGCTGC ATATAATCCC
122551  AGCTGCTCAG CTACTTGGGA GGGTGAGGTG GCGGATCAC TTGAGCCAGG
122601  GAGGTGGAGG TTGCAGTGAG CTGAGATGGC ACCACTGCAC TCCAGCCTGG
122651  GCAATAGAGC CAGACCTTGT CTCAAAATAA ATACATAAAT AACAATAGTA
122701  AAGCCATTAC ATATTAACAT AAATAATACA TTTTAATGAA AACAAANNNN
122751  NNNNNNNNNN NNNNNNNNNN NNNNNNNNNN NNNNNNNNNN NNNNNNAGTT
122801  TGTATTGAGT ATCAAACCAG AAATGGAAAC AAATGGTCTA AAAGTAAAAT
122851  AGAATATTTG AAAGCAGAAT TTTCCTGGCA ATTTTGGGAC ATTTGGTCAC
122901  TGTAATTTAG GCCAGCATAA AGAATAATAT AGGAGTCCTT AATCTCAAAT
122951  ACTTGTATCA TTTCATCCCA AGTAAAATTT AAAGTGTCAG AAATATTTAT
123001  ATTATATTCA GTGTAAATTA ATTTTTTCTC TTCATCCTTA TTTTTATTTT
123051  CCCCACTTAC TATATTAAGT ACGTAATTCC TGAGTATGAT AAGATAAATT
123101  AGGTTATGCT GCAGGAATAA CCAACTAAAA TATTAATGGC TTAAAACAAT
123151  AAGGATTTAT TTCTATCATG CTAAACTTTC ATCAAGATGT AGGAGAGAGG
123201  CTCTGCTCAT TATAATCACT TAGGCCCCCT GTGCTTATAG AAGCTCTAGC
123251  TGGACCTGTG TTTTCTCAGT CACTAAACCA GAAAAAAAGC AATGTGATAA
123301  GTCACACATT GGTACTCATA ACTTCCATTC AAAACTGACA TATGTACACC
123351  CAAGTAGAAT ATACCTGATC CAAATAGCAA AGAAGGCAAA GAAGTACAAT
123401  CTTACCATGT GGTCTAGAAG AAAACCTGGA ATATCTGTGA ACAGCCTAAA
123451  TGGCTAACAT AGCACATGTG TGCGGAGGGG AGGTGGAAGG GACAAGTATG
123501  AAATGTAACT CATACTTTGA GTGGAAATGA ACTTTCTGCA CTGTGTAGAT
123551  ATAATATATA GTTGGCCCTC TGTATCTTCA GGTTCTGCAC CCTTGAACTT
123601  AACTAACTGC AAATCAAAAA TATTTGAAAA GTCAGGGTGC AGTAGCTCAC
123651  ACCTATAATC CCAGCACTTT GGGAGGCCAA GGTGGAGGAT GGTTTGGGGC
123701  CAGGAGTTCA AGACCAGCCC AGGCAACATA GCAAGACTCT GTCTCTACAA
123751  GAAATTTTTT AAAAATTAGC CAGGTTTTGT GGTACACACC TGTAGTCCCA
123801  GCTACTTGGA AGACAGGAGC TTAAGCAGGA GCTTAAGCCT AGGAGTTCAA
123851  GGCTGCAGTG AGGTATGACT GTGCCACTGC ATTCCAGCCT GCATGACAGA
123901  GTGAGACCCT GCCTCTAAAA ACAAAAATCA AAATATTCG AGGGGGGGAC
123951  AATAAAAAAT AACAATGTTA CAATAAAAAT AATATGCATA AAAATTATAC
```

FIGURE 3NN

```
124001  AGTATAATAA ATATATAGCA TATACATTGT ATAGATATTA TAATAATCTA
124051  GAAATGATTT AAAGTACAGA TGCTCCTCAA CTTTCAATGG GGGATTATGT
124101  CCCCCCATTG AAAATATCAT AAGTGAAAC  TATGTTTTTG ACTTATGATA
124151  TTTTCAACTT ATGATAGGTT TATCCAGACT TAACCCCACT GAAAGTTGAG
124201  GAGCCTACTC AATGCATGTC ACTTTTGCAC CATCATAAAG TCAAAAGATT
124251  GTAAGAGAAA CCATAGAAAG TAGGGGATCC TCTAAATATA GGAGTATATG
124301  CATAGGTTAT GTGCAAATAC CACTCCATTT TATGTAAGGA ACTCAAGTAT
124351  CCATAGATTT TGGTATCTGC AGGGAATCCT GGAACCAATC CCTCAAAGAT
124401  ACTGAGGAAT GACTATATAT CCAGAAAATA CTAACATAAC CTTAGTATTA
124451  TTTTCAAAAT GGAAACAAAA TTAACCTTTT AAATTAATTT ATTTATGCCA
124501  GGGTATAAAT ACTGCTGAAA TTCCAACAC  ATTTTACAAA TTTTTATTTC
124551  TATTTGTAAG CAAAGGCTTC CTCCAGAAAC TGATTTCCC  ATACATAAAT
124601  AACTTTGCC  TAATTCTAGT TTAATGAGCT TCCTTTCATC CTCCTTTTTC
124651  TTTCCCTTAC TCCTTCCCTC TAGAAATTTC AACATTCATC TGACATCATA
124701  AGACAAATAG TTACCTATAT GGATCCATAA AATAAATTAT AATATTTTAC
124751  AACATAAACT TCTTTAGAGT CAGAGCTGTC TATTTCTTCA AATTGTTATA
124801  ATCACATGTG AGATAACTGA GTTGAAAACA CTGAACACAT TAATATTTTA
124851  TAATTATTTT TAAGCTATAA ATAATATTTC TATTTCTTCT AAAGGTATTT
124901  CATGATGTTG CCTATAAAGC TAAAGATCGT AATGACTTGG TATCAGGAAT
124951  TGATGAGTTT CTGGATCAGG TTACTGTTCT CCCTCCTGGA GAATGGGATC
125001  CAAGCATTCG AATAGAGCCT CCCAAAAATG TTCCTTCCCA GGTATGTATA
125051  TTTGAAGACA TTCTTTGAAA TTGAATTTTT TTTTGTCTTT TAAATGCATG
125101  TTTTATTTTA TTTTATTTAT TTATTTATTT ATTTTATTAT TATTATACTT
125151  TAAGTTTTAG GGTACATGTG CACAATGTGC CGGCTAGTTA CATATGTATA
125201  CATGTGCCAT GCTGGTGTGC TGCACCCATT AACTCGTCAT TTAGCATTAG
125251  GTATATCTCC TAATGCTATC CCTCCCCCCT CCCCCCACTC CACAACAGTC
125301  CCCAGAGTGT GATGTTCCCC TTCCTGTGTC CATGTGTTCT CATTGTTCAA
125351  TTCCTATCTA TGAGTGAGAA CATGTGGTGT TTGGTTTTTT GCCCTTGCGA
125401  TAGTTTACTG AGAATGATGA TTTCCAATTT CATCCATGTC CCTACAAAGG
125451  ATGTGAACTC ATCATTTTA  TGGCTGCATA GTATTCCATG GTGTATATGT
125501  GCCCCATTTT CTTAATCCAG TCTATCATTG TTGGACATTT GGGTTGGTTC
125551  CAAGTCTTTG CTATTGTGAA TAGTGCCGCA ATAAACATAC ATGTGCATGT
125601  GTCTTTATGG CAGCATGATT TATAGTCCTT TGGGTATATA CCCAGTAATG
125651  GGATGGCTGG GTCAAATGGT ATTTCTAGTT CTAGATCCCT GAGGAATCGC
125701  CACACTGACT TCCACAAGGG TTGAACTAGT TTACAGTCCC ACCAACACTG
125751  TAAAAGTGTT CCTATTTCTG CACATCCTCT CCAGCACCTG TTGTTTCCTG
125801  ACTTTTTAAT GATCACCATT CTAACTGGTG TGAGATGGTA TCTCACTGTG
125851  TTTTTGATTT GCATTTCTCT GATGACCAGT GATGATGAGC ATTTTTTCAT
125901  GTGTCTTTTG GCTGCATAAA TGTCTTCTTT TAAGAAGTGT CTGTTCATAT
125951  CCTTTGCCCA CTTTTTGATG GGGTTGTTTG TTTTTTTCTT GTAAATTTGT
126001  TTGAGTTCAT TGTAGGTTCT GGATATTAGC CCTTTGTCAG ATGAGTAGGT
126051  TGTGAAAATT TTCTTCCATT TTGTAGGTTG CCTGTTCACT CTGATGGTAG
126101  TTTCTTTTGC TGTGCAGAAG CTCTTTAGTT TAATTAGATC CCATTTGTCA
126151  ATTTTGGCTT TTGTTGCCAT TGCTTTTGGT GTTTTAGACA TGAAGTCCTT
126201  GCCCATGCCT ATGTCCTGAA TGGTAATGCC TAGGTTTTCT TCTAGGGTTT
126251  TTATGGTTTT AGGTCTAACA TTTAAGTCTT TAATCCATCT TGAATTAATT
126301  TTTGCCTGAG GTGTAAGGAA GGGATCCACT TTCAGCTTTC TACATATGGC
126351  TAGCCAGTTT TCCCAGCACC ATTTATTAAA TAGGGAATCC TTTCCCCATT
126401  GCTTGTTTTT GTCAGGTTTG TCAAAGATCA GATAGTTCTA GATATGCAGC
126451  GTTATTCTG  AGGGCTCTGT TCTGTTCCAT TGATCTATAT CTCTGTTTTG
126501  GTACCAGTAC CATGCTGTTT TGGTTACTGT AGCCTTGTAG TATAGTTTGA
126551  AGTCAGGTAG TGTGATGCCT CCAGCTTTGT TCTTTTGGCT TAGGATTGAC
126601  TTGGTGATGC AGGCTCTTTT TTAGTTCCAT ATGAACTTTA AAGTAGTTTT
126651  TTTCAATTC  TGTGAAGAAA GTCACTGGTA GCTTGATGGG GCTGGCATTG
126701  AATCTATAAA TTACCTTGGG CAGTATGGCC ATTTTCACGA TATTGATTCT
126751  TCCTATCCAT GAGAGAATAA AATACCTAGG AATCCAACTT ACAAGGGACG
126801  TGAAGGACCT CTTCAAGGAG AACTACAAAC CACTGCTCAA TGAAATAAAA
126851  GAGGATACAA ACAAATGGAA GAACATTCCA TGCTCATAAA TGCATGTTTT
126901  ACAATAGCAT AACCCATCAA GAAGATTCAA ATGATTTAAA GGATAGCCTC
126951  TAAGGCAGAA GGGGCATGAA GTTACAAGAT CTTTCTTAGT ACTACCTAAC
127001  ACACATTACT GAGAAACTTG GCAGTTTGAT GACAACCTAC TAATCAAACA
127051  GTGCCATATG CCTGGAAAGA TTTTAGCCCC TACTTAAAAC ATATTATCCA
```

FIGURE 30O

```
127101  AGAGGAATAT TAAAATTTTA ATAACAACAT TAAATATGGC CTAAGAGAAA
127151  GCGCATTACT GTCCTTGTAT GTTTTGATAC ATCACTTTGA AATTGGCAAG
127201  CATTAGGAAA ATTCAAAGAC ATGACTTAAT CATATTATAT AGAAAACTCC
127251  ATATTTATTA CTGCTAATCA CAGGAAATAT TGGGAAGATT TTAAAATTAT
127301  AATTCTTATA TTTGTATTGC TTTTTTGTGA ATGTATGATA TAAAGATTTT
127351  TTAAATTTTG TTTATGAACA TCTAATGTAT ATTTTACCCA TCATACAATC
127401  CAGAAAGATA GAAATATAAA GCATTGCTAT TTTTTAGGGT CATTTTTTAA
127451  ATTGCAGGCA TGAGTATTAA GAGTGATGAC CAAATATTTG TTAAGCTCAC
127501  TCCTCATACT GCCACCTCTA TGCCTACTGA ATCTGCCTCC CACAACCCTC
127551  CCAAATTGTT GTGTACTTAG TCTTGCCTTT GCGCCTTGCC CTGTGGAGTT
127601  CAGCCTTGCC TGACTCTGCT ACCCTATTGG AAGCGGCAGA TGGTCTAATT
127651  GACCCAGCCC TGGAATTAGA AATTTTCCTG CTTTGCCAGA GGTGGGCAAA
127701  TGAGCAGTTG TACCACTCAA CCATGAGTAC TTAAAAGGG TATCTCAATT
127751  TCACTGTCAA TTTAAAGAAA CTATATGGAT ACCTCATTTT TATATTTTCA
127801  TTTTGAAATC ATTTCATAAT TATTAAAGAC TATTTCCTTT TCTCAAAACT
127851  TACCATTTTG TGATTATGTA ACTGCTACCA CATATTTCAG TTGATCTACT
127901  ATTAAAATAA AAAGTTGCCT AATAATTAAT TGTAGGGTTT ATAGATTGTC
127951  TCATTTCTGT ACTTGTAGAA TACATCTTTG TCTAATGAT ATTAGAAAAG
128001  GCAATATAAT GCTTCCTGAG TATGTAGAAA CTCTTTAATT AATGTTATTT
128051  GGACAAATGC AGCAAATAT TAATACATTC AGAATGAGGC TTTAAAATTC
128101  ACTGTAATAC CCATTAGCTA TTGAAACATT GAAGTTAAGT GTTTTTGAAA
128151  ACACCTTTGT GAACAATAAT GTTTTTGAGG CAAGTTGAGT GATGGGAGGC
128201  CAATATTGTT TATGATTTTA TGACACCCTT TAAAATCGAA TTAATTATTG
128251  GATTCTGGGT ATTGAGAGGC AGTCATAGAA AGAACATCAA ATTAAGAATC
128301  AAAGCATCCG AGTTCTGCAA TTATCTATAT GTATGACCTT GAACAAATGT
128351  TTTAACCTCT CTGTTGATGT TCTGTATCAG CACTGTCCAA CAGAGTTTTC
128401  TGCAATAATG GAAATATTCT ACGTCTATGC TATCCAGTAA TCAAGCCACT
128451  AGTAAGCATT AGAAATGTTG CCATTGTAAC TAAAGATCAG AATTTTTCAT
128501  TTTAATTACC TTAAATGTAA ATAGACATAT GTAGTTTGTG GCTATCATAT
128551  TAGACAGCAT AGTTCTATAC AACAAATTTG AAATTACAGA TATGCTCTAT
128601  GCTTCTTTTC AACATTCATG TTTTAAAAAT ATATGTTGTA ATTGAATAAT
128651  AGATAGCATG AGGCTATGTT TTCTATTAGA CGGAGTGAAA TGAGTTAATA
128701  TACATTAAAC ATTCTGACCT CATACTCTTT CAAATTTTTT CACCATTGGG
128751  ATCATTTCCA TCTTTTTTAT TCATTGAAA TGTGCAAATC CCAGCATTTT
128801  AAATATTTTT TCCCTTTCAG TTAAGAGAAG AATAACCTGT CACCTCCAGG
128851  GATAACCCTG AAAATGTTCA TTAGAACTTT GCATCAGTCA TTAAAATCAC
128901  TCCCTTTTGT GTACCCTCAA CTTATTTGCT CTTCTCTCAT GTCGTGTACT
128951  TGCTTGGCAA AACCACAACC CTGTGAGAAT CCAACACTTT ACTCTGTACC
129001  GCACTGATGA ACTGAAGCTG AAGGAAAACA TGTAACCACA CTAACTGGTC
129051  TCACATAAAT TCATGACCAC ATACCTCAAG TGAGCCCTTT GTGTTGCAGG
129101  TTCATCATAC TACACTTTCC TAGTCCAATC ATTCTCACTT GATGACTATT
129151  TCACACTTAT TCTTCTCTCC TCAAGCCTTC AGCACATCCT TTCTGACCCT
129201  CACTCTCATA TGCTGATGTG CCTTTTATTT CCCTAAGAAA TTTGAAACAA
129251  TCAAAAAGA ACTTCTATAG ATTGCTACAT GCATCCACAT ACTCTGCCTT
129301  CCTGTTCATT ACTATTGATG AAATAGCCAA AGTCAGCCTT CTACTTGTGC
129351  ACTAGAAAGA ACCTATCTCT TCACATCTAC TCAAGAGCAC AACTCTACCA
129401  ATTCTCCTCT TTCTCTTCTA TATCATCAAA TCTTTTTTTC TGTATTTTAT
129451  CACTTTTATT AGCATACAAT ACTATTAAAT TTACCAATCT TAAATAAAAG
129501  AACTCTCTTG ATACCACTAC CCAGCCTGCC ACTCTTATTC ATTCCCTTTT
129551  ATAACAAAAT GCCACAGAAG AGTTCTCTGT GCTACTTGTC TCCAGTTACT
129601  CTCCTCCAAT TCTCTTTTAA CATTCACTCC AAGAGGCTTT TGCCCCTACC
129651  ATTTCACTAA AATACATACG AGAACAATGA TCTCCACCAT GCTAAGTCCC
129701  ATGGTCAATT CTCAGCCTGC ATTTTATCTA ATCTATCAAT GAACAGCATT
129751  TAAGAGTTGA TGACTCCCTT TTCCTTAATA TATGTTCTTT ACTTGGCTCC
129801  CAAAACATCA CCTTCTGTTA GTTTTGTCAT TATAAAATAG AGTTAATTTA
129851  TCTAGTCAGT AGTATTTTCC CAGAAGACCA CATAATAATG CTTGCTTTCT
129901  GAGACCTGTG AAAGCTATGA ATTGTTTTCC TAGGTGATTG GGAAGTAGGT
129951  ATTGAGGGAA ACTCTTAAAT CCCTTTATTA ATGTATCCTA TTTACCTGTA
130001  AAGACAGTTC CTTCATCAGT TGACAGATGC TTCTCTTTTA TCTTTGAACT
130051  TTAGTCTTAC TGCGTCCATC CATTTGCCTG GGAAAATTGT TAAAATATTA
130101  AGCAATAAAC TTTCTTATAT TGAGCATTTT TCAAAACCTT TTTTATGTTT
130151  TAAACCTGTA TCATTCTATC TAAATGTCTC ATGGTAAGTG AGATCAGTTT
```

FIGURE 3PP

```
130201  ATAAGTCACT TTTGTTTTTC ATGTTTACAC TAATTCTATT TTGGAATGGT
130251  GGTCAAGTAA AAATCATAAT TTCACCACTT AAGATTTTTC CTATTATCCT
130301  TTGAAGTGCT TTTGAACACA TTGGTGTGCT CTAAGATCAC CATAGGTAGG
130351  ATTTTAGGTA GAACTTTCTG ATTTTTTAAG AAATCATATT CACCAACAAA
130401  AGCAGGTGGA ATAGACCATG GGAAAACAAT ACTTACCTGA ATCTCTACTA
130451  ATTTGTCATT GGTTAAATTA GAAGCCTCCT TTTACAACAG TCTTTGGCAC
130501  TCTATGAGTT AGAAAGACCT ATATTGTAAA CTATTTACTG GGTAGAAAAA
130551  CACCAGCTGG AATTACACAG AGAAATATAC TTTAAAAATA GTGATGATGG
130601  TTACTGTTCT TTGAACAGTT AAACTATGCC ACGCATATAA CACCACCATA
130651  CTTAACACCT CCTCACGCCA ACCTACCCAC ATCCTGATCT CTCTCTTTGC
130701  CCCTTCCCTT ACTTCATTTT TCTTCATAGC TCCCATCTGT ACCTGATATT
130751  ATAAGGTTAT TGTCTCTTCA CTAACAGAAT GCTTTTCTT GCCCACCTTT
130801  GCAGCTCTAG CATTCATTAC AATGAATGGC ATACACTAGG CACTCAGTTT
130851  TAGTTGAAAG AATAAATAAG TGCCCATCAC CTCATTTAAT TCTCTTAGTC
130901  ACACTATAAG ATAGATACTG TTGTTACCCC CAGTAAACAA AGGAAGAAAC
130951  TAACACTTTA AAAGGCTAAA TAACTTCCTG GAGGTCAAGC AACAAGTAAG
131001  TACAGAGCCT GGGTTCTCAG CTATTGTGCA TATTGCTTCA AGGAAAAATG
131051  AACTGTTATT ATTATTTACA ATTAACACCT GAAATTAAAA CAAAACAAAA
131101  CACATGAACA AAAAACTCTC CACAGGAGAA GAGGAAGATT CCTGCTGTAC
131151  CAAATGGAAC AGCAGCTCAT GGGGAAGCAG AGCCCCACGG AGGACATAGT
131201  GGACCTGAAC TCCAGCGAAC TGGAAGGTTA GTGAAAATCA CTTCTATGGG
131251  ACTTCAAGGA CCAAATGACA TACCATTCTT CTCTGTCAGA AATTGCTATT
131301  TTGGGATCTA ATTTATTGTA TACTTTTAAT ACCTGCTTTT TGAGGGTGAA
131351  AATGCCAATT AGTTTGATTT CTCTGAAGTT ACTAATGATT GTCATTACTG
131401  TTAAACTAAA ACAGTGGATA CACCCTTCCA TTATACTTTA CCTAGTCTTT
131451  CATTTGCTG TGCATAAAAT GCATTCTCAG ATTCTTAGAA TGAAAAGGAA
131501  AACCGTCAAT TGACCCTTCC AAAAGAACCC ATTGAAAGCT TCAAGTTGAA
131551  GATAGAAATA AAACTAAATA CCAACAACTC AGTCTTGTAG GCCCTATCTC
131601  ATTAAATGCA AGTAGGATGT ATATAGTGGT ATTTTTTATT TTTATGGCTG
131651  TGATTTGAAA GAGCTATATG ATTTATTTTT CTAATCACAC ATCTTTGAAG
131701  AGATGAAAGC TTCAATTTAT TTCTTAAAAT GGTGCTTCAT GGTTTTTTTG
131751  ACAGCTTGTC TCTCTCTAAG CAATGTGTGA GCAGAAAATC AGAAACCCTT
131801  GGGTGGGTCT CTCTTCAGGG AATATGTGTA TAGCCTCCAT TATAATTAAA
131851  GGCAGTTGCA AAGGCTTTGC AGGATTGGTG CTCCCCTCCC CTCAAGGCCA
131901  TTTTCTGTAC TGCTTGCAAT GTGTCCTCTA AGCTGACTTT CCAGTTCCTG
131951  AGCACTCTGC ATTTTAATTC TGTGTTCTTT CCCTTTATCT ATGTGTTGTC
132001  TCTGAGGAAA TGTCCTTTAA TGTCTTCCTC AGGCTTGATA CCTAATTTGA
132051  GATGGTTCAA ACAATTTTTT CCTTTTCCCT TCACTGGAAG CTTTGTTACT
132101  CATTCTGTTT GCTTTCATAC TTTCAAATGC TGTCTTTTTA TTTTTGGTGG
132151  TATTTTTTTT CTCTTTCTCA GGTGTAACAT GCCACATAGC TTAGATTTTT
132201  TTCGAAGTTC ACTTTTCCTT ACTGCTTCCT AAATCCTCCC AGGTCACCAA
132251  TATCCGGTAT CTTCGCTTCT CCAGAGTTCT TCCACAGATT CTGTTGCTGA
132301  CATGACTTGA AGTATCCATT ACTCATCTGC TCTCCTGGAG TTGCTGGTGT
132351  ACATCTGGGC TGCTCTTGCA CTGTTCTCTG TAATGAACTC CCACTTCCGG
132401  ATTTAGATTT TTACTGCTAA AAGCACATTT ATTACACAGT ACTATAACAA
132451  CTATTCAGAC TAATGTATGC TCTAATAAGT AATTGATTAG AATCAATGGT
132501  CTAATATAAA GTGCTTTCAA AACTATAAAT ATTAATTACT AATTAATAGC
132551  TCATAACCAC CTCAAATTCT TTTTGGGATT AGGTGGGATA TAAATCATAA
132601  ATGAATGCCT AAATAGACTG GTAGAGTAAA TCTGTTTTGA ATTGTGACTT
132651  TGATAAGTTA ACAAATTATT CAGAAATGAT CCCTAAAATA AAAAAAAGTG
132701  CATATGTTTT ACCAAACATG GGTAGAGAAG CCTAAGGTGA TCTTTATGTG
132751  TACAAATATT TCACAGGTTC TCTGCAAGCT TCTCTGAGTT TCAAATGTCC
132801  TTTTATTCAA TTGAAGTTTC ATTCTTCTCA ACCCTCTCCT ACTCCATAGC
132851  TCTCTAATGG AAGCAATCAC AGGAAAATAT AGTGATCTTA TACCTGCATA
132901  ATAGTAGAAG AGTTATTAAT AGGTAACTAT TACAGATAAA TCAGATCAGG
132951  GAAATTACTT GGTAAAATAT TTAATTATT CATAATATGT ACATCTTTTA
133001  TTTCAAATTC TAAGGAGAAT TTATTTCTAA AAAGGACAGT CCTTTCTGAG
133051  ATGATTCTAG GACTGCCAAA TGAATATTCC TATGCATAAA ATAAATAAGA
133101  AAAATGAAAC AGTTTTTTAT GATCCAAGTA TACTCAGCAT GCTGGCAGTA
133151  TATTGGAGCA TAATAAGATT TTTCACCACT GACATTAACC TTCATGTAGG
133201  AACTTATTCA TAGTCTTATT CATTTTTGCT ATCACATCAT TATTCCATGG
133251  AGCAAAACTT ACAGTAGCCA AATGTTAAGT CTGCGTATTG TTATTAAATG
```

FIGURE 3QQ

```
133301  TTCATAAAAT GAGAATACCT ACTTATTAAT GCTCTCATTT CTTATAGATT
133351  TAAAAAAAGA TCTCAAATTT CAAGCATAAT TTCACAGTTT AATACTTTTC
133401  CCCCAAAATA ATTATCTTTC AAGTGTTTCA ACATGGTTTT GAATATATTT
133451  GGAGTAAATG AATTTATACC AAGTAAGGTC ACTATTGTCT TGTGAATCAC
133501  AGATGCTGGG ATATGTTAAC GCAATAGTGG ATCAAAATTA CATTTATCTA
133551  GTTTTATTAT TATAAGGACT CCCTCCTAGT TTTCTAAAAA TGAAAACAGC
133601  TCTCAAACCT ATCTGTCTCT ACTAAGTATT GCTGCCATCC AAAAGGACAT
133651  TTAGATGTCT TCCTGCAACA ATATCTGGTG AGGGATTTTT GTTTGTTTGT
133701  TTTTTGGCCG AGAGAGTAGG TAACTGGAGC CATGGTTAAA CATTGCTTTT
133751  TCTCTCTAGG GTGATGCTCA CTACTGGAGT ATACAAAAGC CAGCTAACCC
133801  TCCCTCCCTC ACTTCCTGCT ATGCTAAATG GAATTAAACA TTTAGAAATA
133851  CTGCCAATGA TTGAGGGTTG TAGGCCTGAG TTTAGGAGGA GTAGGTTGAC
133901  GTAGAAATGG CACAGAGATT AGAGTAATCC TTGAATCTCA TTATTTGGAT
133951  TATGATTGGT AAACAGCTCT GAACCTTGTT TAAGAGAACC TGGGATTTTT
134001  GGTGGTTGAC ACGATATTGG GTTAGGAATT GAGGTAACGA ACGTAGTTGT
134051  GCAGTGCCTC CCTGTAGATT GTTATAAGAC AATGCAGCAG GTTAATGTGT
134101  GTCTCACCTC TGCTGATGGA AAACGTATAC TGTGACCTGG CAACAAAGCA
134151  AATGAGCATT TTGACTTGTG TGTTTTTTAT ATTTGGGTTT CACTATTGTG
134201  TTTTCCCCCC TGTCTTAGGA TTTTTGGGGG ACTTATTTTA GATATCAAAA
134251  GAAAAGCTCC ATACTTCTGG AGTGACTTCA GAGATGCTTT CAGCCTGCAG
134301  TGCTTAGCAT CTTTTCTATT TCTCTACTGC GCGTGTATGT CTCCTGTCAT
134351  CACGTTGGA GGACTGCTGG GAGAAGCAAC TGAAGGGCGT ATAGTATGTA
134401  TTATGCTTTT CTCTGAACTT TGAAACATAA TCCATTTTA AGATTCATAG
134451  TTAGATAAGT GAGCATTTAA TTTTGGATTC TTTTCTGAGG AGAGATTTGA
134501  GATATGGTCT GGCAGATACA CCTTATATGA ATTTCCTGGA TGGCTAGTGG
134551  AACTGGTAAT CTGGGAGTGG AATGTCTCAG AATAACTAGT TCTGAGTCTT
134601  ACAAAAGGTT CTCATCTGAT GCCTTGCCCT CAGCGCCCCC AATCCTAAGC
134651  TAGGTTTAGT CTCCATTCTT GTCTCACAAG AGGTCCATTT GCTATGTACC
134701  CGGGCCATGT TTCTGTCCAG ACACTAATCC TGAATACATT TAAACCTTTT
134751  GTAAGGCAAC AGAGACGTGA GATAGGAAAG TGAAGAGAAC ACTCCTACCT
134801  TTGCTACTAT GCATTTTCTT CTTGCTGTCA GCCCCTTTAG TCATCCTTCT
134851  ACCCACGTC TTGCCCAGGG TTGCTAGACT TTTCAGGGTG AAGCACAAAG
134901  CACATATCCA TGTATTTTAA ATGTCTTCTC CTTAGCTACA ATGGCCTCCT
134951  GTACAGCTTA GGTAATTGAA CCATTTATAT CTCTACACAG AGTGCAATTG
135001  AATCTCTCTT TGGAGCATCC ATGACCGGGA TAGCCTATTC TCTCTTTGGT
135051  GGACAGCCTC TTACCATATT AGGCAGTACA GGACCAGTTT TGGTGTTTGA
135101  AAAGATTTTG TTTAAATTTT GCAAGTAAGT GTTATGTACT TTTTGGCCCT
135151  TAGCCTCTTC CTTTTTTCTT TACTGTATTT ATACTTCTCC CAACATCACT
135201  TTTGGAGGTC TGTTGATAGA GACAGAATTG CCTGATTTGT TTCAGTTTAT
135251  CATTTTGCT TCATCATGGG AATAGAGGAA AAGTAAAATA TTTATGTATA
135301  TTTTTATGTA ATATTTTAA AAAGTAAGAC TCAGTTATAA GCATCGATAA
135351  ATCCCTTTTG ATTTTGTCCC TTTAGATGTT CCCTTTAGAC CGGTGGTCTG
135401  CAACCATTTT GGCACCAGGG ACTGGTTTCA TGGAAGACAA TTTTTCCACA
135451  AAGAGGGTTG AGGGGATGGT TTTGGAATGA AACTGTTCAC CTCAGATCAT
135501  CAGGCATTAG ATTCTCATAA GGAGCACACA ATCTAGATTC CTCACATGCA
135551  CAGTTCACAA TAGGGCTTGT GCTCCTATGA GAATCTAACG TCCCCACTGA
135601  TCTGACAAGA GTCTGAGCTC AGGCGGTAAT GCTCACTCGC CTGCCACTCA
135651  CCTCCTGCTG TGCAACCCTT TTCATAACAG GCCATGGACC AGGGGTTGGG
135701  GACCCCTGCT TTAGACAGTC TTGAGTTTAG ATACTCATGG GATGTGAAGC
135751  TTATTTACTT TCACTTCCTG AATGAGGTTT ATTTTCATTT GCTTAAAATG
135801  ATAGCAAGCT GTTAAATGAC CTTCTTTTCA CTGTTCTTTC CTTTTCCTCC
135851  TCCCAGAGAA TATGGGCTGT CATACCTATC TTTAAGAGCT AGCATTGGAC
135901  TTTGGACTGC AACTCTATGT ATCATACTTG TGGCCACAGA TGCTAGTTCC
135951  CTTGTCTGCT ACATCACTCG GTTACTGAA GAAGCTTTTG CTTCCCTGAT
136001  TTGCATCATT TTCATTTATG AGGCCCTGGA GAAGTTGTTT GAACTCAGTG
136051  AAGCATATCC AATCAACATG CATAATGATC TGGAACTGCT GACACAATAC
136101  TCGTAAGTAC CATTTCCCCT GCTGGCCTTG GGGCTTTTCT TTTGACAAAT
136151  ATTGCTATTG TTACAAGAAA TATGAGGAAA TTACTCAGCA GAGAATGTGC
136201  CTTAAGTTGA TTCATGACCT AAATCCTGAC TCTCAGAGTC GAACAGGATT
136251  TTAAAAGTTA TTTAATCGGC CACTCATCTG CTACTTGCAT TCTCATTATA
136301  CCATCTCTGC CAAGAGTATC TTTTTAAAGT TCTATTTGTC CAGTGTTCTC
136351  TAAAATAAGT AGATAAGGAA CCAATTCCAT TTTAATATAC ACGAATTTTA
```

FIGURE 3RR

```
136401  CCTTAGCGAA ATATATGTTA TTTGGCGTTA TTTCAGGGTC TTTTTAATTT
136451  ACAATAATCC AAAGAAACAT AGTAATGAAA ATATAAGATT TCAAATTTAG
136501  AGCAATAAGG TAAAATAAAC TTATTGGGTC TAAATCTTAG TAGATGTTTG
136551  AAAGTGTGGT AAAAACATAA ATCACTGAAT GAAAATTTAA TTTTGGTTTT
136601  GGCACTTGTG ACATTTTGAT GGAAATACTC AGATATTAGT TGTTGAAGTT
136651  GATGTTACAG TCCGGGATTG AAGATGTGAT TGGATCTATT GCTTTTTCTA
136701  GTTTTGGTGT ATCAACAGTC TGAAATGTCT CTAAGGCTTT GTCTGCAGAC
136751  TATATGTGGC CATTAAATGA CCCCATTATT TAATTGTAGA ATTTTTTATT
136801  GTGCTTATAT GCAGTTTTTT ATACTGCAAA TATCTGAAGC AATATGTTCT
136851  TTAGGAGACA GTTATAATCT CTGCATCAAC CACCAATCAT TTCCCTATAA
136901  ACTGCTTAGA TATGGCCTTG AACCCTTTTA ATATTTTTTA ATCTTTATTT
136951  ACTATCAGAA GTTTAAATTG TTGAAATCAG ACCAAAATAG TGCAATGTTA
137001  TAATTTTGTT AAGAATGACG AAATGTTGGG AGGCCGAGGC GGGCGGATCA
137051  CGAGGTCAGG AGATCGAGAC CATCCTGGCT AACACAGTGA AACCCCGTCT
137101  CTACTAAAAA ACACAAAAAA ATTAGCCAGG CGTGGTGGCG GGCGCCTGTA
137151  GTCCCAGCTA CGCGGGAGGC TGAGGCAGGA GAATGGCGTG AACCCGGGAG
137201  GCGGAGCTTG CAGTGAGCTG AGATCGCGCC ACTGCACTCC AGCCTGGGCG
137251  ACAGAGCGAG ACTCCGTCTC AAAAAAAAAA AAAAAAAAAA AAAAAAGAAT
137301  CACGAAATGA TATTATGTTG AAAATAATGT GAGTTTTAGT ACTTTCACTT
137351  TTATATTATA TTTAGAGATA ACTTTAAACA ACTGACCCCT ATTTTGAAC
137401  AAGAAAAATC AAAGTGGAAA TATAAAATAA TTTTCCCATT AAAAGCAAAT
137451  AGTGAGAATA TTGTAAACAG GCTAAGAAA GGACTGAGCA TAGGTGTCAG
137501  GGACACTCAG AAAACAGGCA AATGGGAAGA ACAGTTTGAT CAAAACCAGG
137551  GATAACATTG ATACACGCCT TTTCATTTAT CCTTACCTGA AAGAGAATCT
137601  CACTGAATTT GGATATCCTT GCTGGGATAT GTAATTATCT CTGGTTGGAT
137651  TTTCAAATCT ACTACATGCC AGGCACTATA CTAGGTGCTA GGAAAACCAT
137701  GGTGAATCAT ATTCTGTCCT CAGTGAGCTT CCAGTTTAGT AGGGAATGTA
137751  GATAAACAGA CAGCATAAGG AAATGAGTGC CGGGTTAAGA GGTTGGTACA
137801  GAATGCTATA GCAGCACATC AGGAGAGCAC CTAACCCAGA TTTGAGGTTC
137851  AGAGAAGGCT TCCTGGAGGA AATAATGTAG AATAAAAATG CAGTAGAAGT
137901  TAGGAAGGTG CTAAGGAATA GGGCAGAAAA GTAGTTCAGT CAAAGGGCAT
137951  TCACAGGACT AGATGCAAGA GATGCATTCA TGCTTTAAAA TATTTGTCTG
138001  AAGTTATATA GATAGTGGTA AAACAAGAAA TGGAATCCAG GTTTTATTAC
138051  TGATATAATT TTCAGTACAC TGATGAATAC AGATAAACTC TCCAAAAGAA
138101  ACTATGTAAA ACAAATAAAA CAGGTAAAAT CAGAACTATT CTGTTTCAAG
138151  TGGTAGGAAG GCACCCATTG CCTACCCTCT CAGCTGTTCT TTGAACCTTC
138201  ATGGTAGCTT CTTAGGTACT TCAGACTGAG GAACATAGTT TAAAGTCCCT
138251  TGGTCTAGAA AGGAAAAAGA TTGGAAAAGC AAGGTCTGAG CCCTCAACAA
138301  TTTTCACAGC TCTAAAGTAG AATGAGAAAA ATGCAACCAA TAGGCAAAAA
138351  ATAAATAAAT AAAAATAAGA AAGAAGCATC AGAAAAAGAG GAAACTATGG
138401  ATAATGTCAG GTCGCAGAAG GCAAGAAACA AGAAATGTAT CACAAAGTCT
138451  TTAGAGAGGA CAGTGGCATG GACATCAAAC AGAATAAGGA AAAGTGTTTG
138501  AAAAGAGATA CCTGGTAGCT TTAAAAAATT CTCAGCAAAC TATTGCAAGG
138551  ACAAAAAACC AAACACCGCA TGTTCTCATT CATAGGTGGG AACTGAACAA
138601  TGAGAACACA TGGACACAGG AAGGGGAACA TCACACACTG GGGACTGTTG
138651  TGGGGTGGGG GGAGGGGGGA GGGATAGCAT TAGGAGATAT ACCTAATGCT
138701  AAATGACGAG TTGATGGGTG CAGCACACCA ACATGGCACA TGTATACATA
138751  TGTAACAAAC CTGCACGTTG TGCACATGTA CCCTAAAACT TAAAGTATAA
138801  TAATAATAAA ATTAAAAAAA AAAACAACT GGTATTGGGT TGGGAAAGGA
138851  GGCAGAATGG GAAGCCAGTT TGCAAAAACT AACAAGGAAG TGGGTGGTAA
138901  AGAAATGGAG AAAGCTGCAT AGGCCAGTTG GTGTCAAAGA AAGTGGGAAA
138951  CAGAATGCCT TTTGAGGAGG GCAATGAAAT CGTAAGATTG ATAATTTGTG
139001  ACAGAGAAGG ACTATGTGTG TTTGAAAATG GGAGAATAGA GACTGGGGAG
139051  AGGAAGGCAG CAATGATGAA AAGAGTCGAT AAACGTGGGA TTGCAACCTC
139101  CCAGGAGTCA CAAAATAGTA AACTCAAGAG AATAAGTCAA ACAAATGCTC
139151  AAAAGGTAAT TTAACAACAA GAATAGCTTT AAATAAACGT GAACCCAAAC
139201  TGACATGAAA ATAGCAGGAA AATGACGAAA AAAAAAATT CGCCAAAAAA
139251  GACAGTGACA CAAACAGTGC ACACAACACA CAAGAGCGAG AAGAGCAGAA
139301  TGGAGGAGGA CAAGACAAGG CCGGTGCTCA GTGAGAGACG CACCGTATGA
139351  CACCTAGCAG AGGAAGCGAA GAGGGTAGAA GTGCTGANNN NNNNNNNNNN
139401  NNNNNNNNNN NNNNNNNNNN NNNNNNNNNN NNNNNNNNNN NNNNNNNNNN
139451  NNNNNNNNNN NNTCTGAGGC ATGGCTGTGA CACCCTCTTT GGGCTCTGCA
```

FIGURE 3SS

```
139501  GTTCCTGGTG TCTCCAAGCT TCTGGTGCCA CCACGTTCCC CAGAGCCTGC
139551  AGTGTAAGTG GCTTGCAGTA TGCCTGGTCC AGCCACAGCC TTGCACAGAG
139601  CTGGTTCCTG TGCCAGTGTC TGGAACTGCC TGCCCCACCA CAGCAGCCAG
139651  CATGCCTGAC TGTGCACAGT GGCCAGACCA TATGCTTGCT CACTTATGCA
139701  CCCCTCACCT CTGTGCCTTT GGCAGCGCTG GATCCAGGC TGGTAGCACG
139751  AGCTGAGCAC AACCTGCCAG GCCTAGTGGG CAGAATGAGC CAGAGGGCCC
139801  AAGCAAAACT CAGGCAAAGG CACCACTGGC CACAAAGGCT CTGGCTGGA
139851  AGAATGACAC CCCGGGGACC TCATGACAGT AATAACTTGG CTTAAAAGGC
139901  TGGGATAGGG ATCTATGACA TTAACCCAAT TAGTGGCCTT GGGTAAGTCC
139951  CTAAGAACAA CCTCTAGAGA CAATGTCTTA ACTCAAGAAA AAAAAAGTAG
140001  GAAGAATATG GAAAATACAT AGGGAATAAG AAGTCTGGAA GTATTGTATT
140051  AATACCAAAC TTATAGTACT TAAAGGACAA AATAAAGGGT TGCAAAAGAG
140101  TTCACCTTGT TGGTGAAGGA AACCTTGTAC TTTTTATTCT CTGCATATTT
140151  TGAATTGTTC AACTTGCACT GTATGCCTGC ATTATTTGT AATTTCTTTC
140201  TAAAGATGAA TTTTGTGTTG GGAAATTCAA GTCCTGTGAC AAACCATAGT
140251  ATGAGCTAAT CTGGGGGAGG TGGTGCTCTT CAAATTAGTT TCCATGTAAC
140301  AAAATTTATT TTCAAATTCA GGAAAAGAGC AACCTACAAA ACTCAGGAGT
140351  AAAATGGGCA AAATGTTCAA GGAATAATAA GTAGGTTTAC TGTTCTGTTC
140401  ATACATGTGC TTACTCATTC ACTCACTTAG CTCATTCCTT CAACATCCAT
140451  TGATCTTCCT TGTGTATGTC AGTGCTGATG GTATAAAATG AATACAATAT
140501  GGTCCCTACT CTGAAAGACC TTAGTGATTA TCAGACAGTG TCTGGAGATG
140551  TCCTTTGGAC ATGATATCCA CTCAAATAGT ATTTGTTGAA TTAATAAATG
140601  AGGAGAGAGG CTAGAGGATA CACAGTTAAA TAATTGCAAT GTGATATAAC
140651  AAGCACTATA CAAGGTGTCT GTATAATGGC CTAAGAGAAG AAGTAACAGA
140701  GTGCCCTGGA GAGCTCAGAA GCATTCATAG AAAAAGGAAA CCTGAACTTA
140751  TCTCTCCATT TCTGTTGTAC CTGCCACATG AGTTTATTGT ATGTGGCATA
140801  CCTATGTTTC TTTCTCTCTC TCTCTTCATT GTACCTGTGA ATTCCCACAT
140851  GCAGATCATC ACTAGATCTG AGAGTAGTTA CGCAGAGTAG AATGGACCTC
140901  TGGGGACCAA TTGGCAGAGA GCCTTAAAAG TTCTAATAAG TTTTATCTGG
140951  TACAAAGGCC ATCATGGATC ATGACAAGGC TCTGGGAAGA ATTATGTGAC
141001  AATAGGTTAG AAGGTGATCA CAGGAAGCAG AGCAAGGAGC AATACCCTAG
141051  GCATAGAATG TTTAAGTCCT GACTACTGGC TGAGACAATG GTAATGGGAA
141101  GAAAGCAAAA AAACTAAAAA TGGAAAAAAT GAAAAACAAA AATTATCCAG
141151  GATTGATTCA CTTGTTCAAC AAGTAATTGT GGAACAGTGT CTAATTTCTA
141201  GGAGCTATTA TGAAAACTTT GCCTATATGA CTTCATTTGA ACCTCACAAG
141251  AACCTTGTGG GACAAGTATT ATCCCTGCTT TACAAACAAT CAATCTGAGG
141301  CTCCAACAGG TTAAATAATC TTCTCAATAT CACATATACA ATAAACGGTA
141351  AATGGGGTAA ACCCAGGACC ATTTTGTCTT AAAGCTCATA AACTTTCTGA
141401  CATATTAAAG TAAAAATAAT AGCAAATGAT TGCGATGATT ATAACTCCTT
141451  AAAGGTAGGG ACTACGATAT ATGTCTATGT ATCTCCAGTA GGACTTAGCA
141501  CAGTAATCTG TATAAAATAA TTTCAAATTG TTAAATCAGT CAGTTGTCAT
141551  AAGGCTGCCT GCTATGGGCC AGGTGCTTGC TTAAAAAAAA TGAATGCATA
141601  GACAGGATTC CTTCATGGAA CTTATAGTCT GTTGAAAGAA TCAGACATTA
141651  AATATTACAC AAAATTACAT TATACAAATG ACGTAAGTGC TATCATATAA
141701  AAGTATAGGA TGCCAAGACA GTGAGAAATA TTTCCAAACT TATATATTTA
141751  GAGGCTAAGG AGAGGATATG TCTATTTGAA TGAAGATAAA TTTGAGATGA
141801  GAAAAAGTTT AAGAATTTAA TGGAGAGAGT ATTTAAATTT TTAGTGTTAG
141851  CTAATTGTGG TGGTGTTTTA CAAAGCTACG ATGCATATTT TTGAAAAGCT
141901  ATTTTCCTCA TAATATATTA TGGTTATATA CTTAGTGATA TCTTAGAAAA
141951  GTATAAGTAC TAAGCAAACC TCTTCAAATA ATAAGCTCAA AATATGGAAA
142001  TAGGTGTATT CATAAAAGGA TTGTCTCTAT ATTATTTAAA TAGTCATCTT
142051  AATAGTAACA ATTTAATTAA ATGATTAATA ATCCAAGAAT AAGTTATGTT
142101  GTATCCCTTA CAAATAATGG TTCTGAAGGG TAATGTAGCA ATAGGAAAAT
142151  GCTTGCATTC TAGTGCTATG TAAAAAAGGA ATAAAAATAT TGTATGCTCA
142201  TAAAAACATG TTGAAAATAT ACATAAGAAC TACTGAAAGA AGTATACCAA
142251  AAATTTGTAG CAATTATGGT AGAAAGACTA TGAGAGATAC CTTTTTCTTT
142301  TTTATTTTG TAAATATTCT GTAGTGTGAT TTTATTATCA TTGCAATTAA
142351  AAATACTTTC TGAAATAGAA AAAGAATAAT CATAAAAACA CATTTGGCTT
142401  CTATGGATAG ATCCTGATTT TCTGATTGTA TGTTTTGTAT TAATACCTGA
142451  CTTGGTACAT AGCACTCTGG GAGATAATCA AGTCAATAAA AAGACCTGAA
142501  AAATAAATGA ATCACAAACC ATAACTGTTT AGTGCACACA GGAAGGTACT
142551  ATTAATAACT ACAAAGGCAA AAGGAGAGCA TCTGCAACCC AAGGACTAAA
```

FIGURE 3TT

```
142601  ATTAGTAATA ATGTTGAAGG GAGTTCTACC AAATTATGTT TTCCAGAAGA
142651  CAGCGCAGGC TCTTCTTGTG TAAGGAAGAC AGATCACCTC CATTAGCCTT
142701  GAAACAAAAG CAAAGACTTC TGGATGAGGG CATTTAATTA TAATGTTTAT
142751  GTAATCACTC TGTAGCCATT TATATAAACA AGATCGCTTA GAGCACTTGC
142801  TTTTCTGTGG GCAGTAAAGG GTACTAAAAG ATGTATTTTA TAAAAAGTGT
142851  ATTTTAAGCC AAATAATTCA GCACCACAAG TGAAAATTAT TGGCATTTTA
142901  TACTGGTGTT TTTAAACATG TAGAGAAGTG CAGATACAAC CCTTTTTCTG
142951  CTTTATGATT GTTGGACTTT TCAGTCTATG AGCTTGTGAT AGTAACAATA
143001  ATAAATAACC AAAATGAGAT ACCTAACAAT CTCTATTTAC TTATGTCAGG
143051  GCCCATTCTA GGACTTTTAT GTATATTAAT TCATTTAATT TTATAATAAC
143101  CCCTAGAAAG GACATGAACT CAGAAGCTGG AAACCATCAT TCTCAGCAAA
143151  CTATCGCGAG GACAAAAAAC CAAACACTGC ATGTTCTCAC TCACAGGTGG
143201  GAATTGAACA ATGAGAACAC ATGGACACAG GAAGGGGAAC ATCACACACC
143251  GGGGCCTGTT GTGGGTGGG GGGAGTGGGG AAGGATAGCA TTAGGAGATA
143301  TACCTAATGT TAAATGATGA GTTAATGGGT GCAGCACACC AACATGGCAC
143351  ATGTATACAT ATGTAACAAA CCTGCACATT GTGCACATGT ACCCTAAAAC
143401  TTAAAGTATA ATAATAAAAA AAAGAAAAAA AAATAACCCC ATGAGGTTGA
143451  TTATTATCAT TATCTTCACT TTATACATAA GGAAACTGAA ACATAGAGTG
143501  ATTAAATGGC TTGTCCAAGG TTGCTCAGCT AAATGCTTGG ATTTGAATGA
143551  ACATAGGAAA CCTGGCTGGA GACCTCAGTG TTCTAAGCAT ACACTATGCT
143601  ATGCATCAAA AGAAACGTTT TGCATTAATA CTCCATCTTA TTGCCAGAGT
143651  CACTAGAAAT TATTTTTGAT GAGATTAACA AAAAGCTTG TTCCAGACTC
143701  ATATTCTATC TCCTCACAGT GCTATTTCCA TGTTTCTTTT CTCTTTCTTT
143751  CTTCTTTTTT CTTTTTCATT TATCTTCTTT AACTTTTGT AGTTTTAGAA
143801  ATAAGTTCAC CAATACAGAG GAAGACAGGA AAATGGGATT TTTTTCTCAC
143851  ATTTTTCTTG ATTGATTTAT TTAGCATATC TATTTTTGAT ATGTAAGAAC
143901  ATAAGAAGTA AGTAGTCAGA AGTCTTCTTT GAGCCACCAA GAGTTGGTAC
143951  GGAGATATCA AATGTCCTTA CACAACTGGG CAGCCTCTGA GAACTGTCTG
144001  CTGAGATTTT AGATGTCAGA GGTGCAGACT CAAGAAAGAA CAATATTTGC
144051  TTGGGTATAC ATGATATCTG TGATTTTATA CATATATAAA TACAAATAAA
144101  TCTTTAACTT ATTTATTTTT AAATTTGAAT TTATTTATTT ATGTCATATA
144151  TAAATCTTGT ATATTAAAAA CATATTTTCC ACTTTGGAAT TGATTTATAG
144201  GTGAGTAATG TCATAACCTA GAGATAGCTT TGACAGGGAG GCACGTAGGT
144251  AACTAACGTC CACTTGTAGA CTCAACTCTT CAAAAAATGT CTCTCCTATG
144301  ACATTGGTAC ATCAAATTTC TAACTTAGCA TTTTCAAAAA GTCACGGTTA
144351  AAATGTAAGT ACACTACCAG GAATGGAGTA ACACATGCCA TTGTATTCAC
144401  TAACACAGTA TAACCACTTT GGAAAGCAGA GACCATGTTC TTGAGGGAGT
144451  AGTAAAGCAA AATGAATGGA GAAGCCATAT CATCAGGTTT CGATGGGGTT
144501  ATAGGAAACT GGACAGTGGG GCTGAGGAAA ATGTGGATGG TGTAGTTTTC
144551  ATGATAGGAG GGCAGAGCTA CAGGTGTTTT GGAAGAATAC CTTATAGGAG
144601  AGAAGTCTTG AAAGTGGAAG CTAGCAAACT ACACGGTGAA ATGTAGATTA
144651  CTTCATTTGT TCTGGAGTCA TCTCACTCTT CTGGCTATCT TGATAGAAAC
144701  AGCACCAAGT CACATATTGA GGCAGCATAC AATAGCTAAA AGAGTAGGAG
144751  TTTCCATCTG GTCCTGGACT CTTTTTGGTT GGTAAGCTAT TGATTATTGT
144801  CACAATTTCA GAGCCTGTTA TTGGTCTATT CAGAGATTCA GCTTCTTCCT
144851  GGTTTAGTCT TGGGAGGGTG TATGTGTCGA GGAATTTATC CATTTCTTCT
144901  AGATTTTCTA GTTTATTTGC GTAGAGGTGT TTGTAGTATT CTCTGATGGT
144951  AGTTTGTATT TCTGTGGGAT CGGTGGTGAT ATATATCCCC TTTATCATTT
145001  TTTATTGTGT CTATTTGATT CATCTCTCTT TTCTTCTTTA TTAGTCTTCC
145051  TAGCGGTCTA TCAATTTTGT TGATCCTTTC AAAAAACCAG CTCCTGGATT
145101  CATTAACTTT TTGAAGGGTT TTTTATGTCT CTATTTCCCT CAGTTCTGCT
145151  CTGATTTTAG TTATTTCTTG CCTTCTGCTA GTTTTCGAAG GTGTTTGCTC
145201  TTGCTTTTCT GGTTCTTTTA ATTGTGATGT TAGGGTGTCA ATTTGGATC
145251  TTTCCTCCTT TCTCTTGTGG GCATTTAGTG CTATAAACTT CCCTCTACAC
145301  ACTGCTTTGA ATGTGTCCCA GAGATTCTGG TATGTTGTGT CTTTGTTCTC
145351  GTTGGTTTCA AAGAACATCT TTATTTCTGC CTTCATTTCA TTATGTACCC
145401  AGTAGTCATT CAGGAGCAGG TTGTTCAGTT TCCATATAGT TGAGCGGTTT
145451  TGAGTGAGTT TCTTAATCCT GAGTTCTAGT TTGATTGCAC TGTGGTCTGA
145501  GAGACAGTTT GTTATAATTT CTGATCTTTT ACATTTGCTG AGAAGAGCTT
145551  TACTTCCAAC TATGTGGTCA ATTTTGGAAT AGGTGTGGTG TGGTGCTGAA
145601  AAAAATGTAT ATTCTGTTGA TTTGGGGTGG AGAGTTCTGT AGATGTCTAT
145651  TAGGTCCGCT TGGTGCAGAG CTGAGTTCAA TTCCTGGGTA TCCTTGTCAA
```

FIGURE 3UU

```
145701  CTTTCTGTCT CGTTGATCTG TCTAATGTTG ACAGTGGGAT GTTAAAGTCT
145751  CCCATTATTA TTTTGTGGGA GTCTAAGTCT CTTTGTAGGT CACTCAGGAC
145801  TTGCTTTATG AATCTGGGTG CTCCTGTATT AGATACATAT ATATTTAGGA
145851  TAGTTAGCTC TTCTTGTTGA GTTGATCCCT TTACCATTAT GTAATGGCCT
145901  TGTCTCTTTT GATCTTTGTT GGTTTAAAGT CTGTTTTATC AGAGACTATG
145951  ATTGCAACCC CTGCCTTTTT TTGGTTTTTT TTTTTTTTTT TTTTTTGGT
146001  AGATCTTCCT CCATCCCTTT ATTTTGAGCC TATGTGTGTC TCTGCACGTG
146051  TGATGGGTTT CCTGAATACA GCACACTGAT GGGTCTTGAC TCTTTATCCA
146101  ATTTGCCAAT CTGTGTCTTT TAATTAGAGC ATTCAGCCCA TTTACCTTTA
146151  AGGTTAATAT TGTTATGTGT GAATTTGATC CTGTCATTAT GATGTTAGCT
146201  GGTTATTTTG CTTGTTACTT GATGCAGTTA CTTCCTAGCA TCGATGGTCT
146251  TTACAATTTG GCATGTTTTT GCAGTGGCTG GTACCAGTTG TTCCTCTCCA
146301  TGTTTAGTGC TTCCTTCAGG AGCTCTTTTA GGGCAGGCCT GGTGGTGACA
146351  AAATCTCTCA GCATTTGCTT GTCTGTAAAG TATTTTATTT CTCCTTCACT
146401  TATGAAGCTT AGTTTGGCTG GATATGAAAT TCTGGGTTGA AAATTCTTTT
146451  CTTTAAGAAT GTTGAATATT GGCCCCCACT CTCTTCTGGC TTGTAGAGTT
146501  TCTGCTGAGA GATCCGCTGT TAGTCTGATG GGCTTCCCTT TGTGGGTAAC
146551  CCAACCTTTC TCTCTGGCTG CCCTTAACAT TTTTTCCTTC ATTTCAACTT
146601  TGGTGAATCT GAAAATTATG TGTCTTGGAG TTGGTATTCT CGAGGAGTAT
146651  CTTTGTGGTG TTCTCTGTAT TTTCTGAATC TGAATGTTGA CCTGCCTTGC
146701  TAGATTGGGG AAGTTCTCCT GGATAATATC CTGCGGAGTG TTTTCCAACT
146751  TGGTTCCATT CTCCCGGTCA CTTTCAGGTA CACCAATCGG ACGTAGATTT
146801  GTTCTTTTCA CATAGTCCCA TATTTCTTGG AGGCTTTGTT TGTTTCTTTT
146851  TATTCTTTTT TCTCTAAACT TTCCTTCTCA CTTCATTTCA TTCATTTCAT
146901  CTTCCATCAC TGATAACCTT TCTTCCAGTT GATCACATCA GCTCCTGTGG
146951  CTTCTGCATT CTTTACGTAG TTCTCAAGCC TTGGTTTCAG CTCCATCAGC
147001  TCCTTTAAGC ACTTCTCTGT ATTGGTTATT TCAGGACATA GGCATGGGCA
147051  AGGACTTCAT GTCTAAAACA CCAAAAGCAA TGGCAACAAA AGCCAAAATT
147101  GACAAATGGG ATCTAATTAA ACTGAAGAGC TTCTGCACAG TAAAAGAAAC
147151  TACCATCAGA GTGAACAGGC AACCTACAAA ATGGGAGAAA ATTTTCGCAA
147201  CCTACTCATC TGACAAAGGG CTAATATCCA GAACCTACAA TGAACTCAAA
147251  CAAATATACA AGAAAAAAAC AAACAACCCC ATCAAAAAGT GGGCAAAGGA
147301  CATGAACAGA CACTTCTTAA AAGAAGACAT TTATACAGCC AAAAAACACA
147351  TGAAAAAATG CTCACCATCA CTGGCCATCA GAGAAATGCA AATCAAAACC
147401  ACAATGAGAT ACCATCTCAC ACCACTTAGA ATGGCAATCA TTAAAAAGTC
147451  AGGAAACAAC AGGTGCTGGA GAGGATGTGG AGAAATAGAA ACACTTTTAC
147501  ACTGTTGGTG GGACTGTAAA CTAGTTCAAC CATTGTGGAA GTCAGTGTGG
147551  CGATTCCTCA GGGATCTAGA ACTAGAAATA CCATTTGACC CAGCCATCCC
147601  ATTACTGGGT ATATACCCAA AGGACTATAA ATCATGCTGC TATAAAGACA
147651  CATGCACACG TATGTTTATT GTGGCATTAT TCACAATAGC AAAGACTTGG
147701  AACCAACCCA AATGTCCAAC AGTGATAGAC TGGATTAAGA AAATGTGGCA
147751  CATATACACC ATGGAATACT ATGCAGCCAT AAAAAATGAT GAGTTCATGT
147801  CCTTTGTAGG GACATGGATG AAATTGGAAA TCATCATTCT CAGTAAACTA
147851  TCGCAAGAAC AAAAAACCAA ACACGGCATA TTCTCACTCA TAGGCGGGAA
147901  TTGAACAATG AGAACACATG GACACAGGAA GGGGAACATC ACACTCTGGG
147951  GACTGTTGTG GGGTGGGGGG CGGGGGAGG GATAGCTTTA GGAGATATAC
148001  CTAATGCTAA ATGACGAGTT AATGGGTGCA GCACACCAGC ATGGCACATG
148051  TATACATATG TAACTAACCT GCACATTGTG TACATGTACC CTAAACTTA
148101  AAGTATAATA ATAACAGAAT AAAAAAAGTA TAATATATAA TAAAAATATC
148151  TTGAAAATTA AAAAAAAAAA CAAACTTCTC AATGGCTGTC CCTCTCATTC
148201  AAGAGCAAAA ATAAAATCAT AACAATCCTT GAAAGCAAAA AAAAAAAAA
148251  AAAAAGTAGG AGTTTCAGGT TGGGACAGAC CTGGATTCAA GTTTATTTCT
148301  ATCAGTGTAG CCTTGGATAA GTTATCAAAC ATTTAGTTCC TCCCATCTAT
148351  AAAATGTAGC AATTAAACTA TTAAACTAGA AATCCACTA TATGCCATGC
148401  GTATAGCAAC TGTATGCACG CCATACCTAT AGGCATAGAT ATACAGTAGC
148451  TACAGAAAAC ATATATGTAT GTATATACAC ATATACATTT GTACATGGAG
148501  GTATTCACAT ATCTACGATA GTGCTATCTT TCTCCCTCGT TATGTTACTT
148551  CTGCAAGAAA CTTGCCATAT TTTCTCTATT TTATATTTT GTTTCTTATG
148601  TATGGATTTA CTTTTAACAA ATTTTCAAAA TATGCAAATA ACTTTCTGTT
148651  AAACTATAGT ACTGGCCCTT TTATTTCTGA GGTAAACTAA CTGACCATCT
148701  TAGGGAATTC TATTTGTTAG CAACCAAAAA AAAAGGATGT TGCCACTTA
148751  ATAAACAGAT TCAGACAATA TATTACTAAT TTACTTCAAC GAGAAAGAGA
```

FIGURE 3VV

```
148801  CTCTTGCTTC TAGTGAATGA TATTACACAG TTTGTTTTGT TTTGTTGATA
148851  GCACTACTGT GCAATGGTCA CCTGTGATAC AATTATTTGA ATTCATGACA
148901  ATGCTGGGTT AGGAACCGAG GCAGATCCAC TATGCTTCTT TATGTTCAGA
148951  TGTTTTAAAT CAGAATTATA GGACTATATC TATGTGCCTA GGCAAATATC
149001  TAAAATAATT ATTCCATTCT CTGCTAACAG CTTAAACACG TGTTGTAATT
149051  CTAACAGACT TTAGAGAGCA TATGGCAGTT TCAACAAGTC ACACATATTT
149101  TTACATGCAC CTAAGCTAGG GACCCCTGAC CAATGAGTTG AGCATCATCT
149151  ATCAGGATGC TCCCGATAGA TGACAGATCT TCAACCAGCC AGCTAGGTCA
149201  TTTCTGCTTC CTCAATTCCA CATGTTTAGT TAGTTGGGAT TCCCAGTCGG
149251  GAGGCAAAGC AGGTAGCATT TGGGCCCTCC CCTTACTGTG CTCAGTTCAG
149301  TTTATTGATG GAAACATCTC CAAGGATCTT AAAACTTTAA AATAGAAAT
149351  ATCTCTTCCT CACAAAGTTG GAAGCCCTGA ACCTGAGCCT TAAGAGATTT
149401  ATTTTTACAT TTGTTTTCAA ATTCTCACAA TTTATACAGA AAAAAAATC
149451  AGAGTATCCA TTCTGGTTTT TAATTTTTTT ATTTCTTGCC ATAGTATTAT
149501  ATATCAAGAA TATTTATAAG AAGGAAGTAG TTAATACATA TTTGTTATCT
149551  AAGTATAATT TGGGACACTA TATAAATCTT TTAGTTTGTG AGTTACTTCT
149601  GTACCCTGTC ATCTCCTAAG CTACCTGGTC TTTCTTGGAA TAATAAATAT
149651  ACATACCTTT TAGGACCAAG ATCTATAGTT TCACAATATT CATAGCCATC
149701  TGGTTCTGCT ACAGGGTAAA TTTAGACTGG AAATAAGGTA ATATTAAGTA
149751  AGAGAAGCTT CGTTTGTTTA ACCTACCTCC CAAAGGCTCC ATTTGTAAAG
149801  AGTGCAGACC AGAAATCACA TGCACTGCTG GATTCTTTCC ATGAGAAAAG
149851  CCTGTGTTGA GCTTTAGTTT CTTCATTTTC TTTAAACAGA ACAAAAATCT
149901  CTCCTACCAC TCAAAGGAGT GATTTGCAGA TTTAATGCAA TTATATCAAA
149951  GTAGTTTATA ACCCATAAAA CACAAAGTTA TATGACCGTT ACTTTGTATT
150001  GAACATCCAT GAAACTCTAG GAATAGTACT AGAAGCTTTA TACACCATTA
150051  TATATAGAAT GGTGTCTCTT TTAATTCTCA AGAAATCCTG TCCAGTTGTT
150101  ATAATTATAC TTACTGAATA AATTATATTA ATTTATATTA TAATTATATT
150151  AATTAGTTAT ATAATGAATT CATAGAAACT CAGGGGTTGG GTGATTTGCT
150201  AAGATCAATA GCTAGAAAGG GGCAGAATCA GTATTCAACT CAATATTACC
150251  TCCAAATGGA AGTAATTCAG TATTAGTGAG TATTACTAAT TATAGAAGTA
150301  ATACTTCTCC TTTCTACTCA GAGCTAACAC AACAGCATTA TCTAATGTTG
150351  TTAAATGGTA GGTGGAATTA AAAATTGTAG GTAAGATTAA GAAAGGAGGG
150401  AAATCACTGA ATAACCTGCC CTTCCAGCAA AGTTGACAAA GTAGATAAGA
150451  TCTCTGGTAA GATCTAATCT TCATCTCATT CTGCCACATG TTTTTGTTTT
150501  GTTTTGTTTT GTTTTGTTTT GTTTTATTTT GTTTTTTAAG ACGCGTCTCG
150551  CTCTGTGGCC CAAGCTGAAG TGCAGTGGCA CAATCTTGGC TCACTGCAAC
150601  CTCTGCTTCC CAGTTCAAAC AATTCTCCTG CCTCGGCCTC CTGAGTAGCT
150651  GGGATTACAG GCGTGCACCA CCACGCCTGG CTAATTTTTG TATTTCAGC
150701  AGAAAGGGGG TTTCACCATA TTGGCCAGGC TAGTCTCCCC ATGTTTTTA
150751  TCGAAGTCCC TGTGTTCTCA ATATCCTGAG ATGATTGGCT GATTGGCTGT
150801  TGCCACAGCC ATTGGCTTCA GCCACTCTTC TGGCCTGGAC ATCATCCAGT
150851  GCATGTCAAA GACAGGACTC TGGCCTAGCT TCTTTTGGGG ACTTTCTACC
150901  ACAGAATGAG CAAAGGTGAT GTTCGGAACA AAATACCTAT ACGTTCATC
150951  CAGCTGCAAA TAATCAGCTC CAGCTTCTGG AGTTACTTGG TACCTAAATT
151001  GGCCAGGTTG CTGTTGAGGA TGAATGGGCC AATCTTACAG CTGAACACCA
151051  TGATACTGGT TCCCAGGAGC CAAGCATTGC CCCAATCCAG CCTTTTTTA
151101  TTTATTTTAA AAATGTGTTA ATACTTTTA AATCTTTAAG TAGTGACTAA
151151  TTTTCTTTTA AATAAAGATT GTTTTCCTCC AGGATGCATC AGAGTAAAAG
151201  CATAAAATGG AGCTTTAAAA AAATTAATTT AGAATCAGTT GTGTCTTCAG
151251  TTTACTAATC CACGCTTCAA ATGAGTAGAA CTTACAATTT GCTCTGGTTT
151301  TGTTACTTGG GTGGGTAAGA TAACTTAGAA GAGCGACAGG GATTTGCTA
151351  AAATATAAAA ATGGGATAGT TTTAAATCTC TATTGTTGTT ACCGTTGGCA
151401  GTAATATAAA GGAGATCAAA GAACTAATGT GTTTGTTCCC AACCTACCTT
151451  TAAAATAAAT TGTTTTATAG ATGTTATAAA AGTATACCTA TATACACTTT
151501  ATGTACACAC ACATGCATTT CATGTATATA TCCACTATAA TGCTAGTTCT
151551  CTCTTATTAT AACACTCCTG CAAGAAATTT GCCATATTTT CCCTATTTTG
151601  TGTTTTAGTT TCCTTTTTGT CATTAATAAA TATACTAGGT TTTCAGAGTA
151651  TGAAAATGTT TTCCCATCAA ACTCTTATGG TGTTGGGCCT TTTTTTCTG
151701  AGATAAAGTA ACAGAGAAAT CAATTTGGGA GAATCTTCTC ATTAAGGGAG
151751  CATACTACTC CTTACTAGTG AACTGGCTTA CAGACTGAGG TTGGCAGGTT
151801  CAGATATGTA TGAGCAGAAC AGTAGCAAGA CATTTGCAGA CCTATGATCC
151851  TTGCTTGTTC ACCTAATTCT TTTTACCTAA CACTGCCACT ACTGTAAAAC
```

FIGURE 3WW

```
151901  CAAAGCAAGA CATTCAGAAA AAGACATTGC AGACCAAATT GACACTTTGA
151951  GGGAGGCTAC CATGGGTATA ATGTATAAGC CTCCATTTGG AGCAGGATCC
152001  AAGATCAATA TGGATACATT AGATTCTACT TTTTAAAATA AGCACTCATC
152051  TCATTTCAGA CTATGGACAT GCTACTGAGC TTTACTATCC TTAATCCTTA
152101  GTCTAGTACC TCGGTATCTT CATTAAGTAT GAAAGGTTAT TTCTATTAGG
152151  ACTTGCCTCT GAGTCCCAAA CTGGGACTCA GGATCAGATC ATGGAGGAAC
152201  ATGAAACTCT TATGTGGATG ATGACATGGA TTGGGCATCT GTGGTGGTTC
152251  TGGAACTTCA GGATTCACCT GATCTGCCTC CTACTTATCT TTGGAAAAAT
152301  GTAAAGTATA GGATCTTTCT ACCACAATCT TTACTACTGT AGGGAGTTTG
152351  ATCCACTGAC TCTTTTCAAA AGACCTCTCA GTGTTCAAGT ACTTTTCTTT
152401  AATGCCATTT CTTGAGAGTT GGAGCTACAG TTGCTCTAGA TGTGTCTAGG
152451  TCTGATCTTT TCTCCCCATA CTCCTTGAGC CCCTGATAAC CACCATTCTA
152501  CTTTCTATTT CCATGAGTTC AGTCTTTTTA GATTCCCCAT ATAAGTGAGA
152551  TCACAAGGTA TTGGTCTTTC TGTGCCTGGC TTATTCCACT TAACATAATG
152601  TCCTTGAAAT TCATCCAAAT TGTCAAAATG ACAGAATTTT GTTCCTTTTT
152651  AAGGCTGAAA AGTATTCCAC AATGTATATA TGCCACTTAT CTTTCTTTCT
152701  CTTTCTTTCC TGCCTGTTTT TCTTTCTTTT CTTCTTTCTT TCCTCTTTCT
152751  TTCTCTTTCC CCTTCCTTCT TTTCTTTCTT TCTTTCTTTC TTTCTTTCTT
152801  TCTTTCTTTC TTTCTTTCTT TCTTTCTTTC TTTCTTTCTT CTTTCTTTCT
152851  CCTTCCTTCC TTTCTTTTTC TTTCTTTTC TTTGTTTCTT TTTTCTTTAT
152901  TTCTCTCTCT TTTCTCTTTT TTCTTTCTAT TCTTTTCTTT CTCTTTCTCT
152951  CTCTTTCTCT CTTTGTTTCT CCCTTCCCTT CCCTTCCCTT TCCTCTTTCT
153001  TTTACAGGCT CTCACTCTGT CACCCAGTGA GTACAGTGGC ACAATCATAG
153051  CTCACTGCAG CCTGGAACTC CTGGGCTCAA GCAATACTTC TGCCTCAGCC
153101  TCCCGAGTAA CTAGGACAAC ATGCACATGC CACCACATCT GCCTAATTTA
153151  AAAAATTTGT TATAGAGACA ACATTCTTGC TATGTTGCCC AGATTGTTCT
153201  CAAAGGTCTG GCTTCAAGCA ATCCTCCTGC CTTGGCCTCC CAAATGCAG
153251  GGATTACAGG CATGAGCCCC CACACTCAGC CTCAATGCCA TGTTTGACTT
153301  ATCCTTTCGT CCATTGATGG GCACTTAGGT TGATTCCATA TCTTGGCTAC
153351  TGTGAATAAA TGCTACAGTG AACATGGGAA TGCAGATATC TCTTCCATTT
153401  ACTGATTTAA TTACCTTTGG GTACATATCC AGTAGTGGAA TTGATGGATC
153451  ATATGGTAGG TCTATTAATT TTTTGAAGAA ACTCCGTACT GTTTTCCATA
153501  TGGCTGTACT AATTTATATT CCCATCAACA ATGTGAAAAG TTTCCCTTTC
153551  TCCACCTCCT CGCCAACACT TGTTCAGACA CTTTCATCTT TAAAAAAAAA
153601  TTAATTTTTA ATTTTGTGCA CACAGTAAGT GTGTATATGT ATGGGGTGCA
153651  TGAGATATTT TGATACCGGC ATTTTGATGT GTAATGATCA CATCAGAGTA
153701  AATGAGATAT CCATTACCTC AAGCGTTTGT TCTTTCTTTC TGTTACAAAC
153751  AATCCAATTT TGCTCTTTAA ATTATTTTAA AATGTTCAAT CCATTATTGT
153801  TGACTGTAGT CACCCTGTTG TGTTATCAAA TACCAGATCT TATTCATTCT
153851  ACCTAACTAT ATTTTGTAC CCATTAACCA CCCCCACTTG CCTGCCCACC
153901  CCTCATTACC CTTCCCAGCC TCTGATAACC ATCATTATAC TTTTTATCTA
153951  CATGAGGTCG ATTATTTTAA TTTTTAGCTC CCACAAATAA GTGAAAACAT
154001  GCAAAGTCTG TCTTTCAGTG CCTGGCTTAT TTCACTTAAT ATAACGACCT
154051  TCACTTCTAT TCATGTTGAC ACAAATGACA GGATCTCATT CTTTTTATGG
154101  CTGAATAGTA TTTCATCATA TATATGTACC ACATTTTCCT TATTCATTCA
154151  TCTGTTGGTG AATACTTAGG TTGCTTCGAA ATCTTGGCTA CTGTGAGTAG
154201  TTTTCATCTT TTCGATAATA ACCATTCTTA TAGATGTGAG GTAGTATCTC
154251  TGTGGTTTTA ATTTGCATTT CTCTGATCAT TGGTGATTTG AGCATTTTTT
154301  CACATACCAT TGGCTATTTG TATGTCTTCT TTTGAGAAAT GTCTATTCAG
154351  ATACTTTGCC CATTTTTAAC CTTGTTTTTT TCTTACAGT TGTGTTGAGT
154401  TCCTCGTATA TTTTAAACAT TAATCTCTTA TCAGATTTAT GGTTTGTAAA
154451  TATTTTATCT CATTCCATAG GTTGTATATT CACTCTGCTG ATTATTTTCT
154501  TGGCTATGCA GCTTTTTAGT TTGATGTAAT CTCATTTGTC TATCTTTGCT
154551  TTCCCAGTCT GTCATTTGGG GTTAAATCCA AAAAAAAATT ATGCAGACAA
154601  ATGGCAATGT TTTCTTATAG TGGTTTTAGG TATTTAATCC TTTTTTAAAT
154651  ATGGTGTGAG ATAAGGGTCT GATTTCATTC TTCCACATGT GGATATTCAG
154701  TTGTCCCAAC ACCATTTGTT GAAGAGACTG TCCTTTCCCC ACTGTGTGCT
154751  CTCAGCATCT TTGTCGAAAA TCATTTGACC TTAAATACAT GGATTTATTT
154801  CGGGTTGTCT ATTCTGTTCA CTGGCCTCTG TGTCTATTTT TATGCCAGTG
154851  CCATGCTGCC TTGTAATACA GCTTGTGGT GTATTTGAA GTTGATATT
154901  GTGATACTTC CAGGTTTGTT CTTTTGCTC AAGATTTATT TGGTTATTTG
154951  TTTTTTGTGG TTATACAAAG TTAGGATTG CTTTTTCTA TTTTTGTAAA
```

FIGURE 3XX

```
155001 AAATGTCATT GGCATTTTGG CAGGGATTAT ATTGAATCTG TTGATAGCTT
155051 TTGTTAGTAT GGATATTTTA AATATCAGTT CTTCCAATCC ATAAACACAG
155101 GATATTTTTC CTTTTATATG TGTCCTCTAC AATTATTTCA TCAATGTTTT
155151 ATAGTTTCA GTGTACAGGT CTTTCACCTC CTTTGGATTA AATTTATTCC
155201 TAAGTATTTG AAATTTATTT TGGTAACTAT TGCAAACAGG ATTGTTTTCT
155251 TGATTTTATT TTTCAGATAG TTTGTTGTTA GGGTGTTAAA GTGCTACCCA
155301 TTTTTATGTG CAAATAAGGA TAATTTTCTT TCTTTCTTTC TTTCCAATTT
155351 GGATGCCTTT TATTTCTTTC TTTTGCCTAA TGGCTATGAC TAGAACTTCC
155401 AGTACAATGT TGACTAAAAG TGGCAAGAGT AGGCATTCTT GTCTTATTCC
155451 TGATCTTGCA GGAAAACCTT TCAACTTTTC ACCATTGAAT AAGATATTAG
155501 CTGTGGGTTT ATCACATGTG GTCTTTATTG TGTTGGGGTA CATTCCTTCT
155551 ATGTTTAATT TCTGAGAGTT TCTATCATGA AAGAATGTTG AATTTTGTCA
155601 AATGCTTTTT CTGTGTCTGT AGAGATGATC ACATGGTTTT TGTTCTTTAT
155651 TATATTAATG TAGTGTATCA CATTTATAGA TTCGTAAATG TTGAATCATC
155701 CTTGCATCTT TGGGATATAT CTCACTTGAT CATGATGAAT TATTCTTTTA
155751 CTGTGTTGTT GCATTTAATT TGCTGGTATA TTTTGAAGGT TTTTGCATTT
155801 ATGTTCATCA GGGATATTGA CCTATAATAT TTTCTTGTAA TGTTCTTGTC
155851 TGGCTTTGGT ATCATTGTAA TGCTTTCCTC ATAAAATGAG TTTGGATGTA
155901 CTTCTCTTCT TCAATTTTTT GAAAGAGTTT CAGAGGAACT GGTATTATTA
155951 GTTCTTCATT AAATGGTTGA TGATTTCAGC ACTGAAGCCA TCAGGTCGTG
156001 GGCTTTTCTT TCTTGGGAGA GGCTTTTGGT AATTGATTCA ATCTCCTTAC
156051 TTATTATTGG TCTGTTCAGA TCTTCTATTT CTTCCTGATT CAACCTTAGT
156101 AGGTTATATG TGTCTAGGAA TTTATCCATT TTTTTCTAGG TTATTCAATA
156151 TGTTGGATAA TAATTGTTTA TAGCGTTCTT TTATAATCCT TTGCATTTCT
156201 GTAGTGTATT TTAATGTCTC CTCTTTCATT TCTGATTTTA TTTGTTTGAA
156251 TTTTCTTTCC TTTATTCTTG GTCTAGCTCA ACATTTGTTG ATTTTGTTAT
156301 TATTTCAAAA CACCAACCTT TAGTTGAGCT GTTCTATTGT TAGATAGAAT
156351 AGAATAGAAT GTTCTATTTC AACAATAAAA TGTTGAGCAG TTCTATTGTT
156401 TTTCTACTTT GTATTTCACT TATTTCTGCT CTGATTATTA TTTTCCTCCT
156451 TTTAGTAACT CTGTGCTTAG TTTCTTCTTA TTTTGTGTGT CTTAAGGTAC
156501 AATGTTATAG GTTGTTTGAG ATCTTTCTCC CTTTTTGATG TAAGTGTTTA
156551 TTGCCATGAA CTTTCCTCTT AGAACTCTTA CTGTTGCAAT CTACAAAAGT
156601 ATTTGTTTTT GGCAAGTTGT GTTTCCATTT TCATTTGTCT CAATACATTG
156651 TTAAATTTAT CTTTTAACTT CCTCATTGTC CCACTGGTTG TTGAGGAGTA
156701 TGTTGTTTAA TTTCCACATA TTTCTGCATT TTCCAAAATT CTTCCTGTTA
156751 TTGATTTCTA GTCGCATACC ATTGTGTTAA AAAAAAGATA CTCAATATGG
156801 TTTAAAGTAT CATTTCAGTT AATGATCTGG ACCTTAAATG ATGGCAGCAT
156851 AATCAATGTT AATCACAAAC CAAAGGCTAT TTAGTGTTAT TATTTTAATA
156901 TGCAATATAC TTACCAGGCC CCCCAGCACT CAGTCTGCAC AGTCTAGACC
156951 CTGCCTATCT CAGATCCATA CCCCATCTCT TCCTCCACCC CTTCTGTTTC
157001 AACCAAATTA ACACTGTTTA TTCTCTGTAG TTCCCCACCC TCACTGCCGT
157051 GCCCACACTA TGTCTTACCA AATTCTGTCC CTCTTTTAGA TCTCAGTTTT
157101 CCTTGAACAC CCAGACTCAA GGTGTGGATG CCTATTTGTT TATCTTTTTA
157151 GTAGCCCAGA CTTTTTTATA GTACATTTTA CAGATGTAGT CAAATAATTG
157201 TGTAATTGGC TACTTAAGAT TTCTCTCCTG CATTTAAAGA AAGCCCCGAG
157251 ATTATATCTA TCTTGTCCAA CTTAGCATGC TGTCTTGCAT GACAATCATT
157301 AACTTTTTAT TGAGTTAATT AAGCATTGTG CAGAATGCCT AGATGCCTAA
157351 GCTTTCAATG TTACCAAACA TGTGGAACAA AACTTACTGC AATCTAGGTT
157401 CCCCTGAAAA CATAGCCTAA GGTGGAGGCT TACTTGAAGG TTACCGTACC
157451 TTAAGGAGGA GAAGTAAAGA ACAGGAAGTT ACTGTTATAG AGTGAATTTT
157501 TCTCCATACC CCACCCAAAT TCATATGCTG AAGCCCTGTT GACTAAAGAA
157551 AAAAAAAATC AAGCTTTTAA AGTATCAGGC CAGGTACGGT GGCTCATGCC
157601 TATAATCCCA GCACTTTGGG AGGCTGAAGC AGGCAGATTG CTTTAGGCCA
157651 GGAGTTAGAG GCCAGCTGGC AACATGACAA AACCCCGTCT GTACTAAAAA
157701 TACAAAATT AGCCAGGCAC GATGGCGATC ATCTGCAGTC CTAGCTATTC
157751 GGGAGGCTGA GGCACGAGAA TCGCTTGAAC CTGGGAGGCG GAGGTTGCAG
157801 TGAACCGAGA TCATGCCATT GCACTCCAGT CTGGGGGACA GAGAGAAACC
157851 CTGTCTCCAA ATAAATAAAT TAATTAATGA ATTAATTAAA TAAAGAAAAG
157901 TTAGCTTTAT TTGGAAGTCT GAGGACTATG GACCAAGCC TATTGCCTGG
157951 GATCAGTTCT GTTAGACCAT TCCAATGCAG CAATTGAGTT CACAGTTTGT
158001 ATACAAATGG TGAGGATTCA TTACATGCAA AATCACATCC GAGTTCGTGT
158051 ATAAGAGTTG ATATTTATAG ATTATTATTA TTATAGATTA TATTATAGAT
```

FIGURE 3YY

```
158101  TATACATTAT TATCGATAAT AATCTATTAT CGATAATAAT AATCTATAAC
158151  CTATAACATG CTAGGCTGCC TTCTGCTGTT GAAAATAATC CAAATATCTT
158201  GGGCATATAA TTATCATTGA GAAGGGCATG ATATGTACAA GAGAAGTATT
158251  CAACTGGTTT CCCCATGATC GCAAACCTTT GGAGCTTATA GAAGAGAAAA
158301  AAAAAAAGA GAGACAAAGC AAATATAAAA GAGATTTTGA GATAATTTGT
158351  ACACTCTGAA ATGAGAAAGC AAACTTAGGG CTGACACAAG AAGAACTAAT
158401  TATTTTTTTC AAGTACATTT TATTGTTATC AAAATAGTCC ATACATATCC
158451  TAGGGAAAAA AAACCCCACA AATAGTACAG GAAGATTATA ATTTAAAGCA
158501  CCAGTTCACT CAAAGGCAAC ATTTTTAACA AAATTTTTTA AAATTATTTT
158551  TAGTGATCCC TCTAAATTTC TAAATAATAT GCTTATATTT TTTTCTTGTT
158601  TTACCCATGT TAAGTGTGAC AAATTTACTT TTTGCTCTTA TAAATATGGA
158651  TTTAGCTAAT TTTATTTTTA TTTTATTTTA TTGAGACCAG TCTCGCTCTG
158701  TCGCCAGGCA GAGTGTGCAG TGATGCAATC TCTGCTCACT GCAACCTCTG
158751  TCTCCCAGGT TCAAGTGATT CTCCTGCCTC AGCCTCCTCA GTACCTGGGA
158801  GTACAGGCAC TTGCCACCAT GCCTCCCTAA TTTTTGTGTT TTTAGTAGAG
158851  ATGGGGTTTC ACCATGTTGG CCAGGATGGT CTCGATCTCT TGACCTTGTG
158901  ATCTGCCTGC CTCTGCCTCC CAAAGTGCTG GAATTACAGA TGTGAGCCAC
158951  TGCACCTGTC CAGATTTAGC TAATTTTCTA CACTTATCCC CAACCTTCCT
159001  CTTCACTCTA CCTCCCTTTT CAATACGATA ATATCACATC TTAAGTTCCA
159051  TCATCCCTGT AACCTCTGTA GCTATAAGTA TATAGCCACA ATTAACATAT
159101  GTAGATTTCC ATTTCTGATT CTATCAGCCA TAGGTAACTG TCTTTACATT
159151  CCACTTTGTA AGAGGAGATG AATAATTCTC ACCTTTCCTC CCAACTCTGT
159201  GTTCCTCCTT CTACCTCCCC ACCCCCAACT CCGTTGTAGC GGCTATTAAC
159251  ATATATTATT TTGTAACCAT GGGTAAGTGT TAAGTAATTT GCCTAAAGAT
159301  TGATTCTAAA AAATTTAAAA ATATAGAAAT CTATAAAATT CTGTAAATTT
159351  TAGATTTTCT ATAATTATAG AATGTAAAAA TATAGATTTT CTATAAACAT
159401  AGAATGTAAA ATTCTATAAA AATATAGAAA TCTTTATGTA ATTATAACTG
159451  TGTAAGTATT ATTTACTGTA GAACCAAGTA ATGTGCAATG CTTCCTTCTC
159501  CATGGCTCCA GTGTCATGAC ATCTATAGTA CTTTACAAAT AATGTTATGA
159551  GTATATACTT CCAGAATGGT GGTAAAAGAA GCTCTGCAGA CCCTCTCCCC
159601  AGTGAAACAA CCATACTGGT AAAAGTAATT TTAAAAGGCA ATCATGAAAA
159651  GTCTCTGGAA ATTTTCTTAA GGGTATACAG CAAATGAAGA AACATTTATT
159701  CCAAAAAGTG TACTAAATCT TGGTAAGAAC AATGAGTCCA AGGCACCTAA
159751  GTCACAACCC ACTTCCCTTC CTCTCCTCCC AGCTCAGCAT GACAGAAGCT
159801  TAACTCTGGA CAAGAACACA GGGCTTCCTC AGCTTCCAGT TGAGGCCAAC
159851  TGTATGTTCC CAAGAGGAGA AGACCAACAG CGTTTCTTGT CTCCCTTCAC
159901  CCTTCCCCTC CAGAAGCTAA ATTCTGGCTA GATGAATCCA AGATATTGGG
159951  GCTCCCTTCT CTCACCCAGC TCCTACTGGT AGGGTGGAGG TTCAACCTCA
160001  GGCCTGGAAC ACTGAGAATA GTATGGGTTC CAATTATTA ATGAGACTCT
160051  GATTATTGCC CATGCTCAGC TCCCTGCTCC TACAGCAGAG GAGTCACTTA
160101  CAGAGAAACA CAATGCTGTC CCCATCCCTA GCTCTGAAGC CGCGCGTCAG
160151  AGATTTTCCC CAGTGGGAGC ACTGAAGCTC TTTGCAAAGG AACTGACTTT
160201  ATTTGAAGCA GAGTAAAGGG AAGTTCAAGA TAAAGGTATT CTCAAAAATA
160251  ATGTAAGTTC TGGTGGAAAG CAATTAAGGG GAGGTTGGTA GCTTCGTGAA
160301  AGAGACAAGC TAAACCAGAT TAGCTAGTGT ATGAGAGAGA ATCAGGAAAA
160351  GAGATAGCTA AGAAGAGCCC TCCTGGGTCA GAACAAACCT CAAGCACTGA
160401  CCACAGCAGG CAGGGCACTG TGGCTTACAC CTGTAATCCC AGCCCTTTGG
160451  GAGGCTGAGG TGGGAGGATT ACTTGAGCGC AGGAGTTTGA GATTAGCCTG
160501  GGCAACATAA CAAGACTCTG TCTATATTTT AAAAACAAAA AACAAAAGGC
160551  TACCACAGCA AAAAGGCTGG AATTTAGTTG GAGCAGACCC CCAGAGCAAT
160601  TTATGTCCCA GGACATTGTA AAAAATAACA GAACAATCTA GAACAGAATA
160651  GCTGGGTATA TGTGATAAGC CTTAGAGCAA CCACTAAGAA AATAACTCGA
160701  AAAATACATA GTGAAGGAAA GAAAACAACA ATGTTCCTAA CATCACAATC
160751  AAATGAATTC TCCTTTTCAA CATTTCACCA GAGGCTCAAA ATCATTCCAC
160801  GTTTAAAATT TTTTTCTCTT TATAATGTCT ACTGAAAAAG TAGCAAAATC
160851  TACTGAGGAG AGCTTTATTT CTAAAGGGA GTATCACAAC CTGCAAGTGG
160901  GAAATGGAGC CTCTGGTTAA AACTGAAAAG CAGGTGCTTC GAAGGAGGAA
160951  AAATGAGACA GGAATTCATA CTAAATGGAT TGGTTTAGCA TACATATTCA
161001  ACCGGCTATT GGAGGAGCTA TGAATATTCA TGAAGGGGCA CACGTGTAGT
161051  AAGCTAACAT GTCTATTACA TATGTCCCAT GTTCACTTTG GGTGGAAAA
161101  AGCATTTAAA TATACTAAAA TTAAGCTCTA TATGTCAAAA GGTTAAGCAG
161151  AGGACATGAA GGGACTCAGC ATACAGTCTC TGTAAACTGG CCAGAACCAC
```

FIGURE 3ZZ

```
161201  TCCATGTTCA GTGTTCTCTT ATTGGGAAGG AATGCTAGCC AGTTGCTGTG
161251  TCGAAACTAC AAAAAGCAAG GGGCAGCGTA ACATGGTTGG TTGAAATCAG
161301  CCATGGAGCA AGTCTTTCAA AAGAGCTTGT TTCTGTTTAA CCCTTAGGAA
161351  CGAAAGCCTA CTGGTGGTTA ACAAGGTAGG GGGTGTTACA GGGTGTGGCT
161401  GACCTACTGT TCCATCATAG ACAGGAGCTC AGTTTTAAG GTTTCTCTGG
161451  GGTCTCCAAG TGAGCCTCCC TGGAGAATCC TCCAATTTCC CTAGTGAGAG
161501  CAAGAACCAT ATCTGTCTAT ACTGCCCAAC TCAGTTGTTT TTGCAATAAT
161551  AGACAATAAC TCTTTAAAGA ATGAATAAGT GGTGGTGAAA TGAAACAGAG
161601  TAAGTTCCTG ATGTAGAAGG CAGAAGGGAG ACTGTTGCTT AGGCAGACCA
161651  AGTAGAAACT ATACGATATT TTCTATAGTA ATAACCTTAG AAATGGCAAT
161701  TCGGTTCTAT AGTTCAATTA ATATCACTAA AAGAGCTGTC CAATGAACTT
161751  ACAAGTTATG TGGTATATGT GGGTTAATCT GGGAGACCAA CCACCATTTA
161801  TGAAATTCTT CTCTATGAAA ATGCTTTATG AAGGGCAAAT AGCAAGTTTA
161851  CAAATCAATT TTTGGAAAAC AAACTGTAAA TTGAGGTTAA CTTCTAAGGC
161901  TGTTAATTTG TGGGTATCTT TGTCTATATC TTCTTCTCAC TGATATATCC
161951  TCAGGTAGCT AGAGTTCTCC TTTCAACTAG CCTTAATTTT GAATTATATG
162001  CCAGTTATAA ATCATCTTCA GAATATGAAT TAAATACCCC TTTAATTTTA
162051  ATTGATATGA TTTTACAATA TTAACTACAT AGTAACAATG GATTTGGATA
162101  TTTATCATTT TTCTATTTGA TTTATAATTT AGGGCCAAAT GGGTGTCATA
162151  AGGGGCTCTC ATTCCAGGAA ACACTGTAGA GTAGTCTAGT ATCCTAACAG
162201  TCTATCCATC TTGATTTTTG AAAATAGTCT GTTGTGGAGT AGTTTAGGAT
162251  AACCTAACTA CTTGTCTGTC AAATAGAGGA ATGCTGTGAC TGGAGAAAAT
162301  GGAGCCGTTA TACATTAGTC TTCGGTACAG TCACAAAAAG CTACTTATTT
162351  CACAAAAGAC ACTATTTTGC CTTTTCAGGT GTAACTGTGT GGAACCGCAT
162401  AATCCCAGCA ATGGCACATT GAAGGAATGG AGGGAATCCA ATATTTCTGC
162451  CTCTGACATA ATTTGGGAGA ACCTAACTGT GTCAGTAAGT AAAACACTGA
162501  AAAATAGTC ATACCTAAGA GCTTTTGTTG ACATTTTGAC TCAATTATTG
162551  CCATTACAGT AAAATTTTTT TGAATGCATA ATATAAAACT AATAGTTGTG
162601  TTTTAATTTT AATTTCATCA TTTCAGATGC TCATCAGTAA ACTGGGGTTA
162651  TCTTTCATTA TTAAGGTTGT TCTAATAGAA GACCAGAATT GCTCAAATAG
162701  CTCACTTATA CAGAAATATG TGACCGAGAT GGACTGAAAG CACATTAAAT
162751  ATGAGTGGTG TTGACCTAAA TGAAACCATA TGGCAGAACT AAGTCTGCCT
162801  TCTGTGTAAA GAACTCAGAA TGCTCTTACT TTACTCTGTA ATGCTGCTCC
162851  AGCTGTTCCG GATCTGCTGG GGGGAAAGGG ATGTTTCTAA TATTCTAGTG
162901  TCAATACTAA AGTCTTTGGG AGGAACAAAT ATCACTTTTC TTCACAAAAT
162951  TCTGGCACCT CCCTCAACAA GATCTTTCTT TTTTCCATTT TATTCTTATC
163001  TCCCACTCAA GAAAGAGCAT GGCAACATAT TTTCACCTA TAACAGTTCA
163051  ATCCTGTGCC ATTGTCTTAT TTCCTTTGAC TTTTCTCTAC TTTGTGATTT
163101  CTTTTTTCTC ATACCTGCAT TTCTCTATTT TTCTGAATCT ATTCTGTGCC
163151  TCCTTTCCTA TCAATACTTG CATTCTATGC TTCTGGTTCA ATAAAATCTT
163201  GTAATTTGAA AATGTGTTCT ACTTTAAATA AATATTAAAA TCTGAGTAGC
163251  CCTACTTTCT TTTCTATTCT TCCCAGCTAT AAACATTACA GGTTCAAACC
163301  TTCTACCACT TTACCTACCC ATATAGGCTC AAGTTTTATT ATGACTATCA
163351  GCACAAAACT ATTGAGTTCT AGTTCATTTG ATCAAATGCA TACTATTTTA
163401  GTAAGTTGTC TAGTTAGTGA GCATAGAAAT CTTTTTTGGT GTACAGATGC
163451  TATAAAACTC TAAACATGAT TCTTGTAAAG AGCATATGAT CTATTGACTA
163501  TATTCTTGAT TTTCTCTATT GAATATGTTC TTTCAAAATT GAAATCAAAT
163551  TACTTACTCT TTATTTAAAA TTCTATCTTG ACCTATATTT TACTACTTCT
163601  ATTCTTACCC TAGCTGTGTT CTGTAGAATA AGCCTTCAGT TACTCTTATT
163651  GTTTTCTTTT GTTATTGTTA ACATTTATTC TGTTCCACCT ATTTTTCCCT
163701  AGAAAAATAA CATTGCCAGT CTGCTTCCAC TCAAAGAGCC ATTTAAACTG
163751  AACAATAAAA GAATTGATGA GCTGATCAAG AAAAAACACT ATAGTTATTC
163801  AGAATTTAGA CATGGGGTCA TGATTAATGA AATCATTAGT GGGTCTTCTG
163851  TCTACACTTT CTTTGGTAAA CTATATTATG TTTACAGAGC CTCTTGATGT
163901  CTTCTTCAAT ATGAAAACCC AAATGATCCC ATCTCTAAGT TATATAACAT
163951  GATAATTTAC TCTATATGTG TTTTGTATTA TGTGAATAAT TTAATACTAA
164001  ATAATAATAT TCCTTCTATG TATTAGCAAA TCTTGAATTT TGAGAGTTCT
164051  AAGAAGCAGA CATACAGCAC AGTTATCAGG CTAGCTGTGA GTTAGATACC
164101  CTGAGTTTTG AGGTCAAGTA GAATAGTGAA AAATATTTG CAATTAAAGC
164151  AAATACAGCA TTGTGGGGTT GTTGGTTTTT TTCTCTTTTT TTTTGTCATT
164201  TTAAAAAGTT TTGTACTAGG TGTTAACATT TGAGCAGAAA GTTTCATATT
164251  ATTTTTCATT AGTTAAAAGC AGTTTTTGCA ATGGATAATT GCTAAACTTG
```

```
164301  ACCAGAAACA GTCTTTATCA CCAGAGGGAA TACTATATAA TGAAAACAAT
164351  CTTGTAATTT TTAAGTCAAA AAAAGACCAT TAAAATTTTT GTCTAATTGT
164401  TATGCTGAAT TTTTTCCTCA ATATATTCAT AATGTCATCA AAAATATTTT
164451  ATTAATAAAG CACTGAACTA GTGGCTATCA CAACTAATTT TGTTAAAATA
164501  GTGACATAAC ATTTAATTTA CATATTATTT GTTTGGCAGG TCCTGTAATG
164551  TTTTATTGAG TTGTTTGTTA CATATCTCAT GAATTATAAT TTATACCTTG
164601  CCAACTCAGC AAGGGCAAAG AACTTTAGTT TTCTCTGATT CTCCCAAACT
164651  GCTCTATGCA TAGTAAGTGT CAAACATTTG ATAGAAGTAC TTAATGTCTG
164701  TTTGAAACAG TTTCATCTTA CTATTTAATG CAAATATTTA TGGCAAACTG
164751  GAGTACTTAA GTTTGTGTGT ATATATATAT ATATATATAT ATATATATAT
164801  ATATCTCTCT ACATATATAT GCGTGTCGAT ATCGCGAAAA ACCGTCTCTA
164851  TATGATACTC TCGCGCAACG TCGAAGAGTA AGCAGGCGCA GCTCAACCAG
164901  CACGAGGTGT CGCAGTCACT ACCTCGCATA CCTTGCGTGT NNNNNNNNNN
164951  NNNNNNNNNN NNNNNNNNNN NNNNNNNNNN NNNNNNNNNN TATACTATAG
165001  GAGCCAAGTA GCAAAGCATA TGTATGACAC GCAGGATCGA CTCTACGAGG
165051  ATCCCCCTTA GGCAAGATTT AAAATATTCA TAAGCAGTTA ACCAGCATTT
165101  GGTGTTTCAG TGCCTGAATT ACATATTTAG CTTGTACATA TATAAGGGGC
165151  AGGACACTAA TGCCAACTTT AATTTCTTAT TCTAACTTAA TTTTTGCCAA
165201  CTTATAGAAT TGCTGAAACT TAGAATGTGT TTGAAGAGTA ATTAGTAGAA
165251  ATCAGTTTGT CAACAAGCAT TTTTTGAGTA CCCATTGTAA CTGAAACCAT
165301  ATGTTAGACT CAAAAAACGA GAGCAGGATT TGGATTTGGT TTTCATTTCT
165351  AAATTTCAGG ACTTACTCTG TGTGTATGTG TGCATGTATG TATGTGTGCA
165401  TGTGTGAGTG CCCTCTGTGT GTATTGGGG ATACAATTAG TATAAATCTG
165451  AAAATAATTG TTGAATTTAG CAGGTCACAA TTTTTCTCTT TTAAAATTAG
165501  CATTTTGTTT CCTCCCAAAG AGAAAATAAA TAACATTTTC AAATATGCTT
165551  TGAATTAATG TAATTAGGCA GACCATTGGC AAATTATAGA GTGTAAGACA
165601  GCTAAGGAAC CCTTTAAATG TCATCTATGT TCTTAAGAAT TGAGAACAAG
165651  ATCCCGCCAA ATGACTTTTA TACCTGCAGA AATGACAAAA GATGCTCACA
165701  AATTTATAGA TAATGTGTTT ATCATGGAAC TTTTAGCTCC TTTTTCTATG
165751  TAGCAATTTT GCTACCCATT ATATTGCTTA ATAATTGCTC TGCTAGCATT
165801  TCTGGACAGG TGCAGAAGAG GATGAAAAAC ACAAGGATTC ATTTTTGCCA
165851  CCTTATCTAT TTTTAAAGCA TTTTGAAAGA AGGAAAATTA AAACTTTAAT
165901  TAAGGCCTGG GGGATTTTTC TGTGGTTTTT CAATTAGCCA AGTTGCTGTG
165951  CTCTGTATTA GCTTAACATG AATAATTGGA ATTTAACTTT GCCTATCAAG
166001  GAAGATGTTT GCAGTTAAAT TAGAAAAGGA GACAGATTCT TTAAGACAAT
166051  AATAAGGTGT ATTAACTATA TTTCTCAAGA CTCTCAGGCT TAGGGTAGCT
166101  AGCAACTCCA AGTAGATTTT ACTAGTTGTT TGTTTTCAGA TGACAGTGTA
166151  GCTATTTGTA ATTTATTCTA CAATCTTTGG AGTGTATTTA CTTTTTGCTC
166201  TACAAAGATT TCAGGCCTAA AGTTGGGCAG ACTCTGTGTT TGTGATCAAT
166251  CTATCAGTTC ATATTTGTCT CCAAGATCTC TCTGCAATTC AATTTATGTT
166301  CAGGGCAAGA ATATCTCAAG GACTAATGAG ATCACTGGAT CATTTAAACC
166351  ATTATTTCCT GTTTTGAAAT GTAAAAATAC TTTAGTAATC TAATTTTTAA
166401  ATAAGATAAA CCAAAGTAAG TTTAAAATAA CTTTTTTTCA TTCAAAATAT
166451  TTGTTTGAAA TGCTCAGTTT TTCCTGGAGG AAAAAAATTT TTTTGACTTT
166501  GCTGCCACCT CATGGCTAAG GCAGTAATTA GAAATAGTTC TTCAGGCTCT
166551  TACAGAACTA CAGTTGCAGA AGAAAAAATA ATCCATGGAG AAGTCATAGT
166601  AAATATGAGC TTTGCCTTGC TCATGTAGTA ATTTTATTTC ATTTGTTCTT
166651  TAGTCCAAGT TCGATAGTCC CATCTTTGAC TTACAAGTTC ATTTCAGTCA
166701  TTGTATGTCA TAGTTTTCTT GTTGCCTTTC TCATCTTTCT TGGCAGCTTT
166751  TGGACTAGAT AATTCTACAA AGTCATTGTT CTTAGTCAAT AAGCAATAAT
166801  AATCTCACTG CAGAAATCGT GTTTGTATCA CAGCTCTGCG GCCACCCACC
166851  AGTGGTGAGG CCACAACAAA TTATTTAACC CCTTTATGCT TCAGTTTCCT
166901  CAGACATGGA ATATTAATAA TAGCATGAAC ATATTTTATG GTATTGGTGT
166951  GAAAAGTAAT TTAAATGATG TATTTAAATA GCTGGGCATA GTGTCTGACC
167001  TTAGTAACCA ATCACTATTA CATATGTCAT ATTTTCAATA TATCTCGTGT
167051  TAGGAACTTA GTAGATATTA GATTTAATAC ATACTAATTA ATTGGTAAAT
167101  CAATCGTTTT ATACATTTAA ATTTAAAAAG CAGTTCATGT TCAAATTTTT
167151  CATAAACCTT TGCATATTTC TCACCACCCA TCCAAGTTGA ACTTGAAACT
167201  CGTAATGTAA TGCCTGCTAA ATCATTGTGA GAGCCATAAA GGAAAAGCCT
167251  CAGCATCTGA ACTACAATTG ATCAGAAGGT GTTAGTTTTC TGCAAGAAAT
167301  GTGTCCGGTT TTTTCTTAGT AGCTCCATTT GTTTTACTTC CTCTGGCAGG
167351  AATGCAAATC ATTGCATGGA GAGTATGTTG GACGGGCCTG TGGCCATGAT
```

FIGURE 3BBB

```
167401  CACCCATATG TTCCAGATGT TCTATTTTGG TCTGTGATCC TGTTCTTTTC
167451  CACAGTTACT CTGTCAGCCA CCCTGAAGCA GTTCAAGACT AGCAGATATT
167501  TTCCAACCAA GGTACTTAGA CTATTTCTTG ATCTAAATGT AAAATAACAT
167551  AGGACAAAAG AAAGAGTAAT TGATGTAATA AAAGGAGCCA CTGAAAGGCT
167601  TTTGTGTGAG TGAGCTGCCA GGTTAGTTGT GGAGTGAGAT GAGGGGCTGA
167651  AGAGAAAGAA TTTGTGATGC AGGTGCTGGG AGTGCATATG CAGGCTTTTC
167701  TCCTAACTGC AAACCCCACG GATCAACTCC TACTTTCCTA CTGACGTTTT
167751  TGGAAATTCA CAGCACACAC TGCATTACTG ATTGTCACTT TTTTGCCCAG
167801  TGAACAGTGG GAACTATTCC AGCCTGACAG ATACCTCAGA GGAGCCTATG
167851  TTACATTCTC TAATTGGGGA AGCCCCGGCA AGACTCATTG GAACAATATT
167901  CTCTTTTTCA ATGTTTAAAC CGTCAGTCCC TCCCCCTAAC CCACCACGTT
167951  TGCATCTGCA TATTTGGAAA GGAAAGTAAA CAGAGAAACA GCTTAGTTCA
168001  ATATTTAACA CTGCAAAGTA ACACCTATAA TGTCTGATTC CGCCAAAAAA
168051  AATTTAAAAA AAGGAAAAGA AACAAGGAAA CAAGCTTCTG AGGGATGAGC
168101  TATAGATTAT GATCAAAATT CCACTCTGGA AAAATATTTC AAGAACTGTT
168151  CCTTCCGAAG GGGGCTTCTT TTTTGTCACC ACTTTCTTCT ACTAAAGGTG
168201  GAAGATTCAT TTATTTCCCC AAAAATCTTA GTCTGATTAA TACAAAAACA
168251  TTTTTCTAAG CTGAAACAAT AATCTTAAGC ATTTTGTGTA TGCTTGTGTG
168301  TATGTCATAA AGGCATCTTA AAATAAACTA GATCTGGATA ATAATTATAT
168351  GTGAATATTT GCTCAGAATT GGCTTTATAA ATGAGAAATG CTTTAAAAA
168401  TTGGCTCACA TAGAATAAAT TTTAAATTTG CCCACTCTGT TGTGTACATT
168451  CCCAACTGTC ATGCTTATAT TCTAGATAAA CTAAACATT ATGTTTCTTT
168501  GATAAGAACA GATAATTTTA TTTTATGATG CTTCAAGTTT ATCATATTAA
168551  AGTGTTACCT GTGTGAAAGA GATCCCTAAA ATCCAGCCAA ATTCTGCCCA
168601  TGCTACCTTA TTCTGCATTC TGAATATTCA CATGCATGGG TTCATCATAA
168651  AGTTAGATTT TAAATAAACA TTGAAAACAG CACAACCACG ATGTAGCTAT
168701  TCCATAATGC CTCATTCTGG AAAGGTTGAG TGTGTACCAA TCTTAACGAC
168751  AGTGATACAT AAATATATAT TCAGGTTCTG ACAGAGCTAA TGGTAATCTT
168801  ATAGTATGCA TAAAATATAA TATTATGATA TTATGTCATA AAGTGTTTAT
168851  AAAGTGTGAC TCTAGATTAT GTTCCTGAGT ATTCCTTGAT ATTTATAGCT
168901  ACTTTAAGTG ACAAGTGTTT TCATTATTTT TAGGTTCGAT CCATAGTGAG
168951  TGACTTTGCT GTCTTTCTTA CAATTCTGTG TATGGTTTTA ATTGACTATG
169001  CCATTGGGAT CCCATCTCCA AAACTACAAG TACCAAGTGT TTTCAAGGTA
169051  CTTACTATCT CTCTCCCTCT TCCCATCTCT CTCGGTCTAA TCTTCATTTA
169101  GATGATACCT ATAACTCTAG TACTTAGGAT TTTCATGAAA ATATGAAGAA
169151  TTTAGATTAG AAGACCAGTA AATGAAATGC ACACAGCATG GCTAAAATTT
169201  AGGTCTAATA TTTAAAAATA TAAGAATTAC AAAATATAAA TAATTATAAA
169251  TATAAAACTT GCTTGAAAAA AATTTCCTGT CAATTCTGCC AGTTGAAATA
169301  CCTATATATA ACATTCTTAA AAGATAAGGA AGCATTTGAA ACTAAGAGAA
169351  AAGGATTATC TTGGCAGAAT TGTACAGTGA ATAAGGCTTG GAAAACAGAT
169401  AAAAATAGAT TGGGAATAGA ATTCTGACCG TGTTACTAAT GGGGTACAGT
169451  TTGAATATTC CTTATCCAAA GTGCTTGGGA TCGGAAGTGT TTCAGAGTTC
169501  ATTTTTTTTT CAAATTTGA AATATTTGCA AACACATAAT GAGATATGTT
169551  TGGGGTGGGG CCCAAGTCTA AATACAAAAT TTATGTTTCA TATATACCTT
169601  ATACATATAA CCTGAAGGTA ATTTTATACA CTATTCTTAA TAATATATGT
169651  GACCTATCAC ATGATGTGAG GTGTGAATTT TCCGCTTGTG GCATCATGTG
169701  AGCGCTCAAA AGTTTCAGAT TTTGGATCAT TTCAGATTTC AGCTTTTCAA
169751  ATTAGGGGCA CCCCTTTGTT TTCTCTGTCA AACAGGGCTG GGGACTTCTA
169801  TATAGGGCTC TTGTCAGGAT GAAATTTTGA GAATCATCTC AGACAGCAGC
169851  CATGTTTGGA ATCCTTCCCT GAGCCTCTGC TGTGACCAAG TATCTTTTTT
169901  ATCATTTTCA CTCAATAGCC TCTGCACATC AAAAATAACA GTTACAATAC
169951  CATAATGATG TATTTTGTTT AGATGTCTGT CTCTGATTCT AAACTGAAAG
170001  AAGCCTCTGA TTTATCTTTG TATCTCAGTT CTAGCACAGT GGTCAATGTG
170051  TCAATATGCT ATTTGTAAAT TTCAATACAT TTTCCAATAG TAAATAGTAA
170101  ATATTAATAT CATTTTATTT AATACAGGTA TTGATTAATA ACACAGATTT
170151  TTCAACAAGT CTGTCAGAGT TTAAATCCCA TCTCTACCAC GTACTAGCTT
170201  TGGGATCTTG GCAAGTTAC TGGATCTCTC TGTGCCTCAA TTTTCTTATC
170251  TGTGTCATCT TTAGAGTGTT GTGAAGAAAA AAAAATGAG TTAAAATATT
170301  TAAAGCACTT AAAATGGTTT TAAGTGATTT ATGAGTATTA TTATTATTTA
170351  TTATAGGCCA CTCAGCTCCT CTGTTTATAA TTAGGGCTTT CCTAGTAGCA
170401  TCTGTAAGAC CTAATTTGAT CAAGTATTCA TTAATCCAGT TCATAACTAT
170451  GCACATTCTT TACTTTATAC AGCCCACTAG AGATGATCGT GGCTGGTTTG
```

FIGURE 3CCC

```
170501  TTACGCCTTT AGGTCCAAAC CCATGGTGGA CAGTAATAGC TGCTATAATT
170551  CCAGCTCTGC TTTGTACTAT TCTAATTTTT ATGGACCAAC AGATTACAGC
170601  TGTCATCATC AACAGGAAAG AGCATAAGCT AAAGGTATAT TTTAACATCC
170651  ATTTTAATGT AAATAATTAT GACAACTGAT ATCAACTGAT GTTCATTTGA
170701  CTTCTATATT CTGTATTCAT TTGCACAGTG AAATATATAA AATAATGTTT
170751  TTAGATGTAT AATTTTTATT GTCTTACAAG ATACTTGGTC TTACAATGAG
170801  ATGAGAATTT ACTTATTTGT AGCACTTGGC TGAGCTCACG TCTGAGAACT
170851  CACCTCCAAG GCATAAAATA AAAAACTGTC AAAGTTTTAA CTTTTCCATA
170901  CTTAACATAT TTTAATGAAA TAACAATCTG TTCTGGTGAA GTACAACCAT
170951  ACCAACTTGT CTTACATCTG AGATTCCTCT ATTCCTCTAT TTAACCCTAA
171001  ATGTATCTAT TACATTGAAT TCATTATCAG AATAAATTAC AACTTCAACT
171051  ATTTCTCATT TTCTTTAATT ATTTTTCTGT CTGCCTGTAA CAACAAAATC
171101  CAGACATAAA CGTCACAGTT TAGAAGTGAC ATCTTTGAGT TTTATTGCAG
171151  ATTTCACTGT CTCTTTTATA AAAGAATAA CTATAGATGT GTCTTAGTTA
171201  CATTCTGACC TTGCCATTTT GCAATTGTGA ATAATCGAAA TTGTTCACTG
171251  GTATGCAATT TGCCTGAGAT ATGTAATGTA AGCACTGTCA CTTACTTACA
171301  GGAATATGTT AAATAAAATC GATGAAATCA TTAAATGGTT AAAAATAATC
171351  TGCATCAAAC CTTGTAAAAA CATAACATGC ACAATCTTGT TTTGTTTTG
171401  GTATCGTGGG GTAGTTGCCA GCTATTTTCA CATACCCTTT AAACTCTAGG
171451  AGAAAAAATC ATTGTCAGAG CAACAGAAAT CATGCTTTAT AGAATTTTTT
171501  TATAGGAATG TTAGAAAGAT GAAAAATATC TCTGATTAAA CTCTGATGCA
171551  ATATATTGGG TCAATGCAAA AGTAATTGCA GTTTTGCCA TTACTTTTAA
171601  TAATAATAAT TACATAAATG TAAGAAAGCA CACTTATTTG CAATAAATCT
171651  TATGAAGAAG GAATTTTGAG TATATGGTGG AGAGAATGTG TGTCTATCTT
171701  AAAGCAAAGG ACATTTTCA TTCTCTTTGT AGAACGTAAG TTAAGAATTC
171751  TCACAACTTT ATGTATTTTA TTAAATGATA CATTTTAAAA AATCAACTAA
171801  AAAACCTGTT TTAGGAAGAA AGTAAGCCAT ATAATTATA TTTACCTTTC
171851  AAAAAGATTT TTTTAGCCTT TATAATTAGG CAGAAATTCT AGTGTGTTCA
171901  CTGAAAAATT ATCCTCTGTA AGGGCCATCA GTTAAATGGA TTCAGGCAGC
171951  ATTTTTTTCT TATTGTAAGT GGAATCATAT TAAAACAAAG TGTGGAAGTG
172001  AAATGTGTGC TGAGATTGAT ATTACCTTCC TGGCCATTCT GAATCTTTGC
172051  CCTTTCAACC TTATAAATCA CATGACACTT GCTCTTACTC CTTGTTCTTC
172101  ATGAGCCCTT GACATTCACA GCCTTTGTAA AGCTCCACAT TGACAAATAC
172151  ACTAATTTCC CCCTTCACAT ATACTGTGGA ATAACAAAAA TGTAGTAAAG
172201  CATTCTTTAA GTGGTCCTTT CAAGTACTTG CATTTATAGA ATTAAATGCA
172251  GAACTAGAAC TATTTTTGTC ACTGAAATAA ACCTGAGGCT ACATTACTAA
172301  ATCTGTTTTA TTGTGCAAAT AAATGATTAT GTAGTCAAAA GTTGTGTATT
172351  TTTGCCCCTT ACTACTCTGG ATTTAGTAAA TGATACAGCA AATCTGGCTT
172401  AATCATAAAC TCTGCTATAT GCCCACAGGC AGAAGAGTCA GCCTGTTCTT
172451  GGCCACTGTG AATCTGAACT CTCCATCCTC CTTCTTAGAT ATGAATACTT
172501  TTAAAGCAAA TTTCTTCCAG TGAAGATGTA TTTCATCTAC ATTGAACCCC
172551  TATTGGGCCT ATAACTCTTG TCTCCTATAA GCTTCTATAG AGTGTGGTCT
172601  GATGCTACTG GTTTTCCCGT TAACAACAAC AAAATCACCT TCTCAGAATG
172651  TTATTTACTC AGAGTAACGG TTTGTTCCAT AGTCCTTCTC CCCGCCTGTT
172701  GCTTCATTGA AATGTTTGCA AAGTCTCCTG GCTTTGACTT GAACCACATT
172751  TTCACTAAAA GATGTGTTTC TTGAGTATAT CACCAGACCA CAAGCTAACC
172801  ACTTGTGAAA GCATTTTCAG CTTTTACTAA TTTTCTTTTC TCACTTGAAA
172851  ACCCATTTTT GCCTTGGTTG GAGCATTCCC CGAAATTGTT TAATGAATCA
172901  TGTTTTGTAG TTTATGTATC AAACACTTGG TAGACTCCAC ATCATGTATC
172951  TAAGTCTACA TACACCCAAG TCAACTCAGA ATTCCTCATT TCATTCTTTA
173001  TCTCTCCCAA ACATATTTTA GATCTTTTA CTTTTTCTTC ACCTCTATTG
173051  CCAGAACTAG TAGCTGGTTT TCTTTTAGAT GATATTTCTC CTGCTGATAA
173101  AAATGTTTTT ATTGGCCAGG CACAGTGGCT CACGCCTGTA ATCCCAGCAC
173151  TTTGGGAGGC CGAGACAGGT GGATCACGAG GTCAGGAGTT AGAGACCAGC
173201  CTGGCCAACA TGGTGAAACC CCATCTCTAC TAAAAACACA AAGATTAGCT
173251  GGGCGTAGTG GCGGGCACCT GTAATCCCAG CTACTCAGGA GGCTGAGGCA
173301  GGAGAATCGT CTGAACCTGG AAGGCAGAGG TTGCAGTGAG ATGAGATCAT
173351  GCCATTGCAC CCTGGCCTGG GCGACAGGGT GAGACTCCGT CTCAAAAAAA
173401  AAAATGTTT TTATCATTTC ATGAGTGTCA CTATGTACAC AATAAAGCTG
173451  TGTTGCACTG CATAGGTGAC TTACTACTCC GAAGAATGG GGGAGCTCAA
173501  AATCAGTAAA CCTCGAACTC ATTGCATCCT ATGATCCTTT GGATGGCTCC
173551  AGAGTGAAAG AAGAGGCAAA TACAAAATT TGAGAATGTG AAGTATCATG
```

FIGURE 3DDD

```
173601  TATATTATAC ATAAATGTAC ATATAAATCC ATACTCTCTC TAGCATTTGT
173651  TTGTTTGTTT CTCCCTTAGA GAAGTGGATT AGGCATAAGT TAACTGAATC
173701  CTTTTGAAAA GCATTAAAAA TATCTACTTG GGTTTTTTAA AGCACATTCT
173751  CTAAATGTGA AAAGAGAGAT AAAATCTTAT AAAAAAGAAA GTTTCTGTTA
173801  AGATACAACT GTGGGCTTTT CTACATGTTT CTGTAGACAG TTCAGGCTTC
173851  TTTTGACATC ATTTTTAATA AACAGCAATA CAATCCCGGA TCACTTGAGT
173901  AAATGAATGC ATTTGCAACA TTCATTTGGC ACCATATTCT CTTGATGATT
173951  ATGGCATTTG ATATGTTCTT TTTTGCCCTC TTTGTCAGCC TGGTTCTTCA
174001  TGTCAATCTA TAGTCTTTTA TGTGGTTAAC TTGACAGATG CAGGAAATTG
174051  CTGCCAAGCT TTGAAATGAA TTTTTTCAGC AGTGGCATCT GGGTATCAGA
174101  TGGTCCTCTT GGCTGGCCTC TTGTCTTGCT GCATGTTGGT TTTAGTGGGG
174151  TCTGGTGTAG CATCACCTGT TGCTATGCTC CCTTTTCCTC CCATATGTCC
174201  ATTTCCTGTG ATTCATGGAT GAATGTGAGA ATAAAAGCTC TAGCTCTGTC
174251  TTTATTTGAG AAAAAAATCT ACAGAAATAT GTTAGAAGGT GTAGAGTTCT
174301  CTGTCTGACA AAGGGATACT TCTCTTTGGC TGGCATGCCT ATCAGCTAAT
174351  AATTTTGTTA CAAAGTCCAA GTTTTTAAAG ACATTTTAAA TGAAAGGCAA
174401  GAAGGATACT GGTTAGTTAG GGGAAGAGCA AGAACTGCTT TATTTATTTC
174451  CTTTGGTTTA CGTTAAATCA AGATGCTGCC ATTGTTGTAC AGCATAATTA
174501  GGGGAAATTA TATTTTGTT TTTGTTATAT ATTTATATAT TACAAAACTA
174551  GCTTTATAAA TTTAGAAAAG AAATTATTTC CTCTGAAAGA ATTATTTTGC
174601  CTACTTCCTG CAATTCAGAA TCCCACTGTT TACATTTGTA TCATATTTTT
174651  AAAACATTCA ATAAGAGCTA TTGAAATCA CTATCGCGAC AAAGATCTCC
174701  CTCATATTAT TGAGATGTAG TGAATGTGGA CTCTGAGAAA GTCCAGGTGT
174751  GCTAAAAAGT ACAAGCCTGA CTCTCAAGGC CCCCTGTCTT CTGCCCTCCT
174801  CTGATGCTCA TCTCACAGCC ACCAGCTCCT CTTCCATCTT TTGATTTCTC
174851  TTAGCAGTAC CATAATTTTG CAAAATAGCT CCAAGGGGGC ACCATTCACA
174901  TTGTACTCCC TCAGAGGCAG AGGCTTAAGT ATGAGGTCCT TCCCTGTTCT
174951  ACATCCTTCT CACTCCAGAG TTGCTAGGAC AAAACACTTC TCAAACTGCT
175001  TAAGACATTG TCCTTTAAAG GGACCAAAAT CTGAGTTCTA TTCTATGGAA
175051  TTACATCTTC CAAAATGTTT TGCAAAAGGG CCAAGGGATG ATATTATGG
175101  CCTGGCAAAA CTGTTTCCTA TGCTTTTTTG GTTATGCTGA CACCAGGCAG
175151  TTTCTCTTCC TACTCTTCAA CTCTTACTAA TCAAATTCTT TCTTGAGTTA
175201  CTTGCAAAGA AAAGTTTCCA GAGTCATATT CATTCAGGAA ATTGAGTTAG
175251  ATATTTTGGT AAATTGTAGT ATTGCCCCAG TAAGCTGAAT CAATGAAGGG
175301  TACCATTGCT TTGGTGTCAA CATAGGAGGA ACAGGTCCTT AGGCACATAA
175351  CTCTCATTGT CTCCTCACTA TCATCTCTTG CACTTTTATA ATTTGGAAAG
175401  GATGAGCAGA AAGGAAAGAA AGTACAACTG ACTTTAAGAA CCTTCTTACT
175451  AAGAAAACAA GAAAACAAAA TCACAGAGAA AAGACTACCA TGACAAATAT
175501  GCAACAAATA CTCAGTGTGT TTCACACTCC AGGCTATAAG AGCTCTCATA
175551  CTGACTACAA ACTGCTTGAA GTTATATAAA ACTACCTCTA AAAAAGACTA
175601  TTATTCTCCT AGAAGAATTG GTAATTTCTG CTCATGGTCA TAATAACAAA
175651  TTTAACTGCT GTATTTATTT TAAAATTACA CTTACTAAAT TTGATTCTGA
175701  AATGTTTGAT GCGTATTTTA TTTTCAAAAA AGTCAATTTG TAACTTTTAT
175751  TGATTGCTTA TTGTGTGCCA ATGATTGTGC TAAAAACTAG AGGAAATACT
175801  GAGAAATTAT ATAAGTTATC TGATCTTAAG AAACATATTA ATAGTTTTAT
175851  TAAGGAGCCT TGAAACCTAA TGAGTACAAA AGAAACATTT ATTGTTTAAC
175901  CACTAGAATA TAATAGTACC TAACATTTTA CTGATTGCTT TCTATTCAAC
175951  AGATATTATT CCAAATGATT TACAACATCA ACTAATTTAA TTATCACAAC
176001  AGCCCAGTGA GGTGCCTTCT ACTATCATCA TCATCGTTTT TCAGATAGGG
176051  AAAAAGAGGC ACAAGAGCTT AAGTGATTTA TTGGTTGAGC TAGCATTTCA
176101  TTCCAGGCAG TCTGACTCCA GAACTTATAT TCTTAACCAC TTTATTATAC
176151  TGCCTCTCAT AAAGCAGTCA CTAAAAATTA AAAATAAAAG GTGGAACATA
176201  AAATAGGCCA TCCCTTTGGC TGCTTCTGAG GCTCTACACT TCGATTCCTG
176251  CAGGGTATGG AGGGAGTGCT CTTCCCCATC TTTGATTTCC CTCCTCAGAG
176301  AGCACCCTGT CTGCAAGAGG GCAGTTTTCA CACACCCCAT TGCACCTATT
176351  TTTCCTCCTT TACATTTCCT ACCTGGTCCT AGGAGGCACT TAGTTTGCAA
176401  CACCTGGAGA TCAGTGACAG TGGAGTAGCA TAACAGAGGA AATAGAAAAC
176451  AAAAAACCGT GATTTCTAAG GAGGGGCTTA ATTTGTCTAG TGCTGAAACT
176501  GAAGCAAATT AGAACAAGAT AGCACTATAT TAAGGAGAAA ATGACTATAC
176551  AGGGGAGCTT AGGCTCCATG ATATTATTTT TTCTAATAGA AGTCACCCAA
176601  TGAGACAAAC GAGGGCAATT GGAAACTGAG TGTTTGTTTA AGAGTTACTC
176651  CAGGAGATCT GATATGAAGG GCTTGTTGAG TATCATCAGG AAGTGGTTTC
```

FIGURE 3EEE

```
176701 TATTCGCAAT CAGGCCACCC TTAGCCCTGT TATTGACACA GTTTCTTTCT
176751 CTCTTTCTTT CTTTTTTAAA CAGAAAGGTT GTGGGTACCA TCTGGACCTA
176801 TTAATGGTGG CTGTCATGCT CGGTGTATGC TCCATCATGG GCCTGCCATG
176851 GTTTGTGGCT GCCACAGTCC TCTCCATCAC TCATGTCAAT AGCCTAAAAC
176901 TGGAATCAGA ATGCTCAGCT CCAGGAGAAC AACCCAAATT TCTCGGCATT
176951 CGGGAGCAAA GGGTTACTGG GCTTATGATT TTTATTCTTA TGGGTTCATC
177001 AGTCTTTATG ACCAGTATTC TGAAGGTAAC AAAATCTGTC TTTATGAACT
177051 TGAGAGAAAG AATACATTTA TCATCATTTA AGATTTTCAT TTGAATCTGA
177101 GCCATAAATT TGCAAATATT GTGTGGCATG TGATGAAAGT GATGAATTTC
177151 TGAACCATGT TTATATAATT CTTCATAACC TAAGGGAGGG AAATTACGTC
177201 CTATATTTTA AAACCCTTAA ATACATAAAA ATTTAGTCTG GCAAAGTAAA
177251 ATTTGATGAG TAAATTATTG TAACAATTTT GAATCGGTGA TCAAGCTATG
177301 GGAAAAGTC ACTCATTGTT TCTGACTGAC TTGTGACCCG AATCCATTAC
177351 AGGCATTCAT AAAGATTCTA TTTTCTTGTC AGTGGATAAA TATATTAGCA
177401 GTTAATATTA CTTACTATTA ATAAGAGATA GAGGTGAAGG GATGAGCCTG
177451 GTTATAGTCA CATACGCAGT TTTCCATTTT AAGTGCTCTG TAAAACCACT
177501 GTCTGGACAT CATCATTGCA TATAGTGATT TTTTTTTCAC ACAAAACTTG
177551 AAATCTATTT TTAAGAGGAT TAACTAGTAA TTATTTGTC ATGTAATTTT
177601 GTCAGATATT TCCAAGGTGT GTCAATTGCG CTATAAATTA CAACACATTT
177651 TATTTGCCTA TAATTTGACA TTTTAATTAA ATTATTTAAT GATTTACACT
177701 AGTTTACTTG TATTTGATCA TTAACACAAG TACCTTTGCA AGAATTAATC
177751 TCTGTTATAT AAGTAATTAT GTTATAGACA TAAGATGATG TGAACTATTC
177801 CAATAAAAAG AGAAAATCTG AATTATCCAT ATATTTACAA ATACCTGGTA
177851 TAATACAGGA AACACATCTA AATGTTAGCT TCATTTTTAA TCCACCTTTA
177901 ATCCAAATAT CTTATCTTTG TAAAGCAAAA TTCAAGTTGT CTCCAAAGTA
177951 GCATAATAAT AATATTATTG TTCATTATAT ACTACATGGT TTTTAAAAAT
178001 AGATTTTGAC CTATTAAATA ATTATAACAA CCCTATTGTT ATCATCTCCT
178051 TTTAGATATT GGGAAACTAA GGCACAGAGA GCTTAAGTAA CTTACCTAAG
178101 GTTACACAGC TAAAAATGCT AGAGCTGGAA CTTGAATCCT TGTCTTCTGA
178151 ATCTGTACTA TACTGTTTCT ATTCAAAAAT GCCTTTTTTC CCTGTTTTTT
178201 TCTTTGATAA ATGCAAAACC ACAATCTATT TGAAAATGAT TTCTGCCTTT
178251 TCTCCAATTG TTCTTTTACA GTTTATTCCC ATGCCAGTGC TATATGGAGT
178301 GTTTCTTTAT ATGGGTGCTT CATCTCTAAA GGGAATTCAG GTAAATTACT
178351 TACAGTACTA CAGGCACATC TGTGATGACT GACCTTAAGG TCTACTGATA
178401 AGTCATGTGA CAGCTGAGAA AATGCCACCA CCTGAGGAAC AGCTTTTAGA
178451 CCACAATTAA ATTTCTTCAA ACTTGTCAGA GTTACAAAAG TTAAAGAAGA
178501 TTCTCTCCAG CATCTAAGGT TCATAATCTT ATGGTAATTT TCTTTATCAT
178551 AAGTATATTA AAACTGTAAG AGGCTTAGAT TTTACAGCAT TTTTAGAAAA
178601 ATCATAGTAG TATATTTCAA TATATATCCA AATATTTATA ATATTTGACA
178651 CTTTAATCAT GTGTATGGAC ATCTATTGGT AAGAATAGGA AAAGTCTTTA
178701 TGCACGAAGA TGTTCATTGT AACACATACT ATTAAAATAT TGGAAACAAC
178751 CCAATTCTCT AACTGCAGTC AAATAATTAG GTAACCTATG GTATATTCAC
178801 TGAAAATTGA TAATTATAGG AACCACAAAA GTAACATGGC AAAAATGCTT
178851 ACAACATAAT ACAAAGTAAG AAACTATTGA CCATAGGTTT ATAAAGCTAT
178901 GAGTTTGAGC TGGGTTGTGA AGGAAGGTGT AGAAATAAGA ACAATTTGTT
178951 GAGATAGTGA TATCCCGGGG GTTTTCCCCC TTGTTTTGTT TGTTTTACTG
179001 TTATATTTAT AGGATTATTT TTAAAATTAG ACTAAAATAA AGATATAAGC
179051 AGTTTCAAGT ATAAGGGGAA CTTTATGAAT TATTTAAGTA AGTATTGGTT
179101 AAATAAATAT TTTAGGCATG AATTTGGCAA CAGATCAGCC AGATGGTTCT
179151 GGTTCAGGAT GTCCCATGTG GTCACTGTCA GGGTGTGGAC AAGGTCCACA
179201 GCATCTGAAG GTTTGATAGT GCTGGAGGAT CTGCTTGCAA AATGGCTATT
179251 CCACAACTGT GGGCATGAGG GCATCAGTTC TTTTCTACCT GTTGGTAGGA
179301 TGACTCAGTC TTTTGCCACA GTGGCCTCTC CATGGAATCC TTAGTGTGTC
179351 CTCAAACCAT GGAATGTGAC TCCTTCAGAG TGAGCAATAT AAAAGAGAGA
179401 GAGAGAGATA GAGGAGAAAG GAGAGAAGAG AATGAGAAAG AAGATGAAGT
179451 GCTTTTTGAC TTAGTCTTCA AAGTCATACA TGGTCTTTCC ATGTTTTCTA
179501 TTTGTTAGAG GCTATCCACT ACTAAGTCCA GCTTGCACCC AAGTGAAGGG
179551 AAAAGGGAGA CTATCTCTTG AAGAGAAGAG TATCAAAGAA TTTGTAGACA
179601 CATTTTAAAA CCTCCACAAG TGTATTCTAA ATTTTTACAG AAGCTGTAGG
179651 CAAATTCTTC CCACGTATTT CTTTGATGAT ACTGTTATTG GTGAATAGT
179701 GAGTGTTTCC TGAAAATTTA TGTCCACCTG GAGTCTCAAA ATGTGACCTT
179751 ACTTGGGAAA TAGACTATTT GCCTATGTAA TTAGATATGG GTTTCAAGAC
```

FIGURE 3FFF

```
179801  AAGATAATCA TNNNNNNNNN NNNNNNNNNN NNNNNNNNNN NNNNNNNNNN
179851  NNNNNNNNNN NTTGAGTGTG GTGTGGCTCA TGCCTGTAAT CCCAGCACTT
179901  TGGGAAGCCG AGTGGGCGGA TCATGAGGTC AAGAGATCGA GAACATCCTG
179951  GCCAGCATGG TGAAACCCCA TCTCTACTAA AAATATAAAA ATTAGCTGGG
180001  CATGGTGGTG GGCGCCTGTA GTCCTAGCCA CTTGGGAGGC TGAGGCAGGA
180051  GAATTGCTTG AACCTGGGAG GCGGAGGTTG CAGTGAGTGG AAATTGCACC
180101  ACTGCACTCC AGCCTGGGAG GCAGAAAGAG ACTCTGTCTC AAAAAAAAAA
180151  AAAAAAAAAA AAGAAGAGG GGAGAACACA GAGAGACACA GGACAGGGAA
180201  GAAGGCTATA TGAAGATGTA GGAAGGCCAG GCACGGTCAG CTCACACTTC
180251  TAATGCCAGA CCAAGGCGGG TGGATCACCT GAGGTCAGGA GTTCGAGACC
180301  AGCCTGACCA ATATGGCAAA ATCTAGTCTC TACTAAAAAT ACAAAAATCA
180351  GACGGGTGTG GTGGTGCATG CCTGTAATCC CAGCTACTCA GGAGGTTGAG
180401  ATAGAAGAAT TACTTGAACC CGGGAGGTGA AGATCGCATT GAGCCGAGAT
180451  CATGCTACTG CACTCCAGCC TGGACGACAG AGGGATACTC TGTCTCAAAA
180501  AAAAGAAAA AAAAAAAGG GAGAAAGAGA TTAGAGTTTT GTTGCCATAA
180551  ATCAAGGGTG CTAGGAGCCA CCTGGAGCTG GAAGGGGCAA GGAAGTTTTC
180601  TCCCCTAAGA CCTTCAAAGG GAGTGTGGCC CTGGCAATAT CTTGCTTTAG
180651  GCTTCTGGCC TCCACAAGTG TGGAAGAATA TATTTCTATT GATTTAAACC
180701  ACCAAGTTGT GGTAATTTGT TAGGACAGTC CTAGCAAACT AATAGATTTC
180751  TACTTAAATT GTCCCTTGAA AAGTCTTGTT TTATAATTTA ACATTATTTA
180801  GCCCAACACT CCAATGTTCT TGAAAAGAG ACTAGAGACT TATTCATCAT
180851  ATAGTATTTT GTCAACTGAA AAGCAAAAAT AAATTGCAGC TTTTTCTATA
180901  ACACAGCTAG ACTCACTGAT GTTCATAGCA TATAAGAGAA TAGTTAACCT
180951  GCAGGACAGG CAGCACGGGA TCTCTGTTCC TGAGCAAATG ACTAACCAGC
181001  TTCTGACTTT GGGAGAAAAA GCAGAACTTA GGCCTTAAGA CAATACTGGC
181051  TGCCAGTCTG GGGGAAACTT AAGTATGAAG TCATTGCAGG TCACGGAACA
181101  CCCAAAGTTG ATAGTATGAC TGACTCTTCA TCCTGACACT GGGAAAAATG
181151  AACTGGGAGA GGGAGATGGT TGAGCCATGT TATATGTTTT AATTTTACTC
181201  AAATTAGATT TAATTTGCTC ATTTAAAATT TCATGTATGA AAAGTGTAGT
181251  TTGATAGAAT TTGTTTAGTA AGCCATTAGG GAAGAATATG GAAGAGGTTT
181301  TGTTTATTTG TTTTTCTTTT TCCCTTTTTT TTTTTTTGC CTTTGGCAAA
181351  AGTTCCATGA GTACTAATTT CATCTGTAAG TGAAAAGCAT TTATTATTAG
181401  GCCCCAGGCT CACATAAATA CAGCAGCAGA GTTAAGAAA CAATGTAAAA
181451  TCATTTTGAT GATAGGTTTC AACAGATTTT CTCCTCTAAT TCCACATGAT
181501  TTTATACTCA TGAGATTTAG AATTGAACAA GAACGTCAAG TTTTGGAATT
181551  ATTTGGGGTG TGAATCTTTT AAATGAAAAT TGAAGAAAAC GTTATCAAAA
181601  GCCCATGAGT TAAATATAAT GAGTTTTAAA GAACACAAAT GAAACATCAA
181651  TCTGGGCAC ATGTTGATGA ACAGGGTCTC ACACTGAGAA ACAGTGTTCG
181701  TGAAAATTTA AGTGAGCCCC AAGAGCAGGG AGCTGAAATT CCTATTTGGA
181751  ATTGTAGCTA ACTGGGTGGG AAATGTGAT ATTGATACTA GGATATAATA
181801  AAAACCAAAT GTAAAACTCA GAATACATTT ATCATGATGA TGATTATTAT
181851  TTAAACATAT GCTAAATATA ATCAGTTCCA GCAGCATGTT ACTGTCTTAC
181901  CCTATTGAAG GAATCTATGT TACCTGCTTG TTTGGCAATA TTAAGAAACT
181951  TATTATCTGG GCTTCTCACT GTGAAACATG GCAGAAAAAA CAGATCACAG
182001  TGTTCTCATG AATGCTGTTT CTGCATTCAG ATATATACCC ACATCTATAT
182051  TCATTCCAAC ACTTCAGGAA TCCAAAGTAA AGCAAATGTG CCATTTAAAC
182101  AATAACAATT GAAGCACCCA CACACTGAAG TACACTTATG CAATAACATA
182151  GCTTCACAAA TGGAGAAATG GTGGCTGGGA AAAACTAGTT CTATAGAAAA
182201  GGAAATATTC CATTGTAAGC CAGAAGATTT TATTTTATTT CTTTCCTATT
182251  CCTACCTCTA CCATGCACCA AGTTTTTGTT TATTTAATGA CTTTTAAGTT
182301  TAAATAATAT TTAGGAAATA GAAATTTTAA AACTTAATGA CATGTACATG
182351  GACAGAATGG AGAGACATTA TCAGGAATG AGTTCAGCAC TTAGTAGCCT
182401  GCATAGAATG TTTCAATAAT ATTTTTGGAA TATATAAATG AATATGAATA
182451  AATGAATGGT CAGGGAATGA ACTAATATAT GTATGATTCT TATTTAGATA
182501  ACTGAGGAAA GGAAGGCCAT GTCATGCCAT AAGACATAGA ACACAGAAGG
182551  GAAGATAGGT TTATGTTGAG TTTGAGATTC CTATTATGTA TACAAGCAGG
182601  TCTTGGTAAA ACAGGGTGTT TTGACTCTAA CATTTTGACT CAATGGACAA
182651  CTGTTCCTTT GCATATTAAT ATGACACATT TGATGAGAAT TGCCTACAGT
182701  TTTTAAAATA AGTTAGTTAA GAAATAAAAT CTAATATTAC TTTTTGAAAA
182751  TGCATAATGG ATGTTACTGT AGAGATGGCA TGAAATAAAA CAGTGACTGA
182801  CAGTGATTGA AACCATTATT TTCTAAATAA TCGCCTCTAG TTGGAAACAC
182851  TGAAAATTGC AAAAATTGGC CGAAGAACAA TAAACCAAAT AATCTATATA
```

FIGURE 3GGG

```
182901  AAATAAAACT ATCATGCAGT ATGATTTGTT AGTAAATAAA ATGTGATTAA
182951  AGATTTAAGC TTCCTGTGTG CATTTAATTT ATAAAATTCA AAAAAGAAA
183001  AATTGGTTTG CTTGATTAAA AAAGCCCTCA AAGTCAAAGC TGTAACATAA
183051  TAGTATGAAG TACTATAACA ATAGTGTTAT GTAATACTAT GTACTATCTT
183101  TATGGCAAGA TTGAAACAAA TAACATTGAT TGAGATGAAA ATAATTTTAA
183151  TAAAATACAA CTGAAAATAT ATAAATGACG TGACAGTGCT GTATATAAAG
183201  TTAATCAAGA AATTAAATAG AGTTAACAAA ATTTGCTCTG GAACATACTT
183251  TATTAACAAA ATTTATTTAG GTTAAATTTT TATGGTTAAG ATGTTTGTGT
183301  CCATAAAGAC AGCATCTAAA CTTTTGTTGG GGATTAAAGG GACAAAGTCA
183351  AAACAGCAGA GTCAAAATAA GGAGGTTAAA ATACCGTACT TAGCAGCTGG
183401  ATAAGGGTCT AGAACTCAGG AGAGAGCTAA GGCAGAGACG TAGGTCCGTG
183451  AATCATTAGC AAGTCTGTGA AAGTCAAAGC CATGGGTATG GATGAACTAT
183501  TCCAGGAGAA AAGAAAACAG AGAATGAGAG TCCAGGAATC CCAATGTTGA
183551  GGGGCAAATA AAGGAAGAGA TTGTGTTGTG ACAATGAAAA AGAAGATGGT
183601  TAATTATGTT TTGCTTCACA GGGCTCCACT CTTCAAGGTA GCAATATTTA
183651  ACATTGGCTT TCTATTTTTA AACTCTTCTA AATTGTAACC CGTCTCCATA
183701  TTCAAGAAAA TGTGGGCTAT TGTTTAACTG AAATTGTAGT GTTTCAGAGG
183751  GTAAGCATAA CAATCCCATT GTCTTGATGC CGAGATATCA ACTTAGTGTT
183801  ATCCAGGTAT GTCATTTAAC CCAAAATTGT GGACCATATT AAACATCAAC
183851  TTGTCCTACT TTTATTGTTG TCTTACACCT AAAAACAATT TAGTCTGTTT
183901  AATCTTTTAG TTCTTTGATA GGATAAAGCT CTTCTGGATG CCGGCAAAAC
183951  ATCAACCAGA TTTTATATAC CTAAGGCACG TACCGCTTCG AAAAGTGCAT
184001  CTCTTCACAA TTATTCAGAT GAGTTGCCTT GGCCTTTTGT GGATAATAAA
184051  AGTTTCAAGA GCTGCTATTG TCTTTCCCAT GATGGTATGA AACTTCTGTC
184101  AACTATTTTT CTCTTTCTCT GATTTGCTGG TCTCTTTGGA AACATAAACA
184151  CATGAATTGA AACTGGAACA ACAGAGTCAT TTTGAACAAT TATTGGAAAA
184201  TATAAGTTTT GGCACTGAAA GTGTGACTAA GATAGGGTTT AAGAATGCCT
184251  ATGAATTTCA GTGATTCCTA TTAGTTTTGT CTCTATCACT CTGAATGTTT
184301  GTGGTAGTCT GAATTAATTG AAGCTGGATG GAAAAATGCA TTCTTCCAAA
184351  ATTTAACATT AAAGATACTA GCAAATATGA AAAATTAGGA TTTTTAAAAT
184401  AACATTGTAT TAAATGTTTC AGGCAAGTTT CAAATACTTC AAAAACTATA
184451  GTGAATTTGA ATGACTAAAT AATTTCATAA TTATTAGTAT AGATAAGAAT
184501  GTTCTCGTGT TCATTTAATA TAGTATAAAC TATTAACTAC ATGTATTTAA
184551  GGAAACATAG TCAAATACAT TTTATAGGTT TTTTAAAATA GCTTATTTAA
184601  TAGACTCCCA TATTGGTTAA AATCATAGTC ATTATTGTGG TGATGTAGTA
184651  AGAAAAGAAA ATGAAGGAAG CAGAAGACTA GACAATGTTT TATACATATA
184701  TATCTTTAAT TTTTACTTTA ATCTCAGGCC TAATAGAAAT TGTTTCTACC
184751  AAAAACCATA CAGGCAAATC TACACCTCTC ATTTTAATTT TTTTTCCACT
184801  TTAAACTAGT TTATTATTTA CTTCAGGTGT TAGCCCTGGT ATTTGTAAGA
184851  AAGTTGATGG ACTTGTTGTT CACCAAGCGG GAACTCAGCT GGTTGGATGA
184901  TTTGATGCCC GAGAGTAAGA AAAGAAACT GGAAGATGCT GAAAAAGAAG
184951  TAAGAGCAAA ATCAATGTTT TATAAAGAAA GAAAAAAGGA ACATAGTAAT
185001  ATTTCTTTGC AAAACTAAAT TATTGTTTTT ATCTTTAGAC AGTTTGTCT
185051  TTAGACAGTG ATCACTAACA ACCACAAGTA GACTAGTTTG GAAGTTTAAT
185101  GTTTAAAATC ATAAAGATTT GAACAGAGAG AGAATGAAGA TCTTATAGGA
185151  GGAAACCAAA TCCTAATGAA ATATGGAAAT ACTTTGTACT AAAATACCCT
185201  CCAAATTGTA AGGCTCATTT TTCTGATTCC TCTCCTATGG ATGGCAGAAA
185251  CTTGCTAATA CTTAACTATT TCCAAATTAT GATCATGCAG TGATTGTTTT
185301  TTTGTTACAT ATGTGAGAAC AAAAAGAAGA GACATTATTA CTGTTGGTAT
185351  TTTCCTAGGG AACAGAGTTT TAATCAAAAT ATTCTAATGA ATAATTATTT
185401  ATTCTTGAAA TAGGTGAAAT GTTTAGTAGG AAAAATGTTG ATCTGATTTG
185451  CTTTCAAAGT GATTTAAGAT TGAGTAGATG TTGCAGAAAC TTCTGGAATT
185501  TATTTTTACA GGCTACTTAT TTATTTATT CTATTTTATA TGGTATAACA
185551  ATGTATTATA AGTTCGTGG CATATTTAAA GTTTATATGT AAGCCTGAGT
185601  CTATTTTGAA AGCACTTAAT CAACATTTTT TTAAGTATAT AAAAACTACA
185651  AAGAGTGTAA ATGAGGGAAA AATAACTAGC GTAACATTTA GCAGGATGAT
185701  TGAGCCCATA CAATGTAAAA CACAACAAAG TTTTCACATA AATAGAAATG
185751  AGATTGAAAT AAAATATTTG ATGAGAATTA TACTATTTTT CTCTATAAGT
185801  AGTCAGTAAA TGTATTCAAC TTTCTATTTC CTCAAACCAT AGATATATTT
185851  CCTATTTCCT TTGGGGAATT CATTTGCAGA TGTTTCAGAG GTCTTAGTCA
185901  TTTAATGAGG TCAGATCAGG CCATAAATCA AATGAGGTTT TTTCTTTCTC
185951  AGAAATTTAT ACCAATATGG TTACATAATG TGTAATTGG AATTCCCTTA
```

FIGURE 3HHH

```
186001  CTCTACATGG TGTTCTATCA CTAACAATGG ATTCCCACAG ATAGAGATTC
186051  ATCATGATGA TGTGTCTTAA TCCTGTAAGA ATGTTTCAAT TTTTCCAAAT
186101  ATTGTAGAAG GCAATACTTA GACTCATACT TCTAGTAATA TTAATGTTAA
186151  CACAAAAAAT GATATTATAC AATTGTTATT ATTTATTTTT CTGTTTGATA
186201  TATTTTTATT TAAATATTAG TGCTTTTTTA AAAAATAATA CTTTGAGTCA
186251  GGCGCAGTGG CTCATGCCTG TAATGCTAGC AGTTTGGGAG GCTGAGGCGG
186301  GCAGATCACG AGATCAGGAG ATAAGACCAT ATTGGCTAAC ATGGTGAAAC
186351  CCCGTGTCCA CTAAAAATAC AAAAATTAGC TGGGCATGGT GGTGCACACC
186401  TGTAGTCTCA GCTACTCAGG AGGCTGAGGC AGGAGGATCA CTTGAACCGG
186451  GAGGTGGACG TTGCAGTGAG CCACTGCACT CCAGCCTGGT GACAGAGCGA
186501  GACTCCGTCT CAAAAAAAAA AAAACAAAA AACAAAAAAC TTTGACTAGG
186551  ATATTTTGAT AGTCTCTATT TCTTTTTAGG CCTTTAGTAA ACGTTTGCTT
186601  TCATCCTCAG ATACTCTTCA AGAAAATATG GTATAATTTG CACAAGTTA
186651  AATTTAAATA AAACGGACAC TAGAACACAG AAATTCTAAA ATCTTAAGTT
186701  ATCTATATTT GATGTAAATA AAATTATTGA GATCAAACAC AACACCCAAG
186751  AAGGTTTAAA TTAATTTAAT TTTGATGAAA AAGCTCTTGG CTGTGAGCTT
186801  GCCTTTCAGT CTTTTTGATA ATGTCAGTAC AGCAGACCCT TGAATAATAT
186851  AGCATTGTTA TAATGTTGAT GAGAAAAGAA AAAAAAATT CCCTGGCCAG
186901  GGCCACTGTC TGTAGGGAGT TTGCACATTC TCCTCATATC TGTGTGGGTT
186951  TTCTCTGGAC ACTTCGGTTT CCTCCCACAT CCCCAAAATG TGCCCATTAG
187001  GTTCATTGGC GTGTCTACAT TGGCTCAGTG TGAGTGAATG TGGGTGTGTG
187051  TGTGAGTGTG TGCTGCAAGG GAATAGCGTC TTGGCCAGTC TTATTTCTCA
187101  TCTTGTACCC TGAGCTGCCA AGATAGGCTC CAGCCACCCT CGACCTTGAA
187151  CTGGAATAAG TGGGTTGGAA AAGGAATGAA TAAATGAATA CAAATGACTG
187201  TAAAATAAAA ATTCATCAAG TATACGATAA TCACACAAAT GTACGACAAC
187251  AATTTGGTAT GAAAATGCTC AGTGAACCCA GCCATATTTG CTATTGTTTT
187301  TGAACTGCTT GGTGGTAAGA TGTGCTCCTT ACAATTTTCA CTTTGCAAAC
187351  ATTTATTCCT GATTTAATCC ACCCCTACTA TGGCCTCAGT CACTCTCTCA
187401  CTCACCAGAA ATTTGGTAAT TCAATATCTT ACTTGCTTTT ATTAACTTTT
187451  CTTACATGTT TGTATAGCTC ACATTTATTT CAATGTTTAA TATTAAAAAC
187501  ATTTTGGGTC TTTAGTTAGA AGTTTGGTGA TGTTTTTGTG ACCAGATATT
187551  GCCATAGGAA TTTAACTCTT GTTTATATCA ATTAGCCTAT GGTAAAATTG
187601  GTTTTATTTA TTCTTAATGT CACAGTCTCC GAGAACCTAT CAATAACTTT
187651  ATGTGAGCAC TTATTGTACT ATTAATTATA CTCAAGCAGT AACTTACATA
187701  TCTAATTTTG CTTTATTTTT CTGCTTTTTT TTGTTAACTG TCTTTACTGC
187751  TTCTGGAAAA AAAAAAACG AACACAGCCC CAGACATATA ATCATCTCTT
187801  TCACAGTATT CTCCTTAGAT CATACTCATA CCGTGAAACA TTCTTGCCTT
187851  TTAGAAGTTC ACAAAATGAA AAATGATATG TAATCTATTA TGTAATGTTT
187901  AATATTTCTG TGACTGTGAT TCAAAGATAA TTTCAGATTC TCCTTTTATT
187951  TTCTGTGAAA CAGGAGAGAA CAAGTTTAAT AATAATTGTA AATTTATTAG
188001  AATTTGCCAT TCCCACTGCC CAGAACCACT CACATAGCTA TGCATGTATG
188051  GTACTTATAT GTGTGTGTGC CATATGCCCA TTTTGGAATT TATGAATCTC
188101  ATAGGGCAGA GAACATATGT AATCAGTGTC TAATCTTTTT ATATTATATA
188151  CCCACTGTAC TTTAATGGGC ATTTACTGTT CTCTGATTAT GAAGATAAAG
188201  ATTTAAAAG TAACTAAATA GCACTAAATT TCCTAGAACT CATGCTTTCT
188251  GAAAAGATAC AAAAATGGAT TAAAGATTTC CTGGGGCAAT TTTACTGCTA
188301  AATCCTTCAT ATCCAAGTTA GAGGGAAAAG CCTTGCAGTA CATTAACTAG
188351  GCAGGTTTAT AGATCCTTAA AATCTCAGAT GGGTTAATAT GATGATACTT
188401  TCATGTGATC CTCAGTACAT GGAAAGAAAC AAGAAAATCA ATAATATAGT
188451  CAAGAAATAA TCTATAATTG AACAATAAAA TATAGCTCTG ACTAGTGCAA
188501  AGACAGCTAA TTCTCCATCG AACAGGAAAG AAAATAGGAA GTTTAAAGAG
188551  GTTCGCTTTC TAGCTTAGAA TTAGTATTAA AAGAGTATGG TCACTAAAGA
188601  CATTAGGAAG ATTTAGGAAT AATTATACTA AAAGTTAAAT TCCTGGTTGA
188651  TTTGTTTGCC CGGATCTTGG TATTCTATTT TCTTGAGGCT TACAGACTCA
188701  GTAGAAGGAT GTGATCTTAC TGTGGCATCT TATACTAAGG CCCAGTCTTC
188751  TAAGAGATTG TGTGTTAAGG TGGTAAACGG ACAAGTTCTC CAGAAATGTT
188801  GCATTTCTGC AATTGCTCAA ATTAATTGAG TAACTTTGAT CATGAACTGG
188851  CAAGATGGTA AATAGCAGAA ATGTCTCAGC TCCCTGAGAC TTGAATTTAA
188901  AGTAGGCTCA CCTCTTGTCC TTTTGATGAT AGATACAAGC TTTTACCTTT
188951  AGCCTCCAGG GTTTTCCTAT CAGTAGCCCA TTTCTGGTCT TATGGCACTG
189001  AGAAAACATT CATTTGACCT TAAAATTCAA TAATGAGTTA AGCAGAATAA
189051  ATAGCTACAC AGGCCAGTCC AAGGTCGCAG AGCTTCTGTT CCAAATTTTC
```

FIGURE 3III

```
189101  ATGTACTTCA TGCATATGCA TATGCATATG CTTCAGTTTT TAGAAAGAAA
189151  GGATTATAAT CAGGGTAGAA ATGAATATTG GAACCCTGAC ATTTTGCACA
189201  TTGCTCTGTG TAAAGGAAG  ACTGCAGAAT CAAATTCTGG ATGTCCAAAT
189251  GTGCTCAGAG TACCAACATG CCTTCCTTCC TACTTAAATA TTCTCTAGGC
189301  CATTGTACAC ATTTGACAAA AGGCTACTTA CTGTTAAAGG CAGAAAATCC
189351  CAGCAGAATG TTTGCTCCTG GGTAGGAGGA AAGGGGGTTA GTGTTGGATA
189401  AATCCTAGAA ATTCTACTCT GTGGAAGTGA TCATGATAGT GATACTTCTT
189451  GATTTACTGG GGCTTCACTC TTAACATATA CACTATAGGA GAAAACAAAA
189501  AGAGGGCAAA TGGGACCCTG TGATCCCAAT GCAGGATCAT GAAAAAGGTC
189551  AAGAAAAAG  CAATCTAAAA ACAAGTGCAA CTAAACAAAT TACAGAGGAC
189601  GACTTACTGC TAAGATAGGT CAGAATTGGT TATGGATTTG GGAAGCATGG
189651  CCAAATTATT ACANNNNNNN NNNNNNNNNN NNNNNNNNNN NNNNNNNNNN
189701  NNNNNNNNNN NNNAACAAAG TATGCTAGCT ATGGGAAGAT GAGGGCACAG
189751  TACAACTCCC ATTGGAAGGG CACTATAGGT AAGACATAAA TTTAAAAACA
189801  CATCAATTAA AGTAATGAAA TGCATTGTTA TATACTTTAA GAATTTCATA
189851  CTGTGTAGAT CCTCAGAGAG GTTCTTGAA ATTGTATAAG AGTAGAAAGA
189901  ACGAAGAGTT AGATAACATG GGTCCTACTG CTAAGTTTTG CCAATAATAG
189951  CCGTGTGACT ATAATCAAAT TGCATTAAAT GAAGTGAAGC AGGAAGCTGT
190001  TGTCTGAAGT TTTTCTTGCT CCTGTTTTAT AATGTGTATG AAAAATCCCT
190051  TTCATATTCT CAGAAAGTAG CACCAGAAGA CAGATCAAGG TTCCTTTTTT
190101  GTATAAGTGA CTAGTTATTC ACTAAGTTGA TCACAGGTAA ATGTTTTAAC
190151  TCTGGGAATT TGCCGCTAAA AGTGGAATTT CCAATGACAT AATCTATTTC
190201  TTAAGTGATT CAGTTGTATC AGTCATTTTA GGATATATTT ATGCAATTCT
190251  CCAAAATTTT CTAATCTTCT TTATGTACAA AGACATAGCA AAAGAAAGCA
190301  AACTACTGAA GTTATAAAGA AAACATTTGC AAGCATTTGG CCCAGAATTC
190351  TCCCCTCTCT CTCTCTTCTC TGTCTCCCTC TCAATATAGT TTAGTTTAAA
190401  CGGTTATCTT GTACAATTCT AAGTATCAAT TAGTGCCCAA TTTTATAGTC
190451  TCAAAGTCTT TATGAATAAT TTAAGGTTAT GCCAATAAAA ATACAGAGAA
190501  TACTTTTTTA TGAGAAGGGA ATTTGTCATA GTGTTAAAAA CCAAAATAGG
190551  AGAGAATTTT CTAGATCTTT AGGGTCTGAC TCTAAGATTA TATTCCCTAG
190601  AATTTAAGAA AATGTGATTA CCTCCCTCTT AAGAGGGGGC ACAAGTATAA
190651  GATGTTTTAT CTTTTTTTTC TTTTTTACAA CATTTAAATT TTAAAATCCT
190701  GTTGATTTTT TAGCTGAACC AGCATATTTC CAAGTGTATT AGGTAGAAAC
190751  CTAGTCTTGT GTGATACCAC TCTCGAAAGG GCTGTGTGGT TAAATAAGTT
190801  TGAAAAAATG TGCCAAACTG CATTCCAGTT TGGAGATTCA CAATGCATAT
190851  TAGCAAATGA AACAATCTAA GTAGTACTGC ATTTTAAAAA ATTGTATAGC
190901  TTCGTTCAAT CAAGTATTTA AAAAAATCTT TTGCTCAGAA GACTCTTCCT
190951  CACATAATAT CATGAAAAAT GTCTATTCCA CATGATGCTT TTTTTAAGAA
191001  AGTAGTCAAT CTGGTGCTTT GAATTACCAG GAAACTATCT TTCTAGGAAG
191051  ACCAAACAG  CTGGAGGGTT TAGAGGAACT GAAGAACACA TTTCCAGATT
191101  GGGCAAGAGA GGGAGACCCA AGGTTTTGTT CCTCTTAAAA GTTGCATTTG
191151  TTCCTCTCCT GTGACCTATC ACCAATCAGG GTCATATGAA AAGGCGGCAT
191201  TTGAACAAAG AAGGGGCAAG GTTGCTCCAT GTGAAGGGAC ATGATAAGCA
191251  GAGGGAAGAG CAAGGACAAG GCCCCAGGC  AGCACCATGC CCATTGTGTT
191301  CCAGAACAGT CAGGAGGCTA CTGAAATGGG GCTGGAAAGG AGTGAGCAGG
191351  GATGCAGTGG CAGGAGGTGA AATCAGAGTG AGGTGGGGAC AGAGCCTTTA
191401  GGCCATTATA AGGACTTGGC ATTGACTCTG AGTGACTGGG AGCCACTGCA
191451  AGGTCTGAGC AAAGGAGGGA AGTGATCTGG TTGCTATGAT GTTAGGGGCA
191501  AGCGTTTAAG CAATGGACAT GCGGAACCCA TTCTCTGTAA TTTGAAATGA
191551  ATTAAGAATA CCACAGGCCA ACTCAGTATC TATTCAACTA GAATATTTTC
191601  TTTAGTTTTT TTATTTTTCA CAGATTGTTT TCAATAATTG AGAGAAATAT
191651  TCAATACTTC TTCATTTTTA ATTATCAAAA ATATTGTACA ATAAACAAAA
191701  TGGGCATAC  ACATACAATG GAACATTATC CAGGTTTAAA AAGGAGGAAA
191751  TTCTGACATA TGCTACAACA TGGATGCACC TTGAGGATGT TGTACTAACT
191801  GAAATAAACC AGTCACAAAA AGACAAATAC TGTATGATTC TGCTTATATG
191851  AGGCACTTAG AGAAGTCAGA AACCTAGAGA CAGAAAGTGG AATTATAGTT
191901  GCCAGGGACC GGGAACAAGA GGAAATGGAG AGTTGTGGTT TAGTGGGTAT
191951  GGAGTTCCAG TTTTATAGGA TAAAAGAGT  TCTGGAAATG GATGGTGGTG
192001  ATGGTTGCAC AACATTATGA ATGTATTTAG TAACCCTGAA CTGTACTTTT
192051  AAAAATAGTT AAGGTAGTAA ATTTTATGTT ATGTGTATTT TACCACAATT
192101  TAAAAATTGG GAAAATATT  CTTCATAGAT ATATGATTGC CCTATATTTA
192151  GTTTCTGTCA TTGAAAAACT GCAGTTACTT ATGTAATGTT TATTATTTCA
```

FIGURE 3JJJ

```
192201  TTTGGGGAAA CTCCTGTCTA GAGATGATCC ATCTGTGATC AATATATCTG
192251  ATGAAATGTC AAAGACTGCC TTGTGGAGGA ACCTTCTGAT TACTGCCGAT
192301  AACTCAAAAG ATAAGGAGTC AAGCTTTCCT TCCAAAAGGT TTGGATTTTA
192351  AAATAATGAG AATTTATACT AATTCCAATT GTTTTTTGAC ATAAACCATA
192401  AGCAAAGAA  TAATATTAGT TTCCATCAAA TTTAGATATA AAATATTCCA
192451  GAAAATTCTT TCCAAAAGTG GGTAGAAATT GTAATTATTT CAAATGTTGG
192501  TATGTTTTTC ATACCAACTG TGGTATGGGG AACTGTGCTA GAAATGAGTC
192551  ACAATGCATG ACATTTTTGG ACATTCATCT TGGCCTACTG TTTTTCAGTA
192601  TGATTTTATT TTATTCCCTC ATCACCCACT TCCCCCAGGA CCCCTTTAGA
192651  CATCTGGCCA CATTTTGCAC TCCTTTATTT TCCTTTTTT  AGACTGATAT
192701  GCACTGTGTG TATTTTATAT TTATATTTTA TAAATATGCA TAAATATTTA
192751  TATTTAGTAT AGTTCTAGTC CTGACTCCAA CCCCCTGAAA GTCTTCCCTA
192801  AACTTCTTAT CCCAAAACTT TCAACTCCTG AAAGTTCTAT CCATTCTTTC
192851  TTCTCTGTGT GTAAATGTAC AAACAACTCC TGTAGTTGTG GATGGTAGTT
192901  TTAAGTGCAT GCTGGAGGAA GAGTGTGTCC CTAAATATCA ACAGTCATCA
192951  AAGGATTTCC AAGTGAATCT TCTAGGATTT ATAAATAAGA GTTCAAGTCA
193001  CCCAGTCTTC TTAGATGCTG ATCTGAAGAA AGAGGAATTC CTATGTTATG
193051  CTAATATCTC TTTTTGTTAG AGAGTGATTG AGGGAATTGG GACAGTGTTT
193101  ACTATAATTA TAAAGTTCCT TTATTTCGT  AACCTTAAAT TAACTTTTTC
193151  TACTTAATTT TTATATTACA TTTTGTCAT  AAGCTCCCCT TCCTAATCAC
193201  TCTAGAAGCT GATTCCCCAA AGGTAAGACC CTCTCCCTCA AATCTATTCC
193251  TTGGTTGCAT TTCCTTATGT TAAATGGTGT CTTCTAGAAA CCTGGTCAGT
193301  CTATGTCCTC TGTGTGAGTT TTGGGGAGGC AAAAGGCATG GAGAGTGTTG
193351  GGCTCAGATC CAGTAGCAGA CTGAGTTTGA TGATATATCT GTAACAACTC
193401  AGCTCTTTAA GTTAGTCTGA AACTTGAATA AACTTTATTC CTTCCTTGAT
193451  TTATACAGAT GCATCATGTA TAAATCAACA AGTTTCACAG AACTGTAGTT
193501  AGTAATGGCA TCAAATTTCT GGATAGGGAA AATTAAATTT GTCCCTTTAA
193551  GAAATTGAAA AGCTTGCCTG GTGTGGTGAC TCATGCTTGT AATCCCAGCA
193601  TTTTGGGATG CCAAGGTGAG CGGATCACTT GAGGTCAGGA GTTCGAGACA
193651  AGCTTCGTCA ACATGGTGAA ACCTTTTCTG TACTAAAAAT ACAAAAAAAT
193701  TAGCCAGGCG TGGTGGCGGA TGCCTGTAAT CCCAGCTACT TGGAGGATGA
193751  GGCAGGAGGA TCGCTGAGCC CAAGAGGNNN NNNNNNNNNN NNNNNNNNNN
193801  NNNNNNNNNN NNNNNNNNNN NNNNNNNAAA TGCCCTTGAG GTCAATGTGT
193851  TGAGTAATTT GAAACAAACC TGTAAAAAAT TTTCTTCCTG TATTATATGG
193901  ATTCAAAGTC CAAACTTTTC CTCTATTTTT CTTTGGTTCA AGCAAAAGTC
193951  TTGTGACGTG ATATTTTAGC TACTCCTTAA AGTCAAGTGA TACTTTTCAC
194001  CAGAAAAATC TTTTTGTTTT AAAAATATAT ATCCAGATGA CTTCACATAG
194051  TGGGTTGACT CTAGTGAACA ATATAATGTG CTTTAAAGCA GGTCCAATTT
194101  TCAATAGACT ATCCTTTATA TTTAGATATA ACCACTTGTT TCTTATTCTT
194151  TAAATGTACT TTCACTGACG TGAGGTTCAG ACTATTGTGG AATGAAAGTT
194201  TATCCAGCTT TCCTTACCTT TTGATGTGAT CGCATTTGTG GTTTTCCATG
194251  TGAGAAACAT CTTTTGGTTG GTAGTTAATC TCTTTTATCC TCATTACAGT
194301  AGAAACTCTG GCAGAAAGTG TATGACTTAC AGAATTCTAA AACTACTGAT
194351  ACTAATAAGG CTCCCAAAGC CACTTCCTTT TTGTGGTATC TGTTAAAGGC
194401  TTTAAAGCAT CATGACCAGG AACTGTGAAA ATTTAGTACG TGGTAGAGTA
194451  TCCATTGGCA AAAAGAGACC CAAAGAGCAG GTTACTAGGG TCTGAGTCCT
194501  GAGCTGGCAC CCATGCAGCC TTTGACACCC CCCATTCTGA GTTATTTTCC
194551  ATCCTGTGCT GTAATGTGTC AGAGAAGCCT AGAAACCCTT TTTTCATGGA
194601  ATTTTGAATA GAAATTATAT TTTCTCAATT ATATCATTCA CTTTTTGTTG
194651  TCAAAATATA TTTATCTCGT TTAACTGACA GTAGAATCTA AGAACTAACG
194701  GCAAATTCTG TCTTATCTGG AGGATGTCTA ATTTTGATCC TGATGTCATA
194751  CATGCATGTG ACAAGAGCCT CTGCAGCTTA TTAAATGGGC TGGTGAAAT
194801  AGGGCTCATT AACGACCACA TTGCATCAGA ATAGGTTAGC AACTGCTACG
194851  TTTTTAAAC  TGATGCCCAA GATCAGTGTG TCTGGAGGTC CTTGGCAATG
194901  TTAGGAAAAG CAGCACTTAG CTTTGCCTTG GTGACAGAGG CTAGTCTCTG
194951  GGACTATCCG CTCTACCCCC CAACACCCAC CCCTGCACTC CCCCACCACC
195001  TTTTTCTATC CCAGATTCTT TCTTTGCTCT GATTGCCTAG GCTTAGGCTC
195051  TCTCATGACT TCTTGGAAAT ATTATTCATA AAAACAACTT TAGCCTGGGC
195101  GTGGTGGCTC AGGCCTATAA TCTCAGCACT TTGGGAGGCC GAGGCGAGCA
195151  GATCACTTGA GCTCGGGAGC TCAAGATCGG CCTGGCCAAC ATGGTGAAAC
195201  CCCATCTCTA CTAAAAATAC AAAAATTAGT TGGGTATGGT AACGCACACC
195251  TGTAATCCCA GCTACTCAGG AGGCTGAGGC AGGAGAATCC CTTCAACCTG
```

FIGURE 3KKK

```
195301  CGACGTGGAG GTTGCAGTGA GCCAAGATTG TGCCACTGCA CTCCAGCCTG
195351  GGCAACAGAG CAACACTCTG TCTCAAAAAA AACAACCACT ATTTTAGTGA
195401  CATTAAAAAG TAATAGTTTC ATAGTTTACT TAGCATCATG ACAGTACCAG
195451  GTCACTTTTT GCCCTCTTGA AATATTACTT CCTTATATTT TAAATTTTAA
195501  CTCCTCAGGG ACAGGGACAC TCTTATCTAT CTTGTACTCC TAGGTCATTA
195551  TGGAGTTCCT GGCATATAAT AGATATGCAA CATATGTTTA TTACAATGAC
195601  AGATAACAGA TGCATAATAC ATGTTTGTTA CAATGAAAGC TTAAAATTGA
195651  TTGGCCTCCA CAAAAGCGAA CTTAACAAGT AATTCCGAAC AATGGATCCT
195701  AGAGGTCTTG AGCTGGTTAT AAAATTTCTG CTTCATAGTT TGCTGAAATC
195751  TAATCTGATA CCAAAACTAT GGTTATGATG AAGAGGGAAA AAAACCCAGA
195801  CATTTAATAG GTTATTGTTT TGTAACCAAA CAACCAAAGC AGAGTCAGGA
195851  GGAAGCACAT CTATGGATCA AGTTGATATT ATGAATCTTT TTATTTATGA
195901  CTTGGTGACT AATAGTGCCA CTTGGCACAC ATTCATTTAT CAAAAGGTTA
195951  TGGAACACCT CCCACGTTTC AAAGTATTGT GCACACAGTA ATTGCACATG
196001  TGTAGAGACC AGTATATCTC TGTCCTACAA TCTCCTACAT ATAGGATCTG
196051  TTATTCTATC TTTCAAAAAA TAAGAGTTCA TTGGAATTGG GAATACCAGC
196101  CTCAGAATTC TGGAATTCTC ACTACAAGAG AGCCTAGAGG CCATCTAGTC
196151  CAAAACCAAT TTTACAGATG AAGAAACCAA GTCTCAGAGA GATTAAATAA
196201  CTAGTCCAAG GTCATGCAGC TCATTCTGAG TTTCTGAAAA CTGAACCTAG
196251  ATCTTCCAAC ACCAAGCCCA GTGCTGCCCT TTTTCATTGA CTTTGTTTGG
196301  CAAAAGAGAC TGGAAGGCAG GTAGAGCTTA AGGAAAAGTT AATTTGGAAA
196351  GCAGGAGAGC ATACACTTGT CATATAAAAG GAACTTAAAG TAGAAGAAAG
196401  TGAGTCATAC AGATAGAGGA GTTAAAAATA CGAGTTAGGG CTCTCAACAC
196451  ATCATGTGCA CACTGTCATC TTTTCTCATG GAAGGAGAAA AGAAAAGGGA
196501  GGAAAGTTGC TTTGCTCTGA CCTGTAAGTA GTATGTGCTG AGAAGTGTGG
196551  CAGGCACAAA CCCGGGCGCC ATAGACACGC GCTCACACCA GCTCTCAGAG
196601  CTGGCAGCGT GCCACAGATG GCAGAAGCTC CGGCACTTCT TACCTGATGG
196651  TGCCGGGTGG TGGTGACAAC TGAGAAGGGC TGTTTCTAGC TTGAATTGGA
196701  GGAAAAACAA TTTAAAAAAC ACACTCTTAG AATGTGTCTA AGTTATTGAC
196751  CACTTAGAAA GTTGTACAGG AGGCCCCATA GAAAAATGGA GTTTTATTAC
196801  TTTATTACTT GGAGAAGAGT TATAAAACCA AGGGTGCGGT CCATTGTCAA
196851  GTGTTTCATA AATTTATATT AAGGGCCGAA GTTAACAGTA AAAATGTATG
196901  GATACTTACA GCCCAGGGCC TCAGTAGCTG GCTATGGGCT GCCCTTTGTG
196951  TCAGCAGTGG GGAGGGTCAC ATAGAGCCT CAGATGAGGA GGGTTTTGCT
197001  GTGTGCTGCA AGTATCAGGG AGAAAGCATT TCTGCCCTCT CTGGAACATG
197051  GTGTGAACTT CATCCCTGTA ATGATATTGT TTGAATTTTC CATGAAAAAT
197101  TGTCAGCATG AGAGTAAGAA AAGTGTACGA TGGGAAAATA TTGAACCAAA
197151  CAGACAAAAA TGGTAGAGTC ACATGACCAG TTTACTCATT GGTAAAGTTA
197201  ATGAGAGGGT GAGATTAAAC AGAAATTGGT AAAGTTAATG AGAGGGTGAG
197251  ATTAAACAGA GGGTGAGATT AAACTTGGGA ATGAGTTTGT CTGAGGAGTG
197301  AGGTGAAGCA TCATTCCTCT GATGCACAGG GTAAGGGTTT GTCTGTAAAG
197351  AGATAGCACA GGTGTCTGGA GAGCAGCGTG CATGGTAACC TGTCCTCCAG
197401  GCCAGTGGAG CTGTCTGTCT AACCTGGCCA AGGTACAGTC TTCATCAAAG
197451  GTCAGGATCC AGTCCATGCA CAAGGGAGGA GCCATTTGCA GCAGAGCCCA
197501  GAAATGCCTC CTGCGACATC TTGTTTGTGT CATTTACTAG AGTTGGCACT
197551  GTCTTAAGAT GGGGGCATGG CTGACATTTT CAACTATCAT CAGTGAGTCA
197601  CTTGCCCAAA TGAGGACCAT GGTATTAATC TTGCATGTTT TTGGAACTGT
197651  TTAAAAAATG TCTGATTTTT GTTGTTTAGT GTCTGTTTTT GAATTTCCCC
197701  TTCTCTGCAG TTCTTGGTTT CTATCTCACT GAGTGCAGAG GATTTTAATT
197751  GTTGCTGTCT ATCTGTGCTT CGCAGCATGA GAGACAATG CCTACGGGCT
197801  CTTGTGGTGC TTTGGGGTTG ACGGGTTTTA TGTCTGACGA AGCAGAGATGTC
197851  ATAGTAGCCA TGCTGGATTG CAGTAATAAA TGTGTCCTTT TTTTCCTTCT
197901  GTAGCATTGA AAGCCGAAAA GAGAAGAAAG CTGACTCAGG GAAAGGTGTT
197951  GACAGGGAGA CTTGTCTATG ACTCGATCTT CAATTTATTT TTTACATATA
198001  TATGAGAAGA GTGTCACAAT TATTAATAAA ACTGCTTTGA TCATGTATTG
198051  TAAATTCTGT CCCTCAACCC AAATCCACCT TCATACTGTA AGTAGTGCAA
198101  TACTTGTTTC ATTTCTGTGT TTAAACTTCT GAGCAGTGAG ACATCCCTGT
198151  GAGCAGATAC AATAGCCAAT GCAAGAATCT GTGTGTTCCT TGCTGTACGT
198201  TAGACATTTG TAAACTGGAT TCTGATTGTC AGTTTTATGA GAGCAATAGC
198251  TTCCTTAAAG AGATAAGTCA TATTTACCTA GTTTGTATTT TCCTACTTTA
198301  GTGACCTGAA GATGCCTGAT AATTTCATTC AGAAGAATTT TTGAAAGGTA
198351  GTCTTACTTC TTTTTAGTTT TTATAGCTTA GCATTAGTGA CTTATTTCAA
```

FIGURE 3LLL

```
198401  AAGACCCAAA TCAAAAGTT  AGTTTGAAAG CATTTTTTAA TAATTGTATT
198451  TATGCATTTC CTTGATTTAA TATGATAAAT TTAATACTTA ACAATTTATA
198501  TGTAACTAAA ACTTAAAGTC ATTTGAAAAA TATATAGAAA CCTATTTACA
198551  ACTTGTTAAG GACAATCAGA CATAATGCAG AGTTAAGTAG TATTTGCTTA
198601  AAATTCAAGT TGTGACTAAT GATCAAATAC TAGGCTTGTA CGAAATGCTT
198651  TAGAAAAACT TTGTAACAGT TTTGTGGGAT TTTTCAATAT AAACCTTTAT
198701  CAGAAATATA CTAAGTTTGT CTCCCACTGA CAACAGATGT TTTCCAAATA
198751  AACATATTCT ATACATACTT GTGGAATGCC ACATGGTGAA TCATTGTATA
198801  TGAAATTCCA CTCCTGTACA GTTACTCTGC AGCTAATGGT CATGCACTGC
198851  TTAATGCTGG TCCTGAATCA TGTTCTCATG TTAGACCAAC AGCTCTCCAA
198901  TTGTCATTTT TTTTCTGCAG AGTTTTTTTT TTCCACTTTT AAATTAAATG
198951  CATGTTGTGG AAAAACAGTC TTTTAAAATG AAATTTCAGA TTCCATTTGA
199001  GAAGGTTCTG TAGATATTTC AGTCCATATA AAATAATACA TCTTTACTAA
199051  ACTTATATAA GGGGAGAGAA AGTTATGAAG TTTTGGACAT TACTAAAAGT
199101  ACAGTATTTG ATTTCACTTT CAATGAATGG TGAAGTTAAT AAAACTAAAT
199151  CTCATAATGC TCTTGGTTCC TAAGAATGAG TAGTAATCAT CAACTTTATA
199201  ATACTCCAAT ATTCCGTTTT ATAATAATTC AGAGCCCTGT GGCTTTTACA
199251  CACCGTTAAT TATGTACTCT GTTGGAAGTG CACATGAAGA GTGAAGAAAA
199301  GTTCCTCTTG TGATTAAACT AATGGGAGGA AATAAATCAA CAAAGTCTCC
199351  ATTAAGTTCT ACATTTTGAG ACCTTTTAAA AATTCCCCTC ACAATTCTTT
199401  AAGGAGCCCC CCTTTTTATG GAACATGAGC CTAAAAATTA TAGAAAGAAG
199451  AATTTTAAGT TAATAAAGTT TGTATTTATA AATGCTGAAA AAATACAGAA
199501  ACTTTCTGTT CCAAATGTGT TGCCTTTGTG TATTTTATAA TACAGATACT
199551  ACATTGTAAA CATTTCCATT GTTTTATGAT TTAGCCAGTG ATTCCCCAAA
199601  GCAGCCTCTT AGTGTTTTAA TATATTAATA ACTGTTTTGT TAAAAATGAT
199651  CATAGTGAAT TTAAATCTTC ACATGATCAC CTATTTGAAT AAGCAATCAT
199701  ATCCAATGAA ATTCTGTATT TCTGAGTATT TTTATAGTCA TTTTGTTCTT
199751  GTGTGAATTT TAAAGCTATC CCTATGTTAA TCCTAATATT TTGAAATCAT
199801  ATAAAATATA ATAAAAATGT AGTATTATAT ATTTACTTCT AATTTCAGAT
199851  TCCTGGTCAA AATTACTAAA TATCTTGAAT GTAATTTAGT GCCAAGTTTA
199901  AATAATGTGT AAATGTGACT AGGATATTGT GTTTTTCACA ATTAAGAAAT
199951  GTTATGTGGA AATAAATATT TATCCTAACT TCCTTGCACA TTTTAAATTG
200001  TGATACAAAG TGTCTTGTCT TTTTTCTTTG TTTTAATTAG TAAATCAGTG
200051  TAAAACATTT TGATTGTTTG AATATAATAT TTAAATTTAG ACAGCCCCAA
200101  AGCTAAGAAC TCTTGGTGAT GTAAACAATT TATGAGTATG TTTCAAGAGT
200151  AAACAATTTG AACTTTATGA ACAGAAGATT ATGAGAACTA TATAAAGATA
200201  TATTTACTCA TTTTTCCAGA AATGGGTGCA GATGACACGG TTTCTTATGC
200251  TAGGAAAAAC CTCCAAGGTC GTTAGTAGTA GTATTCCTCA TTATTAGAAC
200301  TCTATTTAGA CTTCCGTTTT TAACTTCCAT GGGGAAAGCA TTGCCTAAAA
200351  TTTGTCTCCT CCCTGTTTCT TACAAAGTC AGATGGGACC ATTATTCTTT
200401  GGTAGCCATC TGGCAGTGTG TTGTGGAGAT AATTGCATTC AGAATTCTAT
200451  CTAACCTACT GCTTGGTATT TTTCTCTTGA CTAGTGAGTT TACTTTGTAA
200501  TTGCTCCTGT TTCACAGCCT ACAATATTGG AAAGTTTTTT TCCTGTATAA
200551  TATAATATAG GAATATATAT ATTCCTATGT ATGTATAGGA TATCCTATAT
200601  ATCCTGTATA GATGAATGTC TCCTTGGTAT AGTTTAAACC CGAGTTTGAA
200651  AGAAACTCTC CACTGATGAT CCAAAAGCAA CTTGTATTTC AACATGATTC
200701  CTAGATCTTT TTGGATTTTT CTTGACTCTT AGAAGTGTGA CTTACCTGTT
200751  TTCTATGGCA CTGACCTACC TCTGTTTTGG TTTAACTTTA GCCTATTAGC
200801  TCCTGGGCAC TTGTCTATTT TACTATCATT GCAAGATTGC TCTCTCATTT
200851  TTCCAATATA TTAATATCTA TCTCATATAT TCACACAATG AAATGAAATG
200901  AGATTACATC CATTTGAAAG TTTTATGAGA GTCATTTGGA TAATATGATG
200951  GTTCTCTAAA TGTCTACATC AAGAGGCTAA TTGTAGTTAG TCCCCTTGAA
201001  GAGGCTTAAT AATCAAAGAT TACTGGTAAT ACTTTATTTT AGAGATCTCC
201051  TTCGATGTTC TTCATGGAAT GCTGTGGCTA ACTGATACAA CTGTCACACC
201101  AATTCCGTTC CTGTTGGTGT ACTGGGTACT ATCATTTCTG CTGGAACTTT
201151  GAAAATAGGA CTATGATCCT TGCTTCTAAG GGCAGGGTGG ATACATAGCT
201201  GTAATAATG TGATATGTGC TGAGTTGGCC ATATGAGTAA AGCCATTTTT
201251  TGAATAGGGC AGAGTTTGAC GAAAACATTA TAGTAGAGGT AGCACGTGAA
201301  TTAGAATGGA AATGGGGAAG GAAATGTACT CCAGATGTTG AAGGAACCCC
201351  TGCCTACTAG GCCTCTGGTC TAATGAAGTA TGACCAGAAT GACTCCATCT
201401  TGAAGTGAAG AGCTAGAACA CTCTTAAGGC ACCTATAAGA TTAATGCTTG
201451  TGGTCTGAAA ATAGCCACTT TCCAAGCTGG CTACAACCTA TTATTACAGA
```

FIGURE 3MMM

```
201501 ATATTTATGA CCATACAGAG CATCTCCCAC CATGCCTGCA GAATGTCCCT
201551 ATGTCCTAAG AATTCAGCCC TCCTTACTTA GAGATAACGT TAATGAACAA
201601 GCTTAGGTTA AAAGATTAAG GGTCATGTAA TATCAATGAC ACTGAAGGCC
201651 CCTGCCTTTA GTGAGCACAT AGACACATTC CAAGTTTAAT TGTAGCTCTT
201701 TGTAACTCCT TATAAAAGTA GAGGCGCTAA CAAAGGACAG GGCATTCCTC
201751 CTTTTGCTTT CAGAGGATAT CCCACACTGT AACGAAACGG TTTCTGAAAA
201801 ACTTACTTCT TCCACTATGC TCTGTGGCTT TCCTTGAATT CTCTCCTTTG
201851 CAAGATCCAA GGACCCATTT TTGGGGTCTG GATCAGGACC CCTTTTCCAG
201901 CAACACCGGA ACTACAAAGA TTCTCAAACC TATGTCGGTA TTGAAATAAA
201951 GATGAAATTT AAAAGTAAAG CTATATGGCA TAACTAGAGC CTGGCATATT
202001 T (SEQ ID NO:3)
```

FEATURES:

| | |
|---|---|
| Start: | 3016 |
| Exon: | 3016-3096 |
| Intron: | 3097-11617 |
| Exon: | 11618-11690 |
| Intron: | 11691-37943 |
| Exon: | 37944-38090 |
| Intron: | 38091-76221 |
| Exon: | 76222-76360 |
| Intron: | 76361-91402 |
| Exon: | 91403-91563 |
| Intron: | 91564-99311 |
| Exon: | 99312-99500 |
| Intron: | 99501-108867 |
| Exon: | 108868-108959 |
| Intron: | 108960-110489 |
| Exon: | 110490-110579 |
| Intron: | 110580-115705 |
| Exon: | 115706-115863 |
| Intron: | 115864-118931 |
| Exon: | 118932-119019 |
| Intron: | 119020-124894 |
| Exon: | 124895-125041 |
| Intron: | 125042-131125 |
| Exon: | 131126-131226 |
| Intron: | 131227-134218 |
| Exon: | 134219-134393 |
| Intron: | 134394-134990 |
| Exon: | 134991-135124 |
| Intron: | 135125-135856 |
| Exon: | 135857-136102 |
| Intron: | 136103-162378 |
| Exon: | 162379-162484 |
| Intron: | 162485-167349 |
| Exon: | 167350-167511 |
| Intron: | 167512-168933 |
| Exon: | 168934-169047 |
| Intron: | 169048-170472 |
| Exon: | 170473-170634 |
| Intron: | 170635-176773 |
| Exon: | 176774-177025 |
| Intron: | 177026-178271 |
| Exon: | 178272-178340 |
| Intron: | 178341-183910 |
| Exon: | 183911-184084 |
| Intron: | 184085-184826 |
| Exon: | 184827-184949 |
| Intron: | 184950-189728 |
| Exon: | 189729-189778 |

FIGURE 3NNN

Intron: 189779-192221
Exon(incomplete) 192222-192336
Stop:

CHROMOSOME MAP POSITION:
Bac Accession #: AC008063.2
Chromosome: 2

ALLELIC VARIANTS (SNPs):
DNA

| Position | Major | Minor | |
|---|---|---|---|
| 2180 | T | C | |
| 4693 | T | C | |
| 13759 | T | C | |
| 17580 | T | A | |
| 17701 | G | A | |
| 18151 | A | C | |
| 21076 | A | C | |
| 22984 | T | C | |
| 25961 | - | T | |
| 25962 | - | A | T |
| 29242 | A | T | |
| 29249 | C | T | |
| 34940 | A | C | |
| 35122 | A | G | |
| 35888 | G | A | |
| 37779 | G | A | |
| 40997 | G | C | |
| 45222 | T | C | |
| 45890 | A | G | |
| 49199 | A | G | C |
| 61696 | A | G | C |
| 63810 | G | C | |
| 64061 | C | T | |
| 64186 | T | G | |
| 65909 | G | A | |
| 66361 | C | T | |
| 68545 | C | T | |
| 70223 | A | T | |
| 72117 | C | G | |
| 74720 | A | - | |
| 77206 | G | A | |
| 77426 | A | G | |
| 78935 | C | T | |
| 89179 | A | G | |
| 90081 | T | C | |
| 96033 | T | C | |
| 96808 | A | C | |
| 102300 | A | T | G |
| 105400 | A | G | |
| 105494 | C | T | |
| 105494 | T | C | |
| 105911 | A | T | |
| 110376 | T | C | |
| 111250 | G | A | |
| 111990 | T | C | |
| 112748 | A | G | |
| 112783 | A | G | |
| 114256 | G | A | |
| 118703 | - | T | |
| 120414 | A | G | |
| 127435 | - | T | |

FIGURE 3000

| | | | |
|---|---|---|---|
| 127929 | G | A | |
| 130083 | G | A | |
| 131381 | G | A | |
| 132580 | C | T | |
| 133900 | T | C | |
| 143073 | A | G | |
| 143157 | T | C | |
| 148401 | T | C | G |
| 153365 | G | A | |
| 156875 | T | C | G |
| 159594 | A | T | |
| 160577 | G | A | |
| 161658 | G | A | |
| 165461 | A | T | |
| 166267 | G | T | |
| 169684 | A | G | |
| 171916 | T | C | |
| 173389 | G | A | |
| 173435 | G | T | |
| 174462 | G | A | |
| 176313 | - | T | G |
| 177082 | G | A | |
| 177358 | C | A | |
| 178098 | A | G | |
| 178537 | A | C | |
| 181240 | - | A | |
| 181325 | - | T | |
| 181730 | C | G | |
| 185615 | C | T | |
| 185975 | A | G | |
| 188447 | T | C | |
| 190645 | G | C | |
| 190708 | T | G | |
| 191287 | A | T | |
| 194488 | G | A | |
| 201885 | A | G | |

Context:

DNA

Position

2180   TGTGGTAAAAGAAAACAGTACTCAAACTTTAATAAATAAGACACAGTGAAAATCCATAGT
AAAAATGCCAACAACTTACATAGGTTTCATTACTAGACTTAACCGTGCAGTTTTAGCATT
TGATAATACCACATTATCTTTTGCATGTAAATTCTTTAGAAGAAGATATTAAATAAAAAG
ATAAAATGTATGTTGGTATGAAGAATCTGAAACATAAATGAAATCCCTGAAAATTAAAAG
GTGAATATGTATTTACCTATTTACTATTTACACAACTATCAAAGATTGCCAAAATAAAAA
[T,C]
CCTGTATAGGCGCTCATCATTTTGATGGGTGGATAAGTCGTGATACCCATAGTTTGGAAG
GAAGATTCCTTCAAGAGAGTACAATTTTGCTTGGTAAATCTTTTGCATGTTAAACTTTTT
AGAAGAAGAAATTAAATAAAAATATAAAATGTATGTTGGTATGAAGAATCTGAAACATAA
ATGAAATTCCTGAAAATTAAAGGGTGAATATGTATTTACCTATTTACTATTTATACAACT
ATCAAAGATTGCCAAAATAAAAATCCTTTTTAGGCACTCATCATTTTGATGGGTGGATAA

4693   TTTATATGTTATTCAGGCTACTTAGCCAGCTTATATTCTTATTAGTAGGGAAGATTGGCA
TATTCTTAAGCTTGATTAATTTTGAAATGATTTGAATATACCTTTTAATTGCAACAAAAT
ATGTCTAATCTGTTAGAATTTATTTCCAGTATTTGCATGTATTAGTCATTATGAGTACAT
TCTGTTTCTTGGCATTGCTTTGGGATTCCTCTTGGTATTGGTTTCACAGCATTCTGCTAT
TTTTCACTGTATTCCTGACCTTTCAAGAGAACCAAACTGTAAAGATTTTTAGTTACTTTC
[T,C]
GTTAGTGGCATTTAAATGAGGATATCGATAATTTTGTAAGGTGGAAAAAAATTACTATTT
TAGAATTGTCATTTCTGTCACAAATCAGAGAAATTTTTCTCTATTACTATTTCAAATAT
ACTACAATAAAAAGCAAAGACTGGTTAGAATGTAGTTAAATGCAATGTCAATCTTTCTTC

FIGURE 3PPP

```
         TTGCATGGCAGGATAATCTTGATCTTTGGAATGATAAAACTGATTGTAAACTTGCCCAGT
         AATGATTGGTCATCTTCCTTACAAAGGCTGCCTTCGTTTATACTATTTTACATGCATTTC

13759    AATATATGTGGCTCCATCTTGGTTCACACTGCTACTCAGTGTACTACAAATCACAGTGAG
         TTTGAATGCCATTCATATTACTGCAAACGACATTTTATTTATTTTTATTGCCAGTGCATA
         TCCATCATGCCAGAACAAGAAAATAAGAGAAAAATGAACTTTGATTGTCATGCTTTTATA
         GCACAGTGGAGTGTGAATTATTTTATTTAATTAGATGACAAAATATGTATTTATTATGTA
         AAGACTCTATAGCTATGCTAAAAGAATAGAATATATCTCCACATAACCAGATTAATCACT
         [T,C]
         ATCACAATATTCCTGACTCACAAGAAGACAACAGTCATAAATATTAGAAGGCTTAAAATG
         GAATCTCTCATTATAGCAGAGTTTTCCTACAAAACAAAAAGGACAGTGAGACTTCAACCA
         ATGTACATTTCTGAATGGCTCACTTGTTAGCCAAGTATGCCCTTATAAGACTGTGGCACT
         CTAAACAGGGCTTTCACAATGTCCACCCACACAATACCTGCCTTAATGAAAAGCTCAGTA
         CCAGTTTCAGGCAATTTAAAAATCTTAGCCTTTATTATATTGAAATTAAGTCGAATTATT

17580    AAAAATCAACAAAACATGAAAAATGAGAGCAAGAGAGGAAAAAATGCACAAAATAATTAC
         AAGGCTAACAGAAAACAGTACATGACAATAATAAATCCTTCTCTATCAATAATTACTTTA
         AAACTAAATAAATTATACTTCCCAATCAAAGACATAGGGTGGTTGAATGGATTAAATGTA
         TAATGGAATCACATGCTGTTATCAAGAGACTCCCTTTAGAATTTAGGCTCAATGTGAAAG
         AATGGAAAAAAAATTCCACGAAAATGTTAATGAAAAACGAGCAAGAGTGACTATACTTA
         [T,A]
         ATCAGATAAAATAGACTATAAGTCAAAACTCTCTCAAAAGACTGAGAAAGACATCTTATA
         ATGATAAAAGGATCAATTCACCAGGAATATATAACAATTGTAAGTAGTTATGCACCCAAC
         GATTAAGCACCTAAACATATAAAGCAAACATTGACAAAACTGAAGAGAGAAACAGGCAGC
         AACACAATAATAGTAGGATATTTCAATACCTCATTTTGAATGATGGGTAAAACATATTAT
         CCATTACCCACGGGCAAAACAGAGCAAAAGGAAATAAAGGACTTCAACAACCTTATAGAA

17701    AACTAAATAAATTATACTTCCCAATCAAAGACATAGGGTGGTTGAATGGATTAAATGTAT
         AATGGAATCACATGCTGTTATCAAGAGACTCCCTTTAGAATTTAGGCTCAATGTGAAAGA
         ATGGAAAAAAAATTCCACGAAAATGTTAATGAAAAACGAGCAAGAGTGACTATACTTAT
         ATCAGATAAAATAGACTATAAGTCAAAACTCTCTCAAAAGACTGAGAAAGACATCTTATA
         ATGATAAAAGGATCAATTCACCAGGAATATATAACAATTGTAAGTAGTTATGCACCCAAC
         [G,A]
         ATTAAGCACCTAAACATATAAAGCAAACATTGACAAAACTGAAGAGAGAAACAGGCAGCA
         ACACAATAATAGTAGGATATTTCAATACCTCATTTTGAATGATGGGTAAAACATATTATC
         CATTACCCACGGGCAAAACAGAGCAAAAGGAAATAAAGGACTTCAACAACCTTATAGAAA
         AAAATGGACCCAATAGACATGAACATTTCACTCAATAGCAGCATAATACACATTCTTCTC
         AAGTGCAGCCAGAATATTCTCCAGAATAGATCACATATTAAGCTGAAAAGTATGTTTTAA

18151    GAAATAAAGGACTTCAACAACCTTATAGAAAAAAATGGACCCAATAGACATGAACATTTC
         ACTCAATAGCAGCATAATACACATTCTTCTCAAGTGCAGCCAGAATATTCTCCAGAATAG
         ATCACATATTAAGCTGAAAAGTATGTTTTAAAAATTTAAAGTGATCAAAATTGTACCAAC
         TATTATTTCTGACTACAATGGAATGTGAAAGTAGAAATCAATAGCCATGGGAAAACTGAA
         AATATTATAAATATGTGGACATTAAACAAAACACTCTTGAACAACTAATGGGTCAGAAAG
         [A,C]
         ATTCAAAAGAGACATTAGAAAATATCTTGAGAGACATGAAGATGAAAACATAATATACCA
         AAACTTATGGTATACAGCCAAAGCACTATTAAAAGATAAGTTTATAATGATAAAAGTCTA
         TATGAAAAAAGAAGACAGATCTCAAATTTGCAACCTAATTATACATTTGAAGGGACTAGA
         AAAAAAAAACACACTAGACCCAAAGTTAGCTGATAGGAAGAACTAGCAAAGATCAGAGCA
         GAAATAAACAAAATAGATAATAGAAAACAATAGGAAAAAATCAATGAAATTGGGTTTTTT

21076    CCACTGCTAGTCTGATGGAATTTCCTTTACAGGTGACTTGACTGTTCTCTCTAACTCTCT
         TTAAGATTTTTTCTTTAGCATTGACCTTGGTTAGTCTGATGACTATATGCCTTGATGATG
         TTCATCTTATATAGTATCTTGCAAGTGTTTTCTGAATTTCTTTTATCTGGATGTCTACCT
         CCCAACAAGATCAGGGAAATTTTTCTGAATGATTCCTTTAAATATGTTTCCAAATTGCTT
         ACTTTTCCTTCTTTCTCAGCAATACCTATAAGCTATAGGTTTGGTCAATTTACCCCCTAT
         [A,C]
         CCATCTTTCTCAAATATTTTGTTTATTTTTAAAATGCTTTTCTATTTATTTTTGTCTGAC
         TGGATTAATTTGAAAGACCAATGTTTAAGCTCTGAATTCTTTCTTCTACTTGGTCTAGT
         CTTTTGTTAATGTTTTCAATTGTACATTGAAATTACTTTTGTGAATTTTTTTATTTTCAG
         AAGTTCTATTTTTATAAATATAGCTATCTTGTCTTTCATTTTCTGAGTTGTTCTTCTGGT
         TTCTTTGTATTGGTTTTCAACATTCTCTTGGATATCATTGCACTTCTTTAGAATCCGTAT
```

FIGURE 3QQQ

| | |
|---|---|
| 22984 | AGAGTTCCCAAATTGCCACCAACTGCATTGCCTGGGATTTCAAGGGCAGAGGGGTTCTCT<br>GACAATTTGTCAGTCAGCAGTTAGTCACAGGAGTGAGGGGAGCAGAGAAGCACCCCAACC<br>TATCCTTTACATGGGACTCTGAGTTCCTCAGGAGTCAGTGTCTGCCAGACTTTTGCTGCT<br>TTCCTTGTCTGCACCCCAGTTTCTTCCCATGGGCTCTCTGAAAGCTCGTGGCTCTCTTCC<br>CTCAGCTTTCCATTTGGATCATGACCATTCAACTGTAACTTTGATCTTTCTACAAACTGG<br>[T,C]<br>GTCTGACATCTCTAGTCAGCCATCTTGAAAAAAAAAGCTACATTAAAGTTATAAAAATA<br>AAAGTAATTGCACTGTGATGTTACAAAGGCTACTATATCACTAGGTGACAAGAATTTTTC<br>AGCCCTATTATAGTTTTATGGTACCACTATTTTATATGCGATCCATCATTTGACTGAAAC<br>ATCATTATGTATGACTGTACATAACAAATTGCGAATAGAATTAGAAAGTGCTTTCTACTT<br>CTGGAAATCAATGTTGTCTTCACAGAGACAGAGGTGGGCTTTGAAGGATAAATAGGAGTT |
| 25961 | AGAACTGTGTATTTGTGCGTATATGTATATATAATGTTTTCAACCAATCACTATTTCAGA<br>GAAAAAATGGATGAAAATAAACTTGTATTCATTACATTAAATATAATCCTATACATATTA<br>AGAGGAAATTTTACAGCAGGAAATTGTTCCTTTAATCATTATTTTTCTTGAAAATTATTT<br>AATACTTTTAAGACAAACCACGGATGACCAAAGTCTCTTAATATTTACCACATAGATTTA<br>TATTAACACTATATTTTTGTTTTAAGTTTTCTAGACATCTGAGACTTAAATATGTTCTTA<br>[-,T]<br>TTAAAGACTTTAATAGTATGGCAGTTGTACCATGAAGGTGGCATAGTGAAGGAGATCAAC<br>TTAGTCTACTTTTTGACTAAATTCTTAAATCTCTATTTCAGCTGTCTTCCCCCTAGAACT<br>ATAGCTTAAAAGCTCCTCAGCTGCATACAGCACATAGCCTTCACAGGTTATCGCCTTTCT<br>ATAGAGTCCTCTCACAATATAAACAGGTGTAGCTACCAATTAGGACATGTCTCAAGAAAT<br>TGTTAACACTCACCAATATTAATTAAGTGCTAATAGGGTACTGAGCCAAACACTGAGGGT |
| 25962 | GAACTGTGTATTTGTGCGTATATGTATATATAATGTTTTCAACCAATCACTATTTCAGAG<br>AAAAAATGGATGAAAATAAACTTGTATTCATTACATTAAATATAATCCTATACATATTAA<br>GAGGAAATTTTACAGCAGGAAATTGTTCCTTTAATCATTATTTTTCTTGAAAATTATTTA<br>ATACTTTTAAGACAAACCACGGATGACCAAAGTCTCTTAATATTTACCACATAGATTTAT<br>ATTAACACTATATTTTTGTTTTAAGTTTTCTAGACATCTGAGACTTAAATATGTTCTTAT<br>[-,A,T]<br>TAAAGACTTTAATAGTATGGCAGTTGTACCATGAAGGTGGCATAGTGAAGGAGATCAACT<br>TAGTCTACTTTTTGACTAAATTCTTAAATCTCTATTTCAGCTGTCTTCCCCCTAGAACTA<br>TAGCTTAAAAGCTCCTCAGCTGCATACAGCACATAGCCTTCACAGGTTATCGCCTTTCTA<br>TAGAGTCCTCTCACAATATAAACAGGTGTAGCTACCAATTAGGACATGTCTCAAGAAATT<br>GTTAACACTCACCAATATTAATTAAGTGCTAATAGGGTACTGAGCCAAACACTGAGGGTG |
| 29242 | GTTTGGAATATACACCCATGAAATCATTACTAGCATCAAAGCCACAGATATATCTATCAC<br>CTCCCAAAGCTTCCTAATGCCTTTATTATTATTACTATTATTTTATTATTATTAGTATG<br>TGTGTGTGTGGTAAGAACACAACATAAGATTCAACCTCTTGGAAGATTTTAAGTATACAA<br>TGCAGTATTGTTAGCTATAGGCACTATGCTGTGTAGTAGATCTCTAGAACCTATTTATCG<br>GAAAGTTACTTTTTTGAACCTCAATTTCATTATTTGTAAGTTGGGGAAAATAGTCCATAG<br>[A,T]<br>TTGCAGCGATTTTGTGAAGATTAAATGAGAAAATATAAATAAAACACTTAGCATAGTAGA<br>TGGTACATTGTAGATTTTCTATAAAGGCTAGTTTCTTTTTTTTAACTCTAAACTCTTATA<br>GCTATCTTAAGTGCCAAATGAATCGGCATTTATTTATATTCTGCCTTGGATGTTGCTTGC<br>CTTCTCTAGTATCCTCAGCTTGTACCTTTATGCAGGTTCTTATACATAATTTGTTGTTCC<br>TATCAACATTGATCACAATGTAGTATCAATACTTTCTGATTCTTGGTTCTTAATTTGCCT |
| 29249 | ATATACACCCATGAAATCATTACTAGCATCAAAGCCACAGATATATCTATCACCTCCCAA<br>AGCTTCCTAATGCCTTTATTATTATTACTATTATTTTATTATTATTAGTATGTGTGTGT<br>GTGGTAAGAACACAACATAAGATTCAACCTCTTGGAAGATTTTAAGTATACAATGCAGTA<br>TTGTTAGCTATAGGCACTATGCTGTGTAGTAGATCTCTAGAACCTATTTATCGGAAAGTT<br>ACTTTTTTGAACCTCAATTTCATTATTTGTAAGTTGGGGAAAATAGTCCATAGATTGCAG<br>[C,T]<br>GATTTTGTGAAGATTAAATGAGAAAATATAAATAAAACACTTAGCATAGTAGATGGTACA<br>TTGTAGATTTTCTATAAAGGCTAGTTTCTTTTTTTTAACTCTAAACTCTTATAGCTATCT<br>TAAGTGCCAAATGAATCGGCATTTATTTATATTCTGCCTTGGATGTTGCTTGCCTTCTCT<br>AGTATCCTCAGCTTGTACCTTTATGCAGGTTCTTATACATAATTTGTTGTTCCTATCAAC<br>ATTGATCACAATGTAGTATCAATACTTTCTGATTCTTGGTTCTTAATTTGCCTGCCCATT. |
| 34940 | CTATTCTCTTGCTTTATCTGATAATATAGATAAGGGTGTCACCTGTAATCATTGTTACCA |

FIGURE 3RRR

```
            TATTTCTTGAGGCCATTTTCTTATTCTCATTTAACTTTTCTACTTGTTTCTTCTTTATTT
            GTATTTTTCTCTGTTTTTAATCTTGCTCTTTTTATCATTTCTGTCTCTTTATATCCTACT
            TACCTCTTAATCTTTTTGCCCAACTTCTCTCTTAATATATATATATTTTTGCTCTTTACT
            ATTTCTCTTATCTTTCTATTTCAAAATTACACTGTCTGCTGTTTTCTCCAACTCCCCACA
            [A,C]
            CTCACCTTAGGTGTAGTTGGGACTATGCAATATGCCATCACACAGGTAGTACTAATTTTG
            ACAGGTAGCATCTCTACTTCAAACAAAGAAAGCTTTAACCAAAAAGGAATTACAGGAGAG
            AAGACAGTATTCTCCCCAACTGATGCTAACATTGCCACCTACACTTTTGACGCTTTCTTC
            AACAGTTAAGACGTAGCAACTTATTACTTCCCCAAATTCCCTGTGCTCTGTTGATCTGTC
            TTAAACTCTAAAGGGAGAGAAAGTAGGTTTGTTCATTAGCTGTGGGACTTAAAATGTGAC

35122       CCTCTTAATCTTTTTGCCCAACTTCTCTCTTAATATATATATATTTTTGCTCTTTACTAT
            TTCTCTTATCTTTCTATTTCAAAATTACACTGTCTGCTGTTTTCTCCAACTCCCCACAAC
            TCACCTTAGGTGTAGTTGGGACTATGCAATATGCCATCACACAGGTAGTACTAATTTTGA
            CAGGTAGCATCTCTACTTCAAACAAAGAAAGCTTTAACCAAAAAGGAATTACAGGAGAGA
            AGACAGTATTCTCCCCAACTGATGCTAACATTGCCACCTACACTTTTGACGCTTTCTTCA
            [A,G]
            CAGTTAAGACGTAGCAACTTATTACTTCCCCAAATTCCCTGTGCTCTGTTGATCTGTCTT
            AAACTCTAAAGGGAGAGAAAGTAGGTTTGTTCATTAGCTGTGGGACTTAAAATGTGACTT
            AACTTTTTTGAACCTTTTGTTTCGTGAATGATAAAAAAACACTTTCTGAATGATATAGCT
            ACTAATATTTTCATTTTATAGATAAAGTGAAAGATAAAGTACTTTTTTTAAAGGTTGCAT
            AAATATAAGTGACACACACTGATATGAATGTAAGCATTTGACTCAATCCCAGAGATCATG

35888       TATAATCAGGTACTTGAACCAATTATAATTTTTCACTTGCCTGCATGAATCCATACAGGA
            CAAAAACCTGAATATAGAAACTATCTTTCAGCTTTCGGTTTGCCAGAGGATTAATCTATA
            ATTATTTTTAGGATTATAAAAGATTTACATCCGTTCTTAAAATATACATAATATCGGATT
            TTTTTCCAGCAATAGAGGAATAACTAATTCTATAGTTTCATGCCAATCTCACCTCCAGTC
            CTTCTAGAATTTGGAGGTAATTTAACCCCGTGTATAAAAAATAAATATTTTCTTTTTTGC
            [G,A]
            TTTTATTGAAAAAATCACGTAATTTAAGTACAAATATATCCACTAAAGTAGGCAAATTTA
            TTTTAGTAGAATTCAGTTATCCCTTTCAAAGAAACACTATCAGCCTAAGTGTTATACATT
            GGATATTTTAGAAATCTTACAATTTCAATTACATGTCTTCTGAAACTCATTATTGTAAGG
            CTTTGTTTTAGGCTTTCCTTGCTGTATTAGTTGACTGGGGCTGCCAGAAAAAAATACCAC
            AGGCTGGGCAGCTTAAACTACAGAAATGTATTTTCTCACAGTTCTGGAGGCTGGGACACC

37779       TAGGAAAACAGAAAAACCTCTGTGGAATTTGGCATTAACATAGACCTTAGCGAAACCTGT
            TTTATTAGAGACAGTGATTTTTTAAAAACACTTAACTGTGAAGGGAAGGGATTTGATGAG
            ATAACACAATTGTCTGAAGGTAGAGAGAATAAAAAACAATTTTTTTTCTAATGAGAAGAG
            TATAATTAAGCATGGGGAACAGACACATAGAGATTATAAAGGAAGTGATGATTGCAAAAT
            ATTTAACCAAATAATTAGTATTATACATGTTTGTGATAGAGCTATGGTACACTTAATTAG
            [G,A]
            TAAAATGCCAAAAGACAGTGCCACGCTCCAAGCTTTATGTATCATAAACATCAAAAATGA
            CTTGCTGAATTAAATTAAATTGAGTCTCCATTAACATGTAAATCATCATATCTGTGCCCT
            GGAATAATTCAGAGTTTAATTTGTGGGTTTGCTTCCTTATGAAGGTCATCGAACACTATT
            TATTGGAGTACATGTGCCCTTGGGAGGAAGAAAAAGCCATCGACGTCACAGGCATCGTGG
            TCATAAACACAGAAAGAGAGACAGAGAAAGAGATTCAGGATTAGAGGATGGAAGGGAGTC

40997       CATGTGAGAATTCAAGATGAGATTTGGGTGGGGACACAACCAAACCATATCAAATGTGAA
            CCTTTTACTATTGTGAATGCTCTCTCATTGAAAGCATATTCAGAATACCACAATAAGTGT
            TTTCGTAGTTGTTAAAAGGTTCTGAATGCCATGAGAGCCCATGTACATGACATAACTGAG
            AACCTGGCTCTCAGTTCCTTGACCATCCCATCTCTTATGACCTTCTCTGTCATTGCACTT
            TGTTCACCTTCTCAACCATATTCACTCCATCCCTGAAGTCACTAATTCATTTATCTTTCT
            [G,C]
            TCTGACCACAGCTTCACTCCTTTCTTGCTGTGCAGCTACTTAACCCCTCTACTTTTCTTC
            TATCCATAAGTTTGTCTTTATTTGTTTATCCTAGTCTGATTGCATAGCATGCAGTCTTAG
            GAATACTTTAGCATTACTAGTATTCCATTTGTATTACTAGTAGTCTATTTAGTAATACTA
            GTATTCTAAATATCTTAGGTTCTAAGTTTTAGTTTTCTTCATACCTTTACTGCCTCTTTT
            ATTTTCATTTTTAATAGGAAGCAGCATTTTATTTAAAATGTTTTAATAGATTTCTTAAA

45222       GGGTTCCTCCATTTTTCCATTTTCTCCTTGCCTCCACAAGCAGATATACTCTGCTGGAAA
            TCATCATTCAACAAGGCAGATTGTAACCATTATGAAGTTATGACTCAAGGAGACCTTCAA
            CATCTCCTCCTAATTTCATTGTGTATCTTTTTTGACATTTGAAATAATTATTTTTCAACT
```

FIGURE 3SSS

```
             TTCTTCGCCTTCTTCATCATTCTCCAACATCCTCTCTTTTCACCATTACTTGATAGTAAT
             CTTGCTTTGTACTTCAGAGGGAAAATATATCATCAGAAAGAACTCACTTTACTTTCTTCC
             [T,C]
             GTTAAAAAGTTATAGCTGAAACCTTTCTTCCTATTAAACGGTTAAAACTGCAAGAAAATA
             AGGAAGTTTTCTTTTCCTTTATGTTTATTTTCTATTCCCTCTCACCACTCTGGAAACTTA
             TGCCATTTCTAATTTAATTGACCTCTTCCTCTTGAAATGAATTTTTCTTATCATCTTTGA
             AACATGATAGAGTCTCCACCATTTTAAGCAGTTCTCCAACCTCCTGCAAACCCACCTTTA
             GTCATTCAGATATGTAAGTTAACTGCATATAAATGTTCTGGGTAGCAATTTTACTTTTAA

45890    TATAGTCTCTCTATTTTTATTTTTTAGGTTTATGTATTTTAATCCTGAATGTTTATAGAC
             ATTTTTCTGTGTCCCTTAATGAAGAAAATTGCTAAGATTGACCTAATGGTAGGTGTATTA
             AAAAACTTTTCCATCCCGCATACACGAATAGTTTTCCACCTAGGGAACATTTTCCTATTA
             TGTTTCATTCTGTTCCATTTACTTTGATCTCTTTGTGAAGACTTTCTTTGCTCATATCCC
             TCTACTTTCTTCAAACATTTTAACTACATATATCTTTCATTTTTTTTAACTTTGAATTT
             [A,G]
             GGGGTACATGTGCAGGTTTGTTACATGAGTATGTTGTATGATGCTGAGGTTTGGGGTACA
             GATGGTCCTATCACGCAGGTAGTGAGCACAGAGTATAGTCAATTTTACAACCCTTGTTCC
             CTACCCTCCTTCCCAGCTCCGGTGATTCCAAGTGCCTATTGTTCCCATCTTTATGTCCAT
             GAGTACCCAATGTTTATCTCCCATTTATGAGTAACAACATGCAGTATTTGGTTTTCTGTT
             CCTGAGTTAATTTGCTTAGAGTAATGGCCTCCAGCTGCATTCATGTTACTGCAAAGGAT

49199    AAAGTGCCTACTTCTCCTTCCGCCATGATTGTAAGTTTCCTGAGGCCTCTCCAGGCATAT
             GGAGCTGTGAGACAATTAAACTTCTTTCCTTTATAAATTACCCAGCCTCAGGGAAGCTCT
             TTATCACAGTGGTGAAACAGACTAATAACAGTAACGTATATGAATCTTAAAATTTGACGC
             CAAGCGATGCTCTAGAACATTGCTTATCAAACCCTTCTGGCACATTGGGAATCACTTGAG
             AAGCTTTAAAAAAATTATTGATGCTAGGCTTCAACCTCGAAGGATTTTTATTTAATTAAT
             [A,G,C]
             TTGGGTGTTTCCCTAGGCACTGGTATTTTTAAAAAGTACCCCAAATTATTTAATAACCAC
             TTAAATAATTGACCAAGAATCAGATTCTGAGAAGCTTCTGCCTCTCAATTTGGTGAAACT
             TGGAAATAAGTCGGGTGGCCCAGATTCTCCCTCTTATTTTTTGCCACTATTTTTGGATGC
             CACCTACCTTTTTCCTTCTTCAATCATCTGAGTATCTTCAGTGACATTTAGACCTAAATG
             TGGTTTATCAGTGACAAATGTTTGGCACTTGGTGGTTTCTAAGCAATGGAATTTTCTAGA

61696    CAATGAGGATCAAGTCCTTTATATAATCCATTTTCACTTAATGAGTAGTAAATATATTTT
             CTCTTCTTTGTGATTTTCTTGTTTTCTCCAGTTTATTGTAAAAATACAGTACATAATACA
             CATAATATACACATTATGTGTTAATTGACTATGTTATCATTAAGGCACCTGGTCAACAGT
             AGGCTATTAGTAGTTAAGTTTTGAGGGAGTCAAAAGTTATATACAGATTTTCAGCTGTGT
             GGGAGATCAGCACCTTTAAGACCTGTGTTATTCAAGAGTCAACTGTAGTTGCTTTTTTTT
             [A,G,C]
             TTTTCTACCTTGAACATCTTCCTGCAGATGCTCCATCATCTTCCTAGCTCTAGTTTCTTA
             TCTCTAATGGAGGTAAAGCAGGAAAGTTCTTACTTCACTGCTACTGTGGCAAGTTAATGT
             CACACTCCTTAGGCTTAGCAAGAATTTGAGTTTATTCATTCTCTCCTGGAGGTTTTCTCA
             CCTGCACTCTTTTCTGCGTTACTATTTATTCCTCTTCATCCCCTAGGCATTCAGTTATAA
             TGATAGAGTCTCTCTGCTGAAATATTCTCAGTGCTCTGTGGCAGCCCAAGATGACTCTAT

63810    TGTAATGTATTAATCCTTTTACATATTTATTCCTTTTCCGATTCTTTTGTTAACTTATTT
             TCCTTCTGCCAAATCTTAAACCTTATTACTTCTCCAGTGTTGAGTCTTCTTCTCTCTCAA
             GACTTTCATTTTGAGTCATCATCATCATTGTAATCATGTGATATCTTTAGTTAAATGTTA
             TCTATGTCTCTATCTCTGTCCCTGCTCTCTCTTCCAGAATCCAATCTCAAATCTCCAACT
             GCCTTATGACCTTCTTCATATGATGGTCCCTTAGTCACCTCAAAGTTAGCATATGCAAAA
             [G,C]
             TTATCTTTGGAGCACCCAACCTACAATGCTGGCTCTCATTCTGACAACTCTCTTTTAATT
             AATGGCATGATTATTCTACCTGCTTCAATTTGTAAAGCTCTCTATTTCTGGTAGGTAATT
             CTATATCATCATTATAACCATCACCCCTATCTCTAATATAATCATCAGTAATATTATGT
             GATTCTTTTTTTTTTTGAGACGGAGTCTCGCTCTGTCAACCAGGCTGGAGTGCAGTGG
             CGCGCGATCTCGGCTCACTGCAAGCTCCGCCTCCTGGGTTCACACCATTCTCCTGCCTCA

64061    TTCTTCATATGATGGTCCCTTAGTCACCTCAAAGTTAGCATATGCAAAAGTTATCTTTGG
             AGCACCCAACCTACAATGCTGGCTCTCATTCTGACAACTCTCTTTTAATTAATGGCATGA
             TTATTCTACCTGCTTCAATTTGTAAAGCTCTCTATTTCTGGTAGGTAATTCTATATCATC
             ATTATAACCATCACCCCTATCTCTAATATAATCATCAGTAATATTATGTGATTCTTTTT
             TTTTTTTGAGACGGAGTCTCGCTCTGTCAACCAGGCTGGAGTGCAGTGGCGCGCGATCT
```

FIGURE 3TTT

```
          [C,T]
          GGCTCACTGCAAGCTCCGCCTCCTGGGTTCACACCATTCTCCTGCCTCAGCCTTCCGAGT
          AGCTGGGACTACAGGCACGCCCGCACCAGGCCGGCTAATTTTTTGTATTTTTAGTAGAGA
          CGGGGTTTCGCCATGTTAGCCAGGATGGTCTCGATCTCCTGACCTCGTGATCCGCCCTTC
          TCGGCCTCCCAAAGTGCTGGGATTACAGGCGTGAGCCCCGCGCCCGGCCAATATTTATG
          TGATTCTTTATTGCTTGAAAAGTATTTTTACATCTATAATTTCCTCTTTTGGGGCTTGGT

64186     CTACCTGCTTCAATTTGTAAAGCTCTCTATTTCTGGTAGGTAATTCTATATCATCATTAT
          AACCATCACCCCCTATCTCTAATATAATCATCAGTAATATTATGTGATTCTTTTTTTTTT
          TTTGAGACGGAGTCTCGCTCTGTCAACCAGGCTGGAGTGCAGTGGCGCGCGATCTCGGCT
          CACTGCAAGCTCCGCCTCCTGGGTTCACACCATTCTCCTGCCTCAGCCTTCCGAGTAGCT
          GGGACTACAGGCACGCCCGCACCAGGCCGGCTAATTTTTTGTATTTTTAGTAGAGACGGG
          [T,G]
          TTTCGCCATGTTAGCCAGGATGGTCTCGATCTCCTGACCTCGTGATCCGCCCTTCTCGGC
          CTCCCAAAGTGCTGGGATTACAGGCGTGAGCCCCGCGCCCGGCCAATATTTATGTGATT
          CTTTATTGCTTGAAAAGTATTTTTACATCTATAATTTCCTCTTTTGGGGCTTGGTCCAAT
          CTTCTGGGAGACTAATTCTGGCAGGTAGAAATATAAGGAGGCCAATATCAGTACATTGCT
          TATTCACCATTGCTAGCGTCTTACTCCTGGGTTTACTCTGACTTTGGTCCCCAGCTCTCC

65909     ACATGTTAGTGCTTAATTATTATTGTCTTACATTGTCTGTTATTATGTATTCATCTTATT
          TTTAAAACCAGATTATAAGCAATTTAAGAACAATAAATATGGTATAGCATTTATGTGAAC
          TGGAATAGATACTATCCTACAGTTAATGAATTGACCAAGCAACTATTCAAAGTACAGCCA
          GGCTGAAGACGGCAGTATGTTGTTTTTTAAAAGATACTTTATTTGCTCAATAAATCTAG
          GAAGAAATCAGCCTCACATTTTTTTGAACTGCAACTTCTTTGCTTGCCATCATTTAATTA
          [G,A]
          TTGCCGAGTTAAAGGACCCTCTTGGCTAATAAGATAGCAAAATTGTCATGGATTCTCATC
          AATCTCAATATAATTGAACTTACAATTCATCTAAATTATTCCACTTTGTTTTTTATACTA
          TTTGCAGTAATTTCATTCCACTTGAATAATAAGGGAATGTTTTCTCATGTTCTGTAAATA
          TATTATTTGAGGATATTTTACTTTTTTTCTATATTTATGTATTGGTCTGTTTTCATGCTG
          CTGATAAAGACATACCTGAGACTGGGTAATTTATAAAGAAAAAGAGGTTGAATGGATCAC

66361     AGGGAATGTTTTCTCATGTTCTGTAAATATATTATTTGAGGATATTTTACTTTTTTTCTA
          TATTTATGTATTGGTCTGTTTTCATGCTGCTGATAAAGACATACCTGAGACTGGGTAATT
          TATAAAGAAAAAGAGGTTGAATGGATCACAGTTCCATATGGCTGAGGAGGCCTCACAATC
          ATGGCGGGAAGCAAAAGGAAGGCACATCTTACATGGCAGCAGACAAGAGAGAATAAGAGC
          CAAGCAAAAGGGGTTTCCCCTTATAAAACCATCAGATCTCATGAGACTTATTCACTACCA
          [C,T]
          GGGAACAGTATGGGGAAACTGTCCCCATGATTCAATTATCTCTCACTGGGTCTCTGCCAC
          AACACATAAGAATTATGGGAGCTAAAATTCAAGATGAGATTTGGGTGAGGACACAGCCCA
          ACCATACCAATTTCTTTCTATAGAATATACATTTAAAAATTGACATAAGTGTGCTAAGTG
          CTCTGCACATTTCAGCTCCCAAGGAATGCATATTGTAGGAACTAAAGCAAAAAAAAAAAA
          AAAATAACAACAACCAGGGCAGTTTTATTGAGTTCAGTAAAGAATATGTTTCCCTATATT

68545     AAAAGCTTTTAATTCAAAGATTTTTCTTTCTTTTTCTGAGAGTGATCAGAACATGAAGAT
          GGCTGTTGGGAGACAAATCTCCATGTATCCTTTATGTTCCCAAACATCTTTTGGGCAAAG
          GCACTAAGTGCCTTTGTGCCTGTCTGTCTTTACAAGTATGTTTATATCGTGAACACACTA
          GGAAGATATAGATAGTGTCTCTCTCTGGAGCAAAGGGTAGGTTTTTTATCTTTATACAGT
          AAAGATAATGTCTCCTTATGGGCAACAATCAGTGAGGATTATTGTCCATTATGAAAGAC
          [C,T]
          TGAGTTCCTTACCTTGGTTCTCCCCTGTCACATATCCCGCTACATGTGCAGCATCTCCTG
          GCCCTTTGCACACCCTTCTGTGGGAGTTGGGGCTCAGAATGCAACACAAATGATGATACT
          CTAGGTACTACTATTCTGTGCATAATAAACCATCTTTTGTCTCTGACTCAAGAGTCTCAT
          GGCTTTTGCTAGCATCCATAAAACTGGCAGGGCAAATCCTGATACCCTTCACAATTCTTG
          GCAGTTTTGGCAGTGAGGAAGGGATACTGACAGAGACATGGCTTTTGGAAAAAGAAGGAT

70223     AAATTCTTGTGGTCAGCCTGAAGTTCTAGAAAAGTTCTTTCACCCTTATGTTGGAACCAG
          GCAAGAACTTAATAAATGTTGTATTGATAGTAGGGCAGCAGGTACATCTATCTAGTCTGA
          GGATGTTGTTGCTGTTACAGCCAATTAGTTTATTCTAGACACACCATGTGACCCTTGAAA
          CTAATCTATGTTATGTATTCAGATTTCTGAACCATTCACAGTCAGAGAGTCATGCACTTT
          TTAATCCCCAAAGCCATACAACAATTGGCTGATAATCAAGGTATGTGATAGACCTTCCAC
          [A,T]
          TTTCCTATCATCCATCGGCATCTGGTATTGTTAAATGTTGGAAGGGCTTCTTCAAAAATT
```

FIGURE 3UUU

```
         AAAAAAAGTTTCCAACTCTGCCTCTCTCACCTCCTTCTGGTGCACACATATAAGTAAGAT
         GGTTTGGTCACTGAATGTGGCTTCTGCAGAAACTGATCATCTCCTCTCAGCCTCTATGTG
         GATAATAAGATGAAAGGGTTAAGATTTTATATAAACTTATATTGAAAAATCAGTGTTCCA
         CCATGACCATTTCTGGGCATAATGCGTTATTCTTTCTTATTACAGAAACCTCAGGCCAGC

72117    ATATAGTGACTTGAACCACAGGGATGGTCATAAGAGACCTTTGAATGTTTAAGCAAACAC
         CACCAGTAGATTATGTAAGCTTCAGACGATTTCGGAGAGAACTCCAAAATCTACACTTGG
         CTATGAGGATGAGCTTCCTGGAGGGATAATTGACTTATTAGTTTTGTGTGCCCTACAGGC
         AGTTATCCCTACAATGGTAATCATCAAATTAGAAAAATTGGTGAGAAATTTGCCCCTGAA
         TTTAATCTAAAAGATTAATGATACAATTCCAGTCTTCTTTAGCCTCAGTTCATGGACTAA
         [C,G]
         GTTTTTATGGATGATAGGATTGCCCTCAGCTACCTCCTTGTGGTCCAAGGAAGAGACTGT
         GCAATTGCTTATATATCCTGCTGTACCTGATCTAATGCCTCCGGCCAAGTGGAAAGGTTA
         ATATAGAAACTTAAGGAGAAAGTCACATGGCTTTGTAAGGGAAACCTTTATGGTTTGGGG
         GATTTATTCAGTTTGTTGGGTTCAGCAGCTGAATACATCAGCAGTGTGGTTGAGGTATAT
         ACTGTAGATTGGTCCCATCCTTCTGCTTTGAGTCCTGTTGATAGTGACCTTAAGTAAAGA

74720    TGTTGGCACCCTGATTTCAGACATCCAGGCTTCAGAACTGCAAGAAATAAATTTCTGTTG
         TTTATAAGCCACTCAATCTATGGTACTTTGTTATAGTATCCTGGACTGACTGAAATATAG
         GCCTAGATCAATGGGACATTTTAGAAAGTCCAGAAAAACAGTCCAAACAAATATAACTAA
         TTGATTTTTGAAAACGGCACAAACCATGAAGAATATACTTTTTCTGTGTCTTTTATTTGG
         GTCTTTTCCATAAATGGTATGATATTGGAACAATTTAACATCCATATGCAAAAAATAAAA
         [A,-]
         AAAAACCCTTGAATTAAACCTCATATCTTATACCAAAATTAACTCAAAATGGACCATAGC
         TTCAAGATGTAAAATATAATATATGAAACTTTAGAAGAAAACATAAAAGAAAATCTTTGT
         GACCCTTTAGGCAGAGAGTTTTCAAATTTGATACCAAAGCATAATTTATAACACACACACA
         CAAATCAGAATTTATCAAAATTTAAAACTTTTCCTCAGTGAAAGACACTGCTAAAAGAAT
         ATAAAGTCAAACTATAAATGGGGAGAAAAGACAAATATTGCAAATCATATGTTCAAAAAA

77206    TTGCTATATAATTGATAGAGTTCTGTAAAGTTGGAATTAAATTTTGTGTTTACTTTTCAT
         TCATTCTTTCTGATTTGCTCAGTTAACAAACATTTATGGAGTGTCCATTATGTGCCAAGT
         GCAATGGATATGGCACAACAACAAAAATCTTAGATCTTGCCTTTAGGGATCTTGCAGTCT
         AATTTAGACAAGAAAACAAAGTTGTAAATGCTGTATAATGAAAGCTGTGATACAGGTGTG
         CACAAGAAACTGTGGGCACACCCAGGGTTGTCATTTACCCACTTTTTCACAAATTTTAAT
         [G,A]
         TGACTACCAATCACCTGGAATATTGTTTAAAATGTAGACTTAGTAGGCCTCAGGCATAGT
         CAGACCATGAGGATGTCGTGTAAAATGTTTTGGGTTTGAGAACCAAACTTTGAGTAGCAG
         TTATCTAAACCACGAGGTGAAAGAGAGGATCAGGGTAGCTTCCCTGGAGGAGGCGATTCT
         TGAGCTAGCTCTTGTGAGTTGGGTTGGAGTTAGCTAGGCAGAAAAGCAGAGGGACAGTA
         TTCTAGGCAGAGATAGCAGGACGTGCTTAAATATATCATTGACACAGGTTTAGTGTTTAT

77426    AAAGCTGTGATACAGGTGTGCACAAGAAACTGTGGGCACACCCAGGGTTGTCATTTACCC
         ACTTTTTCACAAATTTTAATGTGACTACCAATCACCTGGAATATTGTTTAAAATGTAGAC
         TTAGTAGGCCTCAGGCATAGTCAGACCATGAGGATGTCGTGTAAAATGTTTTGGGTTTGA
         GAACCAAACTTTGAGTAGCAGTTATCTAAACCACGAGGTGAAAGAGAGGATCAGGGTAGC
         TTCCCTGGAGGAGGCGATTCTTGAGCTAGCTCTTGTGAGTTGGGTTGGAGTTAGCTAGGC
         [A,G]
         GAAAAGCAGAGGGGACAGTATTCTAGGCAGAGATAGCAGGACGTGCTTAAATATATCATT
         GACACAGGTTTAGTGTTTATTTATTTATTTATTTATTTGTCTGAGACAGAGTCTCACTCT
         GTCCCCAGGGTGGAGTGCAGTGACGAGATCTTGGCTCATTGCAACCTCTGCCTCCCTGG
         TTCAAGCCATTCTCCTGCCCCAGCCTCCCTAGTAGCTGAGACCACAGTCATCTGCCACCG
         CGCCCAGCTAATTTTTGTATTTTTAGTAGAGACAGGGTTTCACCATGTTGGCCAGGCTGG

78935    ATGGCAACATATGTAGCAAAGAGAGCAGACATTTTTTCCTTTGATAAATACTGTAAACTT
         ACCTTCATAAAATGTTTTTCTAATTTACACTTCTATCAACAGTGTATGAGAGTGCTTATT
         TCCTCCACATCCTTTCACAGTAAATTATCAAACTGCTTAAAATGTCTTTTCCAGTTTTAT
         AAATAAAACATAAATCTCATTGTTTTAATTTGATTATTCAAATTATTAGTGAGGTACAAC
         ATCTTTTCCTATGTTTTTATTTTTTTCATGTGAACGAACTATTCATTTCCTTTATTTATT
         [C,T]
         TATATAAATCATTCATTATTTTCTTTATTTGCCTTTTGGAACACTTTAAATTGGTGGCAT
         GTTATTCAGTATGAACTAACCTTTTTAATAAAATAATTTACATAAGTTTCCTCATGATGT
         TTTGTATTGTAATACTTTAAATATAGACTTAAATTTAAAATAGTTTTTATTTAACCTGGT
```

FIGURE 3VVV

```
          ACATATTAAGATTAAGAGACTTCTACCTTACTTTTTGTCCCAACTGCATCAAAAACTACG
          TAGTAGTTTTAAAAATGTGTAATATATGTGCTCATCTTCTTTATTTGGTGACAGAAAGGG

89179     TTCCTTATGGAAAGTTTCATTATAGCCCTTCCACAGAATAGTATGTTTGAGTCTTATTCA
          CAAAGGAAAACCATCTATTTTTATCTAGCACAGTAGGCAATAAAGAAAACAAATTGGAAT
          AATATAAAAGAAAAAGTGAGAACAAAGAACATTTTGCAACTTAAGATTGGCTCCAGACAT
          GGATGAAAATTAAATGTTAAATCAGTTGTTTCTGCTATAAGCATTAGCATAAGATCTTTG
          AACTGAAAAGGACTATAAATTCAATTCAAATTACTATATTATGGTGGGAAATGGGCACAG
          [A,G]
          CTCTGGAGAAAAACAAAATTTTAAAAAAAACTTAGAGTTGGATCCTGGCTTGACAAGGTC
          ACTGGCTAGGTGATCTTTGGAAAATTATTTAATGTGTTTAATTTGTCTCATCATTTTACC
          TGTGAGAAAACTGACCCAGAGAAGTTAAAAGACTTTCCTTTTATTACATGGTGGTTTAGC
          TGTATAGAAAAAATATAAATGTCTTTTTATTCTAACTAGTTGAAGACACTTTATGTAAT
          ACTATTCCATTAAAATGTCTGCCAAGAGGTTGTTCCTTTGTGATATTGAAATCATAATGT

90081     CTTGAACTTTGCTTGTTGCATGTCAAGGAAAGGATGAGCTCCAGAGGATATCCTCTTGCC
          AATTAAATACTCCAGTCTGAAAGTGACACACACATAATTTCTGTTCCCACCTCATTTCCA
          GATTTAATCACAGACACATGGACTCACCCAATTAAAAGGGAGCCAGGTAGTGATGTTCTA
          CACTTTCCTAGGAAGAGAGGGAGAACCAGTTATGACATGATATGACCATCACATGATCTA
          TGAGGTATTATGGCCCTGTTTAGGACTGAAAAACTTTAGGAATAACTAATATGAAAACTT
          [T,C]
          CTGTGTAGACAAAAATGTTCTATAAAATTCCCAGCCTTGAAGAGATATACTGTTGGTGAT
          TTGTGGCTTAAATGTAAGTTTTTTCAATATGGCATATCTATTCTTACCTGATTGTAAATT
          TTGGCAGGTATAAGTATTCTTTTCTATTGGCTTCCTTTTCACTTTCTGACATTTTTTTTT
          CTTTTTGCTTCCTAAACACTAAAAACAGATCCATAGCTTTCCTGATCTCTCTTACTACTC
          TGCACATTAATCATTCTGACTGTCTCTTTTGGTTAGTTACTTTTGGCTAATCCACTTGAT

96033     CTTTTTTTTTTTTTTTAGACGAAGTCTCGCTCTGTCGCCAGGCTGGAGTGCAGTGGTGCGA
          TCTCAGCTCACTGCAGCCTCCGCCTCCTGGGTTCAAGCAATTCTCCTACTTCAATCTCTT
          GAGTACCTGGGACTACAGGCACACGGCAACATGCCCAGCTAATTTTTTGTATTTTAGTA
          GAGACGGGGATTCACCACGTTGGACAGGGTGGTCTCAAAGTGCTACTAGTTTTTCTAGAG
          TCTGCTTAGTGTTAGCAGAGTGTGACCTATTTGTCCTTTTTTTCTTTTCTTTTCTTTTCT
          [T,C]
          TTTTTTTTTTTTTTTTTTTTGAGGCGGAGTCTTGCTTTGTCTCCCAGGCTGGAGTGCA
          GTGGCGCAATCTCGGCTCACTGCAAGCTCCGCCTCCCGGGTTCACGCCATTCCCCTGCCT
          CAACCTCCCGAGTCGCTGGGACTACAGGCGCCCGCCACCACGCCCGGCTGATTTTTTGTA
          TTTTTAGAAGTGACGGGGTTTCACCGTGTTAGCCAGGATGGTCTCTATCCCCTGACCTCG
          TGATCCGCCCGCCTCGGCCTCCCAAAGTGCTGGGATTACAGGCGTGAGCCACCGCGCCTT

96808     TTACTAATTCAGATTCCTTTTGGTACTTAAATGTCACCCTAGTATAAATTATATTCTTAA
          GCAAAATGAGTAATTTTTTCCAGACAAGTAGATATAATTTGATACAGTTATACTTTGGAG
          AAGTTTGCTGTGTATTTCTCTGTAACTAATGAACAGATGAGTGTGTTTTTTAATATTTAC
          TTTTCTTTACATAACTGTTTCAAATAAAAATCTTATCTTTGAAAAACTGTGAAGATAGTG
          ACCTATGGCTTTTTTAGTGTTCGAGCCTGGAAACATTGTGCTTTAATAGAAATTAAAAAT
          [A,C]
          ATAAACATATGTAGGGTTTATTATGTGATTACTTTTGATTCTGACTAGAATATTGAACTG
          GGAATTCATATCATGGCTTATATTTGGAACTGCTTTACAATAATATCATATTGATATTCT
          AATAACCTACTTTACAACTTCCATTATGAAGTATATGCATATTTTATATACATTTTTCCA
          TCTTAGCAAGGTTTCAGTGTAATGTCATATACGTTGACAATTTATTATTTCCTTTATTTC
          AGATTAACCCAGGGGTATTATAACTACTGATCTCCAAAGAACTGAAAAATAGATTTAAAT

102300    TATAGACTTCACCAATTTAGAAGTAAATCTCCTACCCAAAAGTGAAAAAAAGTACAAAAG
          ACCTTTACTGCTAAGGTTCTTAATCTACTTATGAACTCTAAAGCCTGACAAACTCTAGAT
          ATATAAACAAATTGAAATTAATAGCCGTAAATGTAAATTGGAAATTCTGTTTTAAATATG
          CAATCAAGATTTAAATTTTTGTGCAATA
          [A,T,G]
          TTCAGAGAGATGCAAAAGGATTTCAAAACATCAAAAAAGTAAAGGTAATACTATTAATTT
          TTAAAAATCTCCTTAGTAAAATCCATTATGCAAAAGATTGACTTTTTTAAAAAAAAAGA
          TTATAGAATAGAAATTAAATAGAGCAAAGATTTTTCCAGAAACTTTAAAACAGAACACAT
          TTTCCTCCCTAAGCATAGTGGTAGAAAT

105400    CACATATGATCCCTACATGAAGACTCAAAGAAAAAAAAATGAATTTGTAACTCAAAGAAA
```

FIGURE 3WWW

```
         AGTAATTCAAACAGGTGCTAATATGAATACTATATAATATATATCTTAATTGGTAAGATA
         TCAAACAAATATTAGAAATTTTGATTTAAGGTGAAGAACTGTTGAGCTTAACAAGTCATA
         AAAATGTATTTAGTAAATAGCAGAGGAGATATTAGGTTTCTCAAATGTTTCCATTTACGT
         TTAAATAGTCACAGATACCAGTTAACCTTAGTGATATCTACTTTTCATCAGTTTTTTAAT
         [A,G]
         ACTTACCATGAATATAATAGATTACTCAATGTCTTTTTTTCATAGTCATCCTCATGCCTC
         AAAATTTTCTAGGTATTATAAAAACAGAAATAATTGAACATTGCAATGACATTCATTTAT
         AGGAAATAATATGGGTAGTGATCAGTGGACAAAGGTAATATAAAGAAACAGGTAAAAAGC
         ATTTGTTTGTAAGTACTGTGGTATAGCACTTTAAAAAAATTACAGTATACAATTAGCATT
         CATAAAGCTTCCACACATATATGAGTGCTAAATCCTAAACTTATA

105494   TAATATATATCTTAATTGGTAAGATATCAAACAAATATTAGAAATTTTGATTTAAGGTGA
         AGAACTGTTGAGCTTAACAAGTCATAAAAATGTATTTAGTAAATAGCAGAGGAGATATTA
         GGTTTCTCAAATGTTTCCATTTACGTTTAAATAGTCACAGATACCAGTTAACCTTAGTGA
         TATCTACTTTTCATCAGTTTTTTAATAACTTACCATGAATATAATAGATTACTCAATGTC
         TTTTTTTCATAGTCATCCTCATGCCTCAAAATTTTCTAGGTATTATAAAAACAGAAATAA
         [C,T]
         TGAACATTGCAATGACATTCATTTATAGGAAATAATATGGGTAGTGATCAGTGGACAAAG
         GTAATATAAAGAAACAGGTAAAAAGCATTTGTTTGTAAGTACTGTGGTATAGCACTTTAA
         AAAAATTACAGTATACAATTAGCATTCATAAAGCTTCCACACATATATGAGTGCTAAATC
         CTAAACTTATA

105494   TTTAAGGTGAAGAACTGTTGAGCTTAACAAGTCATAAAAATGTATTTAGTAAATAGCAGA
         GGAGATATTAGGTTTCTCAAATGTTTCCATTTACGTTTAAATAGTCACAGATACCAGTTA
         ACCTTAGTGATATCTACTTTTCATCAGTTTTTTAATAACTTACCATGAATATAATAGATT
         ACTCAATGTCTTTTTTTCATAGTCATCCTCATGCCTCAAAATTTTCTAGGTATTATAAAA
         ACAGAAATAA
         [T,C]
         TGAACATTGCAATGACATTCATTTATAGGAAATAATATGGGTAGTGATCAGTGGACAAAG
         GTAATATAAAGAAACAGGTAAAAAGCATTTGTTTGTAAGTACTGTGGTATAGCACTTTAA
         AAAAATTACAGTATACAATTAGCATTCATAAAGCTTCCACACATATATGAGTGCTAAATC
         CTAAACTTATACTAATTTTTTTCCGTGAGGGAAAAATATCCTAGCAAATTCTTTGTTATT
         CTATTAGGAAAATTTTTACTTCTGGCTGAACGTAAAATTCTGTACCTGAAAATTGCCATT

105911   TTAAAAAATTACAGTATACAATTAGCATTCATAAAGCTTCCACACATATATGAGTGCTA
         AATCCTAAACTTATACTAATTTTTTTCCGTGAGGGAAAAATATCCTAGCAAATTCTTTGT
         TATTCTATTAGGAAAATTTTTACTTCTGGCTGAAGGTAAAATTCTGTACCTGAAAATTGC
         CATTCTGTGAACCATTATTGCCTTAGACATCAGCAAGAAAATAAGAGATGCCCTTCCAAA
         ATCTGAATTTATTGATTCTTCTTATGTAATAGTATTTCAGTTAATGAAATTAATTTTGAA
         [A,T]
         TTTAATCCATCATCTTCTTTTGAAAGATGGTAATAATTGGCATAAACTAAATAATTGGCA
         TAGAGAAAATATATTTAAACAATGATTACAATTGATAATAGAACTATAAAATCATTTTT
         AATTTATGAGGTTTCAATTAGTTCTATATACTATAATTCATGCTTGAATATTGGTTTTAT
         ATATACAGCAAATAAAATGTTAAGCTTTTTAAAAGACTTCTATTTTTTCAAAATAACCCA
         AATCAAACTTGTTAGCTTAATTTTTAAATAGTATCTATACATCGTTCTATATACTACCAA

110376   GCCTGGGTGACAGAGTGAGACCACATCTCAAAAAAAAAAAAAAAAAAAAAAAAAGACAA
         TGCAAAAGAGAAGGAGTTTGAATACTTGGTGAAAATACGGCAGGTTAACAATTCTCTTTA
         TCTGAGTGGCTGAAATAGAAGTAACTCAGAGTAATATTTTAATAAAGCCCTTAGCACTGG
         CAATAATTATAGTAGTGGGAGGAGGTGGGAATGGATGGAAGCAGTAGAGGAAGTAGCCTG
         AATCAAGGTTCTGAAAAGATTAATAGTGATCAGCTCCTTGGACCTGTTTCAGAATCCCTC
         [T,C]
         GACAATGCCTAAATAATCTAGATCTAGTTACGTGCATGCTCTCCCTCTGGTGCCTGGCGG
         AGTCTCCGTGGGAGCATGGTGTACCAGCTTAAGTCTGTTAATTATGCGTGCAGGGACTGG
         GAGGCCAACAAAAGGGGCATACTAGTCCATGTGGGATGAAACAAAGGCATGAAAAGGAC
         CTCCACACCAGCAAGAGAGAGAGGTGAGGGCATACTCGGGCTCTATTTCTACAGTGGTTC
         AAAGCTCATTTCACTGTATGGAGGCATGTGATTCAAACATTAAGCCAGTTGAAATGTATT

111250   ACCTTTATACACTGATTGTGTATCTCCATATCATGTTGCTTTTGGTTGTGTGACCTGCCT
         TTGCAGCCTTCAAGAATACTTCATCACATATGAAAGAAATGAAGATTGCCAGTTGTAGG
         CAGTAGTCTCATCTTCTGGTCCCCCCTCAAACAGTTAAAACTATGGAAGAGTCAAACTTC
         GATTTCCTTTCTTTTAATCCTTTTCTTTCTCTTCACATTTGCGATCACTGGCCCGTTTCA
```

FIGURE 3XXX

```
              TCTTTTAATAGGCAAGTTAAATTTCTAGAGCCCTCTACTTAGTGTCAGCTGTTGTTCATA
              [G,A]
              CATGGCACACTGGAAAGTCTCTTGTTCATAGCATGGCACACTGGAAAGAATGTGGCTTTT
              GAGAAACAGCATGAGATCTTGAATCCCAACTCTGGCATTATAAACTAGCTGATCTTGGAG
              AAGTTCTCTAAAGTTCAGCCTTCTCATTTGCAAAGTA

111990     AAAAAAGACTAAGTAAGATTTTTTACTTTAAAGTCTGAGAGGGCAGAAAAGTAGAGTTTG
              AAAAGAGCAATTGTGATCTATCACTATGGAAACAAATTTTAGTGCCAGATTTTGCAGGTG
              CATGAGTTGATATTTTTTAGCCTTATGATTTTAGTTTAGTAGTGAATTTATCAGAATTCA
              CCTAGTCTCCAGGTTAGTTCTCTGTTTTAATATTTTAAGTCTTAATATACAGATTCCAAA
              ACCCCAGAATCTTAATATGCAGATTCCAAACATTTTGAGGTGTTAAGAAAAAAAAGGTCT
              [T,C]
              TATTCATCTTATATGATTTGATCATATTTATTCCATCTACATTCAACCTACATATTTGTA
              ACCCTTCCAGTGGATAGACGTATCAAACTTACTTAAGGAATGATTAGGAAAATAACTGGA
              ATTATCAGGTTTTAGCTTCCCATAATACTTTTAAAAAGCAGATGTGTCAAAGCAATATTT
              GTTTTTGTTTTTCAAGCTGACAGTGGAACGTAGGTATTTATGTTGGTGGTGTTTCTTT
              TACTTCAAATGACCCAGAGATGGCTTCACATAATTTTCTACATAGAAAGAACTTCCGTCT

112748     AGACACCATTTCTTCCCAGAGAATCCCTATGAAGTTTCTTGTACTTTCTATAAGGGGCTG
              AAGGCTTAAATTTTCTCCTTAAATTTCCATCTGTTTTTCCTTTAACTCTTAGCGTGTAGT
              TTGCCCAGACACTTCCAATTTCACCTTGGTCTTCTATCTAATCTCATTCCTTGTTCCCTA
              GAAATGTAACTGTTTCTCATCCACAGATTAAGTATCAAAGGCCCAGAAAGAAATCTTTCC
              ACTACCAGCATAAAGGTGAGGTCTGGGCAGCCCAGAAGCATGAGTGTAAATACAGACCCA
              [A,G]
              AAGAGTATAGCTCGATTTCTTCAAGATCCTATTCAGAGGACCAGAAACTTCCAGGATTTC
              CTTCTTGTCCATTCCAAGTGTTTGTGTTCACTTGACAGTTTTCTTAGGGATGTAGTTCAA
              CCTAGATTCTCTAGAGCTGCTTTACATATTTATAATTTTATAAGAGGTCACATTCAGGTC
              TTTAAACATAATATTTTATTATATTAAAAGTTGCTTAGGGGGCCAAGGGCATGGTGGCTG
              ACACCTGTAATCCCAGCATTTTGAGAGGCCAAGTCAGGAGGATCACTTGAGCTTAGGAGT

112783     TTCTTGTACTTTCTATAAGGGGCTGAAGGCTTAAATTTTCTCCTTAAATTTCCATCTGTT
              TTTCCTTTAACTCTTAGCGTGTAGTTTGCCCAGACACTTCCAATTTCACCTTGGTCTTCT
              ATCTAATCTCATTCCTTGTTCCCTAGAAATGTAACTGTTTCTCATCCACAGATTAAGTAT
              CAAAGGCCCAGAAAGAAATCTTTCCACTACCAGCATAAAGGTGAGGTCTGGGCAGCCCAG
              AAGCATGAGTGTAAATACAGACCCAGAAGAGTATAGCTCGATTTCTTCAAGATCCTATTC
              [A,G]
              GAGGACCAGAAACTTCCAGGATTTCCTTCTTGTCCATTCCAAGTGTTTGTGTTCACTTGA
              CAGTTTTCTTAGGGATGTAGTTCAACCTAGATTCTCTAGAGCTGCTTTACATATTTATAA
              TTTTATAAGAGGTCACATTCAGGTCTTTAAACATAATATTTTATTATATTAAAAGTTGCT
              TAGGGGGCCAAGGGCATGGTGGCTGACACCTGTAATCCCAGCATTTTGAGAGGCCAAGTC
              AGGAGGATCACTTGAGCTTAGGAGTTCGAGATCAACCTAGGCAACATGGTAAGACCTCAT

114256     TTAACTGTTTATTCTTTTAGTAACAGAAAGGATTATGAGATTTATTATGTTTTCCTCACA
              GAGCTGATAGTATATGGGAAATCTTCTATTCCCTCCTTGGGAATTTTGGCATTACAATAA
              AAATGTAAAGCATTACTAATTTAAAGCATCTTAAATGTGTACATTTCTCCTAACTAGATA
              AATACCTACAAAAATACCACAATAAATCCCATGAAATTTAACCTTACTTATTATAGTAAA
              TAAATACTTTTGCTATCTATAAACTAAAAGATCAGATTCCACAAAAGCAAAATATTTGCT
              [G,A]
              TATAATCCAGTGTACATTAATTATGAATTTACAAATTTATATTTGGAGTACATTTGTAGC
              TTAAAAATTTTGGATGTATAATATTTGTTAGATATTTTTATAGGCAGTTTTGCTTTGTTA
              AATCATTCTTCCTTTCCTTTAAAATAAAATAATGATTCTATTTAATATTTTGATGGAGT
              ACTGTAGGATATTTTATATTTAATCCTTGTGAAAGAACATATGCTTCCTATACTAGGTT
              ATATATTTTGTGGTATCCTTATTCTTTGGAAAGATTAATTAGTTACAAAACTTACAAATA

118703     CCCCATTTTCTTCTACGTGGCTGATCTTTGATTCCTGACAATAATTTTTTATAATGAAAA
              TTGCACATACACCTACTGTTTTTTGACTCTATATTTTCTCTGTTTTGCTACTGTGTTACC
              TTTGTCCCCTTTGAACTATTCGCCATTTTGCATACAAGTGAGTTTTCTTCCTTCCAATTT
              AGAAAGGTCTAATCAGATTTTACTTTTCCCACTTTCCTTCTCTAAGGATCATAGAATCCT
              TAAAATTCCCAATAACAACTGCACATGCTGTACAGATAACTAAACGGAGAAACACTGTGA
              [-,T]
              AAAAAAAAAAAACACGGAAAACCATGCATTCCCATTGCTTGAGGATCTTAAGCATAAGGG
              TCAATCATGGTAAAATTTTTCAAAATAATAATGAACTATGAAAAACTATGGAAGTATTTG
```

FIGURE 3YYY

```
          CCATCACAATCTCCATTTTCAGTAATTCCTTTGAGATGAGTGATTCTGTATTACTAAAAT
          TATTTTTATATTTCTACCTTAAAACATTTTTTTCTTCTTAATTACAGATTTTTGTTCAT
          TCTTCTGGGACCCCTGGGAAAGGGTCAACAGTACCATGAGATTGGCAGATCAATTGCAAC

120414    ACAACGACTGCCATAAGAAACTACTACAAATTGGGTGGTTTAAAATGACAGTAGTTTGTT
          TTCTAACATTTTTGAGGCTAGAAGTTTGAAGTCAAGGTGTCAGCAGGGCCACAATCCCTT
          CGAAGTCTCTAGGGGAGGATCCTTCCTTGTCTCTTCCATATTCTGGTGGCTCTTGGTCTT
          CCCTGGCTTGTGGCAATAGACCTTTGTTCTCTGTCTCCATCTTCACATGGCTTTCTCCCA
          GTTGTCTCTGTGTGTCTTCTTATTTTCTGTTATGAAGACAGACATTTGTCATTTGATTTA
          [A,G]
          GGCCCATCCTAAATCCATCCAAATCATTGGATTTAGGGCCCATCCTAATTCAGGATAATT
          TCATCTTGAGATACTTACCTTAATTACATCTGCAAAAATCCTTATTTCAAATAAGGCCAC
          ATTCTGCGGCTCCAGGTTGATGTGTATTTTGGGAGGAAATTATTCAATCCACTGTAATGA
          ATAACTTATTCTATTTAGGAAATTTGTGAGAAGACAGGAGGATGAAAAAAATAACTTAAT
          GAGGGCCATACACCTGATTTAGCAGAACTCTCTCTGAGAAAACACTCACAGTATAAAAGC

127435    TATGGCCTAAGAGAAAGCGCATTACTGTCCTTGTATGTTTTGATACATCACTTTGAAATT
          GGCAAGCATTAGGAAAATTCAAAGACATGACTTAATCATATTATATAGAAAACTCCATAT
          TTATTACTGCTAATCACAGGAAATATTGGGAAGATTTTAAAATTATAATTCTTATATTTG
          TATTGCTTTTTTGTGAATGTATGATATAAAGATTTTTTAAATTTTGTTTATGAACATCTA
          ATGTATATTTTACCCATCATACAATCCAGAAAGATAGAAATATAAAGCATTGCTATTTTT
          [-,T]
          AGGGTCATTTTTTAAATTGCAGGCATGAGTATTAAGAGTGATGACCAAATATTTGTTAAG
          CTCACTCCTCATACTGCCACCTCTATGCCTACTGAATCTGCCTCCCACAACCCTCCCAAA
          TTGTTGTGTACTTAGTCTTGCCTTTGCGCCTTGCCCTGTGGAGTTCAGCCTTGCCTGACT
          CTGCTACCCTATTGGAAGCGGCAGATGGTCTAATTGACCCAGCCCTGGAATTAGAAATTT
          TCCTGCTTTGCCAGACGTGGGCAAATGAGCAGTTGTACCACTCAACCATGAGTACTTAAA

127929    GGAAGCGGCAGATGGTCTAATTGACCCAGCCCTGGAATTAGAAATTTTCCTGCTTTGCCA
          GAGGTGGGCAAATGAGCAGTTGTACCACTCAACCATGAGTACTTAAAAAGGGTATCTCAA
          TTTCACTGTCAATTTAAAGAAACTATATGGATACCTCATTTTTATATTTTCATTTTGAAA
          TCATTTCATAATTATTAAAGACTATTTCCTTTTCTCAAAACTTACCATTTTGTGATTATG
          TAACTGCTACCACATATTTCAGTTGATCTACTATTAAAATAAAAAGTTGCCTAATAATTA
          [G,A]
          TTGTAGGGTTTATAGATTGTCTCATTTCTGTACTTGTAGAATACATCTTTGTACTAATGA
          TATTAGAAAAGGCAATATAATGCTTCCTGAGTATCTAGAAACTCTTTAATTAATGTTATT
          TGGAGAAATGCAGCAAAATATTAATACATTCAGAATGAGGCTTTAAAATTCACTGTAATA
          CCCATTAGCTATTGAAACATTGAAGTTAAGTGTTTTTGAAAACACCTTTGTGAACAATAA
          TGTTTTGAGGCAAGTTGAGTGATGGGAGGCCAATATTGTTTATGATTTTATGACACCCT

130083    TGTTCTTTACTTGGCTCCCAAAACATCACCTTCTGTTAGTTTTGTCATTATAAAATAGAG
          TTAATTTATCTAGTCAGTAGTATTTTCCCAGAAGACCACATAATAATGCTTGCTTTCTGA
          GACCTGTGAAAGCTATGAATTGTTTTCCTAGGTGATTGGGAAGTAGGTATTGAGGGAAAC
          TCTTAAATCCCTTTATTAATGTATCCTATTTACCTGTAAAGACAGTTCCTTCATCAGTTG
          ACAGATGCTTCTCTTTTATCTTTGAACTTTAGTCTTACTGCGTCCATCCATTTGCCTGGG
          [G,A]
          AAATTGTTAAAATATTAAGCAATAAACTTTCTTATATTGAGCATTTTTCAAAACCTTTTT
          TATGTTTTAAACCTGTATCATTCTATCTAAATGTCTCATGGTAAGTGAGATCAGTTTATA
          AGTCACTTTTGTTTTTCATGTTTACACTAATTCTATTTTGGAATGGTGGTCAAGTAAAAA
          TCATAATTTCACCACTTAAGATTTTCCTATTATCCTTTGAAGTGCTTTTGAACACATTG
          GTGTGCTCTAAGATCACCATAGGTAGGATTTTAGGTAGAACTTTCTGATTTTTTAAGAAA

131381    GAAATTAAAACAAAACAAAACACATGAACAAAAAACTCTCCACAGGAGAAGAGGAAGATT
          CCTGCTGTACCAAATGGAACAGCAGCTCATGGGAAGCAGAGCCCCACGGAGGACATAGT
          GGACCTGAACTCCAGCGAACTGGAAGGTTAGTGAAAATCACTTCTATGGGACTTCAAGGA
          CCAAATGACATACCATTCTTCTCTGTCAGAAATTGCTATTTTGGGATCTAATTTATTGTA
          TACTTTTAATACCTGCTTTTTGAGGGTGAAAATGCCAATTAGTTTGATTTCTCTGAAGTT
          [G,A]
          CTAATGATTGTCATTACTGTTAAACTAAAACAGTGGATACACCCTTCCATTATACTTTAC
          CTAGTCTTTCATTTTGCTGTGCATAAAATGCATTCTCAGATTCTTAGAATGAAAAGGAAA
          ACCGTCAATTGACCCTTCCAAAAGAACCCATTGAAAGCTTCAAGTTGAAGATAGAAATAA
          AACTAAATACCAACAACTCAGTCTTGTAGGCCCTATCTCATTAAATGCAAGTAGGATGTA
```

FIGURE 3ZZZ

```
             TATAGTGGTATTTTTTATTTTTATGGCTGTGATTTGAAAGAGCTATATGATTTATTTTTC

132580       TTCCACAGATTCTGTTGCTGACATGACTTGAAGTATCCATTACTCATCTGCTCTCCTGGA
             GTTGCTGGTGTACATCTGGGCTGCTCTTGCACTGTTCTCTGTAATGAACTCCCACTTCCG
             GATTTAGATTTTTACTGCTAAAAGCACATTTATTACACAGTACTATAACAACTATTCAGA
             CTAATGTATGCTCTAATAAGTAATTGATTAGAATCAATGGTCTAATATAAAGTGCTTTCA
             AAACTATAAATATTAATTACTAATTAATAGCTCATAACCACCTCAAATTCTTTTTGGGAT
             [C,T]
             AGGTGGGATATAAATCATAAATGAATGCCTAAATAGACTGGTAGAGTAAATCTGTTTTGA
             ATTGTGACTTTGATAAGTTAACAAATTATTCAGAAATGATCCCTAAAATAAAAAAAAGTG
             CATATGTTTTACCAAACATGGGTAGAGAAGCCTAAGGTGATCTTTATGTGTACAAATATT
             TCACAGGTTCTCTGCAAGCTTCTCTGAGTTTCAAATGTCCTTTTATTCAATTGAAGTTTC
             ATTCTTCTCAACCCTCTCCTACTCCATAGCTCTCAATGGAAGCAATCACAGGAAAATAT

133900       CCGAGAGAGTAGGTAACTGGAGCCATGGTTAAACATTGCTTTTTCTCTCTAGGGTGATGC
             TCACTACTGGAGTATACAAAAGCCAGCTAACCCTCCCTCCCTCACTTCCTGCTATGCTAA
             ATGGAATTAAACATTTAGAAATACTGCCAATGATTGAGGGTTGTAGGCCTGAGTTTAGGA
             GGAGTAGGTTGA
             [T,C]
             GTAGAAATGGCACAGAGATTAGAGTAATCCTTGAATCTCATTATTTGGATTATGATTGGT
             AAACAGCTCTGAACCTTGTTTAAGAGAACCTGGGATTTTTGGTGGTTGACACGATATTGG
             GTTAGGAATTGAGGTAACGAACGTAGTTGTGCAGTGCCTCCCTGTAGATTGTTATAAGAC
             AATGCAGCAGGT

143073       TATAAACAAGATCGCTTAGAGCACTTGCTTTTCTGTGGGCAGTAAAGGGTACTAAAAGAT
             GTATTTTATAAAAGTGTATTTTAAGCCAAATAATTCAGCACCACAAGTGAAAATTATTG
             GCATTTTATACTGGTGTTTTTAAACATGTAGAGAAGTGCAGATACAACCCTTTTTCTGCT
             TTATGATTGTTGGACTTTTCAGTCTATGAGCTTGTGATAGTAACAATAATAAATAACCAA
             AATGAGATACCTAACAATCTCTATTTACTTATGTCAGGGCCCATTCTAGGACTTTTATGT
             [A,G]
             TATTAATTCATTTAATTTTATAATAACCCCTAGAAAGGACATGAACTCAGAAGCTGGAAA
             CCATCATTCTCAGCAAACTATCGCGAGGACAAAAAACCAAACACTGCATGTTCTCACTCA
             CAGGTGGGAATTGAACAATGAGAACACATGGACACAGGAAGGGGAACATCACACACCGGG
             GCCTGTTGTGGGTGGGGGGAGTGGGGAAGGATAGCATTAGGAGATATACCTAATGTTAA
             ATGATGAGTTAATGGGTGCAGCACACCAACATGGCACATGTATACATATGTAACAAACCT

143157       AGCCAAATAATTCAGCACCACAAGTGAAAATTATTGGCATTTTATACTGGTGTTTTTAAA
             CATGTAGAGAAGTGCAGATACAACCCTTTTTCTGCTTTATGATTGTTGGACTTTTCAGTC
             TATGAGCTTGTGATAGTAACAATAATAAATAACCAAAATGAGATACCTAACAATCTCTAT
             TTACTTATGTCAGGGCCCATTCTAGGACTTTTATGTATATTAATTCATTTAATTTTATAA
             TAACCCCTAGAAAGGACATGAACTCAGAAGCTGGAAACCATCATTCTCAGCAAACTATCG
             [T,C]
             GAGGACAAAAAACCAAACACTGCATGTTCTCACTCACAGGTGGGAATTGAACAATGAGAA
             CACATGGACACAGGAAGGGGAACATCACACACCGGGGCCTGTTGTGGGTGGGGGGAGTG
             GGGAAGGATAGCATTAGGAGATATACCTAATGTTAAATGATGAGTTAATGGGTGCAGCAC
             ACCAACATGGCACATGTATACATATGTAACAAACCTGCACATTGTGCACATGTACCCTAA
             AACTTAAAGTATAATAATAAAAAAA

148401       AAGTATAATAATAACAGAATAAAAAAAGTATAATATATAATAAAAATATCTTGAAAATTA
             AAAAAAAAAACAAACTTCTCAATGGCTGTCCCTCTCATTCAAGAGCAAAAATAAAATCAT
             AACAATCCTTGAAAGCAAAAAAAAAAAAAAAAAAAGTAGGAGTTTCAGGTTGGGACAGAC
             CTGGATTCAAGTTTATTTCTATCAGTGTAGCCTTGGATAAGTTATCAAACATTTAGTTCC
             TCCCATCTATAAAATGTAGCAATTAAACTATTAAACTAGAAAATCCACTATATGCCATGC
             [T,C,G]
             TATAGCAACTGTATGCACGCCATACCTATAGGCATAGATATACAGTAGCTACAGAAAACA
             TATATGTATGTATATACACATATACATTTGTACATGGAGGTATTCACATATCTACGATAG
             TGCTATCTTTCTCCCTCGTTATGTTACTTCTGCAAGAAACTTGCCATATTTTCTCTATTT
             TATATTTTTGTTTCTTATGTATGGATTTACTTTTAACAAATTTTCAAAATATGCAAATAA
             CTTTCTGTTAAACTATAGTACTGGCCCTTTTATTTCTGAGGTAAACTAACTGACCATCTT

153365       GAACTCCTGGGCTCAAGCAATACTTCTGCCTCAGCCTCCCGAGTAACTAGGACAACATGC
             ACATGCCACCACATCTGCCTAATTTAAAAAATTTGTTATAGAGACAACATTCTTGCTATG
```

FIGURE 3AAAA

```
         TTGCCCAGATTGTTCTCAAAGGTCTGGCTTCAAGCAATCCTCCTGCCTTGGCCTCCCAAA
         ATGCAGGGATTACAGGCATGAGCCCCCACACTCAGCCTCAATGCCATGTTTGACTTATCC
         TTTCGTCCATTGATGGGCACTTAGGTTGATTCCATATCTTGGCTACTGTGAATAAATGCT
         [G,A]
         CAGTGAACATGGGAATGCAGATATCTCTTCCATTTACTGATTTAATTACCTTTGGGTACA
         TATCCAGTAGTGGAATTGATGGATCATATGGTAGGTCTATTAATTTTTTGAAGAAACTCC
         GTACTGTTTTCCATATGGCTGTACTAATTTATATTCCCATCAACAATGTGAAAAGTTTCC
         CTTTCTCCACCTCCTCGCCAACACTTGTTCAGACACTTTCATCTTTAAAAAAAATTAAT
         TTTTAATTTTGTGCACACAGTAAGTGTGTATATGTATGGGGTGCATGAGATATTTTGATA

156875   CTCTTACTGTTGCAATCTACAAAAGTATTTGTTTTTGGCAAGTTGTGTTTCCATTTTCAT
         TTGTCTCAATACATTGTTAAATTTATCTTTTAACTTCCTCATTGTCCCACTGGTTGTTGA
         GGAGTATGTTGTTTAATTTCCACATATTTCTGCATTTTCCAAAATTCTTCCTGTTATTGA
         TTTCTAGTCGCATACCATTGTGTTAAAAAAAGATACTCAATATGGTTTAAAGTATCATT
         TCAGTTAATGATCTGGACCTTAAATGATGGCAGCATAATCAATGTTAATCACAAACCAAA
         [T,C,G]
         GCTATTTAGTGTTATTATTTTAATATGCAATATACTTACCAGGCCCCCAGCACTCAGTC
         TGCACAGTCTAGACCCTGCCTATCTCAGATCCATACCCCATCTCTTCCTCCACCCCTTCT
         GTTTCAACCAAATTAACACTGTTTATTCTCTGTAGTTCCCCACCCTCACTGCCGTGCCCA
         CACTATGTCTTACCAAATTCTGTCCCTCTTTTAGATCTCAGTTTTCCTTGAACACCCAGA
         CTCAAGGTGTGGATGCCTATTTGTTTATCTTTTTAGTAGCCCAGACTTTTTTATAGTACA

159594   TAAAGATTGATTCTAAAAAATTTAAAAATATAGAAATCTATAAAATTCTGTAAATTTTAG
         ATTTTCTATAATTATAGAATGTAAAAATATAGATTTTCTATAAACATAGAATGTAAAATT
         CTATAAAATATAGAAATCTTTATGTAATTATAACTGTGTAAGTATTATTTACTGTAGAA
         CCAAGTAATGTGCAATGCTTCCTTCTCCATGGCTCCAGTGTCATGACATCTATAGTACTT
         TACAAATAATGTTATGAGTATATACTTCCAGAATGGTGGTAAAAGAAGCTCTGCAGACCC
         [A,T]
         CTCCCCAGTGAAACAACCATACTGGTAAAAGTAATTTTAAAAGGCAATCATGAAAAGTCT
         CTGGAAATTTTCTTAAGGGTATACAGCAAATGAAGAAACATTTATTCCAAAAGTGTACT
         AAATCTTGGTAAGAACAATGAGTCCAAGGCACCTAAGTCACAACCCACTTCCCTTCCTCT
         CCTCCCAGCTCAGCATGACAGAAGCTTAACTCTGGACAAGAACACAGGGCTTCCTCAGCT
         TCCAGTTGAGGCCAACTGTATGTTCCCAAGAGGAGAAGACCAACAGCGTTTCTTGTCTCC

160577   CAAGCACTGACCACAGCAGGCAGGGCACTGTGGCTTACACCTGTAATCCCAGCCCTTTGG
         GAGGCTGAGGTGGGAGGATTACTTGAGCGCAGGAGTTTGAGATTAGCCTGGGCAACATAA
         CAAGACTCTGTCTATATTTTAAAAACAAAAAACAAAAGGCTACCACAGCAAAAAGGCTGG
         AATTTA
         [G,A]
         TTGGAGCAGACCCCCAGAGCAATTTATGTCCCAGGACATTGTAAAAAATAACAGAACAAT
         CTAGAACAGAATAGCTGGGTATATGTGATAAGCCTTAGAGCAACCACTAAGAAAATAACT
         CGAAAAATACATAGTGAAGGAAAGAAAACAACAATGTTCCTAACATCACAATCAAATGAA
         TTCTCC

161658   CTACTGGTGGTTAACAAGGTAGGGGGTGTTACAGGGTGTGGCTGACCTACTGTTCCATCA
         TAGACAGGAGCTCAGTTTTTAAGGTTTCTCTGGGGTCTCCAAGTGAGCCTCCCTGGAGAA
         TCCTCCAATTTCCCTAGTGAGAGCAAGAACCATATCTGTCTATACTGCCCAACTCAGTTG
         TTTTTGCAATAATAGACAATAACTCTTTAAAGAATGAATAAGTGGTGGTGAAATGAAACA
         GAGTAAGTTCCTGATGTAGAAGGCAGAAGGGAGACTGTTGCTTAGGCAGACCAAGTAGAA
         [G,A]
         CTATACGATATTTTCTATAGTAATAACCTTAGAAATGGCAATTCGGTTCTATAGTTCAAT
         TAATATCACTAAAAGAGCTGTCCAATGAACTTACAAGTTATGTGGTATATGTGGGTTAAT
         CTGGGAGACCAACCACCATTTATGAAATTCTTCTCTATGAAAATGCTTTATGAAGGGCAA
         ATAGCAAGTTTACAAATGAATTTTTGGAAAACAAACTGTAAATTGAGGTTAACTTCTAAG
         GCTGTTAATTTGTGGGTATCTTTGTCTATATCTTCTTCTCACTGATATATCCTCAGGTAG

165461   CTTTAATTTCTTATTCTAACTTAATTTTTGCCAACTTATAGAATTGCTGAAACTTAGAAT
         GTGTTTGAAGAGTAATTAGTAGAAATCAGTTTGTCAACAAGCATTTTTTGAGTACCCATT
         GTAACTGAAACCATATGTTAGACTCAAAAAACGAGAGCAGGATTTGGATTTGGTTTTCAT
         TTCTAAATTTCAGGACTTACTCTGTGTGTATGTGTGCATGTATGTATGTGTGCATGTGTG
         AGTGCCTCTGTGTGTGTATTGGGGATACAATTAGTATAAATCTGAAAATAATTG
         [A,T]
```

FIGURE 3BBBB

```
           TGAATTTAGCAGGTCACAATTTTTCTCTTTTAAAATTAGCATTTTGTTTCCTCCCAAAGA
           GAAAATAAATAACATTTTCAAATATGCTTTGAATTAATGTAATTAGGCAGACCATTGGCA
           AATTATAGAGTGTAAGACAGCTAAGGAACCCTTTAAATGTCATCTATGTTCTTAAGAATT
           GAGAACAAGATCCCGCCAAATGACTTTTATACCTGCAGAAATGACAAAAGATGCTCACAA
           ATTTATAGATAATGTGTTTATCATGGAACTTTTAGCTCCTTTTTCTATGTAGCAATTTTG

166267   CATGAATAATTGGAATTTAACTTTGCCTATCAAGGAAGATGTTTGCAGTTAAATTAGAAA
           AGGAGACAGATTCTTTAAGACAATAATAAGGTGTATTAACTATATTTCTCAAGACTCTCA
           GGCTTAGGGTAGCTAGCAACTCCAAGTAGATTTTACTAGTTGTTTGTTTTCAGATGACAG
           TGTAGCTATTTGTAATTTATTCTACAATCTTTGGAGTGTATTTACTTTTTGCTCTACAAA
           GATTTCAGGCCTAAAGTTGGGCAGACTCTGTGTTTGTGATCAATCTATCAGTTCATATTT
           [G,T]
           TCTCCAAGATCTCTCTGCAATTCAATTTATGTTCAGGGCAAGAATATCTCAAGGACTAAT
           GAGATCACTGGATCATTTAAACCATTATTTCCTGTTTTGAAATGTAAAATACTTTAGTA
           ATCTAATTTTTAAATAAGATAAACCAAAGTAAGTTTAAAATAACTTTTTTTCATTCAAAA
           TATTTGTTTGAAATGCTCAGTTTTTCCTGGAGGAAAAAAATTTTTTTGACTTTGCTGCCA
           CCTCATGGCTAAGGCAGTAATTAGAAATAGTTCTTCAGGCTCTTACAGAACTACAGTTGC

169684   AGGCTTGGAAAACAGATAAAAATAGATTGGGAATAGAATTCTGACCGTGTTACTAATGGG
           GTACAGTTTGAATATTCCTTATCCAAAGTGCTTGGGATCGGAAGTGTTTCAGAGTTCATT
           TTTTTTTCAAATTTTGAAATATTTGCAAACACATAATGAGATATGTTTGGGGTGGGGCCC
           AAGTCTAAATACAAAATTTATGTTTCATATATACCTTATACATATAACCTGAAGGTAATT
           TTATACACTATTCTTAATAATATATGTGACCTATCACATGATGTGAGGTGTGAATTTTCC
           [A,G]
           CTTGTGGCATCATGTGAGCGCTCAAAAGTTTCAGATTTTGGATCATTTCAGATTTCAGCT
           TTTCAAATTAGGGGCACCCCTTTGTTTTCTCTGTCAAACAGGGCTGGGGACTTCTATATA
           GGGCTCTTGTCAGGATGAAATTTTGAGAATCATCTCAGACAGCAGCCATGTTTGGAATCC
           TTCCCTGAGCCTCTGCTGTGACCAAGTATCTTTTTTATCATTTTCACTCAATAGCCTCTG
           CACATCAAAAATAACAGTTACAATACCATAATGATGTATTTTGTTTAGATGTCTGTCTCT

171916   AAATGTAAGAAAGCACACTTATTTGCAATAAATCTTATGAAGAAGGAATTTTGAGTATAT
           GGTGGAGAGAATGTGTGTCTATCTTAAAGCAAAGGACATTTTTCATTCTCTTTGTAGAAC
           GTAAGTTAAGAATTCTCACAACTTTATGTATTTTATTAAATGATACATTTTAAAAAATCA
           ACTAAAAAACCTGTTTAGGAAGAAAGTAAGCCATATAATTATTATTTACCTTTCAAAAA
           GATTTTTTTAGCCTTTATAATTAGGCAGAAATTCTAGTGTGTTCACTGAAAAATTATCCT
           [T,C]
           TGTAAGGGCCATCAGTTAAATGGATTCAGGCAGCATTTTTTTCTTATTGTAAGTGGAATC
           ATATTAAAACAAAGTGTGGAAGTGAAATGTGTGCTGAGATTGATATTACCTTCCTGGCCA
           TTCTGAATCTTTGCCCTTTCAACCTTATAAATCACATGACACTTGCTCTTACTCCTTGTT
           CTTCATGAGCCCTTGACATTCACAGCCTTTGTAAAGCTCCACATTGACAAATACACTAAT
           TTCCCCCTTCACATATACTGTGGAATAACAAAAATGTAGTAAAGCATTCTTTAAGTGGTC

173389   TCCTGCTGATAAAAATGTTTTTATTGGCCAGGCACAGTGGCTCACGCCTGTAATCCCAGC
           ACTTTGGGAGGCCGAGACAGGTGGATCACGAGGTCAGGAGTTAGAGACCAGCCTGGCCAA
           CATGGTGAAACCCCATCTCTACTAAAAACACAAAGATTAGCTGGGCGTAGTGGCGGGCAC
           CTGTAATCCCAGCTACTCAGGAGGCTGAGGCAGGAGAATCGTCTGAACCTGGAAGGCAGA
           GGTTGCAGTGAGATGAGATCATGCCATTGCACCCTGGCCTGGGCGACAGGGTGAGACTCC
           [G,A]
           TCTCAAAAAAAAAAAAATGTTTTTATCATTTCATGAGTGTCACTATGTACACAATAAAGCT
           GTGTTGCACTGCATAGGTGACTTACTACTCCCGAAGAATGGGGGAGCTCAAAATCAGTAA
           ACCTCGAACTCATTGCATCCTATGATCCTTTGGATGGCTCCAGAGTGAAAGAAGAGGCAA
           ATACAAAATTTGAGAATGTGAAGTATCATGTATATTATACATAAATGTACATATAAATC
           CATACTCTCTCTAGCATTTGTTTGTTTGTTTCTCCCTTAGAGAAGTGGATTAGGCATAAG

173435   CCTGTAATCCCAGCACTTTGGGAGGCCGAGACAGGTGGATCACGAGGTCAGGAGTTAGAG
           ACCAGCCTGGCCAACATGGTGAAACCCCATCTCTACTAAAAACACAAAGATTAGCTGGGC
           GTAGTGGCGGGCACCTGTAATCCCAGCTACTCAGGAGGCTGAGGCAGGAGAATCGTCTGA
           ACCTGGAAGGCAGAGGTTGCAGTGAGATGAGATCATGCCATTGCACCCTGGCCTGGGCGA
           CAGGGTGAGACTCCGTCTCAAAAAAAAAAAATGTTTTTATCATTTCATGAGTGTCACTAT
           [G,T]
           TACACAATAAAGCTGTGTTGCACTGCATAGGTGACTTACTACTCCCGAAGAATGGGGGAG
           CTCAAAATCAGTAAACCTCGAACTCATTGCATCCTATGATCCTTTGGATGGCTCCAGAGT
```

FIGURE 3CCCC

```
           GAAAGAAGAGGCAAATACAAAAATTTGAGAATGTGAAGTATCATGTATATTATACATAAA
           TGTACATATAAATCCATACTCTCTCTAGCATTTGTTTGTTTGTTTCTCCCTTAGAGAAGT
           GGATTAGGCATAAGTTAACTGAATCCTTTTGAAAAGCATTAAAAATATCTACTTGGGTTT

174462     ATCACCTGTTGCTATGCTCCCTTTTCCTCCCATATGTCCATTTCCTGTGATTCATGGATG
           AATGTGAGAATAAAAGCTCTAGCTCTGTCTTTATTTGAGAAAAAAATCTACAGAAATATG
           TTAGAAGGTGTAGAGTTCTCTGTCTGACAAAGGGATACTTCTCTTTGGCTGGCATGCCTA
           TCAGCTAATAATTTTGTTACAAAGTCCAAGTTTTTAAAGACATTTTAAATGAAAGGCAAG
           AAGGATACTGGTTAGTTAGGGGAAGAGCAAGAACTGCTTTATTTATTTCCTTTGGTTTAC
           [G,A]
           TTAAATCAAGATGCTGCCATTGTTGTACAGCATAATTAGGGGAAATTATATTTTTGTTTT
           TGTTATATATTTATATATTACAAAACTAGCTTTATAAATTTAGAAAAGAAATTATTTCCT
           CTGAAAGAATTATTTTGCCTACTTCCTGCAATTCAGAATCCCACTGTTTACATTTGTATC
           ATATTTTAAAACATTCAATAAGAGCTATTGGAAATCACTATCGCGACAAAGATCTCCCT
           CATATTATTGAGATGTAGTGAATGTGGACTCTGAGAAAGTCCAGGTGTGCTAAAAAGTAC

176313     TGCCTTCTACTATCATCATCATCGTTTTTCAGATAGGGAAAAAGAGGCACAAGAGCTTAA
           GTGATTTATTGGTTGAGCTAGCATTTCATTCCAGGCAGTCTGACTCCAGAACTTATATTC
           TTAACCACTTTATTATACTGCCTCTCATAAAGCAGTCACTAAAAATTAAAAATAAAAGGT
           GGAACATAAAATAGGCCATCCCTTTGGCTGCTTCTGAGGCTCTACACTTCGATTCCTGCA
           GGGTATGGAGGGAGTGCTCTTCCCCATCTTTGATTTCCCTCCTCAGAGAGCACCCTGTCT
           [-,T,G]
           CAAGAGGGCAGTTTTCACACACCCCATTGCACCTATTTTTCCTCCTTTACATTTCCTACC
           TGGTCCTAGGAGGCACTTAGTTTGCAACACCTGGAGATCAGTGACAGTGGAGTAGCATAA
           CAGAGGAAATAGAAAACAAAAAACCGTGATTTCTAAGGAGGGGCTTAATTTGTCTAGTGC
           TGAAACTGAAGCAAATTAGAACAAGATAGCACTATATTAAGGAGAAAATGACTATACAGG
           GGAGCTTAGGCTCCATGATATTATTTTTCTAATAGAAGTCACCCAATGAGACAAACGAG

177082     TGGGTACCATCTGGACCTATTAATGGTGGCTGTCATGCTCGGTGTATGCTCCATCATGGG
           CCTGCCATGGTTTGTGGCTGCCACAGTCCTCTCCATCACTCATGTCAATAGCCTAAAACT
           GGAATCAGAATGCTCAGCTCCAGGAGAACAACCCAAATTTCTCGGCATTCGGGAGCAAAG
           GGTTACTGGGCTTATGATTTTTATTCTTATGGGTTCATCAGTCTTTATGACCAGTATTCT
           GAAGGTAACAAAATCTGTCTTTATGAACTTGAGAGAAAGAATACATTTATCATCATTTAA
           [G,A]
           ATTTTCATTTGAATCTGAGCCATAAATTTGCAAATATTGTGTGGCATGTGATGAAAGTGA
           TGAATTTCTGAACCATGTTTATATAATTCTTCATAACCTAAGGGAGGGAAATTACGTCCT
           ATATTTTAAAACCCTTAAATACATAAAAATTTAGTCTGGCAAAGTAAAATTTGATGAGTA
           AATTATTGTAACAATTTTGAATCGGTGATCAAGCTATGGGAAAAGTCACTCATTGTTTC
           TGACTGACTTGTGACCCGAATCCATTACAGGCATTCATAAAGATTCTATTTTCTTGTCAG

177358     AAGAATACATTTATCATCATTTAAGATTTTCATTTGAATCTGAGCCATAAATTTGCAAAT
           ATTGTGTGGCATGTGATGAAAGTGATGAATTTCTGAACCATGTTTATATAATTCTTCATA
           ACCTAAGGGAGGGAAATTACGTCCTATATTTTAAAACCCTTAAATACATAAAAATTTAGT
           CTGGCAAAGTAAAATTTGATGAGTAAATTATTGTAACAATTTTGAATCGGTGATCAAGCT
           ATGGGAAAAGTCACTCATTGTTTCTGACTGACTTGTGACCCGAATCCATTACAGGCATT
           [C,A]
           ATAAAGATTCTATTTTCTTGTCAGTGGATAAATATATTAGCAGTTAATATTACTTACTAT
           TAATAAGAGATAGAGGTGAAGGGATGAGCCTGGTTATAGTCACATACGCAGTTTTCCATT
           TTAAGTGCTCTGTAAAACCACTGTCTGGACATCATCATTGCATATAGTGATTTTTTTTC
           ACACAAAACTTGAAATCTATTTTAAGAGGATTAACTAGTAATTATTTTGTCATGTAATT
           TTGTCAGATATTTCCAAGGTGTGTCAATTGCGCTATAAATTACAACACATTTTATTTGCC

178098     TTCCAATAAAAGAGAAATCTGAATTATCCATATATTTACAAATACCTGGTATAATACA
           GGAAACACATCTAAATGTTAGCTTCATTTTTAATCCACCTTTAATCCAAATATCTTATCT
           TTGTAAAGCAAAATTCAAGTTGTCTCCAAAGTAGCATAATAATAATATTATTGTTCATTA
           TATACTACATGGTTTTTAAAAATAGATTTTGACCTATTAAATAATTATAACAACCCTATT
           GTTATCATCTCCTTTTAGATATTGGGAAACTAAGGCACAGAGAGCTTAAGTAACTTACCT
           [A,G]
           AGGTTACACAGCTAAAAATGCTAGAGCTGGAACTTGAATCCTTGTCTTCTGAATCTGTAC
           TATACTGTTTCTATTCAAAAATGCCTTTTTTCCCTGTTTTTTTCTTTGATAAATGCAAAA
           CCACAATCTATTTGAAAATGATTTCTGCCTTTTCTCCAATTGTTCTTTTACAGTTTATTC
           CCATGCCAGTGCTATATGGAGTGTTTCTTTATATGGGTGCTTCATCTCTAAAGGGAATTC
```

FIGURE 3DDDD

```
         AGGTAAATTACTTACAGTACTACAGGCACATCTGTGATGACTGACCTTAAGGTCTACTGA
178537   TGATTTCTGCCTTTTCTCCAATTGTTCTTTTACAGTTTATTCCCATGCCAGTGCTATATG
         GAGTGTTTCTTTATATGGGTGCTTCATCTCTAAAGGGAATTCAGGTAAATTACTTACAGT
         ACTACAGGCACATCTGTGATGACTGACCTTAAGGTCTACTGATAAGTCATGTGACAGCTG
         AGAAAATGCCACCACCTGAGGAACAGCTTTTAGACCACAATTAAATTTCTTCAAACTTGT
         CAGAGTTACAAAAGTTAAAGAAGATTCTCTCCAGCATCTAAGGTTCATAATCTTATGGTA
         [A,C]
         TTTTCTTTATCATAAGTATATTAAAACTGTAAGAGGCTTAGATTTTACAGCATTTTTAGA
         AAAATCATAGTAGTATATTTCAATATATATCCAAATATTTATAATATTTGACACTTTAAT
         CATGTGTATGGACATCTATTGGTAAGAATAGGAAAAGTCTTTATGCACGAAGATGTTCAT
         TGTAACACATACTATTAAAATATTGGAAACAACCCAATTCTCTAACTGCAGTCAAATAAT
         TAGGTAACCTATGGTATATTCACTGAAAATTGATAATTATAGGAACCACAAAACTAACAT

181240   ATAGTTAACCTGCAGGACAGGCAGCACGGGATCTCTGTTCCTGAGCAAATGACTAACCAG
         CTTCTGACTTTGGGAGAAAAAGCAGAACTTAGGCCTTAAGACAATACTGGCTGCCAGTCT
         GGGGGAAACTTAAGTATGAAGTCATTGCAGGTCACGGAACACCCAAAGTTGATAGTATGA
         CTGACTCTTCATCCTGACACTGGGAAAAATGAACTGGGAGAGGGAGATGGTTGAGCCATG
         TTATATGTTTTAATTTTACTCAAATTAGATTTAATTTGCTCATTTAAAATTTCATGTATG
         [-,A]
         AAAGTGTAGTTTGATAGAATTTGTTTAGTAAGCCATTAGGGAAGAATATGGAAGAGGTTT
         TGTTTATTTGTTTTTCTTTTTCCCTTTTTTTTTTTTGCCTTTGGCAAAAGTTCCATGA
         GTACTAATTTCATCTGTAAGTGAAAAGCATTTATTATTAGGCCCCAGGCTCACATAAATA
         CAGCAGCAGAGTTTAAGAAACAATGTAAAATCATTTTGATGATAGGTTTCAACAGATTTT
         CTCCTCTAATTCCACATGATTTTATACTCATGAGATTTAGAATTGAACAAGAACGTCAAG

181325   AACTTAGGCCTTAAGACAATACTGGCTGCCAGTCTGGGGGAAACTTAAGTATGAAGTCAT
         TGCAGGTCACGGAACACCCAAAGTTGATAGTATGACTGACTCTTCATCCTGACACTGGGA
         AAAATGAACTGGGAGAGGGAGATGGTTGAGCCATGTTATATGTTTTAATTTTACTCAAAT
         TAGATTTAATTTGCTCATTTAAAATTTCATGTATGAAAAGTGTAGTTTGATAGAATTTGT
         TTAGTAAGCCATTAGGGAAGAATATGGAAGAGGTTTTGTTTATTTGTTTTTCTTTTTCCC
         [-,T]
         TTTTTTTTTTTTGCCTTTGGCAAAAGTTCCATGAGTACTAATTTCATCTGTAAGTGAAA
         AGCATTTATTATTAGGCCCCAGGCTCACATAAATACAGCAGCAGAGTTTAAGAAACAATG
         TAAAATCATTTTGATGATAGGTTTCAACAGATTTTCTCCTCTAATTCCACATGATTTTAT
         ACTCATGAGATTTAGAATTGAACAAGAACGTCAAGTTTTGGAATTATTTGGGGTGTGAAT
         CTTTTAAATGAAAATTGAAGAAAACGTTATCAAAAGCCCATGAGTTAAATATAATGAGTT

181730   AGTTTAAGAAACAATGTAAAATCATTTTGATGATAGGTTTCAACAGATTTTCTCCTCTAA
         TTCCACATGATTTTATACTCATGAGATTTAGAATTGAACAAGAACGTCAAGTTTTGGAAT
         TATTTGGGGTGTGAATCTTTTAAATGAAAATTGAAGAAACGTTATCAAAAGCCCATGAG
         TTAAATATAATGAGTTTTAAAGAACACAAATGAAACATCAATCTGGGGCACATGTTGATG
         AACAGGGTCTCACACTGAGAAACAGTGTTCGTGAAATTTAAGTGAGCCCCAAGAGCAGG
         [C,G]
         AGCTGAAATTCCTATTTGGAATTGTAGCTAACTGGGTGGGGAAATGTGATATTGATACTA
         GGATATAATAAAAACCAAATGTAAAACTCAGAATACATTTATCATGATGATGATTATTAT
         TTAAACATATGCTAAATATAATCAGTTCCAGCAGCATGTTACTGTCTTACCCTATTGAAG
         GAATCTATGTTACCTGCTTGTTTGGCAATATTAAGAAACTTATTATCTGGGCTTCTCACT
         GTGAAACATGGCAGAAAAAACAGATCACAGTGTTCTCATGAATGCTGTTTCTGCATTCAG

185615   GAGAACAAAAGAAGAGACATTATTACTGTTGGTATTTTCCTAGGGAACAGAGTTTTAAT
         CAAAATATTCTAATGAATAATTATTTATTCTTGAAATAGGTGAAATGTTTAGTAGGAAAA
         ATGTTGATCTGATTTGCTTTCAAAGTGATTTAAGATTGAGTAGATGTTGCAGAAACTTCT
         GGAATTTATTTTTACAGGCTACTTATTTATTTTATTCTATTTTATATGGTATAACAATGT
         ATTATAAGTTTCGTGGCATATTTAAAGTTTATATGTAAGCCTGAGTCTATTTTGAAAGCA
         [C,T]
         TTAATCAACATTTTTTTAAGTATATAAAAACTACAAAGAGTGTAAATGAGGGAAAAATAA
         CTAGCGTAACATTTAGCAGGATGATTGAGCCCATACAATGTAAAACACAACAAAGTTTTC
         ACATAAATAGAAATGAGATTGAAATAAAATATTTGATGAGAATTATACTATTTTTCTCTA
         TAAGTAGTCAGTAAATGTATTCAACTTTCTATTTCCTCAAACCATAGATATATTTCCTAT
         TTCCTTTGGGGAATTCATTTGCAGATGTTTCAGAGGTCTTAGTCATTTAATGAGGTCAGA
```

FIGURE 3EEEE

185975 ACTAGCGTAACATTTAGCAGGATGATTGAGCCCATACAATGTAAAACACAACAAAGTTTT
CACATAAATAGAAATGAGATTGAAATAAAATATTTGATGAGAATTATACTATTTTTCTCT
ATAAGTAGTCAGTAAATGTATTCAACTTTCTATTTCCTCAAACCATAGATATATTTCCTA
TTTCCTTTGGGGAATTCATTTGCAGATGTTTCAGAGGTCTTAGTCATTTAATGAGGTCAG
ATCAGGCCATAAATCAAATGAGGTTTTTTCTTTCTCAGAAATTTATACCAATATGGTTAC
[A,G]
TAATGTGTAATTGGTAATTCCCTTACTCTACATGGTGTTCTATCACTAACAATGGATTCC
CACAGATAGAGATTCATCATGATGATGTGTCTTAATCCTGTAAGAATGTTTCAATTTTTC
CAAATATTGTAGAAGGCAATACTTAGACTCATACTTCTAGTAATATTAATGTTAACACAA
AAAATGATATTATACAATTGTTATTATTTATTTTTCTGTTTGATATATTTTTATTTAAAT
ATTAGTGCTTTTTTAAAAAATAATACTTTGAGTCAGGCGCAGTGGCTCATGCCTGTAATG

188447 TATACCCACTGTACTTTAATGGGCATTTACTGTTCTCTGATTATGAAGATAAAGATTTTA
AAAGTAACTAAATAGCACTAAATTTCCTAGAACTCATGCTTTCTGAAAAGATACAAAAAT
GGATTAAAGATTTCCTGGGGCAATTTTACTGCTAAATCCTTCATATCCAAGTTAGAGGGA
AAAGCCTTGCAGTACATTAACTAGGCAGGTTTATAGATCCTTAAAATCTCAGATGGGTTA
ATATGATGATACTTTCATGTGATCCTCAGTACATGGAAAGAAACAAGAAAATCAATAATA
[T,C]
AGTCAAGAAATAATCTATAATTGAACAATAAAATATAGCTCTGACTAGTGCAAAGACAGC
TAATTCTCCATCGAACAGGAAAGAAAATAGGAAGTTTAAAGAGGTTCGCTTTCTAGCTTA
GAATTAGTATTAAAAGAGTATGGTCACTAAAGACATTAGGAAGATTTAGGAATAATTATA
CTAAAAGTTAAATTCCTGGTTGATTTGTTTGCCCGGATCTTGGTATTCTATTTTCTTGAG
GCTTACAGACTCAGTAGAAGGATGTGATCTTACTGTGGCATCTTATACTAAGGCCCAGTC

190645 GAATTCTCCCCTCTCTCTCTTCTCTGTCTCCCTCTCAATATAGTTTAGTTTAAACGGT
TATCTTGTACAATTCTAAGTATCAATTAGTGCCCAATTTTATAGTCTCAAAGTCTTTATG
AATAATTTAAGGTTATGCCAATAAAAATACAGAGAATACTTTTTTATGAGAAGGGAATTT
GTCATAGTGTTAAAAACCAAAATAGGAGAGAATTTTCTAGATCTTTAGGGTCTGACTCTA
AGATTATATTCCCTAGAATTTAAGAAAATGTGATTACCTCCCTCTTAAGAGGGGCACAA
[G,C]
TATAAGATGTTTTATCTTTTTTTTCTTTTTTACAACATTTAAATTTTAAAATCCTGTTGA
TTTTTTAGCTGAACCAGCATATTCCAAGTGTATTAGGTAGAAACCTAGTCTTGTGTGAT
ACCACTCTCGAAAGGGCTGTGTGGTTAAATAAGTTTGAAAAAATGTGCCAAACTGCATTC
CAGTTTGGAGATTCACAATGCATATTAGCAAATGAAACAATCTAAGTAGTACTGCATTTT
AAAAAATTGTATAGCTTCGTTCAATCAAGTATTTAAAAAAATCTTTTGCTCAGAAGACTC

190708 CTTGTACAATTCTAAGTATCAATTAGTGCCCAATTTTATAGTCTCAAAGTCTTTATGAAT
AATTTAAGGTTATGCCAATAAAAATACAGAGAATACTTTTTTATGAGAAGGGAATTTGTC
ATAGTGTTAAAAACCAAAATAGGAGAGAATTTTCTAGATCTTTAGGGTCTGACTCTAAGA
TTATATTCCCTAGAATTTAAGAAAATGTGATTACCTCCCTCTTAAGAGGGGCACAAGTA
TAAGATGTTTTATCTTTTTTTCTTTTTACAACATTTAAATTTTAAAATCCTGTTGATT
[T,G]
TTTAGCTGAACCAGCATATTCCAAGTGTATTAGGTAGAAACCTAGTCTTGTGTGATACC
ACTCTCGAAAGGGCTGTGTGGTTAAATAAGTTTGAAAAAATGTGCCAAACTGCATTCCAG
TTTGGAGATTCACAATGCATATTAGCAAATGAAACAATCTAAGTAGTACTGCATTTTAAA
AAATTGTATAGCTTCGTTCAATCAAGTATTTAAAAAAATCTTTTGCTCAGAAGACTCTTC
CTCACATAATATCATGAAAAATGTCTATTCCACATGATGCTTTTTTAAGAAAGTAGTCA

191287 GCTTTTTTTAAGAAAGTAGTCAATCTGGTGCTTTGAATTACCAGGAAACTATCTTTCTAG
GAAGACCAAAACAGCTGGAGGGTTTAGAGGAACTGAAGAACACATTTCCAGATTGGGCAA
GAGAGGGAGACCCAAGGTTTTGTTCCTCTTAAAAGTTGCATTTGTTCCTCTCCTGTGACC
TATCACCAATCAGGGTCATATGAAAAGGCGGCATTTGAACAAAGAAGGGGCAAGGTTGCT
CCATGTGAAGGGACATGATAAGCAGAGGGAAGAGCAAGGACAAGGCCCCCAGGCAGCACC
[A,T]
TGCCCATTGTGTTCCAGAACAGTCAGGAGGCTACTGAAATGGGGCTGGAAAGGAGTGAGC
AGGGATGCAGTGGCAGGAGGTGAAATCAGAGTGAGGTGGGGACAGAGCCTTTAGGCCATT
ATAAGGACTTGGCATTGACTCTGAGTGACTGGGAGCCACTGCAAGGTCTGAGCAAAGGAG
GGAAGTGATCTGGTTGCTATGATGTTAGGGGCAAGCGTTTAAGCAATGGACATGCGGAAC
CCATTCTCTGTAATTTGAAATGAATTAAGAATACCACAGGCCAACTCAGTATCTATTCAA

194488 TGGAATGAAAGTTTATCCAGCTTTCCTTACCTTTTGATGTGATCGCATTTGTGGTTTTCC
ATGTGAGAAACATCTTTTGGTTGGTAGTTAATCTCTTTTATCCTCATTACAGTAGAAACT

FIGURE 3FFFF

```
        CTGGCAGAAAGTGTATGACTTACAGAATTCTAAAACTACTGATACTAATAAGGCTCCCAA
        AGCCACTTCCTTTTTGTGGTATCTGTTAAAGGCTTTAAAGCATCATGACCAGGAACTGTG
        AAAATTTAGTACGTGGTAGAGTATCCATTGGCAAAAAGAGACCCAAAGAGCAGGTTACTA
        [G,A]
        GGTCTGAGTCCTGAGCTGGCACCCATGCAGCCTTTGACACCCCCCATTCTGAGTTATTTT
        CCATCCTGTGCTGTAATGTGTCAGAGAAGCCTAGAAACCCTTTTTTCATGGAATTTTGAA
        TAGAAATTATATTTTCTCAATTATATCATTCACTTTTTGTTGTCAAAAATATTTTATCTC
        GTTTAACTGACAGTAGAATCTAAGAACTAACGGCAAATTCTGTCTTATCTGGAGGATGTC
        TAATTTTGATCCTGATGTCATACATGCATGTGACAAGAGCCTCTGCAGCTTATTAAATGG

201885  TAACGTTAATGAACAAGCTTAGGTTAAAAGATTAAGGGTCATGTAATATCAATGACACTG
        AAGGCCCCTGCCTTTAGTGAGCACATAGACACATTCCAAGTTTAATTGTAGCTCTTTGTA
        ACTCCTTATAAAGTAGAGGCGCTAACAAAGGACAGGGCATTCCTCCTTTTGCTTTCAGA
        GGATATCCCACACTGTAACGAAACGGTTTCTGAAAAACTTACTTCTTCCACTATGCTCTG
        TGGCTTTCCTTGAATTCTCTCCTTTGCAAGATCCAAGGACCCATTTTTGGGGTCTGGATC
        [A,G]
        GGACCCCTTTTCCAGCAACACCGGAACTACAAAGATTCTCAAACCTATGTCGGTATTGAA
        ATAAAGATGAAATTTAAAAGTAAAGCTATATGGCATAACTAGAGCCTGGCATATTT
```

FIGURE 3GGGG

ISOLATED HUMAN TRANSPORTER PROTEINS, NUCLEIC ACID MOLECULES ENCODING HUMAN TRANSPORTER PROTEINS AND USES THEREOF

FIELD OF THE INVENTION

The present invention is in the field of transporter proteins that are related to the sodium bicarbonate cotransporter subfamily, recombinant DNA molecules, and protein production. The present invention specifically provides novel peptides and proteins that effect ligand transport and nucleic acid molecules encoding such peptide and protein molecules, all of which are useful in the development of human therapeutics and diagnostic compositions and methods.

BACKGROUND OF THE INVENTION

Transporters

Transporter proteins regulate many different functions of a cell, including cell proliferation, differentiation, and signaling processes, by regulating the flow of molecules such as ions and macromolecules, into and out of cells. Transporters are found in the plasma membranes of virtually every cell in eukaryotic organisms. Transporters mediate a variety of cellular functions including regulation of membrane potentials and absorption and secretion of molecules and ion across cell membranes. When present in intracellular membranes of the Golgi apparatus and endocytic vesicles, transporters, such as chloride channels, also regulate organelle pH. For a review, see Greger, R. (1988) Annu. Rev. Physiol. 50:111–122.

Transporters are generally classified by structure and the type of mode of action. In addition, transporters are sometimes classified by the molecule type that is transported, for example, sugar transporters, chlorine channels, potassium channels, etc. There may be many classes of channels for transporting a single type of molecule (a detailed review of channel types can be found at Alexander, S. P. H. and J. A. Peters: Receptor and transporter nomenclature supplement. Trends Pharmacol. Sci., Elsevier, pp. 65–68 (1997) and http://www-biology.ucsd.edu/~msaier/transport/titlepage2.html.

The following general classification scheme is known in the art and is followed in the present discoveries.

Channel-type transporters. Transmembrane channel proteins of this class are ubiquitously found in the membranes of all types of organisms from bacteria to higher eukaryotes. Transport systems of this type catalyze facilitated diffusion (by an energy-independent process) by passage through a transmembrane aqueous pore or channel without evidence for a carrier-mediated mechanism. These channel proteins usually consist largely of a-helical spanners, although b-strands may also be present and may even comprise the channel. However, outer membrane porin-type channel proteins are excluded from this class and are instead included in class 9.

Carrier-type transporters. Transport systems are included in this class if they utilize a carrier-mediated process to catalyze uniport (a single species is transported by facilitated diffusion), antiport (two or more species are transported in opposite directions in a tightly coupled process, not coupled to a direct form of energy other than chemiosmotic energy) and/or symport (two or more species are transported together in the same direction in a tightly coupled process, not coupled to a direct form of energy other than chemiosmotic energy).

Pyrophosphate bond hydrolysis-driven active transporters. Transport systems are included in this class if they hydrolyze pyrophosphate or the terminal pyrophosphate bond in ATP or another nucleoside triphosphate to drive the active uptake and/or extrusion of a solute or solutes. The transport protein may or may not be transiently phosphorylated, but the substrate is not phosphorylated.

PEP-dependent, phosphoryl transfer-driven group translocators. Transport systems of the bacterial phosphoenolpyruvate:sugar phosphotransferase system are included in this class. The product of the reaction, derived from extracellular sugar, is a cytoplasmic sugar-phosphate.

Decarboxylation-driven active transporters. Transport systems that drive solute (e.g., ion) uptake or extrusion by decarboxylation of a cytoplasmic substrate are included in this class.

Oxidoreduction-driven active transporters. Transport systems that drive transport of a solute (e.g., an ion) energized by the flow of electrons from a reduced substrate to an oxidized substrate are included in this class.

Light-driven active transporters. Transport systems that utilize light energy to drive transport of a solute (e.g., an ion) are included in this class.

Mechanically-driven active transporters. Transport systems are included in this class if they drive movement of a cell or organelle by allowing the flow of ions (or other solutes) through the membrane down their electrochemical gradients.

Outer-membrane porins (of b-structure). These proteins form transmembrane pores or channels that usually allow the energy independent passage of solutes across a membrane. The transmembrane portions of these proteins consist exclusively of b-strands that form a b-barrel. These porin-type proteins are found in the outer membranes of Gram-negative bacteria, mitochondria and eukaryotic plastids.

Methyltransferase-driven active transporters. A single characterized protein currently falls into this category, the Na+-transporting methyltetrahydromethanopterin:coenzyme M methyltransferase.

Non-ribosome-synthesized channel-forming peptides or peptide-like molecules. These molecules, usually chains of L- and D-amino acids as well as other small molecular building blocks such as lactate, form oligomeric transmembrane ion channels. Voltage may induce channel formation by promoting assembly of the transmembrane channel. These peptides are often made by bacteria and fungi as agents of biological warfare.

Non-Proteinaceous Transport Complexes. Ion conducting substances in biological membranes that do not consist of or are not derived from proteins or peptides fall into this category.

Functionally characterized transporters for which sequence data are lacking. Transporters of particular physiological significance will be included in this category even though a family assignment cannot be made.

Putative transporters in which no family member is an established transporter. Putative transport protein families are grouped under this number and will either be classified elsewhere when the transport function of a member becomes established, or will be eliminated from the TC classification system if the proposed transport function is disproven. These families include a member or members for which a transport function has been suggested, but evidence for such a function is not yet compelling.

Auxiliary transport proteins. Proteins that in some way facilitate transport across one or more biological membranes but do not themselves participate directly in transport are included in this class. These proteins always function in conjunction with one or more transport proteins. They may provide a function connected with energy coupling to transport, play a structural role in complex formation or serve a regulatory function.

Transporters of unknown classification. Transport protein families of unknown classification are grouped under this number and will be classified elsewhere when the transport process and energy coupling mechanism are characterized. These families include at least one member for which a transport function has been established, but either the mode of transport or the energy coupling mechanism is not known.

Ion Channels

An important type of transporter is the ion channel. Ion channels regulate many different cell proliferation, differentiation, and signaling processes by regulating the flow of ions into and out of cells. Ion channels are found in the plasma membranes of virtually every cell in eukaryotic organisms. Ion channels mediate a variety of cellular functions including regulation of membrane potentials and absorption and secretion of ion across epithelial membranes. When present in intracellular membranes of the Golgi apparatus and endocytic vesicles, ion channels, such as chloride channels, also regulate organelle pH. For a review, see Greger, R. (1988) Annu. Rev. Physiol. 50:111–122.

Ion channels are generally classified by structure and the type of mode of action. For example, extracellular ligand gated channels (ELGs) are comprised of five polypeptide subunits, with each subunit having 4 membrane spanning domains, and are activated by the binding of an extracellular ligand to the channel. In addition, channels are sometimes classified by the ion type that is transported, for example, chlorine channels, potassium channels, etc. There may be many classes of channels for transporting a single type of ion (a detailed review of channel types can be found at Alexander, S. P. H. and J. A. Peters (1997). Receptor and ion channel nomenclature supplement. Trends Pharmacol. Sci., Elsevier, pp. 65–68 and http://www-biology.ucsd.edu/~msaier/transport/toc.html.

There are many types of ion channels based on structure. For example, many ion channels fall within one of the following groups: extracellular ligand-gated channels (ELG), intracellular ligand-gated channels (ILG), inward rectifying channels (INR), intercellular (gap junction) channels, and voltage gated channels (VIC). There are additionally recognized other channel families based on ion-type transported, cellular location and drug sensitivity. Detailed information on each of these, their activity, ligand type, ion type, disease association, drugability, and other information pertinent to the present invention, is well known in the art.

Extracellular ligand-gated channels, ELGs, are generally comprised of five polypeptide subunits, Unwin, N. (1993), Cell 72: 31–41; Unwin, N. (1995), Nature 373: 37–43; Hucho, F., et al., (1996) J. Neurochem. 66: 1781–1792; Hucho, F., et al., (1996) Eur. J. Biochem. 239: 539–557; Alexander, S. P. H. and J. A. Peters (1997), Trends Pharmacol. Sci., Elsevier, pp. 4–6; 36–40; 42–44; and Xue, H. (1998) J. Mol. Evol. 47: 323–333. Each subunit has 4 membrane spanning regions: this serves as a means of identifying other members of the ELG family of proteins. ELG bind a ligand and in response modulate the flow of ions. Examples of ELG include most members of the neurotransmitter-receptor family of proteins, e.g., GABAI receptors. Other members of this family of ion channels include glycine receptors, ryandyne receptors, and ligand gated calcium channels.

The Voltage-gated Ion Channel (VIC) Superfamily

Proteins of the VIC family are ion-selective channel proteins found in a wide range of bacteria, archaea and eukaryotes Hille, B. (1992), Chapter 9: Structure of channel proteins; Chapter 20: Evolution and diversity. In: Ionic Channels of Excitable Membranes, 2nd Ed., Sinaur Assoc. Inc., Pubs., Sunderland, Mass.; Sigworth, F. J. (1993), Quart. Rev. Biophys. 27: 1–40; Salkoff, L. and T. Jegla (1995), Neuron 15: 489–492; Alexander, S. P. H. et al., (1997), Trends Pharmacol. Sci., Elsevier, pp. 76–84; Jan, L. Y. et al., (1997), Annu. Rev. Neurosci. 20: 91–123; Doyle, D. A, et al., (1998) Science 280: 69–77; Terlau, H. and W. Stühmer (1998), Naturwissenschaften 85: 437–444. They are often homo- or heterooligomeric structures with several dissimilar subunits (e.g., a1-a2-d-b $Ca^{2+}$ channels, $ab_1b_2$ $Na^+$ channels or $(a)_4$-b $K^+$ channels), but the channel and the primary receptor is usually associated with the a (or a1) subunit. Functionally characterized members are specific for $K^+$, $Na^+$ or $Ca^{2+}$. The $K^+$ channels usually consist of homotetrameric structures with each a-subunit possessing six transmembrane spanners (TMSs). The a1 and a subunits of the $Ca^{2+}$ and $Na^+$ channels, respectively, are about four times as large and possess 4 units, each with 6 TMSs separated by a hydrophilic loop, for a total of 24 TMSs. These large channel proteins form heterotetra-unit structures equivalent to the homotetrameric structures of most $K^+$ channels. All four units of the $Ca^{2+}$ and $Na^+$ channels are homologous to the single unit in the homotetrameric $K^+$ channels. Ion flux via the eukaryotic channels is generally controlled by the transmembrane electrical potential (hence the designation, voltage-sensitive) although some are controlled by ligand or receptor binding.

Several putative $K^+$-selective channel proteins of the VIC family have been identified in prokaryotes. The structure of one of them, the KcsA $K^+$ channel of *Streptomyces lividans*, has been solved to 3.2 Å resolution. The protein possesses four identical subunits, each with two transmembrane helices, arranged in the shape of an inverted teepee or cone. The cone cradles the "selectivity filter" P domain in its outer end. The narrow selectivity filter is only 12 Å long, whereas the remainder of the channel is wider and lined with hydrophobic residues. A large water-filled cavity and helix dipoles stabilize $K^+$ in the pore. The selectivity filter has two bound $K^+$ ions about 7.5 Å apart from each other. Ion conduction is proposed to result from a balance of electrostatic attractive and repulsive forces.

In eukaryotes, each VIC family channel type has several subtypes based on pharmacological and electrophysiological data. Thus, there are five types of $Ca^{2+}$ channels (L, N, P, Q and T). There are at least ten types of $K^+$ channels, each responding in different ways to different stimuli: voltage-sensitive [Ka, Kv, Kvr, Kvs and Ksr], $Ca^{2+}$-sensitive [$BK_{Ca}$, $IK_{Ca}$ and $SK_{Ca}$] and receptor-coupled [$K_M$ and $K_{ACh}$]. There are at least six types of $Na^+$ channels (I, II, III, $\mu$1, H1 and PN3). Tetrameric channels from both prokaryotic and eukaryotic organisms are known in which each a-subunit possesses 2 TMSs rather than 6, and these two TMSs are homologous to TMSs 5 and 6 of the six TMS unit found in the voltage-sensitive channel proteins. KcsA of *S. lividans* is an example of such a 2 TMS channel protein. These channels may include the $K_{Na}$ ($Na^+$-activated) and $K_{Vol}$ (cell volume-sensitive) $K^+$ channels, as well as distantly related channels such as the Tok1 $K^+$ channel of yeast, the TWIK-1 inward rectifier $K^+$ channel of the mouse and the TREK-1 $K^+$ channel of the mouse. Because of insufficient sequence similarity with proteins of the VIC family, inward rectifier $K^+$ IRK channels (ATP-regulated; G-protein-activated)

which possess a P domain and two flanking TMSs are placed in a distinct family. However, substantial sequence similarity in the P region suggests that they are homologous. The b, g and d subunits of VIC family members, when present, frequently play regulatory roles in channel activation/deactivation.

The Epithelial Na$^+$ Channel (ENaC) Family

The ENaC family consists of over twenty-four sequenced proteins (Canessa, C. M., et al., (1994), Nature 367: 463–467, Le, T. and M. H. Saier, Jr. (1996), Mol. Membr. Biol. 13: 149–157; Garty, H. and L. G. Palmer (1997), Physiol. Rev. 77: 359–396; Waldmann, R., et al., (1997), Nature 386: 173–177; Darboux, I., et al., (1998), J. Biol. Chem. 273: 9424–9429; Firsov, D., et al., (1998), EMBO J. 17: 344–352; Horisberger, J.-D. (1998). Curr. Opin. Struc. Biol. 10: 443–449). All are from animals with no recognizable homologues in other eukaryotes or bacteria. The vertebrate ENaC proteins from epithelial cells cluster tightly together on the phylogenetic tree: voltage-insensitive ENaC homologues are also found in the brain. Eleven sequenced C. elegans proteins, including the degenerins, are distantly related to the vertebrate proteins as well as to each other. At least some of these proteins form part of a mechanotransducing complex for touch sensitivity. The homologous Helix aspersa (FMRF-amide)-activated Na$^+$ channel is the first peptide neurotransmitter-gated ionotropic receptor to be sequenced.

Protein members of this family all exhibit the same apparent topology, each with N- and C-termini on the inside of the cell, two amphipathic transmembrane spanning segments, and a large extracellular loop. The extracellular domains contain numerous highly conserved cysteine residues. They are proposed to serve a receptor function.

Mammalian ENaC is important for the maintenance of Na$^+$ balance and the regulation of blood pressure. Three homologous ENaC subunits, alpha, beta, and gamma, have been shown to assemble to form the highly Na$^+$-selective channel. The stoichiometry of the three subunits is alpha$_2$, beta1, gamma1 in a heterotetrameric architecture.

The Glutamate-gated Ion Channel (GIC) Family of Neurotransmitter Receptors

Members of the GIC family are heteropentameric complexes in which each of the 5 subunits is of 800–1000 amino acyl residues in length (Nakanishi, N., et al, (1990), Neuron 5: 569–581; Unwin, N. (1993), Cell 72: 31–41; Alexander, S. P. H. and J. A. Peters (1997) Trends Pharmacol. Sci., Elsevier, pp. 36–40). These subunits may span the membrane three or five times as putative a-helices with the N-termini (the glutamate-binding domains) localized extracellularly and the C-termini localized cytoplasmically. They may be distantly related to the ligand-gated ion channels, and if so, they may possess substantial b-structure in their transmembrane regions. However, homology between these two families cannot be established on the basis of sequence comparisons alone. The subunits fall into six subfamilies: a, b, g, d, e and z.

The GIC channels are divided into three types: (1) a-amino-3-hydroxy-5-methyl-4-isoxazole propionate (AMPA)-, (2) kainate- and (3) N-methyl-D-aspartate (NMDA)-selective glutamate receptors. Subunits of the AMPA and kainate classes exhibit 35–40% identity with each other while subunits of the NMDA receptors exhibit 22–24% identity with the former subunits. They possess large N-terminal, extracellular glutamate-binding domains that are homologous to the periplasmic glutamine and glutamate receptors of ABC-type uptake permeases of Gram-negative bacteria. All known members of the GIC family are from animals. The different channel (receptor) types exhibit distinct ion selectivities and conductance properties. The NMDA-selective large conductance channels are highly permeable to monovalent cations and Ca$^{2+}$. The AMPA-and kainate-selective ion channels are permeable primarily to monovalent cations with only low permeability to Ca$^{2+}$.

The Chloride Channel (ClC) Family

The ClC family is a large family consisting of dozens of sequenced proteins derived from Gram-negative and Gram-positive bacteria, cyanobacteria, archaea, yeast, plants and animals (Steinmeyer, K., et al., (1991), Nature 354: 301–304; Uchida, S., et al., (1993), J. Biol. Chem. 268: 3821–3824; Huang, M. -E., et al., (1994), J. Mol. Biol. 242: 595–598; Kawasaki, M., et al, (1994), Neuron 12: 597–604; Fisher, W. E., et al., (1995), Genomics. 29:598–606; and Foskett, J. K. (1998), Annu. Rev. Physiol. 60: 689–717). These proteins are essentially ubiquitous, although they are not encoded within genomes of *Haemophilus influenzae*, *Mycoplasma genitalium*, and *Mycoplasma pneumoniae*. Sequenced proteins vary in size from 395 amino acyl residues (*M. jannaschii*) to 988 residues (man). Several organisms contain multiple ClC family paralogues. For example, Synechocystis has two paralogues, one of 451 residues in length and the other of 899 residues. *Arabidopsis thaliana* has at least four sequenced paralogues, (775–792 residues), humans also have at least five paralogues (820–988 residues), and *C. elegans* also has at least five (810–950 residues). There are nine known members in mammals, and mutations in three of the corresponding genes cause human diseases. *E. coli, Methanococcus jannaschii* and *Saccharomyces cerevisiae* only have one ClC family member each. With the exception of the larger *Synechocystis* paralogue, all bacterial proteins are small (395–492 residues) while all eukaryotic proteins are larger (687–988 residues). These proteins exhibit 10–12 putative transmembrane a-helical spanners (TMSs) and appear to be present in the membrane as homodimers. While one member of the family, Torpedo ClC-O, has been reported to have two channels, one per subunit, others are believed to have just one.

All functionally characterized members of the ClC family transport chloride, some in a voltage-regulated process. These channels serve a variety of physiological functions (cell volume regulation; membrane potential stabilization; signal transduction; transepithelial transport, etc.). Different homologues in humans exhibit differing anion selectivities, i.e., ClC4 and ClC5 share a NO$_3^-$>Cl$^-$>Br$^-$>I$^-$ conductance sequence, while ClC3 has an I$^-$>Cl$^-$ selectivity. The ClC4 and ClC5 channels and others exhibit outward rectifying currents with currents only at voltages more positive than +20 mV.

Animal Inward Rectifier K$^+$ Channel (IRK-C) Family

IRK channels possess the "minimal channel-forming structure" with only a P domain, characteristic of the channel proteins of the VIC family, and two flanking transmembrane spanners (Shuck, M. E., et al., (1994), J. Biol. Chem. 269: 24261–24270; Ashen, M. D., et al., (1995), Am. J. Physiol. 268: H506–H511; Salkoff, L. and T. Jegla (1995), Neuron 15: 489–492; Aguilar-Bryan, L., et al., (1998), Physiol. Rev. 78: 227–245; Ruknudin, A., et al., (1998), J. Biol. Chem. 273: 14165–14171). They may exist in the membrane as homo- or heterooligomers. They have a greater tendency to let K$^+$ flow into the cell than out. Voltage-dependence may be regulated by external K$^+$, by internal Mg$^{2+}$, by internal ATP and/or by G-proteins. The P domains of IRK channels exhibit limited sequence similarity to those of the VIC family, but this sequence similarity is insufficient to establish homology. Inward rectifiers play a role in setting cellular membrane potentials, and the closing of these channels upon depolarization permits the occurrence of long duration action potentials with a plateau phase. Inward rectifiers lack the intrinsic voltage sensing helices found in VIC family channels. In a few cases, those of Kir1.1a and Kir6.2, for example, direct interaction with a member of the ABC superfamily has been proposed to confer unique functional and regulatory properties to the heteromeric complex, including sensitivity to ATP. The SUR1 sulfonylurea receptor (spQ09428) is the ABC protein that regulates the Kir6.2 channel in response to ATP, and CFTR may regulate Kir1.1a. Mutations in SUR1 are the cause of familial persistent hyperinsulinemic hypoglycemia in infancy (PHHI), an autosomal recessive disorder characterized by unregulated insulin secretion in the pancreas.

ATP-gated Cation Channel (ACC) Family

Members of the ACC family (also called P2X receptors) respond to ATP, a functional neurotransmitter released by exocytosis from many types of neurons (North, R. A. (1996), Curr. Opin. Cell Biol. 8: 474–483; Soto, F., M. Garcia-Guzman and W. Stühmer (1997), J. Membr. Biol. 160: 91–100). They have been placed into seven groups ($P2X_1$-$P2X_7$) based on their pharmacological properties. These channels, which function at neuron-neuron and neuron-smooth muscle junctions, may play roles in the control of blood pressure and pain sensation. They may also function in lymphocyte and platelet physiology. They are found only in animals.

The proteins of the ACC family are quite similar in sequence (>35% identity), but they possess 380–1000 amino acyl residues per subunit with variability in length localized primarily to the C-terminal domains. They possess two transmembrane spanners, one about 30–50 residues from their N-termini, the other near residues 320–340. The extracellular receptor domains between these two spanners (of about 270 residues) are well conserved with numerous conserved glycyl and cysteyl residues. The hydrophilic C-termini vary in length from 25 to 240 residues. They resemble the topologically similar epithelial $Na^+$ channel (ENaC) proteins in possessing (a) N- and C-termini localized intracellularly, (b) two putative transmembrane spanners, (c) a large extracellular loop domain, and (d) many conserved extracellular cysteyl residues. ACC family members are, however, not demonstrably homologous with them. ACC channels are probably hetero- or homomultimers and transport small monovalent cations ($Me^+$). Some also transport $Ca^{2+}$; a few also transport small metabolites.

The Ryanodine-Inositol 1,4,5-triphosphate Receptor $Ca^{2+}$ Channel (RIR-CaC) Family Ryanodine (Ry)-sensitive and inositol 1,4,5-triphosphate (IP3)-sensitive $Ca^{2+}$-release channels function in the release of $Ca^{2+}$ from intracellular storage sites in animal cells and thereby regulate various $Ca^{2+}$-dependent physiological processes (Hasan, G. et al., (1992) Development 116: 967–975; Michikawa, T., et al., (1994), J. Biol. Chem. 269: 9184–9189; Tunwell, R. E. A., (1996), Biochem. J. 318: 477–487; Lee, A. G. (1996) Biomembranes, Vol. 6, Transmembrane Receptors and Channels (A. G. Lee, ed.), JAI Press, Denver, Colo., pp 291–326; Mikoshiba, K., et al., (1996) J. Biochem. Biomem. 6: 273–289). Ry receptors occur primarily in muscle cell sarcoplasmic reticular (SR) membranes, and IP3 receptors occur primarily in brain cell endoplasmic reticular (ER) membranes where they effect release of $Ca^{2+}$ into the cytoplasm upon activation (opening) of the channel.

The Ry receptors are activated as a result of the activity of dihydropyridine-sensitive $Ca^{2+}$ channels. The latter are members of the voltage-sensitive ion channel (VIC) family. Dihydropyridine-sensitive channels are present in the T-tubular systems of muscle tissues.

Ry receptors are homotetrameric complexes with each subunit exhibiting a molecular size of over 500,000 daltons (about 5,000 amino acyl residues). They possess C-terminal domains with six putative transmembrane a -helical spanners (TMSs). Putative pore-forming sequences occur between the fifth and sixth TMSs as suggested for members of the VIC family. The large N-terminal hydrophilic domains and the small C-terminal hydrophilic domains are localized to the cytoplasm. Low resolution 3-dimensional structural data are available. Mammals possess at least three isoforms that probably arose by gene duplication and divergence before divergence of the mammalian species. Homologues are present in humans and Caenorabditis elegans.

$IP_3$ receptors resemble Ry receptors in many respects. (1) They are homotetrameric complexes with each subunit exhibiting a molecular size of over 300,000 daltons (about 2,700 amino acyl residues). (2) They possess C-terminal channel domains that are homologous to those of the Ry receptors. (3) The channel domains possess six putative TMSs and a putative channel lining region between TMSs 5 and 6. (4) Both the large N-terminal domains and the smaller C-terminal tails face the cytoplasm. (5) They possess covalently linked carbohydrate on extracytoplasmic loops of the channel domains. (6) They have three currently recognized isoforms (types 1, 2, and 3) in mammals which are subject to differential regulation and have different tissue distributions.

$IP_3$ receptors possess three domains: N-terminal $IP_3$-binding domains, central coupling or regulatory domains and C-terminal channel domains. Channels are activated by $IP_3$ binding, and like the Ry receptors, the activities of the $IP_3$ receptor channels are regulated by phosphorylation of the regulatory domains, catalyzed by various protein kinases. They predominate in the endoplasmic reticular membranes of various cell types in the brain but have also been found in the plasma membranes of some nerve cells derived from a variety of tissues.

The channel domains of the Ry and $IP_3$ receptors comprise a coherent family that in spite of apparent structural similarities, do not show appreciable sequence similarity of the proteins of the VIC family. The Ry receptors and the $IP_3$ receptors cluster separately on the RIR-CaC family tree. They both have homologues in Drosophila. Based on the phylogenetic tree for the family, the family probably evolved in the following sequence: (1) A gene duplication event occurred that gave rise to Ry and $IP_3$ receptors in invertebrates. (2) Vertebrates evolved from invertebrates. (3) The three isoforms of each receptor arose as a result of two distinct gene duplication events. (4) These isoforms were transmitted to mammals before divergence of the mammalian species.

The Organellar Chloride Channel (O-ClC) Family

Proteins of the O-ClC family are voltage-sensitive chloride channels found in intracellular membranes but not the plasma membranes of animal cells (Landry, D, et al., (1993), J. Biol. Chem. 268: 14948–14955; Valenzuela, Set al., (1997), J. Biol. Chem. 272: 12575–12582; and Duncan, R. R., et al., (1997), J. Biol. Chem. 272: 23880–23886).

They are found in human nuclear membranes, and the bovine protein targets to the microsomes, but not the plasma membrane, when expressed in Xenopus laevis oocytes. These proteins are thought to function in the regulation of the membrane potential and in transepithelial ion absorption and secretion in the kidney. They possess two putative transmembrane a-helical spanners (TMSs) with cytoplasmic N- and C-termini and a large luminal loop that may be glycosylated. The bovine protein is 437 amino acyl residues in length and has the two putative TMSs at positions 223–239 and 367–385. The human nuclear protein is much smaller (241 residues). A C. elegans homologue is 260 residues long.

Sodium Bicarbonate Cotransporters

The novel human protein provided by the present invention is related to the family of sodium bicarbonate cotransporters, and shows a particularly high degree of similarity to the mouse sodium bicarbonate cotransporter isoform kNBC-3.

The sodium bicarbonate cotransporter provides the primary mechanism for transporting bicarbonate across the basolateral membrane in the kidney. At least three sodium bicarbonate cotransporter isoforms are located in the kidney and these may be functionally altered in various pathophysiologic states. For example, sodium bicarbonate cotransporter isoform 1 may be stimulated by metabolic acidosis, potassium depletion, and glucocorticoid excess and may be inhibited by bicarbonate loading or alkalosis. Sodium bicarbonate cotransporters are activated by cystic fibrosis transmembrane conductance regulator (CFTR) and play an important role in bicarbonate secretion in pancreatic duct cells. Furthermore, sodium bicarbonate cotransporters may play an important role in acid-base disorders such as proximal renal tubular acidosis (Soleimani et al., Kidney Int 2000 February;57(2):371–84).

The sodium-driven chloride/bicarbonate exchanger plays an important role in regulating intracellular pH in a wide variety cells by transporting extracellular sodium and bicarbonate into cells in exchange for intracellular chloride and H(+), thereby raising intracellular pH (Wang et al., J Biol Chem 2000 Nov. 10; 275(45):35486–90).

Transporter proteins, particularly members of the sodium bicarbonate cotransporter subfamily, are a major target for drug action and development. Accordingly, it is valuable to the field of pharmaceutical development to identify and characterize previously unknown transport proteins. The present invention advances the state of the art by providing previously unidentified human transport proteins.

SUMMARY OF THE INVENTION

The present invention is based in part on the identification of amino acid sequences of human transporter peptides and proteins that are related to the sodium bicarbonate cotransporter subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate transporter activity in cells and tissues that express the transporter. Experimental data as provided in FIG. 1 indicates expression in humans in the testis, brain (adult and fetal), placenta, and bone marrow.

DESCRIPTION OF THE FIGURE SHEETS

FIG. 1 provides the nucleotide sequence of a cDNA molecule that encodes the transporter protein of the present invention. In addition structure and functional information is provided, such as ATG start, stop and tissue distribution, where available, that allows one to readily determine specific uses of inventions based on this molecular sequence. Experimental data as provided in FIG. 1 indicates expression in humans in the testis, brain (adult and fetal), placenta, and bone marrow.

FIG. 2 provides the predicted amino acid sequence of the transporter of the present invention. In addition structure and functional information such as protein family, function, and modification sites is provided where available, allowing one to readily determine specific uses of inventions based on this molecular sequence.

FIG. 3 provides genomic sequences that span the gene encoding the transporter protein of the present invention. In addition structure and functional information, such as intron/exon structure, promoter location, etc., is provided where available, allowing one to readily determine specific uses of inventions based on this molecular sequence. As illustrated in FIG. 3, SNPs, including insertion/deletion polymorphisms ("indels"), were identifed at 87 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a transporter protein or part of a transporter protein and are related to the sodium bicarbonate cotransporter subfamily. Utilizing these sequences, additional genomic sequences were assembled and transcript and/or cDNA sequences were isolated and characterized. Based on this analysis, the present invention provides amino acid sequences of human transporter peptides and proteins that are related to the sodium bicarbonate cotransporter subfamily, nucleic acid sequences in the form of transcript sequences, cDNA sequences and/or genomic sequences that encode these transporter peptides and proteins, nucleic acid variation (allelic information), tissue distribution of expression, and information about the closest art known protein/peptide/domain that has structural or sequence homology to the transporter of the present invention.

In addition to being previously unknown, the peptides that are provided in the present invention are selected based on their ability to be used for the development of commercially important products and services. Specifically, the present peptides are selected based on homology and/or structural relatedness to known transporter proteins of the sodium bicarbonate cotransporter subfamily and the expression pattern observed. Experimental data as provided in FIG. 1 indicates expression in humans in the testis, brain (adult and fetal), placenta, and bone marrow. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known sodium bicarbonate cotransporter family or subfamily of transporter proteins.

Specific Embodiments

Peptide Molecules

The present invention provides nucleic acid sequences that encode protein molecules that have been identified as being members of the transporter family of proteins and are related to the sodium bicarbonate cotransporter subfamily (protein sequences are provided in FIG. 2, transcript/cDNA sequences are provided in FIGS. 1 and genomic sequences are provided in FIG. 3). The peptide sequences provided in FIG. 2, as well as the obvious variants described herein, particularly allelic variants as identified herein and using the information in FIG. 3, will be referred herein as the transporter peptides of the present invention, transporter peptides, or peptides/proteins of the present invention.

The present invention provides isolated peptide and protein molecules that consist of, consist essentially of, or comprising the amino acid sequences of the transporter peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the transporter peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated transporter peptide can be purified from cells that naturally express it, purified from cells that have been altered to express it (recombinant), or synthesized using known protein synthesis methods. Experimental data as provided in FIG. 1 indicates expression in humans in the testis, brain (adult and fetal), placenta, and bone marrow. For example, a nucleic acid molecule encoding the transporter peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the transporter peptides of the present invention are the naturally occurring mature proteins. A brief description of how various types of these proteins can be made/isolated is provided below.

The transporter peptides of the present invention can be attached to heterologous sequences to form chimeric or fusion proteins. Such chimeric and fusion proteins comprise a transporter peptide operatively linked to a heterologous protein having an amino acid sequence not substantially homologous to the transporter peptide. "Operatively linked" indicates that the transporter peptide and the heterologous protein are fused in-frame. The heterologous protein can be fused to the N-terminus or C-terminus of the transporter peptide.

In some uses, the fusion protein does not affect the activity of the transporter peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant transporter peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A transporter peptide-encoding nucleic acid can be cloned into such an expression vector such that the fusion moiety is linked in-frame to the transporter peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the transporter peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the transporter peptides of the present invention as well as being encoded by the same genetic locus as the transporter peptide provided herein. As indicated by the data presented in FIG. 3, the gene provided by the present invention is located on public BAC AC008063.2, which is known to be mapped to chromosome 2.

Allelic variants of a transporter peptide can readily be identified as being a human protein having a high degree (significant) of sequence homology/identity to at least a portion of the transporter peptide as well as being encoded by the same genetic locus as the transporter peptide provided herein. Genetic locus can readily be determined based on the genomic information provided in FIG. 3, such as the genomic sequence mapped to the reference human. As indicated by the data presented in FIG. 3, the gene provided by the present invention is located on public BAC AC008063.2, which is known to be mapped to chromosome 2. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a transporter peptide encoding nucleic acid molecule under stringent conditions as more fully described below.

FIG. 3 provides information on SNPs that have been found in the gene encoding the transporter protein of the present invention. SNPs, including insertion/deletion polymorphisms ("indels"), were identifed at 87 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. SNP positioning in exons, introns, or outside the ORF can readily be determined based on the genomic features given in FIG. 3.

Paralogs of a transporter peptide can readily be identified as having some degree of significant sequence homology/identity to at least a portion of the transporter peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a transporter peptide encoding nucleic acid molecule under moderate to stringent conditions as more fully described below.

Orthologs of a transporter peptide can readily be identified as having some degree of significant sequence homology/identity to at least a portion of the transporter peptide as well as being encoded by a gene from another organism. Preferred orthologs will be isolated from mammals, preferably primates, for the development of human therapeutic targets and agents. Such orthologs will be encoded by a nucleic acid sequence that will hybridize to a transporter peptide encoding nucleic acid molecule under moderate to stringent conditions, as more fully described below, depending on the degree of relatedness of the two organisms yielding the proteins.

Non-naturally occurring variants of the transporter peptides of the present invention can readily be generated using recombinant techniques. Such variants include, but are not limited to deletions, additions and substitutions in the amino acid sequence of the transporter peptide. For example, one class of substitutions are conserved amino acid substitution. Such substitutions are those that substitute a given amino acid in a transporter peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant transporter peptides can be fully functional or can lack function in one or more activities, e.g. ability to bind ligand, ability to transport ligand, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as transporter activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the transporter peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a transporter peptide. Such fragments can be chosen based on the ability to retain one or more of the biological activities of the transporter peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the transporter peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in transporter peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the transporter peptides of the present invention also encompass derivatives or analogs in which a substituted amino acid residue is not one encoded by the genetic code, in which a substituent group is included, in which the mature transporter peptide is fused with another compound, such as a compound to increase the half-life of the transporter peptide (for example, polyethylene glycol), or in which the additional amino acids are fused to the mature transporter peptide, such as a leader or secretory sequence or a sequence for purification of the mature transporter peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a transporter-effector protein interaction or transporter-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, transporters isolated from humans and their human/mammalian orthologs serve as targets for identifying agents for use in mammalian therapeutic applications, e.g. a human drug, particularly in modulating a biological or pathological response in a cell or tissue that expresses the transporter. Experimental data as provided in FIG. 1 indicates that the transporter protein of the present invention is expressed in humans in the testis, brain (adult and fetal), placenta, and bone marrow, as indicated by PCR-based tissue screening panels. A large percentage of pharmaceutical agents are being developed that modulate the activity of transporter proteins, particularly members of the sodium bicarbonate cotransporter subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the testis, brain (adult and fetal), placenta, and bone marrow. Such uses can readily be determined using the information provided herein, that known in the art and routine experimentation.

The proteins of the present invention (including variants and fragments that may have been disclosed prior to the present invention) are useful for biological assays related to transporters that are related to members of the sodium bicarbonate cotransporter subfamily. Such assays involve any of the known transporter functions or activities or properties useful for diagnosis and treatment of transporter-related conditions that are specific for the subfamily of transporters that the one of the present invention belongs to, particularly in cells and tissues that express the transporter. Experimental data as provided in FIG. 1 indicates that the transporter protein of the present invention is expressed in humans in the testis, brain (adult and fetal), placenta, and bone marrow, as indicated by PCR-based tissue screening panels. The proteins of the present invention are also useful in drug screening assays, in cell-based or cell-free systems ((Hodgson, Bio/technology, Sep. 10, 1992, (9);973–80). Cell-based systems can be native, i.e., cells that normally express the transporter, as a biopsy or expanded in cell culture. Experimental data as provided in FIG. 1 indicates expression in humans in the testis, brain (adult and fetal), placenta, and bone marrow. In an alternate embodiment, cell-based assays involve recombinant host cells expressing the transporter protein.

The polypeptides can be used to identify compounds that modulate transporter activity of the protein in its natural state or an altered form that causes a specific disease or pathology associated with the transporter. Both the transporters of the present invention and appropriate variants and fragments can be used in high-throughput screens to assay candidate compounds for the ability to bind to the transporter. These compounds can be further screened against a functional transporter to determine the effect of the compound on the transporter activity. Further, these compounds can be tested in animal or invertebrate systems to determine activity/effectiveness. Compounds can be identified that activate (agonist) or inactivate (antagonist) the transporter to a desired degree.

Further, the proteins of the present invention can be used to screen a compound for the ability to stimulate or inhibit interaction between the transporter protein and a molecule that normally interacts with the transporter protein, e.g. a substrate or a component of the signal pathway that the transporter protein normally interacts (for example, another transporter). Such assays typically include the steps of combining the transporter protein with a candidate compound under conditions that allow the transporter protein, or fragment, to interact with the target molecule, and to detect the formation of a complex between the protein and the target or to detect the biochemical consequence of the interaction with the transporter protein and the target, such as any of the associated effects of signal transduction such as changes in membrane potential, protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, antiidiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for ligand binding. Other candidate compounds include mutant transporters or appropriate fragments containing mutations that affect transporter function and thus compete for ligand. Accordingly, a fragment that competes for ligand, for example with a higher affinity, or a fragment that binds ligand but does not allow release, is encompassed by the invention.

The invention further includes other end point assays to identify compounds that modulate (stimulate or inhibit) transporter activity. The assays typically involve an assay of events in the signal transduction pathway that indicate transporter activity. Thus, the transport of a ligand, change in cell membrane potential, activation of a protein, a change in the expression of genes that are up-or down-regulated in response to the transporter protein dependent signal cascade can be assayed.

Any of the biological or biochemical functions mediated by the transporter can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the transporter can be assayed. Experimental data as provided in FIG. 1 indicates that the transporter protein of the present invention is expressed in humans in the testis, brain (adult and fetal), placenta, and bone marrow, as indicated by PCR-based tissue screening panels.

Binding and/or activating compounds can also be screened by using chimeric transporter proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a ligand-binding region can be used that interacts with a different ligand then that which is recognized by the native transporter. Accordingly, a different set of signal transduction components is available as an end-point assay for activation. This allows for assays to be performed in other than the specific host cell from which the transporter is derived.

The proteins of the present invention are also useful in competition binding assays in methods designed to discover compounds that interact with the transporter (e.g. binding partners and/or ligands). Thus, a compound is exposed to a transporter polypeptide under conditions that allow the compound to bind or to otherwise interact with the polypeptide. Soluble transporter polypeptide is also added to the mixture. If the test compound interacts with the soluble transporter polypeptide, it decreases the amount of complex formed or activity from the transporter target. This type of assay is particularly useful in cases in which compounds are sought that interact with specific regions of the transporter. Thus, the soluble polypeptide that competes with the target transporter region is designed to contain peptide sequences corresponding to the region of interest.

To perform cell free drug screening assays, it is sometimes desirable to immobilize either the transporter protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of transporter-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a transporter-binding protein and a candidate compound are incubated in the transporter protein-presenting wells and the amount of complex trapped in the well can be quantitated. Methods for detecting such complexes, in addition to those described above for the GST-immobilized complexes, include immunodetection of complexes using antibodies reactive with the transporter protein target molecule, or which are reactive with transporter protein and compete with the target molecule, as well as enzyme-linked assays which rely on detecting an enzymatic activity associated with the target molecule.

Agents that modulate one of the transporters of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of transporter protein activity identified according to these drug screening assays can be used to treat a subject with a disorder mediated by the transporter pathway, by treating cells or tissues that express the transporter. Experimental data as provided in FIG. 1 indicates expression in humans in the testis, brain (adult and fetal), placenta, and bone marrow. These methods of treatment include the steps of administering a modulator of transporter activity in a pharmaceutical composition to a subject in need of such treatment, the modulator being identified as described herein.

In yet another aspect of the invention, the transporter proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the transporter and are involved in transporter activity. Such transporter-binding proteins are also likely to be involved in the propagation of signals by the transporter proteins or transporter targets as, for example, downstream elements of a transporter-mediated signaling pathway. Alternatively, such transporter-binding proteins are likely to be transporter inhibitors.

The two-hybrid system is based on the modular nature of most transcription factors, which consist of separable DNA-binding and activation domains. Briefly, the assay utilizes two different DNA constructs. In one construct, the gene that codes for a transporter protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a transporter-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the transporter protein.

This invention further pertains to novel agents identified by the above-described screening assays. Accordingly, it is within the scope of this invention to further use an agent identified as described herein in an appropriate animal model. For example, an agent identified as described herein (e.g., a transporter-modulating agent, an antisense transporter nucleic acid molecule, a transporter-specific antibody, or a transporter-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The transporter proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the testis, brain (adult and fetal), placenta, and bone marrow. The method involves contacting a biological sample with a compound capable of interacting with the transporter protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered transporter activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the transporter protein in which one or more of the transporter functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and transporter activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the testis, brain (adult and fetal), placenta, and bone marrow. Accordingly, methods for treatment include the use of the transporter protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the transporter proteins. Antibodies can be prepared from any region of the peptide as described herein. However, preferred regions will include those involved in function/activity and/or transporter/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the transporter protein of the present invention is expressed in humans in the testis, brain (adult and fetal), placenta, and bone marrow, as indicated by PCR-based tissue screening panels. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the testis, brain (adult and fetal), placenta, and bone marrow. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the testis, brain (adult and fetal), placenta, and bone marrow. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the testis, brain (adult and fetal), placenta, and bone marrow. Thus, where a specific protein has been correlated with expression in a specific tissue, antibodies that are specific for this protein can be used to identify a tissue type.

The antibodies are also useful for inhibiting protein function, for example, blocking the binding of the transporter peptide to a binding partner such as a ligand or protein binding partner. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a transporter peptide or protein of the present invention (cDNA, transcript and genomic sequence). Such nucleic acid molecules will consist of, consist essentially of, or comprise a nucleotide sequence that encodes one of the transporter peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences that naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprise several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the transporter peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the transporter proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the gene provided by the present invention is located on public BAC AC008063.2, which is known to be mapped to chromosome 2.

FIG. 3 provides information on SNPs that have been found in the gene encoding the transporter protein of the present invention. SNPs, including insertion/deletion polymorphisms ("indels"), were identifed at 87 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. SNP positioning in exons, introns, or outside the ORF can readily be determined based on the genomic features given in FIG. 3.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs, including insertion/deletion polymorphisms ("indels"), were identifed at 87 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the gene provided by the present invention is located on public BAC AC008063.2, which is known to be mapped to chromosome 2.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the transporter protein of the present invention is expressed in humans in the testis, brain (adult and fetal), placenta, and bone marrow, as indicated by PCR-based tissue screening panels.

Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in transporter protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a transporter protein, such as by measuring a level of a transporter-encoding nucleic acid in a sample of cells from a subject e.g., mRNA or genomic DNA, or determining if a transporter gene has been mutated. Experimental data as provided in FIG. 1 indicates that the transporter protein of the present invention is expressed in humans in the testis, brain (adult and fetal), placenta, and bone marrow, as indicated by PCR-based tissue screening panels.

Nucleic acid expression assays are useful for drug screening to identify compounds that modulate transporter nucleic acid expression.

The invention thus provides a method for identifying a compound that can be used to treat a disorder associated with nucleic acid expression of the transporter gene, particularly biological and pathological processes that are mediated by the transporter in cells and tissues that express it. Experimental data as provided in FIG. 1 indicates expression in humans in the testis, brain (adult and fetal), placenta, and bone marrow. The method typically includes assaying the ability of the compound to modulate the expression of the transporter nucleic acid and thus identifying a compound that can be used to treat a disorder characterized by undesired transporter nucleic acid expression. The assays can be performed in cell-based and cell-free systems. Cell-based assays include cells naturally expressing the transporter nucleic acid or recombinant cells genetically engineered to express specific nucleic acid sequences.

The assay for transporter nucleic acid expression can involve direct assay of nucleic acid levels, such as mRNA levels, or on collateral compounds involved in the signal pathway. Further, the expression of genes that are up-or down-regulated in response to the transporter protein signal pathway can also be assayed. In this embodiment the regulatory regions of these genes can be operably linked to a reporter gene such as luciferase.

Thus, modulators of transporter gene expression can be identified in a method wherein a cell is contacted with a candidate compound and the expression of mRNA determined. The level of expression of transporter mRNA in the presence of the candidate compound is compared to the level of expression of transporter mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate transporter nucleic acid expression in cells and tissues that express the transporter. Experimental data as provided in FIG. 1 indicates that the transporter protein of the present invention is expressed in humans in the testis, brain (adult and fetal), placenta, and bone marrow, as indicated by PCR-based tissue screening panels. Modulation includes both up-regulation (i.e. activation or agonization) or down-regulation (suppression or antagonization) or nucleic acid expression.

Alternatively, a modulator for transporter nucleic acid expression can be a small molecule or drug identified using the screening assays described herein as long as the drug or small molecule inhibits the transporter nucleic acid expression in the cells and tissues that express the protein. Experimental data as provided in FIG. 1 indicates expression in humans in the testis, brain (adult and fetal), placenta, and bone marrow.

The nucleic acid molecules are also useful for monitoring the effectiveness of modulating compounds on the expression or activity of the transporter gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in transporter nucleic acid expression, and particularly in qualitative changes that lead to pathology. The nucleic acid molecules can be used to detect mutations in transporter genes and gene expression products such as mRNA. The nucleic acid molecules can be used as hybridization probes to detect naturally occurring genetic mutations in the transporter gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the transporter gene associated with a dysfunction provides a diagnostic tool for an active disease or susceptibility to disease when the disease results from overexpression, underexpression, or altered expression of a transporter protein.

Individuals carrying mutations in the transporter gene can be detected at the nucleic acid level by a variety of techniques. FIG. 3 provides information on SNPs that have been found in the gene encoding the transporter protein of the present invention. SNPs, including insertion/deletion polymorphisms ("indels"), were identifed at 87 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. SNP positioning in exons, introns, or outside the ORF can readily be determined based on the genomic features given in FIG. 3. As indicated by the data presented in FIG. 3, the gene provided by the present invention is located on public BAC AC008063.2, which is known to be mapped to chromosome 2. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a transporter gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant transporter gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al, *Adv. Chromatogr.* 36:127–162 (1996); and Griffin et al, *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al, *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the transporter gene in an individual in order to select an appropriate compound or dosage regimen for treatment. FIG. 3 provides information on SNPs that have been found in the gene encoding the transporter protein of the present invention. SNPs, including insertion/deletion polymorphisms ("indels"), were identifed at 87 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. SNP positioning in exons, introns, or outside the ORF can readily be determined based on the genomic features given in FIG. 3.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control transporter gene expression in cells, tissues, and organisms. A DNA antisense nucleic acid molecule is designed to be complementary to a region of the gene involved in transcription, preventing transcription and hence production of transporter protein. An antisense RNA or DNA nucleic acid molecule would hybridize to the mRNA and thus block translation of mRNA into transporter protein.

Alternatively, a class of antisense molecules can be used to inactivate mRNA in order to decrease expression of transporter nucleic acid. Accordingly, these molecules can treat a disorder characterized by abnormal or undesired transporter nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the transporter protein, such as ligand binding.

The nucleic acid molecules also provide vectors for gene therapy in patients containing cells that are aberrant in transporter gene expression. Thus, recombinant cells, which include the patient's cells that have been engineered ex vivo and returned to the patient, are introduced into an individual where the cells produce the desired transporter protein to treat the individual.

The invention also encompasses kits for detecting the presence of a transporter nucleic acid in a biological sample. Experimental data as provided in FIG. 1 indicates that the transporter protein of the present invention is expressed in humans in the testis, brain (adult and fetal), placenta, and bone marrow, as indicated by PCR-based tissue screening panels. For example, the kit can comprise reagents such as a labeled or labelable nucleic acid or agent capable of detecting transporter nucleic acid in a biological sample; means for determining the amount of transporter nucleic acid in the sample; and means for comparing the amount of transporter nucleic acid in the sample with a standard. The compound or agent can be packaged in a suitable container. The kit can further comprise instructions for using the kit to detect transporter protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS: 1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides that cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/25 1116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the transporter proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the transporter gene of the present invention. FIG. 3 provides information on SNPs that have been found in the gene encoding the transporter protein of the present invention. SNPs, including insertion/deletion polymorphisms ("indels"), were identifed at 87 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. SNP positioning in exons, introns, or outside the ORF can readily be determined based on the genomic features given in FIG. 3.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified transporter gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterotransporter. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed*, Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed, Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as transporters, appropriate secretion signals are incorporated into the vector. The signal sequence can be endogenous to the peptides or heterologous to these peptides.

Where the peptide is not secreted into the medium, which is typically the case with transporters, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a transporter protein or peptide that can be further purified to produce desired amounts of transporter protein or fragments. Thus, host cells containing expression vectors are useful for peptide production.

Host cells are also useful for conducting cell-based assays involving the transporter protein or transporter protein fragments, such as those described above as well as other formats known in the art. Thus, a recombinant host cell expressing a native transporter protein is useful for assaying compounds that stimulate or inhibit transporter protein function.

Host cells are also useful for identifying transporter protein mutants in which these functions are affected. If the mutants naturally occur and give rise to a pathology, host cells containing the mutations are useful to assay compounds that have a desired effect on the mutant transporter protein (for example, stimulating or inhibiting function) which may not be indicated by their effect on the native transporter protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA that is integrated into the genome of a cell from which a transgenic animal develops and which remains in the genome of the mature animal in one or more cell types or tissues of the transgenic animal. These animals are useful for studying the function of a transporter protein and identifying and evaluating modulators of transporter protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the transporter protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the transporter protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, transporter protein activation, and signal transduction, may not be evident from in vitro cell-free or cell-based assays. Accordingly, it is useful to provide non-human transgenic animals to assay in vivo transporter protein function, including ligand interaction, the effect of specific mutant transporter proteins on transporter protein function and ligand interaction, and the effect of chimeric transporter proteins. It is also possible to assess the effect of null mutations, that is mutations that substantially or completely eliminate one or more transporter protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated peptide consisting of an amino acid sequence of SEQ ID NO: 2.

2. A composition comprising the polypeptide of claim 1 and a carrier.

3. An isolated peptide comprising an amino acid sequence of SEQ ID NO: 2.

4. A composition comprising the polypeptide of claim 3 and a carrier.

* * * * *

SEQUENCE LISTING

<160> NUMBER OF SEQ ID NOS: 4

<210> SEQ ID NO 1
<211> LENGTH: 5735
<212> TYPE: DNA
<213> ORGANISM: Human

<400> SEQUENCE: 1

```
cggccgcgtc gacgtgattt gatatcttga tgatggctta aacagatact gatggacaga        60
tctgttgttt gatatttttt tcactagccc tgaagatgct gagacataga gatggctgtg       120
attatctttt gtaagacagg aaatgcagtc tttaggggtt tctggaaata gaaaggtcat       180
gcagtctgga acctgtgagc cttttcaatc tctaagtcat cagagaaatg atgaagaagc       240
agttgtggat agaggtggaa ctcgttctat tctcaaaaca cactttgaga aagaagattt       300
agaaggtcat cgaacactat ttattggagt acatgtgccc ttgggaggaa gaaaaagcca       360
tcgacgtcac aggcatcgtg gtcataaaca cagaaagaga gacagagaaa gagattcagg       420
attagaggat ggaagggagt caccttcttt tgacacccca tcacagaggg tacagtttat       480
tcttggaacc gaggatgatg acgaggaaca cattcctcat gaccttttca cagaactgga       540
tgagatttgt tggcgtgaag gtgaggacgc tgagtggcga gaaacagcca ggtggttgaa       600
gtttgaagaa gatgtggaag atggaggaga aaggtggagc aagccttatg tggctactct       660
ttcattgcac agcttgtttg aattgagaag ttgtattctg aatggaactg tgttgctgga       720
catgcatgcc aacactttag aagaaattgc agatatggtt cttgaccaac aagtgagctc       780
aggtcagctg aatgaagatg tacgccatag ggtccatgag gcattgatga aacagcatca       840
tcatcagaat cagaaaaaac tcaccaacag gattcccatt gttcgttcct ttgctgatat       900
tggcaagaaa cagtcagaac caaattccat ggacaaaaat gcaggtcagg ttgtttctcc       960
tcagtctgct ccagcctgtg ttgaaaataa aaatgatgtt agcagagaaa acagcactgt      1020
tgactttagc aagggactgg gaggccaaca aaagggggcat actagtccat gtgggatgaa      1080
acaaaggcat gaaaaaggac ctccacacca gcaagagaga gaggttgatc tgcattttat      1140
gaaaaagatt cctccaggtg ctgaagcatc gaacatctta gtgggagaac tggagttctt      1200
ggatcgaaca gtagttgcgt ttgtcaggtt gtctccagct gtattgcttc aaggactggc      1260
tgaagtccca atcccaacca gattttttgtt cattcttctg ggaccccctgg gaaagggtca      1320 acagtaccat gagattggca gatcaattgc aaccctaatg acagatgagg tatttcatga      1380
```

-continued

```
tgttgcctat aaagctaaag atcgtaatga cttggtatca ggaattgatg agtttctgga    1440
tcaggttact gttctccctc ctggagaatg ggatccaagc attcgaatag agcctcccaa    1500
aaatgttcct tcccaggaga agaggaagat tcctgctgta ccaaatggaa cagcagctca    1560
tggggaagca gagccccacg gaggacatag tggacctgaa ctccagcgaa ctggaaggat    1620
ttttggggga cttatttag atatcaaaag aaaagctcca tacttctgga gtgacttcag     1680
agatgctttc agcctgcagt gcttagcatc ttttctattt ctctactgcg cgtgtatgtc    1740
tcctgtcatc acgtttggag gactgctggg agaagcaact gaaggcgta taagtgcaat     1800 tgaatctctc tttggagcat ccatgaccgg gatagcctat tctctctttg gtggacagcc    1860
tcttaccata ttaggcagta caggaccagt tttggtgttt gaaagatttt tgtttaaatt    1920
ttgcaaagaa tatgggctgt catacctatc tttaagagct agcattggac tttgactgc     1980 aactctatgt atcatacttg tggccacaga tgctagttcc cttgtctgct acatcactcg    2040
gtttactgaa gaagcttttg cttccctgat ttgcatcatt ttcatttatg aggccctgga    2100
gaagttgttt gaactcagtg aagcatatcc aatcaacatg cataatgatc tggaactgct    2160
gacacaatac tcgtgtaact gtgtggaacc gcataatccc agcaatggca cattgaagga    2220
atggagggaa tccaatattt ctgcctctga cataatttgg gagaacctaa ctgtgtcaga    2280
atgcaaatca ttgcatggag agtatgttgg acgggcctgt ggccatgatc acccatatgt    2340
tccagatgtt ctattttggt ctgtgatcct gttcttttcc acagttactc tgtcagccac    2400
cctgaagcag ttcaagacta gcagatattt tccaaccaag gttcgatcca tagtgagtga    2460
ctttgctgtc tttcttacaa ttctgtgtat ggttttaatt gactatgcca ttgggatccc    2520
atctccaaaa ctacaagtac caagtgtttt caagcccact agagatgatc gtggctggtt    2580
tgttacgcct ttaggtccaa acccatggtg gacagtaata gctgctataa ttccagctct    2640
gctttgtact attctaattt ttatggacca acagattaca gctgtcatca tcaacaggaa    2700
agagcataag ctaaagaaag gttgtgggta ccatctggac ctattaatgg tggctgtcat    2760
gctcggtgta tgctccatca tgggcctgcc atggtttgtg gctgccacag tcctctccat    2820
cactcatgtc aatagcctaa aactggaatc agaatgctca gctccaggag aacaacccaa    2880
atttctcggc attcgggagc aaaggggttac tgggcttatg attttattc ttatgggttc    2940 atcagtcttt atgaccagta ttctgaagtt tattcccatg ccagtgctat atggagtgtt    3000
tctttatatg ggtgcttcat ctctaaaggg aattcagttc tttgatagga taaagctctt    3060
ctggatgccg gcaaaacatc aaccagattt tatataccta aggcacgtac cgcttcgaaa    3120
agtgcatctc ttcacaatta ttcagatgag ttgccttggc cttttgtgga ataaaaagt    3180 ttcaagagct gctattgtct ttcccatgat ggtgttagcc ctggtatttg taagaaagtt    3240
gatggacttg ttgttcacga agcgggaact cagctggttg gatgatttga tgcccgagag    3300
taagaaaaag aaactggaag atgctgaaaa agaagaagaa caaagtatgc tagctatgga    3360
agatgagggc acagtacaac tcccattgga agggcactat agagatgatc catctgtgat    3420
caatatatct gatgaaatgt caaagactgc cttgtggagg aaccttctga ttactgccga    3480
taactcaaaa gataaggagt caagctttcc ttccaaaagc tccccttcct aatcactcta    3540
gaagctgatt ccccaaagca ttgaaagccg aaaagagaag aaagctgact cagggaaagg    3600
tgttgacagg gagacttgtc tatgactcga tcttcaattt atttttaca tatatatgag     3660 aagagtgtca caattattaa taaaactgct ttgatcatgt attgtaaatt ctgtccctca    3720
acccaaatcc accttcatac tgtaagtagt gcaatacttg tttcatttct gtgtttaaac    3780
```

-continued

```
ttctgagcag tgagacatcc ctgtgagcag atacaatagc caatgcaaga atctgtgtgt   3840
tccttgctgt acgttagaca tttgtaaact ggattctgat tgtcagtttt atgagagcaa   3900
tagcttcctt aaagagataa gtcatatttta cctagtttgt attttcctac tttagtgacc   3960
tgaagatgcc tgataatttc attcagaaga attttttgaaa ggtagtctta cttctttttta  4020
gtttttatag cttagcatta gtgacttatt tcaaaagacc caaatcaaaa agttagtttg   4080
aaagcatttt ttaataattg tatttatgca tttccttgat ttaatatgat aaatttaata   4140
cttaacaatt tatatgtaac taaaacttaa agtcatttga aaatatata gaaacctatt    4200
tacaacttgt taaggacaat cagacataat gcagagttaa gtagtatttg cttaaaattc   4260
aagttgtgac taatgatcaa atactaggct tgtacgaaat gctttagaaa aactttgtaa   4320
cagttttgtg ggattttttca atataaacct ttatcagaaa tatactaagt ttgtctccca   4380
ctgacaacag atgttttcca aataaacata ttctatacat acttgtggaa tgccacatgg   4440
tgaatcattg tatatgaaat tccactcctg tacagttact ctgcagctaa tggtcatgca   4500
ctgcttaatg ctggtcctga atcatgttct catgttagac caacagctct ccaattgtca   4560
tttttttttct gcagagtttt ttttttttcca cttttaaatt aaatgcatgt tgtggaaaaa   4620
cagtctttta aaatgaaatt tcagattcca tttgagaagg ttctgtagat atttcagtcc   4680
atataaaata atacatctttt actaaactta tataagggga gagaaagtta tgaagttttg   4740
gacattacta aaagtacagt atttgatttc actttcaatg aatgtgaagt taataaaact   4800
aaatctcata atgctcttgg ttcctaagaa tgagtagtaa tcatcaactt tataatactc   4860
caatattccg ttttataata attcagagcc ctgtggcttt tacacaccgt taattatgta   4920
ctctgttgga agtgcacatg aaaagtgaag aaaagttcct cttgtgatta aactaatggg   4980
aggaaataaa tcaacaaagt ctccattaag ttctacattt tgagaccttt taaaaattcc   5040
cctcacaatt ctttaaggag cccccctttt tatggaacat gagcctaaaa attatagaaa   5100
gaagaatttt aagttaataa agtttgtatt tataaatgct gaaaaaatac agaaactttc   5160
tgttccaaat gtgttgcctt tgtgtatttt ataatacaga tactcattg taaacatttc    5220
cattgttttta tgatttagcc agtgattccc caaagcagcc tcttagtgtt ttaatatatt   5280
aataactgtt ttgttaaaaa tgatcatagt gaatttaaat cttcacatga tcacctattt   5340
gaataagcaa tcatatccaa tgaaattctg tatttctgag tattttttata gtcattttgt   5400
tcttgtgtga atttttaaagc tatccctatg ttaatcctaa tattttgaaa tcatataaaa   5460
tataataaaa atgtagtatt atatatttac ttctaatttc agattcctgg tcaaaattac   5520
taaatatctt gaatgtaatt tagtgccaag tttaaataat gtgtaaatgt gactaggata   5580
ttgtgttttt cacaattaag aaatgttatg tggaaataaa tatttatcct aacttccttg   5640
cacattttaa attgtgatac aaagtgtctt gtcttttttc tttgttttaa ttagtaaatc    5700
agtgtaaaac aaaaaaaaaa aaaaaaaaaa aaaaa                               5735
```

<210> SEQ ID NO 2
<211> LENGTH: 1129
<212> TYPE: PRT
<213> ORGANISM: Human

<400> SEQUENCE: 2

Met Gln Ser Leu Gly Val Ser Gly Asn Arg Lys Val Met Gln Ser Gly
 1               5                  10                  15

Thr Cys Glu Pro Phe Gln Ser Leu Ser His Gln Arg Asn Asp Glu Glu

```
                    20                  25                  30
Ala Val Val Asp Arg Gly Gly Thr Arg Ser Ile Leu Lys Thr His Phe
                35                  40                  45

Glu Lys Glu Asp Leu Glu Gly His Arg Thr Leu Phe Ile Gly Val His
            50                  55                  60

Val Pro Leu Gly Gly Arg Lys Ser His Arg Arg His Arg His Arg Gly
65                  70                  75                  80

His Lys His Arg Lys Arg Asp Arg Glu Arg Asp Ser Gly Leu Glu Asp
                85                  90                  95

Gly Arg Glu Ser Pro Ser Phe Asp Thr Pro Ser Gln Arg Val Gln Phe
                100                 105                 110

Ile Leu Gly Thr Glu Asp Asp Glu Glu His Ile Pro His Asp Leu
                115                 120                 125

Phe Thr Glu Leu Asp Glu Ile Cys Trp Arg Glu Gly Glu Asp Ala Glu
            130                 135                 140

Trp Arg Glu Thr Ala Arg Trp Leu Lys Phe Glu Glu Asp Val Glu Asp
145                 150                 155                 160

Gly Gly Glu Arg Trp Ser Lys Pro Tyr Val Ala Thr Leu Ser Leu His
                165                 170                 175

Ser Leu Phe Glu Leu Arg Ser Cys Ile Leu Asn Gly Thr Val Leu Leu
                180                 185                 190

Asp Met His Ala Asn Thr Leu Glu Glu Ile Ala Asp Met Val Leu Asp
            195                 200                 205

Gln Gln Val Ser Ser Gly Gln Leu Asn Glu Asp Val Arg His Arg Val
    210                 215                 220

His Glu Ala Leu Met Lys Gln His His Gln Asn Gln Lys Lys Leu
225                 230                 235                 240

Thr Asn Arg Ile Pro Ile Val Arg Ser Phe Ala Asp Ile Gly Lys Lys
                245                 250                 255

Gln Ser Glu Pro Asn Ser Met Asp Lys Asn Ala Gly Gln Val Val Ser
                260                 265                 270

Pro Gln Ser Ala Pro Ala Cys Val Glu Asn Lys Asn Asp Val Ser Arg
    275                 280                 285

Glu Asn Ser Thr Val Asp Phe Ser Lys Gly Leu Gly Gly Gln Gln Lys
290                 295                 300

Gly His Thr Ser Pro Cys Gly Met Lys Gln Arg His Glu Lys Gly Pro
305                 310                 315                 320

Pro His Gln Gln Glu Arg Glu Val Asp Leu His Phe Met Lys Lys Ile
                325                 330                 335

Pro Pro Gly Ala Glu Ala Ser Asn Ile Leu Val Gly Glu Leu Glu Phe
                340                 345                 350

Leu Asp Arg Thr Val Val Ala Phe Val Arg Leu Ser Pro Ala Val Leu
            355                 360                 365

Leu Gln Gly Leu Ala Glu Val Pro Ile Pro Thr Arg Phe Leu Phe Ile
    370                 375                 380

Leu Leu Gly Pro Leu Gly Lys Gly Gln Gln Tyr His Glu Ile Gly Arg
385                 390                 395                 400

Ser Ile Ala Thr Leu Met Thr Asp Glu Val Phe His Asp Val Ala Tyr
                405                 410                 415

Lys Ala Lys Asp Arg Asn Asp Leu Val Ser Gly Ile Asp Glu Phe Leu
                420                 425                 430

Asp Gln Val Thr Val Leu Pro Pro Gly Glu Trp Asp Pro Ser Ile Arg
            435                 440                 445
```

```
Ile Glu Pro Pro Lys Asn Val Pro Ser Gln Glu Lys Arg Lys Ile Pro
    450                 455                 460
Ala Val Pro Asn Gly Thr Ala His Gly Glu Ala Glu Pro His Gly
465                 470                 475                 480
Gly His Ser Gly Pro Glu Leu Gln Arg Thr Gly Arg Ile Phe Gly Gly
                    485                 490                 495
Leu Ile Leu Asp Ile Lys Arg Lys Ala Pro Tyr Phe Trp Ser Asp Phe
                500                 505                 510
Arg Asp Ala Phe Ser Leu Gln Cys Leu Ala Ser Phe Leu Phe Leu Tyr
            515                 520                 525
Cys Ala Cys Met Ser Pro Val Ile Thr Phe Gly Gly Leu Leu Gly Glu
530                 535                 540
Ala Thr Glu Gly Arg Ile Ser Ala Ile Glu Ser Leu Phe Gly Ala Ser
545                 550                 555                 560
Met Thr Gly Ile Ala Tyr Ser Leu Phe Gly Gly Gln Pro Leu Thr Ile
                565                 570                 575
Leu Gly Ser Thr Gly Pro Val Leu Val Phe Glu Lys Ile Leu Phe Lys
            580                 585                 590
Phe Cys Lys Glu Tyr Gly Leu Ser Tyr Leu Ser Leu Arg Ala Ser Ile
        595                 600                 605
Gly Leu Trp Thr Ala Thr Leu Cys Ile Ile Leu Val Ala Thr Asp Ala
    610                 615                 620
Ser Ser Leu Val Cys Tyr Ile Thr Arg Phe Thr Glu Glu Ala Phe Ala
625                 630                 635                 640
Ser Leu Ile Cys Ile Ile Phe Ile Tyr Glu Ala Leu Glu Lys Leu Phe
                645                 650                 655
Glu Leu Ser Glu Ala Tyr Pro Ile Asn Met His Asn Asp Leu Glu Leu
            660                 665                 670
Leu Thr Gln Tyr Ser Cys Asn Cys Val Glu Pro His Asn Pro Ser Asn
        675                 680                 685
Gly Thr Leu Lys Glu Trp Arg Glu Ser Asn Ile Ser Ala Ser Asp Ile
    690                 695                 700
Ile Trp Glu Asn Leu Thr Val Ser Glu Cys Lys Ser Leu His Gly Glu
705                 710                 715                 720
Tyr Val Gly Arg Ala Cys Gly His Asp His Pro Tyr Val Pro Asp Val
                725                 730                 735
Leu Phe Trp Ser Val Ile Leu Phe Phe Ser Thr Val Thr Leu Ser Ala
            740                 745                 750
Thr Leu Lys Gln Phe Lys Thr Ser Arg Tyr Phe Pro Thr Lys Val Arg
        755                 760                 765
Ser Ile Val Ser Asp Phe Ala Val Phe Leu Thr Ile Leu Cys Met Val
    770                 775                 780
Leu Ile Asp Tyr Ala Ile Gly Ile Pro Ser Pro Lys Leu Gln Val Pro
785                 790                 795                 800
Ser Val Phe Lys Pro Thr Arg Asp Asp Arg Gly Trp Phe Val Thr Pro
                805                 810                 815
Leu Gly Pro Asn Pro Trp Trp Thr Val Ile Ala Ala Ile Pro Ala
            820                 825                 830
Leu Leu Cys Thr Ile Leu Ile Phe Met Asp Gln Gln Ile Thr Ala Val
        835                 840                 845
Ile Ile Asn Arg Lys Glu His Lys Leu Lys Lys Gly Cys Gly Tyr His
    850                 855                 860
```

-continued

Leu Asp Leu Leu Met Val Ala Val Met Leu Gly Val Cys Ser Ile Met
865                 870                 875                 880

Gly Leu Pro Trp Phe Val Ala Ala Thr Val Leu Ser Ile Thr His Val
            885                 890                 895

Asn Ser Leu Lys Leu Glu Ser Glu Cys Ser Ala Pro Gly Glu Gln Pro
                900                 905                 910

Lys Phe Leu Gly Ile Arg Glu Gln Arg Val Thr Gly Leu Met Ile Phe
            915                 920                 925

Ile Leu Met Gly Ser Ser Val Phe Met Thr Ser Ile Leu Lys Phe Ile
        930                 935                 940

Pro Met Pro Val Leu Tyr Gly Val Phe Leu Tyr Met Gly Ala Ser Ser
945                 950                 955                 960

Leu Lys Gly Ile Gln Phe Phe Asp Arg Ile Lys Leu Phe Trp Met Pro
                965                 970                 975

Ala Lys His Gln Pro Asp Phe Ile Tyr Leu Arg His Val Pro Leu Arg
            980                 985                 990

Lys Val His Leu Phe Thr Ile Ile Gln Met Ser Cys Leu Gly Leu Leu
        995                 1000                1005

Trp Ile Ile Lys Val Ser Arg Ala Ala Ile Val Phe Pro Met Met Val
    1010                1015                1020

Leu Ala Leu Val Phe Val Arg Lys Leu Met Asp Leu Leu Phe Thr Lys
1025                1030                1035                1040

Arg Glu Leu Ser Trp Leu Asp Asp Leu Met Pro Glu Ser Lys Lys Lys
            1045                1050                1055

Lys Leu Glu Asp Ala Glu Lys Glu Glu Gln Ser Met Leu Ala Met
                1060                1065                1070

Glu Asp Glu Gly Thr Val Gln Leu Pro Leu Gly His Tyr Arg Asp
            1075                1080                1085

Asp Pro Ser Val Ile Asn Ile Ser Asp Glu Met Ser Lys Thr Ala Leu
        1090                1095                1100

Trp Arg Asn Leu Leu Ile Thr Ala Asp Asn Ser Lys Asp Lys Glu Ser
1105                1110                1115                1120

Ser Phe Pro Ser Lys Ser Ser Pro Ser
                1125

<210> SEQ ID NO 3
<211> LENGTH: 202001
<212> TYPE: DNA
<213> ORGANISM: Human
<220> FEATURE:
<221> NAME/KEY: misc_feature
<222> LOCATION: (1)...(202001)
<223> OTHER INFORMATION: n = A,T,C or G

<400> SEQUENCE: 3
gccttgggag ctgtgagaaa taaatatttg ttgttgtggc attttgttat agcagcccaa      60
atggactaag atacactctt ttggctctct cttcattcag tccaagggtg ttctgctagg     120
ttttggctac tcttcatttc ttttatcaaa tatttgttaa ggcttattag ggcctaaagt     180
ctagaggcat tctgctttac tattatgacc atatcttaat aacactggta tgagtaacat     240
actgtatgag taaataattt gttttagagc aatggttttc taaaaatggg agatcatagt     300
ttttagtaat taattgtgtt aaattactat taagagggtc aagtaataga tgttaagtaa     360
ttttttggat taaatagatc ttatcaacta gataatagag agattaagag ctgctttgca     420
ctcaggtttc atgtttttat tgcaaagatc aattgtgctt acaagaaaac actgaaggaa     480

```
attggggatt atatatacta attaataaca tccagagaat gataaaaata tcagtgtttg    540
tattcttgct gtgacaaaat acctgaagga aaagttcaat tttcttattt ttcattattg    600
attcatttaa taactttgat atgtaatagt ataggagatt aggaatgaac cttgcttgat    660
gtttcgcttt tcctcatttc tcacattcaa tccctgaatt ctatctttt tcaataagat     720 gtgtatctgg atctattcat ttctcttcat tcctattgcc acttctttgg ttcaggccat    780
catcatcccc tgattgaaat tatttaacat tctcctgatt tgtctcccgt cctccagttt    840
tgttttactc aattgattgt ctatagagta gccgggatat tttaaacctg attatgctga    900
cagtttgtca tttccctaag ggtaaagctc acactcttta aatggctcct gacgcttacc    960
gtgactgggc ctcacttctc atctcttccc tctgttctta cactttatgg tctaacctat   1020
gttgtatttg ccattccttg aatgtgacta gatcagaatc ttctgtttta acagtacttc   1080
cctaaggaaa tcttttctga tccctagatt agggtaggat gccttgctac ggctttcatg   1140
tcaactttta attcttcagt tataacaaaa catgcttgtt tgatttatct gctttctgtg   1200
atggcaggtt ttgtgttgtt tgttatggag tccctagcac ctatatagta cctgacacat   1260
agtaagaatt caatattttc tacaggaaag aatgaatata gaaagagaga cgatgtagct   1320
taggaaggct ttattgagaa gataggtctt aaaggatgag tacctatttt gattataata   1380
agagggtaaa tactacatag atggaaatat ttgtttacat gtgattttc attcagatgt     1440 gttatagtat acatacagca gaataccaag ctctgtgtct ccaacctgtg cagttagagt   1500
cagtagtttt tctaaaagta taatttggat cagcccagtt tcttaagact cattgtgact   1560
agtctccatc aaatgttgtg agtgaaagaa gggaaactat tcacaggtaa ataaagtgtt   1620
catagagtcg tgaattcagg ctattcataa tgtgagggct gtttcaggat aatatgttgc   1680
acttggtgtc ttaattttga atgtagttga attgactata atcttagtct ttttttttt    1740 tggtttgtgt tttctttagt tataaaacac aaccttttgt cacacggtaa agagaaagca   1800
tttccaatta taatttttga gatattgatt ctatattaga acactttatc aatcttaaag   1860
ttccctgatt ctgctatgtt gtggtaaaag aaaacagtac tcaaacttta ataaataaga   1920
cacagtgaaa atccatagta aaaatgccaa caacttacat aggtttcatt actagactta   1980
accgtgcagt tttagcattt gataatacca cattatcttt tgcatgtaaa ttctttagaa   2040
gaagatatta aataaaaaga taaatgtat gttggtatga agaatctgaa acataaatga    2100
aatccctgaa aattaaaagg tgaatatgta tttacctatt tactatttac acaactatca   2160
aagattgcca aaataaaaat cctgtatagg cgctcatcat tttgatgggt ggataagtcg   2220
tgatacccat agtttggaag gaagattcct tcaagagagt acaattttgc ttggtaaatc   2280
ttttgcatgt taaactttt agaagaagaa attaaataaa aatataaat gtatgttggt     2340 atgaagaatc tgaaacataa atgaaattcc tgaaaattaa agggtgaata tgtatttacc   2400
tatttactat ttatacaact atcaaagatt gccaaaataa aaatcctttt taggcactca   2460 tcatttgat gggtggataa gtgatgatat tcagagtttg gagggaaaat tcctttaaga     2520
gagtataatt ttgcttggta agtcataaag cctaaagctt agtcacatat agagaaagct   2580
gcctaataat taagagttga cattttaaca tggtatttgc aacagacaca ttggatactt   2640
aattaaatgg aaaactgctt attttttaaag gactgaaaaa attcaactct ccttggcaaa  2700
tgaagtcttc atagtatcag aaatggggaa atctgaagga tgtggctcat tctctgtttc   2760
gatgatgcag aattgctcta agcagtaagc ttacagtttt cagacagcat cagcaaatac   2820
aactgtgtca gtctctctta gtatggggtg tttgtaactg cacaggggag atgataaata   2880
```

-continued

```
gtatatgtga tttgatatct tgatgatggc ttaaacagat actgatggac agatctgttg   2940
tttgatattt ttttcactag ccctgaagat gctgagacat agagatggct gtgattatct   3000
tttgtaagac aggaaatgca gtctttaggg gtttctggaa atagaaaggt catgcagtct   3060
ggaacctgtg agccttttca atctctaagt catcaggtat gacctcatga attatgatga   3120
taatattaga atgtagggtg cttgcttttt ctagttctta ctcattgaaa atatattcat   3180
taatgtaatt gtttattgtc agactttcct taggatattt gaacaagtaa gatttatggc   3240
agctaaacaa tatgattatt agaaatgtgt gtgtatgtgt gtgcctgtgt gtgtgtatgt   3300
gtttaaattt gtgtttactt tagctttttg ggggagaggg cggtaaagga agagattctt   3360
tgaatgtgat taaagcaag gtttggggca cttcagattt ttccagatta agcctgaata   3420
gagtcaatct ttatatttta cttcaagtga taaaaatagt ataaatcgat caaactgata   3480
aggatacatc gtagctagct gcttacagat actgatatat tgcaaatatt tttattattt   3540
ggaatttctt aaccatagaa actgatgctg ctaccattgt agtgtgctac atagcaaagg   3600
aagtttggtg aatagaatca tctttgtcag catctgacct ataaactaat ttcctgaaat   3660
ttatgttgca ttatctgaac tgttgtaaag acactggttt taatcatttc tcagatctat   3720
tgaaatattg atgctcttgg tgcttttaag gtagatatat actaacgtat tgttcataga   3780
agaaaggaga ctataaatct gtttttcaca agaaagctt gtgacattta agcttgttga   3840 agatttttg acccagagag cttcgtcctt tgcttacttt catttcaaa ctgaaaatac   3900 ttgactatgt taaacatgca aatgatttgg atttcgatgt ccattttgta ctgaaactct   3960
gccatttatt ttaaactatt ttcacccatc aagttatata taatgcattt aactttgatt   4020
tgttacagca tgtcctcaga attatatact tggataagaa actacctata tttgacattc   4080
agattttgaa ggaaatatat ttcattttc aaaatattgt acatgcttct gcctcaatgt   4140
tagagaactt ttcaggtact ccatattaaa tgatcaaaaa gagagaaata tattgcagca   4200
gttctcaaca gcaagatggt tttgtcttta tgattctgta gcctgattgt aatttaatgc   4260
cttatcaggg tgaaatgaca tagattaaaa aaatgaatat atttaaggaa gtctgaaaca   4320
atgaattgat tcagttaagg ggtttctcct ttttaattaa aaacacattc tgcctactga   4380
tattgactat aatttatatg ttattcaggc tacttagcca gcttatattc ttattagtag   4440
ggaagattgg catattctta agcttgatta attttgaaat gatttgaata tacctttta   4500 ttgcaacaaa atatgtctaa tctgttagaa tttatttcca gtatttgcat gtattagtca   4560
ttatgagtac attctgtttc ttggcattgc tttgggattc ctcttggtat tggtttcaca   4620
gcattctgct attttcact gtattcctga cctttcaaga gaaccaaact gtaaagattt   4680
ttagttactt tctgttagtg gcattaaat gaggatatcg ataattttgt aaggtggaaa   4740
aaaattacta tttagaatt gtcatttctg tcacaaatca gagaaatttt tctctattac   4800
tatttcaaaa tatactacaa taaaagcaa agactggtta gaatgtagtt aaatgcaatg   4860
tcaatctttc ttcttgcatg gcaggataat cttgatcttt ggaatgataa aactgattgt   4920
aaacttgccc agtaatgatt ggtcatcttc cttacaaagg ctgccttcgt ttatactatt   4980
ttacatgcat ttcattatac atcataaagg ttttaaggt aagctgccta taaaaactat   5040
ttgagtaatt cttcaattca gtaaacatag taaaggctga gcattggatg atactgtatg   5100
tatttggtgt tatgaggaat gcagaaaaga aaaagtcatt tccggctttc aaggagatta   5160
gtgaatatat gcaatgaatt gtgttcacat tttgaattga ttttttgatag gcagtatgct   5220
```

```
acaatcagtt ttaacttaat ctataagctg atgaatccta gaaggagtta catgtaacct    5280
tttttcctca tgtaaatttc ttgatattag ataaatgaag gcttaggtca aactgtatca    5340
ttatgcatcc cataacttta ttgaaaattg cattaaagac ttttagagtg catagtttct    5400
cgtatagggc tttataaact gtgaatcagt aaaatagcaa aatagctttg catgttgtat    5460
aagccatcat tgtcagtatg agactgaagg tgcacccagt ccactggcag gaggcagaag    5520
tgtcagctca acatagagac ttgatcaatc ctgtctaatt ccaggctcag tgtgggtaat    5580
taagtattat ggaagggggtt ttgactttat agggataaaa cttggaaata aagagtagca    5640
agtatggaag tgtctgttac taactaggtc atttggagag tcctttgaat aaaatggggg    5700
aataggattt acctcaggtt ctgagaaagc ggatcaggac caactaatta tggaagtgga    5760
ccttagctgc tgcttggtga acagtcaggc attactctct tctctttcat tccaatatgt    5820
ttgctgaaag ttgcaggaag gtgggtggag aagatgcaaa gcccttgttt ccccagaatc    5880
ccaaactgga acacgctgcc tgatagtgcc tccaaagtgc ctgtttcctt gtattagagc    5940
aatagaaaat tgatttgcaa attcttctgg tttgtaatgg ctggctgcag taagaggctt    6000
gtgcaatggt tcagtgtctg gactgccatg ttctctgggt tcaaatctta gctatgctac    6060
ttactggctg catgatcttg gcttgtttcc tgatgtgtaa tatagggata ataatggcac    6120
ctacctcaaa gagttgtggt aaacattaag tgagttaatg tatgtgaaac acttataaga    6180
gtacctgaca tatatcaaac atattattgt caacatcctt tgtcgacaga ctttgttata    6240
gacattctaa gaggttggat gggctattgg caagactttg taacagtcat catgcagttt    6300
agttttgttc cctctcccctt aatctcttta tcaaataaga aattcagcca aaaatatatg    6360
ctacactgaa atatagttat aaaaatgcaa acaaagaaca acatgctata tctgattcaa    6420
ttctaacatt tactgacaat aagaattgtg acttgatgaa agattttgtg tttaaacttt    6480
acatctacct gctaggctga tccaaactct cttagaattc tatgtgtgca gattcttttgc    6540 ttctctgtat tacaccaact actttattca tgactgaaag attactagga ctttgggaaa    6600
atttaacagc aacttaaggt ctttcttgtt tattgtttaa gactaaaatt aagggggtaaa    6660 aaaaagcctt tctttaaagg cttaaaaaaa ataatagggg caaatttacc tagcatagat    6720
ttagtgatac ttagtcatca aaaatgtcca agacaaaaaa ttttaccgaa agtcaaacac    6780
aacttgtttt taataatttt atttcttggc atttttattc tagatgaaac actaaatgaa    6840
atatattata aatagaatgc tacatatata agtagaacaa ttcaagttcc catttgatag    6900
agtataatat tttgaattgc tggtgattat ttaatgtaaa aacatttatc tgcttaaaat    6960
tctcaataaa cttcaaagag aagtgagtaa tatgatattt ggattaaatt tacatgctta    7020
aatatggcat tttattacat ctctgaattt cacttctctt ctctgaagaa atttcctcag    7080
tgtgctgctg tttcccccaa attggcagag tcagttgaat ctcagaataa tgcaattttt    7140
aaaaacaaat atacaaaatc ctacaatgtt ctagaaagaa ttgtactggg caaggatata    7200
aaagtctgta ggtctctgcc ttcaggaggt cacaggtaat gggttgtaac tacaaaatac    7260
aagtaactat ggcagaatat gaaagtagtg aatgccatga ggtagtcttg aagactggcc    7320
aacatagaga gaaaggtca tttcaggcag aggaaacaac atcattaaag gtagggaggc    7380
agaaagcaaa taatagaata gttcattttg gctatagcct agtgggataa cttagactta    7440
ccacaggaaa ggtttgttgg gaccagataa gtgtagaatc ttgaatgcta gactatgatt    7500
tctaaactga gaacatttct ttgctgatgt acgtattcct ggaaaaaata aaataaaaaa    7560
aacaaaagag cagtacctat attttgaagt cattttcaga gctctaaccc tcttgagact    7620
```

```
ttgagaatga aaattaaatt cctgagtaga tttagtagtt agtagacaag gtaggggta      7680 gaaacaaact gaaggatttt aataaaattt tctatcaaaa ttgcacatga gagcatttct      7740
cagtctatcc acaagcactc aaaagtccta gatttcagat cctaagagac ctcctgcttg      7800
tccgtgatgt aaactccatt ttattggtac gtaatctgat ttagctttgg ctttgttttt      7860
gacatttcct aaagcaagga caatctagtg ggatcatttt aatacaatga atactcatgt      7920
tactatggtg aatagttgga taaaaaggac tttgtcttag ggaaaattgg aaattaaaat      7980 tgccatttg aatcacggaa gtcgctgaat atttaccttt gttctctgt tcatttaaaa       8040 atcataaagt aaaccatgtt tgcaaatact tttaatatcg ccttcttcta ctccatacac     8100
cagaggcatt ttagtattgc atgaggttag taaaaaagct ggataccttc aagagcaga      8160 tttcctttag atgtgacagc tgggatgtga cttttggtat cagatgcagg aagacgtcat      8220
ttgtacatgg taattgtgaa aaaattggaa cttattactc tcagtataaa tgatccataa     8280
aaagtatgtc agaagtaaaa ctcctggaat tctacaggga gagttaaaat aaaaccagac     8340
acaggtgctc atctgactct attttagaa caataggaga ctcatataac tgagaatgct     8400
ctgtacttcc tgtataaatc tacattattt gaaagtcgta ttttctagaa gttcctgtga     8460
agttgtactt attaatcttt gcaacttcac attgcctagg aaagagccat tcacctggta     8520
ggaacccaac aaattttcag tgcttgtctt agaatcatag tcccatttct gaaagaaacc     8580
ttgaatatca ttgggcttca agttgttcta aaaatgttta agcatttaaa catggttttc     8640
tttctcaaaa agcaaataga aggcatttag aggaaaagga ccctttcttc accttaagac     8700
ttttaaaaat ggcaatatgg gaagattaat aagaagaata agttaaggga gaattcaata    8760
ttcctccatg aaactactct ttctaaaagg caacagagac tggttccagt gaagcatatt    8820
atgatgtgtg gcgtgtaaat gtatatcatt atccctactc atcttttttcc ccaaattcaa   8880 tttaatactc ataagaattt attgaggcta ctgtataaca tggaggaaag ctgtatacca   8940
cagtagcaag gagctagggc tccagagcgg gactcctgtg ttatgatccc atatcttcca   9000 cttactggc aattttttatc ttaggaagtt acttaatctc tcttttcttc agtgttttca   9060
tctgtgaaat gaggacacta atacgttaat ctctagagtt gtaatgaaaa tcaaataaaa    9120
taataaatta atacttcaaa cagtgcctag agtgtttgat acagtgccta gcttttggtt    9180
attataatta tccccactga actaggtaaa tgctacaaat atgtatgtgt atatttgtgt    9240
gtatacacac aaatatgcat atatgtacac acacatactg tacatcctat gtaaacacaa    9300
ttttagtatg tatgtatgtc tatacatacg tatacattct accttaagta tatatagtat    9360
actgaaaaag aaatttagta gtttgcccaa gatcaaaatt gcctgcaaag gataggacaa    9420
tttgagtttc aaacccagaa agtctagctc tacagctgtt ggccttaact actgtttcat    9480
actgtttaga gtataaacac ctgaattaga tagccatga taaattagca tattctaaat     9540
gccaaattga gactaaagac atgaaggtaa actgaaacta ctgtgaaaga cttaatggaa    9600
gaattgtgac ttttatttga ttttaagttc tgggatacat gtgcaggata cgcaggtctg    9660
ttacataggt aaatgtgtgc caaggtggtt tgctgcacct atcaacccat cacctaggta    9720
ttaagcccag catgcattag ctatttttcc ttatgctctc cctcttctca cacacccctc    9780
agcagacccc agtgtgtgtt tttcccctgc ctgtgtccat gtgttctcat ctttcagctc    9840
ccagtgagaa catgtggtat ttggttttct gttcctgcgt tagtttgcag atgataatgg    9900
cttccagctc catccatatc cctgtaaaag acatgatcta attcctttct atggccacat    9960
```

```
agtattccag ggtgtctatg taccacattt tctttatcca gcctatcatt gatgggcatt    10020
tgggttgatt ccatgccttt gatattgtta atagtgctgc aatgaatata cgcacgcatg    10080
tatctttata atagaatgat ttatattcct ttgagtgtat acccagtaat agggtcaaat    10140
ggtatttctg gtgcaggtct ttgaggaatt gccacactgt tttctacaat gtgtgaacta    10200
atttacattc ccaccaaaaa tgtaaaagtg tttctgtttc tccacagccc tcgctagcat    10260
ctgttgtttc ttgacttctt tataatcacc attctgactg gcatgagatg gtatcttatt    10320
gtggttttaa tttgaatttc tctaataatc agcaatatta agctttctct aaatatgttt    10380
tttggctgct tatatatctt cttttgagaa gtgtctgttc atgtcctttg cccacttttt    10440
gatgggtttt ttttttttct tgtaaatttg tttatgttcc ttgtagagtc tggatactag    10500
gcctgtgcca gatggatgga ttgcaaaaat ctcccattct gtaggttgtc tgttttctct    10560
gatgatagtt tcttttgctg tgcagaagtt ctttagttta attagatccc atttgtaaat    10620
ttttgctttt gttgcaattg cttttgatat ttttgtcatg aaatctttgc ccgtgcctat    10680
gtcctgaatg gtattgccta gattttcttc tagggttttt ataatttggg gttttacatt    10740 taagtctttta ctccatcttg agttaatttt tgtaaaagat gtaaggaaaa ggtccatttt    10800 caatttctg cactatttat taaataggga atcctttctc cattgcttgt ttttgtcagg    10860
tttgttgaag atcagacaat tgtaaatgta tggtcttatt tctgagttct ctattctgtt    10920
ccattggtct atgtgtctgt ttttgtacca ataccatgct gctttggtta ctgtagcctt    10980
gtagtacagt ttgaagttgg gtagggtgat gttgccagct ttattctttt tctttaggga    11040
ttgtcttgac tataccagct cttttctggt tccatatgaa ttttaaaatt ttttttctaa    11100
ttctgtgaag aatgtcattg gtagtttaat cattgaatct ataaattact ttgggcagta    11160
tggccatttt catgatgttg attcttctta tccatgagtg tggattgttt ttcgatttgt    11220
ttgagtcatc tctgatttcc ttgagcagtg gtttgtagtt ctccttgaag aggtccttca    11280
cattccttgt tagctgtatt ctaggtattt tattctcttt gtagcaattg tgaatgggag    11340
ttcattcatg atttggcttt atgcttgtct gttgttggtg tataggaata cctgtgattt    11400
ttgcatgttg atttttttatc ctgagatttt gctgaagttg cttatctgct taagaagctt    11460
ttgggctgag atgatggggt tttctaggta tgggatcatg tcatgggcaa agacaatttg    11520
atttcttctc tttctatttg aatacgcttt atttatttct ctttgcctga ttgccctggc    11580
ccagaacttc caatactatt tgaataggag tggtgagaga gcatccttgt cttgtgccag    11640
ttttcaaggg gaatgcttcc agcttttgcc catgcagtat gatattggct gtgagtttgt    11700
cataaatggc ttttattatt ttgaggtatg ttccttcaaa cctagtttat ttagagtttt    11760
taagacgaag ggatgttgaa ctttatcaaa gtccttcttc tgcatctaat gagataatca    11820
cgtggctttt ttctttagtt ctgttcatgt ggtgaattat gtatattgat ttgcatacgc    11880
tgaaccaccc ttgcatccca gggatgaagt agacttgatt gcgatggata agcttttga    11940 tgtgctgctg gattcatttt gccagcattt tcttgaagat ttttgcattg atattcatca    12000
gggatattgg cctgaagttt tctttatttg ttatatctct cccaggtttt ggtgtgagga    12060
tgacgctggc ctcataaaat ggtttacaga ggagtccctc ctttccaatt gtttggaata    12120
gtttcagaag aaatggtacc aactcctctt tgtacctctg gtagaattca gctgtaaatt    12180
catctggtcc tgggctgttt tgtttgggag gctatttttta ctgcctcaat ttcagaactt    12240
gttattggtt attggttatt gattattctt cagggaatca acttcttgt gggtcagtgt    12300 gaggagggtg tatgtgtcca ggaatttatc catttctcct agattttcta gtttgtttgc    12360
```

-continued

```
atagaggtgt ttatagtatt ctctgatggt tgtttgtatt tctgtgatat cccctttatc    12420
atttttactg tgtctatttg attttttctct tttttcttct ttattagtct agctagtggt    12480
ctagctattt tattaatttt ttaaaaaaat cacctcctgg attcgttgat tttttgaagg    12540 gttttttgt gtgtctctct ccttcagttc tgctctgatc ttgcttattt cttgtcttct    12600
gctagctttg gggtttgttt gctcttggtt ctctgtaaat agttctttca gttgtgatgt    12660
taggatgtgg gtttgagata ttgctagcat tttgatggca gcatttagtg ctataaattt    12720
ccctcttaac actgctttag ctgtgtccca gagattctgg tatgctctct tgttctcat    12780 tagtttcaaa gaacttcctg attttttgcct taattatttt attcacccag aagtcattca    12840
ggagtgggtt gttcaatttc catgtagttg tgtagttttg agtgagtttc ttaattttga    12900
attctaattt gattgtgcca tggtctgaga gactgttgtg atttcagttc ttttgcattt    12960
gctgaagagt gttttacttc cacttatgtg atcagttta gagtaggcac catgtagtgc    13020
tgagaagaat gtatattctg ttgttttgg gtggaaagat ctgtagataa ctatcaagtt    13080
cacttgatgc agagctgact tcaagtcctt tgttgatttt ctgtcgtgat gatgagtcta    13140
atattgacag cagggtgtta ttatctccca ctgtttttt tattattata ctttaagttt    13200
tagggtacat gtgcacaatg tgcaggatag ttacatatgt atacatgtgc catgctggtg    13260
tgctgcaccc attaactcct gcttgagcaa tagtggtatc tcctaaggta aactttcccc    13320
ctcccctaac ccacaacagg gcccaaagtg ggttggtccc ccttcttnnn nnnnnnnnn    13380 nnnnnnnnnn nnnnnnnnnn nnnnnnnnnn nnnnnnnnnn nnnnnnnnnn nnnnnnnnnn    13440
nnnnnnnnnn nnnnnnnnaa tatatgtggc tccatcttgg ttcacactgc tactcagtgt    13500
actacaaatc acagtgagtt tgaatgccat tcatattact gcaaacgaca ttttattat    13560 ttttattgcc agtgcatatc catcatgcca gaacaagaaa ataagagaaa atgaacttt    13620 gattgtcatg cttttatagc acagtggagt gtgaattatt ttatttaatt agatgacaaa    13680
atatgtattt attatgtaaa gactctatag ctatgctaaa agaatagaat atatctccac    13740
ataaccagat taatcactca tcacaatatt cctgactcac aagaagacaa cagtcataaa    13800
tattagaagg cttaaaatgg aatctctcat tatagcagag ttttcctaca aaacaaaaag    13860
gacagtgaga cttcaaccaa tgtacatttc tgaatggctc acttgttagc caagtatgcc    13920
cttataagac tgtggcactc taaacagggc tttcacaatg tccacccaca caataccgtc    13980
cttaatgaaa agctcagtac cagtttcagg caatttaaaa atcttagcct ttattatatt    14040
gaaattaagt cgaattattt ttctattatg atccctttg aaataagctt ttacacattt    14100
ctaatgcttt cttcagagcg gctcatataa atcaatgatt ttttaaaaaa ttctttcatt    14160
tcgatttaat ctattaatac tttagatctc actctcaggg aaaaattact ttattgcatg    14220
taaagtaatt caaatagaat atagtttaca attttcttcc aaattaagct tgagcctgga    14280
taaaaatatt tttaagtgcc caacaatatt tagatattat ttgccatgtt tctattttca    14340
taggaagaga taatatgttt aataaaaaat acatatctaa aaggataatc tgatgttgta    14400
aaattataaa ttctaatttt ctgtcaaaac aaccctgaat gtgaacttat cagaatcttg    14460
tctgtgtgac tgcaacccct cccccaacct taaaaaacat accaccagcc ccactctcca    14520
ccagtgtggc caaaccaagg gaagtgagaa gcaggaacat agctacacag gtcagagcta    14580
aatattaaga gtaaaatag tatcttgagc tttcagaacc acaaattttc aaagtgagcc    14640
agaggacaga gcagcagctg cattttcaaa cagaagcaac tacattttc taatcaactg    14700
```

```
ctgtgttatg gaacatgaac tgcaggaaat gatggactaa tgtccttta tgtatcagat   14760 aagcaggagg aagtatcagt ggtgtgcttt acttggtgag tgaatcttga taaacatatt   14820
caataaatat cttccactta tgtcctttaa ttcagtacaa tgcttttaa aaaatattca    14880 acttgtgtgt acatcgacca gaaaatgttc tatataaaaa ctgtattttg cttgggtttc   14940
gagatgaatg tttcataaga tatctatata tgtattaaaa ttatttaaat atgaggaaaa   15000
agaacttgtt tgctgttggc gatgaaatca tgtttaatta tagtactgaa aaaaatgtgc   15060
caagagtaaa caaacttgtt tagtgctgct agtgtttagg tgagaaccat tgcttgaaga   15120 gttgggaca ctgggagcaa catagatggt caatgaaaaa atgacagaag actgatgtca    15180
ccaaagtgtg gagtaggaaa ccttcgtccc caccacaaac acaccaattc aggaacaatt   15240
cacagaaaaa ttccctttgt gggaaatcca gcaactaatt gaagggctcc tgcaccctgg   15300
gtgaatgcaa aatcagatcc atcgaagctg gtgaggatat tcacgacagc tgtctgccaa   15360
aatttctacc cccaacgcaa caccatacaa ttgggaaaag agtctcagct ctcagcttct   15420
cccagaggag gtttgtacat ccaatacccc aacttcgatg ggggctaccc aaaggactgg   15480
cttctgtctt ctctgtctta aagtgctaat ggtgtggaat tatctagcca cctgggggag   15540
aatagagatg gtggcttaga ttggtagcca ccatagcttt tcctccctag ctcagagcat   15600
agagcaagca aacaaaatcc ccacctttca gcttctccct ggggatggaa agagttggta   15660
catacattaa actttctggg ggttttccaa aggattggct gaaatcccaa agaattcagt   15720
ctcactcatc ctggtgcact cacaagacct ggcaaaccct agacacctgg ggctacaaga   15780
aatacacaag caaataagtt gaacaagcat gaggtttaag aagctttaga atctcttcct   15840
ggacttattg gtgggatct tccatataag gccagctctt tgtgaagact cagagagaag    15900
tctgctttat ctgatgcaaa gacaccaatg catagagtca agtaagatga aaaaacagga   15960
aaatgtgttc caaactaggt aacagaaaaa tctccagaaa ttgactctaa tgaaacaaag   16020
atacacaatt tacctggaaa agaatttaga ataactgtca taaagatgct cactgaggat   16080
aagagaacgt tgcatgaaca aagtgagaat ttcagcaaag agatagaaaa tatcttaaaa   16140
gtaccaaaca ggaatcatga agttgaagaa taaataatt aaattgaaaa attcactaga    16200
gggattcaac aacatactag tatcaagcta agaaagaat cagtgaactt aaggacaggc    16260
cattggaact tgctgagtca gagaaacaaa aaggacaaaa taatgaaaaa gaataaaaaa   16320
agcttaaagg acttacgaga caccatcaag tggatcaata tatgcattat gagaattcca   16380
gaaggagaag agagaaggaa agaaccagaa gatttattca aagaaataat agctaaaaac   16440
tcccaagtat ggaaaaggaa atgtgtaatc caaggacccc caaaaaggaa aacttagaga   16500
tatcaacact aagacacctt ataatcaaat tgtcaaaagt caatcacaaa gagaaaaagc   16560
aacaagggaa aagttacttg ttcgggtaca agggaaattt cataagagta taagtagatt   16620
tttcttcagc aacttttttg cagatgagaa ggaaatgaga tgatagattc acaatgctgg   16680
gggaaaaagc caaccaggaa acctagacca aatgaaactg tccttcaacc aggaaaacta   16740
gaccaaatga aactgtcatt caatcatgaa agagagataa agtcttttcc agacaaacaa   16800
aaactaagga agttcatcac caccagacct ccctacaaaa aatgctaagg gaacctcctt   16860
aacttgaaat gaaggacac taaacagcaa caagatagca taagaaagta taaaagtatt    16920
ggtaaaggta aatatataga caaatgcagg accgtaatac tgcaatagtg gtaggtagac   16980
cacttgtaat tcaagtaaaa aagttaaaag acaaagtagc aaaatacttt caataactaa   17040
aatactttta ataagtaaaa ctatgttaat agatacacaa tataaagaaa tgttaactgt   17100
```

```
gacaacaata acaaaatgtg tatgggaagg agagtaaaaa gaggcatatt tttgtatgtc   17160
attgaactta agttgttatc aggaaaaaat agactgtcat tactataagg tattatataa   17220
accccatggt atctaatgag aaaataccta tagaaaggta tcaaagattc caacaaaaa    17280 aaaatcaaca aaacatgaaa aatgagagca agagaggaaa aaatgcacaa ataattaca    17340 aggctaacag aaaacagtac atgacaataa taaatccttc tctatcaata attactttaa   17400
aactaaataa attatacttc ccaatcaaag acataggtg gttgaatgga ttaaatgtat    17460
aatggaatca catgctgtta tcaagagact ccctttagaa tttaggctca atgtgaaaga   17520
atggaaaaaa aaattccacg aaaatgttaa tgaaaaacga gcaagagtga ctatacttat   17580
atcagataaa atagactata agtcaaaact ctctcaaaag actgagaaag acatcttata   17640
atgataaaag gatcaattca ccaggaatat ataacaattg taagtagtta tgcacccaac   17700
gattaagcac ctaaacatat aaagcaaaca ttgacaaaac tgaagagaga acaggcagc    17760 aacacaataa tagtaggata tttcaatacc tcattttgaa tgatgggtaa aacatattat   17820
ccattaccca cgggcaaaac agagcaaaag gaaataaagg acttcaacaa ccttatagaa   17880
aaaaatggac ccaatagaca tgaacatttc actcaatagc agcataatac acattcttct   17940
caagtgcagc cagaatattc tccagaatag atcacatatt aagctgaaaa gtatgtttta   18000
aaaatttaaa gtgatcaaaa ttgtaccaac tattatttct gactacaatg gaatgtgaaa   18060
gtagaaatca atagccatgg gaaaactgaa aatattataa atatgtggac attaaacaaa   18120
acactcttga acaactaatg ggtcagaaag aattcaaaag agacattaga aaatatcttg   18180
agagacatga agatgaaaac ataatatacc aaaacttatg gtatacagcc aaagcactat   18240
taaaagataa gtttataatg ataaaagtct atatgaaaaa agaagacaga tctcaaattt   18300
gcaacctaat tatacatttg aagggactag aaaaaaaaaa cacactagac ccaaagttag   18360
ctgataggaa gaactagcaa agatcagagc agaaataaac aaaatagata atagaaaaca   18420
ataggaaaaa atcaatgaaa ttgggttttt ttttaaaaga taaaattgac aaaacctttgg  18480 ctagacttag aaaaaagaga ggattcaaat aaatataaat catatattaa agaggaggta   18540
ttaccactga tatcacataa gttaaaaagt tcataagtat ctatgataaa caattatatg   18600
ctaagaaact ctatgacctt aaaaatggat aaattcctag gaacataaaa tctaccaaac   18660
acgaaacaag aagatataga aaatctggac agacaaataa caagcaagaa attaaatca    18720 gtaataaaag acctccaaac aaagaaaatc ccaggaacag atggcttcac tggtgaattt   18780
taccaaacat ttgaagaaga tttatgtcaa acttttttt atcttgaaga agaggaaata    18840
cctccaaact cattgtatga tgccagcatt accctgatac caaagccaga caaagacact   18900
gcaagataag aaaattacat aataatatct ctgatgaaca tagatgcaaa aattcttaac   18960
aacaaaaact acctagcaag ctgaattcaa cagtacatta aaaagtcata tgatattttat  19020 tataggaagc aatggatacc ctgggctggg gttcattata tacaaatcaa taaatgtgat   19080
gtgccacatt cacagagtaa agaacaaaaa atatattatt atttaacatc gtttcatgat   19140
aaaaactctc aacaaattag ctgtagaagg gatgtagctc aacacaataa aggccatata   19200
tgacaatcct acagtttaca tcatactcaa tgatgaaaag ttgaaagctt ttcctctaag   19260
ttcaggaaca aggcaaggat gtctactctt gctacttcca ttcaacatag tactagaagt   19320
cctaggaaga gcgattaggc aagaaaattt tttcatgtgc agatgagaaa aaatgtatat   19380
tctgtggtcg ttgaatggaa tgttcagtag atgtttatta ggtccatttg gtcaagagtg   19440
```

```
cagtttaagt tcagagtttc tttgttagtt ttctgctttta atgatctgtc tagtgccatc    19500
attgggatgt tgaagtcctc cactgttatt gtatatctgt ctgtctcttt tctgaggtct    19560
aatggcattt gctttataaa tctgggtggt caggtattgg gtataaatat atttaggata    19620
gttaaatctt cttgtagaat tgaactcttt gtcattatat aatgttattc tttgtctttt    19680
ttttaactat tattggtata aattctgttt ttttctgatg taagaatagc aacctatgct    19740 ctttttgtt ttccattgtg tgatatacct ttctccactc ctttactttg agcctgtggg    19800
tgtcctttca cattagatgg atctcttgta gtcagcagat gttgagtctt gtttcttaaa    19860
tgcaatttga caatctatat cttcatttag gtcatttctg ttcaaagtta atattgacat    19920
gtgaagtttt gttccaatca tagtactgtt agctaattgc tttgtagtct cagtggtgtg    19980
attgctttat aggatctttg gattttgtac ttatatgagc ttttatgaca ggagagtatt    20040
gtcctatatt cttttatgac ataaaagagt atactctttt ctgttcgaag tttatgcttt    20100
atgacataaa agagtatact catttctgtt caaagttaat attgacgtga aattttgttc    20160
caatcatagt attgttagct agttgctttg cagtctcagt agtgtaattg ctttttagga    20220
tctttgagtt ttgtacttat atgagctttt atgacaggag agtattgtcc tatattcttt    20280
tatgacataa aagagtatac tcttttctgt tcaaagttta tgctttatga cataaaagag    20340
tatactcatt tctgttcaaa gttaatattg acatgtgaag ttttgtccca atcatagtat    20400
tgttagctag ttgctttgca gtctcagtgg tgtaattgct ttataggatc tttgaatttt    20460
gtacttatat gagcttttat gacaggagag tattgtccta tgttcttttta tgacataaaa    20520 gagtatactt ttttatgaca aagagtattg tcctttttcc ccacgtttac aacacctttg    20580
agcatttctt atagcaccag tctcatggtg atgaattttc ttaatatttg cttgtttgag    20640
aaagacttta tttctccttt gcttatgaag cttagttagg caggatatac aatttggggc    20700
tataattttt tgtcctcaag aaggctaaaa ataggccccc tatctttttg gcttatatgg    20760
tttctgttga gaaagccact gctagtctga tggaatttcc tttacaggtg acttgactgt    20820
tctctctaac tctctttaag atttttttctt tagcattgac cttggttagt ctgatgacta    20880
tatgccttga tgatgttcat cttatatagt atcttgcaag tgttttctga atttctttta    20940
tctggatgtc tacctcccaa caagatcagg gaaattttc tgaatgattc ctttaaaatat    21000 gtttccaaat tgcttacttt tccttctttc tcagcaatac ctataagcta taggtttggt    21060
caatttaccc cctataccat ctttctcaaa tattttgttt attttttaaaa tgcttttcta    21120 tttattttg tctgactgga ttaatttgaa agaccaatgt ttaagctctg aaattctttc    21180
ttctacttgg tctagtcttt tgttaatgtt tcaattgta cattgaaatt acttttgtga    21240
atttttttat tttcagaagt tctattttta taaatatagc tatcttgtct ttcatttct    21300 gagttgttct tctggtttct ttgtattggt tttcaacatt ctcttggata tcattgcact    21360
tctttagaat ccgtatcttg aattccttat cagtcatttt ttatttttgtt taggatccat    21420 tgctagaaat ctagcctgat cctttcaagg tgttaaaaca ctctgtcttt ttgtaccact    21480
ggagttcttg cactgattcc ttcccatgcg aaggagttgt tgcttctaag ttttgaattt    21540
gctattgttt gaatgggact ttatcatgtt tattcttttt tcccttgagg gtatgactgt    21600
ggtgtatgtt gtatgtgatt gtttggcttc ttttctgggg tttctcggtg ccaagactct    21660
gcatgggctc cttggttatg gatagccttt gtgtggtggc tttctcaaat gctgcttgtt    21720
gtagacatgt attgggcata tgagccaaca cactattttc tgtgtgacta ggagagcaga    21780
ggtctcagta aacttatctt gtacactagt actatacct tctgacagta ggttttttat    21840
```

```
ttggtggtgc aattcagtct tcagtcaagt aggaggtgct taagagtaag aatccactca   21900
ccctcaggca gtctaatgat gaaggaagac aactgtccta attgaggtta gtgtggggag   21960
cttgtgttgg agtgaactgg tcttggtggt aggggcaggg ggcctgcatt agccctcat    22020 cctgggcagg caggaatgtg atccgttttc ctatcacacc tttctgtcac agggctcatg   22080
atcttcagca tatagacatt gttctttggc tcccaagctg aagtgtgact gaggtctgga   22140
gaaatgcccc tttggtggct accaccaaaa tgagctcagg gcagagcctc ttcccagagc   22200
ccagagcaaa cagttttca acttgtctgc ccttcgttgc tgggacactg ccattctgtg    22260
ttgggatggg gagacaggtc ccacctttca tgcatgccta ggtggcattg gctcactttc   22320
aatgaggtgt agctgccacg aagagtgctg gaaaggctgt ctccaagtgc aatcaggtca   22380
gccctcatca ggaaaaagcc tctgctgcat ccacaacagt gcctgcactg agggctagat   22440
ttccatggaa cctgcagctc cccagagacc cgccagtctc ctgtggttgc caaagtcaga   22500
aggggttctg aggtatgttt gcaggggatc ttgtagtgtg gcaacacaag gactaaggtt   22560
ccttggacag ggcactggcc cacaatgagt gcacaaccag tgtggcacct gccatctcag   22620
ttagggcctg aggggagtgt gggcacacca gcacgagctg gccacctgag gctcccaccc   22680
cagagagttc ccaaattgcc accaactgca ttgcctggga tttcaagggc agaggggttc   22740
tctgacaatt tgtcagtcag cagttagtca caggagtgag gggagcagag aagcacccca   22800
acctatcctt tacatgggac tctgagttcc tcaggagtca gtgtctgcca gacttttgct   22860
gctttccttg tctgcacccc agtttcttcc catgggctct ctgaaagctc gtggctctct   22920
tccctcagct ttccatttgg atcatgacca ttcaactgta actttgatct ttctacaaac   22980
tggtgtctga catctctagt cagccatctt gaaaaaaaa agctacatta aagttataaa    23040
aataaaagta attgcactgt gatgttacaa aggctactat atcactaggt gacaagaatt   23100
tttcagccct attatagttt tatggtacca ctatttttata tgcgatccat catttgactg   23160
aaacatcatt atgtatgact gtacataaca aattgcgaat agaattagaa agtgctttct   23220
acttctggaa atcaatgttg tcttcacaga gacagaggtg ggctttgaag gataaatagg   23280
agttcaggag gcaaagaagg aaggatctgt tatattctgg gaatggcaaa tatgatgtgg   23340
ataaagcatt gggattgtgt ctgggggcat aaaatgtgac tggatataaa gtttaaatct   23400
ttacataagg taggtcaaat tgtggagaat gaattaatcc ttgaagtcac tctatctgat   23460
aagcacatta ttatctccat ttcacagata aagaaactaa ggtacagaag attaaatgac   23520
ttaaataggt cacctgacta gtaagtcgta tggcagtgat tcaaacccac aaggaagact   23580
tgtacatatt tattgacttt ttcatgatga ttttttaaaaa gttgagaata ttctattata   23640
aagcaataaa gaatttgata tttagtaacc atatcacaat agttttacaa atgttttagc   23700
aaaagtttga aagttttata gttagaaaat tcccattgaa ctaagattta ttcccataat   23760
taggaaagcc actctcccat tggagactac ttttattata gcctcatgtt ctcttacttt   23820
aaattatctt ctctgctgta ccacaaaata aaaagtctta taatttcctt atttcaaatg   23880
ttttttcttt gaaaaagaac catttatttc tggtattatt agttgattaa tttttgtgca   23940
acttagtagt gttgatatag gatcaatgtc aactggtgga gcaattctaa gggtgtttgc   24000
tccattagta ataaccagtg gagttaatta attacacagg catttgaaat tgtaggtttt   24060
gcctgttaaa cactggatat ttcaggatga gaaatgtgga ggtggactaa tactgaacat   24120
tttatttcag aaaatacagc caatagtaaa tttcagtctt ttattgagct atctttgaca   24180
```

```
cctgtgcaca tcttataata aactgttctg tttttcaatg ggtatcctag gaacaagaac    24240
taaataagag acaattattt taaagtcttc aataatagaa tttacttttg tgtgggcaaa    24300
agacacgaac agacacttct caaaagaaga catacatgcg gctgacatag gaaaaaaaag    24360
ctcaacatca ctaatcatta gagaaatgca atcaaaacc tcaataagat atcatctcac     24420
atcagtcaga atggctatta ttaaaacgtc aagaaacaac agatgctggt gaggttgtgg    24480
agaaaaagga ttcctttaca ctattggtgg aaacgtaaat tagttcaacc attgtggaag    24540
acagtgtggc aattccttaa agacctagag gcagaaatac catttgaccc aacaatgcca    24600
ttaatgtgta tatacccaaa ggaatataaa tcattctatt ataaagatac atgcacgcac    24660
gtgttcattg tagtgctatt cacaatagca aagacatgga accaactaaa atgcccatca    24720
gtgatagact ggataaagaa atgttgcac atgtatcccc tgaaatgcta tgcagccata    24780 aaaggaaca agatcatgtc ctttgcaggg acctggatgg aactggaagc cattaccctc     24840
agcaaactaa agcagtaaca gaaaactaaa taccacatat tctcacttat aagtgggagt    24900
agaatgatga gaacacatgg acacatgaga ggaaacaaca cacactgagg cctgttggag    24960
ggtaggaggt gggaggaggg agcacatcag gaagaatagc tgatggactc tgggcttaat    25020
acctagatga tgggttgatc tgtgcagcaa accaccgtgg tacacattta cctatgcaac    25080
aaaactgcac atattgccct tgtacatctg aacttcaaaa taaagttgg agattaaaaa      25140 acgaaattac ttttgttcca gaattaactc tcagatgttc catgtttcat cactttattt    25200
tttcacataa tttgtgtatg tgactcacat caattcattt tgatatataa ttgatttctg    25260
atattttgtt tgtttgaagt gagaggtaac tgggtaatta tctatactct gcttttacca    25320
tgcattttat ttccaggtaa atttgaaaaa tctaaattat ttttctaaat ttgatcatgg    25380
tttatttgac agtttacaag tacttgcagg catgtgtttg catgtggata ataacaaata    25440
actaagaaat cttacaaaag tatagcttca taatttgggg gtcctggtta tacattttac    25500
atctctaagt taggaactca tattgttaat ctcccttcat agttccttat aactaaactc    25560
tgtttagtat gagtttctac ttatcaaagg cataataact cactcactat ttggtatatt    25620 tgctctcttaa tgtgacatga catgttttct gtggataagg agaactgtgt atttgtgcgt    25680
atatgtatat ataatgtttt caaccaatca ctatttcaga gaaaaaatgg atgaaaataa    25740
acttgtattc attacattaa atataatcct atacatatta agaggaaatt ttacagcagg    25800 aaaattgttcc tttaatcatt attttttcttg aaaattattt aatacttttta agacaaacca   25860 cggatgacca aagtctctta atattacca catagattta tattaacact atattttgt       25920 tttaagtttt ctagacatct gagacttaaa tatgttctta tttaaagact ttaatagtat    25980
ggcagttgta ccatgaaggt ggcatagtga aggagatcaa cttagtctac tttttgacta    26040
aattcttaaa tctctatttc agctgtcttc cccctagaac tatagcttaa aagctcctca    26100
gctgcataca gcacatagcc ttcacaggtt atcgcctttc tatagagtcc tctcacaata    26160
taaacaggtg tagctaccaa ttaggacatg tctcaagaaa ttgttaacac tcaccaatat    26220
taattaagtg ctaataggt actgagccaa acactgaggg tgctgagcca aatttccatt     26280
tcacattctt cattctccaa ggaggtttag atactggtgc tgtcaatagg gtgcttgagt    26340
tctagaaccc atggggaaaa ataaaattact gtggccactt tgcacataaa tgtttaaatt    26400
taaaatatca attgatataa atactgataa taatgaataa atattaaata ataattgaaa    26460
gggatgatgt tcttggtttg ggggataata cccataatct tagcagtacc agaatcattg    26520
caaccctaat aggattaatt ccatttttgga atatcagtat tctgagatta ctattttgaa   26580
```

```
tgttctcgtt tatattttct tcaagtaaac ttttttgctt cttcattctt tttcagaaat   26640
tttattattt ttaaaattga cagataaaat tgtatgtatt tattatgtac aacatgatgc   26700
tttgaaatat atatatctat gcactgtaga ataactaaat atagctaatt aacatatgcc   26760
ttacctcaca tagttattat ttttgtagtg aaaatactta tccactctca ctatttttca   26820
ggaatacaat atgttattaa ctattgtcac tatgctgtac aatagatctc ttgaacttat   26880
ttctgctgtc aaactagaat tttatatcct ttgactagcc ccttcctcag ccccccaagt   26940
gccccagccc ctagtagcca tcattctact ctctagttct atgtgtttgc ctcctcgttc   27000
tatctttcct cttcctcact acctagtcat tcctagtgcc cacagtgtgt cacaactgct   27060
gaaagcatgg tgaaaaaata tctgttttct tttcttccct tctctctctc ttcttaatgc   27120
gtttcaggtg ggaagataat aaaagaaacc aaaatgattg aaatcattat tagcagaaag   27180
taaaatttta atttcctgct ggtacaataa gcttttgtct gggctctggg gacaaaaaga   27240
ttatgaatat tcttttgtgc cactttcaaa ctgcttctaa atatcttagg tacatttgta   27300
atatgaaaat atggcagcct tattagcaaa ataatttcta attttgagct aaattgtata   27360
agattatgca tgttttttctt ttgcataact caatttgttt cctgtaatga taattgccat   27420
gattgaatta gaagataata tagcataaaa aaattttatg acatcacagt gattaatcca   27480
aaactatcag catcaatgaa gttaataaca atattgttca tgaaaacaaa ggtcatgttt   27540
atgaaattga acattgtttt atatgtgagt ggcctatttt tctcatgcta ctgcactaat   27600
tttatcttag ggtttataaa tatgaatcct aaatattaaa gtagtgctat ttatcgccaa   27660
ctctagtggc cttctgtcct cagccttttt gaattcacaa aattcctgta aactgtggac   27720 tatttcccc aacttacaaa taagaaatt gaggttcaaa aaagtaactc gccaataaat   27780
aggttctaga tatctactat acagcatagt gcctatagct aaaaatactg tatcgtatac   27840
ttaaaatctt ccaagagggt ggatcttatg ttgtattctt accacgcaca tacaaataat   27900
aataatgata gtaaaggcat tagggagctt tgggatgtga tagatatatt tccatgtgta   27960
agtgctgtaa gagttcacaa gggcataacc caagtgcccc agatatgcc cttctgtatt   28020 gaatatacct aaggtagaca cactgaagaa gatggatata tgaaaaagtc taatatacta   28080
gccttattga ggtaaattga tcagttcaca ttgggtatag aacattgtca gcaactagaa   28140
aaagaaaatg aggttgttcc gtctctatgt tcacacgagg catgaggcag cgacgttcta   28200
ataatcctcc tgctcttctc ccttacccctc ctgcctcctc aatagcctta atttgtagca   28260
ttttccaata tctgtggtta aattctttcc ctatggccaa ttttataccaa ctgaggtgtt   28320 ttcccctgaa cataaagtta ggaagagatg cgtgtaactg gcactggtga gctggggtaa   28380
gccagctcta gcataccact gctgccaggt tatctaccgt agagtgtaag ccatagtttt   28440
catcaaaagt gtcctgcaaa aaaaaaacat tgaaaaatga gaaacagttt ctgtatgtca   28500
atataagtca attttattg caatgaatat tgaaggaggt aaaatttttt tttacttcct   28560
gatgaaaaca gatgaagtat gttaatatat gtccctgggc cctctgtgtt tctgtgcctc   28620
ccctcacaag gcatgctatt tttctgtacc tgccaataca tatcttatct tccttacagg   28680
cctctctcct ctgtttttga ctatttcagc ctactccagc ttgtagtgct gtagaaaagg   28740
ctttagattc atttatttat tcaagaaaca cttactgagc ttttaatatg ccaggtactg   28800
agaatataaa catgattaga cagaccatgc tatagctttg attgtatggc tttggggcaa   28860 ttgcttttttt tgttttttaa cttactgagg gatgactgac atgtaaaaag ctgtacatat   28920
```

```
ttaatgtata caactcaatg agtttggaat atacacccat gaaatcatta ctagcatcaa    28980
agccacagat atatctatca cctcccaaag cttcctaatg cctttattat tattactatt    29040
atttttatta ttattagtat gtgtgtgtgt ggtaagaaca caacataaga ttcaacctct    29100
tggaagattt taagtataca atgcagtatt gttagctata ggcactatgc tgtgtagtag    29160
atctctagaa cctatttatc ggaaagttac ttttttgaac ctcaatttca ttatttgtaa    29220 gttgggaaa atagtccata gattgcagcg attttgtgaa gattaaatga gaaaatataa     29280
ataaaacact tagcatagta gatggtacat tgtagatttt ctataaaggc tagtttcttt    29340
tttttaactc taaactctta tagctatctt aagtgccaaa tgaatcggca tttatttata    29400
ttctgccttg gatgttgctt gccttctcta gtatcctcag cttgtacctt tatgcaggtt    29460
cttatacata atttgttgtt cctatcaaca ttgatcacaa tgtagtatca atactttctg    29520
attcttggtt cttaatttgc ctgcccattg agatattggt cataagttaa cattttccca    29580
ttattttcca ttttgaatca cttttcctggt actttcaatt ttgtatttta tatcctgtcc    29640 atctgtatt tataattta aatttttct tccaaataaa ttttagcatt cagctattgc       29700
tgtgtcacaa tccatttcca aacgcagtgg cttcaaacag caacatttta tttaggtcat    29760
aattctgtag gttgtgaatt tgggttggac tcagctagtt agttcttcta atgtgaatca    29820
gctggcgccc gcttctacaa tcagctgatg atttcacaac tgaggccggc tggtttgtga    29880
agtcctcagc tggatgactg ccagctaggg cttctctctt catggtctct gatctgatcc    29940
agccagctag gctgggcatg tttacatggt ggcatgactt ccagaagcaa cagcaggtaa    30000
gaacctatgc ataagaaccc ttcaaacctc tgtgtcacat ttgctaatgc cccattgatc    30060
cagattcaag ggttggagga atatattcca actcttgttg gaacaagctg ctaaaatatt    30120
gtggccattt taagagaatc taccacatta tctatgtatt tttcatttgt aaacatctat    30180
acagaaatgc caagtgtttt tatctttgat ttcagatatt ttaattgttt cacagttgaa    30240
tttcataaac tttcctcatg gaaatctgtt tttctcctca gcaacttctc ggttttttcca   30300 ggcaagcctt tctgttctta attactgtaa ttttcagaat gagctacttt ctacatgtgc    30360
acatgtcttt taaattaata taatacaaaa ctaaatctgg aaaatttag ttttacattt     30420 ttttgttcat ctcctaaacct atttccctga agcaaagtga caggtctgtt cagaattat    30480 aatttaatta agatgagatt ggggaggtaa ggaagtacca ctttctcttt tgcattcatt    30540
ttttaaggat ctcaggacat atgttgatct atttcttc tcttccttgc aaattaaaac      30600
aaaatgtttt aaaataaatg ttttaaaata atagtgaaat tgcgagcttt gctgattata    30660
aaaatatatg ctctatgtca tcttgccttt tcttccctgc tctaatatga acttcacatt    30720
atcccttcaa ttgctcttct gttttgctc acgttatctc cttttctaa attttcact      30780 cctctgctga tgtaaaacct gcttattgtt taagagcaac tcaagtccta catcctccat    30840
gaaattttca ctgattgccc aggttatcct tgattttact ctattgtgaa ctcctacagc    30900
atttgatggc tggtaccaca cagtaacatt tgcctcatta caggttggta ttgtttaatg    30960
cttttaatgt gtattttaa tttgtattgt ttgctgctgt tttcattgct gggcttgatt     31020
cgttagccag tttttttttt tactgatttg cactcctggc tctctaagtg ctgtaaatgt    31080
ccaggattaa gctgttttat aatataccaa aatttgggagt tctcaagtca tttttttat    31140 aagaaaacac atatttttag gtttcattca cttattcaag atatattaaa tgcttattat    31200
gtttcaagat taaaaataaa cactatctca agacacaaag ttaatttagt tgctatgttt    31260
tgctcaagac ggtgttataa acttgtaaga aacagtattt ttgaaaatgt gccacagtac    31320
```

```
cttctaaact agtaaatctc agttagtggc cctttggatg agcaacttta ggactttcaa    31380
gatttctact ttctatctag aatagtcata gtcatgaagc ctttgtttt ataatgatta    31440 taaatacccct tcccagggtc aggtaactat gaccagcact agtttaacac tgtcttttc    31500 tttagcaaa acaacacaag gaacaatggc acagtagcct agtaatacct ctttgctata    31560
aacatacact cactcccatc ctctcagtct ctttgtttct ctgttactct cccttagcag    31620
aaattttcca ttggacttct agtgctttga tgtattatga tcaatgatga cttgtgtttt    31680
ctgactctgt tagagtctcc atggaattaa agattatatg cttattcagc ttaatgtact    31740
tgaccttttt gtatgattga cacatctaaa tttctgtagc aactcagtca ttatgcaaca    31800
gctgtgttat attcatttca tgtaaaaagc aaaaacaaaa gacatagagt tctcttcaag    31860
agtagatacc ttgaccccctt ccctcccagc taaataaaga atagtttatt aataacatta    31920
ttaatcagtt tccaaatgcg tctcctttcc tcaccgcatt ttataaacat tcagtatact    31980
gtgaccatag tcacatcaag aatcattca atactgatcc ttattata attaaaatat    32040 tcaataattc tgagtctgtt gaacataata atagccacac aacttaagtg tcaaacatct    32100
aggatttgtt agcaagattt gtgctcagaa aataatatgt acaaaccttt gattttctta    32160
atgatgaaac tgtattttgt ctgaattgac atatgtgtct ttaagttaga gagaaaaaac    32220
cttgacattt ttctgtgact tttccttatc aacagctgtg ttctacctgc gtttattttt    32280
ctcagaattc attatgaatt ctgtataggc cttcagaagg cctatacagg ctttctaaca    32340
gagattctat aggaaaaagt tttggttaac tgtttgaagt attagttgaa gaaggcattc    32400
tagataaggt tttacaagac agaagaaaag aatcaattca tttttagttc tgagcctgaa    32460
ttgtggaaac tgtactaact gcagataaac tctgaataaa ttctagtgtt ctctgcttat    32520
ctcaaaaaat cttttctttt aatgatactg ttccatgctc actaatgttt tcaaaacata    32580
ttcatatcta aatggttttg tattttatt aaatttgga tttttgcat tacataaagt    32640 taattttgtt gaccatttta tgaatttaag aaatgtccac ttgaaaggac tcgctccttt    32700
aattaaattt ttggccttta tttataaaat aaaaattatt cttatatgt tcttgaaaag    32760 taaatcagat taggattaat aattgtcaag tcattttaga acaatgacat ctatcattaa    32820
atttcttgaa ttttttgcct tctcaactga tagctatccg ggtgaaaaat tcaattatgg    32880
atattggaaa aattgatggt aatattaatc tggaaatgtt atttctgtac tattctttac    32940
aggacctgag gggattctct agttcttttag gccagtgtta taatgttagg atttacaaaa    33000
gttggtaata tagagagaaa caggaagaaa atgaaatggg acaggaaaat atcattcctt    33060
cttcttattc cttcctctaa gtcactggca ttgtgaaggg aaaagggaac taacatgtat    33120
tagtgtctac catgtaacag gcattgtctt tcatatttta tatttatcgt attagctcat    33180
gtaatctttg tggaaaatct cctaaatcta ttagtaggtc tttaatatct atgtttattt    33240
attttgtcct gaaaacaaat gaagttttg gatcaagaca gagaattatt attacttata    33300
gcaataacca ccttggaaag aaggcacaca gttatgcgca caggagggga gccatgaaat    33360
tatgaatctg ggaattata taggaattac tatataaact ctttatatag taaatggtct    33420
tctcctgtct tctcctttc tgaaagagga agagaaagtt tatctccgtt atatacaata    33480
agcaaatctt taggggagag aatgagaagg tcctggttta aaccctttga aatgtaaacc    33540
agtagctctg ggattttgtt ctcttttgaa atgtaaacac agagctgtag aaaataagtg    33600
tctgcatatc tctgagggtc tctgtctatt cagtccacct ttaatccaga tttcagtttg    33660
```

```
tcttgctttta taactcctta accatgcaga agcatgaaaa catttctctct gtagttccac  33720
atcatgaatt ttagcagttt tagtactgtt gctaaaaaat tgtggctatt agcttgtttc   33780
cattcctttc ataaagtgtt tagtagcata atgcattatt aggtctactt tctatctatt   33840
atacttgaaa accatcctct ctatgtaaaa tatctattta ttcaatggat atttattgag   33900
caccaaaaac tgtcaagcat tgttctaggt atttgggata catcagtcga caaatcaaag   33960
atacctgcct tgcttgtatt tacaaacttt ggggttagaa tgcataaaat tgagattatg   34020
gagggttgt aattattgcc aatgaaaagc ctaggatgaa agatcactgg aagactaaag    34080
tttaaggaat tgaaaggcca gaatatcaaa agaatcatct atatgtgttt tgaaatctta   34140
tgaattaagg cagtatcgaa gagaatgaca gtatgcaaag agctcaaatg gttgagtggg   34200
aattacctgg accttagtgg ataacagcaa ccatgaggca agtatgtag tgagtaatgt    34260
cgaccatgag atttaaatct gaaggatgtc aggaaggata tggggaaatg gtctgaaaat   34320
gtcagaatgg agcaaagaaa taccactttg cttattccac tcacccaacc agaggtcgca   34380
ggaacaagaa tgacaccttt ccatcttgca taagaactgt gggagagaag cagccatcac   34440
tgagagattg taggggaggc attgtcctcc agagaaagac aggtttatgt ttcagctagg   34500
aaagtaaagg gaacacttag aaaattgatt tttggctcac tggaagggtt tcagcagttg   34560
ggagagaaca aaggtaattt ttaccagctt gtaacttcac atgtattaac tgtgttgcaa   34620
aactaatgaa acttactgtc tattctcttg ctttatctga taatatagat aagggtgtca   34680
cctgtaatca ttgttaccat atttcttgag gccattttct tattctcatt taacttttct   34740
acttgtttct tctttatttg tatttttctc tgttttaat cttgctcttt ttatcatttc    34800
tgtctcttta tatcctactt acctcttaat ctttttgccc aacttctctc ttaatatata   34860
tatattttg ctctttacta tttctcttat ctttctattt caaaattaca ctgtctgctg    34920
ttttctccaa ctccccacaa ctcaccttag gtgtagttgg gactatgcaa tatgccatca   34980
cacaggtagt actaattttg acaggtagca tctctacttc aaacaaagaa agctttaacc   35040
aaaaaggaat tacaggagag aagacagtat tctccccaac tgatgctaac attgccacct   35100
acacttttga cgctttcttc aacagttaag acgtagcaac ttattacttc cccaaattcc   35160
ctgtgctctg ttgatctgtc ttaaaactcta aagggagaga aagtaggttt gttcattagc   35220
tgtgggactt aaaatgtgac ttaactttt tgaacctttt gtttcgtgaa tgataaaaaa    35280
acactttctg aatgatatag ctactaatat tttcatttta tagataaagt gaaagataaa   35340
gtactttttt taaaggttgc ataaatataa gtgacacaca ctgatatgaa tgtaagcatt   35400
tgactcaatc ccagagatca tgttttaatg aatactctat tgtttctcac ataaataac    35460
ttaatattgt ggtcaataaa ataataaata ggaccagaca catatatgta ttaattcact   35520
tcccttatt tccttttcc aaaattgagc cttattggta aagggctttt tgtgcatttt     35580
aattgtctat aatcaggtac ttgaaccaat tataatttt cacttgcctg catgaatcca    35640
tacaggacaa aaacctgaat atagaaacta tctttcagct ttcggtttgc cagaggatta   35700
atctataatt attttttagga ttataaaaga tttcatccg ttcttaaaat atacataata    35760
tcggattttt ttccagcaat agaggaataa ctaattctat agtttcatgc caatctcacc   35820
tccagtcctt ctagaatttg gaggtaattt aaccccgtgt ataaaaaata aatattttct   35880
ttttgcgtt ttattgaaaa aatcacgtaa tttaagtaca aatatatcca ctaaagtagg    35940
caaatttatt ttagtagaat tcagttatcc ctttcaaaga aacactatca gcctaagtgt   36000
tatacattgg atatttaga aatcttacaa tttcaattac atgtcttctg aaactcatta    36060
```

```
ttgtaaggct ttgttttagg ctttccttgc tgtattagtt gactggggct gccagaaaaa   36120
aataccacag gctgggcagc ttaaactaca gaaatgtatt ttctcacagt tctggaggct   36180
gggacaccta agatcaagat ggctagccag gtgggtctca ttctgaagac ttttctcttg   36240
gctttaggtg gttaccatct ccttgcatca ttgtgttacc tctttgtgtg cttggacaga   36300
gagcaagaga ggtagctctt tggtgtttct tcttttaaga acactaattg gatggatcca   36360
gccccactcc tatggcctca tttaaccttg attacctcta taaaggccct atctctaaat   36420
acagtcacat ttggggttgg gactttaaaa tataaacctc gggggacata agccttcatc   36480
cacagtattg ccattataat attttgtgta ctttggcact tgagaaagta agatttttt    36540 taacctagta ttttaatgtt ttctttagag gttttttccc tgatacaaca ctctcctata   36600
catgatctac ttggtaacac aaatatccct ttgtttgctt gtactttgc ttcctcataa   36660 atttttctgt agctacaaat gttaactttg ttggataggc tttatttttt agatcaattt   36720
taagtttata aaaatactgc acagaaagtt gagacagttc ccatgtattt cctctccctg   36780
ctgcacacaa tttcttctct tattaacatt ttacattagt gcagtacatt tgttacaatt   36840
gataaaccaa cattaatagg ttattatcaa ccaaagtcca tagtttacat tagggttcac   36900
tctgtgttat acagttctat tggtctggac aaatgtttaa tgacatgtat ctaccattac   36960
attatcaagg atggtttgac ttccctaaaa atgccctgtg ctccacctgt tcatccctat   37020
accttctccc tgaagccctg acaactgctg atattttac tgtctctata gttttagctt    37080
ttccagaatg tcatacagtt ggaataatac agtatgtagc ttttaaaacc atcttctttc   37140
acctagcaat atgcattaac agttctctca tgtctttttt gtggttgaca gctcatttcc   37200
ttttccagta gtcccacttt atctgtagag gatacgttct aagaccccca aaagatgcct   37260
gaaacctcag atagtactga accctatata tactgtgttt ttccttttaca tacatacccta  37320 tgataaaatt taatttataa attaggcaca gtaagagatt aacagtagct aataataaaa   37380
ttgaacaatt ataacaatat gccagagtcg aaactcttgt gccttgggac tttattaag    37440 tataataggt ggccaatatc aagtgtaaca tagaaaata ggaaaacaga aaaacctctg    37500
tggaatttgg cattaacata gaccttagcg aaacctgttt tattagagac agtgattttt   37560
taaaaacact taactgtgaa gggaagggat ttgatgagat aacacaattg tctgaaggta   37620
gagagaataa aaaacaattt tttttctaat gagaagagta taattaagca tggggaacag   37680
acacatagag attataaagg aagtgatgat tgcaaaatat ttaaccaaat aattagtatt   37740
atacatgttt gtgatagagc tatggtacac ttaattaggt aaaatgccaa aagacagtgc   37800
cacgctccaa gctttatgta tcataaacat caaaaatgac ttgctgaatt aaattaaatt   37860
gagtctccat taacatgtaa atcatcatat ctgtgccctg gaataattca gagtttaatt   37920
tgtgggtttg cttccttatg aaggtcatcg aacactattt attggagtac atgtgccctt   37980
gggaggaaga aaaagccatc gacgtcacag gcatcgtggt cataaacaca gaaagagaga   38040
cagagaaaga gattcaggat tagaggatgg aagggagtca ccttcttttg gtaagaatcc   38100
ttctccttgt ttttattaag ttaattattg taatatactt gcttatacaa ttatgattag   38160
gagtaatacc ttatactcat aaaattgttt atacttttat aaaagacttt gggccggttg   38220
gagagaagtg ggagagataa agcttgatct ttgttttttct cttatatatt tgcattgaga  38280
agctgagaat tgatgaagat ttatgatata ggaaatacaa ttgagtaaag ctcaaaaact   38340
cttgataatt tatacaaata atcatcatta ctcaaagtgg tttgaaaatc cagggcaaaa   38400
```

```
tgccttaatt tagttcccat ttgcactttt actgatagtg cccaagtttc agtcttagga    38460
tgttgtatta gtccgttttc acactgctga taaagacata cccggactag acaatttacc    38520
aaaataaaaa agaggtttaa ttggacttac agtaccacat ggctgtgggaa gcctcacaat   38580
```

```
tgccttaatt tagttcccat ttgcactttt actgatagtg cccaagtttc agtcttagga    38460
tgttgtatta gtccgttttc acactgctga taaagacata cccggactag acaatttacc    38520
aaaataaaaa agaggtttaa ttggacttac agtaccacat ggctgggaa gcctcacaat     38580 tatggtggaa ggcaaggaga agcaagtcat gtcttacatg ggtggcagca ggcaaagaga    38640
gcttgtgcag gaaaactccc ccttataata actatcagat ctcatgagac ttactcacta    38700
tcacgagaaa agcacaggaa agacctgtcc tcattattca attaactccc actgggtccc    38760
tcccacaaca catggaaaat tcaagatgag atttgggtga ggacacagcc aaaccatatc    38820
gttccaccct tgggccctcc caaatctcat gtcctcacat ttcaaaacca atcgtgcctt    38880
cccaacagtc ctccaaggtc ttaacttatt tcagctttaa ttcaaaagtc tatagtccaa    38940
aatctcatct gagataaggc aagtcccttc cacctgtgag cctgtaaaat caaaagcaag    39000
ctagttactt cctagataca actggggtaa aggcattagg taaatacagc cattccaaat    39060
gggagatatt ggccaaaaca aagggctac aggcccaatg caagtccaaa atccagcaag     39120
gcaatcaaat cttaaagctc cgaaatgatc tcctttact ccatgtctca catgcaggtc     39180
atgctgatgg ttctcatggt cttgggcagc tctgccctcg tggctttgca ggatatagcc    39240
cacctcctgg ctgctttcat gggctggcgt tgagtgtctt gttgcttttc cggacacact    39300
attcaagctg tcagtggatc ttccattctg cagtcaggag acagtggcc cttttctcac     39360 agctccacta ggtggtgtcc cagtagggac tctgtggggg ctgtaacccc acatttccct    39420
tctgcactgc cctagcagag gttctccatg agggccctgc ccctgaagca aatttctgcc    39480
tgggcatcca ggcatttcca tacatcctct gaaatctagg cagaggttcc taaacccaa     39540 ttcttgactt ccgtacacct gcaggctcaa caccacatgg aagctgccaa ggcttgaggc    39600
ttgcaccctc tgaagccaca gcctgagctc tacatttgtc cctttcagct atggctggag    39660
cagctgaaac acagggcacc aagtccctag gctgtacaca ggatgggtac cctgtgcctg    39720
actgagaaaa ccactttttc ttcctgggcc tctgggtctg tgatgggagg ggctgccata    39780
aagacctttg acatgccctg gagacatttt ccccattgtc ttggggatta acatttggct    39840
cctcattact tttgtgaatt tctgcatttg gcttgaattt ctcctcagaa aatggaattt    39900
tcttttctat tgcactgtca ggctgcaaat tttctgaact tttatccttt gcttcccttta   39960 taaaaccgaa tgtctttaac agcatccaag tcacttcttg aatgctttgc tgcttagaaa    40020
tttcttctgc cagataccct aaatcatctc tctcaagttc aaagtttcac agatctctag    40080 ggcagggta aaacactgcc agtctctttg ctaaaacata acaagagtca cctttgctcc     40140
agttcccaac acgttcttca tctccacctg agaccacctg agattgcctg gaccttattg    40200
tccatatcat tatcaagctt ttggtcaaag ccattcaaca cgtcactagg aagttccaaa    40260
ctttcccaca ttttcctatc ttcttctgac ccctccaaac tgttccaact tctgcctgtt    40320
acccagttcc aaagtcactt ccacattttc aggtatcttt tcagcagcac cccactctac    40380
tggtatcaat ttactatatt aatatgtttt cacactgctg ataaaaacat acctgagact    40440
aggcaattta cagaagaagg aggtttaatt ggacttacag ttccacatga ctggggaagc    40500
ctcacaatca tagcggaaag caaggaggag caagtcacat cttatgtgaa tggcagcagg    40560
taaagagacc ttgtgcagga aaactctgcc ttataataac catcagatct catggactta    40620
ctcactatca tgagaacagc acaggaaaga cctgccccc atgattcaat tacctcccac     40680
caggtccctc ccacaacatg tgagaattca agatgagatt tgggtgggga cacaaccaaa    40740
ccatatcaaa tgtgaacctt ttactattgt gaatgctctc tcattgaaag catattcaga    40800
```

```
ataccacaat aagtgttttc gtagttgtta aaaggttctg aatgccatga gagcccatgt   40860
acatgacata actgagaacc tggctctcag ttccttgacc atcccatctc ttatgacctt   40920
ctctgtcatt gcactttgtt caccttctca accatattca ctccatccct gaagtcacta   40980
attcatttat ctttctgtct gaccacagct tcactccttt cttgctgtgc agctacttaa   41040
cccctctact tttcttctat ccataagttt gtctttattt gtttatccta gtctgattgc   41100
atagcatgca gtcttaggaa tactttagca ttactagtat tccatttgta ttactagtag   41160
tctatttagt aatactagta ttctaaatat cttaggttct aagttttagt tttcttcata   41220
cctttactgc ctcttttatt ttcatttttta ataggaagca gcatttttatt taaaatgttt   41280 ttaatagatt tcttaaagat gtaaataatc gaattaaact tagtctatat tacttgtatg   41340
aattaattta cattttgttc acattcgtga aaaataattt agctaggtat gcaattccaa   41400
attgacaagt attttaactc agcactttga acataatatc tatttattta tcaatttcat   41460
gaagatgtta agaaaggaga taaaaatcta ttgttgctct acagttaatt tggatttat   41520 attttttatga atttaaatca tttcctttat tttggtattt agttttacat ttattatgat   41580
attttcagac acacatatat gccttttatg cttttcttgg ttgatattta atgagaatgt   41640
atattattag ttcttttaaaa tgcttaaaca tgtcctattt tctattattt tctctcccac   41700
ttatttaaat tctttcttca aatattcatt aagcatattc ctttcaattt cattttcgat   41760
ttattttgat ccctcttttta tattttttca tcattttctc cttgtcctga cattgaagtg   41820
tttattttag ctaattcatt tattcatatt ttagctcata gttttttgcct tgctcatatc   41880 cctttacttt ctttaaacat tttgactaca tgtgtctttc acttctttta ctttggattc   41940
gggggcatgt gtgcaggttt gttacataag tatgttgtgt gatgctgggg tttgggatat   42000
ggatggtcct atcacctagg tagtgagcac agagtatagt tttacaaccc ttgttcccca   42060
ccctccttcc ctgctctggt gattcccagt gcctattgtt cccatcttaa tgtacataag   42120
tacccaatgt ttagccccac ttatgagtga gaacatgcag tatttggttt tctgttcctg   42180 agttaattt tttaggataa tgatctccag ctgcattcat gttgctgcaa aaggatatga   42240
tgtcattctt tttatggcca catagtattc catgatatat atgtaccaca ttttcttcat   42300
ccactttacc ataaggaaac ctagttgatt ccatgtcttt gctatggtga ataacactgc   42360
agtgaacata ccagtgcatg catctttttg gtggaatgat tcatttttct ttgagtatat   42420
acccagtaat gggattgctg ggttgaatgg tagttctgtt ttaatttctt tgataaatct   42480
ccaaactgct ttccacagtg gctgaaccaa tttatattcc caccaacagt gtataagcat   42540
tccgttttct ctgcagcctt gtcagcatct attatttttt gacttttttaa tgttcaccat   42600 tctgactggt gtgacatggt atctcattgt ggttttgact tgcatttcat ttgttgactg   42660
cttgtatgtt ttcttttgag aagtgtctgt tcgtgtcctt tgcccatttt tagtagaatt   42720
atttgttttt tgcttgttga tttgtttaaa ttttgcttgt ggattcgggg tatcagacat   42780
tttttgaatg catagtttgc aaatattttc tcccattctg taagctatct gtttagacta   42840
ttgagatttg ctgtgcagag gctctttagt ttaattaggt cccacttgtc aatttttgtt   42900 tttgttttcaa ttgcttttgg agacttagcc attaattctt tgtcaaagtt aatgttggga   42960
agggtatttc ctaagctttc ttctagaatt attataactt aaagtcttac atttaactct   43020
ttaatccaac ttgagttaat ttttgtatat ggtgaaaagt aggtatccag tttcattatt   43080
ttgcatatgg cttgacagtt atcccagcac catttattta atagggagtc ctttctgtat   43140
```

```
tagttattct tggtgacttt gttgaagagc agactgttgt aggtgtttga ctttatttct   43200
ggattctcta ttctattcca ttagtgtgtg tgtctgtttt ttgtaccagt acaatgctgt   43260
ttgggttaat gtagccatag agtacagttt gaagtcaggt aatatgatgc ctctgacttt   43320
gttcttttg cttagaattg ctttggctat ttgggctctt ttttgattcc atattaattt   43380
tagaatagtt tttctaattc tgtgaaaaac aacattggtg ttttgataga gatcggtatt   43440
gaattctgta aattgctttg ggcagtatgg ccatttttaat gatattgatt cttcctattc   43500
atgagtgtgg aacatttta catttgtttg tgttgtctct gatttctttc agcagtgttt   43560
tgtagttctc cttgtagaaa tctttcacct ctttggttag atgtattaca ttttttttgtg   43620
tgcctattgt aaatgggatt gagtttttga cttggctctc tgatacaatg ttattgctgt   43680
acagaaatac tattgacttt tgtacattga ttttgtctcc tgaaactcta ctgaaattgt   43740
caattctagt tgccttttgg tggagtcttt agggttttct atttctaaaa ttataatcat   43800
cagcaaagga gagatagttt gacttcctct cttcctattt gaatgccttt tatttctttc   43860
tcttgcctga ttgctctggc taggtcttcc ttatactatg ttaaatagga gtggtaagag   43920
taggcatcac tttcttgttc tggttctcca ggggaatagt tatagctttt gcccattcag   43980
tatgatttta gctgtgtgtt tttcatagat ggctcttatt gttttgaggt atgtttcttc   44040
aatgactagc ctgttgaggg tattttatca tgaagggatt tgggattctc ttgaaggcct   44100
tttctgtatc tatcgagata accatatggt tttgattttg attctgttta tgcgatgaat   44160
catatctagt gaattgtgta tgtcgaacca accttgcatt ccaggaatga agcccacttt   44220
tctcatagtg aattagattt tgatgtgctg ctgaattcag tttgctagta ttttgttgag   44280
gattttgtgt ctatgttcat cagggagttt agcctgaagt tttctgtttt tgtgtctctg   44340
ccagattttg gtataaggat gatgatgact ttgtataata tgttagtgag aagcctcccc   44400
tcatcctcaa tttttttggaa gagttttagt aggattggta ccagttcttc tttgtaactc   44460
tagtagaatt cagctgtgaa tccgcctggt tcagggcttt ttttggttgg taggttttttt   44520
taaaattacc gattcaattt cagaacttgt tattggctta ttcatgtttt cacattatcc   44580
cttgttcaac cttggatggt tttgtgtttc tgagaactta tccatttcct ctagattttc   44640
taatttgttt gcacagaggt gttcataata gtctctgaat atcttttgta tttctgtggg   44700
attgggtgta atgtcatttg tcattttga ttgtgcttat ttgggtcttc tcttttttttg   44760
ttaatctaac tagtagtcta tcaatcttat ttattctttc aaaaaacaaa ctctgtttca   44820
tttatctttg tatggacttt tgcatctcaa tttctttcag ttgttctctg attttagtaa   44880
tctctttct tctgctagct tttaaagcca tacttatgtt ggggttcctc catttttcca   44940
ttttctcctt gcctccacaa gcagatatac tctgctggaa atcatcattc aacaaggcag   45000
attgtaacca ttatgaagtt atgactcaag gagaccttca acatctcctc ctaatttcat   45060
tgtgtatctt ttttgacatt tgaaataatt atttttcaac tttcttcgcc ttcttcatca   45120
ttctccaaca tcctctcttt tcaccattac ttgatagtaa tcttgctttg tacttcagag   45180
ggaaaatata tcatcagaaa gaactcactt tactttcttc ctgttaaaaa gttatagctg   45240
aaacctttct tcctattaaa cggttaaaac tgcaagaaaa taaggaagtt ttcttttcct   45300
ttatgttat tttctattcc ctctcaccac tctggaaact tatgccatt ctaatttaat   45360
tgacctcttc ctcttgaaat gaattttttct tatcatcttt gaaacatgat agagtctcca   45420
ccatttttaag cagttctcca acctcctgca aacccacctt tagtcattca gatatgtaag   45480
ttaactgcat ataaatgttc tgggtagcaa ttttactttt aaatatctct ccatattgct   45540
```

```
ttatttggtt tattcaatat ctggcttcag taactattgc agataagtct atagtctctc   45600
tatttttatt ttttaggttt atgtatttta atcctgaatg tttatagaca tttttctgtg   45660
tcccttaatg aagaaaattg ctaagattga cctaatggta ggtgtattaa aaaacttttc   45720
catcccgcat acacgaatag ttttccacct agggaacatt ttcctattat gtttcattct   45780
gttccattta ctttgatctc tttgtgaaga ctttctttgc tcatatccct ctactttctt   45840
caaacatttt aactacatat atctttcatt ttttttttaac tttgaatttg ggggtacatg   45900
tgcaggtttg ttacatgagt atgttgtatg atgctgaggt ttggggtaca gatggtccta   45960
tcacgcaggt agtgagcaca gagtatagtc aattttacaa cccttgttcc ctaccctcct   46020
tcccagctcc ggtgattcca agtgcctatt gttcccatct ttatgtccat gagtacccaa   46080
tgtttatctc ccatttatga gtaacaacat gcagtatttg gttttctgtt cctgagttaa   46140
tttgcttaga gtaatggcct ccagctgcat tcatgttact gcaaaaggat atgatgtcat   46200
tcttttatg gctgcacagt attccatggt gtatatgtac cacattttct ttatccacct   46260
caccctaatg gtacctagtt gattccatgt ctttgctatg gtgaatagca ctaagatgaa   46320
catgcacgta tatgtcagat ttctgatttc tgctctgtat ccttttcctc tgtagtttaa   46380
tgttagtctt ttatattacc atttgattat ctgcagaata aattctgcat tttcctactt   46440
ttattatgag ttttggtttt gctgttgcat ttttagtttt cattaatttc tttcttattt   46500
catcctattt tctttacatt ttagcctgtc ctttcctgaa tacttttttat tttttttctgg   46560
ttggtagagt gtatccccag tgattctggg acgttttcat tttatcctaa agtagacaat   46620
tttcagagct atgcttttcc tttggactgt cagattattt ttactctcca ttgatttta   46680
gtatttttta tggactccta ggttttttcc ttttttttctc attttaaac aaggaaaggt   46740
agattcctac tatatctacc tagctatatc ttaagattgc ttaatgaggc tgctgtcagt   46800
atgctccatg tttccaacag tatgtataat aagcatcaca cttatccaaa tgccctgtac   46860
ttctgccagg ggcagcatag ttgttggtgg cagagtatgt aaagaaaagt actctaggta   46920
tcctgcacca ccatgataaa gaaggatggt tgtccataag aatgggcaga tgggctgaga   46980
gtgtaggata tactaagtat cttctgcatt ttcagatgtt gtctctttca tgaaggaacg   47040
tcttagagtg taaaaaaatg acaatttggc atattttct cattcaagtt ccatctgctt   47100
atagttagca gagatgccct cttagactgc aggaatggat tatctgtagg gctatgcgct   47160
aatgatgagt tttcatcatt ttctagtatt tgagaaaata tatttatatc atcttacaag   47220
tatttcatga gcaaataaaa ataagctgta tttatcattt gtttgttccc tgtgcctctt   47280
cttttattttt ccctaactgg aggcattatg ccagttttc tagaacagtg gttctcaata   47340
atgactgcat ttgagaattc taaaaccgtg ctaatgctca acccgtacac caaccagaat   47400
ctctgtgcct ggggcctaag catgagtatt ttttgaaaag taccccagg tgattcttct   47460
gtggagctgt tgatagctcc acagaaggtt gatatccact gttctggaaa ctttgctatt   47520
taaatttagt tcatcagggg tctaatatcc agaatctata aggaacttaa acaactcaac   47580
aagcaaaaat caacgtgatt aaaaagtggg taaagacatg aacagacact tcttaaaaga   47640
agacatataa gcagccaata aacatatgaa gaaatgctca atatcacgaa tcatcagaga   47700
aatgcaaacc aaaaccacaa tgagatacta tctcacacca gtcaaaatgg tgattatcaa   47760
aaagttaaaa aataacagat tctgacaaag ctgcagagaa aagggtatgc ttacacactg   47820
ttggtgggaa tataaattgg ttcagccact gtggaaagca gtttggagat ttctcgaaga   47880
```

-continued

```
acttaaaaca gaacaactat tgacccagca atgtcattac tgggcatata cccaaaggca   47940
aatgaatcat tctatcaaaa ggcacatgga cacgactgtt aatcacagtg ctattcacca   48000
tggcaaagac atggaatcaa cctaggtgct catcaacagt ggattgaata aagaaaatat   48060
actccatggc atacattgca gccctaaaaa agagcaaaat catgttcttt gcagcaacat   48120
gtatacaact ggaggtcatt atcctaagtg aattaatgca ggaacagaaa accaaatacc   48180
acatgttctc acttataagt gggagctaaa cattgggtag ttgtgaacat aacgatggca   48240
acaatagaca ctggaaacca ccagagagga gagggagggt ggggaactag ggttaaaaaa   48300
gtaactattg ggtactatac tgcccactac ttgggggaca ggatcagtca taccccaaac   48360
ctcagcatca ttcaatatgc ccatataaca agcctgcaca tgtactccct gaatctaaaa   48420
taaaagtaga aattattttt aaaacttacc aaacgtaaag aaagaaacct gtactgctag   48480
cttttaaaag ttatttaata aataaaccta ttttataaca aaaatagtaa aaataaattt   48540
ctacttcaaa gtataaagcc aacaatatta gcattaaatt taaacttgcc agaaatgcag   48600
aatctcaggc cccatccaga cctcttgagt caggacctgt acattaaaaa tatatttagg   48660
taactggtat ggtttggctc tgtgtcccca ccaaaatctc atctccattt ataatcccca   48720
tgtgttgagg gagggacctg taatccccat gtgtccaagg agggaggtga ttggattttg   48780
ggggcggttt ccctcatgct gttctcgtga tggtgagtga tttctcatga gatctgaagg   48840
atttataagg cagtgttccc agctctttgc tcgctcgctc ttctgccgcc ttgtgaagaa   48900
agtgcctact tctccttccg ccatgattgt aagtttcctg aggcctctcc aggcatatgg   48960
agctgtgaga caattaaact tctttccttt ataaattacc cagcctcagg gaagctcttt   49020
atcacagtgg tgaaacagac taataacagt aacgtatatg aatcttaaaa tttgacgcca   49080
agcgatgctc tagaacattg cttatcaaac ccttctggca cattgggaat cacttgagaa   49140
gctttaaaaa aattattgat gctaggcttc aacctcgaag gatttttatt taattaatct   49200
tgggtgtttc cctaggcact ggtatttta aaaagtaccc caaattattt aataaccact   49260
taaataattg accaagaatc agattctgag aagcttctgc ctctcaattt ggtgaaactt   49320
ggaaataagt cgggtggccc agattctccc tcttattttt tgccactatt tttggatgcc   49380
acctaccttt ttccttcttc aatcatctga gtatcttcag tgacatttag acctaaatgt   49440
ggtttatcag tgacaaatgt ttggcacttg gtggtttcta agcaatggaa ttttctagat   49500
ttcacttttt tcagtttctc tagtactaat cttctgcctt catccttatt ccacactcag   49560
tttatttgct ataataagta ctcagtcaca cacagagact tcaaccaaac cctaaacacc   49620
atcctatctg atttgggttt tgatattctg catagtgaga atatatgaca tttccatgct   49680
gaaggcatta agaaaattt ctgcctactt aagaaatagt tattttacgt ggaagcattc   49740
caaagaaaat atttttgaaga tatttctgca ggtgcctcaa aattctttgg aattcaactt   49800
ccgaagaagt ataggataga ggagaattta agagagtatc aggtctctct gctatgaagc   49860
tagatatatg ttgttaattg cagtatgaat ctgtgaaatc atggaatcat tagggcccaa   49920
attatgaagc aagcatcaat ttaacaaaac gattttggga aaaacgtttg aatttgggca   49980
ctctttttt tattattata ctttaagttt tagggtacat gtggacaacg tgcaggtttc   50040
ttacatacgt atacatgtgc catgtgtggt gtgctgcacc cattaactcg tcatttagca   50100
ttaggtatat ctcccaatgc tatccttccc cccctccccc caccccacaa cagtccccag   50160
tgtgtgatgt tccccttccc tgtgtccatg tgttctcatt gttcaattcc cacctgtgag   50220
tgacaacatg cggtgtttgg ttttttgtcc ttgcaatagt ttgctgagaa tgatggtttc   50280
```

-continued

```
cagcttcatc catgtcccta caaaggacat gaactcatca ttttttatgg ctgcatagta    50340
ttccatggtg tatatgtgcc acattttctt aatccagtct atcattgttg gacatttggg    50400
ttggttccaa gtcttttgcta ttctgaatag tgccgcaata aacatacatg tgcatgtgtc    50460
tttatggcag catgatttat agtcctttgg gtatataccc agtaatggga ttgttgggtc    50520
aaatggtatt tctagttcta gatccctgag gaatcgccac actgactttc acaatgattg    50580
aactagttta cagtcccacc aacagtgtaa aagtgttcct atttctccac atcctctcca    50640
gcacctgttg tttcctgact ttttaatgat tgccattcta agtggtatga gatggtatct    50700
cattgtggtt ttgatttgca tttctctgat ggccagtgat gatgagcatt ttttcatgtg    50760
cctgttggct gcataaatgt cttcttttga aagtgtctg ttcatatcct ttgcccactt     50820
tttgatggga ctgtttgttt ttttcttgta aatttgttta agttcattgt agattctgga    50880
tattagccct ttgtcagatg agtaggttgc gaaaattttc tcccattttg taggttgcct    50940
gttcactctg atggtagttt cttttgctgt gcagaagctc tttagtttaa ttagatccca    51000
tttgtcaatt ttggcttttt gttgccattg cttttggtgt tttagacatg aagtccttgc    51060
ccatgcctat gtcctgaatg gtattgccta ggttttcttc tagggttttt atggttttag    51120
gtctaacatt taagtcttta atccatcttg aattaatttt tgtataaggt gtaaggaagg    51180
gatccagttt cagctttcta catatggcta gccagttttc ccagcaccat ttattaaata    51240
gggaatcctt tccccattgc ttgttttttct caggtttgtc aaagatcaga tagttgtaga    51300
tatgcagtgt tatttctgag ggctctgttc tgttccattg atctatatct ctgttttggt    51360
accagtacca tgctgttttg gttactgtag ccttgtagta tagtttgaag tcaggtagcg    51420
tgatgcctcc agctttgttc ttttggctta ggattgactt ggtgatgtgg gttctttttt    51480
ggttccatat gaactttaaa gtagtttttt tccaattctg tgaagaaagt cattggtagc    51540
ttgatgggga tggcattgaa tctataaatt accttgtatc tcccactgtt attgtgtggg    51600
agtctaagtc tcttcatagg tctccaagaa tgtgttttat gaatctgggt gctcctgtat    51660
tgggagcata taattagg acagttagct cctcttgttg aattgaaccc tttaccatta     51720
tataatgccc ttctttgtct ttttcgatct ttgttgggtt aaagtctctt ttgtcagaaa    51780
ctaggatttc aactcctgct tttttctgct ttccatttgc ttggaaaatt ttctccctcc    51840
ctttatttga gcctatctgt atcttggcat gtgagatgga tttcttgaat acagcacgcc    51900
aatgagtctt gactcttttt tttttctttt ttttcttga tgcagagtct tgctctgtca    51960
cccaggctgg agtacagtgg catgatcttg gtcactgcaa cctctgcccc caggttcaag    52020
taattctcct gcctcagcct cccaagtagc tgggattaca ggcatgtgac accacgccca    52080
gctaattttt gtagttttag cagagatggg gtttcaccat gttgatcagg ctggtcttga    52140
actcctgtcc tcaggtgatc cacccacctc ggcctcccca aaagtgcttg gattacaggc    52200
atgagccagg gccttgactc tttatccagc ttaccattct gtgtctttg atttgggcat     52260
ttagcccatt taattgaaga ataatatctt tatgtgtgaa tttgatcctg tcatcatgat    52320
gctagctagt tattttgtag atttgttagt gtagttgctt catagagtca ttggtctgtg    52380
tacttcagtg tgttttttgta gtggctgcta atgattttcc cttttcatatt tagtgctttt    52440
ctcaggagct cttacaaggc aggcaggcca ggtggtgaca aattccctca gtatttgcgt    52500
gtctgaaaag ggttctatttt ctccttcact tatgaagcgt ggtttagcca gatatgaaat    52560
tttgggttag aaattctttt ctttaagact gttgaatatt ggccccagt ctctgctggc    52620
```

```
ttatagggtt tccactgaga tgtttgctgt tagtctgatg gacttccctt tgtaggtgac    52680
ctggcttttc tctctgcgct gcccttaaca ttttttcctt catttctacc tggagaatct    52740
gatgactata nnnnnnnnnn nnnnnnnnnn nnnnnnnnnn nnnnnnnnnn nnnnnnnnnn    52800
ctaaattatt acattcaatg aaatgtaata attgacaaaa ttttatttta ttttattatt    52860
attatacttc tagggcacat gtgcacagca tgcgggtttg ttacttatgt atacatgtgc    52920
catgttggtg tgctgcaccc attaactggt catttacatt aggtatatct cctaatgcta    52980
tccctccccc ctaccccac cccatgacag gccccagtgt gtgatgttcc ccttcctgtg    53040
tccaagtgtt ctcacattgt tcagttccca cctatgagtg agaacatgtg gtgtttggtt    53100
ttttgtcctt gcgatagttt gctgagaatg atggtttcca gcttcatcca tgtccctaca    53160
aaggatatga actcatcctt tttatggctg catagtattc catggtatat atgtgccaca    53220
ttttcttaat ccagtgtatc attgatggac atttgggttg gttccaagtc tttttttttt    53280
ttcattgtta ttttttccag ctttttttt ttttattata ggttccaagt ctttgctatt    53340
gtgaatagtg ccgcaataaa catatgtgtg catgtgtctt catagcagca tgatttataa    53400
tcctttgggt atatacccag taatgggatt gctgggtcaa acggtatttc tagttctaga    53460
tccctgagga atcgccacac tgactttcac aatgattgaa ctagtttaca gtcccaccaa    53520
cagtgtaaaa gtgttcctat ttctccacat cctctccagc acctgttgtt tcctgacttt    53580
ttaatgattg ccattctaag tggtatgaga tggtatctca ttgtggtttt gatttgcatt    53640
tctctgatgg ccagtgatga tgagcatttt ttcatgtgcc tgttggctgc ataaatgtct    53700
tcttttgaga agtgtctgtt catatccttt gcccactttt tgatgggact gtttgttttt    53760
ttcttgtaaa tttgtttaag ttcattgtag attctggcta tcagctcttt gtcagatgag    53820
taggttgcga aaattttctc ccattttgta ggttgcctgt tcactttgat ggtgatttct    53880
tttgctgtgc agaagctctt tagtttaatt agatcccatt tgtcaatttt ggcttttgtt    53940
gccattgctt ttggtgtttt agacatgaag tccttgccca tgcctatgtc ctgaatggta    54000
ttgcctaggt ttttcttctag ggtttttatg gtttagtct aacatgtaag tctttaatcc    54060
atcttgaatt aattttttgta tatggtgtaa ggaagggatc cagtttcagc tttctaccta    54120
tggctagcca gttttcccag caccatttat taaatagggga attctttccc cattgcttgt    54180
ttttgtcagg tttgtcaaag atcagatagt tgtagatatg cggcattatt tctgagggct    54240
ctgttctgtt ccattgatct atatctctgt tttggtacca gtaccatgct gttttggtta    54300
ctgtagcctt gtagtatagt ttgaagtcag gtagcgtgat gcctccagct ttgttctttt    54360
ggcttaggat tgacttggtg atgtgggttc tttttggtt ccatatgaac tttaaagcag    54420 tttttttccaa ttctgtgaag aaagtcattg gtagcttgat ggggatggta ttgaatctat    54480
aaattacctt gggcaatatg gccattttca tgatattgat tcttcctacc catgagcatg    54540
gaatgttctt ccatttgttt gtatcctctt ttatttcatt gagcagtggt ttgtagttct    54600
ccttggacga ggtccttcgc atccctttta agttggagtt ctaggtattt tattctcttt    54660
gaagcaattg tgaatgggag ttcattcatg atttggctct ctgtttgtct gttattggtg    54720
tataagaatg cttatgattt tccacattg attttgtat cctgagactt gttgtagttg    54780
cttatcagct taaggagatt ttgggctgag atgatgggt tttctagtat atacaatcat    54840
gtcatctgca aacaggggac aatgtgactt cttttcctaa ttgaatgccc tttatttcct    54900
tctcctgcct gattgctctg gccagaactt ccaacactat gttgaatagg agtggtgaga    54960
gagggcatcc ctgtcttgtg ccagttttca aagggaatgc ttccagtttt tgtccattca    55020
```

```
gtatgatatt ggctgtgggt ttgtcataga tagctcttat tattttgaga tacatcccat   55080
caatacctaa tttattgaga gttttagca tgaaaggttg ttgaattttg tcaaaggcct   55140
tttctgcatc tgttgaaata atcatgtggt ttttgtcttt ggttctgttt atatactgga   55200
ttacatttat cgatttgcat atgttgaacc agccttgcat cccagggatg aaggccactt   55260
gatcatggtg gataagtttt tgatgtgttg ctgtattcag tttgccagta ttttattgag   55320 gattttgca tcaatattca tcaaggatat tggtctaaaa ttctcttttt ttgttgtgtc   55380
tctgccaggg tttggtatca ggatgatgct ggcctcataa aatgagttag ggaggattcc   55440 ttcttttct atcgattgga atttgggcac tcttaaaaag ttttattact ccaacgtata   55500
agcaacatca gcagaatcct actttattat gagacccaat catagaatac agtgttgtta   55560
aaacatccta gttgcattag tgttgcattc aggtaaaaga ataggccttt aatatagacg   55620
gaagagttta tgcttacatc ataggaaaac aatgactggt tcaagcctac catatgtcat   55680
ggttgggctg tgattcctag gtgagtctaa agaggaactg gcttttggtc tgtgtggtag   55740
tggtggtggt gatgttttgc tcatacaaaa aacttttaat gcccacaaat aagttcaacc   55800
tactttggct actgtactta ataaatataa taaatatatt aatttgttta gatgaatgtg   55860
atgatgatta attaattctc cttcctattg caatcaactc cccagtaaca aagctgctaa   55920
aatttcactt ttttttttg agacagagtc tcactctgtt ggccaggctg cagtgctgta   55980
gcacagtctt ggctcactgc aacctctgcc tccctggttc aagcgattct cctgcctcag   56040
cctcctgagt agctgggatt acaggcacct gccaccacag ccagctaatt ttttgtattt   56100
ttagtagaga cggggtttca ccatgttggc caagctggtc tcgaactcct gacctcgtga   56160
tccacccgca ccagcctccc aaagtgctgg gattacagga atgagccacc gcatccagcc   56220
cacatttgtt attttaatg tcatcttcta ttctctttgt ataatttgaa actatatttt   56280
caactgggaa catggatgag ctgctttaaa ttggtaagtt tgaagcataa gcttgaagtc   56340
agtgaaaata tgaaagatga tgagggaaat ttgtaacact tcaacgttta ttttttttcct   56400 caacctccct gaaaagaatc taatagaaaa gatgatagga ttatgccaat tacaattagc   56460
taatgtataa gaagtagaaa taaatctaaa agatacagac tattaaacac atgttttaaaa   56520 tatggtacac aaagatactg aataaattaa cacagtcctg gaattataat aggattttgt   56580
cagtcttagg tggtaaattg tgcacactct ttaggagaaa tgaagcaaat atagaaaaca   56640
tgacctcaaa gagcaatttt ttgatggaca gtggcttcct gttcctattt taatgaccaa   56700
ttaggtgcta tatgagaata tcaaggtgtt tttacaaatg tattttattg taaagtataa   56760
gacaagcatt cacaagtgtt aaagcataga aacatacata taaaacccaa tgaattatca   56820
caccagaaca tctgtgtaat accaccttgg ctggcactct agaaactcac tttgtgctca   56880
ttaccagtca ttaggttttc catcctcctc aaaagaatct ctggcctttc tttttacaat   56940
gggtattttg cttgttttg aacgttatat aaatgaaatc atataagagg aattaattgc   57000
tcagtgttct gtttatggaa ttcaccaatg ttttttgatgt agcttcagcc tattcatttt   57060
cattattgta tagtatgtta atgtgcttct atatgcacgg tatgtatgca ttctactatt   57120
gatggtcatt tggatcatat gcaattagaa gctactacaa gtaataatgc tgtgaacatt   57180
tttctatatg tcttttggta tacatatgca tttctcatac cgatgaatga aattatcaat   57240
tgctgagtca taggacatgc atattttcag ttttggtaga taatgccaaa tagatttcca   57300
aaattggggt acatatttac attcccacca ataaagtgtg agaacttatg tttttttgca   57360
```

-continued

```
tccttactaa cacttggtaa ttccattctt ttaacattag ccattctctt aaggtatgta    57420
attatatctt attgttttaa tttatatttc ttgattacca atgaaattga gtaactttgc    57480
atatgccttt ggccatttgg atattctctt ctaggaagtg cctaccaaag tcatatttt     57540
aatgagcttt tattgatttg tagaagttct ttacatgtta tggaaataag tcctttgtta    57600
gttttatgtg ttttaaatat cttctcacta ttgtgggttc tgatttcact ctcataatgg    57660
tatttttttg atgtggctac agattccagc agagtctgct aagaggctga tacctttatt    57720
ctttaggcaa attttctat gttatttatt tccattatat gttttagtat atatagaagc     57780
agacccatat cttgatcttc cataatcttg gctgaagttt gtatttcact gctctatggt    57840
ttcagtggct atcataaaaa taaacatcca tcaacacagg agaaatattc tattaactta    57900
gacaattctg ccaggtgctg tagctcacac ctataaaccc agttacttag aaggctgagg    57960
tgagagaatt gcttgagccc aggagttcag ggttacagtg atcatgccat tgcactccag    58020
actgtgtgac agaacaagac agcatctcta ataaaaataa caattttaa caggaagatt     58080
ttttctgatt ttgatagtac tgcaatttac atgaaatatg taatactatt ttaaggtgtc    58140
tatttttaat agacatgaaa aatgggtgtt gaattacaca tttggaaaat ttactgtatt    58200
gaaacataat cttaatccct ttttaagatc ttaaaaatat gttagtagga tggttatgaa    58260
aaatcttttg tgaaaataac ctaataccta taaaatcatt tctattttaa agaatgaagg    58320
cctgatacag ggaaccatac gttatcttga atcaaaataa aatatttctt gtcgctgaat    58380
agatgaccct atttcaataa attattattt tcttaaccat tgctgctatc attgtgtttt    58440
agggaagcct tttgaatacc tgacaccta tctcacactt tcaaatactc cttattcata     58500
actgtgaggg tgttataacc acatgtttac ttacaaatag tattttaaag gtgtgtagtg    58560
agtaagcctc atgctttata aaaggaaaca ctaataagcc ttaaaattaa cactcatgta    58620
catagcaatt gagatttggg ggttggatgc atggtattat agacatccag attactgatg    58680
aagagtgaac tgaaataagt ctttggaaac agtgatgaga gaaaatgttt cagagacatg    58740
gggaccctaa taccaatgtg gaagcatggc tgctatgaga tgtgacctct gagaagtgat    58800
tgggtagtca gaactggttg tcatgcaaca caaaatgact atgtctgctc acactgggtc    58860
agtctaatgg gaatatttaa ttgatttctt agtgtaactc tagaatcaca aattgtgctt    58920
ttttttaaat ggctattcaa agtactgata tttttttctag accaactagt ctgagagata   58980
acaggctaat taaaaatgca gttgacccctt gaacaatatg ggtttgaact gtgcaggtcc   59040
acttacacat agacttttac atttatatgt atattatgta gttttgtat attatgtatt    59100
tttatattaa aaatgtatgg gccaggcgca gtggctcatg cctgtaatcc cagccttttg    59160
ggaggcctag aaacacagat cacttgaggc caggagttgg agaccatcat ggccaacatg    59220
gcaaaacctc ctctctgcta aaaatacaaa aattagctag acatggtgat gcgcacctgt    59280
agtcccagct atttgggagc ctggagcagg agaactgctt gaacccaaga ggtggaggct    59340
gcagtgagcc aagacagtgc cactgcactc cagcctggat ggcagaaaga actgtctca    59400
aaaaaaatta tgtgtatata tatatacttt tttttagat ttgtgacatt ttgaaaaaac     59460
tcacagataa actgcatagc ctagaaatat aaaaaaatta ggaaaaagt atgtcatgaa     59520
tgcataacat ataggtagat actagtctat tgtatcacat actaccataa aatctacaca    59580
aatctattat aaaagttgaa atttatcagg ccttatgtac acaaacactt atagattgtg    59640
catggtgtca ttgcaactg agagaaatgt aaacaagtgc aaaaaatgca gtattaaatc     59700
ataactgcat acagtttact gttgtactta atgtactact gtaataatgt tgtagccact    59760
```

```
tgctgttgct attgtgtgag tgcaagtgtt tccagtatcc acttaaaaca ccttgtgatg   59820
ctaatcacgt ctacctgagc agttcatctc ttcagtaaac agcatattgc cgtaaaaaga   59880
atgatctctc atggttctca catattttc atcatgttta gtataatatt gtgaaccttg    59940
aatataacca cggaacccgt atgaagtgcc acagtgatgc tcgaagtgct cccaagaagc   60000
agagaaaagt cataacatta caagacaaag ttgaattgct tgacatgtac tgcagattga   60060
ggtttgcagc agtggttgcc caccgtttca ggcagataac ataaaagat gcagaaactt    60120 atcaacaaat acagtaaagt actgtaagtg tattttcttt catttatgat ttttgtaaga   60180
gaaaggatat ctgcttgaac aggtttttaa agcagacgaa agtgcccaat tctgggggga   60240
aaatgccaca aaggaagaga acatcagtat taaagcaga aaggaatagg ctaactactg     60300
ttttttggca attgccgcta ggtttatgat caagactacc cttatctata aaactactaa   60360
ccctagatcc ttgaaaggaa aagatgagta ctgcctgcca gtctcttggt tgtactaaaa   60420
ggcctggaca atgagaatcc tttttctact ttggttctat cgatgctttg tccctgaagt   60480
caggaagtac cttaccggta aggaaatgcc tttgaaaatc ctttcaatgt tggacaatgc   60540
ctctggccgt gtagaaaccc aggagctaat gttcatgaag gtgttaaagt gatctacttg   60600
ccccaaaaca caaaacttat aatcagcttc tagatcaggt tttgtaagga cctttaaggt   60660
tcattacaca tggtacccta tggaaagcat cgtcaataat gtggaagaga accccaatag   60720
agaagacatc atgaaactct agatggatta caccattaaa gatgccttca ttgctacaga   60780
aaaatccatg aaagccatca agcttgaaac cacaaattcc tgctggagaa aactgtgttc   60840
cagtgtgcat gacatcacaa gatttacaac acagccaatc aaggaaatta tgaaacagat   60900
tgtgaatatg gcgaaaaagg tgggggtaaa aggtatcagg atatggatct ggagaaaact   60960
caacagcaaa cagaaaccat gtcagaggaa ttaatagaag atgactcgat gaagatgagt   61020
atttctaaac cagcgccaga agataaggaa gaaaacattg aaaagcagt gccagaaaac    61080 aaattcacat tagacaatct ggcagaagag ttacaattat tcaagactag gttcaacttt   61140
ttttacaaca tggacccttc tataatatgt gcactgaaac taaataaat ggtggaagaa     61200 ggatcgcatc tcatggaaac agttttagag aaatgaaaaa gcgaaaggt cagaaattac     61260 aatttatttc cataaagtta catcaagtgt gtctgcctct cttgcctccc cttctacctt   61320
ttctgcctct gccactcctg agatagcaag accaaccct cctcttcctc ctcctcagca    61380
tactcaacat gaagacaatg aggatcaagt cctttatata atccattttc acttaatgag   61440
tagtaaatat attttctctt ctttgtgatt ttcttgtttt ctccagttta ttgtaaaaat   61500
acagtacata atacacataa tatacacatt atgtgttaat tgactatgtt atcattaagg   61560
cacctggtca acagtaggct attagtagtt aagttttgag ggagtcaaaa gttatataca   61620
gattttcagc tgtgtgggag atcagcacct ttaagacctg tgttattcaa gagtcaactg   61680
tagttgcttt ttttcttt ctaccttgaa catcttcctg cagatgctcc atcatcttcc      61740
tagctctagt ttcttatctc taatggaggt aaagcaggaa agttcttact tcactgctac   61800
tgtggcaagt taatgtcaca ctccttaggc ttagcaagaa tttgagttta ttcattctct   61860
cctggaggtt ttctcacctg cactctttc tgcgttacta tttattcctc ttcatcccct    61920
aggcattcag ttataatgat agagtctctc tgctgaaata ttctcagtgc tctgtggcag   61980
cccaagatga ctctatattc cacaccctct ctctctcttc tccccgctcc cctctcatgt   62040
gtgtggctta tgtatgattc acagaagaca cacacacact cagattgagt gctctggtaa   62100
```

```
atactgaaag tgtgtgttat tgaatgcagc aatgtcagcc atcagcagct aggctgactt    62160
tatgtttctc aggtaagaat catacccta ctgccatccc ttttaaggag aataagtaaa    62220
tgtcagactc atgttacagc tctttccgaa gaactctaaa atgtgtctgt ttcatctcat    62280
gatcctttat agccagcctc tgtgtgggtg aaaaattaga gtcacataac taggtttta    62340
gagcatggtt tgcaaattct gcatataatc ttatatccca tgtggaaata aatatctgtt    62400
cttggtgctt catctgaaac attcatttta ccaatctatt accctgtaat gaaattacta    62460
attagaattg ataatattat attatttcaa ttatgtaaat gaattaaaat ctagaaattt    62520
caatgaatag attgtgcatg acattcaaat actatgaaca caattttaaa gttcaactaa    62580
aaatggaaaa tattattgag cttcaaggag actggagaca taaatttgga acagaactac    62640
caaacttgtc ataatttcat aagatagatt atctgaatat ggattcatct gaactataac    62700
aaagataaag aggaagaaaa gtgtctgtga ttcagaaatt cacaatggta agcattttgt    62760
gaatctgttc tcttaagcta aatgtcatag taaccaaggc ttgtgtactt catgacagca    62820
agattacata ttaaaatgga agttttcaa ttcacttctg tcattgtact tgtaatgctg    62880
gcatgataaa tatatattct caacatattt gtaaaatatt gtccagaaag tgtctaaaaa    62940
atagagtgct tttggagagg gcctgcaaaa ggagagtatt ttcactgatt attaggaact    63000
atctctttaa gccctggtta attagtatgt gagttattaa ggcaatataa gtaatatagc    63060
taataatgca aagatagaag tttgctaagg aatttgttgt ttccagttat gattctacaa    63120
gggctttcct cagatagcat aatgatttaa atttgatttt cttaactaat tatttgttga    63180
aaatacagtc catattccaa atggaaatac cttatttgtc tatttctgat tataacagta    63240
ataaatgttc tttggaattc cagtgctatt gaaaattagg ctagccagat cttctttctc    63300
ttaacacagt tctcattgac caccctacaa catccaacat tattgacttc ttattctttt    63360
taaattcttt tctactttgt tcctggttat actactctct ccgtgagatg tatgttccat    63420
gaaggcagag gcttttttc tgtttatatc tgtcttattc actacttagt atggtatctg    63480
acaaagaaa ggtgttcatt aaatgtttgt gtaatgtatt aatcctttta catatttatt    63540
ccttttccga ttcttttgtt aacttatttt ccttctgcca aatcttaaac cttattactt    63600
ctccagtgtt gagtcttctt ctctctcaag actttcattt tgagtcatca tcatcattgt    63660
aatcatgtga tatctttagt taaatgttat ctatgtctct atctctgtcc ctgctctctc    63720
ttccagaatc caatctcaaa tctccaactg ccttatgacc ttcttcatat gatggtccct    63780
tagtcacctc aaagttagca tatgcaaaag ttatctttgg agcacccaac ctacaatgct    63840
ggctctcatt ctgacaactc tcttttaatt aatggcatga ttattctacc tgcttcaatt    63900
tgtaaagctc tctatttctg gtaggtaatt ctatatcatc attataacca tcacccccta    63960
tctctaatat aatcatcagt aatattatgt gattcttttt tttttttga gacggagtct    64020
cgctctgtca accaggctgg agtgcagtgg cgcgcgatct cggctcactg caagctccgc    64080
ctcctgggtt cacaccattc tcctgcctca gccttccgag tagctgggac tacaggcacg    64140
cccgcaccag gccggctaat ttttgtatt tttagtagag acggggtttc gccatgttag    64200
ccaggatggt ctcgatctcc tgacctcgtg atccgccctt ccggcctcc caaagtgctg    64260
ggattacagg cgtgagcccc cgcgcccggc caatatttat gtgattcttt attgcttgaa    64320
aagtattttt acatctataa tttcctcttt tggggcttgg tccaatcttc tgggagacta    64380
attctggcag gtagaaatat aaggaggcca atatcagtac attgcttatt caccattgct    64440
agcgtcttac tcctgggttt actctgactt tggtccccag ctctccagtg ctattatttc    64500
```

```
tttgcttctt tctgttatcc atattcctgt cttgcaacca agtttccctt taatgagata    64560
ttctatttca ctccagtttt cctatgatgg aaccactttg ctagacaaag cctgcgcatt    64620
tggacttgtg ctcattacat gatgcaaact agtgtgataa acctagttat tgtattttat    64680
taacttctta caaaacagta ttcatgactc acttgttcct ttacttctgc ctgcagatct    64740
gcttttggga atttcatttt tgtactactg acccttggat ttgcttacaa aactaaatta    64800
ctgttttttt cttgagcttt tgaatttttg atattgactg cttccagttt ggtccacact    64860
aatttcaacc agtcatcaat tattaaagat ataatcctca tttaaaatgt tatatatctc    64920
tatatatttt aaatatgtag tataatttta tatatgctta ttttttatttg tatatataaa    64980 tatatacata ttatttacca tatattatat atacatgcat aggaaaggac tctttctggt    65040
tccctagtat tggaattttt gcttttcttc tctctggtat ttttttcatcc ttgtttgatt    65100 cagacaacct ggctattgtt ttactgctta cccgggatct taatgcttca ggttcggctg    65160
gattccagct tttccttggt tttaattcta attcatatat atatatatat atatatatat    65220
atatatatat atatatgtat aatctacatc tgcatcaaat ccctctctag agcatgcagt    65280
ggatttcaga cctgggattt catcttgaac ttcagctact gaggatattt tcttgcatta    65340
ttctatttct aaattattct attagaataa ttctattaga attattctat ttctatatta    65400
ttgtatttct aaatccattg cctaaaccaa accattaatt ttgtctcagt aatcctggat    65460 cttttttcttt taccatatag tcaaaaatat tatgtcctta atgctggtgt ggcctgactt    65520
aatcccacct cttcttgtga aaacctcctt gaccgtgtag ccttcatttg tttttacacc    65580
tctttaccct tatagcacta agcaccagac atgttagtgc ttaattatta ttgtcttaca    65640
ttgtctgtta ttatgtattc atcttatttt taaaaccaga ttataagcaa tttaagaaca    65700
ataaatatgg tatagcattt atgtgaactg gaatagatac tatcctacag ttaatgaatt    65760
gaccaagcaa ctattcaaag tacagccagg ctgaagacgg cagtatgttg ttttttttaaa    65820 agatacttta tttgctcaat aaatctagga agaaatcagc ctcacatttt tttgaactgc    65880
aacttctttg cttgccatca tttaattagt tgccgagtta aaggaccctc ttggctaata    65940
agatagcaaa attgtcatgg attctcatga atctcaatat aattgaactt acaattcatc    66000
taaattattc cactttgttt tttatactat ttgcagtaat ttcattccac ttgaataata    66060
agggaatgtt ttctcatgtt ctgtaaatat attatttgag gatattttac ttttttttcta    66120 tatttatgta ttggtctgtt ttcatgctgc tgataaagac atacctgaga ctgggtaatt    66180
tataaagaaa aagaggttga atggatcaca gttccatatg gctgaggagg cctcacaatc    66240
atggcgggaa gcaaaaggaa ggcacatctt acatggcagc agacaagaga gaataagagc    66300
caagcaaaag gggtttcccc ttataaaacc atcagatctc atgagactta ttcactacca    66360
cgggaacagt atgggaaac tgtccccatg attcaattat ctctcactgg gtctctgcca    66420
caacacataa gaattatggg agctaaaatt caagatgaga tttgggtgag gacacagccc    66480
aaccatacca atttctttct atagaatata catttaaaaa ttgacataag tgtgctaagt    66540
gctctgcaca tttcagctcc caaggaatgc atattgtagg aactaaagca aaaaaaaaaa    66600
aaaaataaca acaaccaggg cagttttatt gagttcagta aagaatatgt ttccctatat    66660
tttaataacc acatctattc ttatctgatt tactttaaga atctattttc ctctttaatg    66720
cagttaacta atactatttc ttatacaatg gcagtttgaa atattaatcc aaacattttt    66780
acaatttttc catccatttt cataacatgc cagtgttata tttagtttaa taggctaagg    66840
```

```
ttacctttca tattgatgga tttactctga acttctagct gctcttaagg tagttgtgag    66900
gtttttttt tttcctgtta ttgtaattac agttacagaa taagactgga aactttgagc     66960
aagtttattt tctgttttta aaaaaaaccc agaaacaaac aagctgacat gttgatgaga    67020
tatattttat taccctactt tacccagaaa gctatgcata aagttcatac aacaagataa    67080
aattttaaaa aaaagccaaa agtgtacaaa atacatcttg gcttcatctt ttaaataaat    67140
taatatttgt taaacctttg atatttactg aggatatagc agtgaataaa acaaacatgg    67200
tttctgccct tatatttcat ccattctagc aaaaagatag atgcaaaatc aattattgca    67260
caattaatta ttagttgcaa ttgtgataag tagatcaaga gatgtagggt gctataagtt    67320
aggatagcag gggcctgatt tgtttgtata tgaatatgct tagatgtgga tatgtatgtg    67380
ttcatatgtc tgttttacaa agatgattag gtaggtgtgc caaagtatac tacatttaag    67440
cagagagtag atgtctaaga cagctacaag attctgaggt agggaagagc atgatatttt    67500
taagagtctt aaagaaggct aatgtaccta gactgtaata gcaagggaaa gactggcaga    67560
agatgaggct aatgagttag gcaagagtta ccacagatat ttatttacac agaaatatga    67620
cactatatta tcattgtgtg tttattttc accttgccc tctgaaatac tctcaattat    67680
gacttagttg taatctaatt atttcaataa cttattaatt ggtttatttt catatatgaa    67740
atgattaata ttatagattt cagtaattgc tctatagctg ttactgattt actcattctt    67800
ttgtgtttta aaagtttaa aacataccag atgttttatt gaactaacat tgaattcatg     67860
attttttttt atgactaagg cttcctcatc attcaataaa gttttataat ttttatcaca    67920
aatatgctac ataattttgc tggatttatt cctaatatta tatttttctt ctaaggtaaa    67980
tgaatttttt tctggctaga ctaatagttt ttgctgccct ataggaatag tatggatttt    68040
cttttaaga cctagtaaag atttctaggt aaaaatcata taatctgtac aaaatataat     68100
gaaaaaggaa ataatgaaag caaaatccca agaattcttt tttccccct caaagaatgc     68160
gttgaagaat gggcaaataa aatcgggaat atttagaggt aggaaggtgg tgaaaaggtt    68220
cacaagaag tttcaatttc aacaaaaagc ttttaattca aagattttc tttctttttc      68280
tgagagtgat cagaacatga agatggctgt tgggagacaa atctccatgt atcctttatg    68340
ttcccaaaca tcttttgggc aaaggcacta agtgcctttg tgcctgtctg tctttacaag    68400
tatgtttata tcgtgaacac actaggaaga tatagatagt gtctctctct ggagcaaagg    68460
gtaggttttt tatctttata cagtaaagat aatgtctcct tatggggcaa caatcagtga    68520
ggattattgt ccattatgaa agacctgagt tccttacctt ggttctcccc tgtcacatat    68580
cccgctacat gtgcagcatc tcctggcccct ttgcacaccc ttctgtggga gttgggctc    68640
agaatgcaac acaaatgatg atactctagg tactactatt ctgtgcataa taaccatct    68700
tttgtctctg actcaagagt ctcatggctt ttgctagcat ccataaaact ggcagggcaa    68760
atcctgatac ccttcacaat tcttggcagt tttggcagtg aggaagggat actgacagag    68820
acatggcttt tggaaaaaga aggatgatgg cctcacagct aattaataga ctttgaaaga    68880
agtccattgg tattggtagc aaacttgtgg accaaattgt ctagtaagca gagcaataaa    68940
tattcttcta ctctattgct cattaatgag gaggatttgg ggaggtagtt gcaagctgag    69000
aaccaggcaa cagatatgat ttaactgtcc tttaggcagg gagattacag tctggcagta    69060
gtctcaggtt caccctattgt aacaattagt acttagattc atttgggctg tggggtgggg   69120
agagaggaac aagtttgcat tttctttttt tgttgttgtt gttttgtttt gttttgtttt    69180
gttttttcaga cagagtctca ctctgtcgcc caggctggag tgcagtggcg cgatctcagc    69240
```

```
ttactgcaag ctccgcctcc cgggttcacg ccattcttct gcctctgcct cccgaatagc    69300
tgggattaca ggcgcctgcc accacgcctg gctaattttt tgtattttta gtagagacgg    69360
ggtttcaccg tgttagccag gatggtctcg atctgctgac ctcgtgatcc gcccgcctca    69420
gtctcccaaa gtgcagtgtt gggattacag gcgtgcgcca ccgcgcccgg ccgcattttc    69480
tttcagacaa caattttaga gatacatacc tacagtgagc atgagaggaa aatttatgac    69540
tattatgtac agaaaccagg caaattatta gaactttggc tgattttctt ggaaaatgag    69600
tgaggtgggt catggaatgt tggtaataga agaatggcca aaactgggat atcttttttg    69660
ctcagactct cctaccatca tgccaacttg taatccatct ggagatgaca gtagaaagtc    69720
ttggaatttt ctgtaatggg ttctatctgc tgtaaaataa ctttggccct tttatggaga    69780
tttctctgga agagacaaaa tcaaggggaa actatagatg aggcattaat tagtattgca    69840
ctcttacagc cccagattgg tttcataatg ctaatataag tgaccccctg gagaatgaaa    69900
aggtcatcaa agaaatttag ataaattctt gtggtcagcc tgaagttcta gaaaagttct    69960 ttcacccctta tgttggaacc aggcaagaac ttaataaatg ttgtattgat agtagggcag    70020
caggtacatc tatctagtct gaggatgttg ttgctgttac agccaattag tttattctag    70080
acacaccatg tgaccttga aactaatcta tgttatgtat tcagatttct gaaccattca    70140
cagtcagaga gtcatgcact ttttaatccc caaagccata caacaattgg ctgataatca    70200
aggtatgtga tagaccttcc acatttccta tcatccatcg gcatctggta ttgttaaatg    70260
ttggaagggc ttcttcaaaa attaaaaaaa gtttccaact ctgcctctct cacctccttc    70320
tggtgcacac atataagtaa gatggtttgg tcactgaatg tggcttctgc agaaactgat    70380
catctcctct cagcctctat gtggataata agatgaaagg gttaagattt tatataaact    70440
tatattgaaa aatcagtgtt ccaccatgac catttctggg cataatgcgt tattcttttct   70500 tattacagaa acctcaggcc agcctgattg gtacatcctc caaatggtag tccagctaaa    70560
gggaggcctc aggaattttt atttaattct tgtatagcta actggatatg cttgttggct    70620
tcatttggtc ctacattgta agagtagtaa ccatttagtt gagtacacag cttgccaaga    70680 cccccctgcaa ttgcccaaat gtaccattaa tgtagggac ataatgagtc tctgtaaatt     70740
ttataaaaat gcccttttct cccttattct gaccccttccc aacaaagat ttgggtatga    70800 tagaggatgg ttagaaaaaa agtgaaatta tagctaccgg aatggaacac actctgcatt    70860
tcaggtgcag gagtaaaatc aatgatcttt cagaacttcc cctggagcct cccacataaa    70920
gaaaagtcct tggtgtgagt ctctcaaact gtggtaaatg ctttaaatgt aatttccttc    70980
tggcttaaca ttcttcatca gatgtctctg cctgcatttt gatcatcatt gcttttaacc    71040
ttgaggagaa gtttattaga aacatcaggg aaagatcctt tatcgcctac acacacacac    71100
acacacacac acacacacac acacacacaa aacctattaa caccttttggg tgtcttctttt  71160 acccctcttt ctataaccat caatcactca ttccatgggg tggatgaatg ccatgtagtg    71220
gcttgcatgg ataaatagat cagattggac tgactgtccc caagcagttt ctctaaaaaa    71280
cagcaataat ctcaattatc tgaactgaac tgagaacccc aaggccaact agctggcctg    71340
gaggccctgt tggagacatt gccaatctgt tccttctaac tgcatcggt ccattttggg     71400 ggtcacagtc atcgtaaata acatgttctt tctaggacca ttgtgtgaac ccttaagact    71460
atatgtcttt tttttttttt ttgagacgga gtcttgctct gtcacacagg ctggagcaca    71520
atagcgcaat cttggctcac tgcaaccccc acctgctggg ttcaagcaat tcttctgcct    71580
```

```
cagtctcctg agtatctgag actacaagca cgtgccacca tgcccagcta attttttgta    71640 ttttagtag agatgggatt tcaccatgct ggccaggctg gtcttgaact cctgaccttg    71700
tgatccgtcc acctcggcct cccaaagtgc tgggattaca ggcatgaacc actgcgcccg    71760
gccaagactg catgtcttat gtccaaatca tgcattattt tccctcccta tccaaaatat    71820
agtgacttga accacaggga tggtcataag agacctttga atgtttaagc aaacaccacc    71880
agtagattat gtaagcttca gacgatttcg gagagaactc caaaatctac acttggctat    71940
gaggatgagc ttcctggagg gataattgac ttattagttt tgtgtgccct acaggcagtt    72000
atccctacaa tggtaatcat caaattagaa aaattggtga gaaatttgcc cctgaattta    72060
atctaaaaga ttaatgatac aattccagtc ttctttagcc tcagttcatg gactaacgtt    72120
tttatggatg ataggattgc cctcagctac ctccttgtgg tccaaggaag agactgtgca    72180
attgcttata tatcctgctg tacctgatct aatgcctccg gccaagtgga aggttaata    72240 tagaaactta aggagaaagt cacatggctt tgtaagggaa acctttatgg tttgggggat    72300
ttattcagtt tgttgggttc agcagctgaa tacatcagca gtgtggttga ggtatatact    72360
gtagattggt cccatccttc tgctttgagt cctgttgata gtgaccttaa gtaaagacat    72420
gtatgagaca aagtggatga acttttttcc agcatctgtt ggttagattt atccgtgact    72480
gatggcgtat ttatgggaaa attagtcaga gaaaagatga tgtcaagaca agctgtggct    72540
attgttgatg actgttctca gttgattctg ctgtcactat atcagaagcg aagagaaaga    72600
gtatgaagca aacagacaga aaactatgga agaaataatt gaagacagtt gtggtggctc    72660
atgcctgtaa tcccagcact ttgggaggct gaggcaggca gatcacttga ggtcaggagt    72720
ttgagaccag cctggccaac atggcaaaac cccatctcta ctaaaaatac aaaaattagc    72780
tgggtgtggt ggtgcatgcc tgtaatccca gctactggg aggctgaggc aggagaatca    72840
tttgaacctg ggaggcagag gttgtagtga gcagagatca caccactgca ctccagtgtg    72900
ggtgacagag tgaaagaaag aaaagaaaga aaggaagaa aaagaaagaa agaaagagag    72960
agagagagag agaaagaaag aaagaaagaa aaagaaagaa aaagaaagaa agaaagaaag    73020 aagaaagaa aggaaggaag gaaagaaatg aaagaaaaga aagaaaagaa gaaagaaaat    73080
ttctggaaaa aaaaaaccc cataaactta cacattgaag aagctcaggg ttcccacagg    73140
ataaatgcta aaataaacaa acaccaaaac aaaaccccaa atcccaaaat tattaaaaag    73200
tatcataacc aagcttctga aaactaaaaa caaagaaaat attctaatag tagccagaga    73260
aaaatgcaac aatgattcca atgattgcag atttctcatt aagaaatatg agggctaaaa    73320
ggaaatggaa cagcatttga gaatgctgaa agaacattta gtccaggatt ctatatccac    73380
tgacatattc tttaggcatg aaagttaaat aaaggcattc tcagacaaag ggaaactgac    73440
atcatactta ttcatgaaag actgtttcc ccctgtgacc aggaacaaag taagcctggc    73500
cactctcatc actgccactt aatatcgtac tggaattcta gccagtataa aataaaataa    73560
ataaatagag aaagagcttg gaaggaaaa aataaaatgg ttcatattca catatatatg    73620
atctctacct ggaaaattcc gtggaaccta caaaaaaatt agaataaata agtaagttta    73680
ataaggttga aggatacaag gtcacatgaa aataaatcac atttctctac actagcatta    73740
aaaattggaa acaaattaaa aaatataata gcctcaagaa atgaaatatc taggtataaa    73800
tttaacaaag caggtagaag atctgtgttc tggaaattat aaaacctgat ggaagtaaat    73860
attttgaaat gaaagaagac ctaaataaat gaagatacac atagtttcca tgggttgaa    73920 aaatcattac acttaaggta ctattctccc taaattgatc catagattta gtgcaatatc    73980
```

```
aatcaaattc caagcaggaa ttttgtagat acagaaaaac ttgttctaaa atgtatatca    74040
aaaggcaaaa agattagaat agccaaacag ttttgaaaaa gaagagcaaa gttgggagac    74100
tcataccatc tgactttaag aattactcta aagctatagt aatcaaaaaa gtgtggtatt    74160
gtcaaaggaa tagacaaagc aatgaactaa atgtttgtgt tcccccaaaa ctcataggtt    74220
gatattctca ccccaatatg atggtattag gagatcgggc ctttgggatg aaattaggtc    74280
atgagggtga agcccttatg attgggatta gtgcccttat aaaatgaacc tgctctctca    74340
gccttttcca ccatgtgata ttacaaggag aaaacagcag tttgcaaccc agaataagtc    74400
cttcactaga acctaaccat gttggcaccc tgatttcaga catccaggct tcagaactgc    74460
aagaaataaa tttctgttgt ttataagcca ctcaatctat ggtactttgt tatagtatcc    74520
tggactgact gaaatatagg cctagatcaa tgggacattt tagaaagtcc agaaaaacag    74580
tccaaacaaa tataactaat tgattttga aaacggcaca aaccatgaag aatatacttt    74640
ttctgtgtct tttatttggg tcttttccat aaatggtatg atattggaac aatttaacat    74700
ccatatgcaa aaaataaaaa aaaacccctt gaattaaacc tcatatctta taccaaaatt    74760
aactcaaaat ggaccatagc ttcaagatgt aaaatataat atatgaaact ttagaagaaa    74820
acataaaaga aaatctttgt gacctttagg cagagagttt tcaaatttga taccaaagca    74880
taatttataa cacacacaca caaatcagaa tttatcaaaa tttaaaactt ttcctcagtg    74940
aaagacactg ctaaaagaat ataaagtcaa actataaatg gggagaaaag acaaatattg    75000
caaatcatat gttcaaaaaa tgtcgtgtat ccagaatgta taaagaagtc tcaaaactcg    75060
acagtaagga acagacaacc caataaaaat aagcaaaatg ttttcataaa cactttgcca    75120
gagaataaat atggatgtca aataaactca ggaaaaattg tcaacaataa ccattataga    75180
aatgtaaagt aacaccacaa tgaaatacca ctacatagaa tggctacaaa acaactgata    75240
ataccaagtg ctggtgaaga ttcagaacaa ctgcaactct cttgcattgc tcctgggaat    75300 gcaaatggt acagccattc tggaaagcag tttggcagtg tctcagaaag ctgaacataa    75360
acttatcata tgactagcaa tcctacttct aggtatttac cctagagaaa taaaatttat    75420
gtttacacca aagcctacac aagaatactt atagcagttg tatttataat tgggccaagc    75480
actagaaacc caaatgtcct ccagcaggtg aatgcataag caaagagtgg tacattcctg    75540
caatggactg ttactcagct atgaaaaga atgaactact aatacacaca atgacagata    75600
aatctcaaaa tctcaaaggc atttgctaag tgaataaagc cagtctcaaa aggttatatg    75660
ctgcgtttcc acttacatga cattttgcaa aggcaaagct agcagcagag accagatcag    75720
tggttgctgg gggctacaaa agggaggtag gaatgactac aaaggaggat cacaagggag    75780 ttttttttggt gaataacatt ctgcatagtt ttagtataaa tgaattttat catgatctac    75840
tcttctgaat attaccata aaatatacca tatatgatga gagaaaatga gtatatgtgt    75900
ctgagaaata gaaatagtct ccatgagtgt taaaaataat ccaaaataat aatcatattt    75960
tatttattat ttattatatg tatacattaa tatatacatt ttacatattt atttcccca    76020 attatactgg acttcatgta atgatgaatt tggttttagt tcctgagttt gatttggatg    76080
agtgttgcag tggggagcag gggaggtgtg agcttgggt ggtgcgagct tgggtggtg    76140 ctgaaggcag tgactgggac atttaagct cagggtcgtg gtaatacatg ttcatggtaa    76200
tacatgtctc tgatttttta gacaccccat cacagagggt acagtttatt cttggaaccg    76260
aggatgatga cgaggaacac attcctcatg acctttcac agaactggat gagatttgtt    76320
```

-continued

```
ggcgtgaagg tgaggacgct gagtggcgag aaacagccag gtgaggattt ttgttaaagg    76380
gtgaaggtat actaaagaat tttcatgtta ctagaaaaag agatttctaa tgcaacaatt    76440
ttgcaaacat ctatgattgc tgctgatttt agaagttgct catctagcct gagcatatcc    76500
tataacggga tatgggtcag aaagaaatct gaaggcagta attacagtaa acggtgatgc    76560
agagccagca acagctgcag tcttaaagat aaacagtaac ataatttgtg tgtcatcaac    76620
aaaacaaaag aaatctaaaa gtagtttatt tctatttttt cagctgctgg cttgcaccta    76680
aatttatgat agtatatgat aacttgaaag tgggcttttt ttaaaagaaa gggcaaatat    76740
tatgataaaa tgctttatgt acagtcctgg atttcatgtg ctctttcatg aggataaaaa    76800
taatttgtaa tatgtttcta ggatatgcat acatttaagc atagtggttt ttaaaaatat    76860
cttttaaaat cacttttct atcatttgta attaagattt ttacattgct atataattga    76920
tagagttctg taaagttgga attaaatttt gtgtttactt ttcattcatt ctttctgatt    76980
tgctcagtta acaaacattt atggagtgtc cattatgtgc caagtgcaat ggatatggca    77040
caacaacaaa aatcttagat cttgccttta gggatcttgc agtctaattt agacaagaaa    77100
acaaagttgt aaatgctgta taatgaaagc tgtgatacag gtgtgcacaa gaaactgtgg    77160
gcacacccag ggttgtcatt tacccacttt ttcacaaatt ttaatgtgac taccaatcac    77220
ctggaatatt gttaaaatg tagacttagt aggcctcagg catagtcaga ccatgaggat    77280
gtcgtgtaaa atgttttggg tttgagaacc aaactttgag tagcagttat ctaaaccacg    77340
aggtgaaaga gaggatcagg gtagcttccc tggaggaggc gattcttgag ctagctcttg    77400
tgagttgggt tggagttagc taggcagaaa agcagagggg acagtattct aggcagagat    77460
agcaggacgt gcttaaatat atcattgaca caggtttagt gtttatttat ttatttattt    77520
atttgtctga gacagagtct cactctgtcc cccagggtgg agtgcagtga cgagatcttg    77580
gctcattgca acctctgcct ccctggttca agccattctc ctgccccagc tccctagta    77640 gctgagacca cagtcatctg ccaccgcgcc cagctaattt ttgtatttt agtagagaca    77700 gggtttcacc atgttggcca ggctggtctc gaactcctga cctcaagtcc tctacctgcc    77760
tcagcctccc aaagtgctgg gattgcaggt gtgaaccacc atgcccctgc tgacacaggt    77820
tttattgttt tgttaggcta tctcttccac tgtaggacag cattattatt agaaagactt    77880
tatcttaagc atatttatta gtggtcctca gattgcaatt gctgtctgaa agccacagta    77940
attccattgg atcatgttaa acttgtagct gcatttattc attgacttta ctcagtgtag    78000
aaataaatgc tcaattatga aaagaatgt tgtgaataac aatggcccag ttaattcttg    78060
tttgatatat tttcagtggt ctttacagct ctcctttatt taaaaaacac taaaaacgag    78120
acaaccaaaa tggttaccaa ctagtttatc cttattaaca ttttaaagta aataaaacta    78180
ataactgcca gtatttaaaa ttcacaaggt ataggatggc agaaaagtaa aaatacttct    78240
ctatgcttat tcacagtatc tcttttcaaa agtaatcact gttaatcttt tctgtgcatc    78300 tttccccaa aatttaatag ctaaatctgc gtgtaaatat atgccctttt aaatttacac    78360
aatagggatt atataatata cagtgttcat atcttatctt ttccacttca tatatttgga    78420
acattttcca tatcagcaat tcaaatttat atcatctatt tgatgattgc attgcattca    78480
attatatgga tgaactttca tttattttatt tatcagttag tcttgataga catttaggtt    78540
atttattttt ttccataaaa accactgcag tgattgctca cacaaatatt ttgtcattat    78600
tttgtaggta tttctgtaaa gtgaatttct aacaatggca acatatgtag caaagagagc    78660
agacattttt tcctttgata aatactgtaa acttaccttc ataaaatgtt tttctaattt    78720
```

```
acacttctat caacagtgta tgagagtgct tatttcctcc acatcctttc acagtaaatt   78780
atcaaactgc ttaaaatgtc ttttccagtt ttataaataa aacataaatc tcattgtttt   78840
aatttgatta ttcaaattat tagtgaggta caacatcttt tcctatgttt ttatttttt    78900
catgtgaacg aactattcat ttcctttatt tattttatat aaatcattca ttattttctt   78960
tatttgcctt ttggaacact ttaaattggt ggcatgttat tcagtatgaa ctaaccttt    79020
taataaaata atttacataa gtttcctcat gatgttttgt attgtaatac tttaaatata   79080
gacttaaatt taaaatagtt tttatttaac ctggtacata ttaagattaa gagacttcta   79140
ccttactttt tgtcccaact gcatcaaaaa ctacgtagta gttttaaaaa tgtgtaatat   79200
atgtgctcat cttctttatt tggtgacaga aagggaataa aagatcattt tttccacaga   79260
ttagtgatat aacttgctct tttatgattt tgataagtta aagttcctcc ctccctgttt   79320
aagaccagaa gcatctgtct gccacgagtt acaaggaaca gatgttccta tgtgacttga   79380
aggaaggcga tctggtgatt gtgatgacta gacagctctg gttagttaga gtctctttaa   79440
cctattgcta agaagtattt tgttgaagca tttattttag agttccttct ttaccctcat   79500
actacataat agagctgaaa agtaaaattg gaatatatat ttgggcaaga gtaactcact   79560
tattcttaca gtgattggtg atttttcatc ttacagatca aatagtgacc cattcatttt   79620
aaccaataat ttcttgtaac ttgcccactc tcataaagct aggagattgc agaagcgata   79680
ctagaatata gcactctcac tttgttacag ttgagcaggt aggttttgt tatgctctaa    79740
tggattaact caataacatg tttgtcctaa accatcaaaa tatattgctg ttgatttata   79800
aagaataaaa agatagtcca tttaattata cacattctct aatattatta gatggaccta   79860
tgtttgtagc caagcttcta gaatctaatg catgctatag ctgtttgagc ttcagggaga   79920
catctgatga gcaatggaaa taataacaga tattgaaggg gagggtagat gaattttaac   79980
agagacacaa tgattcaggg aagggcagaa catatttatt gaggatttcg aaaagtaaca   80040
ggttttaaag tggcagaagt aatttttgttc tgattgccct aattcatcta aaaacactaa   80100
ttttttgttaa ttcatgactc catctgattt ttcacatgca atttaattct agaaaatcat  80160
tagcatcacc atttaaagca cttctttctt ttgattagta ttccagatgg gattaataat   80220
tttctaccct cacagcagaa acaaaaagat attttatcag ctcattccac ctgtcacgta   80280
tcacatcttg cataatttat gcccactgtc attgccaagt aaaacttaag caaagtttta   80340
ggttttgaag ctaaattttt gaatcataat tatttaataa atgttcgtaa aaaccagctg   80400
gtcactttta aaaccctaa aagaagccat atgaagagac taatgaaatc aacacaatta    80460
caatgtcctg cttataaata acatgtaatg ttattaatag aaaagtgagc aaagctacca   80520
cagctgtgca gttgtggcga caacatgttt gactcactgt agttacccct tataaaagct   80580
tcccactaat gaactcagaa gaggcaaagc aggggtagc gttaggcttc tgatacatac     80640
atacatggca gaatagaaaa ggattattac atcagaacaa ttttattgat gctgtgaagg   80700
catttgatct tcaaaattag taatggttta agtcatctgg attttttacg ggaaaataat   80760
gtggattaag aacaggtgtg aaaataatat ggattaagaa cagttaatgt ctataaacac   80820
taggtttgga tgtatatcat ttcccttaa gatgactata ggtattcttt gattacatgt     80880
tattctctag ctccacccca gccatgtccc ccaactatcc taaaagagga tgttttttc     80940
ttgagacatc cattatttcc ccgaaggcta aatttggga tgtatataata actccttttg    81000
gatgatagac ttactctttt tttgtttggg tagaatgaga ggattaaaaa tcttagaaaa   81060
```

```
gttaaactga gttagtgaga atagaacacc cagaaagagt taagttctct agaaaaaacc    81120
ttctctagaa gcacctaatt ggcagaataa ttttattctg tatattttaa taggagtatt    81180
gtagaggaga ttataataaa cttaatcctc aaagaattca tgaaacacct atttaatgtt    81240
gcttagtgga aagagactcc aatgtgctaa tcttggatga aaacagatcc agacatactg    81300
aaggaaatga aaataatctt ctcagggttt aaatccaccc ctctctcccc acagaaaagg    81360
tcgtgcaatt ggccaacagt tttatttatt tattttttag cattatccct cacatctcat    81420
tcatgctttg aaactcttgt ttgccttggt ttgctgttca aacaaatgtc agcagagttt    81480
atttgaaaac tggaacaaat tgcagcactt taggtcatta actgcaatca ggcattttgc    81540
aactgacagt atattcagtg attacaaatc ttgaaacagt gtctggtgtg ctcccagatc    81600
tgttcatgtc tatctttgaa ggatgaaatg ggatttaaaa gaacagaaaa gagagatata    81660
gttatgtatt tatgtgtatg tattatttt aatagtctct ttaacaatat tcatttaaat    81720
atctcttaaa gaattggcat cattctggag ctggcataga gcactgaatc ttgaaatgtt    81780
tagtatcttt agtaacttga tatttgtaac atgtgggcac cttttatgg aaagtacctt    81840 ctgcctcctc ctataatact cataaaacct atgggtacat caaaccatcc atgcatataa    81900
cttatatttg gtcatcttaa ctaacaaact gtttggaact ccctgaagtt ccaaactctc    81960
tgaaaagaac tccattcttt tctcagagaa ttaagccctc aacttgaaga aaattattct    82020
aaaggaagga agaataattg gattttttaa aatgtcattt cagacacata aatcactgga    82080
acggaataga gaactaagaa atagaccagc acaagtaaag cttactgatt tttgacaaaa    82140
gacaaaaact attaaatgaa ggaaaaataa tcttttttgaa aaataatgtt ggagcaatta    82200
gacacctaca ggcaaaaaat tagccttgat ataaacctca ccatgtacat aaaaattaat    82260
ttaaaatagt ttatagattt aaatttgaaa cataaagcca tgaaattttt agaagaaaat    82320
attagataaa atcttcagga cctagggcta ggtggcaagt ttttagacat aacaccaaaa    82380
gcgcaattcg taaaaggaaa tatttataga ttgaacttta ccaaaattaa aatgtttgtg    82440
ctgtgaaaga ttctgttaag tggatgaaaa ggcaagctac agacagaaag tatttgtaaa    82500
ccagatattc aacaaaagtg ttatatgtag aacatataaa gaactctcaa agttcaacag    82560
tatgaaaata aatcaactag aaaagtgggc aaaaggcaca aacagacatt tcaccaaaga    82620
agagatacat atggcgaata gcacatggaa aaatgttcaa tatcattagt catcaggaaa    82680
atgcaaatta gaactgctct gagatattac tgcataccta atagaatagt aaaaatgaaa    82740
aaatagtcat aataacaaat gttggtgagg atttgaaaaa actagatctt tcatacattg    82800
ctggtgtgaa tgtaaaatgg tagagccact tatggaaaac agtttgacag tttctgataa    82860
aactaaacat gcatttacta tatgatccag caattggact cttgggcatt tatcccagag    82920
taatgaaaac atgttcacac aaagacctct gcatgagtgt tcacagcaaa tttatttgta    82980
atggcaaaac ctgcaaacaa cctgaatgtc ccccatgggt gactgattaa acaaactgat    83040
acatccatct ttataatgga atattactct gcaataaaaa ggaacaaact actgatacac    83100
acaataactt gaatgtatat caagggcatt atgcttagta aaaagtgtc aatctcaaaa    83160 ggttgcaaac tatatgattc catttatata acaccgtcaa aataacaaaa gtatggtgat    83220
gaagaataga ttagtggttt ccaggggaca gaaatagagt gaggattgag aatataaagg    83280
tgcagcacaa gggatttctt ttgtggtgat ggaacagctt cgtatgttga ttgtggtaga    83340
ggttacatct atctatacat gggataaaaa tgcatagaat ggaggcaggg catggtggct    83400
catgcctgta atcccagcac tttgggtggt cagctaaggc aggaggatta cttgaggcca    83460
```

-continued

```
ggagttcaag accagcctgg gtaacatagt gagaccccca tctctattaa aaaaatacaa   83520
aaaaaaaaaa gccagacata gtacctggct atgtagtccc agctacttgg aaggctgagg   83580
tggaaggatc atctgaaccc aggaggttgt ggctgcagtg agctgtgatt gcaccacagc   83640
actccagtct ggatgacaga gtgagactat gtctcaaaaa agttttttt aatgcataga    83700 actgcacaca cacacacata cacacacaca cacacagcaa cacacagagc ccacatctta   83760
tcagtattct tttttttttt ctttccaact tttattttag gttcaggggg tatatgtgca   83820
gggttgtttc atgggtaaat tgtgtgttac aggtttggtg tacagataat tttgtcagct   83880
gttaggtagt ttttcaatcc tcccattcct ccaccttacc tgatagatat tttttgtcac   83940
tgaataggta gttttcgatc atcccactct ccaccctcaa ctaggcctca gtgtctgttg   84000
ttcccttctt tgtagtccat gtgtatgaat gtttagctcc cacttgtaag aacttgcagt   84060
atttagtttt ctgttcctgc attagttcac ttaggataat ggcctctagc tctattcatg   84120
ttgctgcaaa ggccattatc tcattttta tagctgcata ttattgcatg gtgtatatgt    84180
actacatttt ctttatacag tccaccactg gtaggcacat aggttgattc catgtctttg   84240
ctattgtgaa tagtgctgca atgaacatac atgtgcatgt gtctctatgg tagaacgatt   84300
tatattccat tggttatata ctgagtaata ggattgctgg gatgaatgat agttctgttt   84360
taagttcttt gagaaatgtc cagactgctt tccacagtgg ctgaactaat ttacattccc   84420
accagcaatg tataagcatt ccccttcctc tgcaacctca ccagcttctg ttatttttg    84480 acttttagt aatagccatt ctgactggtg tgtgatggta actcattgta gttttggttt    84540
agatttctgt aatgattagt gatactgagc attttttcat atgcttgttg ctacttgtat   84600
tagtatgtct tcttttgaga agtgtctgtt aatatctttt gcccactttt taaataggt    84660 tgtttgtttt ttgcttgttg atttatttga gttccttaaa gattctggat attaaacctt   84720
agtcagatgc atagtttgca aacatttct cctactctgt aggttgttta ctctgttgat    84780
agtttctttt actgtgcaaa agctctttag gtcaattaaa ttccacttgt caatttttgt   84840
ttttgttgca attgcttttg gcatcttcat catgaagtct tttctttggc tgatgtccag   84900
aatggtattt cctggatttt cttctagagt ttttatagtg tttttggcct tacatttaag   84960
tctttaattc atcttgagtt gacttttgta tatggtgaaa tgtaggggtc ccgtttcaat   85020
cttctgcata tggctagcca gttatcccag cagcatttat tgagtaggga gtcctttcct   85080
cattgcttat ttttattggc tttgttgaag atcagatggt tctacatatg tggctctatt   85140
tctgggtcct ttaacctgtt ccattggtct atgtgtctgt ttttatactg ataccatgct   85200
gttttggtta ctgtagcctt gtagtatagt ttgaagtcag gtagtgtgat gcctccagct   85260
tcattctttt tgttcaggat cactttggct atttgggatc ttttttggtt ccatatgaat   85320
tttagaattt ttttctaatt ttgaaaaatg tgcacttttt tctaattttg taaaaatgtt   85380
attggtaggt tgataggaat agcactgaat ctgtaaattg ctttgggcag tatgccattt   85440
taattttgat ttttttccta tccatgagca tggaatgttt ttccatttgt ttgtgtcatc   85500
tctgatttat ttcagcagtg tcttgtaatt ctcgttgcag agatctttta cgtccctgtt   85560
tagttgtatt cctaggtatt ttatgatttt catggctatt gtgaatggga ttgcattctt   85620
gatttagctc tcagcttgaa tgttattggt gtatataaac ataccatt tgcatattga     85680 tttttgtatc ttaaaacttt gctgaagttg tttagcagat ctaggagcct caagcagaga   85740
ttatggtttt cctaggtata gtatcatatc atttgcgaag agagatgatt tgacttcctc   85800
```

-continued

```
tttctctatc tggatggctt ttattttta ttcttttctg cttctctggt taggacttcc   85860
aggacttatg ttgaataaga atggtgagag tgggcatcct tgtcttgtac cagttttcaa   85920
ggagaatgct ttcagctttt gcccattcag tatgatgttg gctgtaggtt tgttgtagat   85980
aacacttatt atttgtggt gtacaccttc aatgcctagt tttttgcggg tttcaaacat   86040
gaggggatgt ttaattttat caaaagcctt ttctgcatct tctgagatga tcatgtggtt   86100
tttgtttta gttctgttta tgtaataaat aacatttatt gatttgcata tgttgaacca   86160
aacttgcctc ccaggaataa agcctatttg atcatggtgg attagctttt tgatgtgctg   86220
ctggatttgg tttgctagta ttttgtggag gattttttgca tctatgttta tcaggggtat   86280
tggtctgaag atttttgttg tgaatctgcc tggttttagt atgagaatga tgctggcctc   86340
atagaatgaa ttggacagga gcccctcctc cttgtttttt ggaatagttt cagtatccgt   86400
tcttctttac acatctggta gaatttggct gtgactccat ctgatccaag gcttttttct   86460
ggttgatagg tttttttat tactgattca agtttggaac tcattattgg tgtgttcatg   86520
gtttcaattt ctttctggtt aggccaggta cacggctcac acctctaatt ccagcacttt   86580
gggaggttga ggtgggtgga tcacttgagc ccagacattt gagaccagct tggccaaaat   86640
ggcaaaaccc tgtctctact aaaaatacaa aaaattagc tagacacagt ggtgtgcacc   86700
tgtagtccca gctacttgtg atgtgaggca ggagaatcac ttgagtgcag gaacagaggt   86760
tgcagtgagt caagattgtg ccactgcact ccagtctggg tgacagagca agactctgtc   86820
tcaaaaaaat aaaataaaat aaaataaaaa taatttattt ctggtttaat cttgggcagt   86880
tgaatattcc caggaattta tccatttctt ctagcttttc tagtttgtga gcacagaggt   86940
gttcataata gtctcttagg gttttttgtat ttctgtcggg ttagtagtaa tgtctccttt   87000
gttttctgat tgtgtttatc tttatcttct ccctttttaaa aaattagtat agctaatagt   87060
atatcaatgt tattattct ttcaaagagc caagtcttgg ttttgttgat cttttgtgtg   87120
attttttctca tctccatttt attctgttca gctatatttt ggttatttct tttcttctgt   87180
tatatttggg attggttggc ttttgttttt caaattcctt caagtgtaat gttaggttgt   87240
taacttaagt tgtaagtttt tcttttttat gtcgacattt agcagtataa actttcctct   87300
caacactgct tttgccctgt cccagagatt ctagtatgtt gtatctttgt tttcattagt   87360
ttcaaggaat ttctcggttt ctacagttac ttcattgttt acccaaatca ttcaggagta   87420
ggttgtttag tttccatgta attgtatgct tttgagagat cttcttgata ttgatttata   87480
ttttactgc attgtgttct gagagcatgt ttggtatgat tttggttttg taaaatttgt   87540
tgagaattgc tttatggcta agtatgtggt caattttaga atatgtgcca tctgcagatg   87600
aaaagaatgt atattctgtt tttgttgggt ggagtgttct gtagatgtct gttaggttca   87660
tttggtcaag tgttaagttt aggtcccaaa tatctcttgt tagtattctg cctcagtgat   87720
ctgtccaatg ccatcagtag ggtgttgaag tcttccatga ttatattgcc attatctaag   87780
tctcttccta agtctctaag aacttgtttt atgaatctgg gtgttccagt attgggtgca   87840
tatatattta ggatagttaa gtcttcttgt ttaattgaac actttatttt tatgtaatcc   87900
tcttctttt actttctgaa tgttttggt ttaaagtcat tcttttctga aataaaaaca   87960
gcaacccctt tttagcattc ttaaaattta aaattttact ttcaaaggag ccaagatgaa   88020
atgatttaga tgctttgtca cttatttagt catcttcact gttatccaga agtaaatttt   88080
aactataaat tttattataa gaaagggttt tatcattcta tatagatcaa gaggcccagg   88140
agtattttaa aagtgaattt gttattaatg ttattacagc ttacaaacaa tattattgta   88200
```

-continued

```
tgggtaagtt tatagagtta cacttaagta gttaagaaac aatatgattt tttagtaatg   88260
tacgaagact tttcaggatt ttgtacttga gtataatttt tggagattac atttaattca   88320
gtttatttat ttgttctttt gaggcaggat ctcactctat cagccaggct agagtgcagt   88380
ggcgttatca tggctcactc cagcctcgat ctcctgggct caagcaatcc tgccatctta   88440
gccttctgag cagctgggc tacaggcatt cacctctaca cctggttaac atttttatt   88500 tcttgcagag acgtcatctc actgttaccc atcgcctcac tgttacaaca ttttagaatc   88560
aattgtataa acagggatga cagaaagtac catagttcta gaaaccttaa ttgaggacat   88620
tttccataga gaaaaacctg tatttcctta aatagcatta cacccttta aaactctagg   88680 ttttctttac caccaaatag actagaaagt aaatttccaa tttaacaaag ttcttcagtc   88740
aaaataacac cagcatacat gctattatat agtctcccctt cctttttgctc tttttatctg   88800 aaatccacag catatgtcag tagattataa tttaattaga agatttaata aaagttgtat   88860
ccactcccct gatgccactt ccttatggaa agtttcatta tagcccttcc acagaatagt   88920
atgtttgagt cttattcaca aaggaaaacc atctatttt atctagcaca gtaggcaata   88980
aagaaaacaa attggaataa tataaaagaa aaagtgagaa caaagaacat tttgcaactt   89040
aagattggct ccagacatgg atgaaaatta atgttaaat cagttgtttc tgctataagc   89100
attagcataa gatctttgaa ctgaaaagga ctataaattc aattcaaatt actatattat   89160
ggtgggaaat gggcacagac tctgagaaa acaaaatt taaaaaaaac ttagagttgg   89220
atcctggctt gacaaggtca ctggctaggt gatctttgga aaattattta atgtgtttaa   89280
tttgtctcat cattttacct gtgagaaaac tgacccagag aagttaaag actttccttt   89340 tattacatgg tggtttagct gtatagaaaa aatataaatg tcttttttatt ctcaactagt   89400 tgaagacact ttatgtaata ctattccatt aaaatgtctg ccaagaggtt gttcctttgt   89460
gatattgaaa tcataatgtg actatggcct tattctcata tctgacaaga aatagtaatt   89520
tatatttatt aaaatcatat ttactttcac cattaattct gattaggatt tttatgctga   89580
tatgattaac gaaaatggtg atctatgtca gttgggatag gctaaattat gctataaaaa   89640
ataccctgca atctcagtgg cttaaaccca tttatttatg gctcacaatt catgtccatc   89700
atgaatcatt ggggttttgc tcatctgttc attgtattaa atagtgactt agaaacctca   89760
gctgatagat cagtcttcac cttgaacttt gcttgttgca tgtcaaggaa aggatgagct   89820
ccagaggata tcctcttgcc aattaaatac tccagtctga aagtgacaca cacataattt   89880
ctgttcccac ctcatttcca gatttaatca cagacacatg gactcaccca attaaagggg   89940
agccaggtag tgatgttcta cactttccta ggaagagagg gagaaccagt tatgacatga   90000
tatgaccatc acatgatcta tgaggtatta tggccctgtt taggactgaa aaactttagg   90060
aataactaat atgaaaactt tctgtgtaga caaaaatgtt ctataaaatt cccagccttg   90120
aagagatata ctgttggtga tttgtggctt aaatgtaagt tttttcaata tggcatatct   90180
attcttacct gattgtaaat tttggcaggt ataagtattc ttttctattg gcttcctttt   90240
cactttctga catttttttt tcttttttgct tcctaaacac taaaaacaga tccatagctt   90300
tcctgatctc tcttactact ctgcacatta atcattctga ctgtctcttt tggttagtta   90360
cttttggcta atccacttga ttccctaact agttactccc acatatttgt tgtgtgttga   90420
aggtggatca ttttattaca caaaatagta agataatata atatagagga tttgaatgat   90480
attgcttgga gagagaaatt ggggtcaaaa atgactaagg agaaaaggaa tgagggaaat   90540
```

```
ggtggagatg gaggtaggca agaagattta ggctaaggtt cattagaaat ggtgaaacta    90600
aattggtcat ctattaggat tagagaccaa attcctaaac ggataagaat taagtggctt    90660
gtgccagagc aataaaatca ctggtttctc tttatctgtt ccatttatct tgcttataga    90720
caatctaggt attactattc atttcagtcc aagaagacag tggtccccca tttgacatca    90780
tgacatcaag gttcttctct gattatccat cctggcagaa acacccaggg atggggtctg    90840
agctcaattc tcacatattc agtccctagg aagtgactgc tatcactagc tttcatccaa    90900
gcaagcctaa caaggatttt tcctatgcaa caggccccta attatgctag cctccctcaa    90960
gatcttataa gaaaattacc aagagactaa aatattcagg tttaagacct cccactaagg    91020
aaaaataagt attctttcat tttcttttc aattaccatt aactttccat gaagtataca    91080
ctctttatta gtgctacata agattttctc tgaccactgg ttaaacaatt atatttaaat    91140
atttcttcag agttagacaa gttaacaaaa taacatgagt tttccttttt ttcaattatt    91200
ttttaattgc aaaagaata tgagttaaat ggaattaaaa tgaaataagc caaatggctt    91260
agactagctt ttatatactt ccaaaaccta tgaaccaaga cacaatatga ctattttct    91320 atttcaacct tttattttg gtataaagga tcattaacct acaatataat ataaactgtg    91380
ctgataatat ttgtttgtat aggtggttga agtttgaaga agatgtggaa gatggaggag    91440
aaaggtggag caagccttat gtggctactc tttcattgca cagcttgttt gaattgagaa    91500
gttgtattct gaatggaact gtgttgctgg acatgcatgc caacacttta aagaaattg    91560 caggtatatc ttttcccct tagtgtattt tataggtaca gctaattttt tgttactctc    91620 tttcttat aattcaatat acgtatgaac tttggaaaac taattctcat aatcactgca    91680
taaggtctta aaagtcattt tcttttaccc tgttatttga gataaaagaa gttgaatctc    91740
agagaaatat gctctagttt ggcagtgcca agtctaggac aagaacctag atatcttgat    91800
tcccattcac catttatttt cattatcata tttagactct caccattaga aaattaaagg    91860
aaaaaacctt agagctagat acttatttc aatattcaaa catatgaaat aaccaaatga    91920
aaaaatttca atatacagaa aaatgttggt tagaatgga cacagaaagg tacggccatt    91980
cattttaaac ttaattaaaa cccttgaatt ccagaggaag ccaagtgata cagttaggat    92040
tcgttttgta attcaatact ataaactgat gaatgattag tattataatt caatgatatc    92100
ttataataca gacaggtata tttaggaaat gttattatta cagaaattga gtcaaagaac    92160
tcctgtatct tttgaccaga aggcaaacat attttagtaa aaacaaaata atacaaaaag    92220
acagaaatga atttttgaaag agtataaatg aaataattga tggaggtttt aaaaacacaa    92280
acaaagaaaa gaggcagttg aaaagttatt agtttgggaa aaaataaaat tcattccata    92340
tgatttgtat ttgtgaagtg aaaaaactta atatcttaat catattgtag agatgaaaaa    92400
ctatatgtgt gttttttaatc atgtatatga aaataatata ttagaaaaat aacatatcta    92460
ctttaatctg cagaacagcc ccatgaagta gatgtcattc tcatttccta atcacaaaat    92520
agaaactcta aaattgtcat ggcctagatt tcacccaagg gccctgact ttaagcctag    92580 tgttttttct attacactac aactgctgtc tgaagaaaaa gaaatgtctt gaagtgaatg    92640
tcacccaaat tttgatggca catttatcac cttaaaaatt attgatttag tcattggtgc    92700
tgataggcac tgcagtatgt gtgaaaagaa agtaagtac tgaaagatac tttggcttga    92760
aatattaagc aaaaactcca aaaatactaa aacacacaca cacacacaca cacacacaca    92820
cacacacaca cacaccacac tgccccaaat aggaaagata agcggtcctc ttctgtttca    92880 tgtaacaccct ataaagagat tattctttaa gttacatagc tagagcctga aagacttat     92940
```

```
aaagttaaac ataaatgtat aattttcaga aatatccagg ctactgtagc tgcactaaat    93000
caagagaaaa tagagaaaat gattaactca gaaataagca aactccctaa gaatgctgaa    93060
atagttagct atccagctca atttcttagc tttacattat atggtcttgc taatacccaa    93120
taaacatttt tatattttaa ttaggaatga acagcaggc ttttcacagt actttcaagt     93180
atgggaagct cttaagtttg taattatctt tttaatgctc aaacctggtt cttagtatta    93240
ttattgttat ccttatttaa taaagaaaaa aactaagatt taaaaggtta aaggccttgc    93300
tctaaggcgt ttatttctgc cgcttaaatc gatgatggcg ctacctttaa aaatagatta    93360
atccaaatac attttgaaat gggaaacaaa actgtcacat tctaccacct ggcaaaatta    93420
gcctcagaac ataccctta tacttttacc agtcttcaca tttcttaaat tatgtaatt     93480 ctaatgcttt cctcagaaag ttattcctat gaagaaattt tctcccagta atttgactaa    93540
aacacttcat tttatcactt tagttcactt tcattgtcca aaattatgca aattttttcct   93600 aactctgtcc ctgtttccca agctcaattc tgtagaatat gtgaaggtta actgggttaa    93660
atctagcctt ttcaagcaaa ttacattctc taagtctacc cttacagtga aagtagttca    93720
gttgacgtct tgatacccta aatagctttt tagtattctt tctgctcttc taattagtgt    93780
gtatctttct gactttgaag tagcccaacc tgaatgtccc attttttcagt gtagaacagc   93840 ctgtaaaatg acatttagaa tgtgtcagtg gtttaatgct aacatcacaa agaaaaatat    93900
gattacaaat atttgtgttg atcattatta ctttagattc cttactgtc attactaaga    93960 agagatttcc tctcattgaa aactataatt tggctaaatt taaaagttac ttatttatcc    94020
cctcaatata aactcattaa aatatttcct ctctatagtt tgtaattatt ttcttatttt    94080
ttacttctcc tattttcatt ttataaaaat tgagggcat tactaagtt gtaataaata     94140 agcatgcttt ccgttttaa gacttctaac tttgcaaagt atttccacat aattatgttt     94200
tattatcata acaacatata aagtaggaaa gagactattt caccataaac agataaatag    94260 aaagttctt atcaaagatg acctttgcag aaataaaaat aatttttta ttaacctata    94320 atcataaatat ttggggatgg gatctcctat gttgcccagg ctggtcttga actcctgggt   94380
tcaattgatc cacctgcctc agcttcccaa agtgctagga ttacaggcat gagtcactgt    94440
gcccaaccat aatttttgtt ttattctgtt tcatgatcat ttgtggccat agtgattaac    94500
aatcagccct gaaactttt cctcagctct tatttaccat gattttctc tgttagccat     94560 aattcacata cattagtcac tagtttcagt tttacaaacg ctaagtgtaa gagcttacct    94620
ttaagggttc taatccctag tactttgtga atacacaggc tttacagtat tgatgttttt    94680
cagacatttc ctactagatg aatatgaccc agatattgtt ttgtaatgat caaggatttt    94740
tatatcaatg ttttgatatg tttttaacag actcggataa ttccttaaga gattttgta    94800 gacttagtag cagaaaatcc catttgtatc tggcagatct gtcaagaatt tctgatataa    94860
ttaaagtagg attttctttt ggctaagtta atttaaaata tatctgtttc ccaatgtttc    94920
aggaaactca ataaatttaa actttatcct tcaaaatatt acttaacctt ttcaaatcca    94980
aaattctcca gatatatctt cttaccacaa tttactctga tatggagatt aattgtattg    95040
aatatgcttc tgaattatat tcatataaat tacagggaat tttatggtct atgttaatct    95100
ctttgaaatt aagcattata aagattaatg atggaaatat cctctctgca gtgtgtgtat    95160 actttaaccct aattctgtca atgagagtta ggaagaaatt aaaaccaaac caaagttggt   95220
accatggaca gattatcaat catagctccc aactcattta aacaaccttt gttgtttaaa    95280
```

```
atctttcatt gaaggaagaa tctacagttt gctccactga atgtaatctg tagagttggg    95340
agtataggaa taaccatata ttttttaacc tgcctatact gtgacaatcc ttggtctgaa    95400
aagtaagtat tctattacag tttacatctt tagtacacac atccctgtta gtgctggcaa    95460
ccaaaccaca gaatttagga acttcgtatc atattccccc ccacctctcc caatatcttt    95520
taaagttaag acaatggggtt ttcaaagcat tgatatgatg atcttcaaaa aggcagagat    95580
ttatgtagaa tctgcaatat gtcataacct ctagggctt tcattcaaga tacattatga    95640
taaaatagtt atctgatagg atgaaaaaca attttcatt tttctgaggc cttttccac    95700 aagtgctact agttttctt ttcttttctt ttcttttttt ttttttttaga cgaagtctcg    95760 ctctgtcgcc aggctggagt gcagtggtgc gatctcagct cactgcagcc tccgcctcct    95820
gggttcaagc aattctccta cttcaatctc ttgagtacct gggactacag gcacacggca    95880
acatgcccag ctaatttttt tgtattttag tagagacggg gattcaccac gttggacagg    95940
gtggtctcaa agtgctacta gttttttctag agtctgctta gtgttagcag agtgtgacct    96000
atttgtcctt ttttttcttt ctttttcttt cttttttttt tttttttttt tttttgaggc    96060
ggagtcttgc tttgtctccc aggctggagt gcagtggcgc aatctcggct cactgcaagc    96120
tccgcctccc gggttcacgc cattcccctg cctcaacctc ccgagtcgct gggactacag    96180
gcgcccgcca ccacgcccgg ctgatttttt gtattttag aagtgacggg gtttcaccgt    96240
gttagccagg atggtctcta tccctgacc tcgtgatccg cccgcctcgg cctcccaaag    96300
tgctgggatt acaggcgtga gccaccgcgc cttttctctt atcacccaga tcctggggca    96360
gaatagactg tattatgtag gcataatagc ttgctgagat tgcaggactt cactctggac    96420
ccaacgtcat tatggtccgt tattcttttca cacttttcaa attaatacta atatgtattg    96480
tagtggtgaa aagaacaatg taagtgatta ctaattcaga ttccttttgg tacttaaatg    96540
tcaccctagt ataaattata ttcttaagca aaatgagtaa ttttttccag acaagtagat    96600
ataatttgat acagttatac tttggagaag tttgctgtgt atttctctgt aactaatgaa    96660
cagatgagtg tgttttttaa tatttacttt tctttacata actgttttcaa ataaaaatct    96720 tatctttgaa aaactgtgaa gatagtgacc tatggctttt ttagtgttcg agcctggaaa    96780
cattgtgctt taatagaaat taaaaataat aaacatatgt agggtttatt atgtgattac    96840
ttttgattct gactagaata ttgaactggg aattcatatc atggcttata tttggaactg    96900
ctttacaata atatcatatt gatattctaa taacctactt tacaacttcc attatgaagt    96960
atatgcatat tttatataca ttttttccatc ttagcaaggt ttcagtgtaa tgtcatatac    97020
gttgacaatt tattatttcc tttatttcag attaacccag gggtattata actactgatc    97080
tccaaagaac tgaaaaatag atttaaatat tattctatag tatcacacat tttcagaatt    97140
ggaagggacc tttgaggtaa ttatagtgac tgactttcaa acattccagg tatataatat    97200
gggtaacttc caaatattct ttctacctct ttccattgta aacacaaaaa tgatagagca    97260
cactatatcc cacgtgccac atatggccga ctgcctgatt ttgtagggca tttgagctaa    97320
gaatggtgat tatatttaa atggttgaaa ataataaaa aagaagttaa tatgttgtga    97380
tgtgaatatt atatgaaatt caagtttcag catccttaaa aaagtttcat tggagcataa    97440
ccaggctcat ttgtgtacat gttgcctgtg gctgctttct tgctacaaag gcaaaattca    97500
gtatttgtga cagagatcat atggcctaca atgcctaaaa tatttgttat ctggctctgg    97560
acaaaaagag cttgtctttc tctggtttag agaattaact ctagagtgaa gcgcagttct    97620
tgattagcct gtcagtcata tgaataccat ctcctttgcc agtgattggt tcaagatggg    97680
```

```
cagggctatg tcagttagac ttaggataat ttttcctggc caggtgaaaa ataactcatc    97740
taagagaaag tcacaaaaaa acaatatatt tctcactgga tatgaacaaa aatatatatt    97800
tccttgttgc tgctggaagc caccttatga ccataaggaa aatcagcctg aggttaaagc    97860
ttaccctaga ggaggaggaa gttaacaaaa tcacagagaa gcagaattat agccaaccta    97920
actttgatct ttctatttat gtgagccaat aaaattgttt tatgtagttt aatttgggtt    97980
ttctgctatt gataagccca gctttgtctc tacttgataa gctgtcacaa aatatgaaca    98040
tattgaaacc accacaaatt tcaaaccagg aacccataat ctacattatg aaaattacaa    98100
agaaaatctt gttctgggaa atatttactg atagcctcaa tattccaatc agtgcatcag    98160
gtgccttatg tcattagtct tggcaccaat atatgatata gatattatta tctccatttt    98220
acaaataagg acacttaggt tattcaactt tgcaaagttg tctagctaga atgtcataaa    98280
gtggcccaaa tctgtctcct agttcatttc catttcacac tgaaggaaaa cattgttggt    98340
aagggagcat tctgctaact ttgaaacctt tattgtactc aaaaaggcag tggaaggcag    98400
ctcattgtaa tctgctttac ataagatgtt aatgcctaaa aaacaattag agttaatgtt    98460
tgataatcag aaagcagatt aattacacaa acatccattg atgtgatctt tatatcacta    98520
agaaacttaa aataccttta cttatctatt ttactgacat ttttgatact atgtatggta    98580
aataatctgc ttaattatag acttctgaaa tctcaccttc cagtctttgt tttgcaggta    98640
tagaatatct ttttaatcta acattctcaa gggagtgtgt ttccagcaaa gtttgagaaa    98700
gggctgattt tctatccata tgaaacagaa ttgtttactc tccaaattca gtaactatat    98760
cacttcatag gcctctttgc atcagatttt cacagataga cttttgttca cttaatgggg    98820
aaacaaggaa attagtctgt actagaaaat gggaaaaaaa ttaaaatata agtataaaac    98880
caattttcaa attcaaacac gttatgaatt gtgaattcaa acacattatg aattttcaaa    98940
ttcaaacaca ttatgaattt tgatattatc tctacagcta ttcctcccat cagtgtggat    99000
aataaataaa taagaacttt tcttctcaat gcaactattc ccatttgaaa aataatactt    99060
cataagaatt atatatttaa atagaatggt ttataatgaa aatttgccca aatctttctt    99120
attcaacatt tctacaatgg aagataaatt tccatttata acagcatgct tagagatttt    99180
ttaaagaagt tatttctatt tcaagatgaa taatattgtt tagggcttgc atatttggac    99240
tcagtggttc acggctggca cacgttctag aggaaagctg tgcttatctt cttccggcct    99300
tttctcttca gatatggttc ttgaccaaca agtgagctca ggtcagctga atgaagatgt    99360
acgccatagg gtccatgagg cattgatgaa acagcatcat catcagaatc agaaaaaact    99420
caccaacagg attcccattg ttcgttcctt tgctgatatt ggcaagaaac agtcagaacc    99480
aaattccatg gacaaaaatg gtaaatgttt atttattgtg ctctttatgt ctactatagg    99540
tctctgacat atcaaagcgc ttctaaatct ttttaaaactt gttttatttg aaaatgattt    99600
tttgaaattc agattattgt agaattcttt tcacatgagt atatattctt attatcaagc    99660
atcaagttgt aaaaatttta gaaagaact taagtttcct gaaaggttca ggaaaaaaat    99720
gcaaagaaaa ctaatattta ataaaaaaac ttttagattt ggctgcagaa aacataaaca    99780
gagcatctgt ggcataccaa ataaggtcct agtctctgtc ctgtagctta aaaatgtaat    99840
gcagggcttt gacttacgcc atagatggtc ttttagttta aaggaatcat gatcatcatc    99900 tagtgttgt ggaaaaaaga tattggtttc atgttgctca tagtcaacaa attccattag    99960
agaaaatgat tgaaaagacc agccagtgca ttgtttgtgg ctttacatac attatggctg   100020
```

```
attccggttc aagggctcat tgctgtttgt aatgcagcat cttcaacatc catggagcca    100080 cccccacttac tatcttcata aaccaacata gatgaccacc attgtttcct agcaatcaac   100140
ttactatgat ttatgcttca gactattttg tctttcctgt attttttgtt ctctccttgc    100200
gtttatttaa cccctcatca tttgcaataa ggaagttgct taggaatctc ctgttatcat    100260
ccatcctttc tattagtctc atgagagaaa atgaagttac catgaagatg atatgaattt    100320
gttaaacttc tgtaggcttt aaaagtttcc agttctaggc cgggcgcagt ggctcactcc    100380
tgtaatccca gcactttggg aggccgaggc gggcggatca agaggtcagg agatcgtgac    100440
catcctggct aacacggtga aacccgtctc tactaaaaa tacagaaaaa ttagccgggc    100500
gtggtagtgg gtgcctgtag tcccagctac tcgggagact gaggcaggag aatggtgtga    100560
acctgggtgg cggagattgc agtgagccga gatcgcgcca ctgcactcca gcctgggcta    100620
cacagctaga ctctgtctca aaaaaaaaa gtttccagtt ctaaagata aaaattaatg      100680 aaaagtattt tcaaatgctt tactggaaag actgatttcc acgaatggat gaaagcacat    100740
gtaatgacag cgtgaaatat catgtaatct caccttatt ttcaaaagct tcagagatgc     100800
cttaaataaa atgtatgaaa attagttttc ttcagatttg cttcatatta atcagttttc    100860
atgctactgt atcaaatata cataaaaata tagggtaaat gctttattaa atagataaag    100920
atgattagat gtaattttgt ctcagaatgt agaaccagtt cttaatgaca aaatcatttt    100980
tgagatagtt gattttttagg gcttttcaat gactgaatat aagtcatttt tgttacatac   101040
aagagtctat agatgtgcac acttaagttc aataaaatta ttatgaatac tttatggtga   101100
ataccaactt gtgtttgtag attccactga acattctgag gagatataac ttgctttgaa   101160
tcaaatcata tatttaaaac atatttatat tctaaatcac aatttgcttt aaaatatgtg   101220
atacataaga taacaaaact tgaggctttt atattctaag agatgtatta caaatgcagt   101280
gcttttgtta tgcttataat gctagtattt atttggtatg gtagtgttaa atagactca    101340 gttatttact aattttggct atgggattat gtctacatga ttccaaaaac tttattagaa   101400
ttaacttcct aagaatgcat gcagatttta taaaaatgaa ctttttacctt cataactttt   101460 gctagaaatc agataagata tatgtctttta agaaagaggt atgtttcttc aaagaggcaa   101520
ggatcttgca tttttgaacta gttaaaattt ataccttaaa tttcattgga gataatgttt   101580
actataacaa taatttcatt gcattttttt ttcaggcaag agactacaga atttattgga    101640
gcaatgattt attgtaatat gcagatctag gcacactgtt tgttactgct ttaaacttct    101700
attaaacatt agaagagatg ttagaattat aactgtgaat cacaaatcta catatagtca   101760
caaggttttc tgagagcctg ctttttgtct tatttaggaa atggttttagt tttcccaaaa   101820 atcagaatct gagtggttct aaagtgattc tgtcaccatc tgtacaatca gcctttatct    101880
gaacacatac aaatctttttc gaggcatacg taagggcaat aaaaacttgg aaacatttct   101940
aataagattc atataccccaa ttaagtattg ttgtagagta tgctgtcaga agtggttttc   102000
taagcctaag cttataacac ctccttatga ctctgttttg cttcctcaca cactttgcat    102060
aattatgtgt gttgagaatt ctgaaaatat gtatagactt caccaattta gaagtaaatc    102120
tcctacccaa aagtgaaaaa aagtacaaaa gacctttact gctaaggttc ttaatctact    102180
tatgaactct aaagcctgac aaactctaga tatataaaca aattgaaatt aatagccgta    102240
aatgtaaatt ggaaattctg ttttaaatat gcaatcaaga tttaaatttt tgtgcaatag    102300
ttcagagaga tgcaaaagga tttcaaaaca tcaaaaaagt aaaggtaata ctattaattt    102360
ttaaaaatct ccttagtaaa atccattatg caaaaagatt gactttttta aaaaaaaaga   102420
```

-continued

```
ttatagaata gaaattaaat agagcaaaga ttttttccaga aactttaaaa cagaacacat   102480
tttcctccct aagcatagtg gtagaaataa gtccccgttt cttgtttaat gtgctaaaat   102540
tatctcaaaa aggggatcct ctagagtcga nnnnnnnnnn nnnnnnnnnn nnnnnnnnnn   102600
nnnnnnnnnn nnnnnnnnnn tcccggaagc agagcgggag aaagaaggcc ccgtttcggg   102660
gtgaatgtgc gaaaggagc gcaaaaacaa agtgaagctg atgtagataa acctgaaaga    102720
gtcagataga agaaagttag tacgtcctga agtgacttgt gtcttgagca tgttaccttg   102780
tgagtactct ccggggttaa acattcagac actgtatttc aaacgggtc ttccccattt    102840
taaagattag attaataaaa tagtgcattt ccttgctctt ctccttccca agtctaccat   102900
tctttgtcca ttcctttttt agtgatttgt gataatttgt caatctcatc tctaaacaca   102960
ctagttcact cgtttgaata attttttttct tcgtattccg cattctcttc agggctaatg  103020
tgaaggatgc tatggattca ccatgcattt ttaatgccac catgctgtgt ttaactttca   103080
cttttcatta agcatcaaaa ctgtgagaat taaatgtctg attctgatgt ttcaataaaa   103140
agtgacagtt acatttggca aaacaacagc aaaaataata gaaaaataat atctactttg   103200
acattagtac cctgaaaagg gtatgggtgg taaagcactc aaaataaatg tatcgaaaat   103260
attaaaataa ttatttgaat taggaagatt ttctaaaact aaaaataaaa cttttaaggg   103320
atctagaaga caaattttat cagtatctgt atttatcatt taggtcatgt attcaattac   103380
cttttgagac attgggatta taaatctatt ataaaatatt attatcctta tgataatttt   103440
tatattttg aagataattt gggattatta gttttcttaa gtataggatg tctttattct    103500
gctctatcct ttactaataa tttctaactc tgttcgtttt ccttcacata tcttttgtct   103560
ctcctaatct gaatactttc cagttgtacc ttttatttag gatctcaaaa ggagttacag   103620
tgcagaaagt ctctaactac tgttcaacgc ataagttac tgaaaagcag ttagatttgg    103680
gagcctggga cataaagttc actctttagg cctgggtaga tttcagccct taaagcaatg   103740
tacacatatg tattgtgcat aatatttatt tatggttttg gaaatcagac ctattacatt   103800
gtagttactt cttttacaaa tgctgtactt ttaattttca gatgcatgct gtctttcgt    103860
atttagatat atatgctttc ttgcttttttt aatacaatgg tctcataaat aagatatcca   103920
ggatttaaaa tttatccctc ataatgttct acctttgaag aaaaaataaa gctagaataa   103980
taattcttga gattgcttga aagaaaactt attaaaagat ttgtgtatat taaataatta   104040
aacattgttt aataaatatg atattttcca ccgctccaag aaaatcaaga tgacattgtt   104100
gacacaactg atgggcctgc ccagaggcta tattgtcatt acagttttgg aatgtcaaga   104160
ctagattta agagcaaaca taattctagt atgaagtgtt tgaatttgtt atttcttata    104220
ttgcattaat tattttcagg catactaatt tttctccgag tttaattgtt tgcatacttc   104280
tcatgttttt gaagtgtagc tcacctaatc agcattttct aaatatttag cccttctttc   104340
ttcatgtttt ctattcccat gaataaatgt attgttacac atgtatgtaa ctttgtcatt   104400
catctttata tttctttatt ttgctctgtc ttgtgtctgt ctctaacagg ctcatctcat   104460
ctctgtacct ccctcatctc ctacccttg ggtactctaa atgcgttgaa ggtttctgag    104520
gtagtgtaaa ccagcttggt ctctaggtta atagtaatgt acctccatgt cttcatccca   104580
gtttccttct agtgcacgtg atttacagtg gattaagcag tagaaaataa tgatacattt   104640
atgcaatata ttctattgat acgaatttgg ccaactataa atttaaaagt tgctaagctg   104700
ctgttttata atacatatgt gcatacttaa agaagaagag aactatagct aaagacaaat   104760
```

```
gagttaatat aatactcaac agggtttttg agaatatacc tttttttcca ataatgaagt   104820
gttttaaaat actgctatta attaaagtca tgaaatagta cttttgatgt aatctcatgt   104880
tccttccttt atgataaaga aactgtatga taaagaaaat gactttacca gtctcacaat   104940
acacttagtg aaaatttat ggtgtaacaa gcagaaaaac agcttcattt ttctagttag   105000
tatttactca aaatactctc agttttctcc tatgctagcc ccatatctat tataatttgc   105060
cctagaaaaa ttcatggtct ataataactt tttatctgac acatatgatc cctacatgaa   105120
gactcaaaga aaaaaaatg aatttgtaac tcaaagaaaa gtaattcaaa caggtgctaa    105180
tatgaatact atataatata tatcttaatt ggtaagatat caaacaaata ttagaaattt   105240
tgatttaagg tgaagaactg ttgagcttaa caagtcataa aaatgtattt agtaaatagc   105300
agaggagata ttaggtttct caaatgtttc catttacgtt taaatagtca cagataccag   105360
ttaaccttag tgatatctac ttttcatcag ttttttaata acttaccatg aatataatag   105420
attactcaat gtcttttttt catagtcatc ctcatgcctc aaaattttct aggtattata   105480
aaaacagaaa taattgaaca ttgcaatgac attcatttat aggaaataat atgggtagtg   105540
atcagtggac aaaggtaata taagaaaaca ggtaaaaagc atttgtttgt aagtactgtg   105600
gtatagcact ttaaaaaaat tacagtatac aattagcatt cataaagctt ccacacatat   105660
atgagtgcta atcctaaac ttatactaat ttttttccgt gagggaaaaa tatcctagca    105720
aattctttgt tattctatta ggaaaatttt tacttctggc tgaaggtaaa attctgtacc   105780
tgaaaattgc cattctgtga accattattg ccttagacat cagcaagaaa ataagagatg   105840
cccttccaaa atctgaattt attgattctt cttatgtaat agtatttcag ttaatgaaat   105900
taattttgaa atttaatcca tcatcttctt ttgaaagatg gtaataattg gcataaacta   105960
aataattggc atagagaaaa atatatttaa acaatgatta caattgataa tagaactata   106020 aaatcattt taatttatga ggtttcaatt agttctatat actataattc atgcttgaat    106080
attggtttta tatatacagc aaataaaatg ttaagctttt taaaagactt ctatttttc    106140 aaaataaccc aaatcaaact tgttagctta attttttaaat agtatctata catcgttcta   106200
tatactacca agttgtgaaa actgccttga ggatatacac atttaatgta cattgtttca   106260
actttaacaa attaacttac attttttagaa ataatagaca agaaataaca agatttgaag   106320
tgctacttaa acttcgcagg acttttgatg tgattaaata tatttaatta tgaatattaa   106380
cgcctatcat ttaactactg ctctgaaata taaacgatat acaatttgtg gtctttatgt   106440
ctatgtcata ggctagtagt ttttatggct ttttatatta gcatacattc tatacacata   106500
cctagaatct aggactagca agaagtttac tgtcatctga tgtgtctgct gctagttaaa   106560
ctctcaacta ggtcattatc aacatcactt aaaatattta taaaaatagt ttctaaatcc   106620
cttcttcatt atcaaccttta taaagtaata ttttctaaaa ttgttcttgt tttagaacaa   106680
gaatagcata caacaatctc aaaatatatt attataatta ttacataaaa tattaattat   106740
taattactgt aattatttac aaggagaaat acaagtatta atattttaaa catactacct   106800
gagctgaagg taatttatga aatgctctgc ttaaagtata caaatgaaaa cataaggtat   106860
tcaatttctt caaatgttaa gttccgcata ttttctatcc aattcaaaat ttaatctctt   106920
caaagttaat gactttgcac tgggttgact tttgttttgt atgtgtttgg tgatagaact   106980
aaataattgt tcttccatgt agatttatac cacacgaaat gaattattat aagaaagcag   107040
atatgtgttt atttaatta tccatgactt gagtttcacc actcaattt acagaacatt    107100 caataaattt agttttaaat atatctaatg ttctaactca ttaaaatatg gagaaatgat   107160
```

```
gtgaaactgg tgattgaaga catctgttgg tagcacaaat gcattatgta aaagattttt  107220
ttaaaactac agttattatt ttgagaatgg taaattgaat ggctgctaat gaacagttca  107280
cagtcatagc tgcacattgt ggttagaaat gggagaatga gaataattta tgtagcttgt  107340
gtgacattta tctgaagttt atatatttcc ctagaatatg ctatactcag aatttgtgaa  107400
catggtttga ggtgaactta ttttaaaaag tcattttatt ttcatcttct ccaaatatat  107460
tcttttacat tttttaatga aagtagtgaa atccttaagt tctagaagaa tattaagcct  107520
attactttct ggcattataa caactttaaa ccataaaatt actcctatta ataaatgacc  107580
cctgcttgag aggcttacta gtccaaaaag caaacttata gtaatatttg aaagtaaata  107640
attagtattt ttaaccacag ttggtaattt ctaggtaaca aagaataagt gggttttcag  107700
gagagaattt aagggaaagc gttttttgtgg ggttttttttg catttacact gggagtttag  107760
agaatttcag tcagagactg aagtgattag agatgacact aaaggtgaat ttagaataaa  107820
attgggattt aggtaggtag agagaagagc cagacagaga gagtatttct aacatctaca  107880
actgacgtga ataaaagcag tattttgagt cattgagtta ttatcataaa tatgagcaag  107940
gcttcagagt tgagttgtct ttattcattt cacagaaaaa aaaagatgg ggagatgttt  108000 aattttcatt gcattgctaa ctatgaacaa atttcatatg acttactgca aacaatgttt  108060
catatttagt gaatgatgga atttaacctt ttctagccat tgccacactc ccagagctac  108120
tatccactta attctcatca tcttccctat aataggaaa agaactacaa gataattttg  108180 ttttaatta ctgttaatgc aaaactaata caattcaagt ttttatcttt tctcacatca  108240
cagactagta ccagtatgct tatataatag aatagtcaga ggcataaaat catatccata  108300
gtgttcatac tgtgtgaaat aaaggtattt ctaactgaac cccctatat agaaaactgt  108360 aagagttatg gccaaagaaa tttttttcat tggtttggct ttttagatgc aatagaacct  108420
aaaaatatac tgtgtaattt tcagataaat atccgtcctt tttaatgctt tacattttaa  108480
attcttcagg ctgagcttac atcttaacag atgtctatct tgtcttttta tatacgccat  108540
tagttttggt tggaatctag aaatcaatga tgcttcaaaa tcctggtaac atttacatat  108600
tttgtagata tccttattg aaaataatct tttagagttt ttatctgaaa atatgtttat  108660
tttttactga attctcccat ttctacctgt tactgataat aagaatgttt gtattaatat  108720
agatttattt atattgaccc ttcattctta catcataaat ttattaagaa acctgttagt  108780
ctagtttaat tgaagtgcct atttcactca gtatgtctac aactatgtaa gtaattgttt  108840
gtattctgtc acaacaatct cttttagcag gtcaggttgt ttctcctcag tctgctccag  108900
cctgtgttga aaataaaaat gatgttagca gagaaaacag cactgttgac tttagcaagg  108960
tgagcttttc tccctctcat ctaagtaagt tgctaaatta ctactagaaa ttactaccca  109020
ttttaagagg tgttgacaca atattttgca tgcgcttttt gtttcttgtc aaagcttgat  109080
attgttacag aaaatgttag cattaagtcc acatgtaaca ttttgcctat tcaaaaaaaa  109140
aaaaaaaact gaacctgtga gttttatgca tagtattcat gtttcagcca cttggtataa  109200
tgttatctct tccaataaaa agaataactg ggcttcacag ggaatttaac agaagtttaa  109260
tctatttttg tttgtttgtg tttgttgttc tttgtttgtt tgtttgaggc agagtctcgc  109320
tctgtcaccc aggctggaat gcagtggtgc aatcttggct cactgcaacc tccgcctcct  109380
gggttcaagc aattctcaag cctcagcttc ccgagtagct gggattacag gcgtgcacca  109440
ctatgtctga ctaattttg tattttagt agagacgggg tttcaccatc ttggacaggc  109500
```

```
tggtctcgaa ctcctgacct caggtgatcc gtccgcctca gcctctcaaa gtgctgggat 109560
tacaggcgtg agccacccccg cccggccaag tttaatctat tgtttaaaaa ctttggctag 109620
tttgtgttca aaatcacttt tcttctattt gtgggaaagc aaatcataat ataaaactga 109680
attgttaatg taattaagga aaagtcatta ctgtaaggaa atcctagaag acacagcaa 109740 aactgagcag agttttaaat aaaaacatat taagaactga ctgtgttgag ggatacatct 109800
aattggagac aactgaagtg aaatcattaa cttgaatgta ttcttagaaa atgagtcagt 109860
gacaatgatg tgattttgat tagcaaattc ctgacattgt atatgtgcca ttgcaagcta 109920
tggcaaagta acaattgagt ggaaaagagg agtttctagc cgggtgtggt ggcgcgtgcc 109980
tgtggttcca gccacttggg aggctgaggt gggaggattg cttgagccta ggaggcagag 110040
attgcagtga gctgaggtcg tgtcactgca ctccagcctg ggtgacagag tgagaccaca 110100
tctcaaaaaa aaaaaaaaaa aaaaaaaaaa gacaatgcaa aagagaagga gtttgaatac 110160
ttggtgaaaa tacggcaggt taacaattct ctttatctga gtggctgaaa tagaagtaac 110220
tcagagtaat attttaataa agcccttagc actggcaata attatagtag tgggaggagg 110280
tgggaatgga tggaagcagt agaggaagta gcctgaatca aggttctgaa aagattaata 110340
gtgatcagct ccttggacct gtttcagaat ccctctgaca atgcctaaat aatctagatc 110400
tagttacgtg catgctctcc ctctggtgcc tggcggagtc tccgtgggag catggtgtac 110460
cagcttaagt ctgttaatta tgcgtgcagg gactgggagg ccaacaaaag gggcatacta 110520
gtccatgtgg gatgaaacaa aggcatgaaa aaggacctcc acaccagcaa gagagagagg 110580
tgagggcata ctcgggctct atttctacag tggttcaaag ctcatttcac tgtatggagg 110640
catgtgattc aaacattaag ccagttgaaa tgtattccat ctgccactct aagaactatc 110700
tttttaaagc attgcatctt cattcatctg caagttggaa aaagttgtca caaactgcca 110760
tacatttaat ttctgatatt cttaatttga aatgatctta aaagcaataa tgtaacgagc 110820 tgcatatttta tgtataaatg cattaacaac ataaagaagg catatttaac atcctcagaa 110880
acaatcatta taaagcacat agctcctcct ttcaaataaa ttgtgattta acttttttaaa 110940 aataatataa cctttataca ctgattgtgt atctccatat catgttgctt ttggttgtgt 111000
gacctgcctt tgcagccttc aagaatactt catcacatat gaaagaaaat gaagattgcc 111060
agttgtaggc agtagtctca tcttctggtc cccctcaaa cagttaaaac tatggaagag 111120
tcaaacttcg atttcctttc ttttaatcct tttctttctc ttcacatttg cgatcactgg 111180
cccgtttcat cttttaatag gcaagttaaa tttctagagc cctctactta gtgtcagctg 111240
ttgttcatag catggcacac tggaaagtct cttgttcata gcatggcaca ctggaaagaa 111300
tgtggctttt gagaaacagc atgagatctt gaatcccaac tctggcatta taaactagct 111360
gatcttggag aagttctcta aagttcagcc ttctcatttg caaagtaaga aaactattta 111420
caatttcgtt gtgaagattt aatgagctaa tatagaggga ggtgctggaa cagtgcttga 111480
cttgtagcag gtatttaata aaaggtggtt acacttatta gtgtggttat tagtagtagt 111540
agagataata gtgtcagaaa tgaaacacca gaccataatt gaatgttttg gtctccactg 111600
ggtctttagt gccttgaata gtatttggta tatatttgtt gaatgaatcc ttcaagattc 111660
aaaataatgt aagcccagtt ttggaattta aaaaagacta gtaagatttt tttactttaa 111720
agtctgagag ggcagaaaag tagagtttga aaagagcaat tgtgatctat cactatggaa 111780
acaaatttta gtgccagatt ttgcaggtgc atgagttgat attttttagc cttatgattt 111840
tagtttagta gtgaatttat cagaattcac ctagtctcca ggttagttct ctgttttaat 111900
```

-continued

```
attttaagtc ttaatataca gattccaaaa ccccagaatc ttaatatgca gattccaaac 111960
attttgaggt gttaagaaaa aaaaggtctt tattcatctt atatgatttg atcatattta 112020
ttccatctac attcaaccta catatttgta acccttccag tggatagacg tatcaaactt 112080
acttaaggaa tgattaggaa ataactggaa attatcaggt tttagcttcc cataatactt 112140
ttaaaaagca gatgtgtcaa agcaatattt gtttttgttt ttcaagctga cagtggaacg 112200
taggtatttt atgttggtgg tgttttcttt tacttcaaat gacccagaga tggcttcaca 112260
taattttcta catagaaaga acttccgtct gcatctagct ttagtgtatg aaacatatta 112320
gagagagttg tattatttaa tcctagaact gtaggaaacc ttagacatct cctcatttag 112380
tcagcaagaa agctgaatta tagagtgatt aagagagctg ctcaagatca ctggcgagtt 112440
agtgtcaaga caccatttct tcccagagaa tccctatgaa gtttcttgta ctttctataa 112500
ggggctgaag gcttaaattt tctccttaaa tttccatctg tttttccttt aactcttagc 112560
gtgtagtttg cccagacact tccaatttca ccttggtctt ctatctaatc tcattccttg 112620
ttccctagaa atgtaactgt ttctcatcca cagattaagt atcaaaggcc cagaaagaaa 112680
tctttccact accagcataa aggtgaggtc tgggcagccc agaagcatga gtgtaaatac 112740
agacccagaa gagtatagct cgatttcttc aagatcctat tcagaggacc agaaacttcc 112800
aggatttcct tcttgtccat tccaagtgtt tgtgttcact tgacagtttt cttagggatg 112860
tagttcaacc tagattctct agagctgctt tacatattta aattttata agaggtcaca 112920 ttcaggtctt taaacataat attttattat attaaaagtt gcttagggg ccaagggcat 112980 ggtggctgac acctgtaatc ccagcatttt gagaggccaa gtcaggagga tcacttgagc 113040
ttaggagttc gagatcaacc taggcaacat ggtaagacct catctctaca aaatctagaa 113100
aaaatcagcc aggcatggtg gcgcacctgt agtcccagct actcagaagg ctgaaatgga 113160
aggatcagga tggcttgagc caggaagttc gaggctgcag tgagctggga tcgcaccact 113220
gcactccact ctggatgaca caaggagacc ctgtctcaaa aacttaacca aaccaaaaaa 113280
gatagttggt ttgtcaaata agtttcttca tgaagtatat agtacacaaa cacaaaatat 113340
agggttgccc cacgaataat ataatatgta actatacata atataggaat aatataatta 113400
gataatatat aatcgattac ttcccaaagt atatgattac tccaagaata atgtaatgta 113460
atgagtataa tacaatggct accccagata tgtgctatag tactataact tattccattt 113520
gaagtcaaaa gatgaatttg cttatcctga atttaaattc tgtatatttt aatgttttt 113580 ctaaataaca ggtatcaatg atatattagg tattttgtaa atttaaagat catatgtaat 113640
gaccatatat tttcttttac aaaatttaac tattttaaca tactatgtac ttcttgattt 113700
aattaaattt catctttaaa cagttatttc tataatcacc agttgcccga ggcacagact 113760
ttcatagtta agacaatggc atttgtcaag caataaatga gttatagaa ttttcaaggt 113820 ggaatttaaa tttcaggtat tatcaatata attcatatta tcaattatgg attttaaaaa 113880
aagatgtttt ctcattttaa attttgttca gtatatttat attgtatcat tgttctttcc 113940
attgagagag aaaacttaac tgtttattct tttagtaaca gaaaggatta tgagatttat 114000 tatgtttttcc tcacagagct gatagtatat gggaaatctt ctattccctc cttgggaatt 114060
ttggcattac aataaaaatg taaagcatta ctaatttaaa gcatcttaaa tgtgtacatt 114120
tctcctaact agataaatac ctacaaaaat accacaataa atcccatgaa atttaacctt 114180
acttattata gtaaataaat acttttgcta tctataaact aaaagatcag attccacaaa 114240
```

```
agcaaaatat ttgctgtata atccagtgta cattaattat gaatttacaa atttatattt 114300
ggagtacatt tgtagcttaa aaattttgga tgtataatat ttgttagata tttttatagg 114360
cagttttgct ttgttaaatc attcttcctt tcctttaaaa taaataatg attctattta 114420 atatttttga tggagtactg taggatattt ttatatttaa tccttgtgaa agaacatatg 114480
cttcctatac taggttatat attttgtggt atccttattc tttggaaaga ttaattagtt 114540
acaaaactta caaatagctg tactatcatc ttgatttcag aaagcaacat atttaatgta 114600
gtcactaagt attactatgg atttttttcat tttaaatttt tgagaaaaat attctcaaat 114660
cattaaacct gcaaaagaac tatctaggct aaaaaaaatc ttctcagccc cactcatatt 114720
tgccagagct cattcctctc tcggctattc tcactttgat ctttggccct catttcatta 114780
acatcagagc ataagatcaa ttactagagc agataaattc ttactcccct aaaaacagag 114840
tttcataaaa agctactcaa gtgaattaga aacaagacat agatcttgta caatttacat 114900
taaagtcact gcttgtcttt cactgaggcc ctatgcataa aaattgatat ttattgttaa 114960
ggatattttg cattcatttt ttagacttca ccctttattc ttagcatttc ttctcgttaa 115020
tgatcacttt tgctttgtgt acattcattt cgatcacaaa catctcatgt cagaaattca 115080
actatagctc ttcagtaact ccaaatgtta atattttttt cttatttttt tctactgtgt 115140
catatctaaa ttctcagatg aaaaaccaat attgaagaat taccaggcca agtatataat 115200
gtgaagaata tagaacaact agaaaagaga agaaggttaa agtcataatt tatactgtaa 115260
agagaaacag gattatattt cttttgacat aagcatattt gagtatcaat taaaatgtat 115320
tatgtacaaa aattaggtaa tgtagtataa aatattaaat ctgttggcaa atgctaatta 115380
aattatggtt aaagaatagt tatttaactg aactcacata cttttccctg tctaaaattt 115440
caagattgtt gaggctggag aaacttcttt taaaaataat aaatagaagt accagagtac 115500
tcagcttatt gatgacaagt taaaataatc cacaagtaaa gaaaaaaggt tattatagaa 115560
aaagggcaaa tgagatgttt aactgtgtgt atttatttaa actatattta ttcatggatt 115620
actatatgtg aagcactgtg caagaatatg atttaccaga ttttttccaat tttgatttat 115680 catatttacc tggtgatgct tgcaggttga tctgcatttt atgaaaaaga ttcctccagg 115740
tgctgaagca tcgaacatct tagtgggaga actggagttc ttggatcgaa cagtagttgc 115800
gtttgtcagg ttgtctccag ctgtattgct tcaaggactg gctgaagtcc caatcccaac 115860
caggtaaaaa gtataaaagc gtcttttgta ttttttcttaa accatctttt catggaaaga 115920
aaatgaggat tcaatgtaat tttctgttag agttttgact agaaactaat gtgaaatcca 115980
caaaactact attaattttt gtttgtggag gaggggaaaa gtgctttaaa aattattctc 116040
ttctttcctc ccttctctca aacttctgct tcattttagg cacattcctc atctcaaggt 116100
accctgaagc catatgaatc cttttttttt tttttttttt tacatttttg gtaaagaag 116160 tggtaacatg ttagcttttt ctcaaagatt gcattaaatt gtctgctata gaagaaagg 116220 atcctgtgca tgagtgcggt caaactcaaa aacagcaaag ttactaaggt ttgcttacac 116280
ttgaataaga aggccttcaa aatgcatgta agtgccatcg ttaggatagc gtcaaatata 116340
tgtttcaatc ctaggcacag tgggcttccg acacacaggg tctgtagaaa cactggtaga 116400
agtattatcg cagtgtggtt ggatgtgagt taaggtaca aatttaattt gatgatcaga 116460
acttgtttct catttaacaa taaaataaca acttagggat aatacaaact gaattatgct 116520
tttctcattt tttagaataa ggctatccat tactaaaact gtaaaaaaaa gaaaagata 116580 aaaaaagaa aggaaacaca gaatattgac tttagcacat taatttccaa gcaatttacc 116640
```

-continued

```
caggaacctt gttttcttcc atacttctac catcagtgtg attccaaaat gcagatagcc    116700
ttttactcta gtcctattcc cacagcaaaa catgtatatt tagggccccg ttcccatatg    116760
gctggtgccc tttgtttgat gctacagcta tctcaaaagc tgttagtgcg cctcctcttc    116820
caaacattga ataccttagc caagttactt gatgaaaagt tcaggtactg tatcaactgt    116880
agaatatatg tcctctatga atctttggcc ttaactcaaa atatagcaga ttacataact    116940
ccatgctttg attatggata aaatattcta caactatgga acagcacagc caggagaggc    117000
ctcatttttt aagagctcag ctgactggaa cgggattcag tggttaagta cctatgtctg    117060
actatggttt gggggaggaa tctagttact gttcagatta tagaaagaag tctatgttta    117120
tcctgtttga gagttactga gatgactgat acacatcaac ttttatgtac aaagggaaag    117180
gatgaactga gcacattaaa gtggcatctg actgtgtgat tcaggctata tgttttctat    117240
ggacaacctg taacctattc aaggtttctg ggagtctggg atttatatct aagatgttaa    117300
acttgctaat ggtagagtta ctattatagc agtttaaaat ttcttttcag tcctccaagc    117360
agtgcatttg tgttccacca cttaggaagg tgtctggtga actatgagca aatgatggct    117420
atttacgaca atgatagtgc ttgtatttca aagaaggaa aagaaaaatt cccatgagta     117480
gaaaaagcc gtgatggggt tatataccct tactgtgaaa actgtcaggt ttaagtgacc     117540
ttatttcata ctgagatagc aaaatatgtg tagagaacaa cggagaaaaa aattagggcc    117600
actgtagagc aactgtatga gaaaagattt aaagacaaga ctatttagtt aggaaaggtg    117660
aaaaatggaa gattagttgg acaaacaaaa taagaaagc cattcagggt ttcttattat     117720
ccttttttg ggaagacaaa aggcatccta ttaatacgat ggcaacacat agtagaaagg     117780
tcagaaaata atcttttaga tctttaaaaa tagcccatgg aatggaaacc tgaaaaatag    117840
caagatgtac ataggttagg aagtttctta aaaagctatt atagttgata aagcacctgc    117900
taccgaatta aaccattcct gtttttaatg tatactggac atttctacat agtagaaatt    117960
ggcttgggtt cagttgtcac tggcacacac aaaaaatatt gtcatatcct ctacaattgt    118020
gtaatatttg cctcatgtaa aaacatgtac aatctctaaa gattacaact aaatgaggag    118080
tagaattata gtaactattt tagtacacct tgtgaagtca ttagtcttca tacttaacag    118140
cataaaccat ttaacaaatt aacaccacag aatgatatgg cagaatatag ggcattcttt    118200
aattttcaaa atttcccaga aggattgacc ttctcagaga cagggcaatt accagtctgc    118260
taaagttaga gtatctattg atttctttaa aagcaccact tgtgatgatg aatttgccaa    118320
atgttcgacc taatatagat ggaatattat agtgcagatg ctattttat tcctcagcat     118380
tataaataat agatcattaa ctccccattt tcttctacgt ggctgatctt tgattcctga    118440
caataatttt ttataatgaa aattgcacat acacctactg ttttttgact ctatattttc    118500
tctgtttgc tactgtgtta ccttgtccc ctttgaacta ttcgccattt tgcatacaag      118560
tgagttttct tccttccaat ttagaaaggt ctaatcagat tttacttttc ccactttcct    118620
tctctaagga tcatagaatc cttaaaattc ccaataacaa ctgcacatgc tgtacagata    118680
actaaacgga gaaacactgt gataaaaaaa aaaacacgg aaaccatgc attcccattg      118740
cttgaggatc ttaagcataa gggtcaatca tggtaaaatt tttcaaaata ataatgaact    118800
atgaaaaact atggaagtat ttgccatcac aatctccatt tcagtaatt cctttgagat     118860
gagtgattct gtattactaa aattatttt atatttctac cttaaaacat ttttttttctt    118920
cttaattaca gattttttgtt cattcttctg ggaccctgg gaaggggtca acagtaccat    118980
```

```
gagattggca gatcaattgc aaccctaatg acagatgagg tatttattca agttctttgg  119040 gaacatttc ccccattagg tatacctaaa acttttggag gtcctctttt catgacagtt  119100
tgttgtgaat cagatttctc tgtattgaat cccattctcc catgcttctg ctataaaatc  119160
tcctttagaa aaatgtttcc caaagggata ataaattaac acccatgaat ataatatttt  119220
aaaacttcat agtgtaaaga aatttttca gtgacactta gaatatatta ttaatattcc  119280
ctttatggta tatgtgctac caaagtaagc accattgtta atatcaatgg aaatcttgtt  119340
ttgagtaaag aatttcgaag tctaaagaaa aaacaatagc agtttatctg aatagtatac  119400
atgacaccaa aatgcatgca acatctatca actctctaca gttgcctgaa tgtagatatt  119460
tttaacctgg gagtctgggg actattagag aagctgtaga tagatttcaa ggagcttgtg  119520
atttctgtaa cagagcatgt aaattttct atgtaaaaaa tttgtatgta gatttttgg  119580 gactggaaaa agctttcatc agctcttcaa agaagtgtat gtctcaaaaa tataagatct  119640
ttaaagtaag aacataaaaa gtagcatcat accactattt tcctttactt gggttctcca  119700
acacattatg gaaatttgtt gttattgtta acgggaagag cagatgcagt agatcacaga  119760
aggggcatta aatcaaaatt cagttgtaaa tgaacaaatg ggattatata cttctagatt  119820
tcatctaaat aatttaataa tgttttatt gaaatacatg gctgcagata tttgaaaatt  119880
ctgtaaaaag agccaattag tattgtatat tactttttct atgttacaa tagctaaaat  119940 ttgaacttgt tttgggggtt aaatattata aattcttcaa tctgtccaaa ttatgtttta  120000
tagtgttata tgaattagtt tttgatattt atgcacaaga aagcaaaagc aagaagaaaa  120060 acattttc cctcagtttt caaaaggaac caacttaatg agtgtattag tttacaacga  120120
ctgccataag aaactactac aaattgggtg gtttaaaatg acagtagttt gttttctaac  120180 attttgagg ctagaagttt gaagtcaagg tgtcagcagg gccacaatcc cttcgaagtc  120240
tctaggggag gatccttcct tgtctcttcc atattctggt ggctcttggt cttccctggc  120300
ttgtggcaat agacctttgt tctctgtctc catcttcaca tggctttctc ccagttgtct  120360
ctgtgtgtct tcttatttc tgttatgaag acagacattt gtcatttgat ttagggccca  120420
tcctaaatcc atccaaatca ttggatttag ggcccatcct aattcaggat aatttcatct  120480
tgagatactt accttaatta catctgcaaa aatccttatt tcaaataagg ccacattctg  120540
cggctccagg ttgatgtgta ttttgggagg aaattattca atccactgta atgaataact  120600
tattctattt aggaaatttg tgagaagaca ggaggatgaa aaaaataact taatgagggc  120660
catacacctg atttagcaga actctctctg agaaaacact cacagtataa aagctcttag  120720
tatttctata ttgatttgta ttgttattct atgatttaag tattatcact ttcacataca  120780
tttgtttaat attttgttat atttcagaca aaaaatgttt ccccatctaa gaaattaggg  120840
caatatttta agatatctgt ggggcatgag acacgtgata atgtgagagg atcctactat  120900
gtcatgggaa gtacatgtat atcaatgtat ctctcttctc ttcatcctct acttccccaa  120960
ttgggaatca agattttct cgacagaaag atgtcagttc caaagttttc ttgactaacc  121020
aagtggacac agaacaggga acatccatg ttctataaat ttcagattta ggatgagaac  121080
agagaagggg cttccaccta tttctttgat tagtgagagc tacctaattt gagaataagc  121140
atcaatcaca taataaagac tgaaattga gcataagcat cagtcatcta ttttttcaat  121200
tatttagact tgaaagttc agagcatggc tttaggtaat cattgtagat tatgggatag  121260
agaagcagaa actcaaccag aaagctactc taaaagataa gagccattag ttataatagg  121320
acatgttaat tacaacagga cattgattga atatcaaaga atgtttaaat atttttaaa  121380
```

-continued

```
agagaaaaca gatttgtatt tctcaaagcc tcggtgaggc aattgttctg cttatctaat 121440
tgctttgaag gctattgaat aattgtacta ggccaggtgt aatggcttac atctgtaatc 121500
ccagcacttt gggaggccaa ggtggatgga tcacctgaag tcaggagttc gagatcagcc 121560
tggccaacat ggtgaaacct cgtctctact aaaaatacaa aaattagctg ggtgtggtgg 121620
caggtgcctg tggtcccagc tacttgagag gctgagaggg gagaatcact tgaacctggg 121680
aagtggagat ggcaatgagc caagattgca tcactgcact ccagcctggg tgatggagcg 121740
agactctgtc tcaaaaataa ataaatagat aaataaataa gaaagaaaaa gaaaaagaa 121800
aagaacaatt gtactcatta agaatagaat ttaatatgtt gattcatagt ttactttggt 121860
taaaaaaat agtgcattgg agtgcattat caaacataaa ttccatgaga acagttagca 121920
ttttagcatt cagtattcgt ttttatgacc tgattcttcc aagtgctcaa ataaatatcc 121980
attgagctaa gttctgtttt ctttcccttc tctgtacttg aacactttc taggtagact 122040
gtcttccttt tgtattttta gacttattat gagtgtctga ccctcagtca gggttcaata 122100
aatctttaga acatgaatca attactgaat attctagaca tcataccaat attctatctt 122160
gaatcaagcc aataatttat tttcttcatt tctgttgagc tttgctagag ataaatcata 122220
tgattatgct tatcaacact gctaccaatg tgttgatccc ttcacattct caaaaattac 122280
taagcacccc aaagaacttt tgtgtatgta gatatgttgg tatttaccat aggagaactt 122340
aaaactgaga aatttaaaaa gtatgtgtta atgaattcat ttaaaaataa taatagaacg 122400
ggttcagtgg ctcacacctg taatcccaga actttcagag cctaaggcga gtggatcact 122460
tgatgtcaca agtttgagac cagcctgggc agcatggtga agccctgtct ctaccaaaaa 122520
attcaaaaaa atttagctgc atataatccc agctgctcag ctacttggga gggtgaggtg 122580
ggcggatcac ttgagccagg gaggtggagg ttgcagtgag ctgagatggc accactgcac 122640
tccagcctgg gcaatagagc cagaccttgt ctcaaaataa atacataaat aacaatagta 122700
aagccattac atattaacat aaataataca ttttaatgaa acaaannnn nnnnnnnnn 122760
nnnnnnnnn nnnnnnnnn nnnnnnnnn nnnnnagtt tgtattgagt atcaaaccag 122820
aaatggaaac aaatggtcta aaagtaaaat agaatatttg aaagcagaat ttcctggca 122880
attttgggac atttggtcac tgtaatttag gccagcataa agaataatat aggagtcctt 122940
aatctcaaat acttgtatca tttcatccca agtaaaattt aaagtgtcag aaatatttat 123000
attatattca gtgtaaatta atttttttctc ttcatcctta ttttttatttt ccccacttac 123060
tatattaagt acgtaattcc tgagtatgat aagataaatt aggttatgct gcaggaataa 123120
ccaactaaaa tattaatggc ttaaaacaat aaggatttat ttctatcatg ctaaactttc 123180
atcaagatgt aggagagagg ctctgctcat tataatcact taggccccct gtgcttatag 123240
aagctctagc tggacctgtg ttttctcagt cactaaacca gaaaaaaagc aatgtgataa 123300
gtcacacatt ggtactcata acttccattc aaaactgaca tatgtacacc caagtagaat 123360
atacctgatc caaatagcaa agaaggcaaa gaagtacaat cttaccatgt ggtctagaag 123420
aaaacctgga atatctgtga acagcctaaa tggctaacat agcacatgtg tgcggagggg 123480
aggtggaagg gacaagtatg aaatgtaact catactttga gtggaaatga actttctgca 123540
ctgtgtagat ataatatata gttggccctc tgtatcttca ggttctgcac ccttgaactt 123600
aactaactgc aaatcaaaaa tatttgaaaa gtcagggtgc agtagctcac acctataatc 123660
ccagcacttt gggaggccaa ggtggaggat ggtttggggc caggagttca agaccagccc 123720
```

-continued

```
aggcaacata gcaagactct gtctctacaa gaaattttt aaaaattagc caggttttgt 123780
ggtacacacc tgtagtccca gctacttgga agacaggagc ttaagcagga gcttaagcct 123840
aggagttcaa ggctgcagtg aggtatgact gtgccactgc attccagcct gcatgacaga 123900
gtgagaccct gcctctaaaa acaaaaatca aaatattcg agggggggac aataaaaaat 123960
aacaatgtta caataaaaat aatatgcata aaaattatac agtataataa atatatagca 124020
tatacattgt atagatatta taataatcta gaaatgattt aaagtacaga tgctcctcaa 124080
ctttcaatgg gggattatgt cccccccattg aaaatatcat aagtggaaac tatgttttg 124140
acttatgata ttttcaactt atgataggtt tatccagact taaccccact gaaagttgag 124200
gagcctactc aatgcatgtc acttttgcac catcataaag tcaaagatt gtaagagaaa 124260
ccatagaaag taggggatcc tctaaatata ggagtatatg cataggttat gtgcaaatac 124320
cactccattt tatgtaagga actcaagtat ccatagattt tggtatctgc agggaatcct 124380
ggaaccaatc cctcaaagat actgaggaat gactatatat ccagaaaata ctaacataac 124440
cttagtatta ttttcaaaat ggaaacaaaa ttaacctttt aaattaattt atttatgcca 124500
gggtataaat actgctgaaa tttccaacac attttacaaa tttttatttc tatttgtaag 124560
caaaggcttc ctccagaaac tgattttccc atacataaat aacttttgcc taattctagt 124620
ttaatgagct tcctttcatc ctcctttttc tttcccttac tccttccctc tagaaatttc 124680
aacattcatc tgacatcata agacaaatag ttacctatat ggatccataa aataaattat 124740
aatattttac aacataaact tctttagagt cagagctgtc tatttcttca aattgttata 124800
atcacatgtg agataactga gttgaaaaca ctgaacacat taatatttta taattatttt 124860
taagctataa ataatatttc tatttcttct aaaggtattt catgatgttg cctataaagc 124920
taaagatcgt aatgacttgg tatcaggaat tgatgagttt ctggatcagg ttactgttct 124980
ccctcctgga gaatgggatc caagcattcg aatagagcct cccaaaatg ttccttccca 125040
ggtatgtata tttgaagaca ttcttgaaa ttgaatttt ttttgtcttt taaatgcatg 125100
ttttatttta ttttatttat ttatttattt attttattat tattatactt taagttttag 125160
ggtacatgtg cacaatgtgc cggctagtta catatgtata catgtgccat gctggtgtgc 125220
tgcacccatt aactcgtcat ttagcattag gtatatctcc taatgctatc cctcccccct 125280
cccccactc cacaacagtc cccagagtgt gatgttcccc ttcctgtgtc catgtgttct 125340
cattgttcaa ttcctatcta tgagtgagaa catgtggtgt ttggtttttt gcccttgcga 125400
tagtttactg agaatgatga tttccaattt catccatgtc cctacaaagg atgtgaactc 125460
atcatttta tggctgcata gtattccatg gtgtatatgt gccccatttt cttaatccag 125520
tctatcattg ttggacattt gggttggttc caagtctttg ctattgtgaa tagtgccgca 125580
ataaacatac atgtgcatgt gtctttatgg cagcatgatt tatagtcctt tgggtatata 125640
cccagtaatg ggatggctgg gtcaaatggt atttctagtt ctagatccct gaggaatcgc 125700
cacactgact tccacaaggg ttgaactagt ttacagtccc accaacactg taaaagtgtt 125760
cctatttctg cacatcctct ccagcacctg ttgtttcctg acttttaat gatcaccatt 125820
ctaactggtg tgagatggta tctcactgtg tttttgattt gcatttctct gatgaccagt 125880
gatgatgagc atttttcat gtgtcttttg gctgcataaa tgtcttcttt taagaagtgt 125940
ctgttcatat cctttgccca cttttttgatg gggttgtttg ttttttctt gtaaatttgt 126000
ttgagttcat gtaggttct ggatattagc cctttgtcag atgagtaggt tgtgaaaatt 126060
ttcttccatt ttgtaggttg cctgttcact ctgatggtag tttcttttgc tgtgcagaag 126120
```

```
ctctttagtt taattagatc ccatttgtca attttggctt ttgttgccat tgcttttggt    126180
gttttagaca tgaagtcctt gcccatgcct atgtcctgaa tggtaatgcc taggttttct    126240
tctagggttt ttatggtttt aggtctaaca tttaagtctt taatccatct tgaattaatt    126300
tttgcctgag gtgtaaggaa gggatccact ttcagctttc tacatatggc tagccagttt    126360
tcccagcacc atttattaaa tagggaatcc tttccccatt gcttgttttt gtcaggtttg    126420
tcaaagatca gatagttgta gatatgcagc gttatttctg agggctctgt tctgttccat    126480
tgatctatat ctctgttttg gtaccagtac catgctgttt tggttactgt agccttgtag    126540
tatagtttga agtcaggtag tgtgatgcct ccagctttgt tcttttggct taggattgac    126600
ttggtgatgc aggctctttt ttagttccat atgaacttta aagtagtttt tttccaattc    126660
tgtgaagaaa gtcactggta gcttgatggg gctggcattg aatctataaa ttaccttggg    126720
cagtatggcc attttcacga tattgattct tcctatccat gagagaataa ataccctagg    126780
aatccaactt acaagggacg tgaaggacct cttcaaggag aactacaaac cactgctcaa    126840
tgaaataaaa gaggatacaa acaaatggaa gaacattcca tgctcataaa tgcatgtttt    126900
acaatagcat aacccatcaa gaagattcaa atgatttaaa ggatagcctc taaggcagaa    126960
ggggcatgaa gttacaagat cttcttagt actacctaac acacattact gagaaacttg    127020
gcagtttgat gacaacctac taatcaaaca gtgccatatg cctggaaaga ttttagcccc    127080
tacttaaaac atattatcca agaggaatat taaaatttta ataacaacat taaatatggc    127140
ctaagagaaa gcgcattact gtccttgtat gttttgatac atcactttga aattggcaag    127200
cattaggaaa attcaaagac atgacttaat catattatat agaaaactcc atattatta    127260 ctgctaatca caggaaatat tgggaagatt ttaaaattat aattcttata tttgtattgc    127320
ttttttgtga atgtatgata taaagatttt ttaaattttg tttatgaaca tctaatgtat    127380
attttaccca tcatacaatc cagaaagata gaaatataaa gcattgctat tttttagggt    127440
cattttttaa attgcaggca tgagtattaa gagtgatgac caaatatttg ttaagctcac    127500
tcctcatact gccacctcta tgcctactga atctgcctcc cacaaccctc ccaaattgtt    127560
gtgtacttag tcttgccttt gcgccttgcc ctgtggagtt cagccttgcc tgactctgct    127620
accctattgg aagcggcaga tggtctaatt gacccagccc tggaattaga aattttcctg    127680
ctttgccaga ggtgggcaaa tgagcagttg taccactcaa ccatgagtac ttaaaaaggg    127740
tatctcaatt tcactgtcaa tttaaagaaa ctatatggat acctcatttt tatatttca    127800 ttttgaaatc atttcataat tattaaagac tatttccttt tctcaaaact taccattttg    127860
tgattatgta actgctacca cattttcag ttgatctact attaaaataa aaagttgcct    127920
aataattaat tgtagggttt atagattgtc tcatttctgt acttgtagaa tacatctttg    127980
tactaatgat attagaaaag gcaatataat gcttcctgag tatgtagaaa ctctttaatt    128040
aatgttattt ggagaaatgc agcaaaatat taatacattc agaatgaggc tttaaaattc    128100
actgtaatac ccattagcta ttgaaacatt gaagttaagt gttttgaaa acacctttgt    128160 gaacaataat gtttttgagg caagttgagt gatgggaggc caatattgtt tatgatttta    128220
tgacaccctt taaaatcgaa ttaattattg gattctgggt attgagaggc agtcatagaa    128280
agaacatcaa attaagaatc aaagcatccg agttctgcaa ttatctatat gtatgacctt    128340
gaacaaatgt tttaacctct ctgttgatgt tctgtatcag cactgtccaa cagagttttc    128400
tgcaataatg gaaatattct acgtctatgc tatccagtaa tcaagccact agtaagcatt    128460
```

```
agaaatgttg ccattgtaac taaagatcag aattttttcat tttaattacc ttaaatgtaa 128520
atagacatat gtagtttgtg gctatcatat tagacagcat agttctatac aacaaatttg 128580
aaattacaga tatgctctat gcttcttttc aacattcatg tttttaaaaat atatgttgta 128640 attgaataat agatagcatg aggctatgtt ttctattaga cggagtgaaa tgagttaata 128700
tacattaaac attctgacct catactcttt caaatttttt caccattggg atcatttcca 128760 tctttttat tcatttgaaa tgtgcaaatc ccagcatttt aaatattttt tcccttttcag 128820 ttaagagaag aataacctgt cacctccagg gataaccctg aaaatgttca ttagaacttt 128880
gcatcagtca ttaaaatcac tccctttttgt gtaccctcaa cttatttgct cttctctcat 128940
gtcgtgtact tgcttggcaa aaccacaacc ctgtgagaat ccaacacttt actctgtacc 129000
gcactgatga actgaagctg aaggaaaaca tgtaaccaca ctaactggtc tcacataaat 129060
tcatgaccac atacctcaag tgagcccttt gtgttgcagg ttcatcatac tacactttcc 129120
tagtccaatc attctcactt gatgactatt tcacacttat tcttctctcc tcaagccttc 129180
agcacatcct ttctgaccct cactctcata tgctgatgtg ccttttattt ccctaagaaa 129240
tttgaaacaa tcaaaaaaga acttctatag attgctacat gcatccacat actctgcctt 129300
cctgttcatt actattgatg aaatagccaa agtcagcctt ctacttgtgc actagaaaga 129360
acctatctct tcacatctac tcaagagcac aactctacca attctcctct ttctcttcta 129420
tatcatcaaa tcttttttttc tgtatttat cacttttatt agcatacaat actattaaat 129480
ttaccaatct taaataaaag aactctcttg ataccactac ccagcctgcc actcttattc 129540
attccctttt ataacaaaat gccacagaag agttctctgt gctacttgtc tccagttact 129600
ctcctccaat tctcttttaa cattcactcc aagaggcttt tgcccctacc atttcactaa 129660
aatacatacg agaacaatga tctccaccat gctaagtccc atggtcaatt ctcagcctgc 129720
attttatcta atctatcaat gaacagcatt taagagttga tgactccctt ttccttaata 129780
tatgttcttt acttggctcc caaaacatca ccttctgtta gtttttgtcat tataaaatag 129840 agttaattta tctagtcagt agtatttcc cagaagacca cataataatg cttgctttct 129900
gagacctgtg aaagctatga attgttttcc taggtgattg ggaagtaggt attgagggaa 129960
actcttaaat ccccttatta atgtatccta tttacctgta aagacagttc cttcatcagt 130020
tgacagatgc ttctctttta tctttgaact ttagtcttac tgcgtccatc catttgcctg 130080
ggaaaattgt taaatatta agcaataaac tttcttatat tgagcatttt tcaaaacctt 130140
ttttatgttt taaacctgta tcattctatc taaatgtctc atggtaagtg agatcagttt 130200
ataagtcact tttgttttc atgtttacac taattctatt ttggaatggt ggtcaagtaa 130260
aaatcataat ttcaccactt aagattttc ctattatcct ttgaagtgct tttgaacaca 130320
ttggtgtgct ctaagatcac cataggtagg attttaggta gaactttctg attttttaag 130380
aaatcatatt caccaacaaa agcaggtgga atagaccatg ggaaaacaat acttacctga 130440
atctctacta atttgtcatt ggttaaatta gaagcctcct tttacaacag tctttggcac 130500
tctatgagtt agaaagacct atattgtaaa ctatttactg ggtagaaaaa caccagctgg 130560
aattacacag agaaatatac tttaaaaata gtgatgatgg ttactgttct ttgaacagtt 130620
aaactatgcc acgcatataa caccaccata cttaacacct cctcacgcca acctacccac 130680
atcctgatct ctctcttttgc cccttccctt acttcatttt tcttcatagc tcccatctgt 130740
acctgatatt ataaggttat tgtctcttca ctaacagaat gctttttctt gcccacccttt 130800 gcagctctag cattcattac aatgaatggc atacactagg cactcagttt tagttgaaag 130860
```

```
aataaataag tgcccatcac ctcatttaat tctcttagtc acactataag atagatactg  130920
ttgttacccc cagtaaacaa aggaagaaac taacactttta aaaggctaaa taacttcctg  130980
gaggtcaagc aacaagtaag tacagagcct gggttctcag ctattgtgca tattgcttca  131040
aggaaaaatg aactgttatt attatttaca attaacacct gaaattaaaa caaaacaaaa  131100
cacatgaaca aaaaactctc cacaggagaa aggaagatt cctgctgtac caatggaac   131160
agcagctcat ggggaagcag agccccacgg aggacatagt ggacctgaac tccagcgaac  131220
tggaaggtta gtgaaaatca cttctatggg acttcaagga ccaaatgaca taccattctt  131280
ctctgtcaga aattgctatt ttgggatcta atttattgta tacttttaat acctgctttt  131340
tgagggtgaa aatgccaatt agtttgattt ctctgaagtt actaatgatt gtcattactg  131400
ttaaactaaa acagtggata caccettcca ttatacttta cctagtcttt cattttgctg  131460
tgcataaaat gcattctcag attcttagaa tgaaaaggaa aaccgtcaat tgacccttcc  131520
aaaagaaccc attgaaagct tcaagttgaa gatagaaata aaactaaata ccaacaactc  131580
agtcttgtag gccctatctc attaaatgca gtaggatgt atatagtggt attttttatt   131640
tttatggctg tgatttgaaa gagctatatg atttatttt ctaatcacac atctttgaag   131700
agatgaaagc ttcaattat ttcttaaaat ggtgcttcat ggtttttttg acagcttgtc   131760
tctctctaag caatgtgtga gcagaaaatc agaaaccctt gggtgggtct ctcttcaggg  131820
aatatgtgta tagcctccat tataattaaa ggcagttgca aaggctttgc aggattggtg  131880
ctcccctccc ctcaaggcca ttttctgtac tgcttgcaat gtgtcctcta agctgacttt  131940
ccagttcctg agcactctgc attttaattc tgtgttcttt cccttatct atgtgttgtc    132000
tctgaggaaa tgtcctttaa tgtcttcctc aggcttgata cctaatttga gatggttcaa  132060
acaattttt ccttttcccct tcactggaag ctttgttact cattctgttt gctttcatac   132120
tttcaaatgc tgtcttttta ttttggtgg tattttttt ctctttctca ggtgtaacat     132180
gccacatagc ttagattttt ttcgaagttc acttttcctt actgcttcct aaatcctccc  132240
aggtcaccaa tatccggtat cttcgcttct ccagagttct tccacagatt ctgttgctga  132300
catgacttga agtatccatt actcatctgc tctcctggag ttgctggtgt acatctgggc  132360
tgctcttgca ctgttctctg taatgaactc ccacttccgg atttagattt ttactgctaa  132420
aagcacattt attacacagt actataacaa ctattcagac taatgtatgc tctaataagt  132480
aattgattag aatcaatggt ctaatataaa gtgctttcaa aactataaat attaattact  132540
aattaatagc tcataaccac ctcaaattct ttttgggatt aggtgggata taaatcataa  132600
atgaatgcct aaatagactg gtagagtaaa tctgttttga attgtgactt tgataagtta  132660
acaaattatt cagaaatgat ccctaaaata aaaaaaagtg catatgtttt accaaacatg  132720
ggtagagaag cctaaggtga tcttatgtg tacaaatatt tcacaggttc tctgcaagct   132780
tctctgagtt tcaaatgtcc ttttattcaa ttgaagtttc attcttctca accctctcct  132840
actccatagc tctctaatgg aagcaatcac aggaaaatat agtgatctta tacctgcata  132900
atagtagaag agttattaat aggtaactat tacagataaa tcagatcagg gaaattactt  132960
ggtaaaatat tttaattatt cataatatgt acatctttta tttcaaattc taaggagaat  133020
ttatttctaa aaaggacagt cctttctgag atgattctag gactgccaaa tgaatattcc  133080
tatgcataaa ataaataaga aaaatgaaac agtttttat gatccaagta tactcagcat   133140
gctggcagta tattggagca taataagatt tttcaccact gacattaacc ttcatgtagg  133200
```

```
aacttattca tagtcttatt cattttttgct atcacatcat tattccatgg agcaaaactt 133260
acagtagcca aatgttaagt ctgcgtattg ttattaaatg ttcataaaat gagaatacct 133320
acttattaat gctctcattt cttatagatt taaaaaaaga tctcaaattt caagcataat 133380
ttcacagttt aatactttc ccccaaaata attatctttc aagtgtttca acatggtttt 133440
gaatatattt ggagtaaatg aatttatacc aagtaaggtc actattgtct tgtgaatcac 133500
agatgctggg atatgttaac gcaatagtgg atcaaaatta catttatcta gttttattat 133560
tataaggact ccctcctagt tttctaaaaa tgaaaacagc tctgaaacct atctgtctct 133620
actaagtatt gctgccatcc aaaaggacat ttagatgtct tcctgcaaca atatctggtg 133680
agggattttt gtttgtttgt tttttggccg agagagtagg taactggagc catggttaaa 133740
cattgctttt tctctctagg gtgatgctca ctactggagt atacaaaagc cagctaaccc 133800
tccctccctc acttcctgct atgctaaatg gaattaaaca tttagaaata ctgccaatga 133860
ttgagggttg taggcctgag tttaggagga gtaggttgac gtagaaatgg cacagagatt 133920
agagtaatcc ttgaatctca ttatttggat tatgattggt aaacagctct gaaccttgtt 133980
taagagaacc tgggattttt ggtggttgac acgatattgg gttaggaatt gaggtaacga 134040
acgtagttgt gcagtgcctc cctgtagatt gttataagac aatgcagcag gttaatgtgt 134100
gtctcacctc tgctgatgga aaacgtatac tgtgacctgg caacaaagca aatgagcatt 134160
ttgacttgtg tgtttttttat atttgggttt cactattgtg ttttccccc tgtcttagga 134220 tttttggggg acttattta gatatcaaaa gaaaagctcc atacttctgg agtgacttca 134280
gagatgcttt cagcctgcag tgcttagcat ctttttctatt tctctactgc gcgtgtatgt 134340
ctcctgtcat cacgtttgga ggactgctgg gagaagcaac tgaagggcgt atagtatgta 134400
ttatgctttt ctctgaactt tgaaacataa tccatttta agattcatag ttagataagt 134460
gagcatttaa ttttggattc ttttctgagg agagatttga gatatggtct ggcagataca 134520
ccttatatga atttcctgga tggctagtgg aactggtaat ctgggagtgg aatgtctcag 134580
aataactagt tctgagtctt acaaaaggtt ctcatctgat gccttgccct cagcgccccc 134640
aatcctaagc taggtttagt ctccattctt gtctcacaag aggtccattt gctatgtacc 134700
cgggccatgt ttctgtccag acactaatcc tgaatacatt taaaccttt gtaaggcaac 134760 agagacgtga gataggaaag tgaagagaac actcctacct ttgctactat gcattttctt 134820
cttgctgtca gcccctttag tcatccttct accccacgtc ttgcccaggg ttgctagact 134880
tttcagggtg aagcacaaag cacatatcca tgtatttttaa atgtcttctc cttagctaca 134940
atggcctcct gtacagctta ggtaattgaa ccatttatat ctctacacag agtgcaattg 135000
aatctctctt tggagcatcc atgaccggga tagcctattc tctctttggt ggacagcctc 135060
ttaccatatt aggcagtaca ggaccagttt tggtgtttga aaagattttg tttaaatttt 135120
gcaagtaagt gttatgtact ttttggcccct tagcctcttc cttttttctt tactgtattt 135180
atacttctcc caacatcact tttggaggtc tgttgataga gacagaattg cctgatttgt 135240
ttcagtttat cattttgct tcatcatggg aatagaggaa aagtaaaata tttatgtata 135300
tttttatgta atattttaa aaagtaagac tcagttataa gcatcgataa atccctttg 135360 attttgtccc tttagatgtt cccttttagac cggtggtctg caaccatttt ggcaccaggg 135420
actggtttca tggaagacaa ttttttccaca aagagggttg aggggatggt tttggaatga 135480
aactgttcac ctcagatcat caggcattag attctcataa ggagcacaca atctagattc 135540
ctcacatgca cagttcacaa tagggcttgt gctcctatga gaatctaacg tccccactga 135600
```

```
tctgacaaga gtctgagctc aggcggtaat gctcactcgc ctgccactca cctcctgctg   135660
tgcaacccTT ttcataacag gccatggacc aggggttggg gacccctgct ttagacagtc   135720
ttgagtttag atactcatgg gatgtgaagc ttatttactt tcacttcctg aatgaggttt   135780
attttcattt gcttaaaatg atagcaagct gttaaatgac cttcttttca ctgttctttc   135840
cttttcctcc tcccagagaa tatgggctgt catacctatc tttaagagct agcattggac   135900
tttggactgc aactctatgt atcatacttg tggccacaga tgctagttcc cttgtctgct   135960
acatcactcg gttactgaa gaagcttttg cttccctgat ttgcatcatt ttcatttatg   136020
aggccctgga gaagttgttt gaactcagtg aagcatatcc aatcaacatg cataatgatc   136080
tggaactgct gacacaatac tcgtaagtac catttcccct gctggccttg ggcttttct    136140 tttgacaaat attgctattg ttacaagaaa tatgaggaaa ttactcagca gagaatgtgc   136200
cttaagttga ttcatgacct aaatcctgac tctcagagtc gaacaggatt ttaaaagtta   136260
tttaatcggc cactcatctg ctacttgcat tctcattata ccatctctgc caagagtatc   136320
tttttaaagt tctatttgtc cagtgttctc taaaataagt agataaggaa ccaattccat   136380
tttaatatac acgaatttta ccttagcgaa atatatgtta tttggcgtta tttcagggtc   136440
tttttaattt acaataatcc aaagaaacat agtaatgaaa ataaagatt tcaaatttag    136500 agcaataagg taaaataaac ttattgggtc taaatcttag tagatgtttg aaagtgtggt   136560
aaaaacataa atcactgaat gaaaatttaa ttttggtttt ggcacttgtg acattttgat   136620
ggaaatactc agatattagt tgttgaagtt gatgttacag tccgggattg aagatgtgat   136680
tggatctatt gcttttcta gttttggtgt atcaacagtc tgaaatgtct ctaaggcttt    136740
gtctgcagac tatatgtggc cattaaatga ccccattatt taattgtaga atttttatt    136800 gtgcttatat gcagttttt atactgcaaa tatctgaagc aatatgttct ttaggagaca   136860
gttataatct ctgcatcaac caccaatcat ttccctataa actgcttaga tatggccttg   136920 aacccttttta atatttttta atctttattt actatcagaa gtttaaattg ttgaaatcag   136980
accaaaatag tgcaatgtta taattttgtt aagaatgacg aaatgttggg aggccgaggc   137040
gggcggatca cgaggtcagg agatcgagac catcctggct aacacagtga aaccccgtct   137100
ctactaaaaa acacaaaaaa attagccagg cgtggtggcg ggcgcctgta gtcccagcta   137160
cgcgggaggc tgaggcagga gaatggcgtg aacccgggag gcggagcttg cagtgagctg   137220
agatcgcgcc actgcactcc agcctgggcg acagagcgag actccgtctc aaaaaaaaaa   137280
aaaaaaaaaa aaaaagaat cacgaaatga tattatgttg aaaataatgt gagttttagt   137340
actttcactt ttatattata tttagagata actttaaaca actgacccct attttttgaac  137400 aagaaaaatc aaagtggaaa tataaaataa ttttcccatt aaaagcaaat agtgagaata   137460
ttgtaaacag ggctaagaaa ggactgagca taggtgtcag ggacactcag aaaacaggca   137520
aatgggaaga acagtttgat caaaaccagg gataacattg atacacgcct tttcatttat   137580
ccttacctga aagagaatct cactgaattt ggatatcctt gctgggatat gtaattatct   137640
ctggttggat tttcaaatct actacatgcc aggcactata ctaggtgcta ggaaaaccat   137700
ggtgaatcat attctgtcct cagtgagctt ccagtttagt agggaatgta gataaacaga   137760
cagcataagg aaatgagtgc cgggttaaga ggttggtaca gaatgctata gcagcacatc   137820
aggagagcac ctaacccaga tttgaggttc agagaaggct tcctggagga aataatgtag   137880
aataaaaatg cagtagaagt taggaaggtg ctaaggaata gggcagaaaa gtagttcagt   137940
```

```
caaagggcat tcacaggact agatgcaaga gatgcattca tgctttaaaa tatttgtctg    138000
aagttatata gatagtggta aaacaagaaa tggaatccag gttttattac tgatataatt    138060
ttcagtacac tgatgaatac agataaactc tccaaaagaa actatgtaaa acaaataaaa    138120
caggtaaaat cagaactatt ctgtttcaag tggtaggaag gcacccattg cctaccctct    138180
cagctgttct ttgaaccttc atggtagctt cttaggtact tcagactgag gaacatagtt    138240
taaagtccct tggtctagaa aggaaaaaga ttggaaaagc aaggtctgag ccctgaacaa    138300
ttttcacagc tctaaagtag aatgagaaaa atgcaaccaa taggcaaaaa ataaataaat    138360
aaaaataaga aagaagcatc agaaaagag gaaactatgg ataatgtcag gtcgcagaag    138420
gcaagaaaca agaaatgtat cacaaagtct ttagagagga cagtggcatg gacatcaaac    138480
agaataagga aaagtgtttg aaaagagata cctggtagct ttaaaaaatt ctcagcaaac    138540
tattgcaagg acaaaaaacc aaacaccgca tgttctcatt cataggtggg aactgaacaa    138600
tgagaacaca tggacacagg aaggggaaca tcacacactg gggactgttg tggggtgggg    138660 ggaggggga gggatagcat taggagatat acctaatgct aaatgacgag ttgatgggtg    138720
cagcacacca acatggcaca tgtatacata tgtaacaaac ctgcacgttg tgcacatgta    138780
ccctaaaact taaagtataa taataataaa attaaaaaa aaaacaact ggtattgggt    138840 tgggaaagga ggcagaatgg gaagccagtt tgcaaaaact aacaaggaag tgggtggtaa    138900
agaaatggag aaagctgcat aggccagttg gtgtcaaaga aagtgggaaa cagaatgcct    138960
tttgaggagg gcaatgaaat cgtaagattg ataatttgtg acagaagg actatgtgtg    139020 tttgaaaatg ggagaataga gactggggag aggaaggcag caatgatgaa aagagtcgat    139080
aaacgtggga ttgcaacctc ccaggagtca caaatagta aactcaagag aataagtcaa    139140
acaaatgctc aaaaggtaat ttaacaacaa gaatagcttt aaataaacgt gaacccaaac    139200
tgacatgaaa atagcaggaa aatgacgaaa aaaaaaatt cgccaaaaaa gacagtgaca    139260
caaacagtgc acacaacaca caagagcgag aagagcagaa tggaggagga caagacaagg    139320
ccggtgctca gtgagagacg caccgtatga cacctagcag aggaagcgaa gagggtagaa    139380
gtgctgannn nnnnnnnnn nnnnnnnnnn nnnnnnnnn nnnnnnnnnn nnnnnnnnnn    139440
nnnnnnnnnn nnnnnnnnnn nntctgaggc atggctgtga caccctcttt gggctctgca    139500
gttcctggtg tctccaagct tctggtgcca ccacgttccc cagagcctgc agtgtaagtg    139560
gcttgcagta tgcctggtcc agccacagcc ttgcacagag ctggttcctg tgccagtgtc    139620
tggaactgcc tgccccacca cagcagccag catgcctgac tgtgcacagt ggccagacca    139680
tatgcttgct cacttatgca cccctcacct ctgtgccttt ggcagcgctg ggatccaggc    139740
tggtagcacg agctgagcac aacctgccag gcctagtggg cagaatgagc cagagggccc    139800
aagcaaaact caggcaaagg caccactggc cacaaaggct tctggctgga agaatgacac    139860 cccgggggacc tcatgacagt aataacttgg cttaaaggc tgggatagg atctatgaca    139920 ttaacccaat tagtggcctt gggtaagtcc ctaagaacaa cctctagaga caatgtctta    139980
actcaagaaa aaaaagtag gaagaatatg gaaaatacat agggaataag aagtctggaa    140040
gtattgtatt aataccaaac ttatagtact taaggacaa ataaagggt tgcaaaagag    140100 ttcaccttgt tggtgaagga aaccttgtac ttttattct ctgcatattt tgaattgttc    140160
aacttgcact gtatgcctgc attattttgt aatttctttc taaagatgaa ttttgtgttg    140220
ggaaattcaa gtcctgtgac aaaccatagt atgagctaat ctgggggagg tggtgctctt    140280
caaattagtt tccatgtaac aaaatttatt ttcaaattca ggaaaagagc aacctacaaa    140340
```

-continued

```
actcaggagt aaaatgggca aaatgttcaa ggaataataa gtaggtttac tgttctgttc   140400
atacatgtgc ttactcattc actcacttag ctcattcctt caacatccat tgatcttcct   140460
tgtgtatgtc agtgctgatg gtataaaatg aatacaatat ggtccctact ctgaaagacc   140520
ttagtgatta tcagacagtg tctggagatg tcctttggac atgatatcca ctcaaatagt   140580
atttgttgaa ttaataaatg aggagagagg ctagaggata cacagttaaa taattgcaat   140640
gtgatataac aagcactata caaggtgtct gtataatggc ctaagagaag aagtaacaga   140700
gtgccctgga gagctcagaa gcattcatag aaaaaggaaa cctgaactta tctctccatt   140760
tctgttgtac ctgccacatg agtttattgt atgtggcata cctatgtttc tttctctctc   140820
tctcttcatt gtacctgtga attcccacat gcagatcatc actagatctg agagtagtta   140880
cgcagagtag aatggacctc tggggaccaa ttggcagaga gccttaaaag ttctaataag   140940
ttttatctgg tacaaaggcc atcatggatc atgacaaggc tctgggaaga attatgtgac   141000
aataggttag aaggtgatca caggaagcag agcaaggagc aatacccttag gcatagaatg   141060
tttaagtcct gactactggc tgagacaatg gtaatgggaa gaaagcaaaa aaactaaaaa   141120
tggaaaaaat gaaaaacaaa aattatccag gattgattca cttgttcaac aagtaattgt   141180
ggaacagtgt ctaatttcta ggagctatta tgaaaacttt gcctatatga cttcatttga   141240
acctcacaag aaccttgtgg gacaagtatt atccctgctt tacaaacaat caatctgagg   141300
ctccaacagg ttaaataatc ttctcaatat cacatataca ataaacggta aatgggtaa    141360
acccaggacc attttgtctt aaagctcata aactttctga catattaaag taaaaataat   141420
agcaaatgat tgcgatgatt ataactcctt aaaggtaggg actacgatat atgtctatgt   141480
atctccagta ggacttagca cagtaatctg tataaaataa tttcaaattg ttaaatcagt   141540
cagttgtcat aaggctgcct gctatgggcc aggtgcttgc ttaaaaaaaa tgaatgcata   141600
gacaggattc cttcatggaa cttatagtct gttgaaagaa tcagacatta aatattacac   141660
aaaattacat tatacaaatg acgtaagtgc tatcatataa aagtatagga tgccaagaca   141720
gtgagaaata tttccaaact tatatattta gaggctaagg agaggatatg tctatttgaa   141780
tgaagataaa tttgagatga gaaaagtttt aagaatttaa tggagagagt atttaaattt   141840
ttagtgttag ctaattgtgg tggtgttttta caaagctacg atgcatattt ttgaaaagct   141900
attttcctca taatatatta tggttatata cttagtgata tcttagaaaa gtataagtac   141960
taagcaaacc tcttcaaata ataagctcaa aatatggaaa taggtgtatt cataaaagga   142020
ttgtctctat attatttaaa tagtcatctt aatagtaaca atttaattaa atgattaata   142080
atccaagaat aagttatgtt gtatcccetta caaataatgg ttctgaaggg taatgtagca   142140
ataggaaaat gcttgcattc tagtgctatg taaaaaagga ataaaaatat tgtatgctca   142200
taaaacatg ttgaaaatat acataagaac tactgaaaga agtataccaa aaatttgtag    142260
caattatggt agaaagacta tgagagatac cttttttcttt ttttattttg taaatattct   142320
gtagtgtgat tttattatca ttgcaattaa aaatactttc tgaaatagaa aaagaataat   142380
cataaaaaca catttggctt ctatggatag atcctgattt tctgattgta tgttttgtat   142440
taataccctga cttggtacat agcactctgg gagataatca agtcaataaa aagacctgaa   142500
aaataaatga atcacaaacc ataactgttt agtgcacaca ggaaggtact attaataact   142560
acaaaggcaa aaggagagca tctgcaaccc aaggactaaa attagtaata atgttgaagg   142620
gagttctacc aaattatgtt ttccagaaga cagcgcaggc tcttcttgtg taaggaagac   142680
```

```
agatcacctc cattagcctt gaaacaaaag caaagacttc tggatgaggg catttaatta  142740
taatgtttat gtaatcactc tgtagccatt tatataaaca agatcgctta gagcacttgc  142800
ttttctgtgg gcagtaaagg gtactaaaag atgtatttta taaaaagtgt attttaagcc  142860
aaataattca gcaccacaag tgaaaattat tggcatttta tactggtgtt tttaaacatg  142920
tagagaagtg cagatacaac cctttttctg ctttatgatt gttggacttt tcagtctatg  142980
agcttgtgat agtaacaata ataaataacc aaaatgagat acctaacaat ctctatttac  143040
ttatgtcagg gcccattcta ggactttat gtatattaat tcatttaatt ttataataac  143100
ccctagaaag gacatgaact cagaagctgg aaaccatcat tctcagcaaa ctatcgcgag  143160
gacaaaaaac caaacactgc atgttctcac tcacaggtgg gaattgaaca atgagaacac  143220
atggacacag gaaggggaac atcacacacc ggggcctgtt gtggggtggg gggagtgggg  143280
aaggatagca ttaggagata tacctaatgt taaatgatga gttaatgggt gcagcacacc  143340
aacatggcac atgtatacat atgtaacaaa cctgcacatt gtgcacatgt accctaaaac  143400
ttaaagtata ataataaaaa aaagaaaaaa aaataacccc atgaggttga ttattatcat  143460
tatcttcact ttatacataa ggaaactgaa acatagagtg attaaatggc ttgtccaagg  143520
ttgctcagct aaatgcttgg atttgaatga acataggaaa cctggctgga gacctcagtg  143580
ttctaagcat acactatgct atgcatcaaa agaaacgttt tgcattaata ctccatctta  143640
ttgccagagt cactagaaat tattttttgat gagattaaca aaaaagcttg ttccagactc  143700
atattctatc tcctcacagt gctatttcca tgtttctttt ctctttcttt cttctttttt  143760 cttttttcatt tatcttcttt aacttttttgt agttttagaa ataagttcac caatacagag  143820
gaagacagga aaatgggatt tttttctcac attttttcttg attgatttat ttagcatatc  143880
tatttttgat atgtaagaac ataagaagta agtagtcaga agtcttcttt gagccaccaa  143940
gagttggtac ggagatatca aatgtcctta cacaactggg cagcctctga gaactgtctg  144000
ctgagatttt agatgtcaga ggtgcagact caagaaagaa caatatttgc ttgggtatac  144060
atgatatctg tgattttata catatataaa tacaaataaa tctttaactt atttattttt  144120
aaatttgaat ttatttattt atgtcatata taaatcttgt atattaaaaa catattttcc  144180
actttggaat tgatttatag gtgagtaatg tcataaccta gagatagctt tgacagggag  144240
gcacgtaggt aactaacgtc cacttgtaga ctcaactctt caaaaaatgt ctctcctatg  144300
acattggtac atcaaatttc taacttagca ttttcaaaaa gtcacggtta aaatgtaagt  144360
acactaccag gaatggagta acacatgcca ttgtattcac taacacagta taaccacttt  144420
ggaaagcaga gaccatgttc ttgagggagt agtaaagcaa aatgaatgga gaagccatat  144480
catcaggttt cgatggggtt ataggaaact ggacagtggg gctgaggaaa atgtggatgg  144540
tgtagttttc atgataggag ggcagagcta caggtgtttt ggaagaatac cttataggag  144600
agaagtcttg aaagtggaag ctagcaaact acacggtgaa atgtagatta cttcattgt  144660 tctggagtca tctcactctt ctggctatct tgatagaaac agcaccaagt cacatattga  144720
ggcagcatac aatagctaaa agagtaggag tttccatctg gtcctggact cttttggtt  144780 ggtaagctat tgattattgt cacaatttca gagcctgtta ttggtctatt cagagattca  144840
gcttcttcct ggtttagtct tgggagggtg tatgtgtcga ggaatttatc catttcttct  144900
agattttcta gtttatttgc gtagaggtgt ttgtagtatt ctctgatggt agtttgtatt  144960
tctgtgggat cggtggtgat atatatcccc tttatcattt tttattgtgt ctatttgatt  145020
catctctctt ttcttctta ttagtcttcc tagcggtcta tcaattttgt tgatcctttc  145080
```

```
aaaaaaccag ctcctggatt cattaacttt ttgaagggtt ttttatgtct ctatttccct 145140
cagttctgct ctgattttag ttatttcttg ccttctgcta gttttcgaag gtgtttgctc 145200
ttgcttttct ggttctttta attgtgatgt tagggtgtca attttggatc tttcctcctt 145260
tctcttgtgg gcatttagtg ctataaactt ccctctacac actgctttga atgtgtccca 145320
gagattctgg tatgttgtgt ctttgttctc gttggtttca agaacatct ttatttctgc 145380 cttcatttca ttatgtaccc agtagtcatt caggagcagg ttgttcagtt tccatatagt 145440
tgagcggttt tgagtgagtt tcttaatcct gagttctagt ttgattgcac tgtggtctga 145500
gagacagttt gttataattt ctgatctttt acatttgctg agaagagctt tacttccaac 145560
tatgtggtca atttggaat aggtgtggtg tggtgctgaa aaaatgtat attctgttga 145620 tttggggtgg agagttctgt agatgtctat taggtccgct tggtgcagag ctgagttcaa 145680
ttcctgggta tccttgtcaa ctttctgtct cgttgatctg tctaatgttg acagtgggat 145740
gttaaagtct cccattatta ttttgtggga gtctaagtct ctttgtaggt cactcaggac 145800
ttgctttatg aatctgggtg ctcctgtatt agatacatat atatttagga tagttagctc 145860
ttcttgttga gttgatccct ttaccattat gtaatggcct tgtctctttt gatctttgtt 145920
ggtttaaagt ctgttttatc agagactatg attgcaaccc ctgcctttt ttggttttt 145980 tttttttttt ttttttggt agatcttcct ccatcccttt attttgagcc tatgtgtgtc 146040
tctgcacgtg tgatgggttt cctgaataca gcacactgat gggtcttgac tctttatcca 146100
atttgccaat ctgtgtcttt taattagagc attcagccca tttaccttta aggttaatat 146160
tgttatgtgt gaatttgatc ctgtcattat gatgttagct ggttattttg cttgttactt 146220
gatgcagtta cttcctagca tcgatggtct ttacaatttg gcatgttttt gcagtggctg 146280
gtaccagttg ttcctctcca tgtttagtgc ttccttcagg agctctttta gggcaggcct 146340
ggtggtgaca aaatctctca gcatttgctt gtctgtaaag tattttattt ctccttcact 146400
tatgaagctt agtttggctg gatatgaaat tctgggttga aaattctttt ctttaagaat 146460
gttgaatatt ggcccccact ctcttctggc ttgtagagtt tctgctgaga gatccgctgt 146520
tagtctgatg ggcttccctt tgtgggtaac ccaacctttc tctctggctg cccttaacat 146580
tttttccttc atttcaactt tggtgaatct gaaaattatg tgtcttggag ttggtattct 146640
cgaggagtat ctttgtggtg ttctctgtat tttctgaatc tgaatgttgg cctgccttgc 146700
tagattgggg aagttctcct ggataatatc ctgcggagtg ttttccaact tggttccatt 146760
ctcccggtca ctttcaggta caccaatcgg acgtagattt gttcttttca catagtccca 146820
tatttcttgg aggctttgtt tgtttctttt tattcttttt tctctaaact ttccttctca 146880
cttcatttca ttcatttcat cttccatcac tgataacctt tcttccagtt gatcacatca 146940
gctcctgtgg cttctgcatt cttttacgtag ttctcaagcc ttggtttcag ctccatcagc 147000
tcctttaagc acttctctgt attggttatt tcaggacata ggcatgggca aggacttcat 147060
gtctaaaaca ccaaaagcaa tggcaacaaa agccaaaatt gacaaatggg atctaattaa 147120
actgaagagc ttctgcacag taaaagaaac taccatcaga gtgaacaggc aacctacaaa 147180
atgggagaaa attttcgcaa cctactcatc tgacaaaggg ctaatatcca gaacctacaa 147240
tgaactcaaa caaatataca agaaaaaaac aaacaacccc atcaaaaagt gggcaaagga 147300
catgaacaga cacttcttaa aagaagacat ttatacagcc aaaaaacaca tgaaaaaatg 147360
ctcaccatca ctggccatca gagaaatgca aatcaaaacc acaatgagat accatctcac 147420
```

```
accacttaga atggcaatca ttaaaaagtc aggaaacaac aggtgctgga gaggatgtgg  147480
agaaatagaa acacttttac actgttggtg ggactgtaaa ctagttcaac cattgtggaa  147540
gtcagtgtgg cgattcctca gggatctaga actagaaata ccatttgacc cagccatccc  147600
attactgggt atatacccaa aggactataa atcatgctgc tataaagaca catgcacacg  147660
tatgtttatt gtggcattat tcacaatagc aaagacttgg aaccaaccca aatgtccaac  147720
agtgatagac tggattaaga aaatgtggca catatacacc atggaatact atgcagccat  147780
aaaaaatgat gagttcatgt cctttgtagg acatggatg aaattggaaa tcatcattct  147840
cagtaaacta tcgcaagaac aaaaaaccaa acacggcata ttctcactca taggcgggaa  147900
ttgaacaatg agaacacatg gacacaggaa ggggaacatc acactctggg gactgttgtg  147960
gggtgggggg cggggggagg gatagcttta ggagatatac ctaatgctaa atgacgagtt  148020
aatgggtgca gcacaccagc atggcacatg tatacatatg taactaacct gcacattgtg  148080
tacatgtacc ctaaaactta aagtataata ataacagaat aaaaaaagta taatatataa  148140
taaaaatatc ttgaaaatta aaaaaaaaaa caaacttctc aatggctgtc cctctcattc  148200
aagagcaaaa ataaaatcat aacaatcctt gaaagcaaaa aaaaaaaaaa aaaaagtagg  148260
agtttcaggt tgggacagac ctggattcaa gtttatttct atcagtgtag ccttggataa  148320
gttatcaaac atttagttcc tcccatctat aaaatgtagc aattaaacta ttaaactaga  148380
aaatccacta tatgccatgc gtatagcaac tgtatgcacg ccatacctat aggcatagat  148440
atacagtagc tacagaaaac atatatgtat gtatatacac atatacattt gtacatggag  148500
gtattcacat atctacgata gtgctatctt tctccctcgt tatgttactt ctgcaagaaa  148560
cttgccatat tttctctatt ttatatttt gtttcttatg tatggattta cttttaacaa  148620
attttcaaaa tatgcaaata actttctgtt aaactatagt actggcccctt ttatttctga  148680 ggtaaactaa ctgaccatct tagggaattc tatttgttag caaccaaaaa aaaaggatgt  148740
ttgccactta ataaacagat tcagacaata tattactaat ttacttcaac gagaaagaga  148800
ctcttgcttc tagtgaatga tattacacag tttgttttgt tttgttgata gcactactgt  148860
gcaatggtca cctgtgatac aattatttga attcatgaca atgctgggtt aggaaccgag  148920
gcagatccac tatgcttctt tatgttcaga tgtttttaaat cagaattata ggactatatc  148980
tatgtgccta ggcaaatatc taaaataatt attccattct ctgctaacag cttaaacacg  149040
tgttgtaatt ctaacagact ttagagagca tatggcagtt tcaacaagtc acacatattt  149100
ttacatgcac ctaagctagg gacccctgac caatgagttg agcatcatct atcaggatgc  149160
tcccgataga tgacagatct tcaaccagcc agctaggtca tttctgcttc ctcaattcca  149220
catgtttagt tagttgggat tcccagtcgg gaggcaaagc aggtagcatt tgggccctcc  149280
ccttactgtg ctcagttcag tttattgatg gaaacatctc caaggatctt aaaactttaa  149340
aatagaaaat atctcttcct cacaaagttg gaagccctga acctgagcct taagagattt  149400
atttttacat ttgttttcaa attctcacaa tttatacaga aaaaaaaatc agagtatcca  149460
ttctggtttt taatttttt atttcttgcc atagtattat atatcaagaa tatttataag  149520
aaggaagtag ttaatacata tttgttatct aagtataatt tgggacacta tataaatctt  149580
ttagtttgtg agttacttct gtaccctgtc atctcctaag ctacctggtc tttcttgaa  149640 taataaatat acatacctttt taggaccaag atctatagtt tcacaatatt catagccatc  149700
tggttctgct acagggtaaa tttagactgg aaataaggta atattaagta agagaagctt  149760
cgtttgttta acctacctcc caaaggctcc atttgtaaag agtgcagacc agaaatcaca  149820
```

```
tgcactgctg gattctttcc atgagaaaag cctgtgttga gctttagttt cttcattttc 149880
tttaaacaga acaaaaatct ctcctaccac tcaaaggagt gatttgcaga tttaatgcaa 149940
ttatatcaaa gtagtttata acccataaaa cacaaagtta tatgaccgtt actttgtatt 150000
gaacatccat gaaactctag gaatagtact agaagcttta tacaccatta tatatagaat 150060
ggtgtctctt ttaattctca agaaatcctg tccagttgtt ataattatac ttactgaata 150120
aattatatta atttatatta taattatatt aattagttat ataatgaatt catagaaact 150180
caggggttgg gtgatttgct aagatcaata gctagaaagg ggcagaatca gtattcaact 150240
caatattacc tccaaatgga agtaattcag tattagtgag tattactaat tatagaagta 150300
atacttctcc tttctactca gagctaacac aacagcatta tctaatgttg ttaaatggta 150360
ggtggaatta aaaattgtag gtaagattaa gaaaggaggg aaatcactga ataacctgcc 150420
cttccagcaa agttgacaaa gtagataaga tctctggtaa gatctaatct tcatctcatt 150480
ctgccacatg ttttttgtttt gttttgtttt gttttgtttt gtttttattt gtttttttaag 150540
acgcgtctcg ctctgtggcc caagctgaag tgcagtggca caatcttggc tcactgcaac 150600
ctctgcttcc cagttcaaac aattctcctg cctcggcctc ctgagtagct gggattacag 150660
gcgtgcacca ccacgcctgg ctaattttg tattttcagc agaaagggg tttcaccata 150720
ttggccaggc tagtctcccc atgtttttta tcgaagtccc tgtgttctca atatcctgag 150780
atgattggct gattggctgt tgccacagcc attggcttca gccactcttc tggcctggac 150840
atcatccagt gcatgtcaaa gacaggactc tggcctagct tcttttgggg actttctacc 150900
acagaatgag caaggtgat gttcggaaca aaatacctat acgtttcatc cagctgcaaa 150960
taatcagctc cagcttctgg agttacttgg tacctaaatt ggccaggttg ctgttgagga 151020
tgaatgggcc aatcttacag ctgaacacca tgatactggt tcccaggagc caagcattgc 151080
cccaatccag cctttttta tttattttaa aatgtgtta atactttta aatctttaag 151140
tagtgactaa ttttctttta aataaagatt gttttcctcc aggatgcatc agagtaaaag 151200
cataaaatgg agcttaaaaa aaattaattt agaatcagtt gtgtcttcag tttactaatc 151260
cacgcttcaa atgagtagaa cttacaattt gctctggttt tgttacttgg gtgggtaaga 151320
taacttagaa gagcgacagg gattttgcta aaatataaaa atgggatagt tttaaatctc 151380
tattgttgtt accgttggca gtaatataaa ggagatcaaa gaactaatgt gtttgttccc 151440
aacctacctt taaataaaat tgtttatag atgttataaa agtataccta tatacacttt 151500
atgtacacac acatgcattt catgtatata tccactataa tgctagttct ctcttattat 151560
aacactcctg caagaaattt gccatatttt ccctattttg tgtttagtt tcctttttgt 151620
cattaataaa tatactaggt tttcagagta tgaaaatgtt ttcccatcaa actcttatgg 151680
tgttgggcct ttttttctg agataaagta acagagaaat caatttggga gaatcttctc 151740
attaagggag catactactc cttactagtg aactggctta cagactgagg ttggcaggtt 151800
cagatatgta tgagcagaac agtagcaaga catttgcaga cctatgatcc ttgcttgttc 151860
acctaattct tttacctaa cactgccact actgtaaaac caaagcaaga cattcagaaa 151920
aagacattgc agaccaaatt gacactttga gggaggctac catgggtata atgtataagc 151980
ctccatttgg agcaggatcc aagatcaata tggatacatt agattctact ttttaaaata 152040
agcactcatc tcatttcaga ctatggacat gctactgagc tttactatcc ttaatcctta 152100
gtctagtacc tcggtatctt cattaagtat gaaaggttat ttctattagg acttgcctct 152160
```

```
gagtcccaaa ctgggactca ggatcagatc atggaggaac atgaaactct tatgtggatg   152220
atgacatgga ttgggcatct gtggtggttc tggaacttca ggattcacct gatctgcctc   152280
ctacttatct ttggaaaaat gtaaagtata ggatctttct accacaatct ttactactgt   152340
agggagtttg atccactgac tcttttcaaa agacctctca gtgttcaagt acttttcttt   152400
aatgccattt cttgagagtt ggagctacag ttgctctaga tgtgtctagg tctgatcttt   152460
tctccccata ctccttgagc ccctgataac caccattcta ctttctattt ccatgagttc   152520
agtcttttta gattccccat ataagtgaga tcacaaggta ttggtctttc tgtgcctggc   152580
ttattccact aacataatg tccttgaaat tcatccaaat tgtcaaaatg acagaatttt   152640
gttccttttt aaggctgaaa agtattccac aatgtatata tgccacttat ctttctttct   152700 ctttcttttcc tgcctgtttt tctttctttt cttctttctt tcctctttct ttctctttcc   152760
ccttccttct tttctttctt tctttctttc tttctttctt tctttctttc tttctttctt   152820
tctttctttc tttctttctt ctttctttct ccttccttcc tttcttttc tttctctttc    152880 tttgtttctt ttttctttat ttctctctct tttctcttt ttctttctat tcttttcttt    152940
ctctttctct ctctttctct ctttgtttct cccttccctt cccttccctt tcctctttct   153000
tttacaggct ctcactctgt cacccagtga gtacagtggc acaatcatag ctcactgcag   153060
cctggaactc ctgggctcaa gcaatacttc tgcctcagcc tcccgagtaa ctaggacaac   153120
atgcacatgc caccacatct gcctaattta aaaaatttgt tatagagaca acattcttgc   153180
tatgttgccc agattgttct caaaggtctg gcttcaagca atcctcctgc cttggcctcc   153240
caaaatgcag ggattacagg catgagcccc cacactcagc ctcaatgcca tgtttgactt   153300
atcctttcgt ccattgatgg gcacttaggt tgattccata tcttggctac tgtgaataaa   153360
tgctacagtg aacatgggaa tgcagatatc tcttccattt actgatttaa ttacctttgg   153420
gtacatatcc agtagtggaa ttgatggatc atatggtagg tctattaatt ttttgaagaa   153480
actccgtact gttttccata tggctgtact aatttatatt cccatcaaca atgtgaaaag   153540
tttccctttc tccacctcct cgccaacact tgttcagaca ctttcatctt taaaaaaaaa   153600 ttaatttta attttgtgca cacagtaagt gtgtatatgt atgggtgca tgagatattt     153660 tgataccggc attttgatgt gtaatgatca catcagagta aatgagatat ccattacctc   153720
aagcgtttgt tctttctttc tgttacaaac aatccaattt tgctcttaa attatttaa     153780 aatgttcaat ccattattgt tgactgtagt caccctgttg tgttatcaaa taccagatct   153840
tattcattct acctaactat atttttgtac ccattaacca cccccacttg cctgcccacc   153900
cctcattacc cttcccagcc tctgataacc atcattatac ttttatcta catgaggtcg    153960 attatttta ttttagctc ccacaaataa gtgaaaacat gcaaagtctg tctttcagtg     154020
cctggcttat ttcacttaat ataacgacct tcacttctat tcatgttgac acaaatgaca   154080
ggatctcatt cttttatgg ctgaatagta tttcatcata tatatgtacc acattttcct    154140
tattcattca tctgttggtg aatacttagg ttgcttcgaa atcttggcta ctgtgagtag   154200
ttttcatctt ttcgataata accattctta tagatgtgag gtagtatctc tgtggtttta   154260
atttgcattt ctctgatcat tggtgatttg agcattttt cacataccat tggctatttg    154320
tatgtcttct tttgagaaat gtctattcag atacttgcc catttttaac cttgtttttt    154380
ttcttacagt tgtgttgagt tcctcgtata ttttaaacat taatctctta tcagatttat   154440
ggtttgtaaa tattttatct cattccatag gttgtatatt cactctgctg attatttct    154500 tggctatgca gcttttagt ttgatgtaat ctcatttgtc tatctttgct ttcccagtct    154560
```

```
gtgatttggg gttaaatcca aaaaaaaatt atgcagacaa atggcaatgt tttcttatag    154620
tggttttagg tatttaatcc ttttttaaat atggtgtgag ataagggtct gatttcattc    154680
ttccacatgt ggatattcag ttgtcccaac accatttgtt gaagagactg tcctttcccc    154740
actgtgtgct ctcagcatct ttgtcgaaaa tcatttgacc ttaaatacat ggatttattt    154800
cgggttgtct attctgttca ctggcctctg tgtctatttt tatgccagtg ccatgctgcc    154860
ttgtaataca gctttgtggt gtattttgaa gtttgatatt gtgatacttc caggtttgtt    154920
ctttttgctc aagatttatt tggttatttg ttttttgtgg ttatacaaag tttaggatta    154980
ctttttcta tttttgtaaa aaatgtcatt ggcattttgg cagggattat attgaatctg    155040
ttgatagctt ttgttagtat ggatatttta aatatcagtt cttccaatcc ataaacacag    155100
gatatttttc cttttatatg tgtcctctac aattatttca tcaatgtttt atagtttca     155160
gtgtacaggt ctttcacctc ctttggatta aatttattcc taagtatttg aaatttattt    155220
tggtaactat tgcaaacagg attgttttct tgattttatt tttcagatag tttgttgtta    155280
gggtgttaaa gtgctaccca tttttatgtg caaataagga taattttctt tctttctttc    155340
tttccaattt ggatgccttt tatttctttc ttttgcctaa tggctatgac tagaacttcc    155400
agtacaatgt tgactaaaag tggcaagagt aggcattctt gtcttattcc tgatcttgca    155460
ggaaaacctt tcaactttc accattgaat aagatattag ctgtgggttt atcacatgtg     155520
gtctttattg tgttggggta cattccttct atgtttaatt tctgagagtt tctatcatga    155580
aagaatgttg aattttgtca aatgctttt ctgtgtctgt agagatgatc acatggtttt      155640
tgttctttat tatattaatg tagtgtatca catttataga ttcgtaaatg ttgaatcatc    155700
cttgcatctt tgggatatat ctcacttgat catgatgaat tattcttta ctgtgttgtt      155760
gcatttaatt tgctggtata ttttgaaggt ttttgcattt atgttcatca gggatattga    155820
cctataatat tttcttgtaa tgttcttgtc tggctttggt atcattgtaa tgctttcctc    155880
ataaaatgag tttggatgta cttctcttct tcaatttttt gaaagagttt cagaggaact    155940
ggtattatta gttcttcatt aaatggttga tgatttcagc actgaagcca tcaggtcgtg    156000
ggcttttctt tcttgggaga ggcttttggt aattgattca atctccttac ttattattgg    156060
tctgttcaga tcttctatt cttcctgatt caaccttagt aggttatatg tgtctaggaa      156120
tttatccatt ttttctagg ttattcaata tgttggataa taattgttta tagcgttctt      156180
ttataatcct ttgcatttct gtagtgtatt ttaatgtctc ctctttcatt tctgatttta    156240
tttgtttgaa ttttctttcc tttattcttg gtctagctca acatttgttg attttgttat    156300
tatttcaaaa caccaacctt tagttgagct gttctattgt tagatagaat agaatagaat    156360
gttctatttc aacaataaaa tgttgagcag ttctattgtt tttctacttt gtatttcact    156420
tatttctgct ctgattatta ttttcctcct tttagtaact ctgtgcttag tttcttctta    156480
ttttgtgtgt cttaaggtac aatgttatag gttgtttgag atctttctcc cttttttgatg   156540
taagtgttta ttgccatgaa cttttcctctt agaactctta ctgttgcaat ctacaaaagt    156600
atttgttttt ggcaagttgt gtttccattt tcatttgtct caatacattg ttaaatttat    156660
cttttaactt cctcattgtc ccactggttg ttgaggagta tgttgtttaa tttccacata    156720
tttctgcatt ttccaaaatt cttcctgtta ttgatttcta gtcgcatacc attgtgttaa    156780
aaaaagata ctcaatatgg tttaaagtat catttcagtt aatgatctgg accttaaatg      156840
atggcagcat aatcaatgtt aatcacaaac caaaggctat ttagtgttat tattttaata    156900
```

```
tgcaatatac ttaccaggcc ccccagcact cagtctgcac agtctagacc ctgcctatct 156960
cagatccata ccccatctct tcctccaccc cttctgtttc aaccaaatta acactgttta 157020
ttctctgtag ttccccaccc tcactgccgt gcccacacta tgtcttacca aattctgtcc 157080
ctctttttaga tctcagtttt ccttgaacac ccagactcaa ggtgtggatg cctatttgtt 157140
tatcttttta gtagcccaga cttttttata gtacatttta cagatgtagt caaataattg 157200
tgtaattggc tacttaagat ttctctcctg catttaaaga aagccccgag attatatcta 157260
tcttgtccaa cttagcatgc tgtcttgcat gacaatcatt aactttttat tgagttaatt 157320
aagcattgtg cagaatgcct agatgcctaa gctttcaatg ttaccaaaca tgtggaacaa 157380
aacttactgc aatctaggtt cccctgaaaa catagcctaa ggtggaggct tacttgaagg 157440
ttaccgtacc ttaaggagga gaagtaaaga acaggaagtt actgttatag agtgaatttt 157500
tctccatacc ccacccaaat tcatatgctg aagccctgtt gactaaagaa aaaaaaaatc 157560
aagcttttaa agtatcaggc caggtacggt ggctcatgcc tataatccca gcactttggg 157620
aggctgaagc aggcagattg ctttaggcca ggagttagag gccagctggc aacatgacaa 157680
aaccccgtct gtactaaaaa tacaaaaatt agccaggcac gatggcgatc atctgcagtc 157740
ctagctattc gggaggctga ggcacgagaa tcgcttgaac ctgggaggcg gaggttgcag 157800
tgaaccgaga tcatgccatt gcactccagt ctgggggaca gagagaaacc ctgtctccaa 157860
ataaataaat taattaatga attaattaaa taaagaaaag ttagctttat ttggaagtct 157920
gaggactatg gaccaaggcc tattgcctgg gatcagttct gttagaccat tccaatgcag 157980
caattgagtt cacagtttgt atacaaatgg tgaggattca ttacatgcaa aatcacatcc 158040
gagttcgtgt ataagagttg atatttatag attattatta ttatagatta tattatagat 158100
tatacattat tatcgataat aatctattat cgataataat aatctataac ctataacatg 158160
ctaggctgcc ttctgctgtt gaaaataatc caaatatctt gggcatataa ttatcattga 158220
gaagggcatg atatgtacaa gagaagtatt caactggttt ccccatgatc gcaaaccttt 158280
ggagcttata gaagagaaaa aaaaaaaaga gagacaaagc aaatataaaa gagattttga 158340
gataaatttgt acactctgaa atgagaaagc aaacttaggg ctgacacaag aagaactaat 158400
tatttttttc aagtacattt tattgttatc aaaatagtcc atacatatcc tagggaaaaa 158460
aaaccccaca aatagtacag gaagattata atttaaagca ccagttcact caaaggcaac 158520
atttttaaca aaatttttta aaattatttt tagtgatccc tctaaatttc taaataatat 158580
gcttatattt ttttcttgtt ttacccatgt taagtgtgac aaatttactt tttgctctta 158640
taaatatgga tttagctaat tttatttta tttatttta ttgagaccag tctcgctctg 158700
tcgccaggca gagtgtgcag tgatgcaatc tctgctcact gcaacctctg tctcccaggt 158760
tcaagtgatt ctcctgcctc agcctcctca gtacctggga gtacaggcac ttgccaccat 158820
gcctccctaa ttttttgtgtt tttagtagag atggggtttc accatgttgg ccaggatggt 158880
ctcgatctct tgaccttgtg atctgcctgc ctctgcctcc caaagtgctg gaattacaga 158940
tgtgagccac tgcacctgtc cagatttagc taattttcta cacttatccc caaccttcct 159000
cttcactcta cctcccttttt caatacgata atatcacatc ttaagttcca tcatccctgt 159060
aacctctgta gctataagta tatagccaca attaacatat gtagatttcc atttctgatt 159120
ctatcagcca taggtaactg tctttacatt ccactttgta agaggagatg aataattctc 159180
acctttcctc ccaactctgt gttcctcctt ctacctcccc accccaact ccgttgtagc 159240
ggctattaac atatattatt ttgtaaccat gggtaagtgt taagtaattt gcctaaagat 159300
```

-continued

```
tgattctaaa aaatttaaaa atatagaaat ctataaaatt ctgtaaattt tagattttct 159360
ataattatag aatgtaaaaa tatagatttt ctataaacat agaatgtaaa attctataaa 159420
aatatagaaa tctttatgta attataactg tgtaagtatt atttactgta gaaccaagta 159480
atgtgcaatg cttccttctc catggctcca gtgtcatgac atctatagta ctttacaaat 159540
aatgttatga gtatatactt ccagaatggt ggtaaaagaa gctctgcaga ccctctcccc 159600
agtgaaacaa ccatactggt aaaagtaatt ttaaaaggca atcatgaaaa gtctctggaa 159660
attttcttaa gggtatacag caaatgaaga aacatttatt ccaaaaagtg tactaaatct 159720
tggtaagaac aatgagtcca aggcacctaa gtcacaaccc acttcccttc ctctcctccc 159780
agctcagcat gacagaagct taactctgga caagaacaca gggcttcctc agcttccagt 159840
tgaggccaac tgtatgttcc caagaggaga agaccaacag cgtttcttgt ctcccttcac 159900
ccttcccctc cagaagctaa attctggcta gatgaatcca agatattggg gctcccttct 159960
ctcacccagc tcctactggt agggtggagg ttcaacctca ggcctggaac actgagaata 160020
gtatgggttc ccaattatta atgagactct gattattgcc catgctcagc tccctgctcc 160080
tacagcagag gagtcactta cagagaaaca caatgctgtc cccatcccta gctctgaagc 160140
cgcgcgtcag agattttccc cagtgggagc actgaagctc tttgcaaagg aactgacttt 160200
atttgaagca gagtaaaggg aagttcaaga taaaggtatt ctcaaaaata atgtaagttc 160260
tggtggaaag caattaaggg gaggttggta gcttcgtgaa agagacaagc taaaccagat 160320
tagctagtgt atgagagaga atcaggaaaa gagatagcta agaagagccc tcctgggtca 160380
gaacaaacct caagcactga ccacagcagg cagggcactg tggcttacac ctgtaatccc 160440
agcccttggg gaggctgagg tgggaggatt acttgagcgc aggagtttga gattagcctg 160500
ggcaacataa caagactctg tctatatttt aaaacaaaa acaaaaggc taccacagca 160560 aaaaggctgg aatttagttg gagcagaccc ccagagcaat ttatgtccca ggacattgta 160620
aaaaataaca gaacaatcta gaacagaata gctgggtata tgtgataagc cttagagcaa 160680
ccactaagaa aataactcga aaaatacata gtgaaggaaa gaaaacaaca atgttcctaa 160740
catcacaatc aaatgaattc tccttttcaa catttcacca gaggctcaaa atcattccac 160800
gtttaaaatt tttttctctt tataatgtct actgaaaaag tagcaaaatc tactgaggag 160860 agctttatt ctaaaaggga gtatcacaac ctgcaagtgg gaaatggagc ctctggttaa 160920
aactgaaaag caggtgcttc gaaggaggaa aaatgagaca ggaattcata ctaaatggat 160980
tggtttagca tacatattca accggctatt ggaggagcta tgaatattca tgaaggggca 161040
cacgtgtagt aagctaacat gtctattaca tatgtcccat gttcactttg gggtggaaaa 161100
agcatttaaa tatactaaaa ttaagctcta tatgtcaaaa ggttaagcag aggacatgaa 161160
gggactcagc atacagtctc tgtaaactgg ccagaaccac tccatgttca gtgttctctt 161220
attgggaagg aatgctagcc agttgctgtg tcgaaactac aaaaagcaag gggcagcgta 161280
acatggttgg ttgaaatcag ccatggagca agtctttcaa aagagcttgt ttctgtttaa 161340
cccttaggaa cgaaagccta ctggtggtta acaaggtagg gggtgttaca gggtgtggct 161400
gacctactgt tccatcatag acaggagctc agttttaag gtttctctgg ggtctccaag 161460
tgagcctccc tggagaatcc tccaatttcc ctagtgagag caagaaccat atctgtctat 161520
actgcccaac tcagttgttt ttgcaataat agacaataac tctttaaaga atgaataagt 161580
ggtggtgaaa tgaaacagag taagttcctg atgtagaagg cagaagggag actgttgctt 161640
```

```
aggcagacca agtagaaact atacgatatt ttctatagta ataaccttag aaatggcaat    161700
tcggttctat agttcaatta atatcactaa aagagctgtc caatgaactt acaagttatg    161760
tggtatatgt gggttaatct gggagaccaa ccaccattta tgaaattctt ctctatgaaa    161820
atgctttatg aagggcaaat agcaagttta caaatgaatt tttggaaaac aaactgtaaa    161880
ttgaggttaa cttctaaggc tgttaatttg tgggtatctt tgtctatatc ttcttctcac    161940
tgatatatcc tcaggtagct agagttctcc tttcaactag ccttaatttt gaattatatg    162000
ccagttataa atcatcttca gaatatgaat taaatacccc tttaatttta attgatatga    162060
ttttacaata ttaactacat agtaacaatg gatttggata tttatcattt ttctatttga    162120
tttataattt agggccaaat gggtgtcata aggggctctc attccaggaa acactgtaga    162180
gtagtctagt atcctaacag tctatccatc ttgattttg aaaatagtct gttgtggagt     162240
agtttaggat aacctaacta cttgtctgtc aaatagagga atgctgtgac tggagaaaat    162300
ggagccgtta tacattagtc ttcggtacag tcacaaaaag ctacttattt cacaaaagac    162360
actattttgc cttttcaggt gtaactgtgt ggaaccgcat aatcccagca atggcacatt    162420
gaaggaatgg agggaatcca atatttctgc ctctgacata atttgggaga acctaactgt    162480
gtcagtaagt aaaacactga aaaataagtc atacctaaga gcttttgttg acattttgac    162540
tcaattattg ccattacagt aaaatttttt tgaatgcata atataaaact aatagttgtg    162600
ttttaatttt aatttcatca tttcagatgc tcatcagtaa actggggtta tctttcatta    162660
ttaaggttgt tctaatagaa gaccagaatt gctcaaatag ctcacttata cagaaatatg    162720
tgaccgagat ggactgaaag cacattaaat atgagtggtg ttgacctaaa tgaaaccata    162780
tggcagaact aagtctgcct tctgtgtaaa gaactcagaa tgctcttact ttactctgta    162840
atgctgctcc agctgttccg gatctgctgg ggggaaaggg atgtttctaa tattctagtg    162900
tcaatactaa agtctttggg aggaacaaat atcactttc ttcacaaaat ctggcacct     162960 ccctcaacaa gatctttctt ttttccattt tattcttatc tcccactcaa gaaagagcat    163020
ggcaacatat ttttcaccta taacagttca atcctgtgcc attgtcttat ttcctttgac    163080
ttttctctac tttgtgattt cttttttctc ataccctgcat ttctctattt ttctgaatct   163140
attctgtgcc tcctttccta tcaatacttg cattctatgc ttctggttca ataaaatctt    163200
gtaatttgaa aatgtgttct actttaaata aatattaaaa tctgagtagc cctactttct    163260
tttctattct tcccagctat aaacattaca ggttcaaacc ttctaccact ttacctaccc    163320 ataggctc aagttttatt atgactatca gcacaaaact attgagttct agttcatttg       163380
atcaaatgca tactattta gtaagttgtc tagttagtga gcatagaaat cttttttggt     163440
gtacagatgc tataaaactc taaacatgat tcttgtaaag agcatatgat ctattgacta    163500
tattcttgat tttctctatt gaatatgttc tttcaaaatt gaaatcaaat tacttactct    163560
ttatttaaaa ttctatcttg acctatattt tactacttct attcttaccc tagctgtgtt    163620
ctgtagaata agccttcagt tactcttatt gttttctttt gttattgtta acatttattc    163680
tgttccacct attttccct agaaaaataa cattgccagt ctgcttccac tcaaagagcc     163740
atttaaactg aacaataaaa gaattgatga gctgatcaag aaaaacact atagttattc      163800 agaatttaga catgggtca tgattaatga aatcattagt gggtcttctg tctacactt      163860 ctttggtaaa ctatattatg tttacagagc ctcttgatgt cttcttcaat atgaaaccc     163920 aaatgatccc atctctaagt tatataacat gataatttac tctatatgtg ttttgtatta    163980
tgtgaataat ttaatactaa ataataatat tccttctatg tattagcaaa tcttgaattt    164040
```

```
tgagagttct aagaagcaga catacagcac agttatcagg ctagctgtga gttagatacc  164100
ctgagttttg aggtcaagta gaatagtgaa aaatattttg caattaaagc aaatacagca  164160 ttgtgggggtt gttggttttt ttctcttttt ttttgtcatt ttaaaaagtt ttgtactagg  164220
tgttaacatt tgagcagaaa gtttcatatt attttcatt agttaaaagc agttttgca    164280 atggataatt gctaaacttg accagaaaca gtctttatca ccagagggaa tactatataa  164340
tgaaaacaat cttgtaattt ttaagtcaaa aaaagaccat taaaattttt gtctaattgt  164400
tatgctgaat tttttcctca atatattcat aatgtcatca aaaatatttt attaataaag  164460
cactgaacta gtggctatca caactaattt tgttaaaata gtgacataac atttaattta  164520
catattattt gtttggcagg tcctgtaatg ttttattgag ttgtttgtta catatctcat  164580
gaattataat ttataccttg ccaactcagc aagggcaaag aactttagtt ttctctgatt  164640
ctcccaaact gctctatgca tagtaagtgt caaacatttg atagaagtac ttaatgtctg  164700
tttgaaacag tttcatctta ctatttaatg caaatattta tggcaaactg gagtacttaa  164760
gtttgtgtgt atatatatat atatatatat atatatatat atatctctct acatatatat  164820
gcgtgtcgat atcgcgaaaa accgtctcta tatgatactc tcgcgcaacg tcgaagagta  164880
agcaggcgca gctcaaccag cacgaggtgt cgcagtcact acctcgcata ccttgcgtgt  164940
nnnnnnnnnn nnnnnnnnnn nnnnnnnnnn nnnnnnnnnn nnnnnnnnnn tatactatag  165000
gagccaagta gcaaagcata tgtatgacac gcaggatcga ctctacgagg atcccccttta 165060 ggcaagattt aaaatattca taagcagtta accagcattt ggtgtttcag tgcctgaatt  165120
acatatttag cttgtacata tataagggc aggacactaa tgccaacttt aatttcttat   165180
tctaacttaa ttttgccaa cttatagaat tgctgaaact tagaatgtgt ttgaagagta    165240
attagtagaa atcagtttgt caacaagcat tttttgagta cccattgtaa ctgaaaccat   165300
atgttagact caaaaaacga gagcaggatt tggatttggt tttcatttct aaatttcagg   165360
acttactctg tgtgtatgtg tgcatgtatg tatgtgtgca tgtgtgagtg cctctgtgtg   165420
tgtattgggg atacaattag tataaatctg aaaataattg ttgaatttag caggtcacaa   165480
tttttctctt ttaaaattag catttttgttt cctcccaaag agaaaataaa taacatttc    165540 aaatatgctt tgaattaatg taattaggca gaccattggc aaattataga gtgtaagaca    165600
gctaaggaac ccttaaatg tcatctatgt tcttaagaat tgagaacaag atcccgccaa    165660
atgactttta tacctgcaga aatgacaaaa gatgctcaca aatttataga taatgtgttt   165720
atcatggaac ttttagctcc ttttctatg tagcaattt gctacccatt atattgctta     165780
ataattgctc tgctagcatt tctggacagg tgcagaagag gatgaaaaac acaaggattc   165840
atttttgcca ccttatctat ttttaaagca ttttgaaaga aggaaaatta aactttaat    165900 taaggcctgg gggattttc tgtggttttt caattagcca agttgctgtg ctctgtatta    165960
gcttaacatg aataattgga atttaacttt gcctatcaag gaagatgttt gcagttaaat   166020
tagaaaagga gacagattct ttaagacaat aataaggtgt attaactata tttctcaaga   166080
ctctcaggct tagggtagct agcaactcca agtagatttt actagttgtt tgttttcaga   166140
tgacagtgta gctatttgta atttattcta caatctttgg agtgtattta cttttgctc    166200 tacaaagatt tcaggcctaa agttgggcag actctgtgtt tgtgatcaat ctatcagttc   166260
atatttgtct ccaagatctc tctgcaattc aatttatgtt cagggcaaga atatctcaag   166320
gactaatgag atcactggat catttaaacc attatttcct gttttgaaat gtaaaaatac   166380
```

```
tttagtaatc taatttttaa ataagataaa ccaaagtaag tttaaaataa ctttttttca 166440
ttcaaaatat ttgtttgaaa tgctcagttt ttcctggagg aaaaaaattt ttttgacttt 166500
gctgccacct catggctaag gcagtaatta gaaatagttc ttcaggctct tacagaacta 166560
cagttgcaga agaaaaaata atccatggag aagtcatagt aaatatgagc tttgccttgc 166620
tcatgtagta atttttatttc atttgttctt tagtccaagt tcgatagtcc catctttgac 166680
ttacaagttc atttcagtca ttgtatgtca tagttttctt gttgcctttc tcatctttct 166740
tggcagcttt tggactagat aattctacaa agtcattgtt cttagtcaat aagcaataat 166800
aatctcactg cagaaatcgt gttttgtatca cagctctgcg gccacccacc agtggtgagg 166860
ccacaacaaa ttatttaacc cctttatgct tcagtttcct cagacatgga atattaataa 166920
tagcatgaac atattttatg gtattggtgt gaaaagtaat ttaaatgatg tatttaaata 166980
gctgggcata gtgtctgacc ttagtaacca atcactatta catatgtcat attttcaata 167040
tatctcgtgt taggaactta gtagatatta gatttaatac atactaatta attggtaaat 167100
caatcgtttt atacatttaa atttaaaaag cagttcatgt tcaaattttt cataaacctt 167160
tgcatatttc tcaccaccca tccaagttga acttgaaact cgtaatgtaa tgcctgctaa 167220
atcattgtga gagccataaa ggaaaagcct cagcatctga actacaattg atcagaaggt 167280
gttagttttc tgcaagaaat gtgtccggtt ttttcttagt agctccatttt gttttacttc 167340 ctctggcagg aatgcaaatc attgcatgga gagtatgttg gacgggcctg tggccatgat 167400
cacccatatg ttccagatgt tctatttttgg tctgtgatcc tgttcttttc cacagttact 167460
ctgtcagcca ccctgaagca gttcaagact agcagatatt ttccaaccaa ggtacttaga 167520
ctatttcttg atctaaatgt aaaataacat aggacaaaag aaagagtaat tgatgtaata 167580
aaaggagcca ctgaaaggct tttgtgtgag tgagctgcca ggttagttgt ggagtgagat 167640
gaggggctga agagaaagaa tttgtgatgc aggtgctggg agtgcatatg caggcttttc 167700
tcctaactgc aaacccccacg gatcaactcc tactttccta ctgacgtttt tggaaaattca 167760 cagcacacac tgcattactg attgtcactt ttttgcccag tgaacagtgg gaactattcc 167820
agcctgacag ataccctcaga ggagcctatg ttacattctc taattgggga agccccggca 167880
agactcattg gaacaatatt ctcttttttca atgtttaaac cgtcagtccc tcccctaac 167940 ccaccacgtt tgcatctgca tatttggaaa ggaaagtaaa cagagaaaca gcttagttca 168000
atatttaaca ctgcaaagta acacctataa tgtctgattc cgccaaaaaa aatttaaaaa 168060
aaggaaaaga aacaaggaaa caagcttctg agggatgagc tatagattat gatcaaaatt 168120
ccactctgga aaaatatttc aagaactgtt ccttccgaag ggggcttctt ttttgtcacc 168180
actttcttct actaaaggtg gaagattcat ttatttcccc aaaaatctta gtctgattaa 168240
tacaaaaaca tttttctaag ctgaaacaat aatcttaagc attttgtgta tgcttgtgtg 168300
tatgtcataa aggcatctta aaataaacta gatctggata ataattatat gtgaatattt 168360
gctcagaatt ggctttataa atgagaaatg gctttaaaaa ttggctcaca tagaataaat 168420
tttaaatttg cccactctgt tgtgtacatt cccaactgtc atgcttatat tctagataaa 168480
ctaaaacatt atgtttcttt gataagaaca gataattttta ttttatgatg cttcaagttt 168540
atcatattaa agtgttacct gtgtgaaaga gatccctaaa atccagccaa attctgccca 168600
tgctacctta ttctgcattc tgaatattca catgcatggg ttcatcataa agttagattt 168660
taaataaaca ttgaaaacag cacaaccacg atgtagctat tccataatgc ctcattctgg 168720
aaaggttgag tgtgtaccaa tcttaacgac agtgatacat aaatatatat tcaggttctg 168780
```

```
acagagctaa tggtaatctt atagtatgca taaaatataa tattatgata ttatgtcata 168840
aagtgtttat aaagtgtgac tctagattat gttcctgagt attccttgat atttatagct 168900
actttaagtg acaagtgttt tcattatttt taggttcgat ccatagtgag tgactttgct 168960
gtctttctta caattctgtg tatggtttta attgactatg ccattgggat cccatctcca 169020
aaactacaag taccaagtgt tttcaaggta cttactatct ctctccctct tcccatctct 169080
ctcggtctaa tcttcattta gatgatacct ataactctag tacttaggat tttcatgaaa 169140
atatgaagaa tttagattag aagaccagta atgaaatgc acacagcatg gctaaaattt 169200
aggtctaata tttaaaaata taagaattac aaaatataaa taattataaa tataaaactt 169260
gcttgaaaaa aatttcctgt caattctgcc agttgaaata cctatatata acattcttaa 169320
aagataagga agcatttgaa actaagagaa aaggattatc ttggcagaat tgtacagtga 169380
ataaggcttg gaaaacagat aaaaatagat tgggaataga attctgaccg tgttactaat 169440
ggggtacagt ttgaatattc cttatccaaa gtgcttggga tcggaagtgt ttcagagttc 169500 atttttttt caaattttga aatatttgca aacacataat gagatatgtt tggggtgggg 169560
cccaagtcta aatacaaaat ttatgtttca tatataccgtt atacatataa cctgaaggta 169620
attttataca ctattcttaa taatatatgt gacctatcac atgatgtgag gtgtgaattt 169680
tccgcttgtg gcatcatgtg agcgctcaaa agtttcagat tttggatcat ttcagatttc 169740
agcttttcaa attaggggca ccctttgtt ttctctgtca aacagggctg gggacttcta 169800
tatagggctc ttgtcaggat gaaattttga gaatcatctc agacagcagc catgtttgga 169860
atccttccct gagcctctgc tgtgaccaag tatctttttt atcattttca ctcaatagcc 169920
tctgcacatc aaaaataaca gttacaatac cataatgatg tattttgttt agatgtctgt 169980
ctctgattct aaactgaaag aagcctctga tttatcttg tatctcagtt ctagcacagt 170040
ggtcaatgtg tcaatatgct atttgtaaat ttcaatacat tttccaatag taaatagtaa 170100
atattaatat cattttattt aatacaggta ttgattaata acacagattt ttcaacaagt 170160
ctgtcagagt ttaaatccca tctctaccac gtactagctt tgggatcttg ggcaagttac 170220
tggatctctc tgtgcctcaa ttttcttatc tgtgtcatct ttagagtgtt gtgaagaaaa 170280
aaaaaatgag ttaaaatatt taaagcactt aaaatggttt taagtgattt atgagtatta 170340
ttattattta ttataggcca ctcagctcct ctgtttataa ttagggcttt cctagtagca 170400 tctgtaaagac ctaatttgat caagtattca ttaatccagt tcataactat gcacattctt 170460
tactttatac agcccactag agatgatcgt ggctggtttg ttacgccttt aggtccaaac 170520
ccatggtgga cagtaatagc tgctataatt ccagctctgc tttgtactat tctaattttt 170580
atggaccaac agattacagc tgtcatcatc aacaggaaag agcataagct aaaggtatat 170640
tttaacatcc atttaatgt aaataattat gacaactgat atcaactgat gttcatttga 170700
cttctatatt ctgtattcat ttgcacagtg aaatatataa aataatgttt ttagatgtat 170760
aatttttatt gtcttacaag atacttggtc ttacaatgag atgagaattt acttatttgt 170820
agcacttggc tgagctcacg tctgagaact cacctccaag gcataaaata aaaaactgtc 170880
aaagttttaa cttttccata cttaacatat tttaatgaaa taacaatctg ttctggtgaa 170940
gtacaaccat accaacttgt cttacatctg agattcctct attcctctat ttaacctaa 171000 atgtatctat tacattgaat tcattatcag aataaattac aacttcaact atttctcatt 171060
ttctttaatt attttttctgt ctgcctgtaa caacaaaatc cagacataaa cgtcacagtt 171120
```

```
tagaagtgac atctttgagt tttattgcag atttcactgt ctctttata aaaagaataa 171180
ctatagatgt gtcttagtta cattctgacc ttgccatttt gcaattgtga ataatcgaaa 171240
ttgttcactg gtatgcaatt tgcctgagat atgtaatgta agcactgtca cttacttaca 171300
ggaatatgtt aaataaaatc gatgaaatca ttaaatggtt aaaaataatc tgcatcaaac 171360
cttgtaaaaa cataacatgc acaatcttgt ttttgttttg gtatcgtggg gtagttgcca 171420
gctattttca catcccttt aaactctagg agaaaaaatc attgtcagag caacagaaat 171480
catgctttat agaatttttt tataggaatg ttagaaagat gaaaaatatc tctgattaaa 171540
ctctgatgca atatattggg tcaatgcaaa agtaattgca gttttttgcca ttacttttaa 171600
taataataat tacataaatg taagaaagca cacttatttg caataaatct tatgaagaag 171660
gaattttgag tatatggtgg agagaatgtg tgtctatctt aaagcaaagg acattttcta 171720
ttctctttgt agaacgtaag ttaagaattc tcacaacttt atgtatttta ttaaatgata 171780
cattttaaaa aatcaactaa aaaacctgtt ttaggaagaa agtaagccat ataattatta 171840
tttacctttc aaaaagattt ttttagcctt tataattagg cagaaattct agtgtgttca 171900
ctgaaaaatt atcctctgta agggccatca gttaaatgga ttcaggcagc attttttct 171960
tattgtaagt ggaatcatat taaaacaaag tgtggaagtg aaatgtgtgc tgagattgat 172020
attaccttcc tggccattct gaatctttgc ccttcaacc ttataaatca catgacactt 172080
gctcttactc cttgttcttc atgagcccct gacattcaca gcctttgtaa agctccacat 172140
tgacaaatac actaatttcc cccttcacat atactgtgga ataacaaaaa tgtagtaaag 172200
cattctttaa gtggtccttt caagtacttg catttataga attaaatgca gaactagaac 172260
tatttttgtc actgaaataa acctgaggct acattactaa atctgtttta ttgtgcaaat 172320
aaatgattat gtagtcaaaa gttgtgtatt tttgcccctt actactctgg attttagtaaa 172380
tgatacagca aatctggctt aatcataaac tctgctatat ggccacaggc agaagagtca 172440
gcctgttctt ggccactgtg aatctgaact ctccatcctc cttcttagat atgaatactt 172500
ttaaagcaaa tttcttccag tgaagatgta tttcatctac attgaacccc tattgggcct 172560
ataactcttg tctcctataa gcttctatag agtgtggtct gatgctactg ttttccctgt 172620
taacaacaac aaaatcacct tctcagaatg ttatttactc agagtaacgg tttgttccat 172680
agtccttctc cccgcctgtt gcttcattga aatgtttgca aagtctcctg gctttgactt 172740
gaaccacatt ttcactaaaa gatgtgtttc ttgagtatat caccagacca caagctaacc 172800
acttgtgaaa gcattttcag cttttactaa ttttcttttc tcacttgaaa acccattttt 172860
gccttggttg gagcattccc cgaaattgtt taatgaatca tgttttgtag tttatgtatc 172920
aaacacttgg tagactccac atcatgtatc taagtctaca tacacccaag tcaactcaga 172980
attcctcatt tcattcttta tctctcccaa acatattta gatcttttta ctttttcttc 173040
acctctattg ccagaactag tagctggttt tcttttagat gatatttctc ctgctgataa 173100
aaatgttttt attggccagg cacagtggct cacgcctgta atcccagcac tttgggaggc 173160
cgagacaggt ggatcacgag gtcaggagtt agagaccagc ctggccaaca tggtgaaacc 173220
ccatctctac taaaaacaca aagattagct gggcgtagtg gcgggcacct gtaatcccag 173280
ctactcagga ggctgaggca ggagaatcgt ctgaacctgg aaggcagagg ttgcagtgag 173340
atgagatcat gccattgcac cctggcctgg gcgacagggt gagactccgt ctcaaaaaaa 173400
aaaaatgttt ttatcatttc atgagtgtca ctatgtacac aataaagctg tgttgcactg 173460
cataggtgac ttactactcc cgaagaatgg gggagctcaa aatcagtaaa cctcgaactc 173520
```

```
attgcatcct atgatccttt ggatggctcc agagtgaaag aagaggcaaa tacaaaaatt  173580
tgagaatgtg aagtatcatg tatattatac ataaatgtac atataaatcc atactctctc  173640
tagcatttgt ttgtttgttt ctcccttaga gaagtggatt aggcataagt taactgaatc  173700
cttttgaaaa gcattaaaaa tatctacttg ggtttttaa agcacattct ctaaatgtga   173760
aaagagagat aaaatcttat aaaaaagaaa gtttctgtta agatacaact gtgggctttt  173820
ctacatgttt ctgtagacag ttcaggcttc ttttgacatc attttaata aacagcaata   173880 caatcccgga tcacttgagt aaatgaatgc atttgcaaca ttcatttggc accatattct  173940
cttgatgatt atggcatttg atatgttctt ttttgccctc tttgtcagcc tggttcttca   174000
tgtcaatcta tagtctttta tgtggttaac ttgacagatg caggaaattg ctgccaagct  174060
ttgaaatgaa ttttttcagc agtggcatct gggtatcaga tggtcctctt ggctggcctc   174120
ttgtcttgct gcatgttggt tttagtgggg tctggtgtag catcacctgt tgctatgctc   174180 cctttcctc ccatatgtcc atttcctgtg attcatggat gaatgtgaga ataaaagctc    174240
tagctctgtc tttatttgag aaaaaaatct acagaaatat gttagaaggt gtagagttct  174300
ctgtctgaca aagggatact tctctttggc tggcatgcct atcagctaat aattttgtta  174360
caaagtccaa gttttaaag acattttaaa tgaaaggcaa gaaggatact ggttagttag   174420
gggaagagca agaactgctt tatttatttc ctttggttta cgttaaatca agatgctgcc  174480
attgttgtac agcataatta ggggaaatta tatttttgtt tttgttatat atttatatat   174540
tacaaaacta gctttataaa tttagaaaag aaattatttc ctctgaaaga attattttgc   174600
ctacttcctg caattcagaa tcccactgtt tacatttgta tcatattttt aaaacattca  174660
ataagagcta ttggaaaatca ctatcgcgac aaagatctcc ctcatattat tgagatgtag  174720
tgaatgtgga ctctgagaaa gtccaggtgt gctaaaaagt acaagcctga ctctcaaggc  174780
cccctgtctt ctgccctcct ctgatgctca tctcacagcc accagctcct cttccatctt  174840
ttgatttctc ttagcagtac cataattttg caaatagct ccaaggggggc accattcaca   174900 ttgtactccc tcagaggcag aggcttaagt atgaggtcct tccctgttct acatccttct  174960
cactccagag ttgctaggac aaaacacttc tcaaactgct taagacattg tcctttaaag  175020
ggaccaaaat ctgagttcta ttctatggaa ttacatcttc caaatgtttt tgcaaaaggg  175080
ccaagggatg atattatggt cctggcaaaa ctgtttccta tgcttttttg gttatgctga  175140
caccaggcag tttctcttcc tactcttcaa ctcttactaa tcaaattctt tcttgagtta   175200
cttgcaaaga aaagtttcca gagtcatatt cattcaggaa attgagttag atattttggt   175260
aaattgtagt attgccccag taagctgaat caatgaaggg taccattgct ttggtgtcaa  175320
cataggagga acaggtcctt aggcacataa ctctcattgt ctcctcacta tcatctcttg   175380 cactttata atttggaaag gatgagcaga aggaaagaa agtacaactg actttaagaa    175440
ccttcttact aagaaaacaa gaaaacaaaa tcacagagaa aagactacca tgacaaatat  175500
gcaacaaata ctcagtgtgt ttcacactcc aggctataag agctctcata ctgactacaa   175560
actgcttgaa gttatataaa actacctcta aaaagactta ttattctcct agaagaattg   175620
gtaatttctg ctcatggtca taataacaaa tttaactgct gtatttattt taaaattaca  175680
cttactaaat ttgattctga aatgtttgat gcgtatttta ttttcaaaaa agtcaatttg  175740
taacttttat tgattgctta ttgtgtgcca atgattgtgc taaaaactag aggaaatact  175800
gagaaattat ataagttatc tgatcttaag aaacatatta atagttttat taaggagcct  175860
```

-continued

```
tgaaacctaa tgagtacaaa agaaacattt attgtttaac cactagaata taatagtacc 175920 taacattta  ctgattgctt tctattcaac agatattatt ccaaatgatt tacaacatca 175980
actaatttaa ttatcacaac agcccagtga ggtgccttct actatcatca tcatcgtttt 176040
tcagataggg aaaagaggc  acaagagctt aagtgattta ttggttgagc tagcatttca 176100
ttccaggcag tctgactcca gaacttatat tcttaaccac tttattatac tgcctctcat 176160
aaagcagtca ctaaaaatta aaataaaag  gtggaacata aataggcca  tcctttggc  176220 tgcttctgag gctctacact tcgattcctg cagggtatgg agggagtgct cttccccatc 176280
tttgatttcc ctcctcagag agcaccctgt ctgcaagagg gcagttttca cacacccat  176340 tgcacctatt tttcctcctt tacatttcct acctggtcct aggaggcact tagtttgcaa 176400
cacctggaga tcagtgacag tggagtagca taacagagga aatagaaaac aaaaaaccgt 176460
gatttctaag gaggggctta atttgtctag tgctgaaact gaagcaaatt agaacaagat 176520
agcactatat taaggagaaa atgactatac agggagctt  aggctccatg atattattt  176580 ttctaataga agtcacccaa tgagacaaac gagggcaatt ggaaactgag tgtttgttta 176640
agagttactc caggagatct gatatgaagg gcttgttgag tatcatcagg aagtggttc  176700 tattcgcaat caggccaccc ttagccctgt tattgacaca gtttctttct ctctttcttt 176760
cttttttaaa cagaaaggtt gtgggtacca tctggaccta ttaatggtgg ctgtcatgct 176820
cggtgtatgc tccatcatgg gcctgccatg gtttgtggct gccacagtcc tctccatcac 176880
tcatgtcaat agcctaaaac tggaatcaga atgctcagct ccaggagaac aacccaaatt 176940
tctcggcatt cgggagcaaa gggttactgg gcttatgatt tttattctta tgggttcatc 177000
agtctttatg accagtattc tgaaggtaac aaaatctgtc tttatgaact tgagagaaag 177060
aatacattta tcatcattta agattttcat ttgaatctga gccataaatt tgcaaatatt 177120
gtgtggcatg tgatgaaagt gatgaatttc tgaaccatgt ttatataatt cttcataacc 177180
taagggaggg aaattacgtc ctatatttta aaacccttaa atacataaaa atttagtctg 177240
gcaaagtaaa atttgatgag taaattattg taacaatttt gaatcggtga tcaagctatg 177300
ggaaaaagtc actcattgtt tctgactgac ttgtgacccg aatccattac aggcattcat 177360
aaagattcta ttttcttgtc agtggataaa tatattagca gttaatatta cttactatta 177420
ataagagata gaggtgaagg gatgagcctg gttatagtca catacgcagt tttccatttt 177480
aagtgctctg taaaaccact gtctggacat catcattgca tatagtgatt ttttttttcac 177540 acaaacttg  aaatctattt ttaagaggat taactagtaa ttattttgtc atgtaatttt 177600
gtcagatatt tccaaggtgt gtcaattgcg ctataaatta caacacattt tatttgccta 177660
taatttgaca ttttaattaa attatttaat gatttacact agtttacttg tatttgatca 177720
ttaacacaag tacctttgca agaattaatc tctgttatat aagtaattat gttatagaca 177780
taagatgatg tgaactattc aataaaag   agaaaatctg aattatccat atatttacaa 177840
atacctggta taatacagga aacacatcta aatgttagct tcatttttaa tccaccttta 177900
atccaaatat cttatctttg taaagcaaaa ttcaagttgt ctccaaagta gcataataat 177960
aatattattg ttcattatat actacatggt ttttaaaaat agattttgac ctattaaata 178020
attataacaa ccctattgtt atcatctcct tttagatatt gggaaactaa ggcacagaga 178080
gcttaagtaa cttacctaag gttacacagc taaaatgct  agagctggaa cttgaatcct 178140
tgtcttctga atctgtacta tactgttcct attcaaaaat gccttttttc cctgttttt  178200 tctttgataa atgcaaaacc acaatctatt tgaaaatgat ttctgccttt tctccaattg 178260
```

```
ttcttttaca gtttattccc atgccagtgc tatatggagt gtttctttat atgggtgctt    178320
catctctaaa gggaattcag gtaaattact tacagtacta caggcacatc tgtgatgact   178380
gaccttaagg tctactgata agtcatgtga cagctgagaa aatgccacca cctgaggaac   178440
agcttttaga ccacaattaa atttcttcaa acttgtcaga gttacaaaag ttaaagaaga   178500
ttctctccag catctaaggt tcataatctt atggtaattt tctttatcat aagtatatta   178560
aaactgtaag aggcttagat tttacagcat ttttagaaaa atcatagtag tatatttcaa   178620
tatatatcca aatatttata atatttgaca ctttaatcat gtgtatggac atctattggt   178680
aagaatagga aaagtcttta tgcacgaaga tgttcattgt aacacatact attaaaatat   178740
tggaaacaac ccaattctct aactgcagtc aaataattag gtaacctatg gtatattcac   178800
tgaaaattga taattatagg aaccacaaaa gtaacatggc aaaaatgctt acaacataat   178860
acaaagtaag aaactattga ccataggttt ataaagctat gagtttgagc tgggttgtga   178920
aggaaggtgt agaaataaga acaatttgtt gagatagtga tatcccgggg gttttccccc   178980
ttgttttgtt tgttttactg ttatatttat aggattattt ttaaaattag actaaaataa   179040
agatataagc agtttcaagt ataaggggaa ctttatgaat tatttaagta agtattggtt   179100
aaataaatat tttaggcatg aatttggcaa cagatcagcc agatggttct ggttcaggat   179160
gtcccatgtg gtcactgtca gggtgtggac aaggtccaca gcatctgaag gtttgatagt   179220
gctggaggat ctgcttgcaa aatggctatt ccacaactgt gggcatgagg gcatcagttc   179280
ttttctacct gttggtagga tgactcagtc ttttgccaca gtggcctctc catggaatcc   179340
ttagtgtgtc ctcaaaccat ggaatgtgac tccttcagag tgagcaatat aaaagagaga   179400
gagagagata gaggagaaag gagagaagag aatgagaaag aagatgaagt gcttttttgac  179460
ttagtcttca aagtcataca tggtctttcc atgttttcta tttgttagag gctatccact   179520
actaagtcca gcttgcaccc aagtgaaggg aaaagggaga ctatctcttg aagagaagag   179580
tatcaaagaa tttgtagaca cattttaaaa cctccacaag tgtattctaa attttttacag  179640
aagctgtagg caaattcttc ccacgtattt cttttgatgat actgttattg gttgaatagt   179700
gagtgtttcc tgaaaattta tgtccacctg gagtctcaaa atgtgacctt acttgggaaa   179760
tagactattt gcctatgtaa ttagatatgg gtttcaagac aagataatca tnnnnnnnn    179820
nnnnnnnnn nnnnnnnnnn nnnnnnnnnn nnnnnnnnnn nttgagtgtg gtgtggctca    179880
tgcctgtaat cccagcactt tgggaagccg agtgggcgga tcatgaggtc aagagatcga   179940
gaacatcctg gccagcatgg tgaaacccca tctctactaa aaatataaaa attagctggg   180000
catggtggtg ggcgcctgta gtcctagcca cttgggaggc tgaggcagga gaattgcttg    180060
aacctgggag gcggaggttg cagtgagtgg aaattgcacc actgcactcc agcctgggag    180120
gcagaaagag actctgtctc aaaaaaaaaa aaaaaaaaa aaagaagagg ggagaacaca    180180
gagagacaca ggacagggaa gaaggctata tgaagatgta ggaaggccag gcacggtcag   180240
ctcacacttc taatgccaga ccaaggcggg tggatcacct gaggtcagga gttcgagacc   180300
agcctgacca atatggcaaa atctagtctc tactaaaaat acaaaaatca gacgggtgtg   180360
gtggtgcatg cctgtaatcc cagctactca ggaggttgag atagaagaat tacttgaacc   180420
cgggaggtga agatcgcatt gagccgagat catgctactg cactccagcc tggacgacag   180480
agggatactc tgtctcaaaa aaaagaaaa aaaaaaagg gagaaagaga ttagagtttt    180540
gttgccataa atcaagggtg ctaggagcca cctggagctg gaaggggcaa ggaagttttc   180600
```

```
tcccctaaga ccttcaaagg gagtgtggcc ctggcaatat cttgctttag gcttctggcc 180660
tccacaagtg tggaagaata tatttctatt gatttaaacc accaagttgt ggtaatttgt 180720
taggacagtc ctagcaaact aatagatttc tacttaaatt gtcccttgaa aagtcttgtt 180780
ttataattta acattattta gcccaacact ccaatgttct tgaaaagag actagagact 180840
tattcatcat atagtatttt gtcaactgaa aagcaaaaat aaattgcagc tttttctata 180900
acacagctag actcactgat gttcatagca tataagagaa tagttaaccct gcaggacagg 180960
cagcacggga tctctgttcc tgagcaaatg actaaccagc ttctgacttt gggagaaaaa 181020
gcagaactta ggcctaaaga caatactggc tgccagtctg ggggaaactt aagtatgaag 181080
tcattgcagg tcacggaaca cccaaagttg atagtatgac tgactcttca tcctgacact 181140
gggaaaaatg aactgggaga gggagatggt tgagccatgt tatatgtttt aattttactc 181200
aaattagatt taatttgctc atttaaaatt tcatgtatga aaagtgtagt ttgatagaat 181260
ttgtttagta agccattagg gaagaatatg gaagaggttt tgtttatttg tttttctttt 181320
tccctttttt tttttttttgc ctttggcaaa agttccatga gtactaattt catctgtaag 181380
tgaaaagcat ttattattag gccccaggct cacataaata cagcagcaga gtttaagaaa 181440
caatgtaaaa tcattttgat gataggtttc aacagatttt ctcctctaat tccacatgat 181500
tttatactca tgagatttag aattgaacaa gaacgtcaag ttttggaatt atttggggtg 181560
tgaatctttt aaatgaaaat tgaagaaaac gttatcaaaa gcccatgagt taaatataat 181620
gagttttaaa gaacacaaat gaaacatcaa tctggggcac atgttgatga acagggtctc 181680
acactgagaa acagtgttcg tgaaaattta agtgagcccc aagagcaggg agctgaaatt 181740
cctatttgga attgtagcta actgggtggg gaaatgtgat attgatacta ggatataata 181800
aaaccaaat gtaaaactca gaatacattt atcatgatga tgattattat ttaaacatat 181860
gctaaatata atcagttcca gcagcatgtt actgtcttac cctattgaag gaatctatgt 181920
tacctgcttg tttggcaata ttaagaaact tattatctgg gcttctcact gtgaaacatg 181980
gcagaaaaaa cagatcacag tgttctcatg aatgctgttt ctgcattcag atatataccc 182040
acatctatat tcattccaac acttcaggaa tccaaagtaa agcaaatgtg ccatttaaac 182100
aataacaatt gaagcaccca cacactgaag tacacttatg caataacata gcttcacaaa 182160
tggagaaatg gtggctggga aaactagtt ctatagaaaa ggaaatattc cattgtaagc 182220
cagaagattt tattttatt ctttcctatt cctacctcta ccatgcacca agttttgtt 182280
tatttaatga ctttttaagtt taaataatat ttaggaaata gaaattttaa aacttaatga 182340
catgtacatg gacagaatgg agagacatta ttcaggaatg agttcagcac ttagtagcct 182400
gcatagaatg tttcaataat attttggaa tatataaagt aatatgaata atgaatggt 182460
cagggaatga actaatatat gtatgattct tatttagata actgaggaaa ggaaggccat 182520
gtcatgccat aagacataga acacagaagg gaagataggt ttatgttgag tttgagattc 182580
ctattatgta tacaagcagg tcttggtaaa acagggtgtt ttgactctaa cattttgact 182640
caatggacaa ctgttccttt gcatattaat atgcacatt tgatgagaat tgcctacagt 182700
ttttaaaata agttagttaa gaaataaaat ctaatattac ttttttgaaaa tgcataatgg 182760
atgttactgt agagatggca tgaaataaaa cagtgactga cagtgattga accattatt 182820
ttctaaataa tcgcctctag ttggaaacac tgaaaattgc aaaaattggc cgaagaacaa 182880
taaaccaaat aatctatata aaataaaact atcatgcagt atgatttgtt agtaaataaa 182940
atgtgattaa agatttaagc ttcctgtgtg catttaattt ataaaattca aaaaagaaa 183000
```

```
aattggtttg cttgattaaa aaagccctca aagtcaaagc tgtaacataa tagtatgaag  183060
tactataaca atagtgttat gtaatactat gtactatctt tatggcaaga ttgaaacaaa  183120
taacattgat tgagatgaaa ataattttaa taaaatacaa ctgaaaatat ataaatgacg  183180
tgacagtgct gtatataaag ttaatcaaga aattaaatag agttaacaaa atttgctctg  183240
gaacatactt tattaacaaa atttatttag gttaaatttt tatggttaag atgtttgtgt  183300
ccataaagac agcatctaaa cttttgttgg ggattaaagg gacaaagtca aaacagcaga  183360
gtcaaaataa ggaggttaaa ataccgtact tagcagctgg ataagggtct agaactcagg  183420
agagagctaa ggcagagacg taggtccgtg aatcattagc aagtctgtga aagtcaaagc  183480
catgggtatg gatgaactat tccaggagaa aagaaaacag agaatgagag tccaggaatc  183540
ccaatgttga ggggcaaata aaggaagaga ttgtgttgtg acaatgaaaa agaagatggt  183600
taattatgtt ttgcttcaca gggctccact cttcaaggta gcaatattta acattggctt  183660 tctatttta aactcttcta aattgtaacc cgtctccata ttcaagaaaa tgtgggctat  183720
tgtttaactg aaattgtagt gtttcagagg gtaagcataa caatcccatt gtcttgatgc  183780
cgagatatca acttagtgtt atccaggtat gtcatttaac ccaaaattgt ggaccatatt  183840
aaacatcaac ttgtcctact tttattgttg tcttacacct aaaaacaatt tagtctgttt  183900
aatcttttag ttctttgata ggataaagct cttctggatg ccggcaaaac atcaaccaga  183960
ttttatatac ctaaggcacg taccgcttcg aaaagtgcat ctcttcacaa ttattcagat  184020
gagttgcctt ggccttttgt ggataataaa agtttcaaga gctgctattg tctttcccat  184080
gatggtatga aacttctgtc aactattttt ctctttctct gatttgctgg tctctttgga  184140
aacataaaca catgaattga aactggaaca acagagtcat tttgaacaat tattggaaaa  184200
tataagtttt ggcactgaaa gtgtgactaa gatagggttt aagaatgcct atgaatttca  184260
gtgattccta ttagttttgt ctctatcact ctgaatgttt gtggtagtct gaattaattg  184320
aagctggatg gaaaaatgca ttcttccaaa atttaacatt aaagatacta gcaaatatga  184380
aaaattagga tttttaaaat aacattgtat taaatgtttc aggcaagttt caaatacttc  184440
aaaaactata gtgaatttga atgactaaat aatttcataa ttattagtat agataagaat  184500
gttctcgtgt tcatttaata tagtataaac tattaactac atgtatttaa ggaaacatag  184560
tcaaatacat tttataggtt ttttaaaata gcttatttaa tagactccca tattggttaa  184620
aatcatagtc attattgtgg tgatgtagta agaaaagaaa atgaaggaag cagaagacta  184680
gacaatgttt tatacatata tatctttaat ttttactta atctcaggcc taatagaaat  184740
tgtttctacc aaaaaccata caggcaaatc tacacctctc attttaattt tttttccact  184800
ttaaactagt ttattattta cttcaggtgt tagccctggt atttgtaaga agttgatgg  184860 acttgttgtt cacgaagcgg gaactcagct ggttggatga tttgatgccc gagagtaaga  184920 aaagaaact ggaagatgct gaaaagaag taagagcaaa atcaatgttt tataaagaaa  184980
gaaaaaagga acatagtaat atttctttgc aaaactaaat tattgttttt atctttagac  185040
agttttgtct ttagacagtg atcactaaca accacaagta gactagtttg gaagtttaat  185100
gtttaaaatc ataagagttt gaacagagag agaatgaaga tcttatagga ggaaaccaaa  185160
tcctaatgaa atatggaaat actttgtact aaaatacct ccaaattgta aggctcattt  185220
ttctgattcc tctcctatgg atggcagaaa cttgctaata cttaactatt tccaaattat  185280
gatcatgcag tgattgtttt tttgttacat atgtgagaac aaaaagaaga gacattatta  185340
```

```
ctgttggtat tttcctaggg aacagagttt taatcaaaat attctaatga ataattattt 185400
attcttgaaa taggtgaaat gtttagtagg aaaaatgttg atctgatttg ctttcaaagt 185460
gatttaagat tgagtagatg ttgcagaaac ttctggaatt tatttttaca ggctacttat 185520
ttattttatt ctattttata tggtataaca atgtattata agtttcgtgg catatttaaa 185580
gtttatatgt aagcctgagt ctattttgaa agcacttaat caacatttt ttaagtatat 185640
aaaaactaca aagagtgtaa atgagggaaa ataactagc gtaacattta gcaggatgat 185700
tgagcccata caatgtaaaa cacaacaaag ttttcacata aatagaaatg agattgaaat 185760
aaaatatttg atgagaatta tactattttt ctctataagt agtcagtaaa tgtattcaac 185820
tttctatttc ctcaaaccat agatatattt cctatttcct ttggggaatt catttgcaga 185880
tgtttcagag gtcttagtca tttaatgagg tcagatcagg ccataaatca aatgaggttt 185940
tttctttctc agaaatttat accaatatgg ttacataatg tgtaattggt aattccctta 186000
ctctacatgg tgttctatca ctaacaatgg attcccacag atagagattc atcatgatga 186060
tgtgtcttaa tcctgtaaga atgtttcaat ttttccaaat attgtagaag gcaatactta 186120
gactcatact tctagtaata ttaatgttaa cacaaaaaat gatattatac aattgttatt 186180
atttattttt ctgtttgata tatttttatt taaatattag tgcttttta aaaaataata 186240
cttttgagtca ggcgcagtgg ctcatgcctg taatgctagc agtttgggag gctgaggcgg 186300
gcagatcacg agatcaggag ataagaccat attggctaac atggtgaaac cccgtgtcca 186360
ctaaaaatac aaaaattagc tgggcatggt ggtgcacacc tgtagtctca gctactcagg 186420
aggctgaggc aggaggatca cttgaaccgg gaggtggacg ttgcagtgag ccactgcact 186480
ccagcctggt gacagagcga gactccgtct caaaaaaaaa aaaaacaaaa acaaaaaac 186540
tttgactagg atattttgat agtctctatt tcttttagg cctttagtaa acgtttgctt 186600
tcatcctcag atactcttca agaaaatatg gtataatttg gcacaagtta aatttaaata 186660
aaacggacac tagaacacag aaattctaaa atcttaagtt atctatattt gatgtaaata 186720
aaattattga gatcaaacac aacacccaag aaggtttaaa ttaatttaat tttgatgaaa 186780
aagctcttgg ctgtgagctt gcctttcagt cttttttgata atgtcagtac agcagaccct 186840
tgaataatat agcattgtta taatgttgat gagaaaagaa aaaaaaatt ccctggccag 186900
ggccactgtc tgtagggagt ttgcacattc tcctcatatc tgtgtgggtt ttctctggac 186960
acttcggttt cctcccacat ccccaaaatg tgcccattag gttcattggc gtgtctacat 187020
tggctcagtg tgagtgaatg tgggtgtgtg tgtgagtgtg tgctgcaagg gaatagcgtc 187080
ttggccagtc ttatttctca tcttgtaccc tgagctgcca agataggctc cagccaccct 187140
cgaccttgaa ctgaataag tgggttggaa aaggaatgaa taaatgaata caaatgactg 187200
taaaataaaa attcatcaag tatacgataa tcacacaaat gtacgacaac aatttggtat 187260
gaaaatgctc agtgaaccca gccatatttg ctattgtttt tgaactgctt ggtggtaaga 187320
tgtgctcctt acaattttca ctttgcaaac atttattcct gatttaatcc accctacta 187380
tggcctcagt cactctctca ctcaccagaa atttggtaat tcaatatctt acttgctttt 187440
attaactttt cttacatgtt tgtatagctc acatttattt caatgtttaa tattaaaaac 187500
atttgggtc tttagttaga agtttggtga tgttttgtg accagatatt gccataggaa 187560
tttaactctt gttatatca attagcctat ggtaaaattg gtttattta ttcttaatgt 187620
cacagtctcc gagaacctat caataacttt atgtgagcac ttattgtact attaattata 187680
ctcaagcagt aacttacata tctaatttg ctttattttt ctgctttttt ttgttaactg 187740
```

```
tctttactgc ttctggaaaa aaaaaaaacg aacacagccc cagacatata atcatctctt    187800
tcacagtatt ctccttagat catactcata ccgtgaaaca ttcttgcctt ttagaagttc    187860
acaaaatgaa aaatgatatg taatctatta tgtaatgttt aatatttctg tgactgtgat    187920
tcaaagataa tttcagattc tcctttatt ttctgtgaaa caggagagaa caagtttaat     187980
aataattgta aatttattag aatttgccat tcccactgcc cagaaccact cacatagcta    188040
tgcatgtatg gtacttatat gtgtgtgtgc catatgccca ttttggaatt tatgaatctc    188100
ataggggcaga gaacatatgt aatcagtgtc taatcttttt atattatata cccactgtac   188160
tttaatgggc atttactgtt ctctgattat gaagataaag attttaaaag taactaaata    188220
gcactaaatt tcctagaact catgctttct gaaaagatac aaaaatggat taaagatttc    188280
ctggggcaat tttactgcta aatccttcat atccaagtta gagggaaaag ccttgcagta    188340
cattaactag gcaggtttat agatccttaa aatctcagat gggttaatat gatgatactt    188400
tcatgtgatc ctcagtacat ggaaagaaac aagaaaatca ataatatagt caagaaataa    188460
tctataattg aacaataaaa tatagctctg actagtgcaa agacagctaa ttctccatcg    188520
aacaggaaag aaaataggaa gtttaaagag gttcgctttc tagcttagaa ttagtattaa    188580
aagagtatgg tcactaaaga cattaggaag atttaggaat aattatacta aaagttaaat    188640
tcctggttga tttgtttgcc cggatcttgg tattctattt tcttgaggct tacagactca    188700
gtagaaggat gtgatcttac tgtggcatct tatactaagg cccagtcttc taagagattg    188760
tgtgttaagg tggtaaacgg acaagttctc cagaaatgtt gcattctgc aattgctcaa     188820
attaattgag taactttgat catgaactgg caagatggta aatagcagaa atgtctcagc    188880
tccctgagac ttgaatttaa gtaggctca cctcttgtcc ttttgatgat agatacaagc     188940
ttttacctttt agcctccagg gttttcctat cagtagccca tttctggtct tatggcactg   189000
agaaaacatt catttgacct taaaattcaa taatgagtta agcagaataa atagctacac    189060
aggccagtcc aagtcgcag agcttctgtt ccaaattttc atgtacttca tgcatatgca     189120
tatgcatatg cttcagtttt tagaaagaaa ggattataat cagggtagaa atgaatattg    189180
gaaccctgac attttgcaca ttgctctgtg taaagggaag actgcagaat caaattctgg    189240
atgtccaaat gtgctcagag taccaacatg ccttccttcc tacttaaata ttctctaggc    189300
cattgtacac atttgacaaa aggctactta ctgttaaagg cagaaaatcc cagcagaatg    189360
tttgctcctg ggtaggagga aaggggggtta gtgttggata aatcctagaa attctactct   189420
gtggaagtga tcatgatagt gatacttctt gatttactgg ggcttcactc ttaacatata   189480
cactatagga gaaaacaaaa agagggcaaa tgggaccctg tgatcccaat gcaggatcat    189540
gaaaaaggtc aagaaaaaag caatctaaaa acaagtgcaa ctaaacaaat tacagaggac    189600
gacttactgc taagataggt cagaattggt tatggatttg ggaagcatgg ccaaattatt    189660
acannnnnnn nnnnnnnnnn nnnnnnnnnn nnnnnnnnnn nnnnnnnnnn nnnaacaaag    189720
tatgctagct atgggaagat gagggcacag tacaactccc attggaaggg cactataggt    189780
aagacataaa tttaaaaaca catcaattaa agtaatgaaa tgcattgtta tatactttaa    189840
gaatttcata ctgtgtagat cctcagagag gtttcttgaa attgtataag agtgaaagaa    189900
acgaagagtt agataacatg ggtcctactg ctaagttttg ccaataatag ccgtgtgact    189960
ataatcaaat tgcattaaat gaagtgaagc aggaagctgt tgtctgaagt ttttcttgct    190020
cctgttttat aatgtgtatg aaaaatccct ttcatattct cagaaagtag caccagaaga    190080
```

```
cagatcaagg ttcctttttt gtataagtga ctagttattc actaagttga tcacaggtaa    190140
atgttttaac tctgggaatt tgccgctaaa agtggaattt ccaatgacat aatctatttc    190200
ttaagtgatt cagttgtatc agtcatttta ggatatattt atgcaattct ccaaaatttt    190260
ctaatcttct ttatgtacaa agacatagca aaagaaagca aactactgaa gttataaaga    190320
aaacatttgc aagcatttgg cccagaattc tccctctct ctctcttctc tgtctccctc     190380
tcaatatagt ttagtttaaa cggttatctt gtacaattct aagtatcaat tagtgcccaa    190440
ttttatagtc tcaaagtctt tatgaataat ttaaggttat gccaataaaa atacagagaa    190500 tacttttta tgagaaggga atttgtcata gtgttaaaaa ccaaaatagg agagaatttt     190560
ctagatcttt agggtctgac tctaagatta tattccctag aatttaagaa aatgtgatta    190620
cctccctctt aagaggggc acaagtataa gatgttttat ctttttttc ttttttacaa      190680 catttaaatt ttaaaatcct gttgatttt tagctgaacc agcatatttc caagtgtatt     190740
aggtagaaac ctagtcttgt gtgataccac tctcgaaagg gctgtgtggt taaataagtt    190800 tgaaaaatg tgccaaactg cattccagtt tggagattca caatgcatat tagcaaatga     190860
aacaatctaa gtagtactgc atttaaaaa attgtatagc ttcgttcaat caagtattta     190920
aaaaaatctt ttgctcagaa gactcttcct cacataatat catgaaaaat gtctattcca    190980
catgatgctt tttttaagaa agtagtcaat ctggtgcttt gaattaccag gaaactatct    191040
ttctaggaag accaaaacag ctggagggtt tagaggaact gaagaacaca tttccagatt    191100
gggcaagaga gggagaccca aggttttgtt cctcttaaaa gttgcatttg ttcctctcct    191160
gtgacctatc accaatcagg gtcatatgaa aaggcggcat ttgaacaaag aagggcaag     191220 gttgctccat gtgaagggac atgataagca gaggaagag caaggacaag gcccccaggc     191280
agcaccatgc ccattgtgtt ccagaacagt caggaggcta ctgaaatggg gctggaaagg    191340
agtgagcagg gatgcagtgg caggaggtga atcagagtg aggtggggac agagccttta     191400
ggccattata aggacttggc attgactctg agtgactggg agccactgca aggtctgagc    191460
aaaggaggga agtgatctgg ttgctatgat gttaggggca agcgtttaag caatggacat    191520
gcggaaccca ttctctgtaa tttgaaatga attaagaata ccacaggcca actcagtatc    191580
tattcaacta gaatattttc tttagttttt ttattttca cagattgttt tcaataattg      191640
agagaaatat tcaatacttc ttcatttta attatcaaaa atattgtaca ataaacaaaa     191700
tggggcatac acatacaatg gaacattatc caggtttaaa aaggaggaaa ttctgacata    191760
tgctacaaca tggatgcacc ttgaggatgt tgtactaact gaaataaacc agtcacaaaa    191820
agacaaatac tgtatgattc tgcttatatg aggcacttag agaagtcaga acctagaga     191880 cagaaagtgg aattatagtt gccagggacc gggaacaaga ggaaatggag agttgtggtt    191940
tagtgggtat ggagttccag ttttatagga taaaaagagt tctggaaatg atggtggtg     192000 atggttgcac aacattatga atgtatttag taaccctgaa ctgtacttt aaaaatagtt     192060 aaggtagtaa attttatgtt atgtgtattt taccacaatt taaaaattgg gaaaatatt     192120 cttcatagat atatgattgc cctatattta gtttctgtca ttgaaaaact gcagttactt    192180
atgtaatgtt tattatttca tttggggaaa ctcctgtcta gagatgatcc atctgtgatc    192240
aatatatctg atgaaatgtc aaagactgcc ttgtggagga accttctgat tactgccgat    192300
aactcaaaag ataaggagtc aagctttcct tccaaaaggt ttggatttta aaataatgag    192360
aatttatact aattccaatt gttttttgac ataaaccata agcaaagaa taatattagt       192420 ttccatcaaa tttagatata aaatattcca gaaaattctt tccaaaagtg ggtagaaatt    192480
```

```
gtaattattt caaatgttgg tatgtttttc ataccaactg tggtatgggg aactgtgcta    192540
gaaatgagtc acaatgcatg acattttttgg acattcatct tggcctactg tttttcagta   192600
tgattttatt ttattccctc atcacccact tccccccagga cccctttaga catctggcca   192660
cattttgcac tcctttattt tccctttttt agactgatat gcactgtgtg tattttatat   192720
ttatatttta taaatatgca taaatattta tatttagtat agttctagtc ctgactccaa    192780 cccccctgaaa gtcttcccta aacttcttat cccaaaactt tcaactcctg aaagttctat   192840
ccattctttc ttctctgtgt gtaaatgtac aaacaactcc tgtagttgtg atggtagtt    192900 ttaagtgcat gctggaggaa gagtgtgtcc ctaaatatca acagtcatca aaggatttcc   192960
aagtgaatct tctaggattt ataaataaga gttcaagtca cccagtcttc ttagatgctg    193020
atctgaagaa agaggaattc ctatgttatg ctaatatctc tttttgttag agagtgattg    193080
agggaattgg gacagtgttt actataatta taaagttcct ttatttttcgt aaccttaaat   193140 taacttttttc tacttaattt ttatattaca tttttgtcat aagctcccct tcctaatcac   193200
tctagaagct gattccccaa aggtaagacc ctctcccctca aatctattcc ttggttgcat   193260
ttccttatgt taaatggtgt cttctagaaa cctggtcagt ctatgtcctc tgtgtgagtt    193320
ttggggaggc aaaaggcatg gagagtgttg ggctcagatc cagtagcaga ctgagtttga    193380
tgatatatct gtaacaactc agctctttaa gttagtctga aacttgaata aactttattc    193440
cttccttgat ttatacagat gcatcatgta taaatcaaca agtttcacag aactgtagtt    193500
agtaatggca tcaaatttct ggatagggaa aattaaattt gtccctttaa gaaattgaaa    193560
agcttgcctg gtgtggtgac tcatgcttgt aatcccagca ttttgggatg ccaaggtgag    193620
cggatcactt gaggtcagga gttcgagaca agcttcgtca acatggtgaa accttttctg    193680
tactaaaaat acaaaaaaat tagccaggcg tggtggcgga tgcctgtaat cccagctact    193740
tggaggatga ggcaggagga tcgctgagcc caagaggnnn nnnnnnnnn nnnnnnnnn    193800 nnnnnnnnn nnnnnnnnnn nnnnnnnaaa tgcccttgag gtcaatgtgt tgagtaattt   193860
gaaacaaacc tgtaaaaaat tttcttcctg tattatatgg attcaaagtc caaacttttc    193920
ctctattttt ctttggttca agcaaaagtc ttgtgacgtg atattttagc tactccttaa    193980
agtcaagtga tactttttcac cagaaaaatc tttttgtttt aaaaatatat atccagatga   194040
cttcacatag tgggttgact ctagtgaaca atataatgtg ctttaaagca ggtccaattt    194100
tcaatagact atcctttata tttagatata accacttgtt tcttattctt taaatgtact   194160
ttcactgacg tgaggttcag actattgtgg aatgaaagtt tatccagctt tccttacctt    194220
ttgatgtgat cgcatttgtg gttttccatg tgagaaacat ttttggttg gtagttaatc    194280 tcttttatcc tcattacagt agaaactctg gcagaaagtg tatgacttac agaattctaa    194340
aactactgat actaataagg ctcccaaagc cacttccttt ttgtggtatc tgttaaaggc    194400
tttaaagcat catgaccagg aactgtgaaa atttagtacg tggtagagta tccattggca    194460
aaaagagacc caaagagcag gttactaggg tctgagtcct gagctggcac ccatgcagcc   194520
tttgacaccc cccattctga gttattttcc atcctgtgct gtaatgtgtc agagaagcct    194580 agaaacccctt ttttcatgga attttgaata gaaattatat tttctcaatt atatcattca   194640 cttttttgttg tcaaaaatat tttatctcgt ttaactgaca gtagaatcta agaactaacg    194700
gcaaattctg tcttatctgg aggatgtcta attttgatcc tgatgtcata catgcatgtg    194760
acaagagcct ctgcagctta ttaaatgggc tggtgaaaat agggctcatt aacgaccaca    194820
```

```
ttgcatcaga ataggttagc aactgctacg tttttttaaac tgatgcccaa gatcagtgtg   194880
tctggaggtc cttggcaatg ttaggaaaag cagcacttag ctttgccttg gtgacagagg   194940
ctagtctctg ggactatccg ctctaccccc aacacccac ccctgcactc ccccaccacc    195000
tttttctatc ccagattctt tctttgctct gattgcctag gcttaggctc tctcatgact   195060
tcttggaaat attattcata aaaacaactt tagcctgggc gtggtggctc aggcctataa   195120
tctcagcact ttgggaggcc gaggcgagca gatcacttga gctcgggagc tcaagatcgg   195180
cctggccaac atggtgaaac cccatctcta ctaaaaatac aaaaattagt tgggtatggt   195240
aacgcacacc tgtaatccca gctactcagg aggctgaggc aggagaatcc cttcaacctg   195300
cgacgtggag gttgcagtga gccaagattg tgccactgca ctccagcctg gcaacagag   195360
caacactctg tctcaaaaaa aacaaccact attttagtga cattaaaaag taatagtttc   195420
atagtttact tagcatcatg acagtaccag gtcactttt gccctcttga aatattactt   195480
ccttatattt taaattttaa ctcctcaggg acagggacac tcttatctat cttgtactcc   195540
taggtcatta tggagttcct ggcatataat agatatgcaa catatgttta ttacaatgac   195600
agataacaga tgcataatac atgtttgtta caatgaaagc ttaaaattga ttggcctcca   195660
caaaagcgaa cttaacaagt aattccgaac aatggatcct agaggtcttg agctggttat   195720
aaaatttctg cttcatagtt tgctgaaatc taatctgata ccaaaactat ggttatgatg   195780
aagagggaaa aaacccaga catttaatag gttattgttt tgtaaccaaa caaccaaagc   195840
agagtcagga ggaagcacat ctatggatca agttgatatt atgaatcttt ttatttatga   195900
cttggtgact aatagtgcca cttggcacac attcatttat caaaaggtta tggaacacct   195960
cccacgtttc aaagtattgt gcacacagta attgcacatg tgtagagacc agtatatctc   196020
tgtcctacaa tctcctacat ataggatctg ttattctatc tttcaaaaaa taagagttca   196080
ttggaattgg gaataccagc ctcagaattc tggaattctc actacaagag agcctagagg   196140
ccatctagtc caaaaccaat tttacagatg aagaaaccaa gtctcagaga gattaaataa   196200
ctagtccaag gtcatgcagc tcattctgag ttctgaaaaa ctgaacctag atcttccaac   196260
accaagccca gtgctgccct ttttcattga ctttgtttgg caaagagac tggaaggcag    196320
gtagagctta aggaaaagtt aatttggaaa gcaggagagc atacacttgt catataaaag   196380
gaacttaaag tagaagaaag tgagtcatac agatagagga gttaaaaata cgagttaggg   196440
ctctcaacac atcatgtgca cactgtcatc ttttctcatg gaaggagaaa agaaaaggga   196500
ggaaagttgc tttgctctga cctgtaagta gtatgtgctg agaagtgtgg caggcacaaa   196560
cccgggcgcc atagacacgc gctcacacca gctctcagag ctggcagcgt gccacagatg   196620
gcagaagctc cggcacttct tacctgatgg tgccgggtgg tggtgacaac tgagaagggc   196680
tgtttctagc ttgaattgga ggaaaaacaa tttaaaaaac acactcttag aatgtgtcta   196740
agttattgac cacttagaaa gttgtacagg aggccccata gaaaatgga gttttattac    196800
tttattactt ggagaagagt tataaaacca agggtgcggt ccattgtcaa gtgtttcata   196860
aatttatatt aagggccgaa gttaacagta aaaatgtatg gatacttaca gcccaggggcc  196920
tcagtagctg gctatgggct gccctttgtg tcagcagtgg ggagggtcac atagaagcct   196980
cagatgagga gggtttttgct gtgtgctgca agtatcaggg agaaagcatt tctgccctct   197040
ctggaacatg gtgtgaactt catccctgta atgatattgt ttgaattttc catgaaaaat   197100
tgtcagcatg agagtaagaa aagtgtacga tgggaaaata ttgaaccaaa cagacaaaaa   197160
tggtagagtc acatgaccag tttactcatt ggtaaagtta atgagagggt gagattaaac   197220
```

```
agaaattggt aaagttaatg agagggtgag attaaacaga gggtgagatt aaacttggga   197280
atgagtttgt ctgaggagtg aggtgaagca tcattcctct gatgcacagg gtaagggttt   197340
gtctgtaaag agatagcaca ggtgtctgga gagcagcgtg catggtaacc tgtcctccag   197400
gccagtggag ctgtctgtct aacctggcca aggtacagtc ttcatcaaag gtcaggatcc   197460
agtccatgca caagggagga gccatttgca gcagagccca gaaatgcctc ctgcgacatc   197520
ttgtttgtgt catttactag agttggcact gtcttaagat gggggcatgg ctgacatttt   197580
caactatcat cagtgagtca cttgcccaaa tgaggaccat ggtattaatc ttgcatgttt   197640
ttggaactgt ttaaaaaatg tctgattttt gttgtttagt gtctgttttt gaatttcccc   197700
ttctctgcag ttcttggttt ctatctcact gagtgcagag gattttaatt gttgctgtct   197760
atctgtgctt cgcagcatga gagagcaatg cctacgggct cttgtggtgc tttggggttg   197820
acgggtttta tgtctgagca agcagatgtc atagtagcca tgctggattg cagtaataaa   197880
tgtgtccttt ttttccttct gtagcattga aagccgaaaa gagaagaaag ctgactcagg   197940
gaaaggtgtt gacagggaga cttgtctatg actcgatctt caatttattt tttacatata   198000
tatgagaaga gtgtcacaat tattaataaa actgctttga tcatgtattg taaattctgt   198060
ccctcaaccc aaatccacct tcatactgta agtagtgcaa tacttgtttc atttctgtgt   198120
ttaaacttct gagcagtgag acatccctgt gagcagatac aatagccaat gcaagaatct   198180
gtgtgttcct tgctgtacgt tagacatttg taaactggat tctgattgtc agttttatga   198240
gagcaatagc ttccttaaag agataagtca tatttaccta gtttgtattt tcctacttta   198300
gtgacctgaa gatgcctgat aatttcattc agaagaattt ttgaaaggta gtcttacttc   198360
tttttagttt ttatagctta gcattagtga cttatttcaa aagacccaaa tcaaaaagtt   198420
agtttgaaag cattttttaa taattgtatt tatgcatttc cttgatttaa tatgataaat   198480
ttaatactta acaatttata tgtaactaaa acttaaagtc atttgaaaaa tatatagaaa   198540
cctatttaca acttgttaag gacaatcaga cataatgcag agttaagtag tatttgctta   198600
aaattcaagt tgtgactaat gatcaaatac taggcttgta cgaaatgctt tagaaaaact   198660
ttgtaacagt tttgtgggat ttttcaatat aaaccttttat cagaaatata ctaagtttgt   198720
ctcccactga caacagatgt tttccaaata aacatattct atacatactt gtggaatgcc   198780
acatggtgaa tcattgtata tgaaattcca ctcctgtaca gttactctgc agctaatggt   198840
catgcactgc ttaatgctgg tcctgaatca tgttctcatg ttagaccaac agctctccaa   198900
ttgtcatttt ttttctgcag agtttttttt ttccactttt aaattaaatg catgttgtgg   198960
aaaaacagtc ttttaaaatg aaatttcaga ttccatttga gaaggttctg tagatatttc   199020
agtccatata aaataataca tctttactaa acttatataa ggggagagaa agttatgaag   199080
ttttggacat tactaaaagt acagtatttg atttcacttt caatgaatgg tgaagttaat   199140
aaaactaaat ctcataatgc tcttggttcc taagaatgag tagtaatcat caactttata   199200
atactccaat attccgtttt ataataattc agagccctgt ggcttttaca caccgttaat   199260
tatgtactct gttggaagtg cacatgaaaa gtgaagaaaa gttcctcttg tgattaaact   199320
aatgggagga aataaatcaa caaagtctcc attaagttct acattttgag accttttaaa   199380 aattccctc acaattcttt aaggagcccc ccttttatg gaacatgagc ctaaaaatta   199440
tagaaagaag aattttaagt taataaagtt tgtatttata aatgctgaaa aaatacagaa   199500
actttctgtt ccaaatgtgt tgcctttgtg tattttataa tacagatact acattgtaaa   199560
```

```
catttccatt gttttatgat ttagccagtg attccccaaa gcagcctctt agtgttttaa 199620
tatattaata actgttttgt taaaaatgat catagtgaat ttaaatcttc acatgatcac 199680
ctatttgaat aagcaatcat atccaatgaa attctgtatt tctgagtatt tttatagtca 199740
ttttgttctt gtgtgaattt taaagctatc cctatgttaa tcctaatatt ttgaaatcat 199800
ataaaatata ataaaaatgt agtattatat atttacttct aatttcagat tcctggtcaa 199860
aattactaaa tatcttgaat gtaatttagt gccaagttta ataatgtgt aaatgtgact 199920
aggatattgt gtttttcaca attaagaaat gttatgtgga aataaatatt tatcctaact 199980
tccttgcaca ttttaaattg tgatacaaag tgtcttgtct tttttctttg ttttaattag 200040
taaatcagtg taaaacattt tgattgtttg aatataatat ttaaatttag acagccccaa 200100
agctaagaac tcttggtgat gtaaacaatt tatgagtatg tttcaagagt aaacaatttg 200160
aactttatga acagaagatt atgagaacta tataagata tatttactca tttttccaga 200220
aatgggtgca gatgacacgg tttcttatgc taggaaaaac ctccaaggtc gttagtagta 200280
gtattcctca ttattagaac tctatttaga cttccgtttt taacttccat ggggaaagca 200340
ttgcctaaaa tttgtctcct ccctgtttct tacaaaagtc agatgggacc attattcttt 200400
ggtagccatc tggcagtgtg ttgtggagat aattgcattc agaattctat ctaacctact 200460
gcttggtatt tttctcttga ctagtgagtt tactttgtaa ttgctcctgt ttcacagcct 200520
acaatattgg aaagtttttt tcctgtataa tataatatag gaatatatat attcctatgt 200580
atgtatagga tatcctatat atcctgtata gatgaatgtc tccttggtat agtttaaacc 200640
cgagtttgaa agaaactctc cactgatgat ccaaaagcaa cttgtatttc aacatgattc 200700
ctagatcttt ttggattttt cttgactctt agaagtgtga cttacctgtt ttctatggca 200760
ctgacctacc tctgttttgg tttaacttta gcctattagc tcctgggcac ttgtctattt 200820
tactatcatt gcaagattgc tctctcattt ttccaatata ttaatatcta tctcatatat 200880
tcacacaatg aaatgaaatg agattacatc catttgaaag ttttatgaga gtcatttgga 200940
taatatgatg gttctctaaa tgtctacatc aagaggctaa ttgtagttag tccccttgaa 201000
gaggcttaat aatcaaagat tactggtaat actttatttt agagatctcc ttcgatgttc 201060
ttcatggaat gctgtggcta actgatacaa ctgtcacacc aattccgttc ctgttggtgt 201120
actgggtact atcatttctg ctggaacttt gaaaatagga ctatgatcct tgcttctaag 201180
ggcagggtgg atacatagct gtaaataatg tgatatgtgc tgagttggcc atatgagtaa 201240
agccattttt tgaatagggc agagtttgac gaaaacatta tagtagaggt agcacgtgaa 201300
ttagaatgga aatgggggaag gaaatgtact ccagatgttg aaggaacccc tgcctactag 201360
gcctctggtc taatgaagta tgaccagaat gactccatct tgaagtgaag agctagaaca 201420
ctcttaaggc acctataaga ttaatgcttg tggtctgaaa atagccactt tccaagctgg 201480
ctacaaccta ttattacaga atatttatga ccatacagag catctcccac catgcctgca 201540
gaatgtccct atgtcctaag aattcagccc tccttactta gagataacgt taatgaacaa 201600
gcttaggtta aaagattaag ggtcatgtaa tatcaatgac actgaaggcc cctgccttta 201660
gtgagcacat agacacattc caagtttaat tgtagctctt tgtaactcct tataaaagta 201720
gaggcgctaa caaaggacag ggcattcctc cttttgcttt cagaggatat cccacactgt 201780
aacgaaacgg tttctgaaaa acttacttct tccactatgc tctgtggctt tccttgaatt 201840
ctctcctttg caagatccaa ggacccattt tggggtctg gatcaggacc ccttttccag 201900
caacaccgga actacaaaga ttctcaaacc tatgtcggta ttgaaataaa gatgaaattt 201960
```
aaaagtaaag ctatatggca taactagagc ctggcatatt t    202001

<210> SEQ ID NO 4
<211> LENGTH: 1085
<212> TYPE: PRT
<213> ORGANISM: Mus musculus

<400> SEQUENCE: 4

```
Met Pro Ala Gly Ser Asn Glu Pro Asp Gly Val Leu Ser Tyr Gln Arg
 1               5                  10                  15

Pro Asp Glu Glu Ala Val Val Asp Gln Gly Gly Thr Ser Thr Ile Leu
            20                  25                  30

Asn Ile His Tyr Glu Lys Glu Leu Glu Gly His Arg Thr Leu Tyr
        35                  40                  45

Val Gly Val Arg Met Pro Leu Gly Arg Gln Ser His Arg His Arg
    50                  55                  60

Thr His Gly Gln Lys His Arg Arg Gly Arg Gly Lys Gly Ala
65                  70                  75                  80

Ser Gln Gly Glu Glu Gly Leu Glu Ala Leu Ala His Asp Thr Pro Ser
                85                  90                  95

Gln Arg Val Gln Phe Ile Leu Gly Thr Glu Glu Asp Glu His Val
            100                 105                 110

Pro His Glu Leu Phe Thr Leu Asp Glu Ile Cys Met Lys Glu Gly
        115                 120                 125

Glu Asp Ala Glu Trp Lys Glu Thr Ala Arg Trp Leu Lys Phe Glu Glu
    130                 135                 140

Asp Val Glu Asp Gly Gly Glu Arg Trp Ser Lys Pro Tyr Val Ala Thr
145                 150                 155                 160

Leu Ser Leu His Ser Leu Phe Glu Leu Arg Ser Cys Leu Ile Asn Gly
                165                 170                 175

Ser Val Leu Leu Asp Met Arg Ala Ser Ser Ile Glu Ile Ser Asp
            180                 185                 190

Leu Ile Leu Asp Gln Gln Glu Leu Leu Arg Asp Leu Ser Asp Ser Val
    195                 200                 205

Arg Val Lys Val Arg Glu Ala Leu Leu Lys Lys His His His Gln Asn
210                 215                 220

Glu Arg Arg Arg Asn Asn Leu Ile Pro Ile Val Arg Ser Phe Ala Glu
225                 230                 235                 240

Val Gly Lys Lys Gln Ser Asp Pro His Ser Met Asp Arg Asp Gly Gln
                245                 250                 255

Thr Met Ser Pro Gln Ser Ala Thr Asn Leu Glu Val Lys Asn Gly Val
            260                 265                 270

Asn Cys Glu His Ser Pro Val Asp Leu Ser Lys Val Asp Leu His Phe
        275                 280                 285

Met Lys Lys Ile Pro Thr Gly Ala Glu Ala Ser Asn Val Leu Val Gly
    290                 295                 300

Glu Val Asp Thr Leu Asp Arg Pro Ile Val Ala Phe Val Arg Leu Ser
305                 310                 315                 320

Pro Ala Val Leu Leu Ser Gly Leu Thr Glu Val Pro Ile Pro Thr Arg
                325                 330                 335

Phe Leu Phe Ile Leu Leu Gly Pro Val Gly Lys Gly Gln Gln Tyr His
            340                 345                 350

Glu Ile Gly Arg Ser Met Ala Thr Ile Met Thr Asp Glu Ile Phe His
        355                 360                 365
```

-continued

```
Asp Val Ala Tyr Lys Ala Lys Glu Arg Asp Asp Leu Leu Ala Gly Ile
    370                 375                 380

Asp Glu Phe Leu Asp Gln Val Thr Val Leu Pro Pro Gly Glu Trp Asp
385                 390                 395                 400

Pro Ser Ile Arg Ile Glu Pro Pro Lys Asn Val Pro Ser Gln Glu Lys
            405                 410                 415

Arg Lys Met Pro Gly Val Pro Asn Gly Asn Val Cys His Ile Glu Pro
            420                 425                 430

Glu Pro His Gly Gly His Ser Gly Pro Glu Leu Glu Arg Thr Gly Arg
        435                 440                 445

Leu Phe Gly Gly Leu Val Leu Asp Val Lys Lys Ala Pro Trp Tyr
    450                 455                 460

Trp Ser Asp Tyr Arg Asp Ala Leu Ser Leu Gln Cys Leu Ala Ser Phe
465                 470                 475                 480

Leu Phe Leu Tyr Cys Ala Cys Met Ser Pro Val Ile Thr Phe Gly Gly
                485                 490                 495

Leu Leu Gly Glu Ala Thr Glu Gly Arg Ile Ser Ala Ile Glu Ser Leu
            500                 505                 510

Phe Gly Ala Ser Met Thr Gly Ile Ala Tyr Ser Leu Phe Ala Gly Gln
        515                 520                 525

Pro Leu Thr Ile Leu Gly Ser Thr Gly Pro Val Leu Val Phe Glu Lys
    530                 535                 540

Ile Leu Phe Lys Phe Cys Lys Asp Tyr Ala Leu Ser Tyr Leu Ser Leu
545                 550                 555                 560

Arg Ala Leu Ile Gly Leu Trp Thr Ala Phe Leu Cys Ile Val Leu Val
                565                 570                 575

Ala Thr Asp Ala Ser Ser Leu Val Cys Tyr Ile Thr Arg Phe Thr Glu
            580                 585                 590

Glu Ala Phe Ala Ser Leu Ile Cys Ile Ile Phe Ile Tyr Glu Ala Ile
        595                 600                 605

Glu Lys Leu Ile His Leu Ala Glu Thr Tyr Pro Ile His Met His Ser
    610                 615                 620

Gln Leu Asp His Leu Ser Leu Tyr Tyr Cys Arg Cys Val Leu Pro Glu
625                 630                 635                 640

Asn Pro Asn Asn His Thr Leu Gln Tyr Trp Lys Asp His Asn Ile Leu
                645                 650                 655

Ala Ala Glu Val Asn Trp Ala Asn Leu Thr Val Ser Glu Cys Gln Glu
            660                 665                 670

Met His Gly Glu Phe Met Gly Ser Ala Cys Gly His His Gly Pro Tyr
        675                 680                 685

Thr Pro Asp Val Leu Phe Trp Ser Cys Ile Leu Phe Phe Ala Thr Phe
    690                 695                 700

Ile Val Pro Ser Thr Leu Lys Thr Phe Lys Thr Ser Arg Tyr Phe Pro
705                 710                 715                 720

Thr Arg Val Arg Ser Met Val Ser Asp Phe Ala Val Phe Leu Thr Ile
                725                 730                 735

Phe Thr Met Val Val Leu Asp Phe Leu Ile Gly Val Pro Ser Pro Lys
            740                 745                 750

Leu Gln Val Pro Asn Val Phe Lys Pro Thr Arg Asp Asp Arg Gly Trp
        755                 760                 765

Phe Ile Asn Pro Ile Gly Pro Asn Pro Trp Trp Thr Val Ile Ala Ala
    770                 775                 780
```

-continued

```
Ile Ile Pro Ala Leu Leu Cys Thr Ile Leu Ile Phe Met Asp Gln Gln
785                 790                 795                 800

Ile Thr Ala Val Ile Ile Asn Arg Lys Glu His Lys Leu Lys Lys Gly
                805                 810                 815

Cys Gly Tyr His Leu Asp Leu Leu Met Val Ala Val Met Leu Gly Val
                820                 825                 830

Cys Ser Ile Met Gly Leu Pro Trp Phe Val Ala Thr Val Leu Ser
            835                 840                 845

Ile Thr His Val Asn Ser Leu Lys Leu Glu Ser Glu Cys Ser Ala Pro
        850                 855                 860

Gly Glu Gln Pro Lys Phe Leu Gly Ile Arg Glu Gln Arg Val Thr Gly
865                 870                 875                 880

Leu Met Ile Phe Val Leu Met Gly Cys Ser Val Phe Met Thr Ala Val
                885                 890                 895

Leu Lys Phe Ile Pro Met Pro Val Leu Tyr Gly Val Phe Leu Tyr Met
                900                 905                 910

Gly Val Ser Ser Leu Gln Gly Ile Gln Phe Phe Asp Arg Leu Lys Leu
            915                 920                 925

Phe Gly Met Pro Ala Lys His Gln Pro Asp Phe Ile Tyr Leu Arg His
        930                 935                 940

Val Pro Leu Arg Lys Val His Leu Phe Thr Leu Val Gln Leu Thr Cys
945                 950                 955                 960

Leu Val Leu Leu Trp Val Ile Lys Ala Ser Pro Ala Ala Ile Val Phe
                965                 970                 975

Pro Met Met Val Leu Ala Leu Val Phe Val Arg Lys Val Met Asp Leu
            980                 985                 990

Cys Phe Ser Lys Arg Glu Leu Ser Trp Leu Asp Asp Leu Met Pro Glu
        995                 1000                1005

Ser Lys Lys Lys Lys Leu Asp Asp Ala Lys Lys Glu Glu Glu Glu
    1010                1015                1020

Ala Glu Lys Met Leu Asp Ile Gly Gly Asp Lys Phe Pro Leu Glu Ser
1025                1030                1035                1040

Arg Lys Leu Leu Ser Ser Pro Gly Lys Ser Ser Phe Arg Cys Asp
                1045                1050                1055

Pro Ser Glu Ile Asn Ile Ser Asp Glu Met Pro Lys Thr Thr Val Trp
            1060                1065                1070

Lys Ala Leu Ser Ile Asn Ser Gly Asn Thr Lys Glu Lys
            1075                1080                1085
```